(12) United States Patent
Jin et al.

(10) Patent No.: US 11,352,351 B2
(45) Date of Patent: *Jun. 7, 2022

(54) COMPOUNDS AND METHODS FOR THE TARGETED DEGRADATION OF ANDROGEN RECEPTOR

(71) Applicant: Arvinas, Inc., New Haven, CT (US)

(72) Inventors: Meizhong Jin, East Northport, NY (US); Andrew P. Crew, Guilford, CT (US); Hanqing Dong, Madison, CT (US); Jing Wang, Milford, CT (US); Xin Chen, Trumbull, CT (US); Yimin Qian, Plainsboro, NJ (US)

(73) Assignee: ARVINAS OPERATIONS, INC., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/002,303

(22) Filed: Jan. 20, 2016

(65) Prior Publication Data

US 2016/0214972 A1 Jul. 28, 2016

Related U.S. Application Data

(60) Provisional application No. 62/105,210, filed on Jan. 20, 2015.

(51) Int. Cl.

| | | |
|---|---|---|
| *C07D 417/14* | (2006.01) | |
| *C07D 413/14* | (2006.01) | |
| *A61K 31/422* | (2006.01) | |
| *A61K 31/4439* | (2006.01) | |
| *C07D 417/12* | (2006.01) | |
| *A61K 45/06* | (2006.01) | |
| *A61K 31/4545* | (2006.01) | |
| *C07D 233/86* | (2006.01) | |
| *C07D 401/04* | (2006.01) | |
| *C07D 491/107* | (2006.01) | |
| *C07D 471/10* | (2006.01) | |
| *A61K 31/427* | (2006.01) | |
| *C07D 413/12* | (2006.01) | |
| *C07K 5/078* | (2006.01) | |
| *A61P 35/00* | (2006.01) | |
| *A61P 25/28* | (2006.01) | |

(52) U.S. Cl.
CPC .......... *C07D 417/14* (2013.01); *A61K 45/06* (2013.01); *A61P 25/28* (2018.01); *A61P 35/00* (2018.01); *C07D 233/86* (2013.01); *C07D 401/04* (2013.01); *C07D 413/12* (2013.01); *C07D 413/14* (2013.01); *C07D 417/12* (2013.01); *C07D 471/10* (2013.01); *C07D 491/107* (2013.01); *C07K 5/06165* (2013.01)

(58) Field of Classification Search
None
See application file for complete search history.

(56) References Cited

U.S. PATENT DOCUMENTS

| | | |
|---|---|---|
| 6,306,663 B1 | 10/2001 | Kenten et al. |
| 6,670,348 B1 | 12/2003 | Rosen et al. |
| 7,041,298 B2 | 5/2006 | Deshaies et al. |
| 7,208,157 B2 | 4/2007 | Sakamoto et al. |
| 7,244,851 B2 | 7/2007 | Cohen et al. |
| 7,345,081 B2 | 3/2008 | Cohen et al. |
| 7,419,975 B2 | 9/2008 | Palermo et al. |
| 7,517,906 B2 | 4/2009 | Condon et al. |
| 7,915,293 B2 | 3/2011 | Ramesh |
| 9,500,653 B2 | 11/2016 | Crews et al. |
| 9,632,089 B2 | 4/2017 | Crews et al. |
| 2006/0128632 A1 | 6/2006 | Sharma et al. |
| 2007/0254933 A1 | 11/2007 | Jung et al. |
| 2008/0051432 A1 | 2/2008 | Zhang |
| 2008/0214501 A1 | 9/2008 | Zhengying et al. |
| 2008/0269140 A1 | 10/2008 | Wang et al. |
| 2009/0035362 A1 | 2/2009 | Shih et al. |
| 2010/0048517 A1 | 2/2010 | Hu et al. |
| 2010/0203012 A1 | 8/2010 | Laurent et al. |
| 2011/0195043 A1 | 8/2011 | Sun et al. |
| 2012/0270800 A1 | 10/2012 | Verdine et al. |
| 2014/0235629 A1 | 8/2014 | Bartberger et al. |

(Continued)

FOREIGN PATENT DOCUMENTS

| | | |
|---|---|---|
| EP | 2985285 | 2/2016 |
| JP | 2004-509072 | 3/2004 |

(Continued)

OTHER PUBLICATIONS

Grant & Hackh's Chemical Dictionary (5th Ed. 1987) at p. 148.*
Federal Register (published on 2011, vol. 76, No. 27, p. 7166).*
Ahn, et al., "HIF-lalpha peptide derivatives with modifications at the hydroxyproline residue as activators of HIF-lalpha", Bioorg Med Chem Lett. 19(15), 2009, 4403-4405.
Allan, GF, et al., "Therapeutic androgen receptor ligands", Nuclear Receptor Signaling, 2003, 1, e009 DOI:10.621.01009 9 1-4.
Ardecky, RJ, et al., "Design, synthesis and evaluation of inhibitor of apoptosis protein (IAP) antagonists that are highly selective for the BIR2 domain ofXIAP", Bioorg. Med. Chem., 23(14): 4253-4257 (2013).
Asangani, I.A. et al., "Therapeutic Targeting of BET Bromodomain Proteins in Castration-Resistant Prostate Cancer", Nature, 2014, 510: 278-282.

(Continued)

*Primary Examiner* — Po-Chih Chen
(74) *Attorney, Agent, or Firm* — Bryan D. Zerhusen, Esq.; Nicholas R. Herrel, Esq.; Cantor Colburn LLP

(57) ABSTRACT

The present invention relates to bifunctional compounds, which find utility to degrade and (inhibit) Androgen Receptor. In particular, the present invention is directed to compounds, which contain on one end a VHL ligand which binds to the ubiquitin ligase and on the other end a moiety which binds Androgen Receptor such that Androgen Receptor is placed in proximity to the ubiquitin ligase to effect degradation (and inhibition) of Androgen Receptor. The present invention exhibits a broad range of pharmacological activities associated with compounds according to the present invention, consistent with the degradation/inhibition of Androgen Receptor.

16 Claims, 8 Drawing Sheets

(56) References Cited

U.S. PATENT DOCUMENTS

| | | |
|---|---|---|
| 2014/0243372 A1 | 8/2014 | Rew |
| 2014/0302523 A1 | 10/2014 | Crews et al. |
| 2014/0356322 A1 | 12/2014 | Crews et al. |
| 2015/0119435 A1 | 4/2015 | Crews et al. |
| 2015/0291562 A1 | 10/2015 | Crew et al. |
| 2015/0344473 A1 | 10/2015 | Du et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0136230 A1 | 5/2016 | Campos et al. |
| 2016/0176916 A1 | 6/2016 | Bradner et al. |
| 2016/0214972 A1 | 7/2016 | Jin et al. |
| 2016/0272639 A1 | 9/2016 | Crew et al. |
| 2016/0368911 A1 | 12/2016 | Campos et al. |
| 2017/0008904 A1 | 1/2017 | Crew et al. |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0281784 A1 | 10/2017 | Wang et al. |
| 2017/0307614 A1 | 10/2017 | Crews et al. |
| 2017/0327469 A1 | 11/2017 | Crew et al. |
| 2018/0099940 A1 | 4/2018 | Crew et al. |
| 2018/0125821 A1 | 5/2018 | Crew et al. |
| 2018/0147202 A1 | 5/2018 | Crew et al. |
| 2018/0155322 A1 | 6/2018 | Crew et al. |
| 2018/0177750 A1 | 6/2018 | Crew et al. |
| 2018/0179183 A1 | 6/2018 | Crew et al. |
| 2018/0228907 A1 | 8/2018 | Crew et al. |

FOREIGN PATENT DOCUMENTS

| | | |
|---|---|---|
| JP | A 2004-525889 | 8/2004 |
| JP | 2005-523257 A | 8/2005 |
| JP | 2008-505880 | 2/2008 |
| JP | A 2010-502627 | 1/2010 |
| JP | 2013-508447 A | 3/2013 |
| JP | 2013-519733 | 5/2013 |
| JP | 2014-511895 | 5/2014 |
| JP | 2014-511895 A | 5/2014 |
| RU | 2008112221 A | 10/2009 |
| RU | 2448101 C2 | 4/2012 |
| RU | 2011121567 A | 10/2012 |
| RU | 2012138709 A | 3/2014 |
| WO | WO 1998/003502 | 1/1998 |
| WO | WO 2000/066119 | 11/2000 |
| WO | WO 2002/000617 | 1/2002 |
| WO | WO 2002/066512 | 8/2002 |
| WO | WO 2002/100845 | 12/2002 |
| WO | WO 2005/097791 | 10/2005 |
| WO | WO 2006/028226 | 3/2006 |
| WO | WO 2006/069063 | 6/2006 |
| WO | WO 2006/113942 | 10/2006 |
| WO | WO 2007/101347 | 9/2007 |
| WO | WO 2007/106670 | 9/2007 |
| WO | WO 2007/130626 | 11/2007 |
| WO | WO 2008/011392 | 1/2008 |
| WO | WO 2008/014236 | 1/2008 |
| WO | WO 2008/109057 | 9/2008 |
| WO | WO 2008/128121 | 10/2008 |
| WO | WO 2008/128171 | 10/2008 |
| WO | WO 2008/134679 | 11/2008 |
| WO | WO 2009/015254 | 1/2009 |
| WO | WO 2009/060292 | 5/2009 |
| WO | WO 2010/107485 | 9/2010 |
| WO | WO 2010/141805 | 12/2010 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/071035 | 5/2013 |
| WO | WO 2013/071039 | 5/2013 |
| WO | WO 2013/106643 | 7/2013 |
| WO | WO 2013/106646 | 7/2013 |
| WO | WO 2013/170147 | 11/2013 |
| WO | WO 2013/175417 | 11/2013 |
| WO | WO 2013/178570 | 12/2013 |
| WO | WO 2014/011712 | 1/2014 |
| WO | WO 2014/020502 | 2/2014 |
| WO | WO 2014/025759 | 2/2014 |
| WO | WO 2014/036897 | 3/2014 |
| WO | WO 2014/038606 | 3/2014 |
| WO | WO 2014/047024 | 3/2014 |
| WO | WO 2014/055461 | 4/2014 |
| WO | WO 2014/074658 | 5/2014 |
| WO | WO 2014/100065 | 6/2014 |
| WO | WO 2014/100071 | 6/2014 |
| WO | WO 2014/107713 | 7/2014 |
| WO | WO 2014/108452 | 7/2014 |
| WO | WO 2014/123418 | 8/2014 |
| WO | WO 2014/134201 | 9/2014 |
| WO | WO 2014/151863 | 9/2014 |
| WO | WO 2014/202827 | 12/2014 |
| WO | WO2015/000867 | * 1/2015 |
| WO | WO 2015/000868 | 1/2015 |
| WO | WO 2015/006524 | 1/2015 |
| WO | WO 2015/160845 | 10/2015 |
| WO | WO 2016/105518 | 6/2016 |
| WO | WO 2016/146985 | 9/2016 |
| WO | WO 2016/172134 | 10/2016 |
| WO | WO 2016/197114 | 12/2016 |
| WO | WO 2017/007612 | 1/2017 |
| WO | WO 2017/011590 | 1/2017 |
| WO | WO 2017/024317 | 2/2017 |
| WO | WO 2017/024318 A1 | 2/2017 |
| WO | WO 2017/024319 A1 | 2/2017 |
| WO | WO 2017/030814 | 2/2017 |
| WO | WO 2017/079267 | 5/2017 |

OTHER PUBLICATIONS

Asano M, et al., "Design, sterioselective synthesis, and biological evaluation of novel tri-cyclic compounds as inhibitor of apoptosis proteins (IAP) antagonists", Bioorg. Med. Chem., 21(18): 5725-5737 (2013).

Bargagna-Mohan, et al., "Use of PROTACS as molecular probes of angiogenesis", Bioorg Med Chem Left. 15(11) 2005, 2724-2727.

Bondeson, et al., "Catalytic in vivo protein knockdown by small-molecule PROTACS", National Chem Biol. 11(8) Aug. 2015, 611-617.

Bradbury, RH, et. al, "Small-molecule androgen receptor downregulators as an approach to treatment of advanced prostate cancer", Bioorganic & Medicinal Chemistry Letters, 2011, 21: 5442-5445.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIFla", Angew Chem Int Ed Engl.51(46), Oct. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Capitosti, S., et al., "Thalidomide analogues demonstrate dual inhibition of both angiogenesis and prostate cancer", Bioorganic & Medicinal Chemistry 12, (2004) 327-336.

Carmony, KC, et al., "PROTAC-Induced Proteolytic Targeting", Methods Mol. Biol., 2012, vol. 832, pp. 627-638.

CAS 155180-53-3 published 1994.

CAS 155255-73-5 published 1995. (Year 1995).

CAS 186040-53-9 published 1997.

CAS 186798-71-0 published 1997.

CAS 186798-85-6 published 1997.

CAS 534612-78-7 published 2003.

CAS Registry No. 1004933-70-3, which entered STN on Feb. 21, 2008.

CAS Registry No. 871986-52-6 entered STN Jan. 16, 2006.

Chene, P., et al., "Inhibiting the p53-MDM2 interaction: an important target for cancer therapy" Nat. Rev. Cancer (2003), 3, 102-109.

Cohen, F, et al., "Orally bioavailable antagonists of inhibitor of apoptosis proteins based on an azabicyclooctane scaffold", J. Med. Chem., 52(6), 1723-1730 (2009).

(56) References Cited

OTHER PUBLICATIONS

Cohen, F. et al., "Antogonists of inhibitors of apoptosis proteins based on thiazole amide isosteres", Bioorg. Med. Chem. Lett., 20(7), 2229-2233 (2010).

Contino-Pepin, Christiane, et al., "Preliminary biological evaluations of new thalidomide analogues for multiple sclerosis application", Bioorganic & Medicinal Chemistry Letter 19 (2009), 878-881.

Corson, et al., "Design and applications of bifunctional small molecules: why two heads are better than one", ACS Chemical Biology vol. 3 No. 11, pp. 677-692; Nov. 21, 2008.

Crews, C. M., "Targeting the undruggable proteome: the small molecules of my dreams", Chem Biol 17, 551-555, doi:S1074-5521(10)00196-1 [pii] 10.1016/j.chembiol.2010.05.011 (2010).

Cyrus, et al., "Jostling for position: optimizing linker location in the design of estrogen receptor-targeting PROTACs", Chem Med Chem. 5(7), Jul. 5, 2010, 979-985.

Cyrus, K. et al., "Impact of Linker Length on the Activity of PROTACs," Mol. Biosyst., 2011, vol. 7, No. 2, pp. 359-364.

Cyrus, K. et al., "Two-Headed PROTAC: An Effective New Tool for Targeted Protein Degradation," Chembiochem., 2010, vol. 11, pp. 1531-1534.

Di, J et al. "Reactivation of p53 by inhibiting Mdm2 E3 Ligase: a novel antitumor approach", Current Cancer Drug Targets (2011), 11(8), 987-994.

Ding, Q, et al., "Discovery of RG7388, a potent and selective p53-MDM2 inhibitor in clinical development", J Med Chem. Jul. 25, 2013; 56(14):5979-83. doi: 10.1021/jm400487c. Epub Jul. 16, 2013. PubMed PMID: 23808545 (J. Med. Chem. (2013) 56, 5979-5983 Ding, et al).

Dixon, S. J. et al., "Identifying druggable disease-modifying gene products",. Curr Opin Chem Biol 13, 549-555, doi:S1367-5931(09)00107-0 [pii] 10.1016/j.cbpa.2009.08.003 (2009).

Fischer, et al., "Structure of the DDB1-DRBN E3 Ubiquitin ligase in complex with thalidomide", Nature, vol. 000, pp. 1-5 (2014).

Flygare, J.A., et al. "Small-molecule pan-IAP antagonists: a patent review", Expert Opin. Ther. Pat., 20 (2), 251-267 ( 2010).

Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.

Gosink, M et al., "Redirecting the specificity of ubiquitination by modifying ubiquitin-conjugating enzymes", Pro. Natl. Acad Sci, vol. 92, pp. 9117-9121, 1995.

Guo C., et al., "Design of oxobenzimidazoles and oxindoles as novel androgen receptor antagonists", Bioorganic & Medicinal Chemistry Letters, 2012, 22:2572-2578.

Guo, C. et al "Discovery of Aryloxy Tetramethylcyclobutanes as Novel Androgen Receptor Antagonists", J. Med. Chem. 2011, 54, 7693-7704.

Gustafson, et al., "Small-Molecule-Mediated Degradation of the Androgen Receptor through Hydrophobic Tagging", Agnew Chem Int Ed., 54: 9659-9662 (2015).

Haupt, Y. et al., "Mdm2 promotes the rapid degradation of p53", Nature 387, 296-299 (1997).

Hennessy, EJ, et al., "Discovery of aminopiperidine-based Smac mimetics as IAP antagonists", Bioorg. Med. Chem. Lett., 22(4), 1690-1694 (2012).

Hines, J., et al., "Posttranslational protein knockdown coupled to receptor tyrosine kinase activation with phosphoPROTACs", Proc Natl Acad Sci USA 110, 8942-8947 (2013).

Hird, AW, et al., "Structure-based design and synthesis of tricyclic IAP (Inhibitors of Apoptosis Proteins) inhibitors", Bioorg. Med. Chem. Lett., 24(7): 1820-1824 (2014).

Hon, et al., "Structural basis for the recognition of hydroxyproline in Hlf-1 alpha by pVHL", Nature 417, Jun. 27, 2002, 975-978.

Ivan, M., et al., "HIFa Targeted for VHL-Mediated Destruction by Proline Hydroxylation: Implications for O2 Sensing", Science, vol. 292, No. 5516, pp. 464-468, 2001.

Jang, E.R. et al., "Targeted Degradation of Proteins by PROTACs," Curr. Protoc. Chem. Biol., 2010, vol. 2, No. 2, pp. 71-87.

Jung, M. E. et al "Structure-Activity Relationship for Thioydantoin Androgen Receptor Antagonists for Castration-Resistant Prostate Cancer (CRPC)", J. Med. Chem. 2010, 53, 2779-2796.

Kim, K.S., "Discovery of tetrahydroisoquinoline-based bivalent heterodimeric IAP antagonists", Bioorg. Med. Chem. Lett. 24(21), 5022-5029 (2014).

Knott, Edward (1955). "Compounds containing sulphur chromophores. Part I. The action of bases on heterocyclic sulphide quarternary salts", Journal of The Chemical Society (resumed). 10.1039/jr9550000916. 949-954) (USPTO summary attached).

Kronke, et al, "Lenalidomide Causes Selective Degradation of IKZF1 and IKZF3 in Multiple Myeloma Cells", Science 343, 301-305 (2014).

Lai, A.C., et al., "Modular PROTAC Design for the Degradation of Oncogenic BCR-ABL", Angew Chem Int Ed Engl 55, 807-810 (2016).

Lebraud, H., et al., "Protein Degradation by In-Cell Self-Assembly of Proteolysis Targeting Chimeras", ACS Central Science, 2, 927-934 (2016).

Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.

Li, Yan, et al., "Single polymer-drug conjugate carrying two drugs for fixed-dose co-delivery", Medicinal Chemistry, 2014, vol. 4(10): 676-683.

Liu, K., et al., "Design and biological characterization of hybrid compounds of curcumin and thalidomide for multiple myeloma", Org. Biomol. Chem. 2013, 11, 4757-4763.

Lopez-Girona, A. et al., "Cereblon is a direct protein target for immunomodulatory and antiproliferative activities of lenalidomide and pomalidomide, Leukemia 26: 2326-2335, 2012).

Lu, et al., "Hijacking the E3 ubiquitin ligase cereblon to efficiently target BRD4", Chem Biol 22(6), 2015, 755-763.

Lu, et al., "The myeloma drug lenalidomide promotes the cereblon-dependent destruction of ikaros proteins", Science 343, 305-309 (2014).

Lu, NZ, et al., "International Union of Pharmacology. LXV. The pharmacology and classification of the nuclear receptor superfamily: glucocorticoid, mineralocorticoid, progesterone, and androgen receptors", Pharmacol Rev. Dec. 2006;58(4):782-797. Review. PubMed PMID: 17132855.

Mannhold, R., et al., "IAP antagonists: promising candidates for cancer therapy", Drug Discov. Today, 15 (5-6), 210-219 (2010).

Min, Jung-hyun, et al., "Structure of an HIV-1-alpha—pVHL complex: hydroxyproline recognition in signaling", Jun. 7, 2002, 296: 1886-1889.

Miyazaki, M., et al., "Discovery of DS-5272 as a promising candidate: a potent and orally active p53-MDM2 interaction inhibitor", Bioorg. Med. Chem. Lett. (2015) 23, 2360-2367.

Muller, G., et al., "Amino-Substituted Thalodomide Analogs: Potent Inhibitors of TNF-αProduction", Bioorganic & Medicinal Chemistry Letters 9 (1999) 1625-1630.

Ndubaku, C, et al., "Antagonism of c-IAP and XIAP proteins is required for efficient induction of cell death by small-molecule IAP antagonists", ACS Chem Biol. Jul. 17, 2009;4(7):557-566.

Neklesa, T.K., et al., "Chemical biology: Greasy tags for protein removal", Nature 487, 308-309 (2012).

Nikolovska-Coleska, et al., "Interaction of a cyclic, Bivalent Smac Mimetic with the X-linked inhibitor of apoptosis protein", Biochemistry, 2008, 47(37), pp. 9811-9824.

Oost, T.K. et al., "Discovery of potent antagonists of the antiapoptotic protein XIAP for the treatment of cancer", Journal of Medicinal Chemistry 2004, 47, 4417-4426.

Pepe, A. et al., "Synthesis and structure-activity relationship studies of novel dihydropyridones as androgen receptor modulators", J. Med. Chem. 2013, 56, 8280-8297.

(56) References Cited

OTHER PUBLICATIONS

Perez, HL, "Discovery of potent heterodimeric antagonists of inhibitor of apoptosis proteins (IAPs) with sustained antitumor activity", J. Med. Chem. 58(3), 1556-1562 (2015).
Poutiainen, PK, et. al., "Design, synthesis, and biological evaluation of nonsteroidal cycloalkane[d]isoxazole-containing androgen receptor modulators", J. Med. Chem. 55, 6316-6327 (2012).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Raina, K., et al., "PROTAC-induced BET protein degradation as a therapy for castration-resistant prostate cancer", Proc Natl Acad Sci USA 113, 7124-7129 (2016).
Rew, Y, et al., "Discovery of AM-7209, a potent and selective 4-amidobenzoic acid inhibitor of the MDM2-p53 interaction", J Med Chem. Dec. 26, 2014;57(24):10499-10511. doi: 10.1021/jm501550p. Epub Dec. 4, 2014. PubMed PMID: 25384157. (J. Med. Chem. (2014) 57, 10499-10511 Rew, et al.).
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Ruchelman, A., et al., "Isosteric analogs of lenalidomide and pomalidomide: Synthesis and biological activity", Bioorganic & Medicinal Chemistry Letters 23 (2013) 360-365.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1 -Cullin-F box complex for ubiquitination and degradation", Proc Natl Acad Sci U S A.98(15), Jul. 17, 2001, 8554-8559.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stewart, Scott G., et al., "Efforts toward elucidating Thalidomide's molecular target: An Expedient Synthesis of the first Thalidomide Biotin Analogue" Org. Biomol., Chem., 2010, 8, 4059-4062.
Sun, D, et al., "Discovery of AMG 232, a potent, selective, and orally bioavailable MDM2-p53 inhibitor in clinical development", J Med Chem. Feb. 27, 2014;57(4):1454-72. doi: 10.1021/jm401753e. Epub Feb. 5, 2014. PubMed PMID: 24456472.
Sun, et al., "Potent bivalent Smac mimetics: effect of the linker on binding to inhibitor apoptosis proteins (IAPs) and anticancer activity", J. Med. Chem. 53, 3306-3318 (2011).
Trewartha D, Carter K. "Advances in prostate cancer treatment", Nat Rev Drug Discov. Nov. 2013;12(11):823-824. doi: 10.1038/nrd4068. PubMed PMID: 24172327.
Turk, B. E., "Binding of thalidomide to alpha1-acid glycoprotein may be involved in its inhibition of tumor necrosis factor alpha production", Proc. Natl. Acad. Sci. U.S.A. 1996, 93, 7552-7556.
Vamos M., et al., "Expedient synthesis of highly potent antagonists of inhibitor of apoptosis proteins (IAPs) with unique selectivity for ML-IAP", ACS Chem. Biol., 8(4), 725-732 (2013).
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.
Vassilev, et al., "In vivo activation of the p53 pathway by small-molecule antagonists of MDM2", Science 303, Feb. 6, 2004, 844-848.

Vazquez, A. et al., "The genetics of the p53 pathway, apoptosis and cancer therapy", Nat. Rev. Drug. Dis., 7, 979-982 (2008).
Vu, B. et al. "Discovery of RG7112: a small-molecule MDM2 inhibitor in clinical development", ACS Med. Chem. Lett. (2013) 4, 466-469.
Wang J, et al., "Discovery of novel second mitochondrial-derived activator of caspase mimetics as selective inhibitor or apoptosis protein inhibitors", J. Pharmacol. Exp. Ther., 349(2): 319-29 (2014).
Wang, S., et al. "Small-molecule inhibitors of the MDM2-p53 protein-protein interaction (MDM2 inhibitors) in clinical trials for cancer treatment", J. Med. Chem. (2015) 58, 1038-1052.
Wang, S., et al. "Temporal activation of p53 by a specific MDM2 inhibitor is selectively toxic to tumors and leads to complete tumor growth inhabitation", PNAS USA (2008) 105, 3933-3938.
Winter, et al., "Phthalimide Conjugation as a strategy for in vivo target protein degradation", Science, 2015 vol. 348 (6241), pp. 1376-1381 [Pub online: May 21, 2015].
Zengerle, et al., "Selective Small Molecule Induced Degradation of the BET Bromodomain Protein BRD4" ACS Chemical Biology, Jun. 2, 2015, vol. 10, pp. 1770-1777.
Zhang B.et al., "Small-molecule MDM2-p53 inhibitors: recent advances", Future Med. Chem. (2015) 7, 631-645.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Golub, et al., "Molecular classification of cancer: class discovery and class prediction by gene expression monitoring", Science 286, 531-537 (1991).
Huang, et al., (2016) "Drugging the undruggables: exploring the ubiquitin system for drug development." *Cell Res* 26(4):484-498.
Lala, et al., "Role of nitric oxide in tumor progression: Lessons from experimental tumors", Cancer and Metastasis Reviews 17:91-106 (1998).
Levine, et al., Targeting the androgen receptor with steroid conjugates, J. Med. Chem., vol. 57., No. 20. pp. 8224-8237, (2014).
MEDLINE Plus Trusted Health Information for You, www.nlm.nih.gov/medlineplus/cancer.html pp. 1-10, (2007).
Mohler, M.L., et al., Androgen receptor antagonists: a patent review (2008-2011), Expert Opinion on Therapeutic Patents, vol. 22, No. 5. pp. 541-565, (2012).
Toure, et al., (2016) "Small-Molecule PROTACS: New Approaches to Protein Degradation." *Angew Chem Int Ed Engl* 55(6):1966-1973.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).
International Preliminary Report on Patentability for PCT/US2018/044051, dated Jan. 28, 2020.
Sakamoto, KM., et al., "Protacs for Treatment of Cancer", Pediatric Res., May 2010, 67(5) 505-508.
Schafer, S., et al., "Failure is an option: learning from unsuccessful proof-of-concept trials", Drug Discovery Today, vol. 13, Nos. 21/22, Nov. 2008, pp. 913-916.
Horig, H., et al., From bench to clinic and back: Perspective on the 1st IQPC Transactional Research conference, Journal of Translation Medicine, Dec. 2004, 2:44.
CAS Registry No. 1558960-34-1, Feb. 28, 2014.
CAS Registry No. 1556793-88-4, Feb. 26, 2014.
CAS Registry No. 1554948-46-7, Feb. 25, 2014.
CAS Registry No. 1489731-17-0, Dec. 8, 2013.
CAS Registry No. 1485649-65-7, Dec. 2, 2013.
CAS Registry No. 1436227-05-2, Jun. 9, 2013.
CAS Registry No. 112026-68-3, Dec. 25, 1987.
CAS Registry No. 93743-04-5, Dec. 18, 1984.

* cited by examiner

COMPOUNDS AND METHODS FOR THE TARGETED DEGRADATION OF ANDROGEN RECEPTOR

CROSS-REFERENCE TO RELATED APPLICATIONS

This application claims the benefit of U.S. Provisional Patent Application Ser. No. 62/105,210, filed 20 Jan. 2015 and entitled: Compounds and Methods for the Targeted Degradation of the Androgen Receptor, which is incorporated herein by reference in its entirety.

BACKGROUND

1. Field of the Discovery

The present description relates to bifunctional compounds, which are useful for the modifying the ubiquitination and subsequent degradation of target polypeptides and proteins, in particular, androgen receptor. In certain aspects, the compounds comprise a Von Hippel-Lindau (VHL) binding moiety, which binds to the VHL E3 ubiquitin ligase, a target protein binding moiety, which binds to the target protein (e.g., androgen receptor), and optionally a linker moiety which links the VHL binding moiety and target protein binding moiety. These compounds work in such way that the target protein/polypeptide is placed in proximity to the ubiquitin ligase to effect degradation (and inhibition) of that protein (e.g., androgen receptor).

2. Background Information

Androgen Receptor (AR) belongs to a nuclear hormone receptor family that is activated by androgens, such as testosterone and dihydrotestosterone (*Pharmacol. Rev.* 2006, 58(4), 782-97; *Vitam. Horn.* 1999, 55:309-52.). In the absence of androgens, AR is bound by Heat Shock Protein 90 (Hsp90) in the cytosol. When an androgen binds AR, its conformation changes to release AR from Hsp90 and to expose the Nuclear Localization Signal (NLS). The latter enables AR to translocate into the nucleus where AR acts as a transcription factor to promote gene expression responsible for male sexual characteristics (*Endocr. Rev.* 1987, 8(1):1-28; *Mol. Endocrinol.* 2002, 16(10), 2181-7). AR deficiency leads to Androgen Insensitivity Syndrome, formerly termed testicular feminization.

While AR is responsible for development of male sexual characteristics, it is also a well-documented oncogene in certain forms cancers including prostate cancers (*Endocr. Rev.* 2004, 25(2), 276-308). A commonly measured target gene of AR activity is the secreted Prostate Specific Antigen (PSA) protein. The current treatment regimen for prostate cancer involves inhibiting the androgen-AR axis by two methods. The first approach relies on reduction of androgens, while the second strategy aims to inhibit AR function (Nat. Rev. Drug Discovery, 2013, 12,823-824). Despite the development of effective targeted therapies, most patients develop resistance and the disease progresses. An alternative approach for the treatment of prostate cancer involves eliminating the AR protein. Because AR is a critical driver of tumorigenesis in many forms of prostate cancers, its elimination should lead to therapeutically beneficial response.

There exists an ongoing need in the art for effective treatments for diseases and conditions that are related to aberrant AR regulation or activity, such as, for example, cancer, prostate cancer, and Kennedy's Disease.

SUMMARY

The present disclosure describes compounds, including compositions comprising the same, which function to recruit endogenous proteins to an E3 ubiquitin ligase, e.g., Von Hippel-Lindau (VHL) E3 ubiquitin ligase, for ubiquitination and subsequent degradation, and methods of using the same. In particular, the present disclosure provides bifunctional or proteolysis targeting chimeric (PROTAC) compounds, which find utility as modulators of targeted ubiquitination and degradation of androgen receptor (AR). In addition, the description provides methods of using an effective amount of the compounds as described herein for the treatment or amelioration of a disease condition including cancer, e.g., prostate cancer, and Kennedy's Disease.

Thus, in one aspect, the disclosure provides compounds which function to recruit endogenous proteins, e.g., AR proteins, to E3 Ubiquitin Ligase for ubiquintination and degradation. In certain embodiments, the compounds have the following general structure:

$$\text{ABM-L-ULM} \quad (I),$$

wherein ABM is an AR binding moiety, ULM is an E3 ligase binding moiety, e.g., a VHL E3 ligase binding moiety (VLM), and L is a bond or a linker moiety which links the ABM and ULM. As such, in certain embodiments, the description provides compounds having the following general structure:

$$\text{ABM-L-VLM} \quad (II),$$

wherein ABM is an AR binding moiety, VLM is a VHL E3 ligase binding moiety and L is a bond or a linker moiety which links the ABM and VLM. In certain embodiments, the VLM comprises a hydroxyl prolyl moiety.

In certain embodiments, the ULM is a moiety specific for an E3 ubiquitin ligase such as, e.g., cereblon, mouse double minute 2 homolog (Mdm2), or inhibitor of apoptosis (IAP), wherein the ULM moiety is coupled to an ABM as described herein.

It will be understood that the general structures are exemplary and the respective moieties can be arranged spatially in any desired order or configuration, e.g., ULM-L-ABM, and VLM-L-ABM respectively.

In another aspect, the description provides AR binding moieties (ABM). In an additional embodiment, the description provides compounds having the following general structure: ABM-L, wherein ABM is an AR binding moiety as described herein, and L is a chemical linker moiety, or optionally a bond. In certain embodiments, the ABM and/or L are coupled to a ULM as described herein.

In any of the aspects or embodiments described herein, the ABM is selected from following structures:

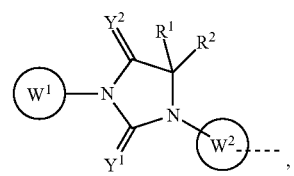
ABM-a

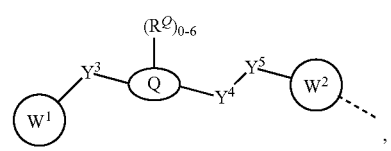
ABM-b

-continued

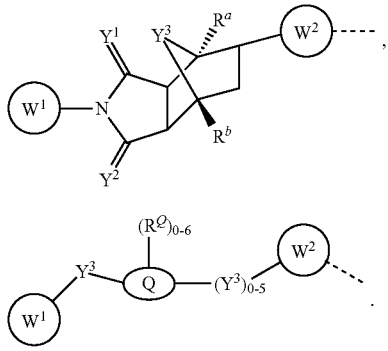

ABM-c

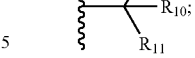

ABM-d

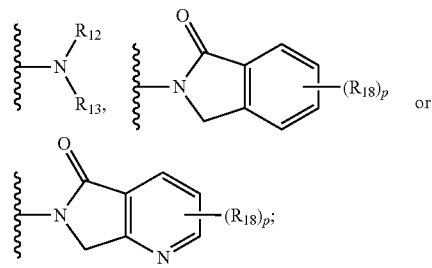

wherein $W^1$ is aryl or heteroaryl, independently substituted by 1 or more halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl;

$Y^1$, $Y^2$ are each independently $NR^{Y1}$, O, S;

$Y^3$, $Y^4$, $Y^5$ are each independently a bond, O, $NR^{Y2}$, $CR^{Y1}R^{Y2}$, C=O, C=S, SO, $SO_2$;

Q is a 3-6 membered alicyclic or aromatic ring with 0-4 heteroatoms, optionally substituted with 0-6 $R^Q$, each $R^Q$, is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

$W^2$ is a bond, $C_{1-6}$ alkyl, $C_{1-6}$ alicyclic, heterocyclic, aryl, or heteroaryl, each optionally substituted by 1, 2 or 3 $R^{W2}$; and each $R^{W2}$ is independently H, halo, $C_{1-6}$ alkyl (optionally substituted by 1 or more F), $OC_{1-3}$alkyl (optionally substituted by 1 or more —F), OH, $NH_2$, $NR^{Y1}R^{Y2}$, CN.

In any of the aspects or embodiments described herein, the ABM can comprise or consist of a structure as set forth herein, in particular in any of the ABMs as provided in Examples 1-593.

In certain embodiments, the ULM (derivatized or configured to be linked or coupled to an ABM via a linker (as indicated by the dashed line)) has the structure,

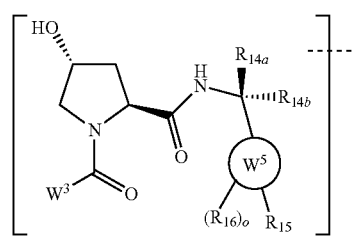

wherein, $W^3$ is optionally substituted aryl, optionally substituted heteroaryl, or

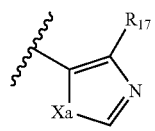

each $R_9$ and $R_{10}$ is independently hydrogen, optionally substituted alkyl, optionally substituted cycloalkyl, optionally substituted hydroxyalkyl, optionally substituted heteroaryl, or haloalkyl; or $R_9$, $R_{10}$, and the carbon atom to which they are attached form an optionally substituted cycloalkyl;

$R_{11}$ is optionally substituted heterocyclic, optionally substituted alkoxy, optionally substituted heteroaryl, optionally substituted aryl, $R_{12}$ is H or optionally substituted alkyl;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, is each independently H, haloalkyl, or optionally substituted alkyl;

$W^5$ is a phenyl or a 5-10 membered heteroaryl, $R_{15}$ is H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, cycloheteroalkyl each $R_{16}$ is independently halo, optionally substituted alkyl, optionally substituted haloalkyl, hydroxy, or optionally substituted haloalkoxy; or wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl, and Xa is S or O;

o is 0, 1, 2, 3, or 4;

each $R_{18}$ is independently halo, optionally substituted alkoxy, cyano, optionally substituted alkyl, haloalkyl, haloalkoxy or a linker; and p is 0, 1, 2, 3, or 4.

In another embodiments, the ULM has the structure

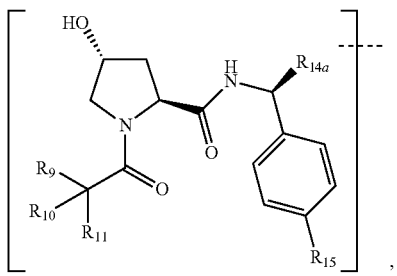

wherein
$R_9$ is H;
$R_{10}$ is isopropyl, tert-butyl, sec-butyl, cyclopentyl, or cyclohexyl;
$R_{11}$ is

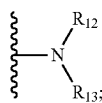

$R_{12}$ is H;
$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;
$R_{14a}$ is H, haloalkyl, or optionally substituted methyl, ethyl, isopropyl, cyclopropyl, or other alkyl; and
$R_{15}$ is

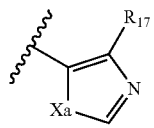

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.

In certain embodiments, an androgen receptor binding moiety has a structure of

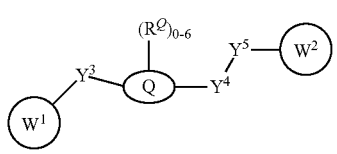

ABM-e wherein $W^1$ is aryl or heteroaryl, independently substituted by 1 or more halo, hydroxyl, nitro, CN, C≡CH, $C_{1-6}$ alkyl (linear, branched, optionally substituted by 1 or more halo, $C_{1-6}$ alkoxyl), $C_{1-6}$ alkoxyl (linear, branched, optionally substituted by 1 or more halo), $C_{2-6}$ alkenyl, $C_{2-6}$ alkynyl;
$Y^1$, $Y^2$ are each independently $NR^{Y1}$, O, S;
$Y^3$, $Y^4$, $Y^5$ are each independently a bond, O, $NR^{Y2}$, $CR^{Y1}R^{Y2}$, C=O, C=S, SO, $SO_2$;

Q is a 3-6 membered alicyclic or aromatic ring with 0-4 heteroatoms, optionally substituted with 0-6 $R^Q$, each $R^Q$, is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);
$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);
$W^2$ is a bond, $C_{1-6}$ alkyl, $C_{1-6}$ alicyclic, heterocyclic, aryl, or heteroaryl, each optionally substituted by 1, 2 or 3 $R^{W2}$; and each $R^{W2}$ is independently H, halo, $C_{1-6}$ alkyl (optionally substituted by 1 or more F), $OC_{1-3}$alkyl (optionally substituted by 1 or more —F), OH, $NH_2$, $NR^{Y1}R^{Y2}$, CN.

In certain additional embodiments, the compounds comprise a plurality of E3 ligase binding moieties and/or a plurality of ABMs.

In certain embodiments, the linker group (L) comprises a chemical structural unit represented by the formula:

$$-A_q-$$

wherein
q is an integer greater than 1; and
A is independently selected from the group consisting of a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}$, $C(=NCN)NR^{L4}$, $NR^{L3}C(=NCN)$, $NR^{L3}C(=CNO_2)NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups;
wherein $R^{L1}$, $R^{L2}$, $R^{L3}$, $R^{L4}$ and $R^{L5}$ are each, independently, selected from the group consisting of H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, C≡CH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)CONH($C_{1-8}$alkyl), $N(C_{1-8}$alkyl)CON($C_{1-8}$alkyl$)_2$, $NHCONH(C_{1-8}$alkyl), $NHCON(C_{1-8}$alkyl$)_2$, $NHCONH_2$, $N(C_{1-8}$alkyl)$SO_2NH(C_{1-8}$alkyl), $N(C_{1-8}$alkyl)$SO_2N(C_{1-8}$alkyl$)_2$, $NHSO_2NH(C_{1-8}$alkyl), $NHSO_2N(C_{1-8}$alkyl$)_2$, and $NHSO_2NH_2$; and wherein when q is greater than 1, $R^{L1}$ or $R^{L2}$ each, independently, can be linked to another A group to form cycloalkyl and/or heterocyclyl moiety that can be further substituted with 0-4 $R^{L5}$ groups.

In certain embodiments, the description provides a bifunctional compound having a structure selected from the group consisting of Examples 1-593, a salt, a polymorph, and a prodrug thereof.

In another aspect, the description provides compositions comprising compounds as described herein, and a pharmaceutically acceptable carrier. In certain embodiments, the compositions are therapeutic or pharmaceutical compositions comprising an effective amount of a compound as described herein and a pharmaceutically acceptable carrier. In certain embodiments, the therapeutic or pharmaceutical compositions comprise an additional biologically active agent, e.g., an agent effective for the treatment of cancer.

In any of the aspects or embodiments described herein, the therapeutic compositions comprising compounds described herein can be in any suitable dosage form, e.g., solid, or liquid, and configured to be delivered by any suitable route, e.g., oral, parenteral, intravenous, intraperitoneal, subcutaneous, intramuscular, etc., and in any desired unit dosage form. For example, in certain embodiments, the therapeutic composition as described herein is configured to be administered or consumed by a subject one or more times over a descired time period, e.g., day, week, month, etc.

In another aspect, the disclosure provides methods of modulating protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating protein ubquitination and degrnation of the protein in the subject. In certain embodiments, the protein is androgen receptor (AR).

In another aspect, the disclosure provides methods of modulating AR protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating AR protein ubiquitination and degrnation of the protein in the subject.

In another aspect, the disclosure provides methods of treating or ameliorating a symptom of a disease related to AR activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to AR activity in the subject. In certain embodiments, the disease to be treated is cancer, e.g., prostate cancer, or Kennedy's Disease. In a preferred embodiment, the subject is a human.

In another aspect, the disclosure provides methods for identifying the effects of the degradation of proteins of interest in a biological system using compounds according to the present invention.

In another aspect, the description provides kits comprising compounds or compositions as described herein. The kit may be promoted, distributed, or sold as a unit for performing the methods of the present invention. In addition, the kits of the present invention may preferably contain instructions which describe a suitable use. Such kits can be conveniently used, e.g., in clinical settings, to treat patients exhibiting symptoms of, e.g., cancer or Kennedy's Disease.

Where applicable or not specifically disclaimed, any one of the embodiments described herein are contemplated to be able to combine with any other one or more embodiments, even though the embodiments are described under different aspects of the invention. As such, the preceding general areas of utility are given by way of example only and are not intended to be limiting on the scope of the present disclosure and appended claims. Additional objects and advantages associated with the compositions, methods, and processes of the present invention will be appreciated by one of ordinary skill in the art in light of the instant claims, description, and examples. For example, the various aspects and embodiments of the invention may be utilized in numerous combinations, all of which are expressly contemplated by the present description. These additional advantages objects and embodiments are expressly included within the scope of the present invention. The publications and other materials used herein to illuminate the background of the invention, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which:

FIG. 1A: Exemplary PROTACs comprise an androgen receptor targeting moiety (ABM; darkly shaded rectangle), a Von Hippel-Lindau (VHL) E3 ubiquitin ligase binding moiety (VLM; lightly shaded triangle), and a linker moiety (L; black line) coupling or tethering the ABM to the VLM (as described herein, L can be absent or a bond or a chemical linker moiety). FIG. 1B Illustrates the functional use of the PROTACs as described herein. Briefly, the VLM recognizes and binds to Von Hippel-Lindau (VHL) E3 ubiquitin ligase, and the ABM binds and recruits androgen receptor and brings it into close proximity to the Von Hippel-Lindau (VHL) E3 ubiquitin ligase. Typically, the E3 ubiquitin ligase is complexed with an E2 ubiquitin-conjugating protein, and either alone or via the E2 protein catalyzes attachment of ubiquitin (dark circles) to a lysine on the target protein via an isopeptide bond. The poly-ubiquitinated protein (far right) is then targeted for degration by the proteosomal machinery of the cell.

FIG. 7A: AR PROTAC Example 1 was added to LNCaP cells at indicated concentrations for 24 hours in the presence or absence of 10 uM VHL E3 ligase ligand compound B. FIG. 7B: LNCaP cells were treated with AR PROTAC Example 1 and its inactive epimer analog compound C which is unable to bind to VHL E3 ligase."

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Figure 1A:
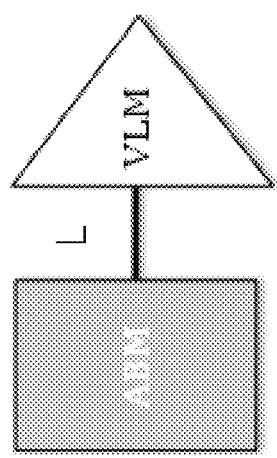
FIG. 1A and FIG. 1B. Illustration of general principle for PROTAC function.
Figure 1B:
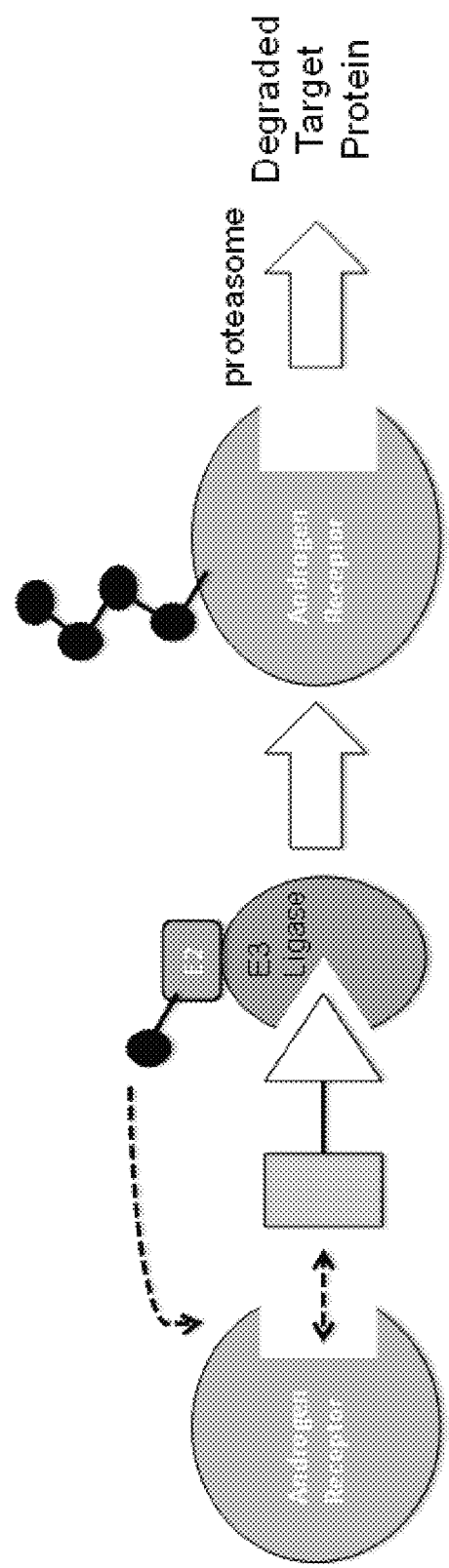

The present description relates to the surprising and unexpected discovery that an E3 ubiquitin ligase protein can ubiquitinate a target protein, in particular androgen receptor, once the E3 ubiquitin ligase protein and the target protein are brought into proximity by a chimeric construct (e.g., PROTAC) as described herein, in which a moiety that binds the E3 ubiquitin ligase protein is coupled, e.g., covalently, to a moiety that bind the androgen receptor target protein. Accordingly, the present description provides compounds, compositions comprising the same, and associated methods of use for ubiquitination and degradation of a chosen target protein, e.g., androgen receptor (See FIG. 1A and FIG. 1B).

The present description is related in certain aspects to U.S. Patent Publication 2014/0356322A1, which is incorporated herein by reference in its entirety for all purposes.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

The term "about" and the like, as used herein, in association with numeric values or ranges, reflects the fact that there is a certain level of variation that is recognized and tolerated in the art due to practical and/or theoretical limitations. For example, minor variation is tolerated due to inherent variances in the manner in which certain devices operate and/or measurements are taken. In accordance with the above, the phrase "about" is normally used to encompass values within the standard deviation or standard error.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" can refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are coadministered in combination with at least one additional bioactive agent, especially including an anticancer agent. In particularly preferred aspects, the co-administration of compounds results in synergistic activity and/or therapy, including anticancer activity.

The term "effective" can mean, but is in no way limited to, that amount/dose of the active pharmaceutical ingredient, which, when used in the context of its intended use, effectuates or is sufficient to prevent, inhibit the occurrence, ameliorate, delay or treat (alleviate a symptom to some extent, preferably all) the symptoms of a condition, disorder or disease state in a subject in need of such treatment or receiving such treatment. The term effective subsumes all other effective amount or effective concentration terms, e.g., "effective amount/dose," "pharmaceutically effective amount/dose" or "therapeutically effective amount/dose," which are otherwise described or used in the present application.

The effective amount depends on the type and severity of disease, the composition used, the route of administration, the type of mammal being treated, the physical characteristics of the specific mammal under consideration, concurrent medication, and other factors which those skilled in the medical arts will recognize. The exact amount can be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

The term "pharmaceutically acceptable" or "pharmacologically acceptable" can mean, but is in no way limited to, entities and compositions that do not produce an adverse, allergic or other untoward reaction when administered to an animal, or a human, as appropriate.

The term "pharmaceutically acceptable carrier" or "pharmacologically acceptable carrier" can mean, but is in no way limited to, any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The term "systemic administration" refers to a route of administration that is, e.g., enteral or parenteral, and results in the systemic distribution of an agent leading to systemic absorption or accumulation of drugs in the blood stream followed by distribution throughout the entire body. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect. Administration routes which lead to systemic absorption include, without limitations: intravenous, subcutaneous, intraperitoneal, inhalation, oral, intrapulmonary and intramuscular. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful.

The term "local administration" refers to a route of administration in which the agent is delivered to a site that is apposite or proximal, e.g., within about 10 cm, to the site of the lesion or disease.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described.

It is understood by those of ordinary skill that molecules which are described herein are stable compounds as generally described hereunder. When the bond  is shown, both a double bond and single bond are represented within the context of the compound shown.

As used herein, "derivatives" can mean compositions formed from the native compounds either directly, by modification, or by partial substitution. As used herein, "analogs" can mean compositions that have a structure similar to, but not identical to, the native compound.

The term "Ubiquitin Ligase" refers to a family of proteins that facilitate the transfer of ubiquitin to a specific substrate protein, targeting the substrate protein for degradation. By way of example, Von Hippel-Lindau E3 Ubiquitin Ligase or VCB E3 Ubiquitin Ligase is protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "subject" is used throughout the specification to describe a cell, tissue, or animal, preferably a mammal, e.g., a human or a domesticated animal, to whom treatment, including prophylactic treatment, with the compositions according to the present invention is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present invention, the term patient refers to a human patient unless otherwise stated or implied from the context of the use of the term.

Compounds

In one aspect, the present invention provides compounds useful for regulating protein activity. The composition comprises a ubiquitin pathway protein binding moiety (preferably for an E3 ubiquitin ligase, alone or in complex with an E2 ubiquitin conjugating enzyme which is responsible for the transfer of ubiquitin to targeted proteins) according to a defined chemical structure and a protein targeting moiety which are linked or coupled together, preferably through a linker, wherein the ubiquitin pathway protein binding moiety recognizes an ubiquitin pathway protein and the targeting moiety recognizes a target protein (e.g., androgen receptor). Such compounds may be referred to herein as PROTAC compounds or PROTACs.

In one aspect, the description provides AR binding moieties (ABM). In certain embodiments, the compounds having the following general structure: ABM-L, wherein ABM is an AR binding moiety as described herein, and L is a chemical linker moiety, e.g., a linker as described herein, or optionally a bond. In certain embodiments, the ABM and/or L are coupled to a ULM as described herein below.

In another aspect, the disclosure provides compounds which function to recruit androgen receptor (AR) proteins to E3 Ubiquitin Ligase for ubiquintination and degradation. In certain embodiments, the compounds have the following general structure:

$$ABM\text{-}L\text{-}ULM \qquad (I),$$

wherein ULM is an E3 ligase binding moiety, ABM is an AR binding moiety, which binds to an AR protein and L is a bond or a chemical linker moiety which links the ABM and ULM.

In certain embodiments, the ULM is a moiety specific for an E3 ubiquitin ligase such as, e.g., Von Hippel-Lindau E3 ubiquitin ligase (VHL), cereblon, mouse double minute 2 homolog (Mdm2), or inhibitor of apoptosis (IAP), wherein the ULM moiety is coupled to an ABM as described herein.

Without being bound by any particular theory, it is hypothesized that due at least in part to the proximity of AR and the E3 ubiquitin ligase, the AR is ubiquitinated by the ubiquitin ligase and degraded. In certain embodiments, the ABM is chemically linked or coupled directly to the ULM group. In certain additional embodiments, the ABM is chemically linked or coupled to the ULM via a chemical linker moiety. In additional embodiments, the description provides compounds having the following general structure:

$$ABM\text{-}L\text{-}VLM \qquad (II),$$

wherein ABM is an AR binding moiety and VLM is a Von Hippel-Lindau E3 Ubiquitin Ligase (VHL) binding moiety, and L is a bond or a chemical linker moiety which links the ABM and VLM. The ULM or VLM group and ABM group may be covalently linked to the linker group through any covalent bond which is appropriate and stable to the chemistry of the linker.

In certain embodiments, the ULM or VLM comprises a hydroxyprolyl moiety. The hydroxyl prolyl moiety has been shown to be important for binding and recruiting of the VHL protein.

It will be understood that the general structures are exemplary and the respective moieties can be arranged in any desired order or configuration, e.g., ULM-L-ABM, and VLM-L-ABM respectively. In certain additional embodiments, the compounds comprise a plurality of E3 ligase binding moieties and/or a plurality of ABMs.

In certain embodiments, ABM alone, without forming ABM-L-ULM, provides desired properties in regulating protein activity.

In any of the aspects or embodiments of compounds described herein, unless indicated otherwise, the compounds are intended to encompass pharmaceutically acceptable salts, enantiomers, stereoisomers, solvates or polymorphs thereof.

Exemplary ULMs

In certain embodiments of the compounds as described herein, the ULM comprises a chemical structure selected from the group ULM-a:

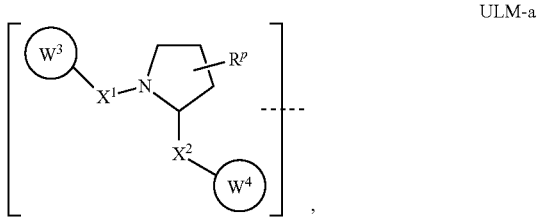

ULM-a where a dashed line indicates the attachment of at least one ABM, another ULM or VLM (i.e., ULM' or VLM'), or a chemical linker moiety coupling at least one ABM, a ULM' or VLM' to the other end of the linker;

$X^1$, $X^2$ are each independently a bond, O, $NR^{Y3}$, $CR^{Y3}R^{Y4}$, C=O, C=S, SO, $SO_2$;

$R^{Y3}$, $R^{Y4}$ are each independently H, $C_{1-6}$ alkyl (linear, branched, optionally substituted by 1 or more halo, $C_{1-6}$ alkoxyl);

optionally substituted by 1-3 $R^P$ groups in the pyrrolidine moiety, wherein each $R^P$ is independently H, halo, —OH, $C_{1-3}$alkyl;

$W^3$ is an optionally substituted -T-N($R^{1a}R^{1b}$), -T-Aryl, an optionally substituted -T-Heteroaryl, an optionally substituted -T-Heterocycle, an optionally substituted —$NR^1$-T-Aryl, an optionally substituted —$NR^1$-T-Heteroaryl or an optionally substituted —$NR^1$-T-Heterocycle, where T is covalently bonded to $X^1$;

each $R^1$, $R^{1a}$, $R^{1b}$ is independently H, a $C_1$-$C_6$ alkyl group (linear, branched, optionally substituted by 1 or more halo, —OH), $R^{Y3}$C=O, $R^{Y3}$C=S, $R^{Y3}$SO, $R^{Y3}SO_2$, N($R^{Y3}R^{Y4}$)C=O, N($R^{Y3}R^{Y4}$)C=S, N($R^{Y3}R^{Y4}$)SO, N($R^{Y3}R^{Y4}$)$SO_2$;

T is an optionally substituted —$(CH_2)_n$— group, wherein each one of the methylene groups may be optionally substituted with one or two substituents, preferably selected from halogen, a $C_1$-$C_6$ alkyl group (linear, branched, optionally substituted by 1 or more halogen, —OH) or the sidechain of an amino acid as otherwise described herein, preferably methyl, which may be optionally substituted; and n is 0 to 6, often 0, 1, 2, or 3, preferably 0.

Alternatively, T may also be a —$(CH_2O)_n$— group, a —$(OCH_2)_n$— group, a —$(CH_2CH_2O)_n$— group, a —$(OCH_2CH_2)_n$— group, each of which groups is optionally substituted; and $W^4$ is an optionally substituted —$NR^1$-T-Aryl, an optionally substituted —$NR^1$-T-Heteroaryl group or an optionally substituted —$NR^1$-T-Heterocycle, where —$NR^1$ is covalently bonded to $X^2$; $R^1$ is H or $CH_3$, preferably H, and T is an optionally substituted —$(CH_2)_n$— group, wherein each one of the methylene groups may be optionally substituted with one or two substituents, preferably selected from halogen, an amino acid sidechain as otherwise described herein or a $C_1$-$C_6$ alkyl group (linear, branched, optionally substituted by 1 or more halo, —OH), preferably one or two methyl groups, which may be optionally substituted; and n is 0 to 6, often 0, 1, 2 or 3, preferably 1.

Alternatively, T may also be a —$(CH_2O)_n$— group, a —$(OCH_2)_n$— group, a —$(CH_2CH_2O)_n$— group, a —$(OCH_2CH_2)_n$— group, all of which groups are optionally substituted.

In any of the embodiments described herein, $W^3$ and/or $W^4$ can be attached to a linker moiety as described herein.

In certain embodiments, aryl groups for $W^3$ include optionally substituted phenyl or naphthyl groups, preferably phenyl groups, wherein the phenyl or naphthyl group is optionally substituted with a linker group to which is attached a ABM group (including a ULM' group) and/or a halogen (preferably F or Cl), an amine, monoalkyl- or dialkyl amine (preferably, dimethylamine), an amido group (preferably a —$(CH_2)_n$—$NR_1C(O)R_2$ group where m, $R_1$ and $R_2$ are the same as for $R^1$), a halogen (often F or Cl), OH, $CH_3$, $CF_3$, OMe, $OCF_3$, $NO_2$, CN or a $S(O)_2R_S$ group ($R_S$ is a $C_1$-$C_6$ alkyl group, an optionally substituted aryl, heteroaryl or heterocycle group or a —$(CH_2)$—$NR_1R_2$ group), each of which may be substituted in ortho-, meta- and/or para-positions of the phenyl ring, preferably para-), or an Aryl (preferably phenyl), heteroaryl or heterocycle. Preferably said substituent phenyl group is an optionally substituted phenyl group (i.e., the substituent phenyl group itself is preferably substituted with at least one of F, Cl, OH, SH, COOH, $CH_3$, $CF_3$, OMe, $OCF_3$, $NO_2$, CN or a linker group to which is attached a ABM group (including a ULM' group), wherein the substitution occurs in ortho-, meta- and/or para-positions of the phenyl ring, preferably para-), a naphthyl group, which may be optionally substituted including as described above, an optionally substituted heteroaryl (preferably an optionally substituted isoxazole including a methylsubstituted isoxazole, an optionally substituted oxazole including a methylsubstituted oxazole, an optionally substituted thiazole including a methyl substituted thiazole, an optionally substituted pyrrole including a methylsubstituted pyrrole, an optionally substituted imidazole including a methylimidazole, a benzylimidazole or methoxybenzylimidazole, an oximidazole or methyloximidazole, an optionally substituted diazole group, including a methyldiazole group, an optionally substituted triazole group, including a methylsubstituted triazole group, a pyridine group, including a halo-(preferably, F) or methylsubstitutedpyridine group or an oxapyridine group (where the pyridine group is linked to the phenyl group by an oxygen) or an optionally substituted heterocycle (tetrahydrofuran, tetrahydrothiophene, pyrrolidine, piperidine, morpholine, piperazine, tetrahydroquinoline, oxane or thiane. Each of the aryl, heteroaryl or heterocyclic groups may be optionally substituted with a linker group to which is attached a ABM group (including a ULM' group).

In certain embodiments, heteroaryl groups for $W^3$ include an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

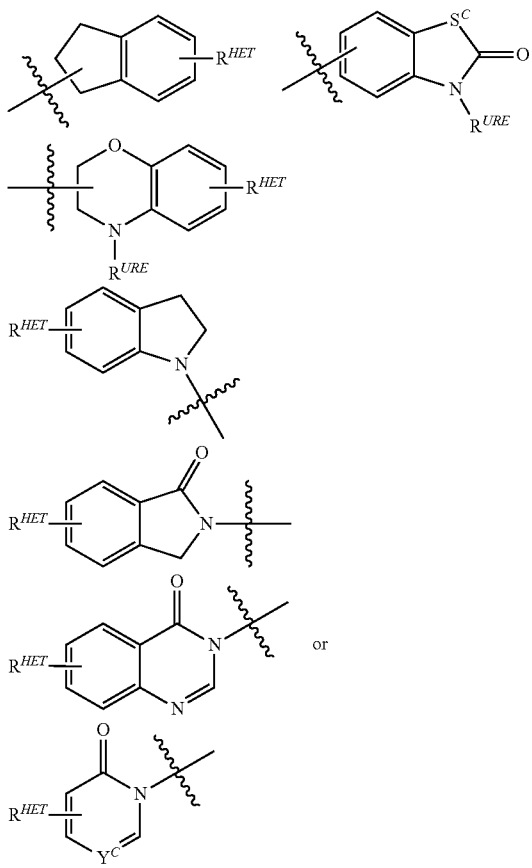
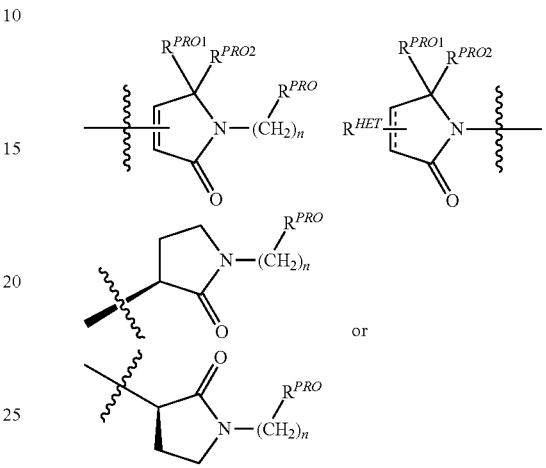

where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted; and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl). Each of said heteroaryl groups may be optionally substituted with a linker group to which is attached a ABM group (including a ULM' group).

In additional embodiments, heterocycle groups for $W^3$ include tetrahydroquinoline, piperidine, piperazine, pyrrolidine, morpholine, tetrahydrofuran, tetrahydrothiophene, oxane and thiane, each of which groups may be optionally substituted or a group according to the chemical structure:

group;

where $R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group, and each n is 0, 1, 2, 3, 4, 5, or 6 (preferably 0 or 1), wherein each of said Heteocycle groups may be optionally substituted with a linker group to which is attached a ABM group (including a ULM' group) or a pharmaceutically acceptable salt, stereoisomer, solvate or polymorph thereof.

In certain embodiments, $W^3$ substituents for use in the present invention also include specifically (and without limitation to the specific compound disclosed) the $W^3$ substituents which are found in the identified compounds disclosed herein (which includes the specific compounds which are disclosed in the present specification, and the figures which are attached hereto). Each of these $W^3$ substituents may be used in conjunction with any number of $W^4$ substituents, which are also disclosed herein.

In certain embodiments, Aryl groups for $W^4$ include optionally substituted phenyl or naphthyl groups, preferably phenyl groups, wherein the phenyl group is optionally substituted with a linker group to which is attached an ABMABM group (including a ULM' group), a halogen (preferably F or Cl), an amine, monoalkyl- or dialkyl amine (preferably, dimethylamine), F, Cl, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a ABM group, including a ULM' group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo- (preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, an optionally substituted group according to the chemical structure:

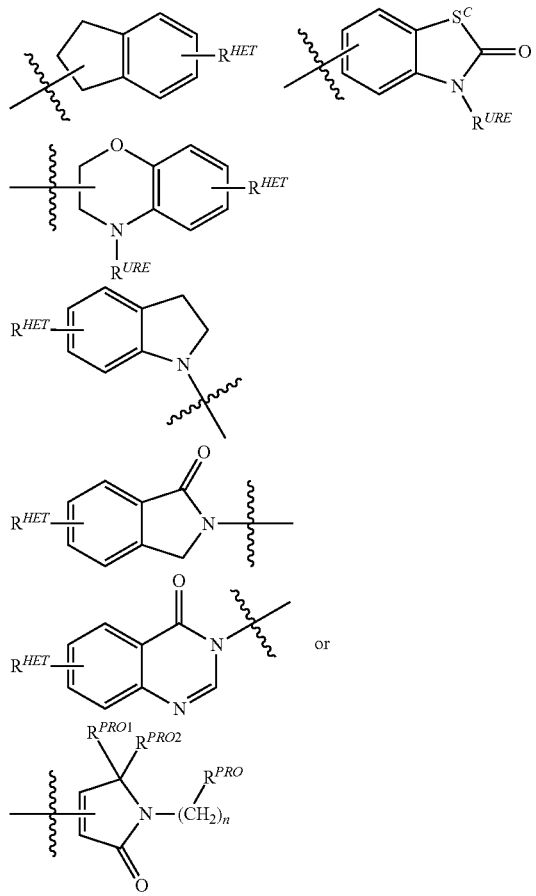

where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl) each of which groups is optionally substituted with one or two hydroxyl groups or up to three halogen, preferably fluorine groups, or an optionally substituted phenyl group, an optionally substituted heteroaryl, or an optionally substituted heterocycle, preferably for example piperidine, morpholine, pyrrolidine, tetrahydrofuran);

$R^{PRO}$ is H, optionally substituted $C_1$-$C_6$ alkyl or an optionally substituted aryl (phenyl or napthyl), heteroaryl or heterocyclic group selected from the group consisting of oxazole, isoxazole, thiazole, isothiazole, imidazole, diazole, oximidazole, pyrrole, pyrollidine, furan, dihydrofuran, tetrahydrofuran, thiene, dihydrothiene, tetrahydrothiene, pyridine, piperidine, piperazine, morpholine, quinoline, (each preferably substituted with a $C_1$-$C_3$ alkyl group, preferably methyl or a halo group, preferably F or Cl), benzofuran, indole, indolizine, azaindolizine;

$R^{PRO1}$ and $R^{PRO2}$ are each independently H, an optionally substituted $C_1$-$C_3$ alkyl group or together form a keto group; and each n is independently 0, 1, 2, 3, 4, 5, or 6 (preferably 0 or 1), or an optionally substituted heterocycle, preferably tetrahydrofuran, tetrahydrothiene, piperidine, piperazine or morpholine (each of which groups when substituted, are preferably substituted with a methyl or halo (F, Br, Cl), each of which groups may be optionally substituted with a linker group to which is attached a ABM group (including a ULM' group).

In certain preferred aspects,

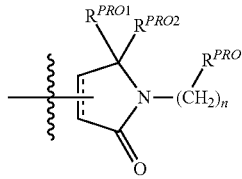

is a

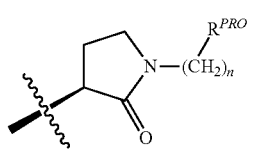

or or

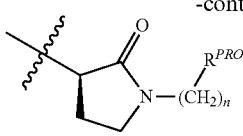

group, where $R^{PRO}$ and n are the same as above.

In certain embodiments, heteroaryl groups for $W^4$ include an optionally substituted quinoline (which may be attached to the pharmacophore or substituted on any carbon atom within the quinoline ring), an optionally substituted indole, an optionally substituted indolizine, an optionally substituted azaindolizine, an optionally substituted benzofuran, including an optionally substituted benzofuran, an optionally substituted isoxazole, an optionally substituted thiazole, an optionally substituted isothiazole, an optionally substituted thiophene, an optionally substituted pyridine (2-, 3-, or 4-pyridine), an optionally substituted imidazole, an optionally substituted pyrrole, an optionally substituted diazole, an optionally substituted triazole, a tetrazole, an optionally substituted oximidazole, or a group according to the chemical structure:

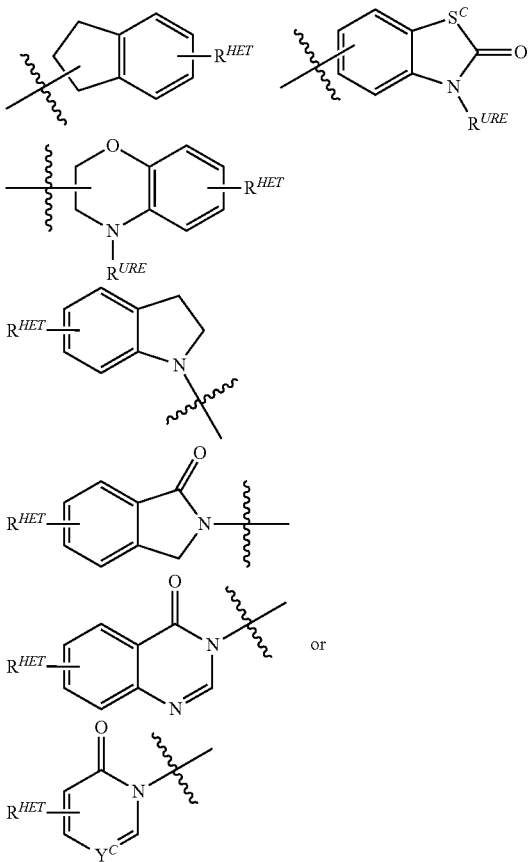

where $S^c$ is $CHR^{SS}$, $NR^{URE}$, or O;

$R^{HET}$ is H, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl);

$R^{SS}$ is H, CN, $NO_2$, halo (preferably F or Cl), optionally substituted $C_1$-$C_6$ alkyl (preferably substituted with one or two hydroxyl groups or up to three halo groups), optionally substituted O—($C_1$-$C_6$ alkyl) (preferably substituted with one or two hydroxyl groups or up to three halo groups) or an optionally substituted —C(O)($C_1$-$C_6$ alkyl) (preferably substituted with one or two hydroxyl groups or up to three halo groups);

$R^{URE}$ is H, a $C_1$-$C_6$ alkyl (preferably H or $C_1$-$C_3$ alkyl) or a —C(O)($C_1$-$C_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—$R^{YC}$, where $R^{YC}$ is H, OH, CN, $NO_2$, halo (preferably Cl or F), optionally substituted $C_1$-$C_6$ alkyl (preferably substituted with one or two hydroxyl groups or up to three halo groups (e.g. $CF_3$), optionally substituted $O(C_1$-$C_6$ alkyl) (preferably substituted with one or two hydroxyl groups or up to three halo groups) or an optionally substituted acetylenic group —C≡C—$R_a$ where $R_a$ is H or a $C_1$-$C_6$ alkyl group (preferably $C_1$-$C_3$ alkyl), each of which groups may be optionally substituted with a linker group to which is attached a ABM group (including a ULM' group).

In certain embodiments, heterocycle groups for $W^4$ include tetrahydrofuran, tetrahydrothiene, tetrahydroquinoline, piperidine, piperazine, pyrrollidine, morpholine, oxane or thiane, each of which groups may be optionally substituted, or a group according to the chemical structure:

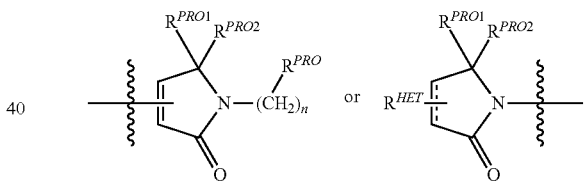

preferably, a

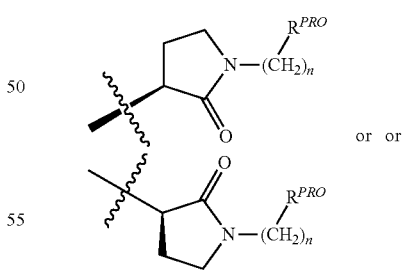

group, where $R^{PRO}$ is H, optionally substituted $C_1$-$C_6$ alkyl or an optionally substituted aryl, heteroaryl or heterocyclic group;

$R^{PRO1}$ and $R^{PRO2}$ are each independently H, an optionally substituted $C_1$-$C_3$ alkyl group or together form a keto group and each n is independently 0, 1, 2, 3, 4, 5, or 6 (often 0 or 1), each of which groups may be optionally substituted with a linker group to which is attached a ABM group (including a ULM' group) In additional embodiments, $W^4$ substituents for use in the present invention also include specifically (and without limitation to the specific compound disclosed) the $W^4$ substituents which are found in the identified compounds disclosed herein (which includes the specific compounds which are disclosed in the present specification, and the figures which are attached hereto). Each of these $W^4$ substituents may be used in conjunction with any number of $W^3$ substituents which are also disclosed herein.

In certain additional embodiments, ULM-a, is optionally substituted by 1-3 $R^P$ groups in the pyrrolidine moiety. Each $R^P$ is independently H, halo, —OH, $C_{1-3}$alkyl.

In any of the embodiments described herein, the $W^3$, $W^4$ can independently be covalently coupled to a linker which is attached one or more ABM groups.

In certain embodiments, ULM is a group (derivatized or configured to be linked or coupled to an ABM via a linker (as indicated by the dashed line) according to the chemical structure:

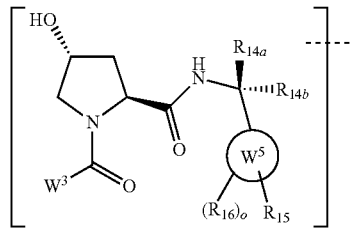

wherein, $W^3$ is optionally substituted aryl, optionally substituted heteroaryl, or

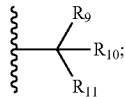

each $R_9$ and $R_{10}$ is independently hydrogen, optionally substituted alkyl, optionally substituted cycloalkyl, optionally substituted hydroxyalkyl, optionally substituted heteroaryl, or haloalkyl; or $R_9$, $R_{10}$, and the carbon atom to which they are attached form an optionally substituted cycloalkyl;

$R_{11}$ is optionally substituted heterocyclic, optionally substituted alkoxy, optionally substituted heteroaryl, optionally substituted aryl,

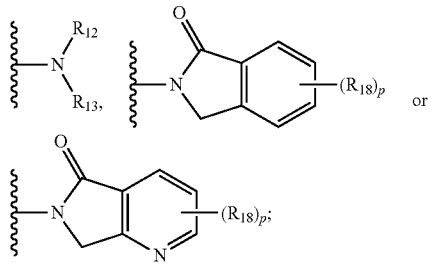

$R_{12}$ is H or optionally substituted alkyl;
$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$, $R_{14b}$, is each independently H, haloalkyl, or optionally substituted alkyl;

$W^5$ is a phenyl or a 5-10 membered heteroaryl,
$R_{15}$ is H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy; aryl, heteroaryl, cycloalkyl, cycloheteroalkyl each $R_{16}$ is independently halo, optionally substituted alkyl, optionally substituted haloalkyl, hydroxy, or optionally substituted haloalkoxy;

o is 0, 1, 2, 3, or 4;
each $R_{18}$ is independently halo, optionally substituted alkoxy, cyano, optionally substituted alkyl, haloalkyl, haloalkoxy or a linker; and p is 0, 1, 2, 3, or 4.
In certain embodiments, $R_{15}$ is

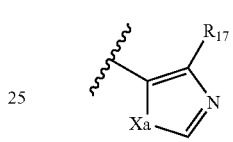

wherein $R_{17}$ is H, halo, optionally substituted $C_{3-6}$cycloalkyl, optionally substituted $C_{1-6}$alkyl, optionally substituted $C_{1-6}$alkenyl, and $C_{1-6}$haloalkyl; and Xa is S or O.
In certain embodiments, $R_{17}$ is selected from the group methyl, ethyl, isopropyl, and cyclopropyl.

In certain additional embodiments, $R_{15}$ is selected from the group consisting of:

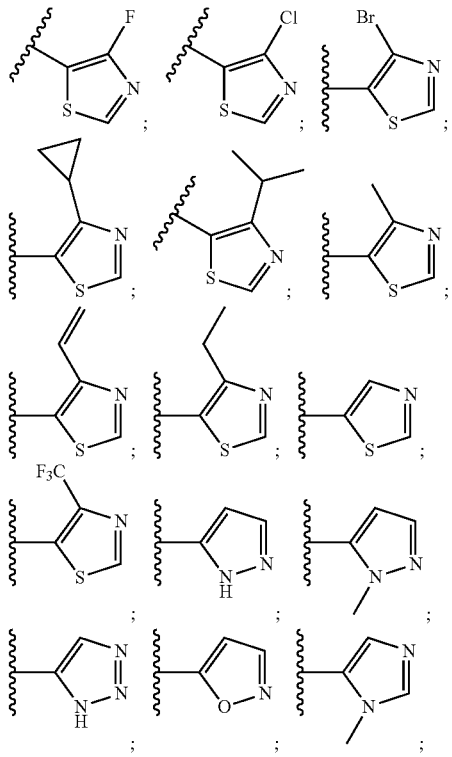

-continued

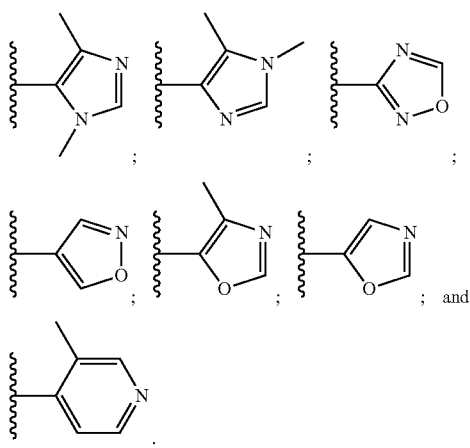

.

In certain embodiments, $R_{11}$ is selected from the group consisting of:

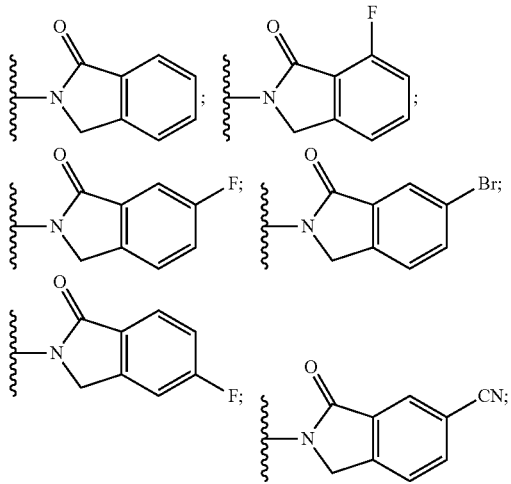

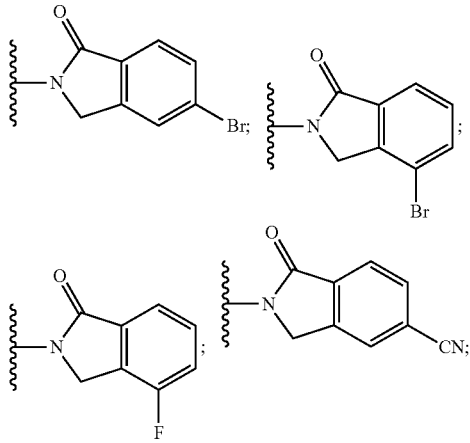

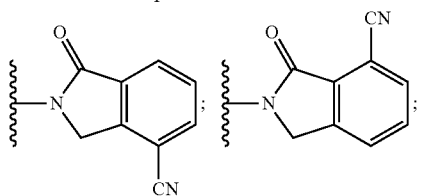

-continued

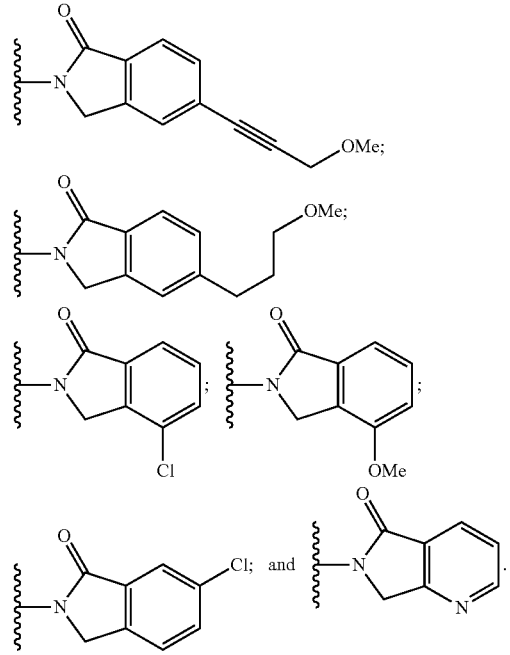

In certain embodiments, the ULM (derivatized or configured to be linked or coupled to an ABM via a linker (as indicated by the dashed line)) has the structure:

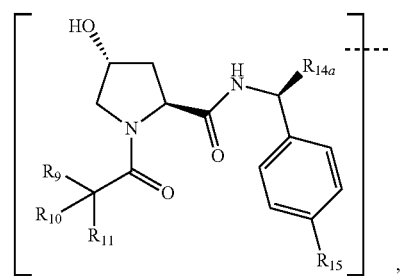

wherein $R_9$ is H;

$R_{10}$ is isopropyl, tert-butyl, sec-butyl, cyclopentyl, or cyclohexyl;

$R_{11}$ is

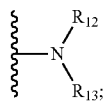

$R_{12}$ is H;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

R14a is H, haloalkyl, or optionally substituted methyl, ethyl, isopropyl, cyclopropyl, or other alkyl; and R15 is
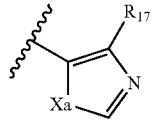
wherein R17 is H, halo, optionally substituted C3-6cycloalkyl, optionally substituted C1-6alkyl, optionally substituted C1-6alkenyl, and C1-6haloalkyl; and Xa is S or O.
In certain embodiments, the ULM or VLM is selected from the group consisting of:
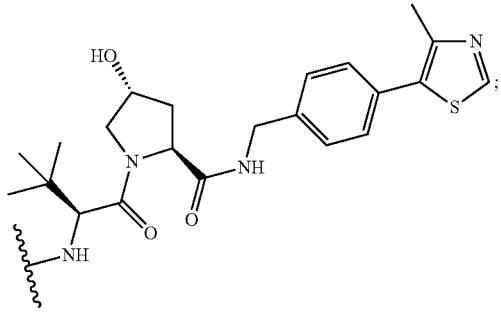
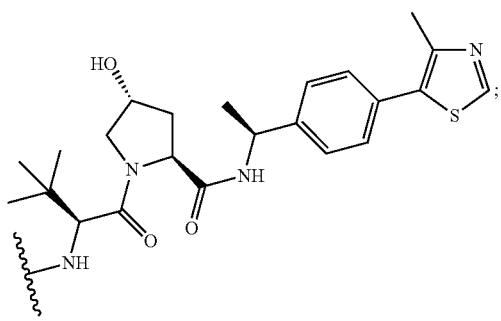
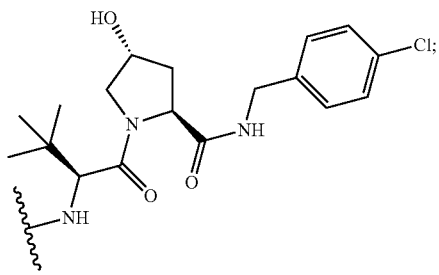
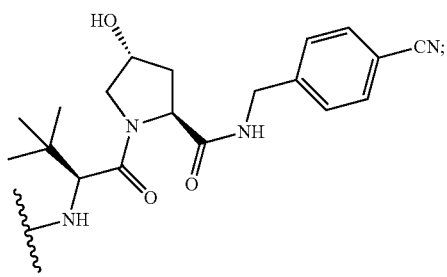
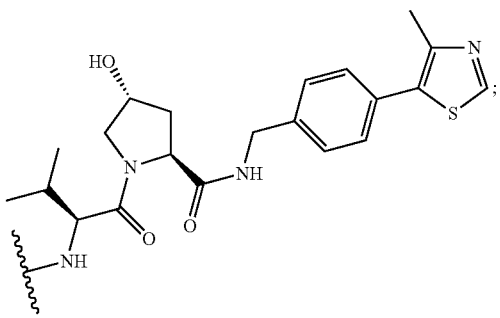
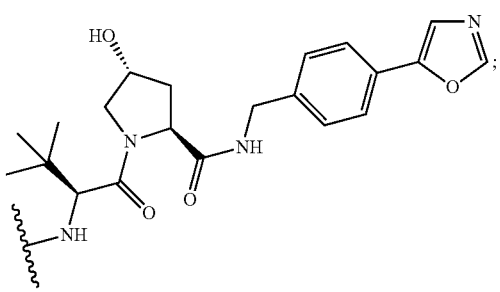
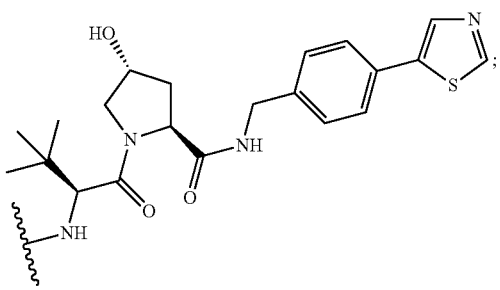
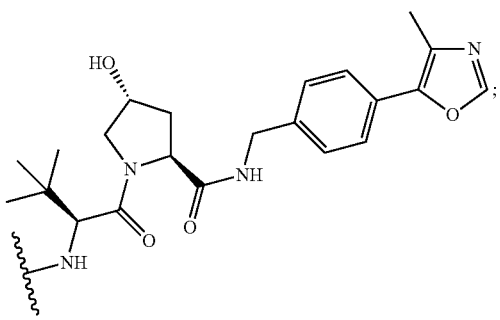
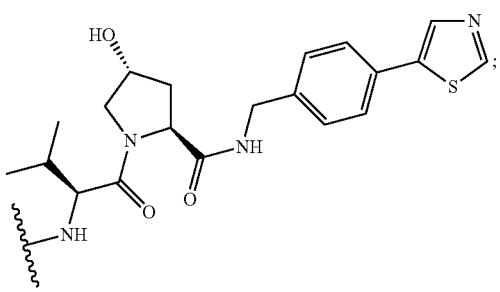

-continued

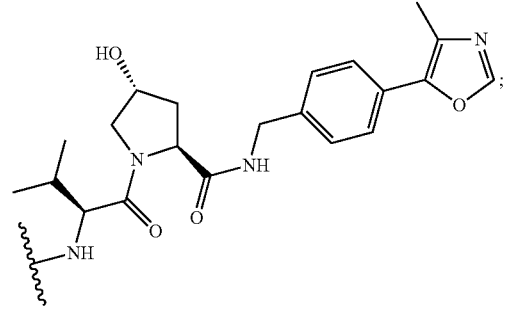

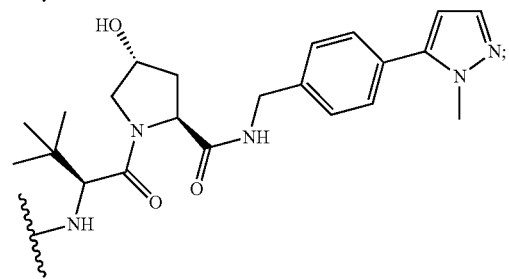

and

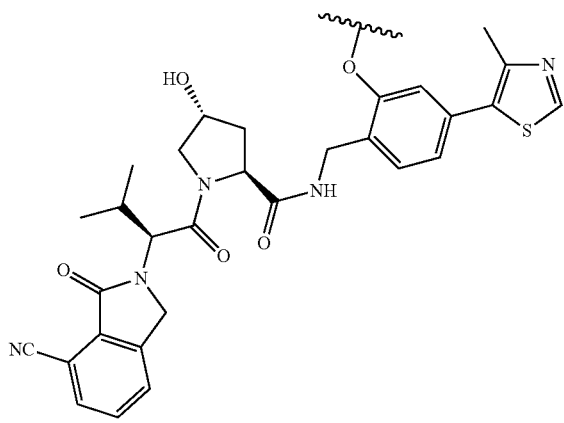

attached to the linker moiety at the position indicated.

Exemplary Linkers

In certain embodiments, the compounds as described herein include one or more ABM chemically linked or coupled to one or more ULMs or VLMs via a chemical linker (L). In certain embodiments, the linker group L is a group comprises one or more covalently connected structural units of A (e.g. -$A_1 \ldots A_q$-), wherein $A_1$ is coupled to an ABM moiety, and q is an integer greater than or equal to 0. In certain embodiments, q is an integer greater than or equal to 1.

In certain embodiments, e. g., where q is greater than 2, $A_q$ is a group which is connected to a ULM or VLM moiety, and $A_1$ and $A_q$ are connected via structural units of A (number of such structural units of A: q-2).

In certain embodiments, e. g., where q is 2, $A_q$ is a group which is connected to $A_1$ and to a ULM or VLM moiety.

In certain embodiments, e. g., where q is 1, the structure of the linker group L is -$A_1$-, and $A_1$ is a group which is connected to a ULM or VLM moiety and an ABM moiety.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, $A_1$ to $A_q$ are, each independently, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C$(=NCN)$NR^{L4}$, $NR^{L3}C$(=NCN), $NR^{L3}C$(=$CNO_2$)$NR^{L4}$, $C_{3-11}$cycloalkyl optionally substituted with 0-6 $R^{L1}$ and/or $R^{L2}$ groups, $C_{3-11}$heteocyclyl optionally substituted with 0-6 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, wherein $R^{L1}$ or $R^{L2}$, each independently, can be linked to other A groups to form cycloalkyl and/or heterocyclyl moiety which can be further substituted with 0-4 $R^{L5}$ groups;

wherein $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}$cycloalkyl$)_2$, $N(C_{1-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, Si(OH$)_3$, Si($C_{1-8}$alkyl$)_3$, Si(OH)($C_{1-8}$alkyl$)_2$, $COC_{1-8}$alkyl, $CO_2$H, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, CON($C_{1-8}$alkyl$)_2$, $N(C_{1-8}$alkyl)CONH($C_{1-8}$alkyl), $N(C_{1-8}$alkyl)CON($C_{1-8}$alkyl$)_2$, NHCONH($C_{1-8}$alkyl), NHCON($C_{1-8}$alkyl$)_2$, $NHCONH_2$, $N(C_{1-8}$alkyl)$SO_2NH(C_{1-8}$alkyl), $N(C_{1-8}$alkyl)$SO_2N(C_{1-8}$alkyl$)_2$, $NHSO_2NH(C_{1-8}$alkyl), $NHSO_2N(C_{1-8}$alkyl$)_2$, $NHSO_2NH_2$.

In certain embodiments, the linker (L) is selected from the group consisting of):

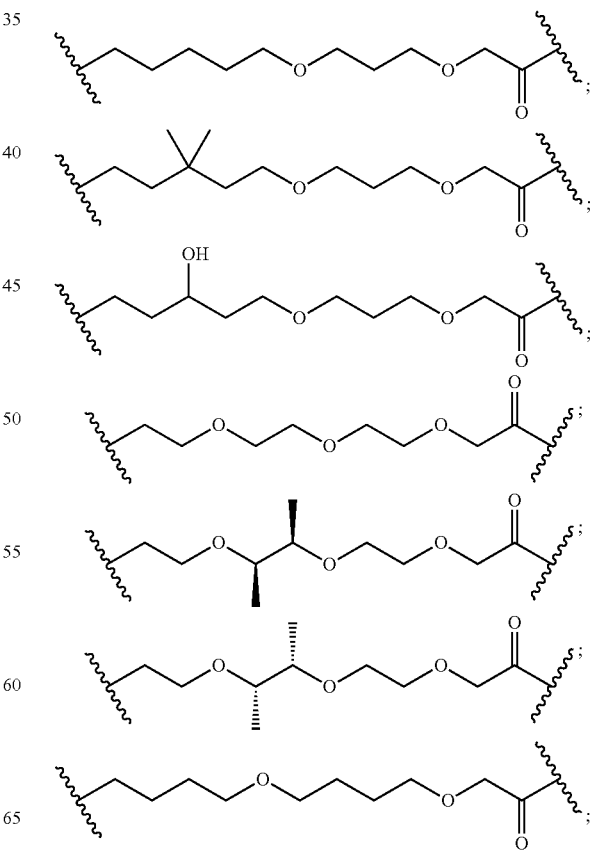

31
-continued

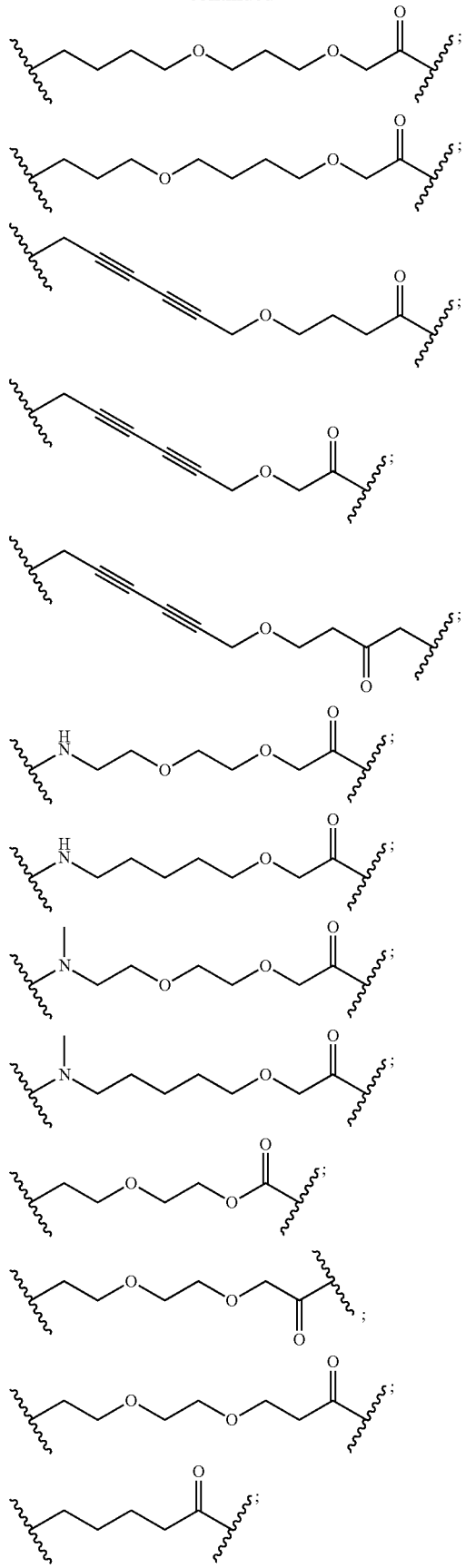

32
-continued

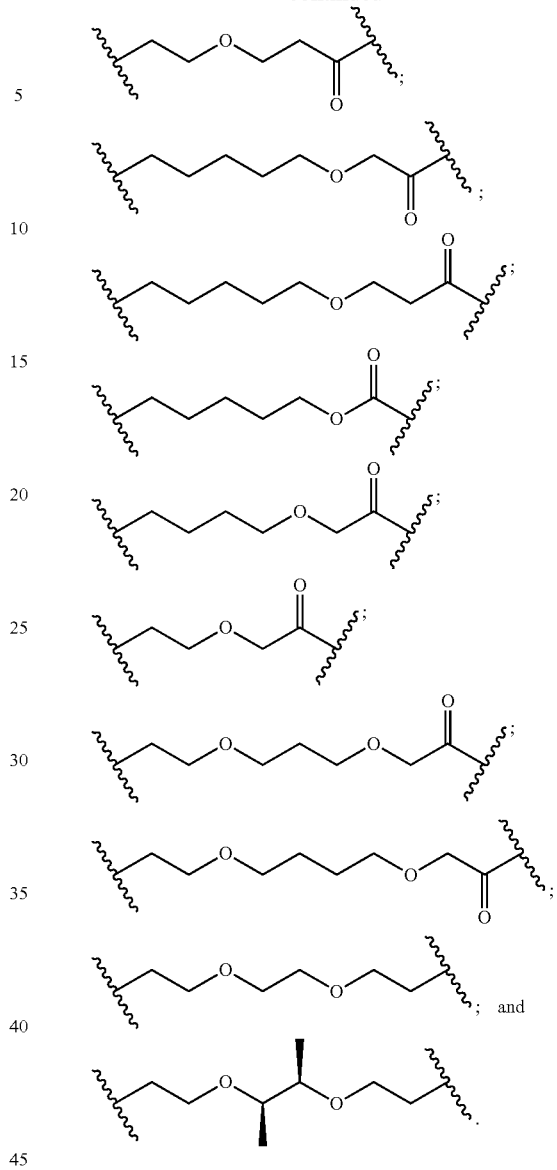

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In certain aspects the description provides a PROTAC compound in which the linker is cleavable in vivo into a functional E3 ligase binding moiety, and target protein binding moiety. In this regard, and without being bound by any particular theory, it is hypothesized that such a configuration can potentiate the beneficial effects of the degradation activity of the intact PROTAC molecule. Thus, in certain embodiments, the linker is configured or "tuned" to have the desired kinetics of cleavage into functional component molecules or active metabolites. In certain embodiments, the enzyme responsible for cleavage of the linker is a liver enzyme, such as, e.g., oxidases, peroxidase, reductases, transferases, dehydrogenases, peroxidases. In certain embodiments, the enzyme is at least one of cytochrome P450 oxidase, e.g., CYP3A4, Flavin-containing monooxygenase, alcohol dehydrogenase, aldehyde dehydrogenase, monoamine oxidase, peroxidase, glutathione S-transferase, cytochrome P450 reductase, sulfotransferase, methyltransferase, N-acetyltransferase, glucuronosyltransferase, transpeptidase, or combination thereof.

Exemplary Androgen Binding Moieties (ABMs)

In another aspect, the description provides AR binding moieties (ABM), which in certain aspects and embodiments are coupled to a linker and/or a ULM as described herein.

In any of the compounds described herein, the ABM comprises a chemical moiety that binds to the androgen receptor (AR). Various androgen receptor binding compounds have been described in literature, including various androgen derivatives such as testosterone, dihydrotestosterone, and metribolone (also known as methyltrienolone or R1881), and non-steroidal compounds such as bicalutamide, enzalutamide. Those of ordinary skill in the art would appreciate that these androgen receptor binding compounds could be potentially used as an ABM moiety in a PROTAC compound. Such literature includes, but not limited to, G. F. Allan et. al, *Nuclear Receptor Signaling*, 2003, 1, e009; R. H. Bradbury et. al, *Bioorganic & Medicinal Chemistry Letters*, 2011 5442-5445; C. Guo et. al, *Bioorganic & Medicinal Chemistry Letters*, 2012 2572-2578; P. K. Poutiainen et. al, *J. Med. Chem.* 2012, 55, 6316-6327 A. Pepe et. al, *J. Med. Chem.* 2013, 56, 8280-8297; M. E. Jung et al, *J. Med. Chem.* 2010, 53, 2779-2796, which are incorporated by reference herein.

In certain embodiments, the ABM comprises a structure selected from, but not limited to the structures shown below, where a dashed line indicates the attachment point of linker moiety:

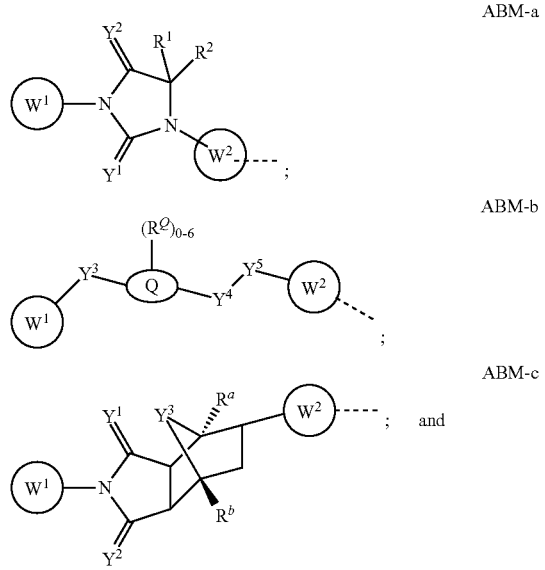

ABM-a

ABM-b

ABM-c

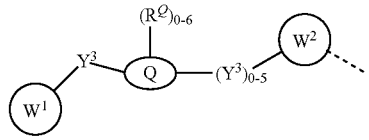

ABM-d wherein $W^1$ is aryl or heteroaryl, independently substituted by 1 or more halo, hydroxyl, nitro, CN, C≡CH, $C_{1-6}$ alkyl (linear, branched, optionally substituted by 1 or more halo, $C_1$-6 alkoxyl), $C_1$-6 alkoxyl (linear, branched, optionally substituted by 1 or more halo), $C_{2-6}$ alkenyl, $C_{2-6}$ alkynyl;

$Y^1$, $Y^2$ are each independently $NR^{Y1}$, O, S;

$Y^3$, $Y^4$, $Y^5$ are each independently a bond, O, $NR^{Y2}$, $CR^{Y1}R^{Y2}$, C=O, C=S, SO, $SO_2$;

Q is a 3-6 membered ring with 0-4 heteroatoms, optionally substituted with 0-6 $R^Q$, each $R^Q$, is independently H, $C_1$-6 alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^1$, $R^2$, $R^a$, $R^b$, $R^{Y1}$, $R^{Y2}$ are each independently H, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms);

$W^2$ is a bond, $C_{1-6}$ alkyl, or aryl, or heteroaryl, each optionally substituted by 1, 2 or 3 $R^{W2}$; and each $R^{W2}$ is independently H, halo, $C_{1-6}$ alkyl (optionally substituted by 1 or more F), $OC_{1-3}$alkyl (optionally substituted by 1 or more —F).

In any of the embodiments described herein, the $W^2$ is covalently coupled to one or more ULM or VLM groups, or a linker to which is attached one or more ULM or VLM groups as described herein.

In certain embodiments, $W^1$ is

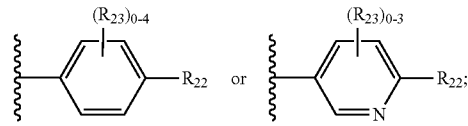

wherein each $R_{22}$ is independently halo, optionally substituted alkyl, haloalkyl, cyano, or nitro; and each $R_{23}$ is independently H, halo, optionally substituted alkyl, haloalkyl, cyano, or nitro.

In certain additional embodiments, $W^1$ is selected from the group consisting of:

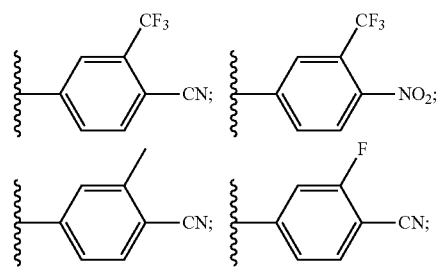

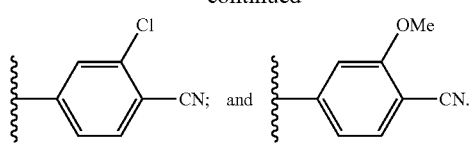
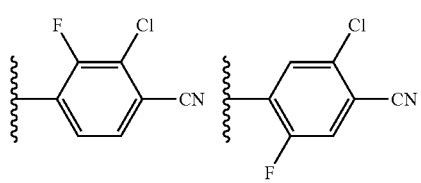
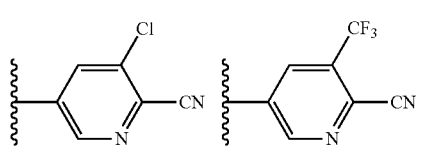
In certain embodiments, ABM is selected from the group consisting of:
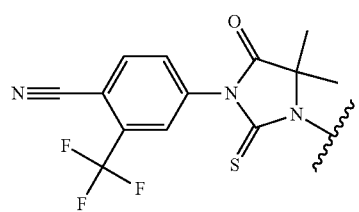
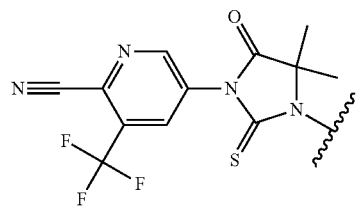
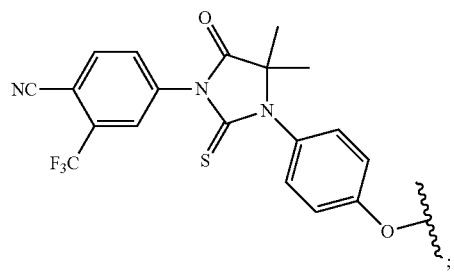
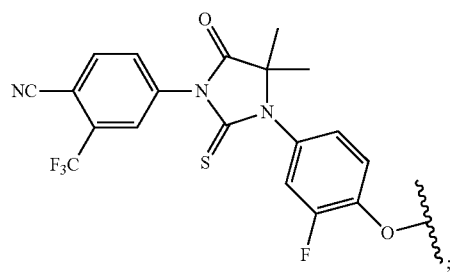
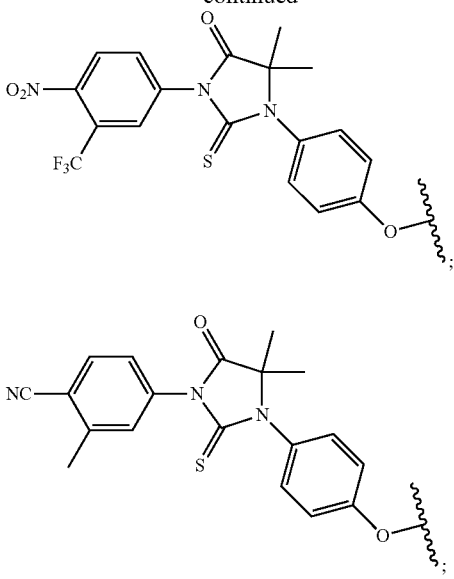
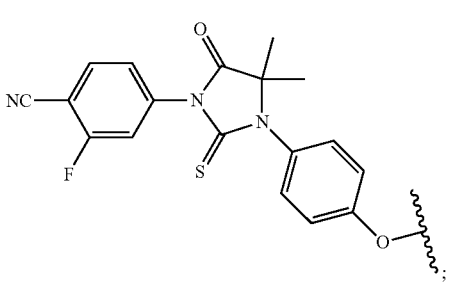
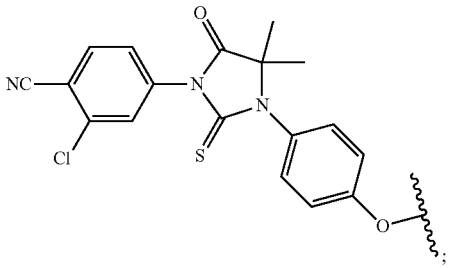
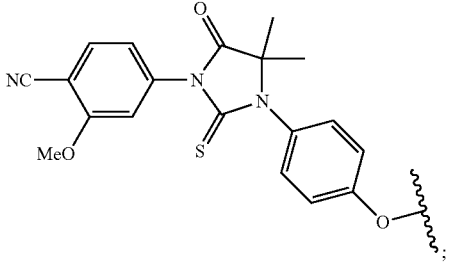
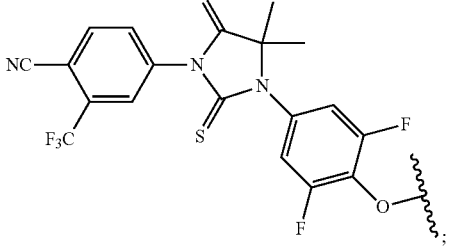

-continued
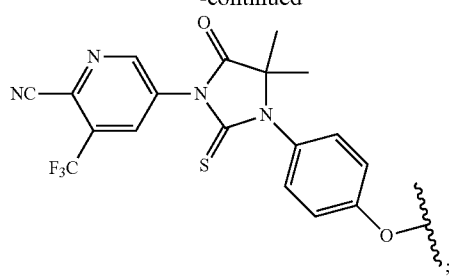
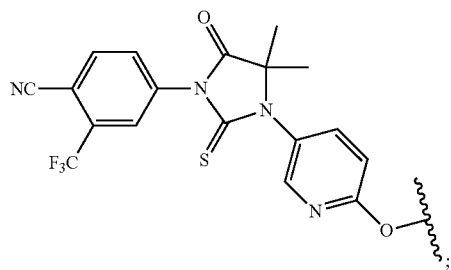
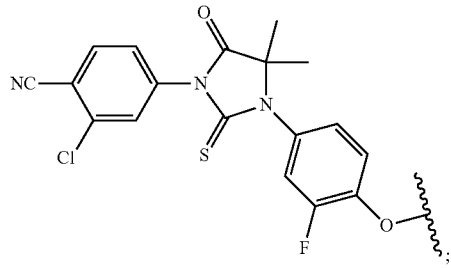
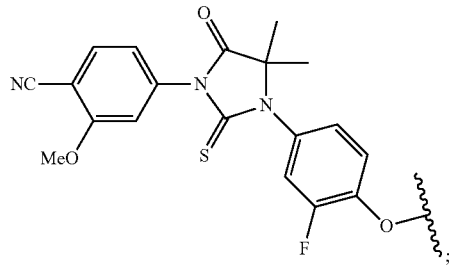
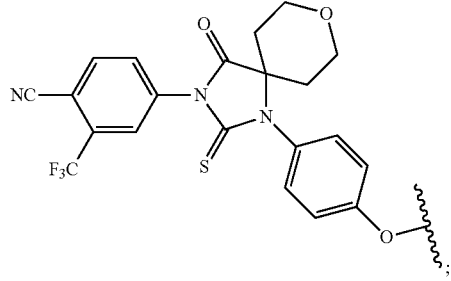
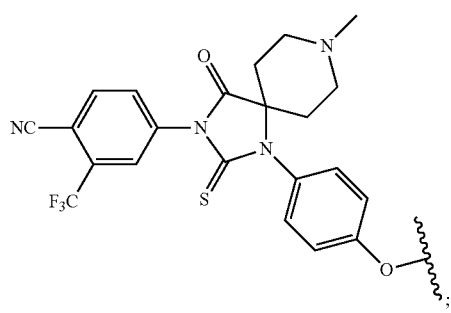
-continued
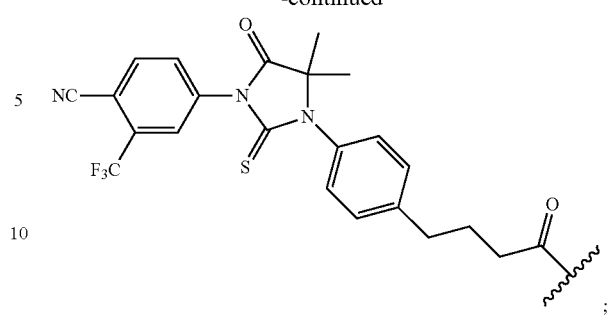
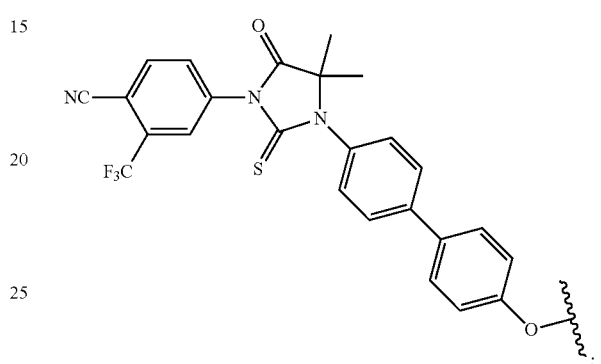
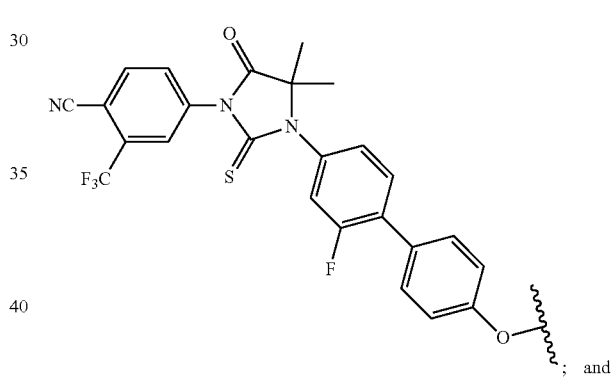
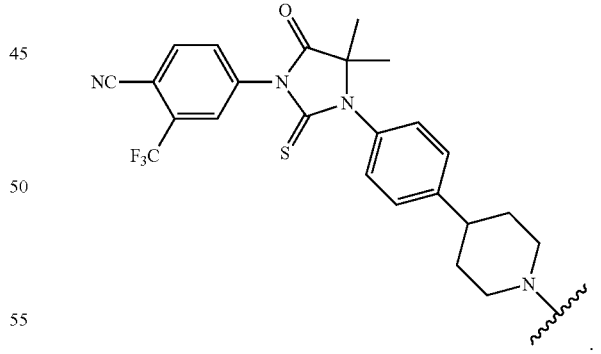
; and
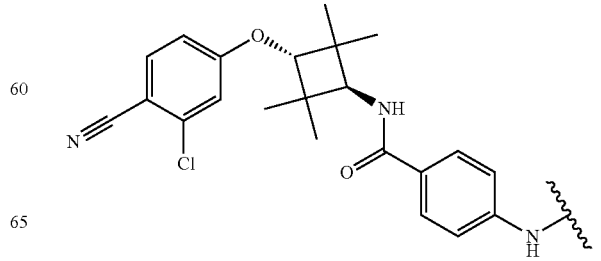
.

-continued
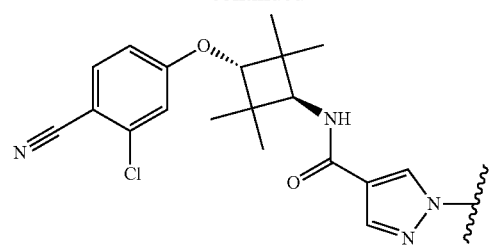
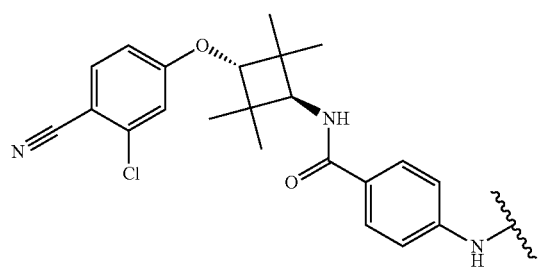
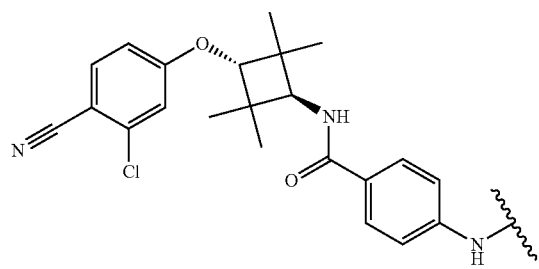
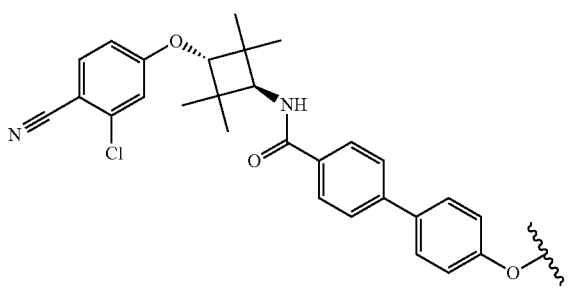
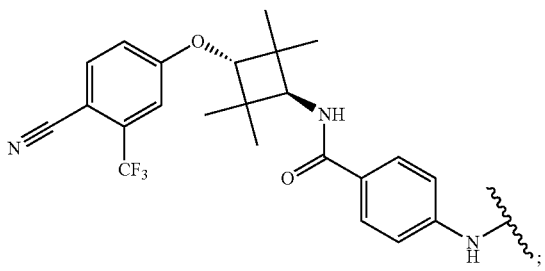
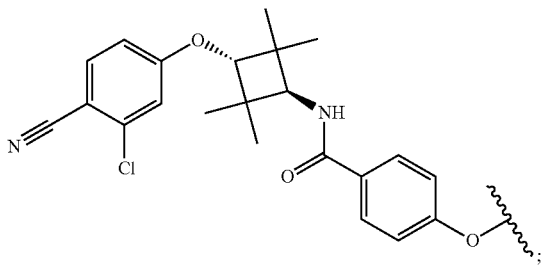
-continued
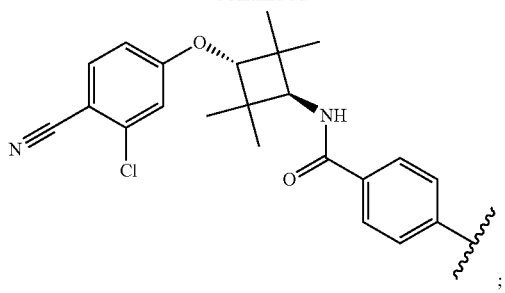;
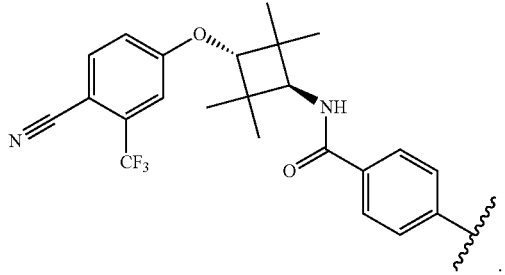;
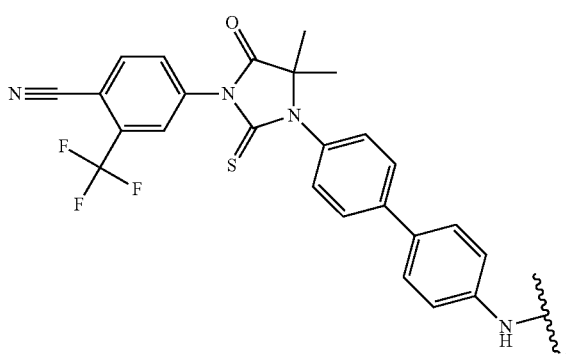;
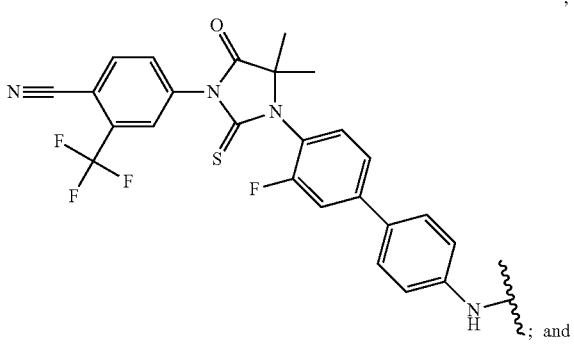; and
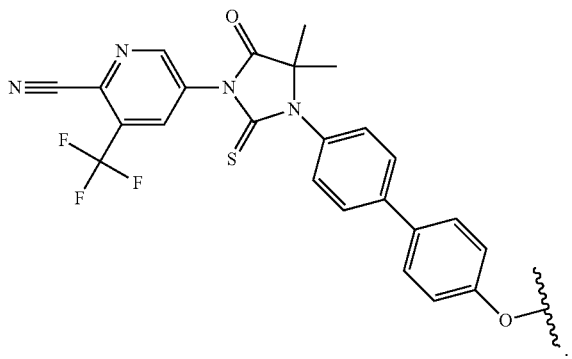 [SMILES: *Oc1ccc(-c2ccc(N3C(=S)N(c4cnc(C#N)c(C(F)(F)F)c4)C(=O)C3(C)C)cc2)cc1].

In certain embodiments, the ABM comprises the structure:

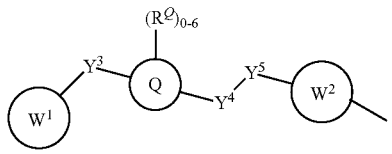

ABM-b wherein W$^1$ is aryl or heteroaryl, independently substituted by 1 or more halo, hydroxyl, nitro, CN, C≡CH, C$_{1-6}$ alkyl (linear, branched, optionally substituted by 1 or more halo, C$_{1-6}$ alkoxyl), C$_{1-6}$ alkoxyl (linear, branched, optionally substituted by 1 or more halo), C$_{2-6}$ alkenyl, C$_{2-6}$ alkynyl;

Y$^3$, Y$^4$, Y$^5$ are each independently a bond, O, NR$^{Y2}$, CR$^{Y1}$R$^{Y2}$, C=O, C=S, SO, SO$_2$;

Q is a 4 membered alicyclic ring with 0-2 heteroatoms, optionally substituted with 0-6 R$^Q$, each R$^Q$, is independently H, C$_{1-6}$ alkyl (linear, branched, optionally substituted by 1 or more halo, C$_{1-6}$ alkoxyl), or 2 R$^Q$ groups taken together with the atom they are attached to, form a 3-8 membered ring system containing 0-2 heteroatoms);

R$^{Y1}$, R$^{Y2}$ are each independently H, C$_{1-6}$ alkyl (linear, branched, optionally substituted by 1 or more halo, C$_{1-6}$ alkoxyl);

W$^2$ is a bond, C$_{1-6}$ alkyl, C$_{1-6}$ alicyclic, heterocyclic, aryl, or heteroaryl, each optionally substituted by 1, 2 or 3 R$^{W2}$; and each R$^{W2}$ is independently H, halo, C$_{1-6}$ alkyl (optionally substituted by 1 or more F), OC$_{1-3}$alkyl (optionally substituted by 1 or more —F), OH, NH$_2$, NR$^{Y1}$R$^{Y2}$, CN.

In an additional aspect, the description provides an androgen receptor binding compound comprising a structure of:

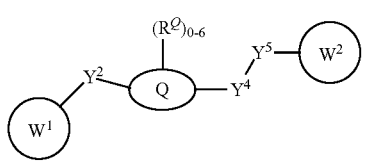

ABM-e wherein W$^1$ is aryl or heteroaryl, independently substituted by 1 or more halo, hydroxyl, nitro, CN, C≡CH, C$_{1-6}$ alkyl (linear, branched, optionally substituted by 1 or more halo, C$_{1-6}$ alkoxyl), C$_{1-6}$ alkoxyl (linear, branched, optionally substituted by 1 or more halo), C$_{2-6}$ alkenyl, C$_{2-6}$ alkynyl;

Y$^1$, Y$^2$ are each independently NR$^{Y1}$, O, S;

Y$^3$, Y$^4$, Y$^5$ are each independently a bond, O, NR$^{Y2}$, CR$^{Y1}$R$^{Y2}$, C=O, C=S, SO, SO$_2$;

Q is a 3-6 membered alicyclic or aromatic ring with 0-4 heteroatoms, optionally substituted with 0-6 R$^Q$, each R$^Q$, is independently H, C$_{1-6}$ alkyl (linear, branched, optionally substituted by 1 or more halo, C$_{1-6}$ alkoxyl), or 2 R$^Q$ groups taken together with the atom they are attached to, form a 3-8 membered ring system containing 0-2 heteroatoms);

R$^1$, R$^2$, R$^a$, R$^b$, R$^{Y1}$, R$^{Y2}$ are each independently H, C$_{1-6}$ alkyl (linear, branched, optionally substituted by 1 or more halo, C$_{1-6}$ alkoxyl), or R$^1$, R$^2$ together with the atom they are attached to, form a 3-8 membered ring system containing 0-2 heteroatoms);

W$^2$ is a bond, C$_{1-6}$ alkyl, C$_{1-6}$ alicyclic, heterocyclic, aryl, or heteroaryl, each optionally substituted by 1, 2 or 3 R$^{W2}$; and each R$^{W2}$ is independently H, halo, C$_{1-6}$ alkyl (optionally substituted by 1 or more F), OC$_{1-3}$alkyl (optionally substituted by 1 or more —F), OH, NH$_2$, NR$^{Y1}$R$^{Y2}$, CN.

In certain embodiments, the androgen receptor binding compound of ABM-e is selected from the group consisting of:

trans-2-Chloro-4-[3-amino-2,2,4,4-tetramethylcyclobutoxy]benzonitrile;

cis-2-Chloro-4-[3-amino-2,2,4,4-tetramethylcyclobutoxy]benzonitrile;

trans 6-Amino-N-[3-(3-chloro-4-cyanophenoxy)-2,2,4,4-tetramethylcyclobutyl]pyridazine-3-carboxamide;

trans tert-Butyl N-[3-(3-chloro-4-cyanophenoxy)-2,2,4,4-tetramethylcyclobutyl]carbamate;

trans 4-Amino-N-[3-(3-chloro-4-cyanophenoxy)-2,2,4,4-tetramethylcyclobutyl]benzamide;

trans 5-Amino-N-[3-(3-chloro-4-cyanophenoxy)-2,2,4,4-tetramethylcyclobutyl]pyrazine-2-carboxamide;

trans 2-Amino-N-[3-(3-chloro-4-cyanophenoxy)-2,2,4,4-tetramethylcyclobutyl]pyrimidine-5-carboxamide;

4-Methoxy-N-[(1r,3r)-3-(3-chloro-4-cyanophenoxy)-2,2,4,4-tetramethylcyclobutyl]benzamide;

trans 1-(2-Hydroxyethyl)-N-[3-(3-chloro-4-cyanophenoxy)-2,2,4,4-tetramethylcyclobutyl]-1H-pyrazole-4-carboxamide;

trans 6-Amino-N-[3-(3-chloro-4-cyanophenoxy)-2,2,4,4-tetramethylcyclobutyl]pyridine-3-carboxamide;

trans 4-[(5-Hydroxypentyl)amino]-N-[3-(3-chloro-4-cyanophenoxy)-2,2,4,4-tetramethylcyclobutyl]benzamide; and trans tert-Butyl 2-({5-[(4-{[3-(3-chloro-4-cyanophenoxy)-2,2,4,4-tetramethylcyclobutyl]carbamoyl}phenyl)aminopentyl}oxy)acetate.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "alkyl" shall mean within its context a linear, branch-chained or cyclic fully saturated hydrocarbon radical or alkyl group, preferably a C$_1$-C$_{10}$, more preferably a C$_1$-C$_6$, alternatively a C$_1$-C$_3$ alkyl group, which may be optionally substituted. Examples of alkyl groups are methyl, ethyl, n-propyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain preferred embodiments, compounds according to the present invention which may be used to covalently bind to dehalogenase enzymes. These compounds generally contain a side chain (often linked through a polyethylene glycol group) which terminates in an alkyl group which has a halogen substituent (often chlorine or bromine) on its distil end which results in covalent binding of the compound containing such a moiety to the protein.

The term "Alkenyl" refers to linear, branch-chained or cyclic C$_2$-C$_{10}$ (preferably C$_2$-C$_6$) hydrocarbon radicals containing at least one C=C bond.

The term "Alkynyl" refers to linear, branch-chained or cyclic C$_2$-C$_{10}$ (preferably C$_2$-C$_6$) hydrocarbon radicals containing at least one CC bond.

The term "alkylene" when used, refers to a —(CH$_2$)$_n$— group (n is an integer generally from 0-6), which may be optionally substituted. When substituted, the alkylene group preferably is substituted on one or more of the methylene groups with a C$_1$-C$_6$ alkyl group (including a cyclopropyl group or a t-butyl group), more preferably a methyl group, but may also be substituted with one or more halo groups, preferably from 1 to 3 halo groups or one or two hydroxyl groups, O—(C$_1$-C$_6$ alkyl) groups or amino acid sidechains as otherwise disclosed herein. In certain embodiments, an alkylene group may be substituted with a urethane or alkoxy group (or other group) which is further substituted with a polyethylene glycol chain (of from 1 to 10, preferably 1 to 6, often 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (often, a methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon. The term "substituted" or "optionally substituted" shall mean independently (i.e., where more than substituent occurs, each substituent is independent of another substituent) one or more substituents (independently up to five substitutents, preferably up to three substituents, often 1 or 2 substituents on a moiety in a compound according to the present invention and may include substituents which themselves may be further substituted) at a carbon (or nitrogen) position anywhere on a molecule within context, and includes as substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl for example benzyl or benzoyl), alkoxy group (preferably, $C_1$-$C_6$ alkyl or aryl, including phenyl and substituted phenyl), thioether ($C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which is preferably substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present invention may include, for example —$SiR_1R_2R_3$ groups where each of $R_1$ and $R_2$ is as otherwise described herein and $R_3$ is H or a $C_1$-$C_6$ alkyl group, preferably $R_1$, $R_2$, $R_3$ in this context is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteraryl moiety) through an optionally substituted —$(CH_2)_m$— or alternatively an optionally substituted —$(OCH_2)_m$—, —$(OCH_2CH_2)_m$— or —$(CH_2CH_2O)_m$— group, which may be substituted with any one or more of the above-described substituents. Alkylene groups —$(CH_2)_m$— or —$(CH_2)_m$— groups or other chains such as ethylene glycol chains, as identified above, may be substituted anywhere on the chain. Preferred substituents on alkylene groups include halogen or $C_1$-$C_6$ (preferably $C_1$-$C_3$)alkyl groups, which may be optionally substituted with one or two hydroxyl groups, one or two ether groups (O—$C_1$-$C_6$ groups), up to three halo groups (preferably F), or a sideshain of an amino acid as otherwise described herein and optionally substituted amide (preferably carboxamide substituted as described above) or urethane groups (often with one or two $C_0$-$C_6$ alkyl substitutents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present invention, a moiety in a molecule may be optionally substituted with up to five substituents, preferably up to three substituents. Most often, in the present invention moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—$NR_1R_2$ or —N($R_1$)—C(O)—O—$R_1$, nitro, cyano and amine (especially including a $C_1$-$C_6$ alkylene-$NR_1R_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —$(CH_2)_m$— (here, m and n are in context, 1, 2, 3, 4, 5 or 6), —S—, —S(O)—, $SO_2$— or —NH—C(O)—NH—, —$(CH_2)_n$OH, —$(CH_2)_n$SH, —$(CH_2)_n$COOH, $C_1$-$C_6$ alkyl, —$(CH_2)_n$O—($C_1$-$C_6$ alkyl), —$(CH_2)_n$C(O)—($C_1$-$C_6$ alkyl), —$(CH_2)_n$OC(O)—($C_1$-$C_6$ alkyl), —$(CH_2)_n$C(O)O—($C_1$-$C_6$ alkyl), —$(CH_2)_n$NHC(O)—$R_1$, —$(CH_2)_n$C(O)—$NR_1R_2$, —$(OCH_2)_n$OH, —$(CH_2O)_n$COOH, $C_1$-$C_6$ alkyl, —$(OCH_2)_n$O—($C_1$-$C_6$ alkyl), —$(CH_2O)_n$C(O)—($C_1$-$C_6$ alkyl), —$(OCH_2)_n$NHC(O)—$R_1$, —$(CH_2O)_n$C(O)—$NR_1R_2$, —$S(O)_2$—$R_S$, —S(O)—$R_S$ ($R_S$ is $C_1$-$C_6$ alkyl or a —$(CH_2)_n$—$NR_1R_2$ group), $NO_2$, CN or halogen (F, Cl, Br, I, preferably F or Cl), depending on the context of the use of the substituent. $R_1$ and $R_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—$NR_1R_2$ group where $R_1$ and $R_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical having a single ring (e.g., benzene, phenyl, benzyl) or condensed rings (e.g., naphthyl, anthracenyl, phenanthrenyl, etc.) and can be bound to the compound according to the present invention at any available stable position on the ring(s) or as otherwise indicated in the chemical structure presented. Other examples of aryl groups, in context, may include heterocyclic aromatic ring systems "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —$(CH_2)_n$OH, —$(CH_2)_n$—O—$(C_1$-$C_6)$alkyl, —$(CH_2)_n$—O—$(CH_2)_n$—$(C_1$-$C_6)$alkyl, —$(CH_2)_n$—C(O)$(C_0$-$C_6)$alkyl, —$(CH_2)_n$—C(O)O$(C_0$-$C_6)$alkyl, —$(CH_2)_n$—OC(O)$(C_0$-$C_6)$alkyl, amine, mono- or di-$(C_1$-$C_6$ alkyl)amine wherein the alkyl group on the amine is optionally substituted with 1 or 2 hydroxyl groups or up to three halo (preferably F, Cl) groups, OH, COOH, $C_1$-$C_6$ alkyl, preferably $CH_3$, $CF_3$, OMe, $OCF_3$, $NO_2$, or CN group (each of which may be substituted in ortho-, meta- and/or para-positions of the phenyl ring, preferably para-), an optionally substituted phenyl group (the phenyl group itself is preferably substituted with a linker group attached to a ABM group, including a ULM group), and/or at least one of F, Cl, OH, COOH, $CH_3$, $CF_3$, OMe, $OCF_3$, $NO_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methylsubstituted isoxazole, an optionally substituted oxazole including a methylsubstituted oxazole, an optionally substituted thiazole including a methyl substituted thiazole, an optionally substituted isothiazole including a methyl substituted isothiazole, an optionally substituted pyrrole including a methylsubstituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methylsubstituted triazole group, an optionally substituted pyridine group, including a halo-(preferably, F) or methylsubstitutedpyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —$(CH_2)_m$—O—$C_1$-$C_6$ alkyl group or an optionally substituted —$(CH_2)_m$—C(O)—O—$C_1$-$C_6$ alkyl group), an optionally substituted pyridine (2-, 3, or 4-pyridine) or a group according to the chemical structure:

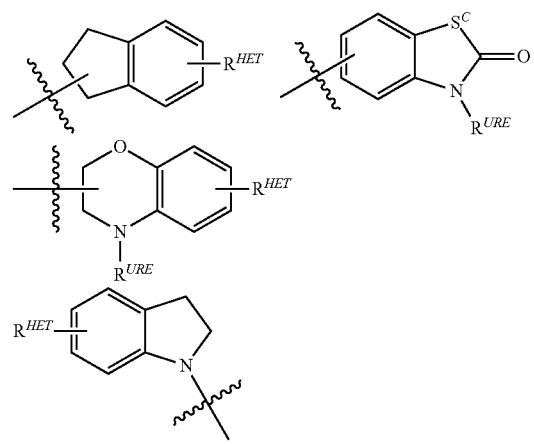

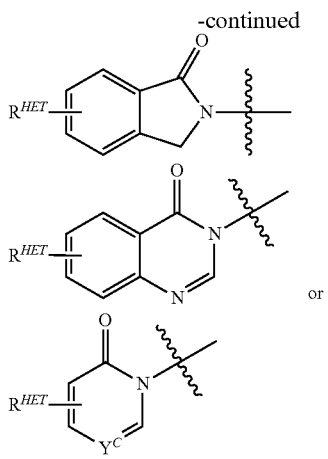

where $S^c$ is $CHR^{SS}$, $NR^{URE}$, or O;

$R^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);

$R^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O)(C$_1$-C$_6$ alkyl) (preferably substituted with one or two hydroxyl groups or up to three halo groups);

$R^{URE}$ is H, H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and $Y^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl).

The terms "arylkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "heterocycle" refers to a cyclic group which contains at least one heteroatom, i.e., O, N or S, and may be aromatic (heteroaryl) or non-aromatic. Thus, the heteroaryl moieties are subsumed under the definition of heterocycle, depending on the context of its use. Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

Exemplary AR-PROTAC Compounds

As described above, in certain aspects, the description provides bifunctional PROTAC compounds comprising at least one ABM group, a linker, and at least one ULM (or VLM) group as described herein.

In certain embodiments, the compound is selected from the group consisting of compounds 1-593 (as described in Tables 2-17), and salts and polymorphs thereof.

In certain embodiments, the compound is selected from the group consisting of:

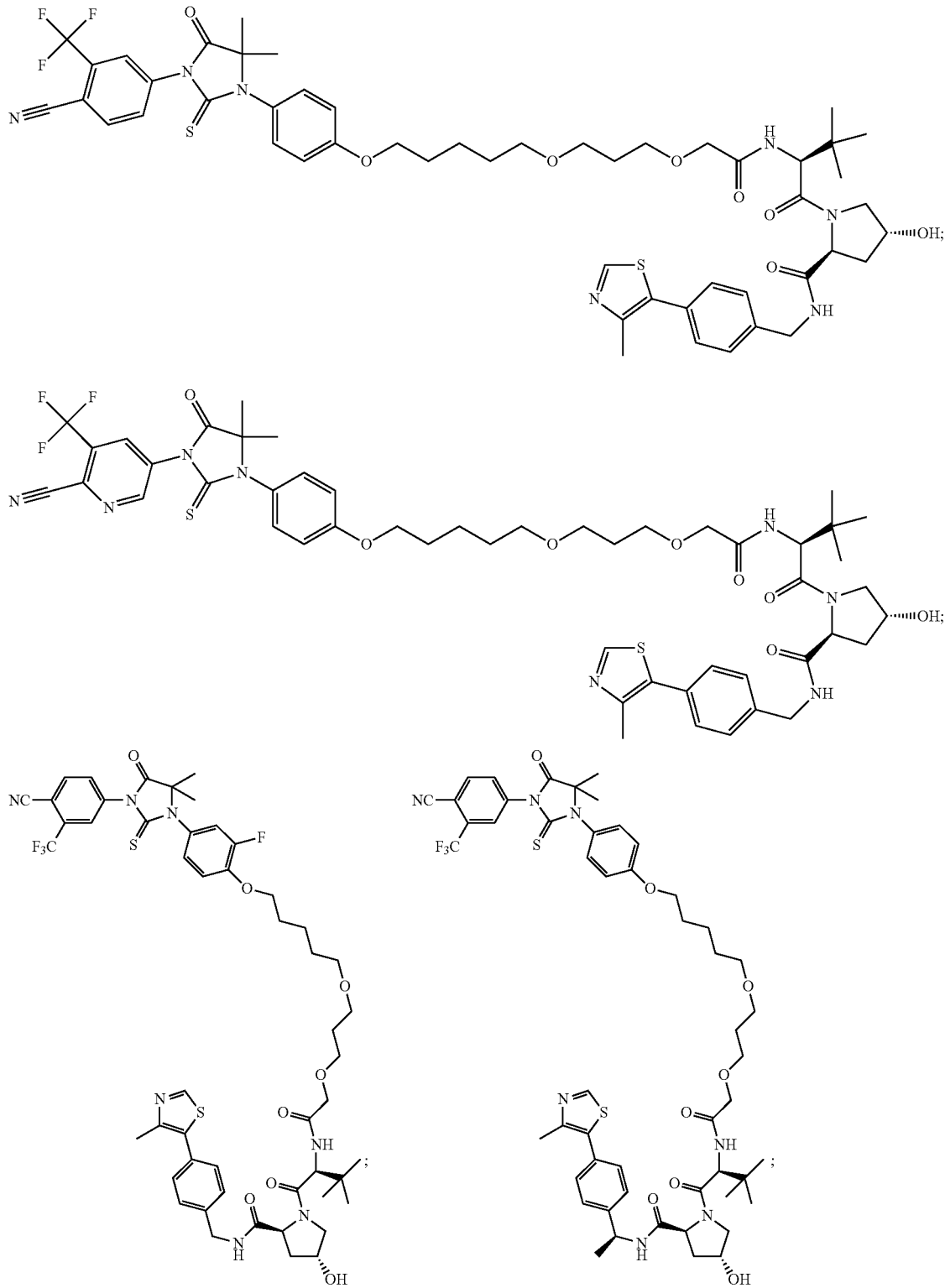

-continued
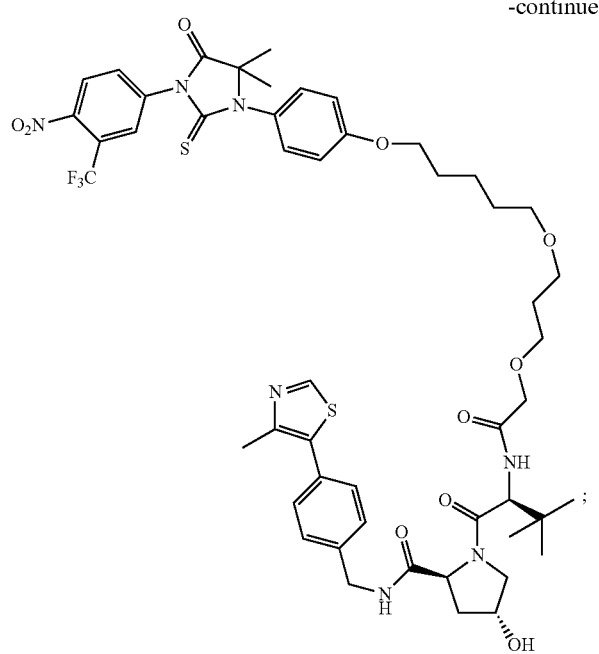
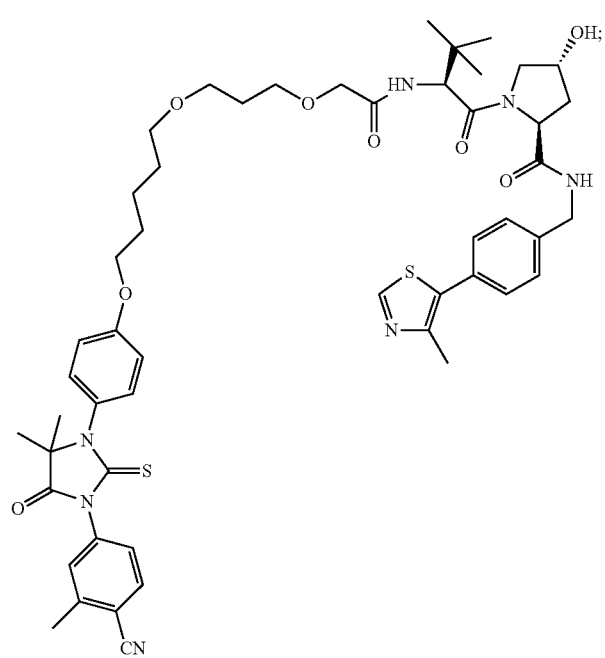

-continued
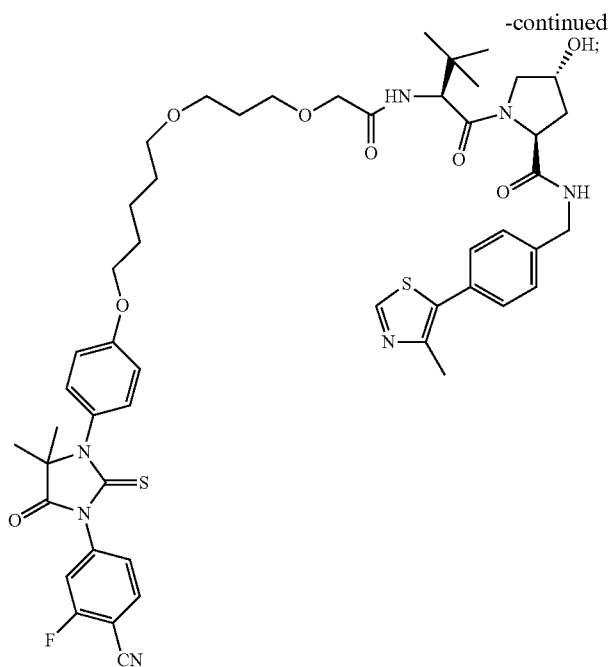
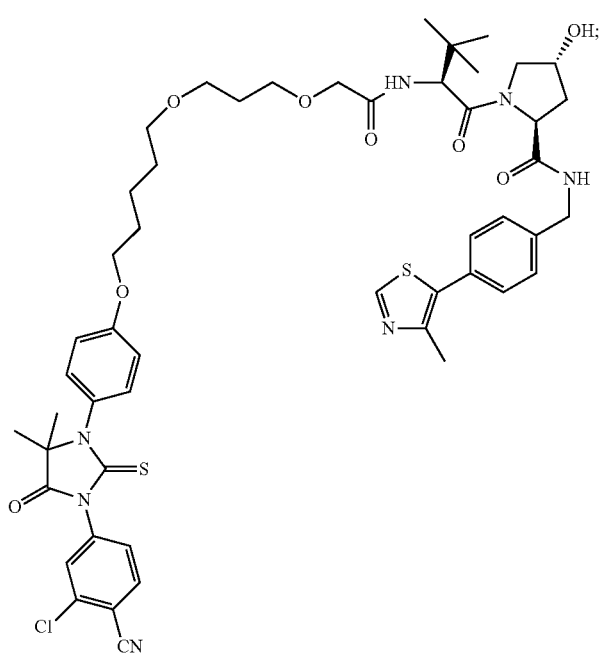 [SMILES: Cc1ncsc1-c1ccc(CNC(=O)[C@@H]2C[C@@H](O)CN2C(=O)[C@@H](NC(=O)COCCCOCCCCCOc2ccc(N3C(=S)N(c4ccc(C#N)c(Cl)c4)C(=O)C3(C)C)cc2)C(C)(C)C)cc1]

-continued
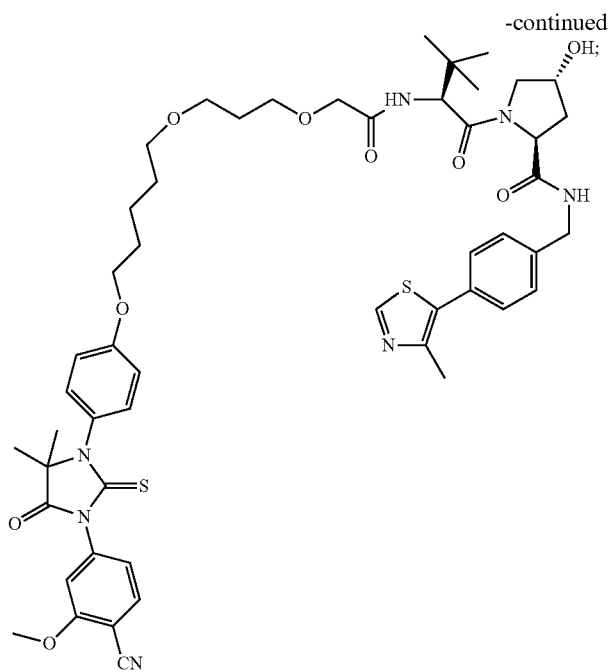
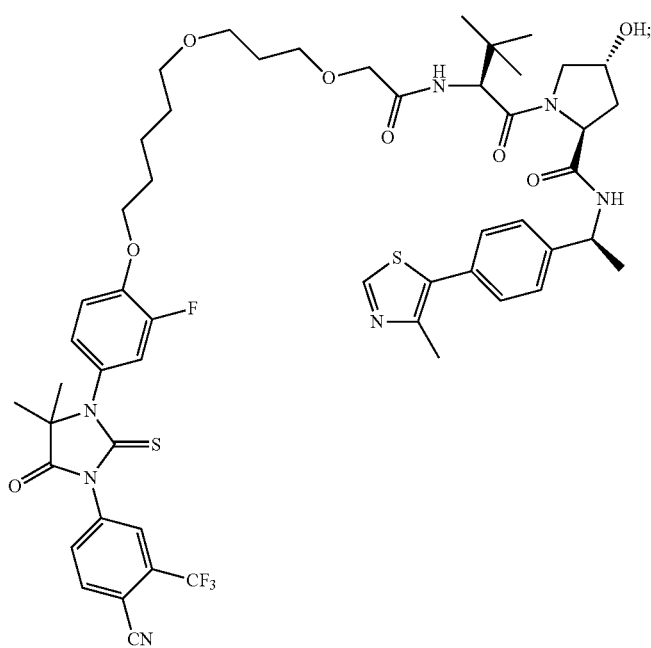

-continued
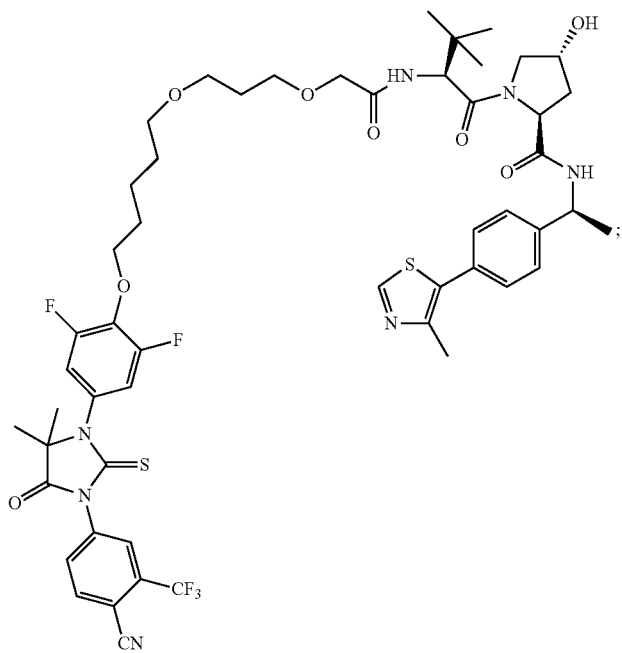
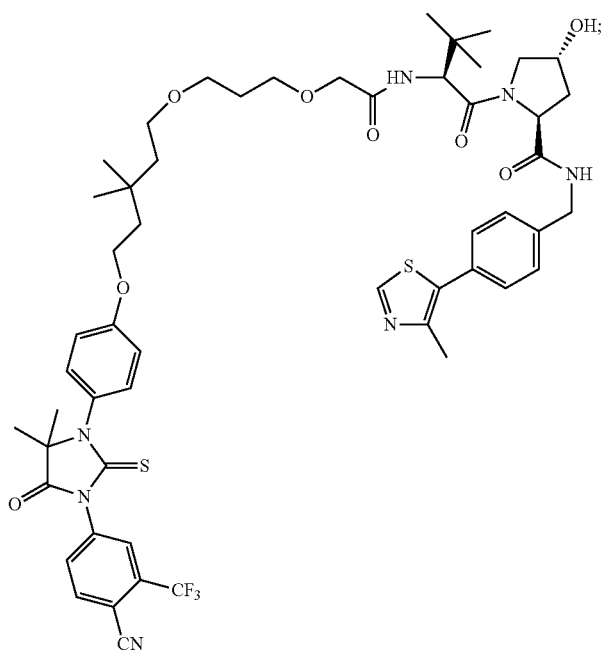

59 60
-continued
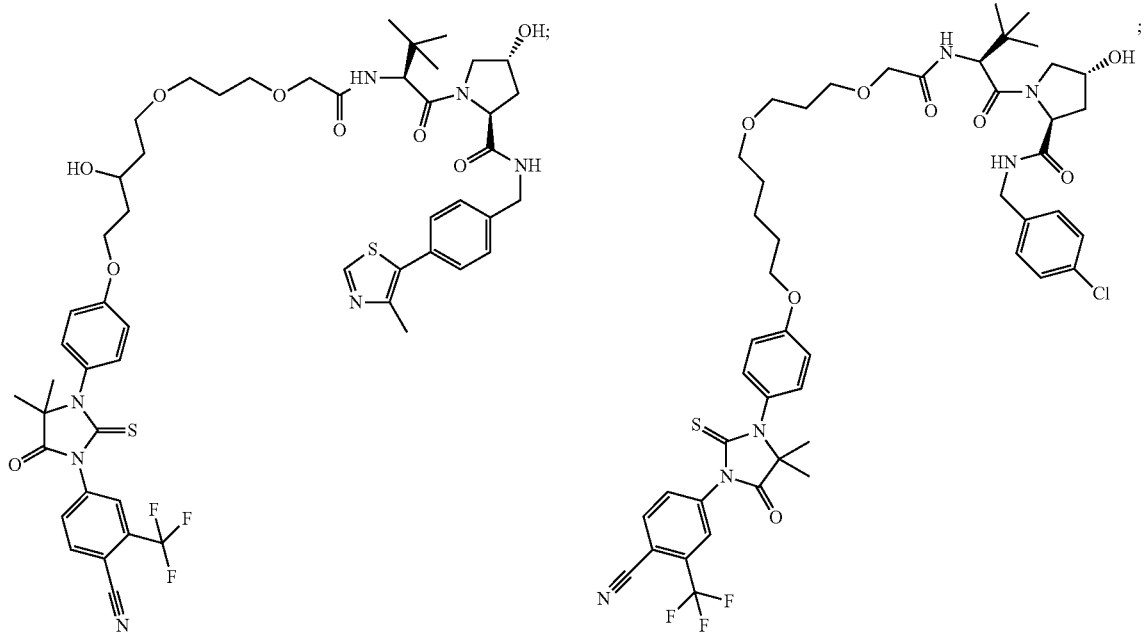
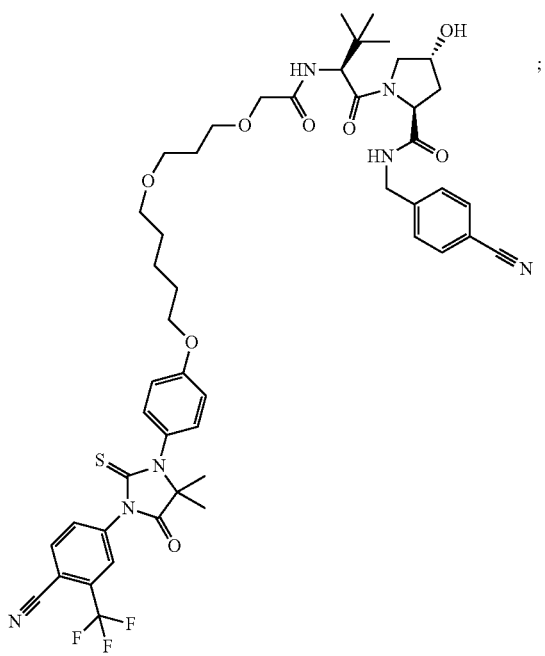

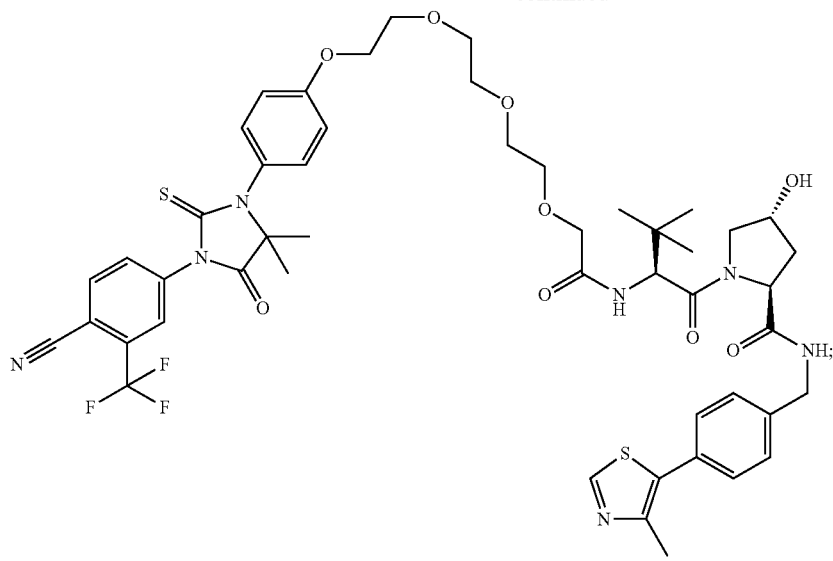
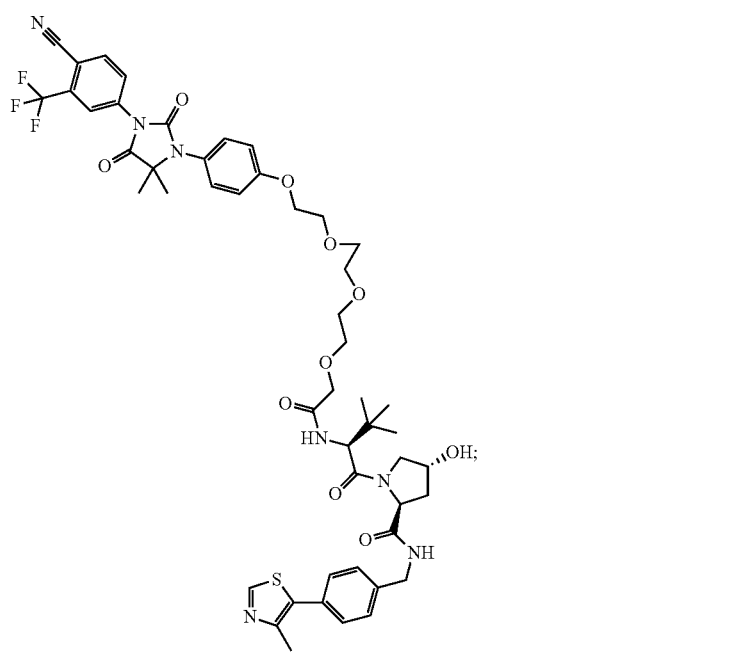
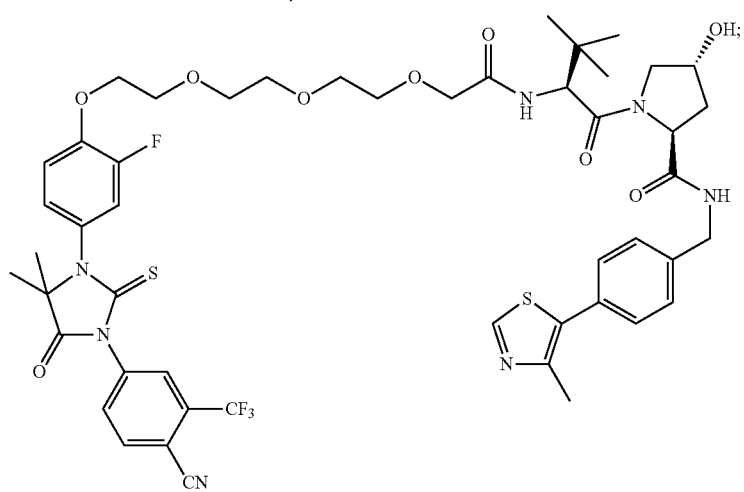

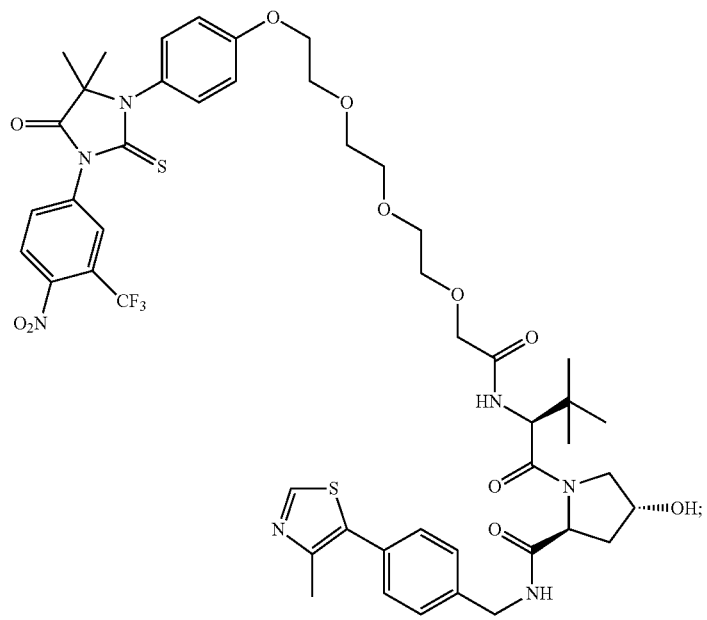
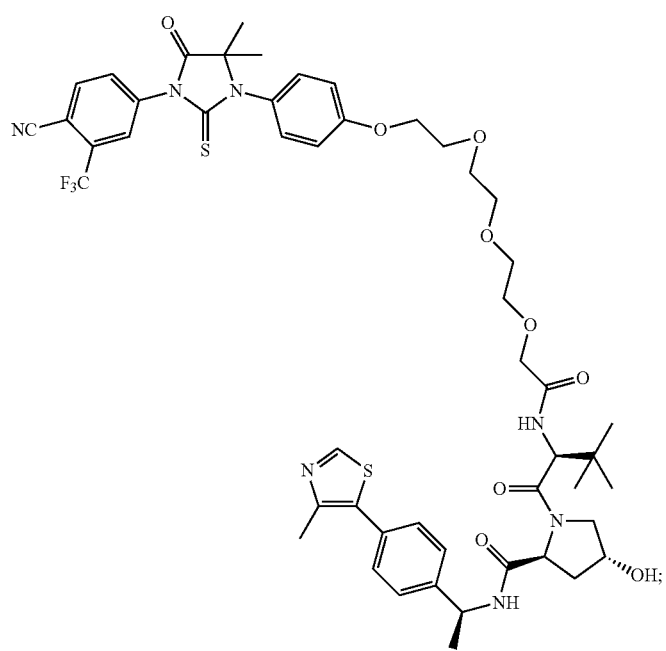

-continued
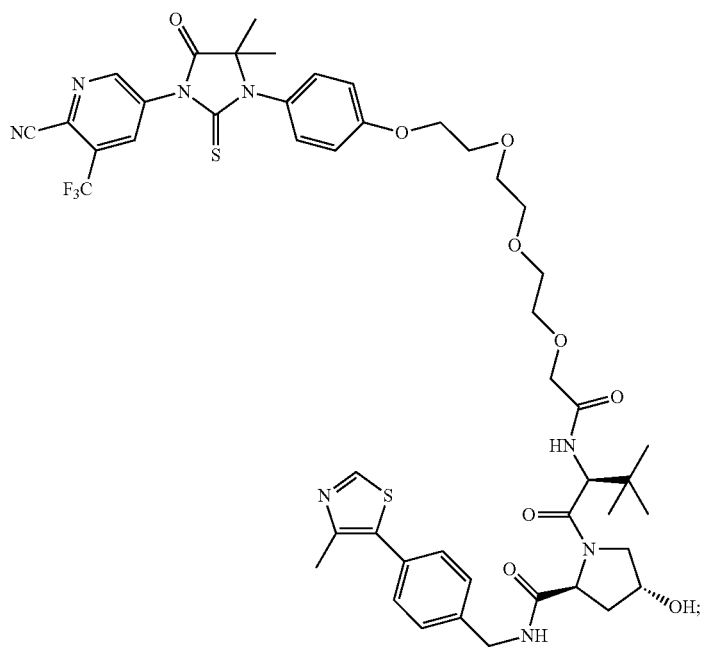
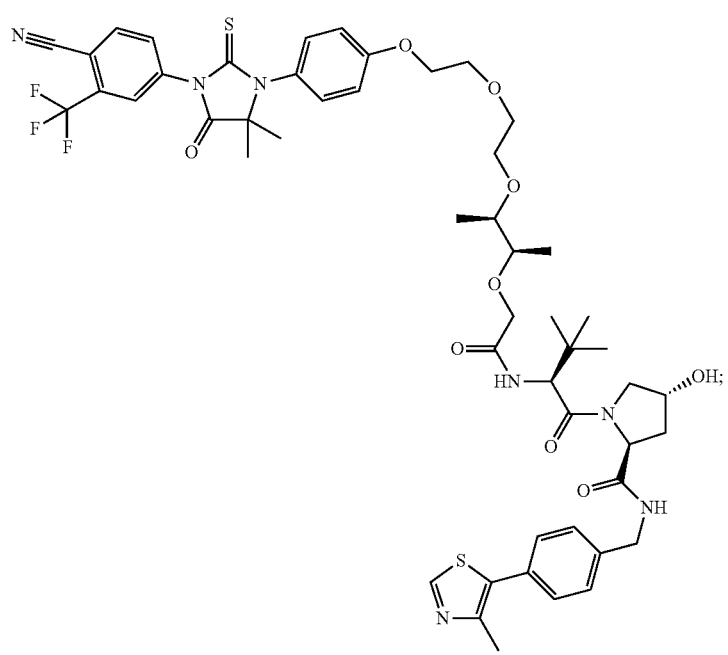

-continued
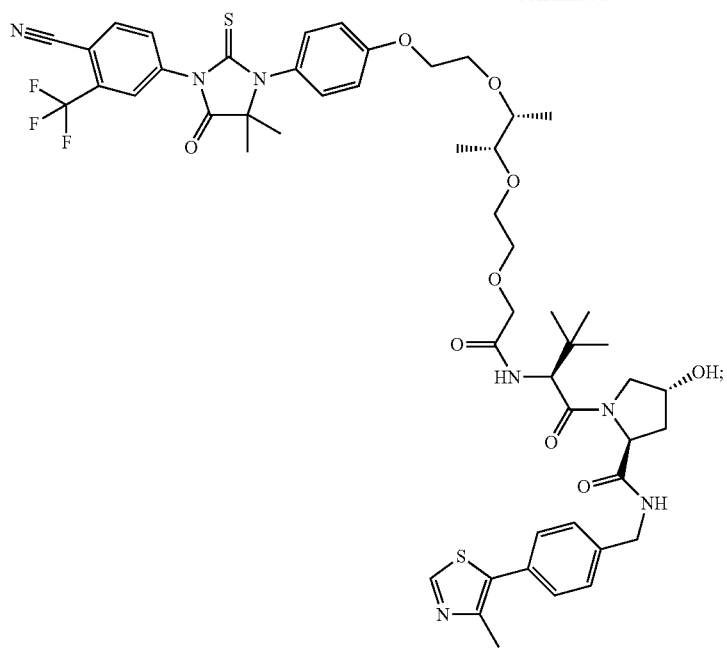
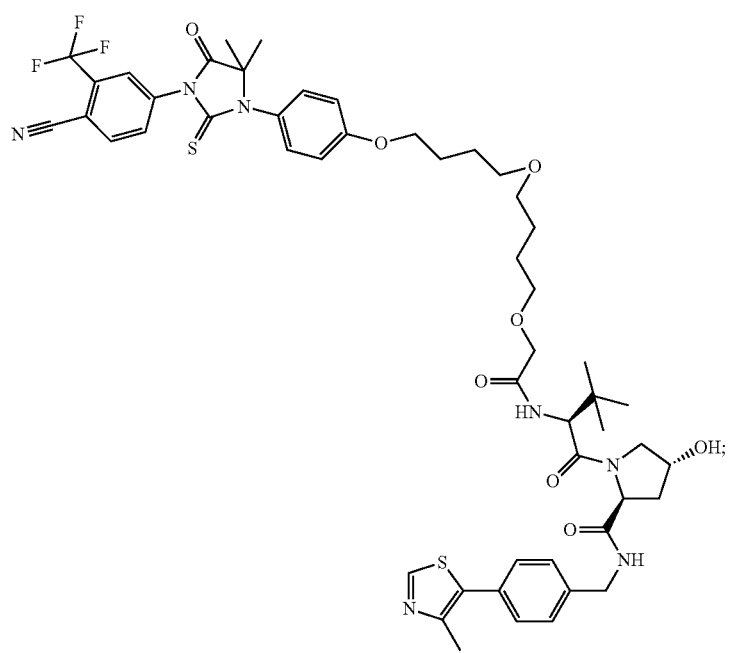

-continued
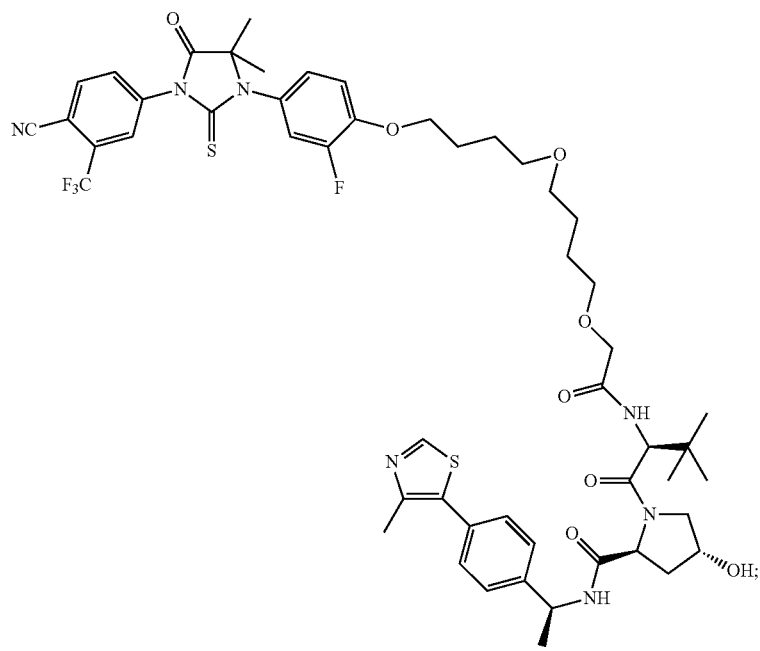
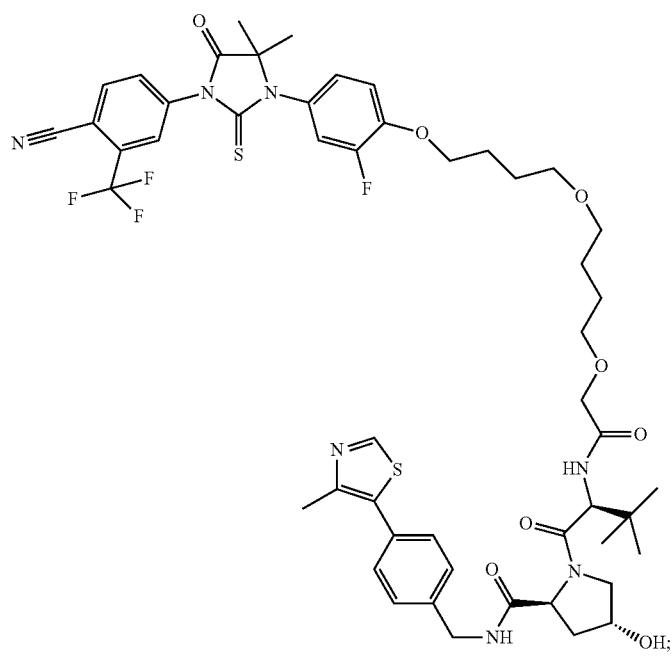

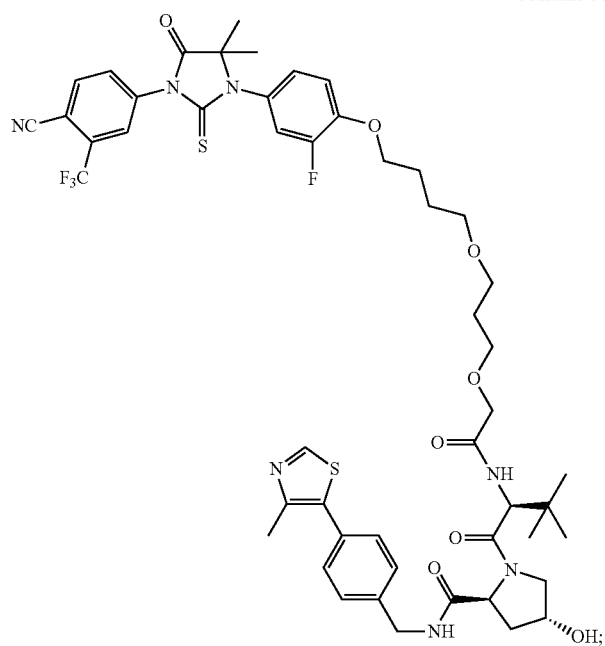
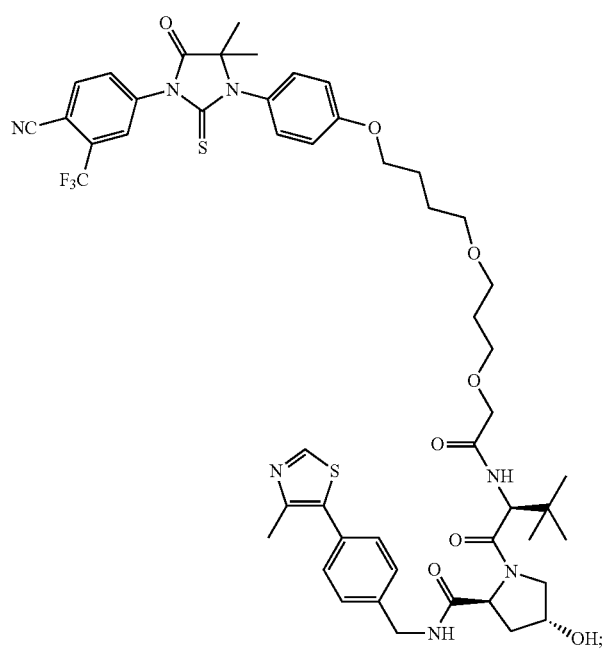

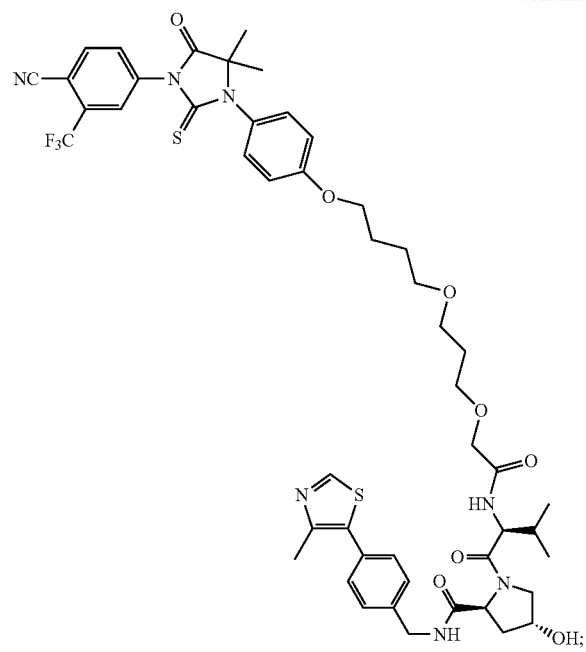
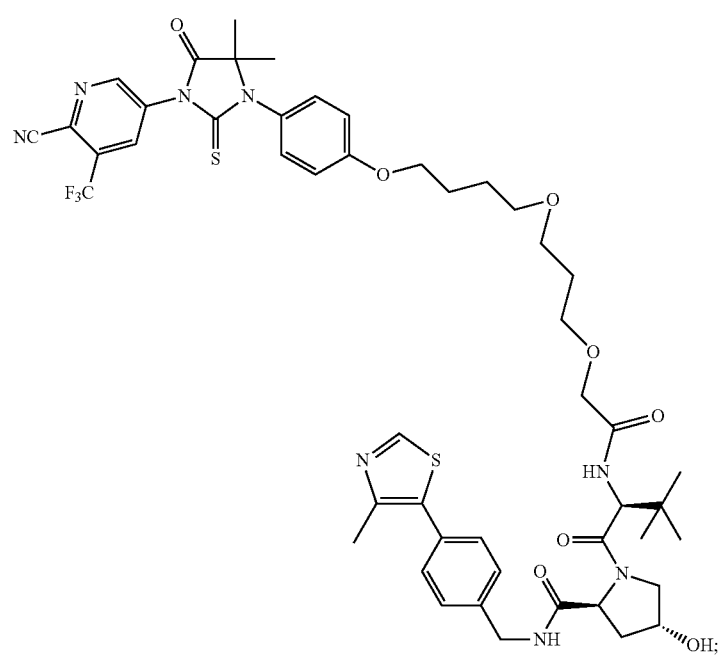

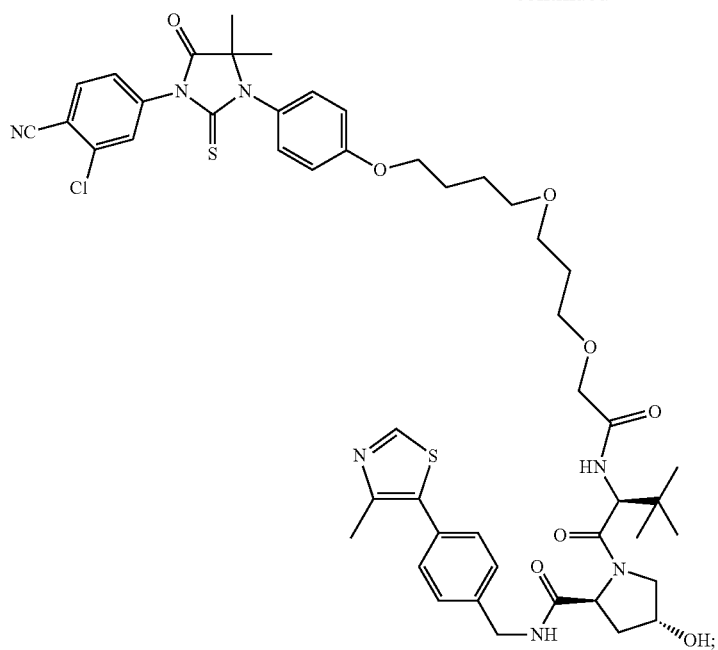
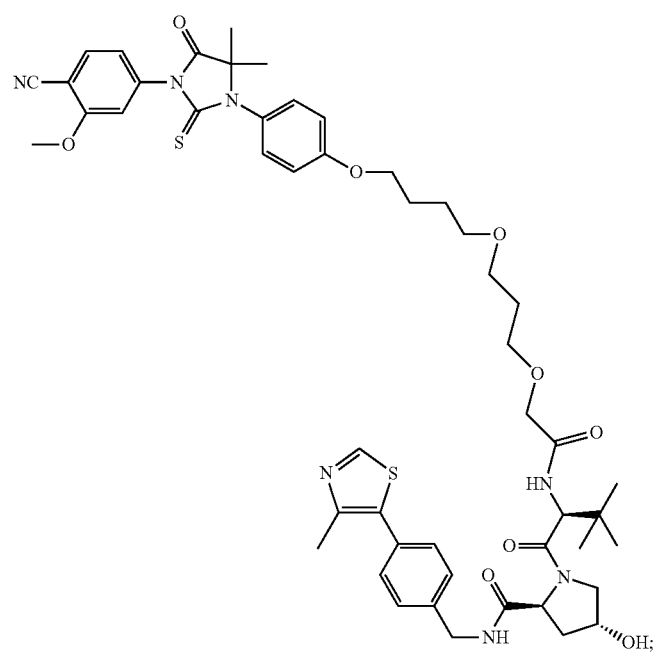

77
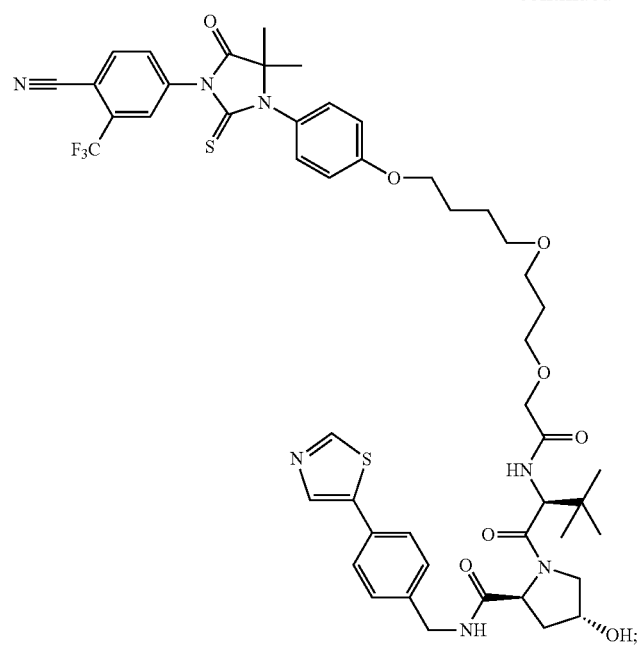
78
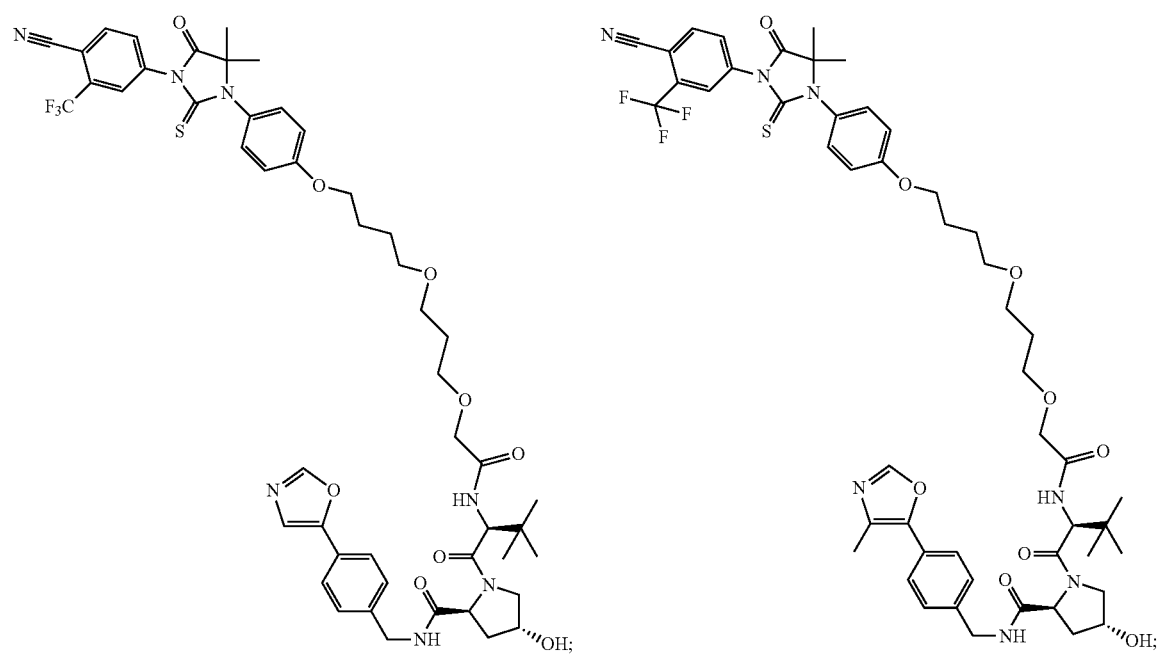

-continued
79
80
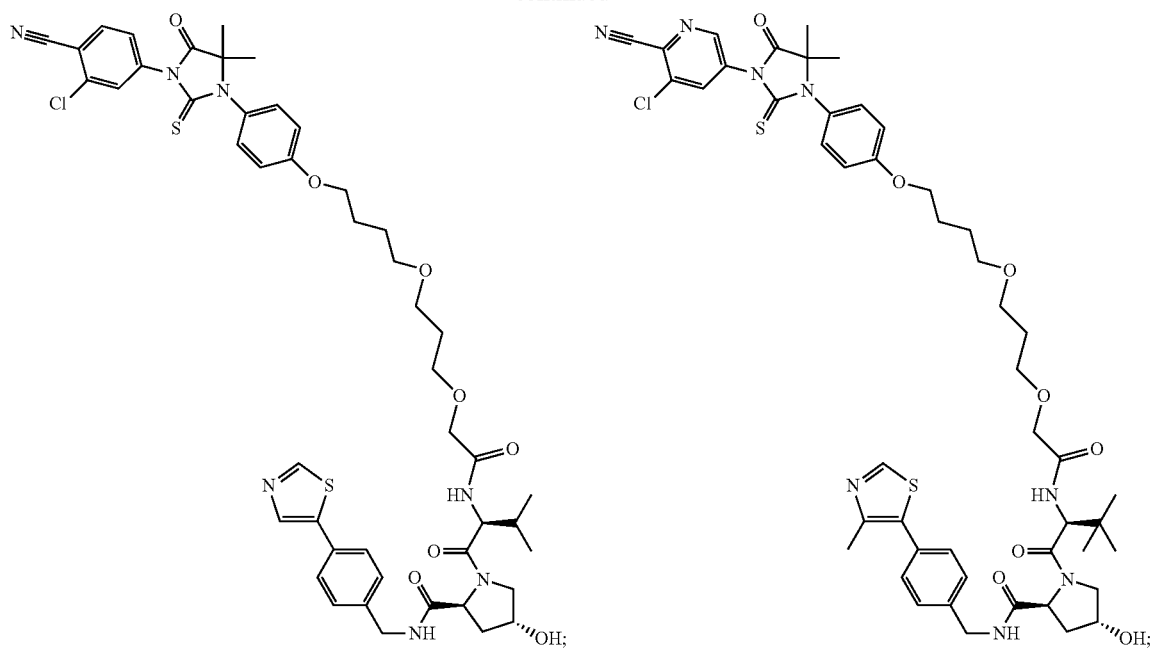
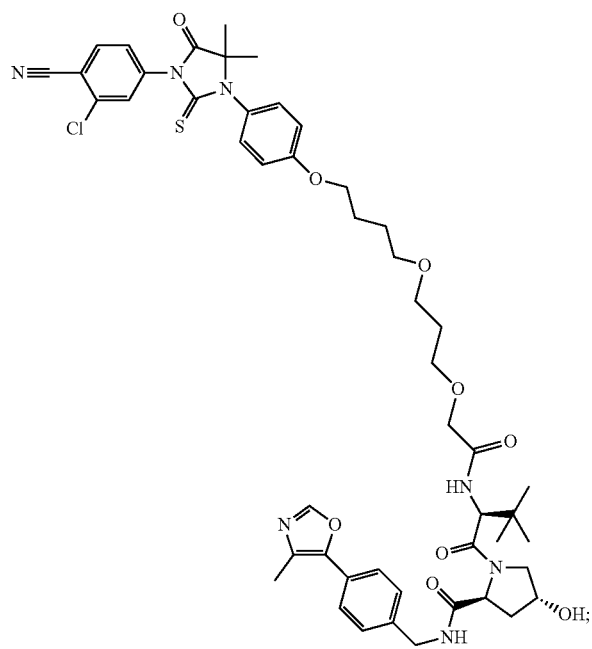

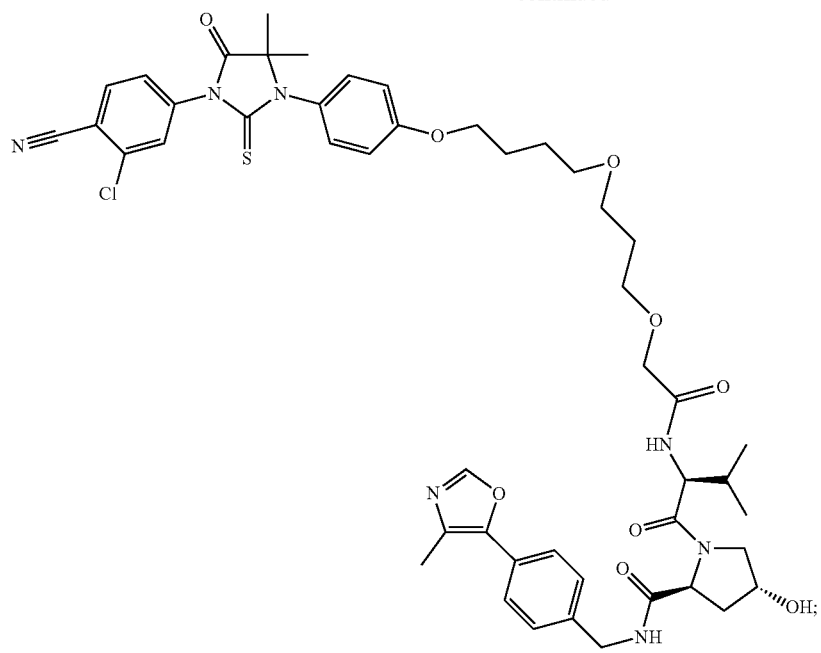
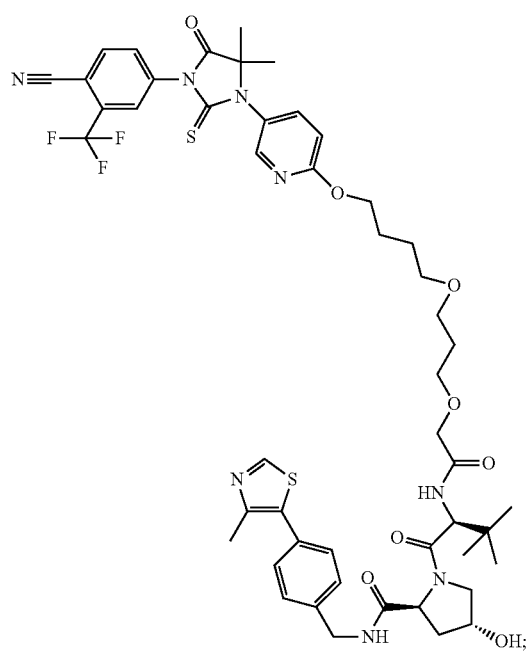

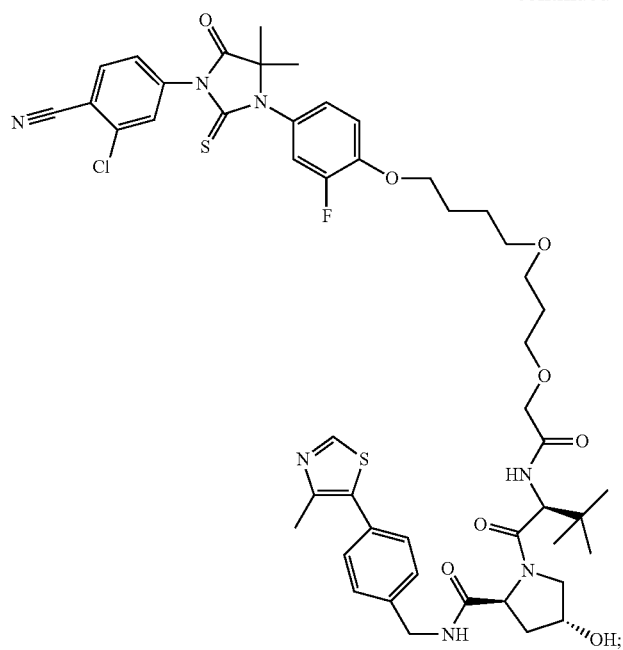 [SMILES: COc1cc(N2C(=O)C(C)(C)N(c3ccc(OCCCCOCCCOCC(=O)N[C@H](C(=O)N4C[C@H](O)C[C@H]4C(=O)NCc4ccc(-c5scnc5C)cc4)C(C)(C)C)c(F)c3)C2=S)ccc1C#N]
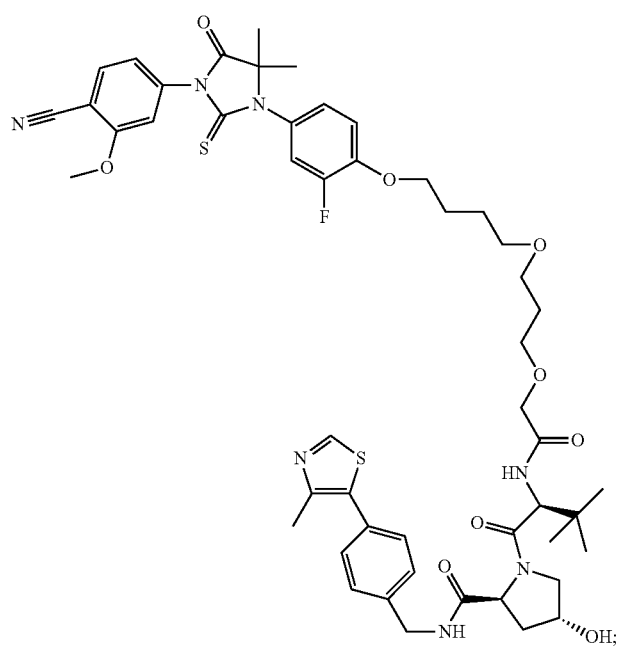

85
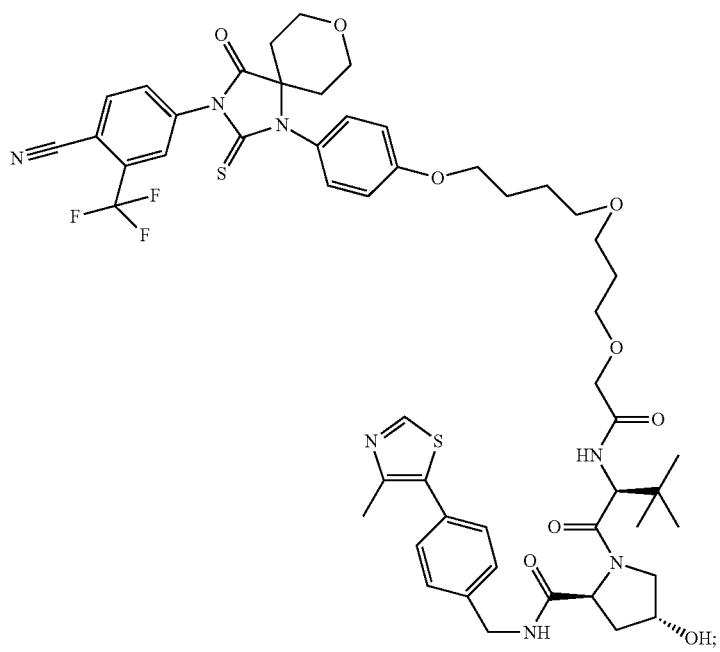
86
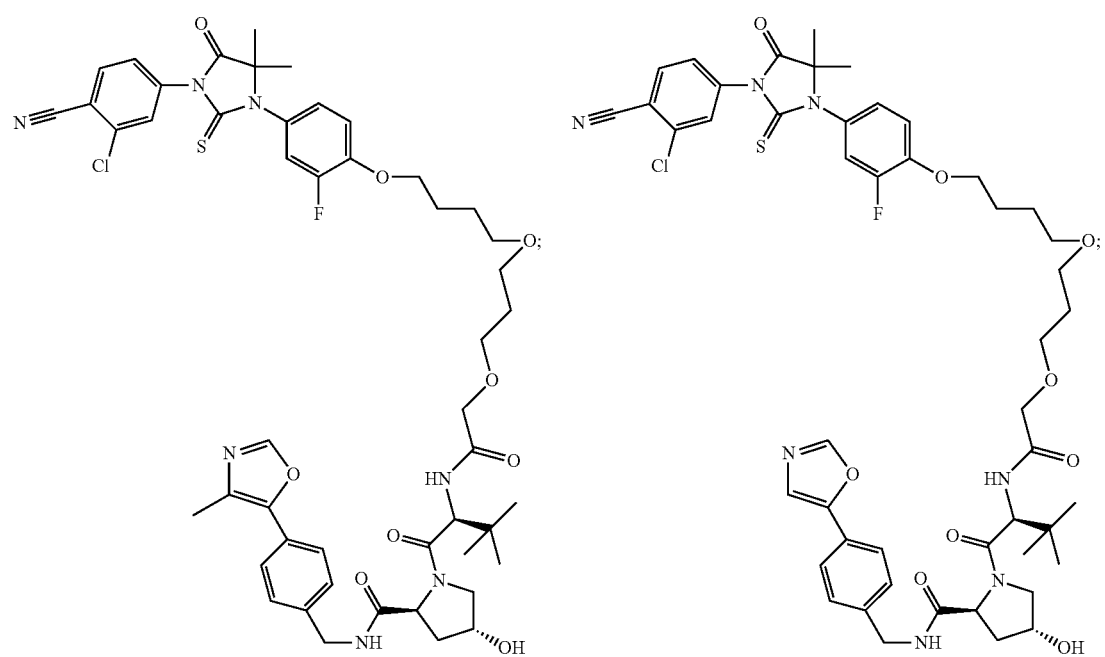

87 88
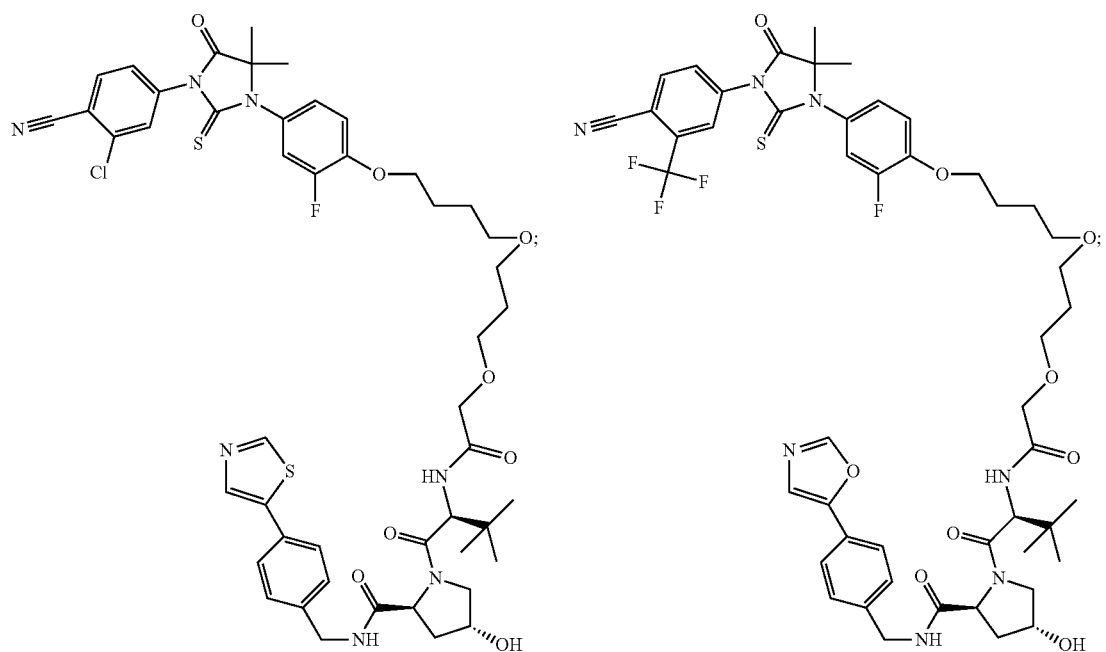
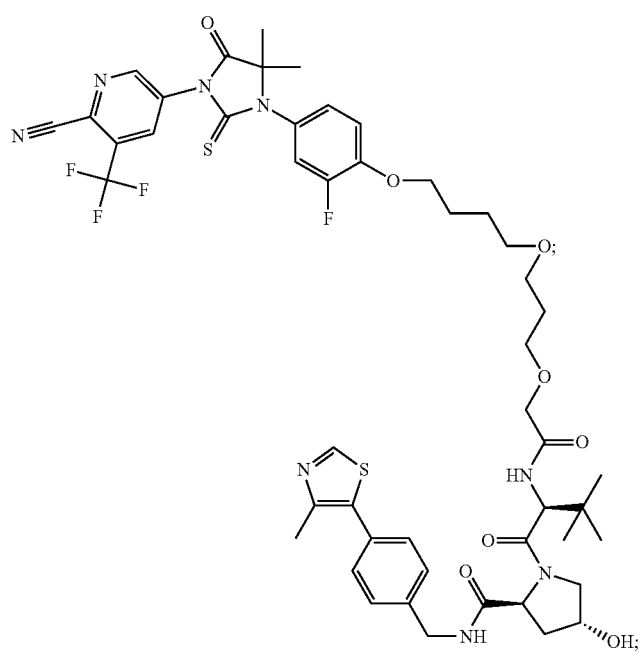

89
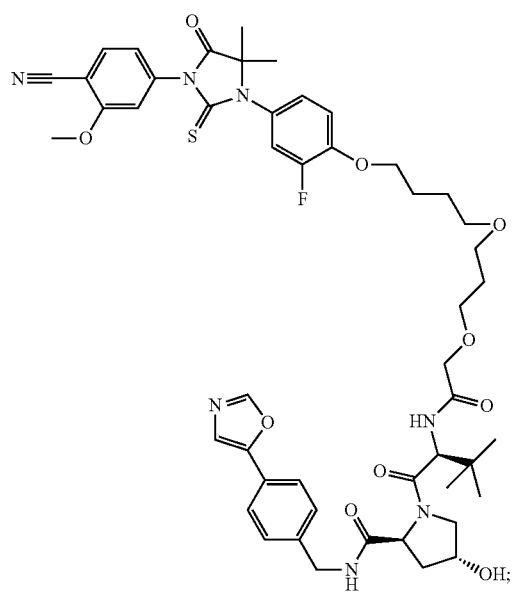
90
-continued
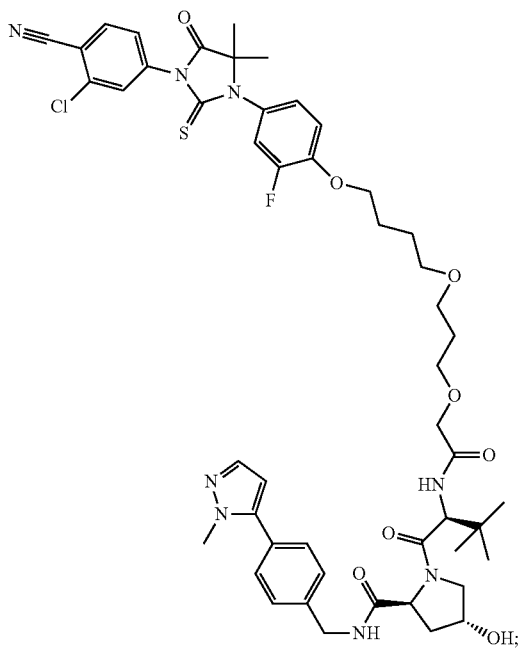
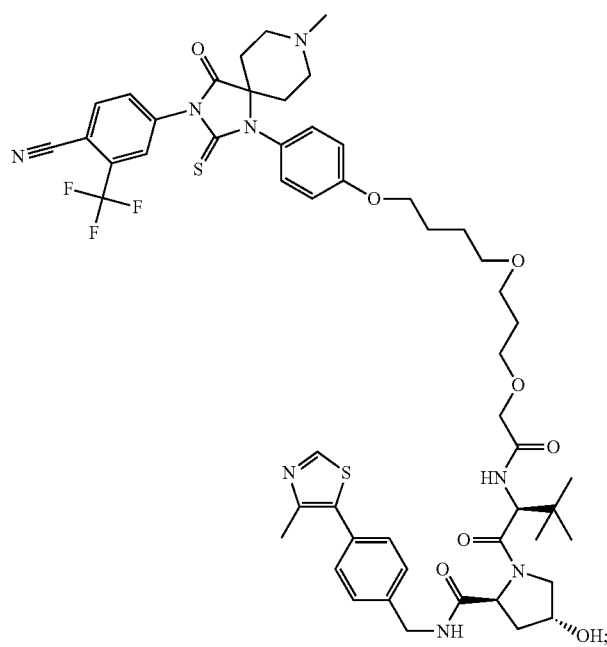

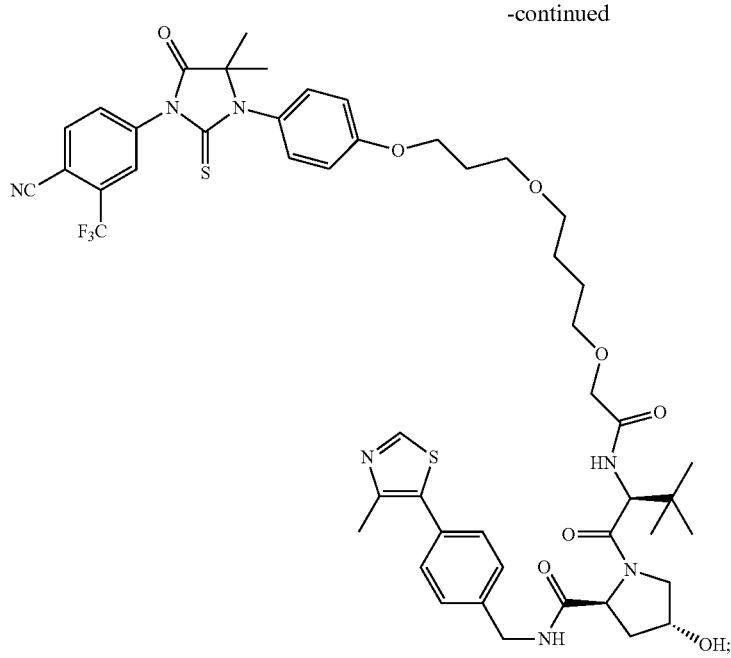
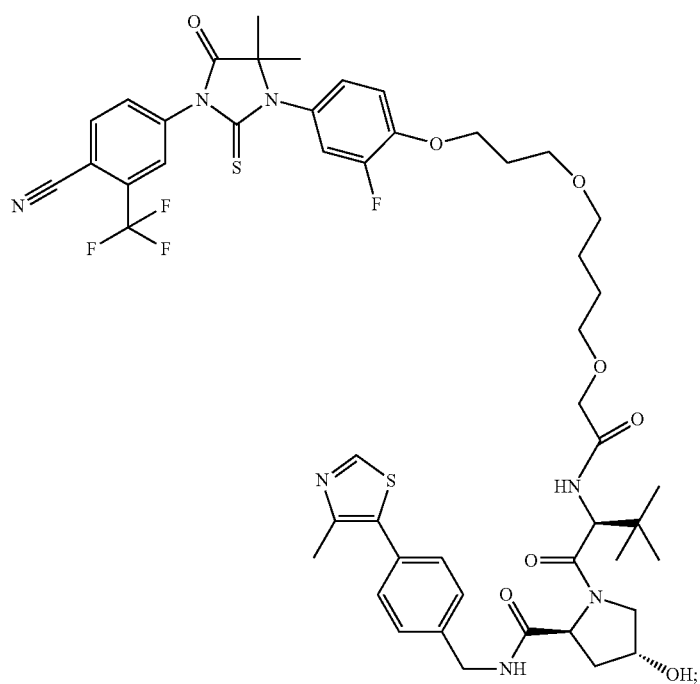

-continued
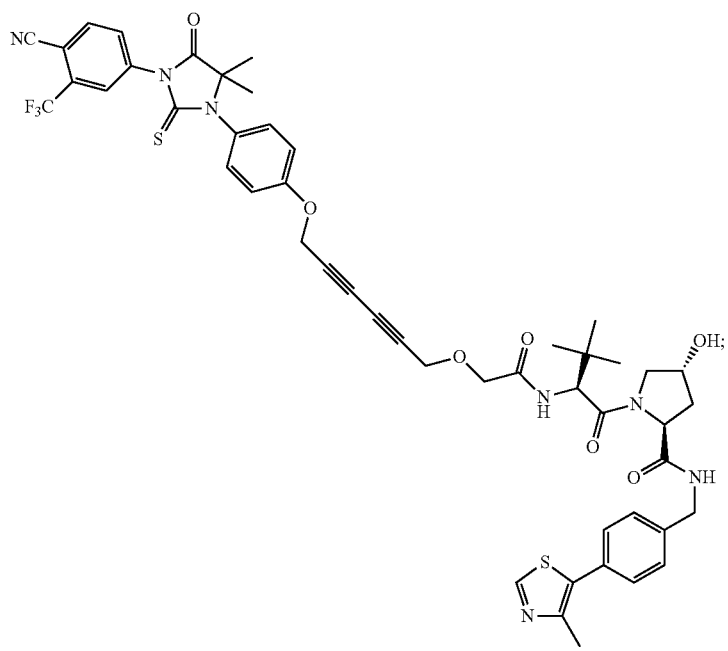
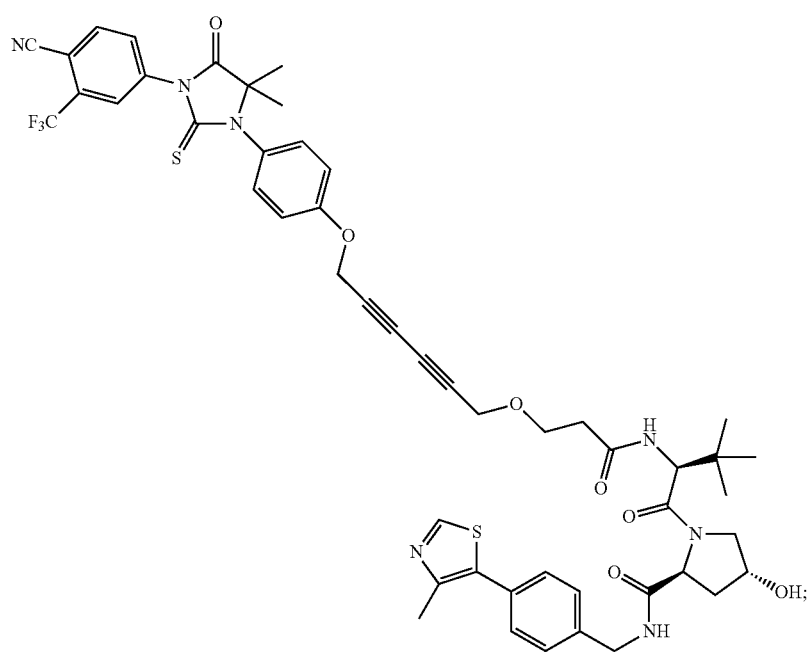

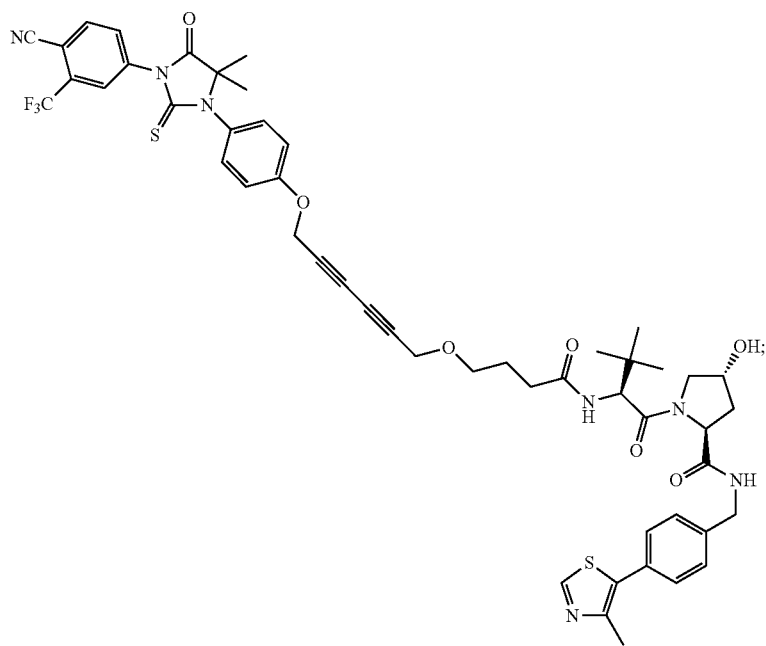
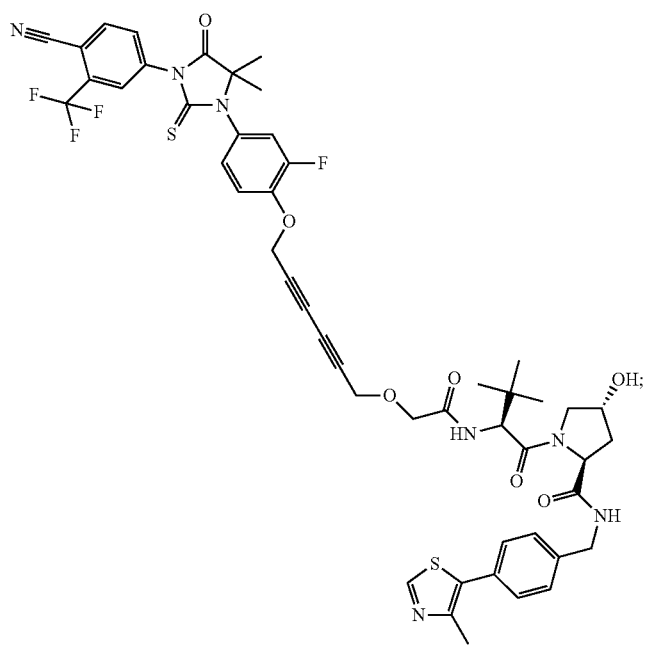

-continued
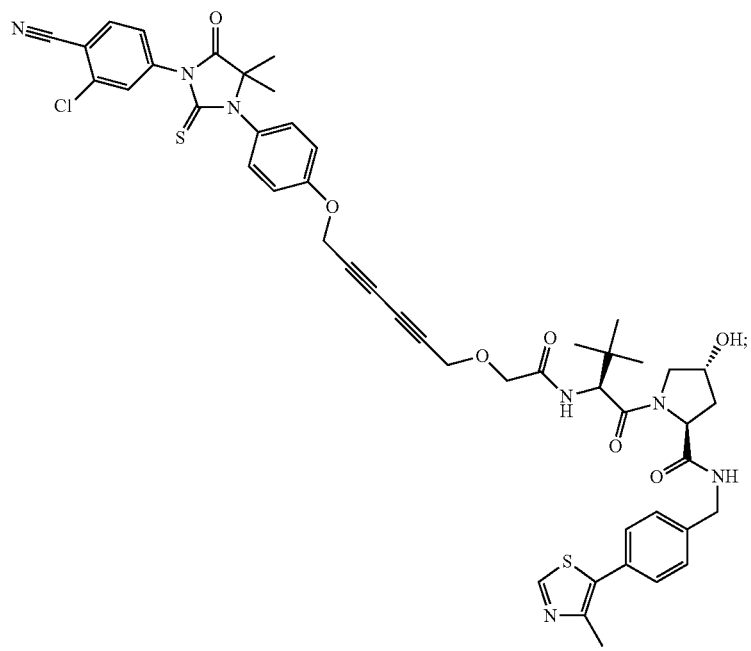
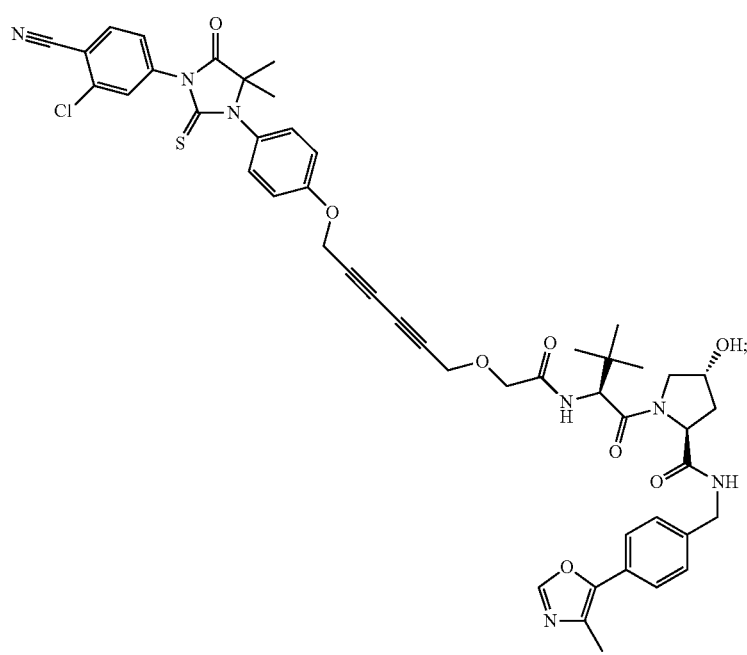

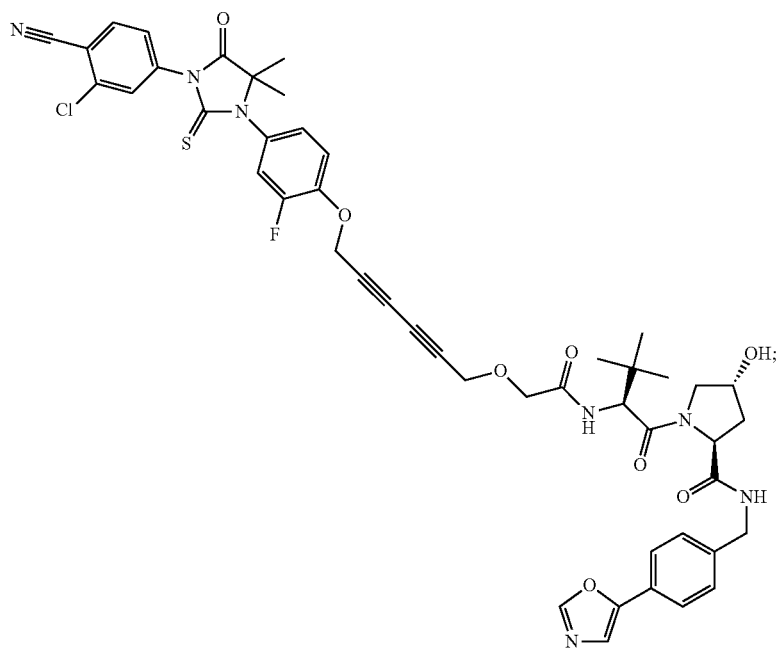
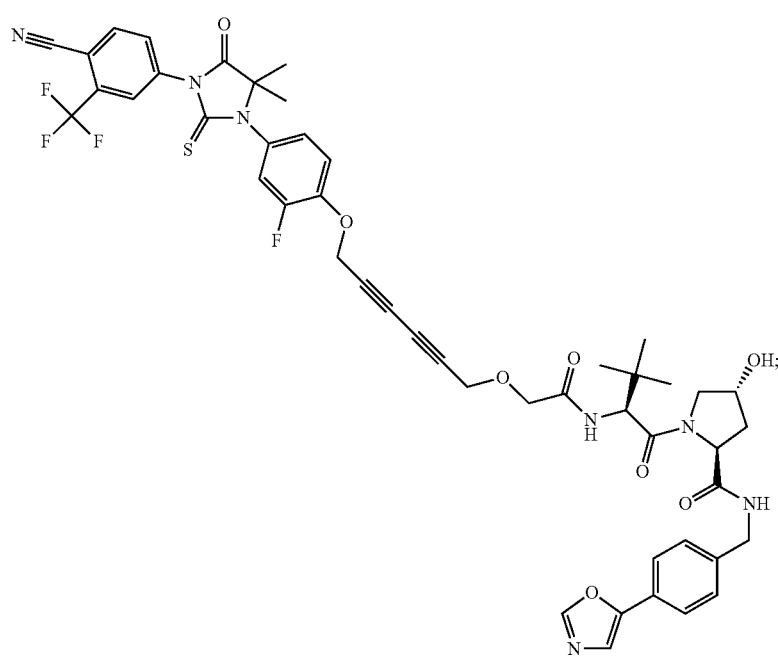

-continued
101
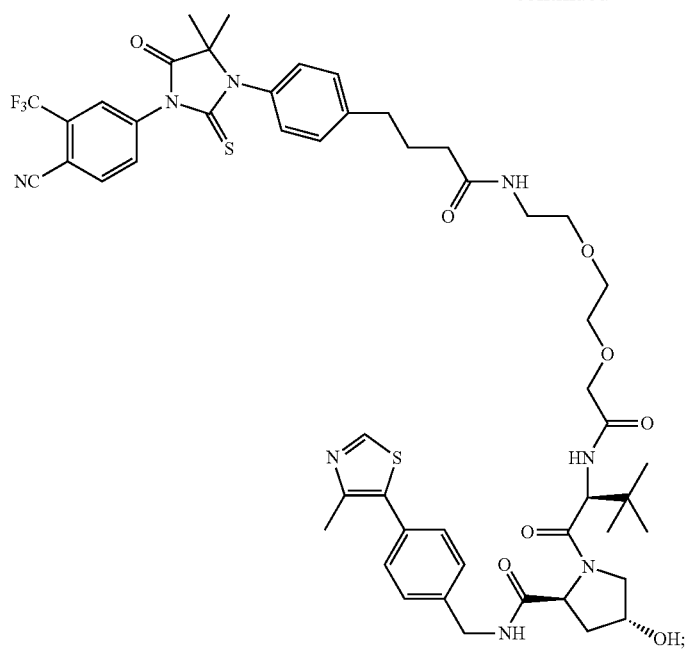
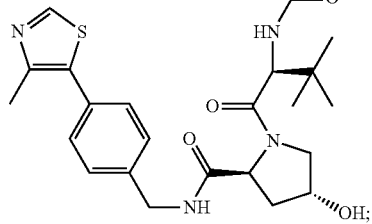
102
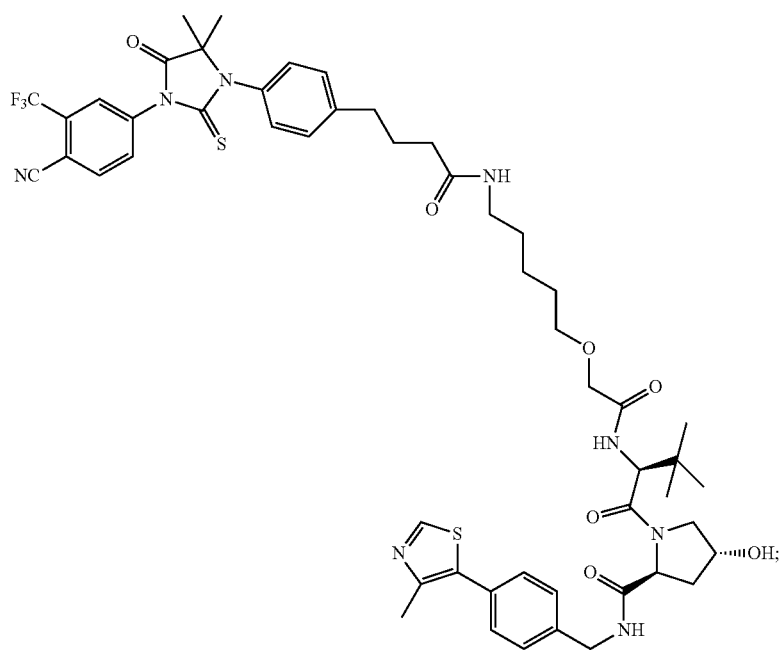
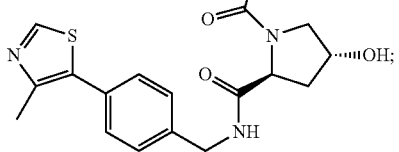

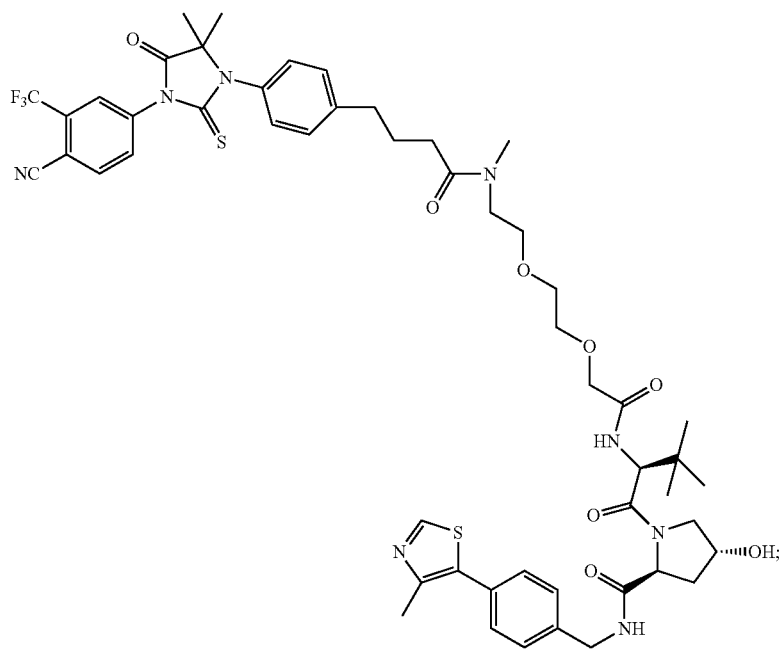
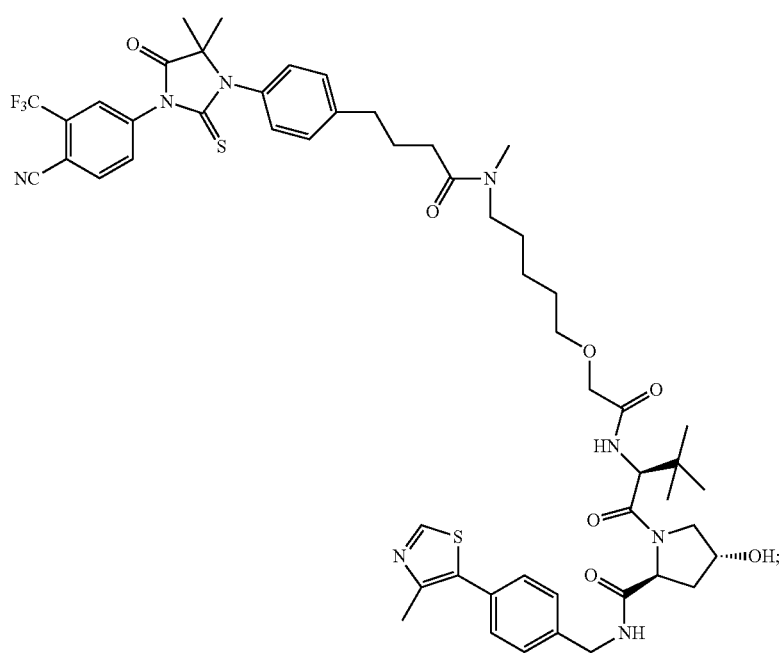

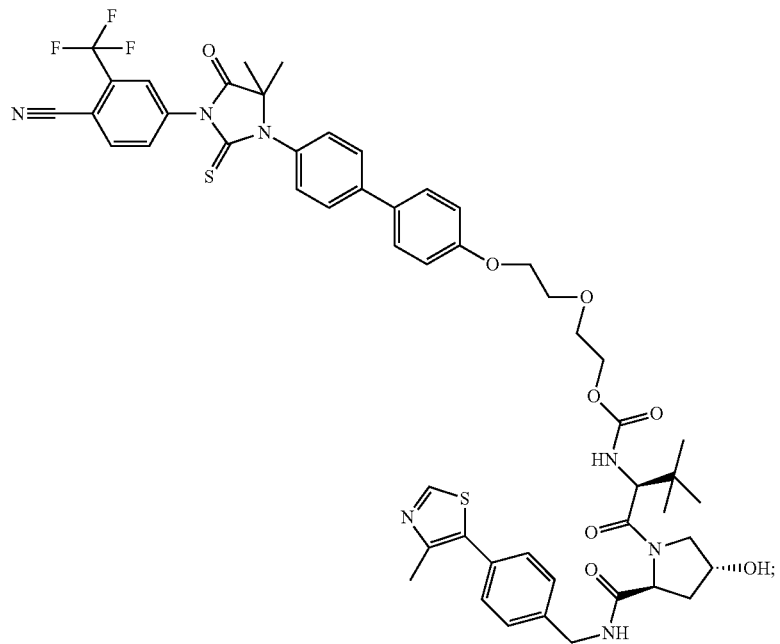
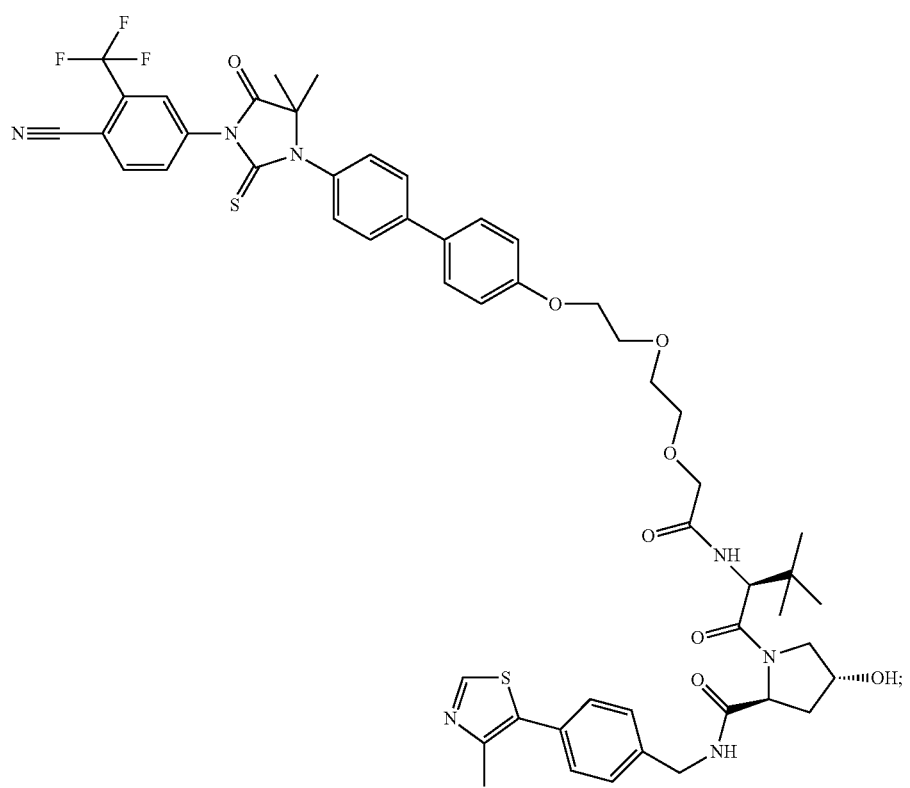

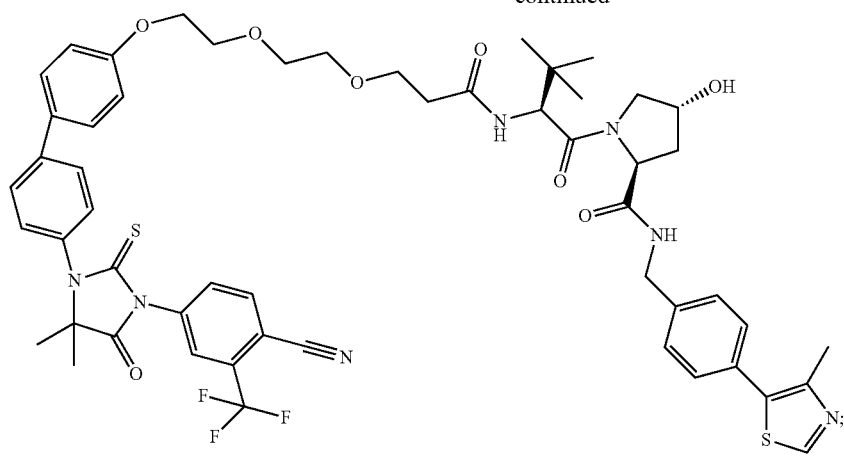
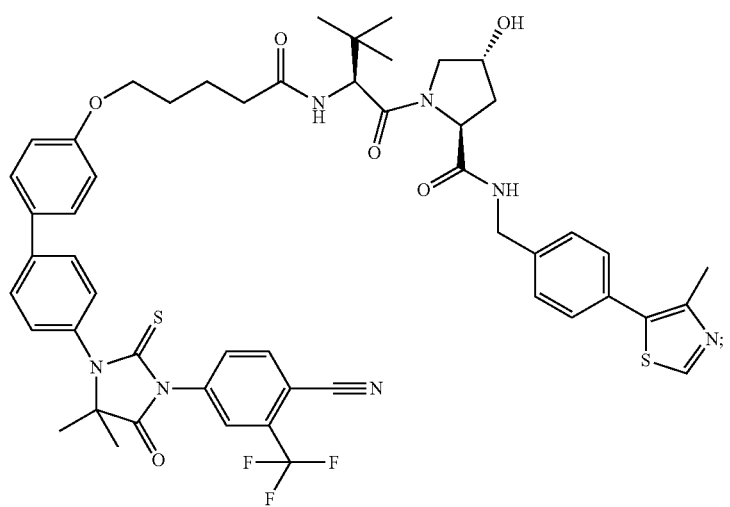
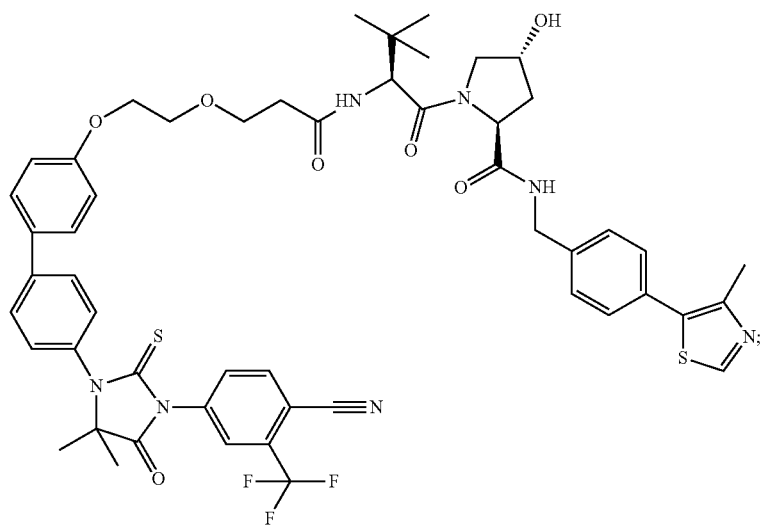

-continued
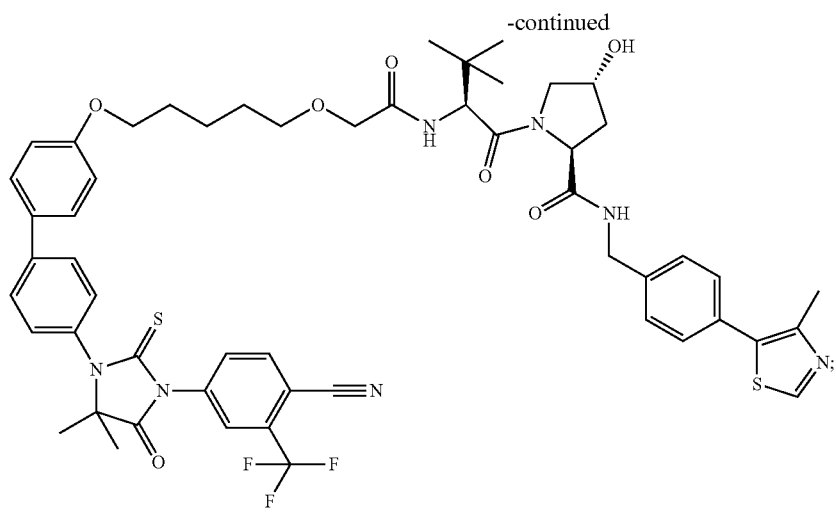
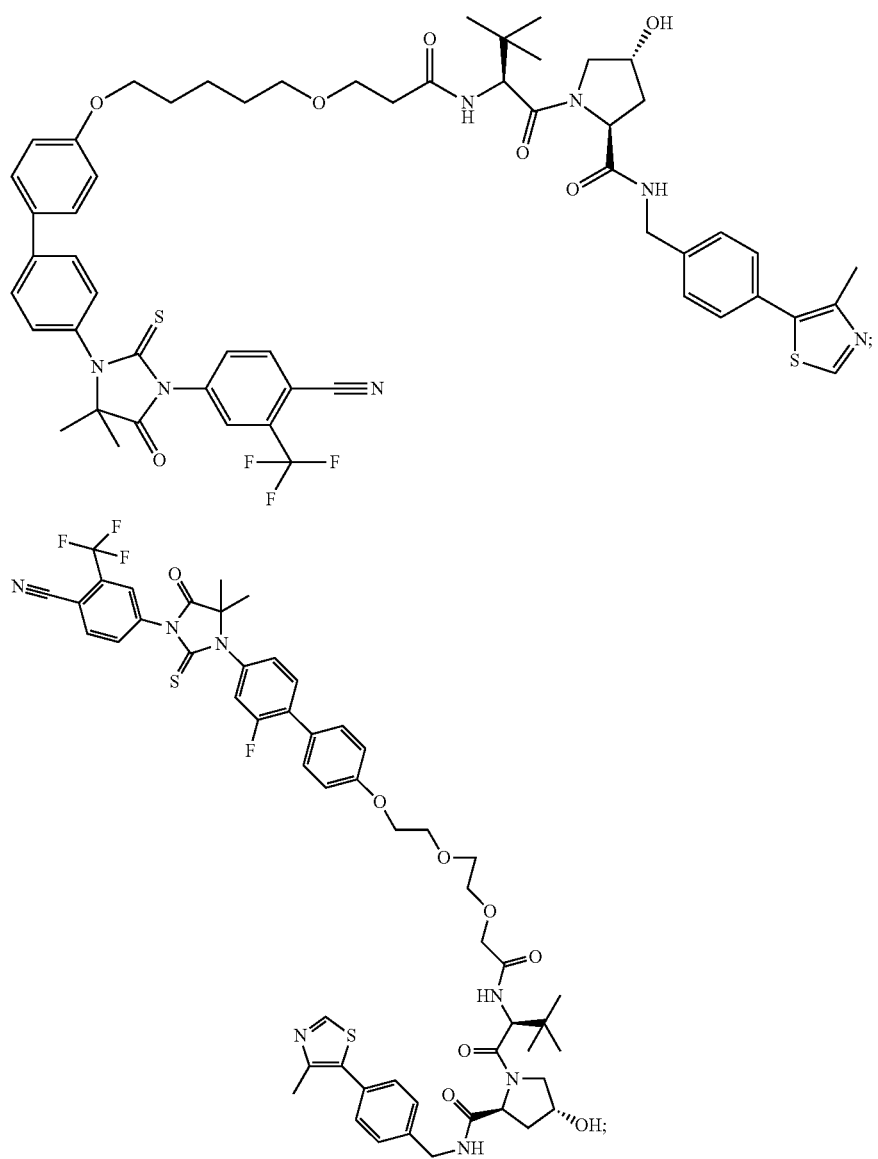

-continued
111
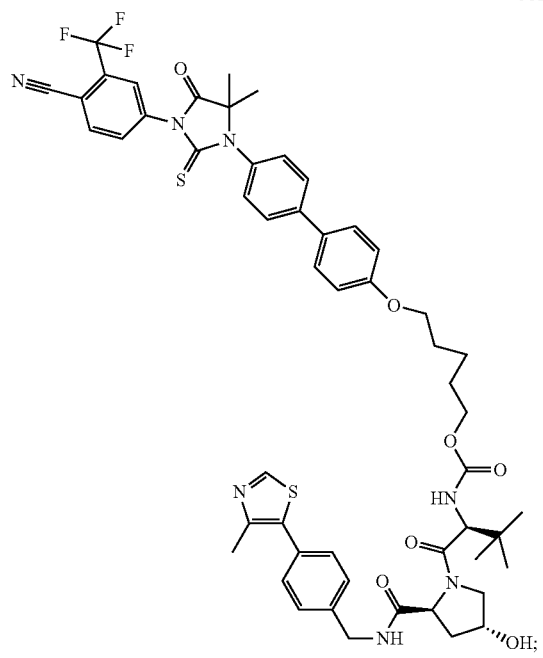
112
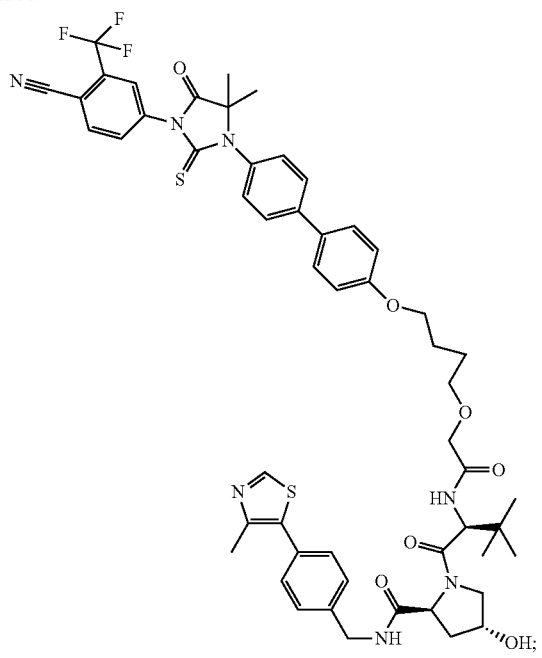
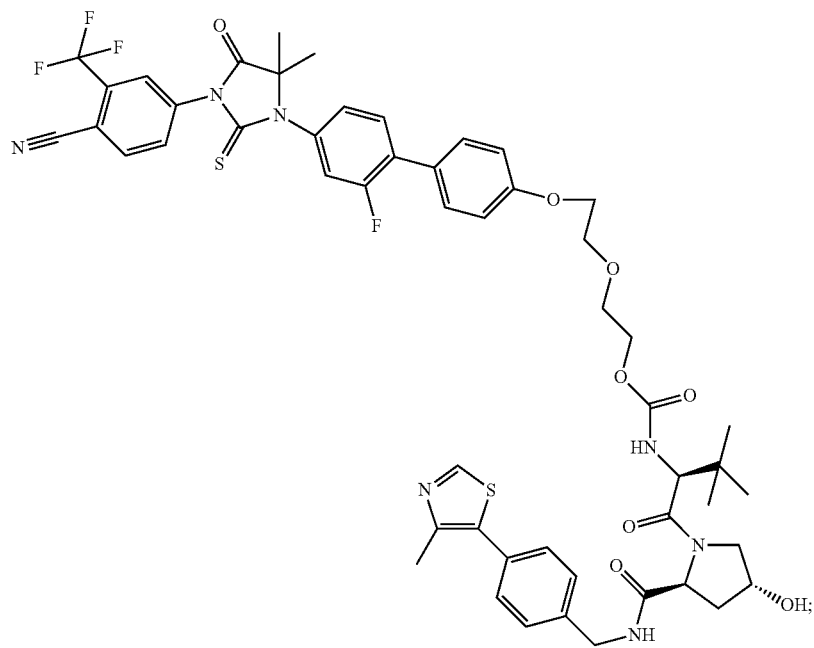

-continued
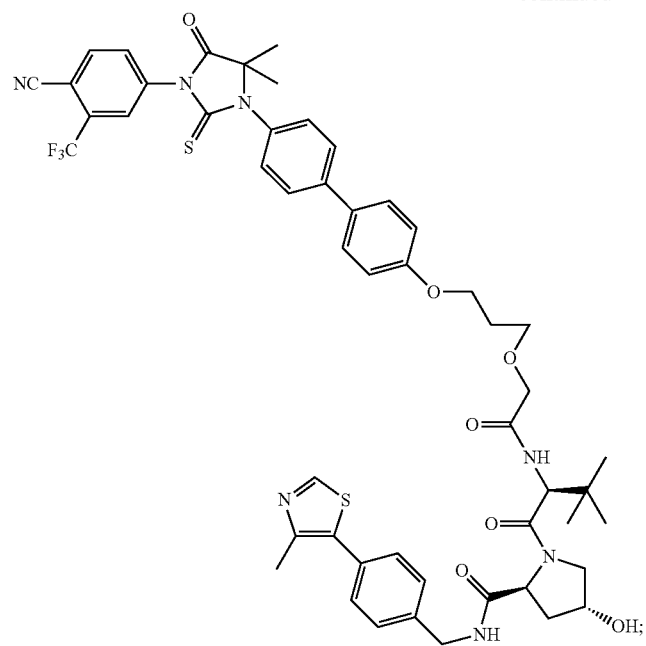
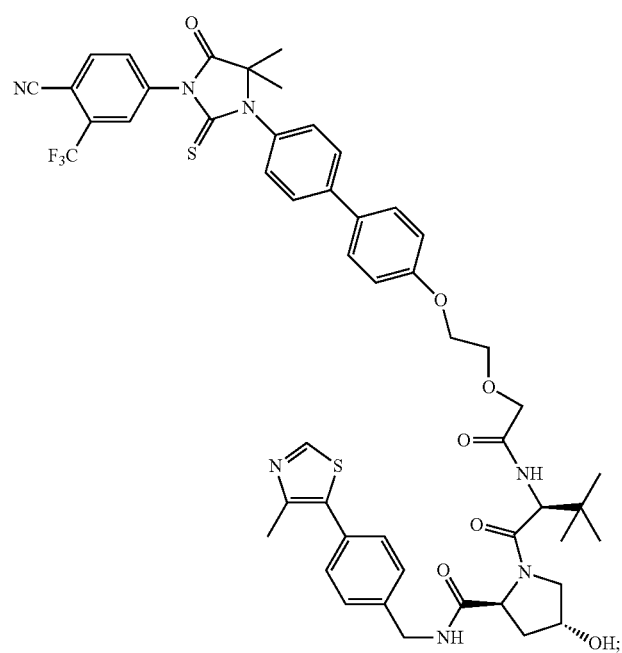

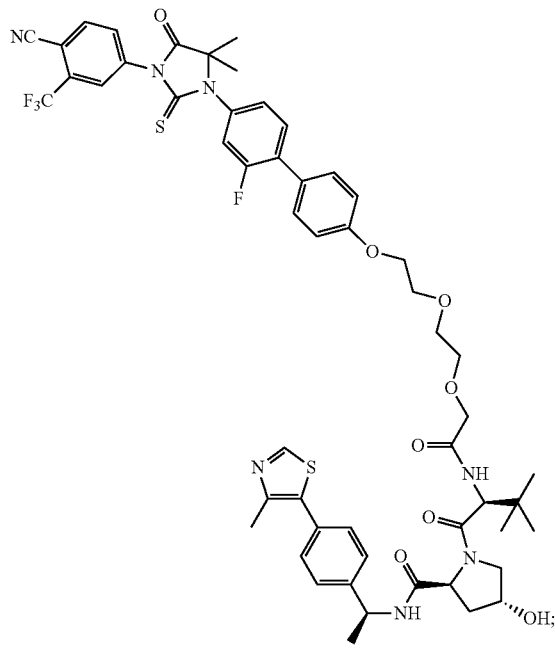
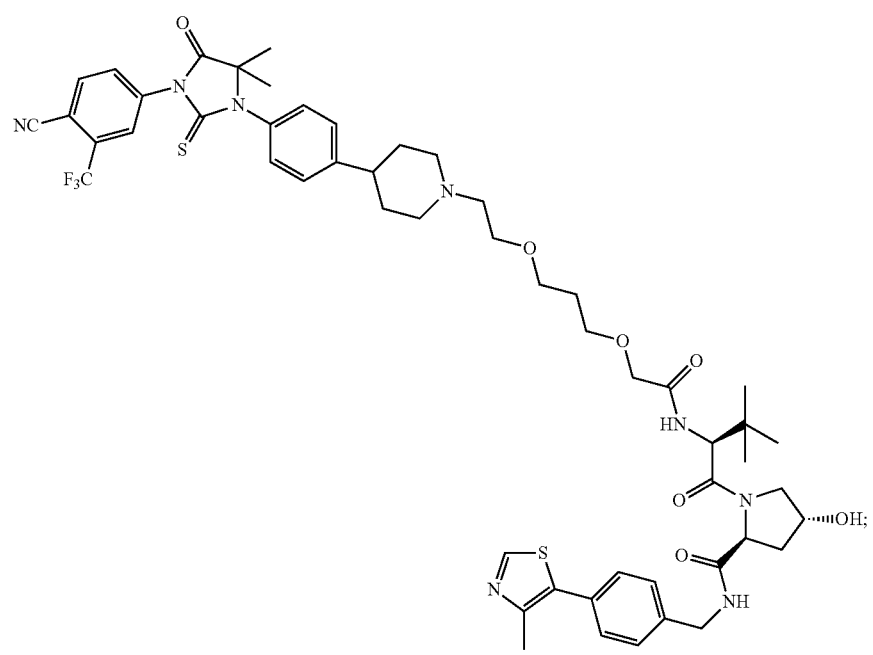

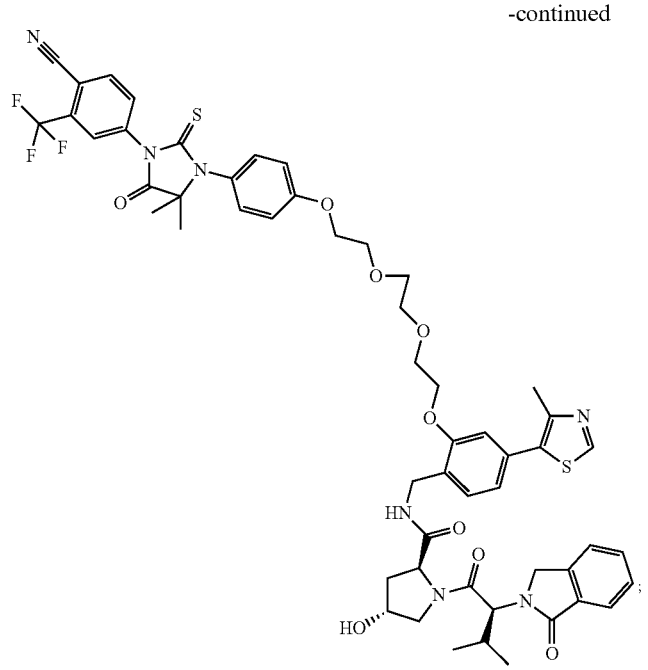
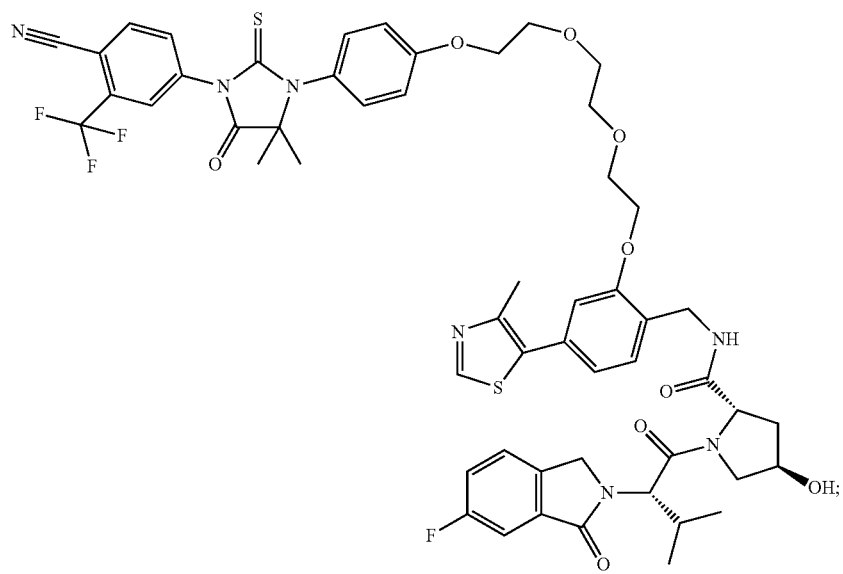

-continued
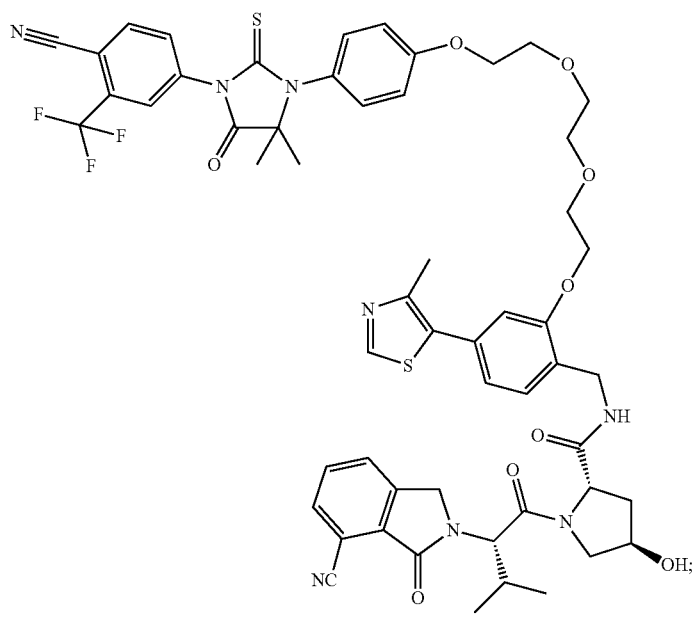
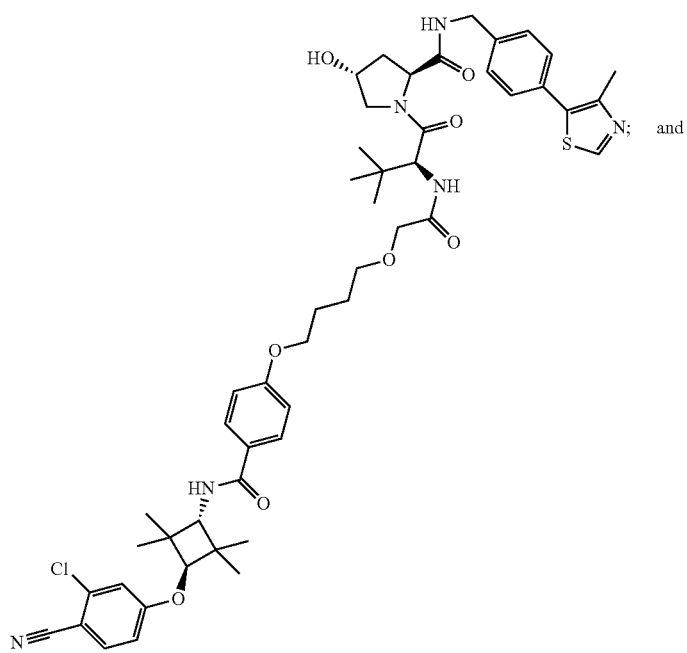

-continued

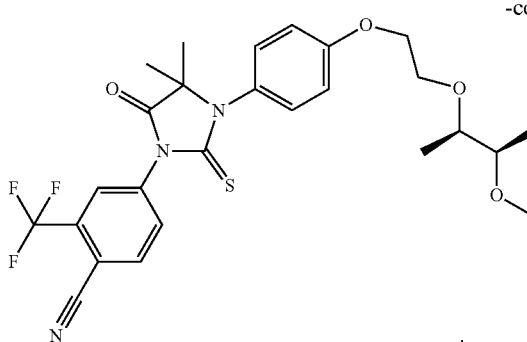
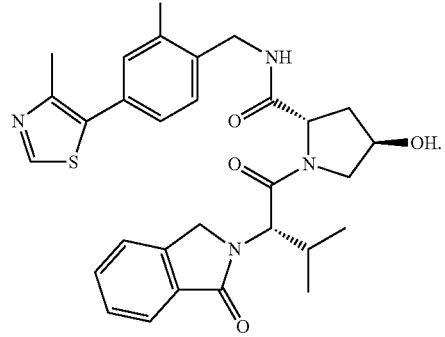

In another embodiment, the present invention provides a library of compounds. The library comprises more than one compound wherein each compound has a formula of ABM-L-ULM, wherein ULM is a ubiquitin pathway protein binding moiety (preferably, an E3 ubiquitin ligase moiety as otherwise disclosed herein), e.g., a VLM, and ABM is an AR protein binding moiety, wherein ABM is coupled (preferably, through a linker moiety) to ULM, and wherein the ubiquitin pathway protein binding moiety recognizes an ubiquitin pathway protein, in particular, an E3 ubiquitin ligase.

The present description includes, where applicable, the compositions comprising the pharmaceutically acceptable salts, in particular, acid or base addition salts of compounds of the present invention.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present invention.

The acids which are used to prepare the pharmaceutically acceptable acid addition salts of the aforementioned base compounds useful in this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds or derivatives according to the present invention. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

Compositions

In another aspect, the description provides compositions comprising compounds as described herein, including salts thereof, and a pharmaceutically acceptable carrier. In certain embodiments, the compositions are therapeutic or pharmaceutical compositions comprising an effective amount of a compound as described herein and a pharmaceutically acceptable carrier.

The amount of compound in a pharmaceutical composition of the instant invention that may be combined with the carrier materials to produce a single dosage form will vary depending upon the host and disease treated, the particular mode of administration. Generally, an amount between 0.1 mg/kg and 1000 mg/kg body weight/day of active ingredients is administered dependent upon potency of the agent. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 µM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Modes of Administration

In any of the aspects or embodiments described herein, the therapeutic compositions comprising compounds described herein can be in any suitable dosage form configured to be delivered by any suitable route. For example, the compounds can be administered by any appropriate route, for example, orally, parenterally, intravenously, intradermally, subcutaneously, or topically, including transdermally, in liquid, cream, gel, or solid form, rectally, nasally, buccally, vaginally or via an implanted reservoir or by aerosol form.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The compounds as described herein may be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient.

Administration of compounds as sprays, mists, or aerosols for intra-nasal, intra-tracheal or pulmonary administration may also be used. Compounds as described herein may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added. Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials are included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions of this invention may also be administered topically. Suitable topical formulations are readily prepared for each of these areas or organs. Topical application for the lower intestinal tract can be effected in a rectal suppository formulation (see above) or in a suitable enema formulation. Topically-acceptable transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. In certain preferred aspects of the invention, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds as described herein can be treated by administering to the patient (subject) an effective amount of the compound including pharmaceutically acceptable salts, solvates or polymorphs, thereof optionally in a pharmaceutically acceptable carrier or diluent, either alone, or in combination with other known agents.

Co-Administration

Disease states of conditions which may be treated using compounds or compositions according to the present description include, but not limited to, for example, cancer (e.g., prostate cancer), and Kennedy's disease. In certain embodiments, the therapeutic or pharmaceutical compositions comprise an effective amount of an additional biologically or bioactive active agent, e.g., an agent effective for the treatment of cancer, that is co-administered.

The term "coadministration" or "combination therapy" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. In certain preferred aspects of the present invention, one or more of the present compounds described above, are coadministered in combination with at least one additional bioactive agent, especially including an anticancer agent. In particularly preferred aspects of the invention, the co-administration of compounds results in synergistic therapeutic, including anticancer therapy.

In another aspect, the description provides a composition comprising an effective amount of two or more of the PROTAC compounds as described herein, and a pharmaceutically acceptable carrier. In certain embodiments, the composition further comprises an effective or synergistic amount of another bioactive agent that is not a PROTAC compound.

Pharmaceutical compositions comprising combinations of an effective amount of at least one bifunctional compound according to the present invention, and one or more of the compounds otherwise described herein, all in effective amounts, in combination with a pharmaceutically effective amount of a carrier, additive or excipient, represents a further aspect of the present invention.

The term "bioactive agent" is used to describe an agent, other than the PROTAC compounds described herein, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents.

The term "additional anti-cancer agent" is used to describe an anti-cancer agent, which may be combined with PROTAC compounds according to the present description to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, an androgen receptor inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INTO 1001, IPdR$_1$ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolylj-quinolone, vatalanib, AG-013736, AVE-0005, the acetate salt of [D-Ser(Bu t) 6, Azgly 10] (pyro-Glu-His-Trp-Ser-Tyr-D-Ser(Bu t)-Leu-Arg-Pro-Azgly-NH$_2$ acetate[C$_{59}$H$_{84}$N$_{18}$Oi$_4$-(C$_2$H$_4$O$_2$)$_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

Methods of Treatment

In another aspect, the disclosure provides methods of modulating protein ubiquitination and degradation in a subject, e.g., a cell, a tissue, mammal, or human patient, the method comprising administering an effective amount of a PROTAC compound as described herein or a composition comprising an effective amount of the same to a subject, wherein the compound or composition comprising the same is effective in modulating protein ubiquitination and degradation of the protein in the subject. In certain embodiments, the protein is androgen receptor (AR).

In certain embodiments, the description provides a method for regulating protein activity of the androgen receptor in a patient in need comprising administering to said patient an amount of a compound as described herein to a patient.

In still additional embodiments, the description provides a method of treating a disease state or condition in a patient wherein dysregulated protein activity is responsible for said disease state or condition, said method comprising administering to said patient an effective amount of a compound as described herein to said patient in order to regulate said protein activity in said patient. In certain embodiments, the protein is AR.

The terms "treat", "treating", and "treatment", etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present invention are set forth hereinabove.

In another aspect, the disclosure provides methods of modulating AR protein ubiquitination and degradation in a subject, e.g., a cell, a tissue, mammal, or human patient, the method comprising administering an effective amount of a compound as described herein or a composition comprising an effective amount of the same to a subject, wherein the compound or composition comprising the same is effective in modulating AR protein ubiquitination and degradation of the protein in the subject.

In another aspect, the disclosure provides methods of treating or ameliorating a symptom of a disease related to AR activity in a subject, e.g., a cell, a tissue, mammal, or human patient, the method comprising administering an effective amount of a compound as described herein or a composition comprising an effective amount of the same to a subject in need thereof, wherein the compound or composition comprising the same is effective in treating or ameliorating a symptom of a disease related to AR activity in the subject.

In certain embodiments, the disease or disorder is asthma, multiple sclerosis, cancer, prostate cancer, Kenney's disease, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome. The method according to claim 48 wherein said cancer is squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor or teratocarcinomas. In certain embodiments, the disease to be treated is cancer, e.g., prostate cancer, or Kennedy's Disease. In a preferred embodiment, the subject is a human.

In another aspect, the disclosure provides methods of treating or ameliorating a symptom of a disease related to AR activity in a subject, e.g., a cell, a tissue, mammal, or human patient, the method comprising administering an effective amount of a compound as described herein or a composition comprising an effective amount of the same and an effective or synergistic amount of another bioactive agent to a subject in need thereof, wherein the composition comprising the same is effective in treating or ameliorating a symptom of a disease related to AR activity in the subject. In certain embodiments, the disease to be treated is cancer, e.g., prostate cancer, or Kennedy's Disease. In a preferred embodiment, the subject is a human. In certain additional embodiments, the additional bioactive agent is an anti-cancer agent.

In alternative aspects, the present invention relates to a method for treating a disease state by degrading a protein or polypeptide through which a disease state or condition is modulated comprising administering to said patient or subject an effective amount of at least one compound as described hereinabove, optionally in combination with an additional bioactive agent. The method according to the present invention may be used to treat a large number of disease states or conditions including cancer, by virtue of the administration of effective amounts of at least one compound described herein.

In another aspect, the disclosure provides methods for identifying the effects of the degradation of proteins of interest in a biological system using compounds according to the present invention.

Kits

In another aspect, the description provides kits comprising compounds or compositions as described herein. The kit may be promoted, distributed, or sold as a unit for performing the methods of the present invention. In addition, the kits of the present invention may preferably contain instructions which describe a suitable use. Such kits can be conveniently used, e.g., in clinical settings, to treat patients exhibiting symptoms of, e.g., cancer or Kennedy's Disease.

EXAMPLES

General Chemistry—Analysis and Synthesis

Unless otherwise noted, all materials/reagents were obtained from commercial suppliers and used without further purification. Reactions were monitored by LC-MS and/or thin layer chromatography (TLC) on silica gel 60 F254 (0.2 mm) pre-coated aluminum foil or glass-backed and visualized using UV light. Flash chromatography (alternatively called "ISCO chromatography") was performed using an ISCO CombiFlash RF 75 PSI or equivalent with RediSep normal-phase silica gel cartridges. Preparative TLC was performed on Whatman LK6F Silica Gel 60A size 20×20 cm plates with a thickness of 1000 μm or equivalent.

$^1$HNMR (300 or 400 MHz) and $^{13}$CNMR (100.6 MHz) spectra were recorded on Bruker spectrometers at rt with TMS or the residual solvent peak as the internal standard. The line positions or multiples are given in (δ) and the coupling constants (J) are given as absolute values in Hertz (Hz). The multiplicities in $^1$HNMR spectra are abbreviated as follows: s (singlet), d (doublet), t (triplet), q (quartet), m (multiplet), br or broad (broadened).

Preparative HPLC purifications were performed on a Waters® UV-Directed Purification System equipped with 2545 Binary Gradient Module, 2767 Sample Manager and 2489 UV/Visible Detector, controlled by MassLynx V4.1 software. All purification work was completed using the following columns: Atlantis Prep T3 OBD Column, SunFire Prep C18 OBD Column and XBridge Prep Phenyl OBD Column. The mobile phases were water (with 0.1% TFA or 0.01% $NH_4HCO_3$) and acetonitrile; all reagents used were of HPLC grade. The flow rate was 30 ml/min. After the columns, a 1:1000 LC packings flow splitter allowed transfer of a small portion of the eluent into the UV detector. The electrospray source was set at 3.0 kV capillary voltage, 30 V conevoltage, 110° C. source temperature, 350° C. desolvation temperature, 600 L/h desolvation gas flow, and 60 L/h cone gas flow. For the analyzer, the multiplier was set at 550 for preparative tune method.

Analytical LC-MS data was collected on a Shimadzu LCMS-2020 with a mobile phase of 0.05% TFA in Acetonitrile (A) and 0.05% TFA in HPLC grade water (B); 0.1% FA in Acetonitrile (A) and 0.1% FA in HPLC grade water (B); Acetonitrile (A) and 5 mM ammonium bicarbonate in HPLC grade water (B).

Shimadzu LCMS-2020 equipped with LC-20AD or 30AD pumps, SPD-M20A PDA and Alltech 3300 ELSD. The system uses the following conditions for 2.0 min, 2.6 min, 3 min, 3.6 min, 5 min or 5.6 min run time.

2.0 minute run: Kinetex XB-C 18 100A column, 2.6 μm, 3.0×50 mm. The flow rate is 1.5 mL/min, the run time is 2.0 min, and the gradient profiles are 0.01 min 10% A, 1.10 min 100% A, 1.60 min 100% A, 1.70 min 10% A, 2.00 min 10% A.

2.6 minute run: Shim-pack VP-ODS column, 2.2 μm, 3.0×50 mm. The flow rate is 1.5 mL/min, the run time is 2.6 min, and the gradient profiles are 0.01 min 5% A, 1.20 min 100% A, 2.20 min 100% A, 2.30 min 5% A, 2.60 min 5% A.

3.0 minute run: ACE UltraCore Super C18 column, 2.5 μm, 3.0×50 mm. The flow rate is 1.5 mL/min, the run time is 3.0 min, and the gradient profiles are 0.01 min 10% A, 2.00 min 95% A, 2.60 min 95% A, 2.70 min 10% A, 3.00 min 10% A.

3.6 minute run: Shim-pack VP-ODS column, 2.2 μm, 3.0×50 mm. The flow rate is 1.5 mL/min, the run time is 3.6 min, and the gradient profiles are 0.01 min 5% A, 2.20 min 100% A, 3.20 min 100% A, 3.30 min 5% A, 3.60 min 5% A.

5.0 minute run: ACE UltraCore Super C18 column, 2.5 μm, 3.0×50 mm. The flow rate is 1.5 mL/min, the run time is 5.0 min, and the gradient profiles are 0.01 min 10% A, 4.00 min 60% A, 4.70 min 60% A, 4.80 min 10% A, 5.00 min 10% A.

5.6 minute run: Shim-pack VP-ODS column, 2.2 μm, 3.0×50 mm. The flow rate is 1.5 mL/min, the run time is 5.6 min, and the gradient profiles are 0.01 min 5% A, 3.00 min 50% A, 5.00 min 50% A, 5.20 min 5% A, 5.60 min 5% A Alternatively, analytical LC-MS data was collected on Agilent infinity 1260 LC, Agilent 6230 TOF mass spectrometer. The analysis is conducted on a Poroshell 120 EC C18 column (50 mm×3.0 mm internal diameter 2.7 μm packing diameter) at 45° C.

The solvents employed are:
A=0.1% v/v solution of formic acid in water.
B=0.1% v/v solution of formic acid in acetonitrile.
The gradient employed are as follows:

TABLE 1

Exemplary Column Gradients.

| Time (minutes) | Flow Rate (mL/min) | % A | % B |
|---|---|---|---|
| 0 | 1 | 95 | 5 |
| 0.5 | 1 | 95 | 5 |
| 3.0 | 1 | 1 | 99 |
| 4.0 | 1 | 1 | 99 |
| 4.1 | 1 | 95 | 5 |
| 4.5 | 1 | 95 | 5 |

The UV detection is an averaged signal from wavelength of 210 nm to 350 nm and mass spectra are recorded on a mass spectrometer using positive mode electrospray ionization.

Unless otherwise noted, all compounds were prepared with LC-MS purity >95%.

Chemical Synthesis

A PROTAC of ABM-L-ULM, or their pharmaceutically acceptable salts, polymorphic forms, prodrugs, solvate forms and isotope containing derivatives thereof, may be prepared by the general approaches described below (scheme 3-4), together with synthetic methods known in the art of organic chemistry, or modifications and derivatizations that are familiar to those of ordinary skill in the art.

Scheme 3

Scheme 3:

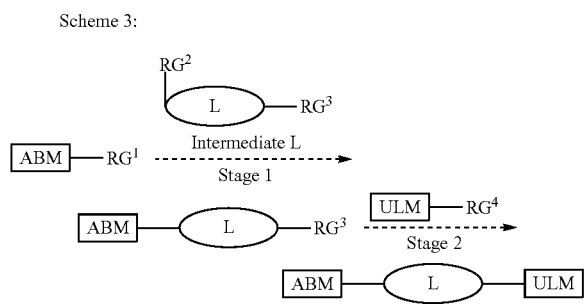

Scheme 4

Scheme 4:

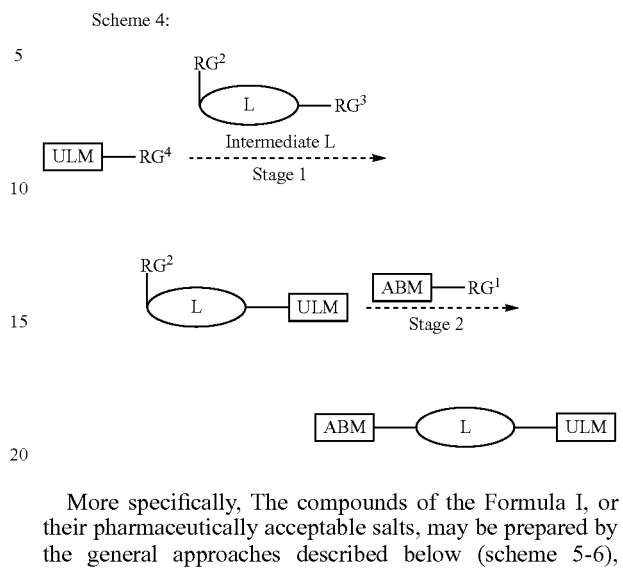

More specifically, The compounds of the Formula I, or their pharmaceutically acceptable salts, may be prepared by the general approaches described below (scheme 5-6), together with synthetic methods known in the art of organic chemistry, or modifications and derivatizations that are familiar to those of ordinary skill in the art.

Scheme 5

Scheme 5:

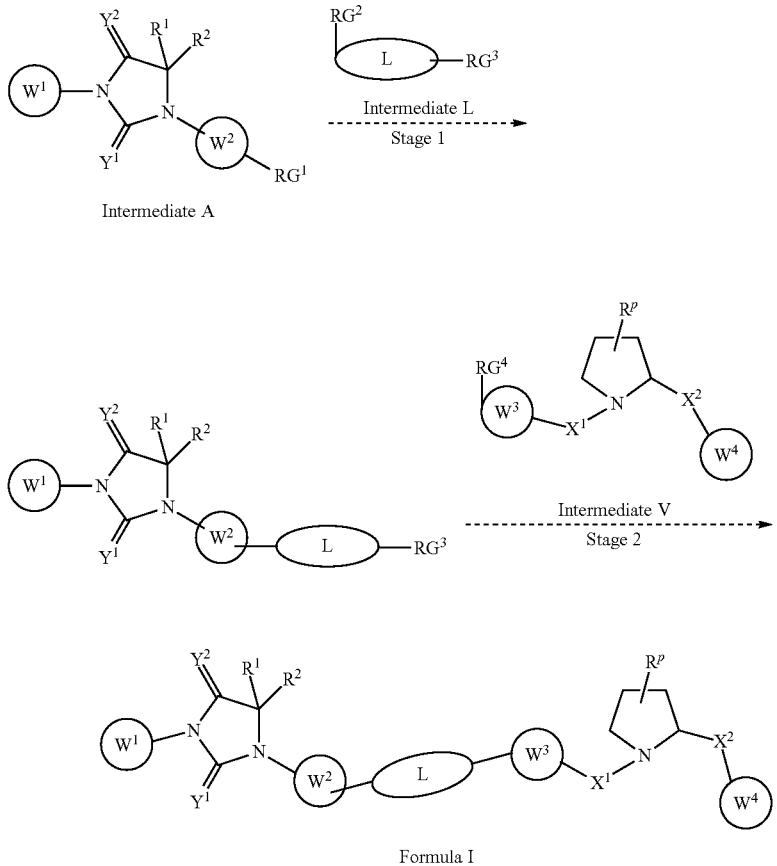

Formula I

Scheme 6

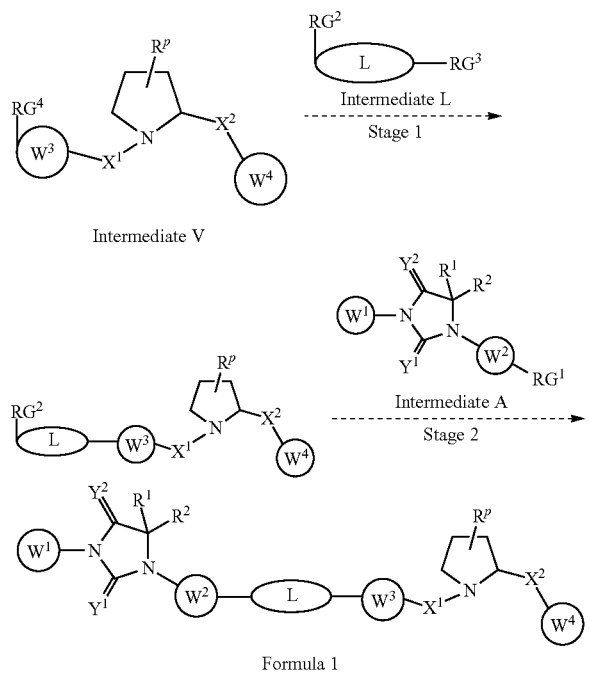

Formula 1

In schemes 3-6, L, ABM, ULM groups, $W^1$, $W^2$, $W^3$, $W^4$, $X^1$, $X^2$, $Y^1$, $Y^2$, $R^1$, $R^2$, and $R^P$ are as define above. $RG^1$, $RG^2$, $RG^3$ and $RG^4$ are moieties with suitable reacting groups that would be necessary to enable the synthetic chemistry to connect intermediate A, intermediate L and intermediate V together into PROTAC compounds of Formula I via covalent bond formation chemistries. These chemistries, depends on specific reacting groups, include but not limited to, amide formation, ester formation, carbamate formation, urea formation, ether formation, amine formation and various C—C, C=C bond formation. The stage 1 and stage 2 transformations in scheme 5 and scheme 6 may involve 1 or multiple synthetic steps. These are routine methods known in the art such as those methods disclosed in standard reference books such as the *Compendium of Organic Synthetic Methods*, Vol. I-VI (Wiley-Interscience); or the *Comprehensive Organic Transformations*, by R. C. Larock (Wiley-Interscience). Unless otherwise indicated, the substituents in the schemes are defined as above. Isolation and purification of the products is accomplished by standard procedures, which are known to a chemist of ordinary skill.

In certain examples, for the chemistry described in schemes 3-6, $RG^1$ is a moiety with a suitable nucleophile such as —OH and $RG^2$ is a moiety with a suitable leaving group such as halogen, —OMs, or —OTs. In a typical procedure, a $RG^1$ containing intermediate is reacted with a $RG^2$ containing intermediate in a suitable solvent. Suitable solvents include, but are not limited to, water, ethers such as THF, glyme, and the like; chlorinated solvents such as DCM, 1,2-dichloroethane (DCE) or CHCl3 and the like, toluene, benzene and the like, DMF, DMSO, MeCN. If desired, mixtures of these solvents are used. A base may be added to the reaction to facilitate the reaction. Suitable bases include, but are not limited to, $Cs_2CO_3$, $K_2CO_3$, and the like. The above process may be carried out at temperatures between about −78° C. and about 150° C. Preferably, the reaction is carried out between about 20° C. and about 120° C.

In another example, chemistry described in in schemes 3-6, $RG^3$ is a moiety contains a —COOH group and $RG^4$ is a moiety contains a suitable amine group. In a typical procedure, a $RG^3$ containing intermediate is reacted with a $RG^4$ containing intermediate in a suitable solvent in the presence of a suitable amide coupling reagent. Suitable solvents include, but are not limited to, water, ethers such as THF, glyme, and the like; chlorinated solvents such as DCM, 1,2-dichloroethane (DCE) or CHCl3 and the like, toluene, benzene and the like, DMF, DMSO, MeCN. If desired, mixtures of these solvents are used. In this case, the preferred solvents are DMF or DCM. A suitable amide coupling reagent include, but are not limited to, DCC, EDC, HATU, HBTU, PyBOP and the like. A base is often added to the reaction. Suitable bases include, but are not limited to, TEA, DIPEA, and the like. The above process may be carried out at temperatures between about −78° C. and about 150° C. Preferably, the reaction is carried out between about 0° C. and about 100° C.

Although not explicitly shown in schemes 3-6, a chemist of ordinary skill would realize that during any of the synthetic sequences it may be necessary and/or desirable to protect sensitive or reactive groups on any of the molecules concerned. This can be achieved by means of conventional protecting groups, such as those described in T. W. Greene, *Protective Groups in Organic Chemistry*, John Wiley & Sons (1981); T. W. Greene and P. G. M. Wuts, *Protective Groups in Organic Chemistry*, John Wiley & Sons (1991), and T. W. Greene and P. G. M. Wuts, *Protective Groups in Organic Chemistry*, John Wiley & Sons, 1999, which are hereby incorporated by reference in their entireties.

When a general or exemplary synthetic procedure is referred to, one skilled in the art can readily determine the appropriate reagents, if not indicated, extrapolating from the general or exemplary procedures. Some of the general procedures are given as examples for preparing specific compounds. One skilled in the art can readily adapt such procedures to the synthesis of other compounds. Representation of an unsubstituted position in structures shown or referred to in the general procedures is for convenience and does not preclude substitution as described elsewhere herein. For specific groups that can be present, either as R groups in the general procedures or as optional substituents not shown, refer to the descriptions in the remainder of this document, including the claims, summary and detailed description.

The process to produce compounds of the present invention is preferably carried out at about atmospheric pressure although higher or lower pressures can be used if desired. Substantially equimolar amounts of reactants are preferably used although higher or lower amounts can also be used.

The compounds of Formulae II-IV (below), or their pharmaceutically acceptable salts, may be prepared by the methods similar to chemistry illustrated above for synthesis of compounds of Formula I (scheme 3-6), together with synthetic methods known in the art of organic chemistry, or modifications and derivatizations that are familiar to those of ordinary skill in the art:

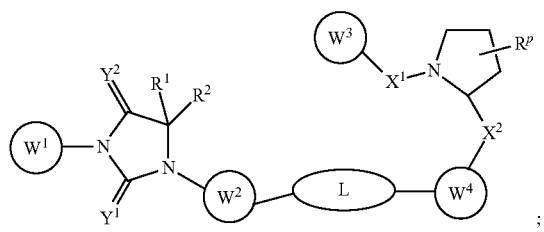

Formula II

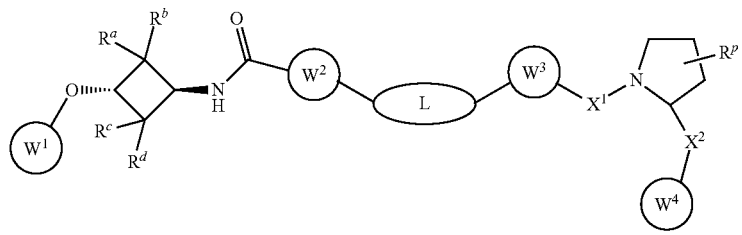

Formula III

; and

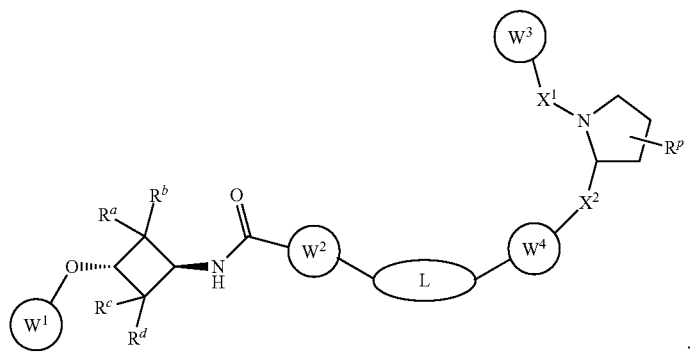

Formula IV

For compounds of Formulae II-IV, L, ABM, ULM groups, $W^1$, $W^2$, $W^3$, $W^4$, $X^1$, $X^2$, $Y^1$, $Y^2$, $R^1$, $R^2$, $R^P$, $R^a$, $R^b$, $R^c$ and $R^d$ are as define above.

In certain embodiments, ABM compounds are active without forming bifunctional compounds of formula II-IV.

Synthesis of ABM Moieties

ABM-1: 2-chloro-4-(3-(4-hydroxyphenyl)-4,4-dimethyl-5-oxo-2-thioxoimidazolidin-1-yl)benzonitrile

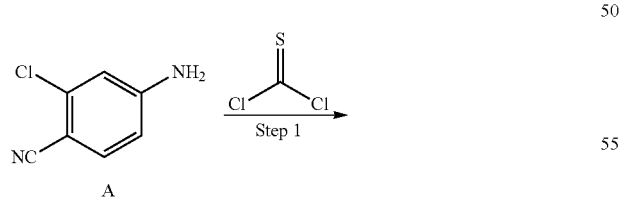

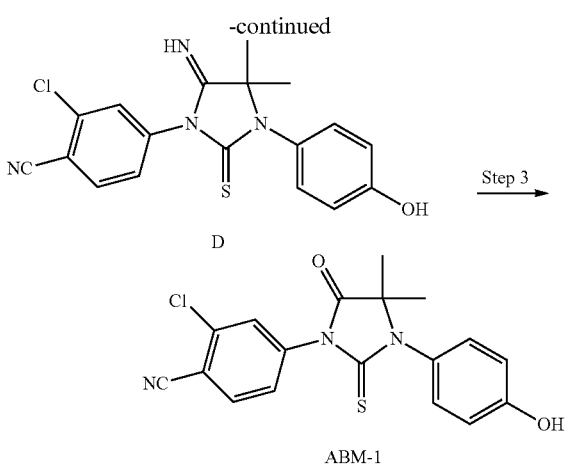

Step 1: Synthesis of 2-chloro-4-isothiocyanatobenzonitrile (B)

To a stirred solution of 4-amino-2-chlorobenzonitrile (A, 1 g, 6.55 mmol) in dichloromethane (9 mL) was added sodium bicarbonate (2.21 g, 26.31 mmol) and water (9 mL). The resulting mixture was cooled to 0° C., to which thiophosgene (817 mg, 7.11 mmol) was added in drop wise in 30 min at 0° C. The resulting mixture was then warmed up to rt and stirred at rt for 1 h. The reaction mixture was diluted with dichloromethane (200 mL), washed with brine (50 mL×2), dried over anhydrous sodium sulfate and then concentrated under reduced pressure to give a crude residue. The residue was purified by flash silica gel chromatography (eluent: ethyl acetate/petroleum ether (v:v=1:30)) to give desired product (yield: 71%) $^1$HNMR (400 MHz, CDCl$_3$): δ 7.69 (d, J=8.0 Hz, 1H), 7.38 (s, 1H), 7.28 (m, 1H);

Step 2: Synthesis of 2-chloro-4-[3-(4-hydroxyphenyl)-5-imino-4, 4-dimethyl-2-sulfanylideneimidazolidin-1-yl]benzonitrile (D)

To a stirred solution of 2-chloro-4-isothiocyanatobenzonitrile (B, 399 mg, 2.05 mmol) in toluene (5 mL) was added 2-[(4-hydroxyphenyl)amino]-2-methylpropanenitrile (C, 300 mg, 1.70 mmol) and 4-dimethylaminopyridine (312 mg, 2.55 mmol). The resulting solution was then heated in an oil bath to 100° C. and stirred at the same temperature for 16 h. LC-MS indicated formation of the desired product. The reaction mixture was concentrated under vacuum to give a crude reside which was purified by flash silica gel chromatography (eluent: ethyl acetate/petroleum ether (v:v=1:1)) to give desired product (yield: 48%) as a brown solid. LC-MS (ES$^+$): m/z 370.95 [MH$^+$], t$_R$=0.74 min (2.0 minute run);

Step 3: Synthesis of 2-chloro-4-[3-(4-hydroxyphenyl)-4,4-dimethyl-5-oxo-2-sulfanylideneimidazolidin-1-yl]benzonitrile (ABM-1)

To a stirred solution of 2-chloro-4-[3-(4-hydroxyphenyl)-5-imino-4,4-dimethyl-2-sulfanylideneimidazolidin-1-yl]benzonitrile (D, 300 mg, 0.81 mmol) in methanol (6 mL) was added aqueous hydrogen chloride (2N, 3.0 mL). The resulting solution was then heated in an oil bath to 100° C. and stirred at the same temperature for 2 h. The reaction mixture was diluted with water (30 mL), extracted with ethyl acetate (60 mL×3), washed with water (50 mL), dried over anhydrous sodium sulfate and concentrated under vacuum to give titled product (yield: 93%) as a yellow solid, which was used for the next step without any further purifications. LC-MS (ES$^+$): m/z 372.00 [MH$^+$], t$_R$=0.97 min (2.0 minute run).

Unless otherwise noted, the following intermediates and their analogs (for examples, but not limited to, analogs with substitutions such as halogens) were synthesized according to similar procedures described above for the synthesis of ABM-1, by utilizing corresponding starting materials and reagents.

ABM-2: 2-fluoro-4-(3-(4-hydroxyphenyl)-4,4-dimethyl-5-oxo-2-thioxoimidazolidin-1-yl)benzonitrile

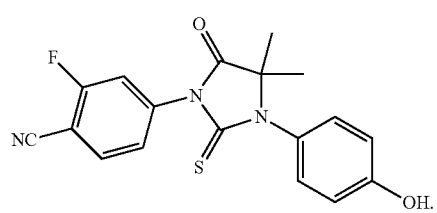

ABM-2

ABM-3: 4-(3-(4-hydroxyphenyl)-4,4-dimethyl-5-oxo-2-thioxoimidazolidin-1-yl)-2-(trifluoromethyl)benzonitrile

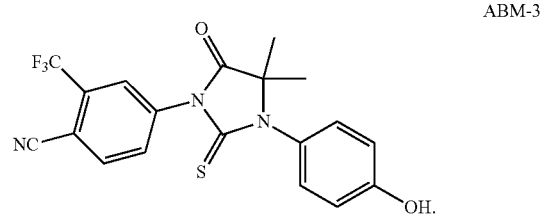 [SMILES: CC1(C)C(=O)N(c2ccc(C#N)c(C(F)(F)F)c2)C(=S)N1c1ccc(O)cc1]

ABM-3

ABM-4: 5-(3-(4-hydroxyphenyl)-4,4-dimethyl-5-oxo-2-thioxoimidazolidin-1-yl)-3-(trifluoromethyl)picolinonitrile

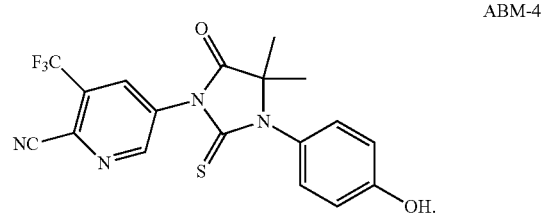 [SMILES: CC1(C)C(=O)N(c2cnc(C#N)c(C(F)(F)F)c2)C(=S)N1c1ccc(O)cc1]

ABM-4

ABM-5: 4-(3-(4-hydroxyphenyl)-4,4-dimethyl-5-oxo-2-thioxoimidazolidin-1-yl)-2-methoxybenzonitrile

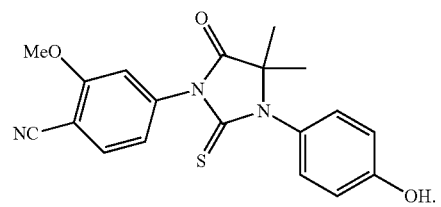

ABM-5

ABM-6: 4-(3-(4-hydroxyphenyl)-4,4-dimethyl-5-oxo-2-thioxoimidazolidin-1-yl)-2-methylbenzonitrile

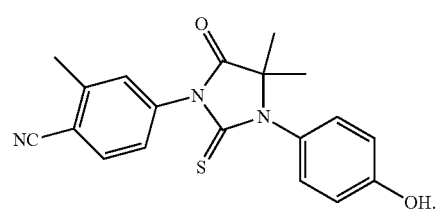

ABM-6

ABM-7: 3-chloro-5-(3-(4-hydroxyphenyl)-4,4-dimethyl-5-oxo-2-thioxoimidazolidin-1-yl)picolinonitrile

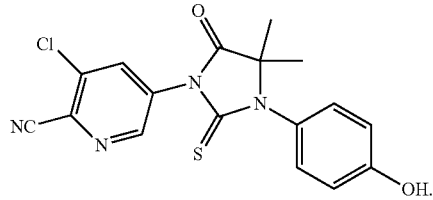
ABM-7

ABM-8: 4-(1-(4-hydroxyphenyl)-4-oxo-2-thioxo-8-oxa-1,3-diazaspiro[4.5]decan-3-yl)-2-(trifluoromethyl)benzonitrile

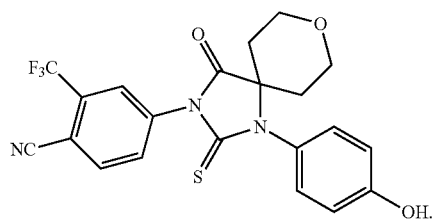
ABM-8

ABM-9: 4-(1-(4-hydroxyphenyl)-8-methyl-4-oxo-2-thioxo-1,3,8-triazaspiro[4.5]decan-3-yl)-2-(trifluoromethyl)benzonitrile

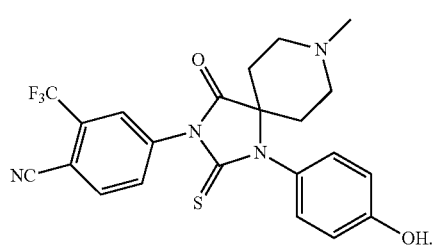
ABM-9

ABM-10: 4-(5-(4-hydroxyphenyl)-8-oxo-6-thioxo-5,7-diazaspiro[3.4]octan-7-yl)-2-(trifluoromethyl)benzonitrile

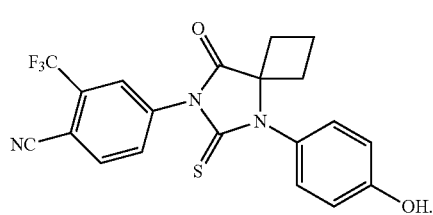
ABM-10

ABM-11: 5-(5-(4-hydroxyphenyl)-8-oxo-6-thioxo-5,7-diazaspiro[3.4]octan-7-yl)-3-(trifluoromethyl)picolinonitrile

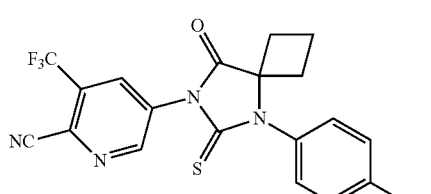
ABM-11

ABM-12: 4-(4-(3-(4-cyano-3-(trifluoromethyl)phenyl)-5,5-dimethyl-4-oxo-2-thioxoimidazolidin-1-yl)phenyl)butanoic acid

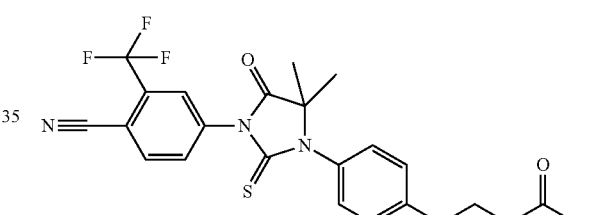
ABM-12

ABM-13: 2-chloro-4-(3-(4'-hydroxybiphenyl-4-yl)-4,4-dimethyl-5-oxo-2-thioxoimidazolidin-1-yl)benzonitrile

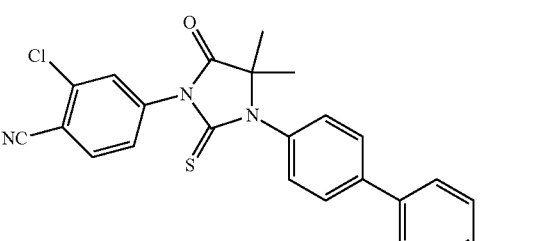
ABM-13

ABM-14: 4-(3-(4'-hydroxybiphenyl-4-yl)-4,4-dimethyl-5-oxo-2-thioxoimidazolidin-1-yl)-2-(trifluoromethyl)benzonitrile

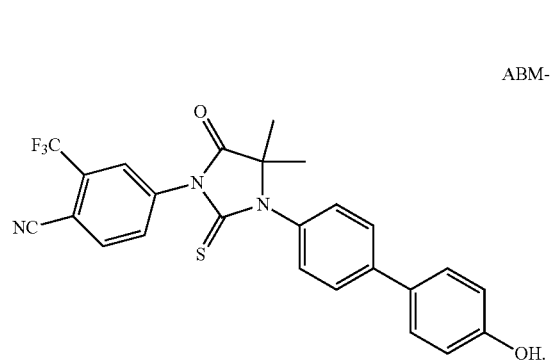

ABM-15: 5-(3-(4'-hydroxybiphenyl-4-yl)-4,4-dimethyl-5-oxo-2-thioxoimidazolidin-1-yl)-3-(trifluoromethyl)picolinonitrile

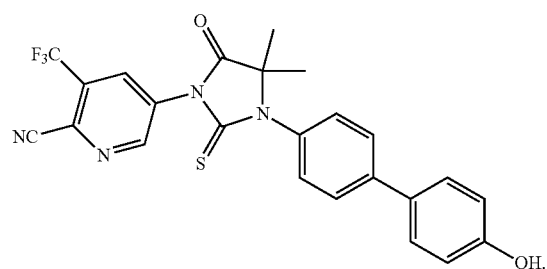

ABM-16: 4-(3-(3-fluoro-4-hydroxyphenyl)-4,4-dimethyl-5-oxo-2-thioxoimidazolidin-1-yl)-2-(trifluoromethyl)benzonitrile

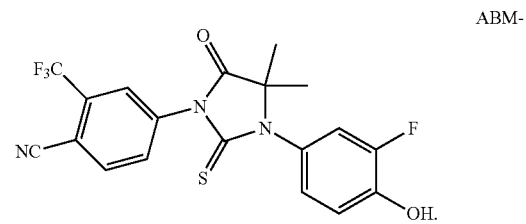

ABM-17: 1-(4-hydroxyphenyl)-5,5-dimethyl-3-(4-nitro-3-(trifluoromethyl)phenyl)-2-thioxoimidazolidin-4-one

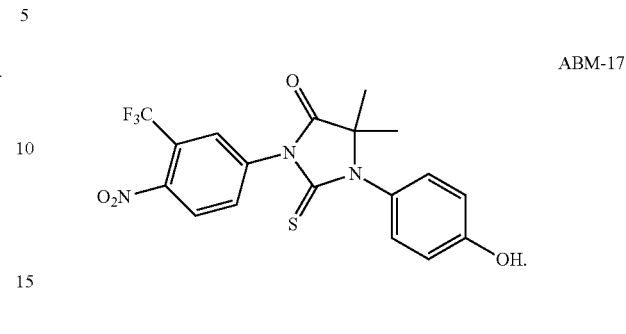

ABM-18: 4-(3-(3,5-difluoro-4-hydroxyphenyl)-4,4-dimethyl-5-oxo-2-thioxoimidazolidin-1-yl)-2-(trifluoromethyl)benzonitrile

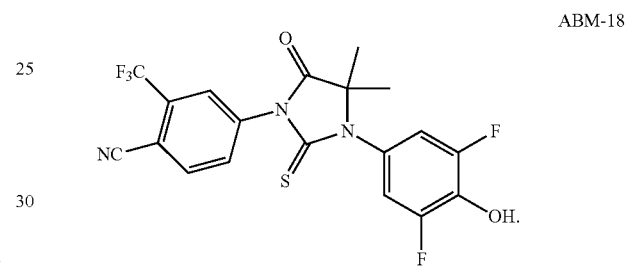

ABM-19: 4-(3-(4-hydroxyphenyl)-4,4-dimethyl-2,5-dioxoimidazolidin-1-yl)-2-(trifluoromethyl)benzonitrile

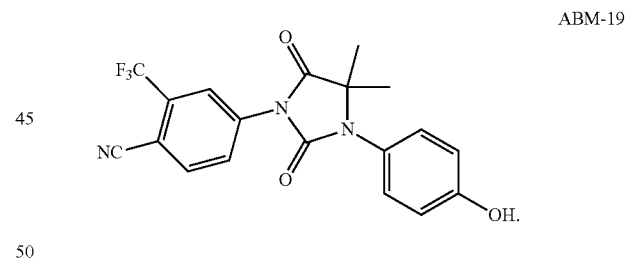

ABM-20: 4-(3-(6-hydroxypyridin-3-yl)-4,4-dimethyl-5-oxo-2-thioxoimidazolidin-1-yl)-2-(trifluoromethyl)benzonitrile

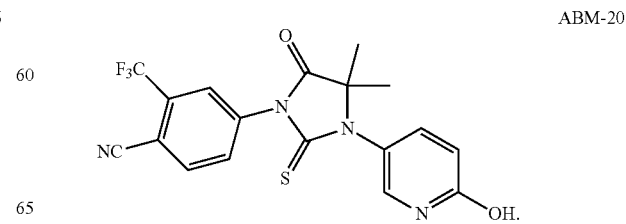

ABM-21: 2-chloro-4-(3-(3-fluoro-4-hydroxyphenyl)-4,4-dimethyl-5-oxo-2-thioxoimidazolidin-1-yl)benzonitrile

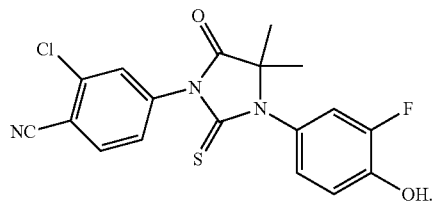

ABM-22: 4-(3-(3-fluoro-4-hydroxyphenyl)-4,4-dimethyl-5-oxo-2-thioxoimidazolidin-1-yl)-2-methoxybenzonitrile

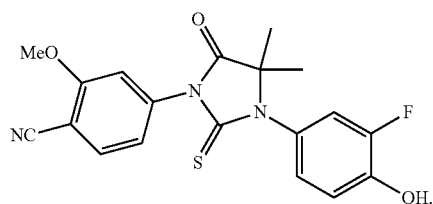

ABM-23: 5-(3-(3-fluoro-4-hydroxyphenyl)-4,4-dimethyl-5-oxo-2-thioxoimidazolidin-1-yl)-3-(trifluoromethyl)picolinonitrile

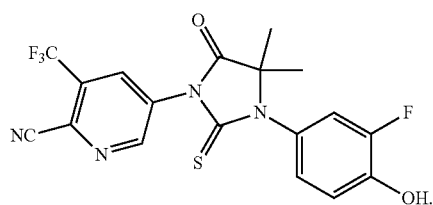

ABM-24: 5-(3-(2-fluoro-4'-hydroxybiphenyl-4-yl)-4,4-dimethyl-5-oxo-2-thioxoimidazolidin-1-yl)-3-(trifluoromethyl)picolinonitrile

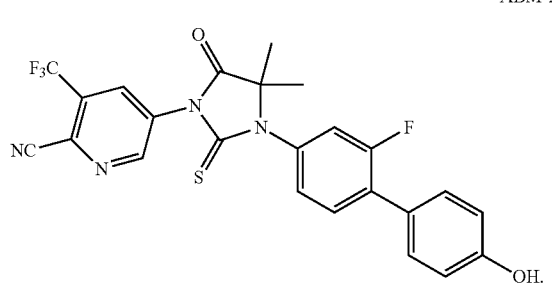

ABM-25: 4-(4,4-dimethyl-5-oxo-3-(4-(piperidin-4-yl)phenyl)-2-thioxoimidazolidin-1-yl)-2-(trifluoromethyl)benzonitrile

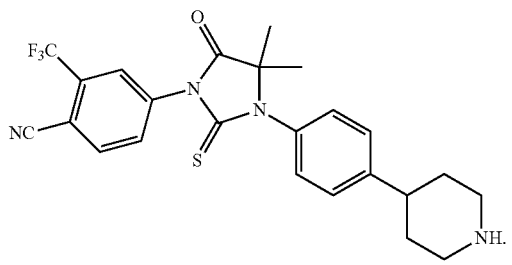

ABM-26: trans-2-Chloro-4-[3-amino-2,2,4,4-tetramethylcyclobutoxy]benzonitrile

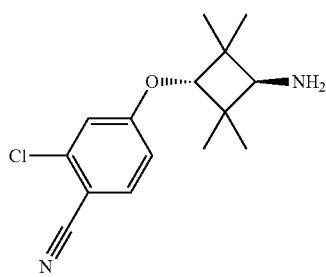 [SMILES: CC1(C)[C@H](N)C(C)(C)[C@H]1Oc1ccc(C#N)c(Cl)c1]

ABM-27: cis-2-Chloro-4-[3-amino-2,2,4,4-tetramethylcyclobutoxy]benzonitrile

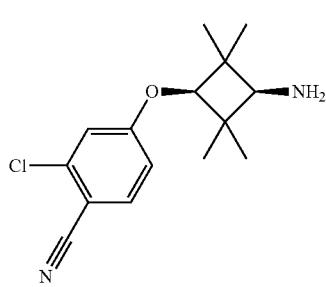 [SMILES: CC1(C)[C@H](N)C(C)(C)[C@@H]1Oc1ccc(C#N)c(Cl)c1]

ABM-28: trans 6-Amino-N-[3-(3-chloro-4-cyanophenoxy)-2,2,4,4-tetramethylcyclobutyl]pyridazine-3-carboxamide

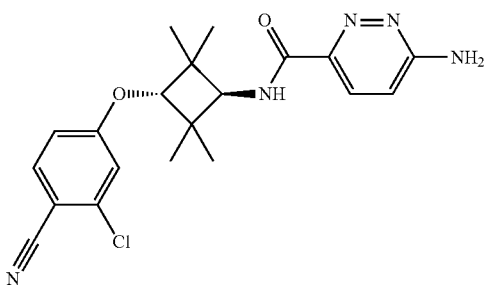 [SMILES: CC1(C)[C@H](NC(=O)c2ccc(N)nn2)C(C)(C)[C@H]1Oc1ccc(C#N)c(Cl)c1]

ABM-29: trans tert-Butyl N-[3-(3-chloro-4-cyanophenoxy)-2,2,4,4-tetramethylcyclobutyl]carbamate

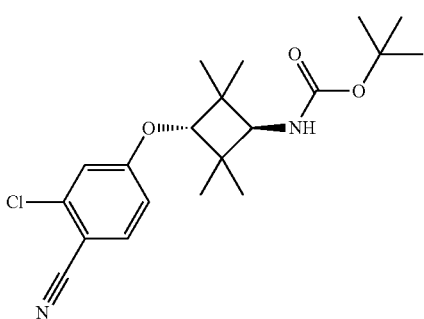 [SMILES: CC(C)(C)OC(=O)N[C@H]1C(C)(C)[C@H](Oc2ccc(C#N)c(Cl)c2)C1(C)C]

ABM-30: trans 4-Amino-N-[3-(3-chloro-4-cyanophenoxy)-2,2,4,4-tetramethylcyclobutyl]benzamide

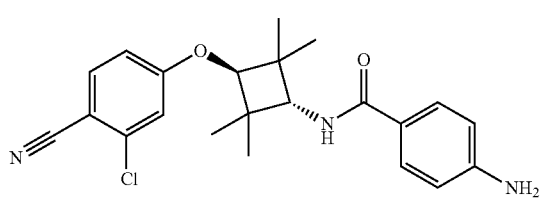 [SMILES: CC1(C)[C@H](NC(=O)c2ccc(N)cc2)C(C)(C)[C@H]1Oc1ccc(C#N)c(Cl)c1]

Step 1: Synthesis of tert-butyl(4-((trans-3-(3-chloro-4-cyanophenoxy)-2,2,4,4-tetramethylcyclobutyl)carbamoyl)phenyl)carbamate A suspension of 4-((tert-butoxycarbonyl)amino)benzoic acid (1.50 g, 6.34 mmol) in methylene dichloride (40 mL) was charged with N,N-diisopropylethylamine (3.30 mL, 19.0 mmol), followed by 4-(trans-3-amino-2,2,4,4-tetramethylcyclobutoxy)-2-chlorobenzonitrile hydrochloride (2.0 g, 6.34 mmol). The mixture was stirred for several minutes and then charged with HATU (2.41 g, 6.34 mmol). The reaction mixture was allowed to stir at room temperature for 2 h. The mixture was diluted with methylene dichloride (40 mL), washed with aqueous 1N HCl (2×), saturated aqueous sodium bicarbonate (2×), brine, and dried over anhydrous Na₂SO₄. The crude product was used in next step;

Step 2: synthesis of trans 4-Amino-N-[3-(3-chloro-4-cyanophenoxy)-2,2,4,4-tetramethylcyclobutyl]benzamide 4M HCl in Dioxane (1.38 mL, 40.0 mmol) was added to a pre-mixed solution of tert-butyl(4-((trans-3-(3-chloro-4-cyanophenoxy)-2,2,4,4-tetramethylcyclobutyl)carbamoyl)phenyl)carbamate (2.00 g, 4.01 mmol) in MeOH (2 mL) and left to stir at rt for 1 h till completion. The reaction mixture was concentrated in vacuo to a solid, which was dissolved with 5% MeOH in DCM. The organic layer was washed with sodium bicarbonate (2×), filtered through a Biotage Universal Phase Separator and then concentrated in vacuo to a solid. The crude product was recrystallized from EtOH/Heptanes to afford the desired product as a white solid, 1.2 g, 75% yield. $^1$H NMR (400 MHz, METHANOL-d4) δ 7.72 (d, J=8.80 Hz, 1H), 7.61 (d, J=8.61 Hz, 2H), 7.13 (d, J=2.35 Hz, 1H), 6.98 (dd, J=2.45, 8.71 Hz, 1H), 6.69 (d, J=8.61 Hz, 2H), 4.28 (s, 1H), 4.12 (s, 1H), 1.27 (s, 6H), 1.22 (s, 6H). LC-MS (ES+): m/z 398.16/400.15 [MH$^+$].

ABM-31: trans 5-Amino-N-[3-(3-chloro-4-cyanophenoxy)-2,2,4,4-tetramethylcyclobutyl]pyrazine-2-carboxamide

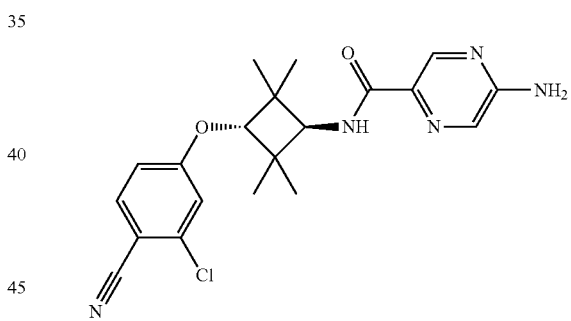

ABM-32: trans 2-Amino-N-[3-(3-chloro-4-cyanophenoxy)-2,2,4,4-tetramethylcyclobutyl]pyrimidine-5-carboxamid

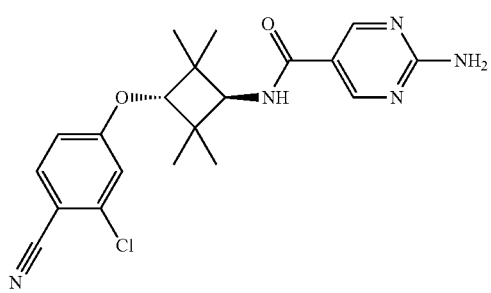 [SMILES: CC1(C)[C@H](NC(=O)c2cnc(N)nc2)C(C)(C)[C@H]1Oc1ccc(C#N)c(Cl)c1]

149

ABM-33: 4-Methoxy-N-[(1r,3r)-3-(3-chloro-4-cyanophenoxy)-2,2,4,4-tetramethylcyclobutyl]benzamide

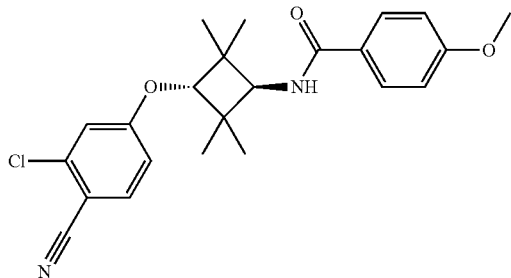 [SMILES: COc1ccc(C(=O)N[C@H]2C(C)(C)[C@H](Oc3ccc(C#N)c(Cl)c3)C2(C)C)cc1]

ABM-34: trans 1-(2-Hydroxyethyl)-N-[3-(3-chloro-4-cyanophenoxy)-2,2,4,4-tetramethylcyclobutyl]-1H-pyrazole-4-carboxamide

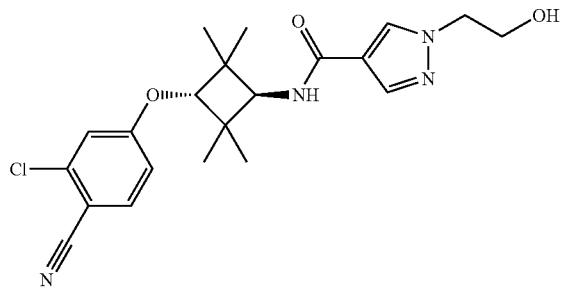 [SMILES: CC1(C)[C@H](NC(=O)c2cnn(CCO)c2)C(C)(C)[C@H]1Oc1ccc(C#N)c(Cl)c1]

ABM-35: trans 6-Amino-N-[3-(3-chloro-4-cyanophenoxy)-2,2,4,4-tetramethylcyclobutyl]pyridine-3-carboxamide

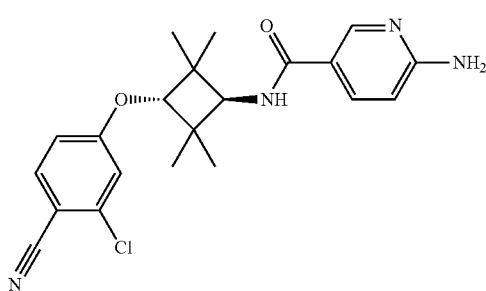 [SMILES: CC1(C)[C@H](NC(=O)c2ccc(N)nc2)C(C)(C)[C@H]1Oc1ccc(C#N)c(Cl)c1]

150

ABM-36: trans 4-[(5-Hydroxypentyl)amino]-N-[3-(3-chloro-4-cyanophenoxy)-2,2,4,4-tetramethylcyclobutyl]benzamide

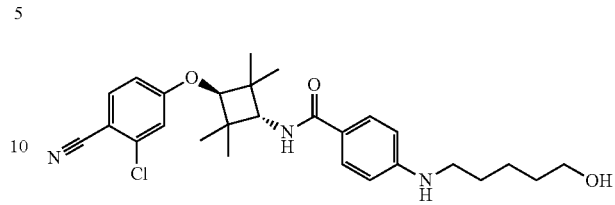

ABM-37: trans tert-Butyl 2-({5-[(4-{[3-(3-chloro-4-cyanophenoxy)-2,2,4,4-tetramethylcyclobutyl]carbamoyl}phenyl)aminopentyl}oxy)acetate

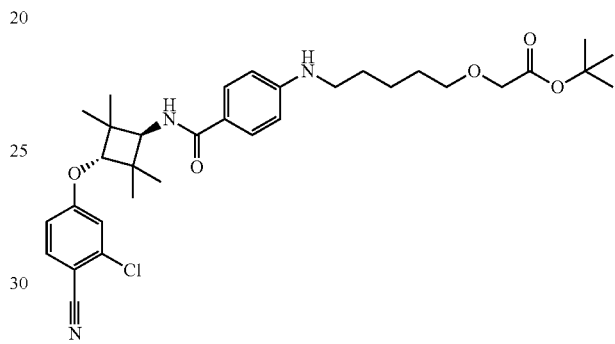

Synthesis of ULM Moieties

ULM-1: (2S,4R)-1-((S)-2-amino-3,3-dimethylbutanoyl)-4-hydroxy-N-(4-(4-methylthiazol-5-yl)benzyl)pyrrolidine-2-carboxamide

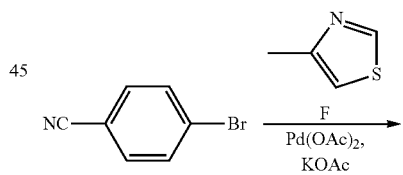

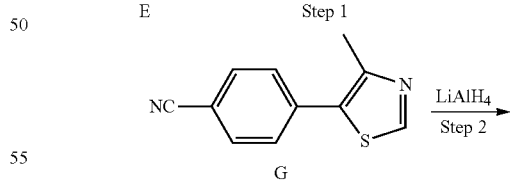

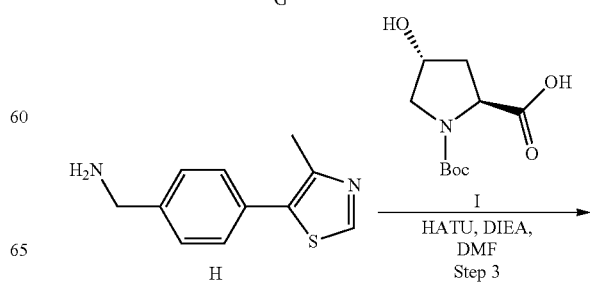

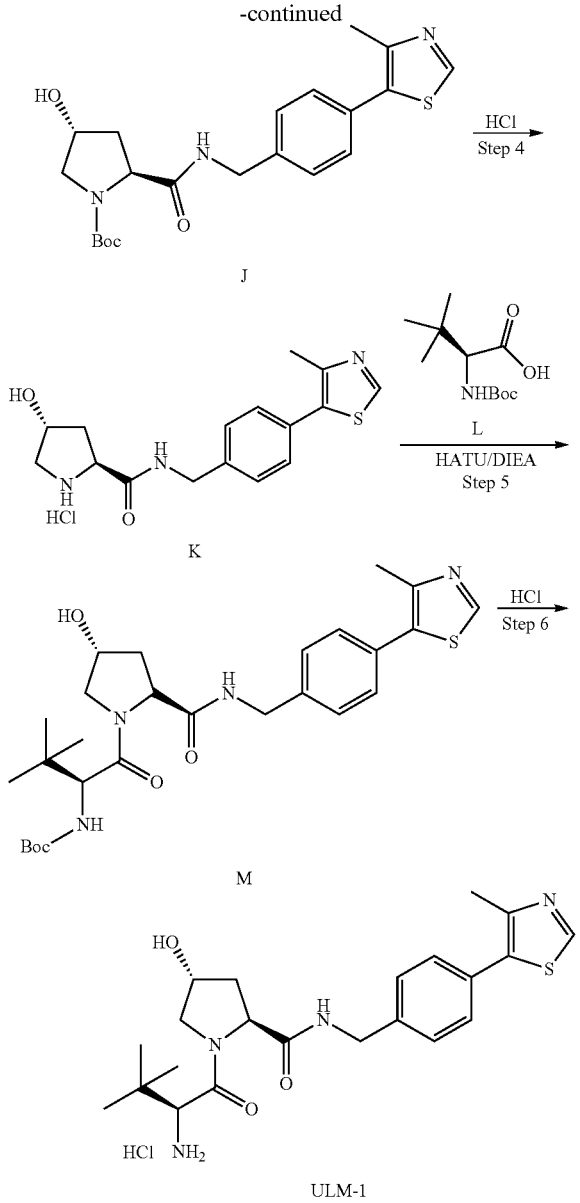

J

K

M

ULM-1

Step 1: Synthesis of
4-(4-methyl-1,3-thiazol-5-yl)benzonitrile (G)

To a stirred solution of 4-bromobenzonitrile (E, 20 g, 109.88 mmol) in DMA (250 mL) under a nitrogen atmosphere was added 4-methyl-1,3-thiazole (F, 21.88 g, 220.67 mmol), palladium (II) acetate (743 mg, 3.31 mmol) and potassium acetate (21.66 g, 220.71 mmol) at rt. The resulting solution was heated to 150° C. and stirred at this temperature for 5 h, LC-MS indicated formation of the desired product. The reaction was cooled to rt, diluted with 1 L of water and extracted with ethyl acetate (300 mL×3). The organic layers were combined, washed with saturated aqueous solution of sodium chloride (200 mL), dried over anhydrous sodium sulfate and then concentrated under reduced pressure to give a crude residue, which was purified by flash silica gel chromatography (eluent: ethyl acetate/petroleum ether, v:v=1:5) to give the G (yield: 91%) as a white solid.

Step 2: Synthesis of [4-(4-methyl-1,3-thiazol-5-yl)phenyl]methanamine (H)

To a stirred solution of 4-(4-methyl-1,3-thiazol-5-yl)benzonitrile (G, 35.0 g, 174.8 mmol) in tetrahydrofuran (1000 mL) was added LiAlH$_4$ (20.0 g, 526.3 mmol) in portions at 0° C. in 10 min under a nitrogen atmosphere. The resulting solution was then stirred at 60° C. for 3 h. LC-MS indicated formation of the desired product. The reaction was then cooled to 0° C., quenched by the addition water (20 mL, added slowly), aq. solution of NaOH (15%, 20 mL) and water (60 mL). The resulting mixture was then extracted with ethyl acetate (300 mL×2). The organic layers were combined, washed with saturated aqueous solution of sodium chloride (100 mL), dried over anhydrous sodium sulfate and then concentrated under reduced pressure to give a crude residue, which was purified by flash silica gel chromatography (eluent: dichloromethane/methanol (v:v=10:1)) to give H (yield: 56%) as a yellow oil.

Step 1: synthesis of tert-butyl(2S,4R)-4-hydroxy-2-({[4-(4-methyl-1,3-thiazol-5-yl)phenyl]methyl}carbamoyl)pyrrolidine-1-carboxylate (J)

To a stirred solution of (2S,4R)-1-[(tert-butoxy)carbonyl]-4-hydroxypyrrolidine-2-carboxylic acid (I, 2.7 g, 11.7 mmol) in N,N-dimethylformamide (20 mL) was added DIEA (2.52 g, 19.50 mmol), HATU (4.47 g, 11.76 mmol) and [4-(4-methyl-1,3-thiazol-5-yl)phenyl]methanamine (H, 2.0 g, 9.79 mmol) at rt. The resulting mixture was stirred at rt overnight, LC-MS indicated formation of the desired product. The reaction mixture was diluted with water (20 mL) and extracted with ethyl acetate (50 mL×3). The organic layers were combined, washed with saturated aqueous solution of sodium chloride (50 mL), dried over anhydrous sodium sulfate and then concentrated under reduced pressure to give a crude residue, which was purified by flash silica gel chromatography (eluent: dichloromethane/methanol (v:v=20:1)) to give J (yield: 56%) as a yellow solid.

Step 2: Synthesis of (2S,4R)-4-hydroxy-N-{[4-(4-methyl-1,3-thiazol-5-yl)phenyl]methyl}pyrrolidine-2-carboxamide hydrochloride (K)

To a stirred solution of tert-butyl(2S,4R)-4-hydroxy-2-({[4-(4-methyl-1,3-thiazol-5-yl)phenyl]methyl}carbamoyl)pyrrolidine-1-carboxylate (J, 45 g, 107.78 mmol), was added a solution of hydrogen chloride in dioxane (4N, 300 mL). The resulting solution was stirred at 20° C. for 2 h. The solids were collected by filtration to give K (yield: 98%) as a yellow solid, which was used for the next step without any further purification.

Step 3: Synthesis of tert-butyl N-[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamate (M)

To a stirred solution of (2S)-2-{[(tert-butoxy)carbonyl]amino}-3,3-dimethylbutanoic acid (L, 15.7 g, 68.0 mmol) in N,N-dimethylformamide (500 mL) was added DIEA (29.2 g, 225.9 mmol), HATU (25.9 g, 68.1 mmol) and (2S,4R)-4-hydroxy-N-{[4-(4-methyl-1,3-thiazol-5-yl)phenyl]methyl}pyrrolidine-2-carboxamide hydrochloride (K, 20.0 g, 56.5 mmol) at rt.
The resulting solution was stirred at rt for 16 h, LC-MS indicated formation of the desired product. The reaction mixture was diluted by water (200 mL) and extracted with ethyl acetate (200 mL×3). The organic layers were combined, washed with saturated aqueous solution of sodium chloride (50 mL×2), dried over anhydrous sodium sulfate and then concentrated under reduced pressure to give a crude residue, which was purified by flash silica gel chromatography (eluent: ethyl acetate/petroleum ether (v:v=2:1)) to give M (yield: 51%) as a yellow solid.

Step 4: Synthesis of (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1)

To a stirred solution of tert-butyl N-[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamate (M, 12 g, 22.61 mmol) in dioxane (20 mL) was added a solution of hydrogen chloride in dioxane (4N, 80 mL) at rt. The resulting solution was stirred at rt for 2 h, LC-MS indicated formation of the desired product. Precipitated solids were collected by filtration to give ULM-1 (yield: 48%) as a yellow solid. $^1$HNMR (400 MHz, CD$_3$OD): δ 9.84-9.82 (s, 1H), 7.58-7.54 (m, 4H), 4.71-4.41 (m, 4H), 4.13-4.08 (m, 1H), 3.86-3.71 (m, 2H), 3.36 (s, 1H), 2.60-2.58 (s, 3H), 2.35-2.07 (m, 2H), 1.19-1.12 (m, 9H). LC-MS (ES$^+$): m/z 431.11 [MH$^+$], t$_R$=0.73 min (2.0 minute run).

ULM-2: (2S,4R)-1-((S)-2-amino-3,3-dimethylbutanoyl)-4-hydroxy-N-(4-(thiazol-5-yl)benzyl)pyrrolidine-2-carboxamide

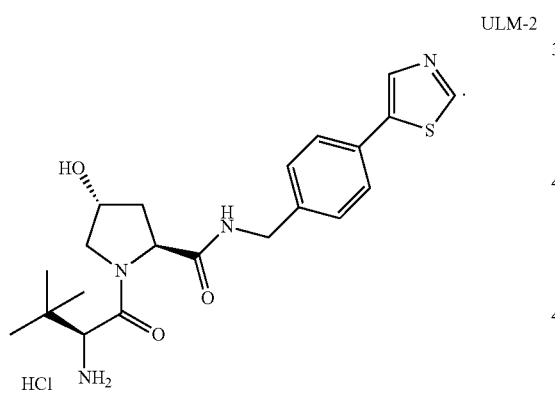

ULM-2

ULM-2 was synthesized according to similar procedure described above for the synthesis of ULM-1, utilizing 4-bromobenzonitrile and 1,3-thiazole as starting materials. LC-MS (ES$^+$): m/z 417.10 [MH$^+$], t$_R$=0.51 min (2.0 minute run).

ULM-3: (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide

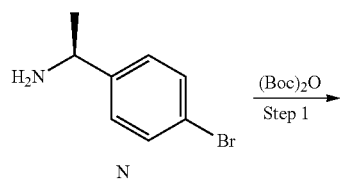

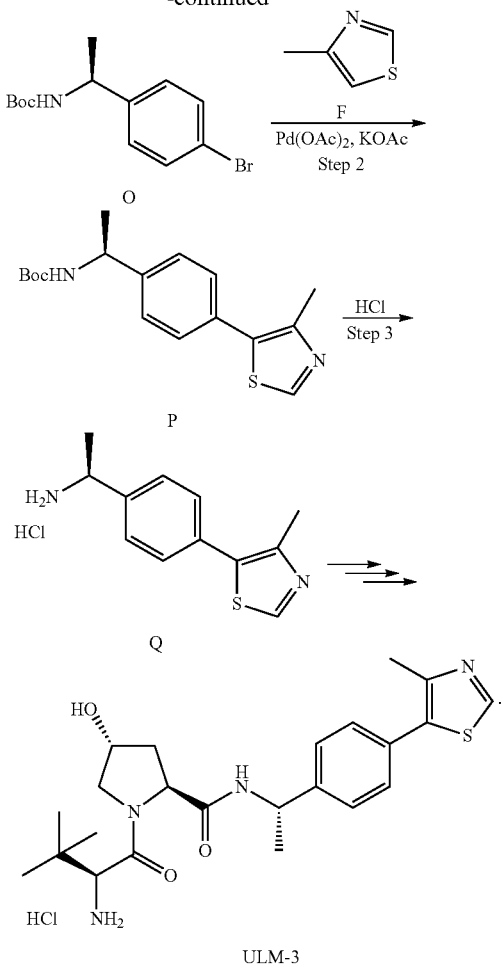

Step 1: Synthesis of tert-butyl N-[(1S)-1-(4-bromophenyl)ethyl]carbamate (O)

To a stirred mixture of (1S)-1-(4-bromophenyl)ethan-1-amine (N, 10.0 g, 49.98 mmol) in dichloromethane (100 mL) was added Et$_3$N (10.0 g, 99.01 mmol) and (Boc)$_2$O (13.0 g, 59.63 mmol). The resulting mixture was stirred at rt for 2 h. The bulk of solvent was then removed under reduced pressure to give a crude residue, which was purified by flash silica gel chromatography (eluent: ethyl acetate/petroleum ether, v:v=1:10) to give O (yield: 99%) as a white solid.

Step 2: Synthesis of tert-butyl N-[(1S)-1-[4-(4-methyl-1,3-thiazol-5-yl)phenyl]ethyl]carbamate (P)

To a stirred solution of tert-butyl N-[(1S)-1-(4-bromophenyl)ethyl]carbamate (O, 15.0 g, 49.97 mmol) in DMA (100 mL), under an atmosphere of nitrogen, was added 4-methyl-1,3-thiazole (9.9 g, 99.84 mmol), potassium acetate (9.8 g, 99.86 mmol) and Pd(OAc)$_2$ (112.5 mg, 0.50 mmol) at rt. The resulting mixture was then stirred at 120° C. for 2 h. The reaction mixture was then cooled to rt, diluted by water (120 mL), and extracted with ethyl acetate (200 mL×3). The organic layers were combined, dried over anhydrous sodium sulfate and then concentrated under reduced pressure to give a crude residue, which was purified by flash silica gel chromatography (eluent: ethyl acetate/petroleum ether, v:v=1:5) to give P (yield: 47%) as a white solid. LC-MS (ES+): m/z 319.13 [MH+], $t_R$=0.97 min (2.0 minute run).

Step 3. Synthesis of (1S)-1-[4-(4-methyl-1,3-thiazol-5-yl)phenyl]ethan-1-amine hydrochloride (Q)

To a stirred solution of tert-butyl N-[(1S)-1-[4-(4-methyl-1,3-thiazol-5-yl)phenyl]ethyl]carbamate (P, 7.5 g, 23.55 mmol) in methanol (20 mL) was bubbled in hydrogen chloride (gas) at rt for 2 h. Then the resulting mixture was concentrated under vacuum to give Q (yield: 86%) as a white solid, which was used in the next step without any further purifications.

Intermediate Q was converted to ULM-3 in a similar manner as described for the conversion of H to ULM-1. $^1$H NMR (300 MHz, DMSO): δ 8.99 (s, 1H), 8.57-8.55 (d, J=7.8 Hz, 1H), 8.01 (br. s, 3H), 7.46-7.43 (d, J=8.4 Hz, 2H), 7.39-7.37 (d, J=8.4 Hz, 2H), 4.98-4.90 (m, 1H), 4.57-4.51 (m, 1H), 4.34 (br. s, 1H), 3.94-3.92 (m, 1H), 3.69-3.66 (m, 1H), 3.53-3.49 (m, 1H), 2.52 (s, 3H), 2.10-2.07 (m, 1H), 1.83-1.81 (m, 1H), 1.40-1.30 (m, 3H), 1.03 (s, 9H). LC-MS (ES+): m/z 445.05 [MH+], $t_R$=0.53 min (2.0 minute run).

ULM-4: (2S,4R)-1-((S)-2-amino-3,3-dimethylbutanoyl)-4-hydroxy-N-(4-(oxazol-5-yl)benzyl)pyrrolidine-2-carboxamide hydrochloride

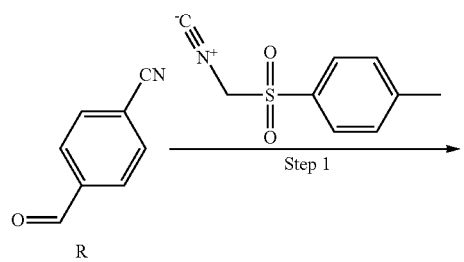

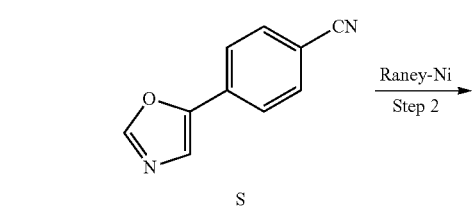

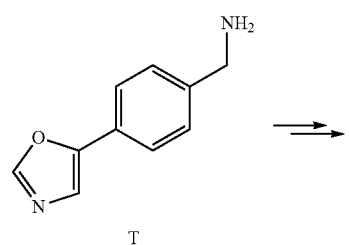

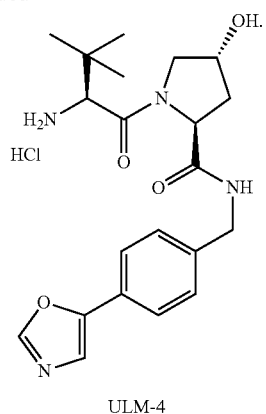

ULM-4

Step 1: 1. Synthesis of 4-(1,3-oxazol-5-yl)benzonitrile (S)

To a stirred solution of 4-formylbenzonitrile (R, 1.0 g, 7.63 mmol) in methanol (40 mL) was added [[(4-methylbenzene)sulfonyl]methyl](methyliumylidyne)azanuide (1.6 g, 8.40 mmol) and potassium carbonate (1.4 g, 9.91 mmol), the resulting mixture was stirred at rt for 1.5 h. The bulk of solvent was then removed under reduced pressure. The residue was diluted with saturated aqueous sodium bicarbonate (20 mL) and was extracted with dichloromethane (30 mL×3). The organic layers were combined, washed with brine (30 mL), dried over anhydrous sodium sulfate and concentrated under vacuum to give a crude product, which was purified by re-crystallization using dichloromethane and hexane to give S (1.0 g) as a white solid. $^1$H NMR (400 MHz, DMSO) δ 8.56 (s, 1H), 7.97-7.83 (m, 5H); LC-MS (ES+): m/z 170.95 [MH+], $t_R$=0.79 min (2.0 minute run).

Step 2. Synthesis of [4-(1,3-oxazol-5-yl)phenyl]methanamine (T)

To a stirred solution of 4-(1,3-oxazol-5-yl)benzonitrile (S, 900.0 mg, 5.29 mmol) in methanol (15 mL) was added Raney-Ni (900 mg) and aq. ammonium hydroxide (3.0 mL). Hydrogen gas was then introduced into the reaction mixture via a balloon. The resulting mixture was stirred at rt for 16 h. The solids were then removed by filtration and the solution was concentrated under vacuum to give T (yield: 81%) as brown oil, which was used in the next step without any further purifications. LC-MS (ES+): m/z 175.90 [MH+], $t_R$=0.26 min (2.0 minute run).

Intermediate T was converted to ULM-4 in a similar manner as described for the conversion of H to ULM-1. LC-MS (ES+): m/z 400.96 [MH+], $t_R$=0.66 min (2.0 minute run).

ULM-5: (2S,4R)-1-((S)-2-amino-3,3-dimethylbutanoyl)-4-hydroxy-N-(4-(4-methyloxazol-5-yl)benzyl)pyrrolidine-2-carboxamide

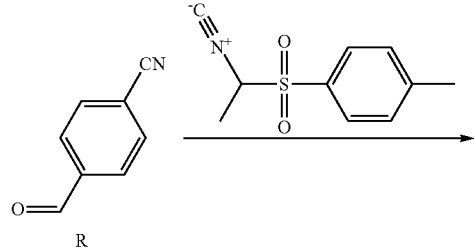

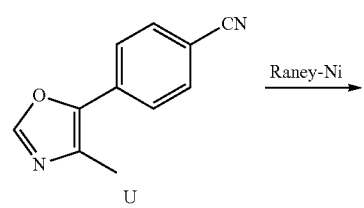

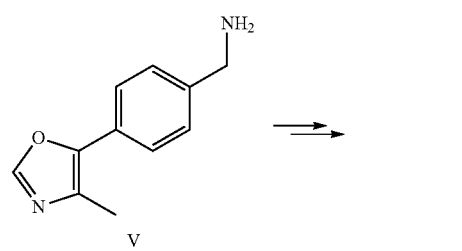

ULM-5

[4-(4-methyl-1,3-oxazol-5-yl)phenyl]methanamine (V) was synthesized according to similar procedure described above for the synthesis of [4-(1,3-oxazol-5-yl)phenyl]methanamine (T).

Intermediate V was converted to ULM-5 in a similar manner as described for the conversion of H to ULM-1. LC-MS (ES$^+$): m/z 415.10 [MH$^+$], t$_R$=1.17 min (2.6 minute run).

ULM-6: (2S,4R)-1-((S)-2-amino-3,3-dimethylbutanoyl)-N-(4-chlorobenzyl)-4-hydroxypyrrolidine-2-carboxamide Hydrochloride

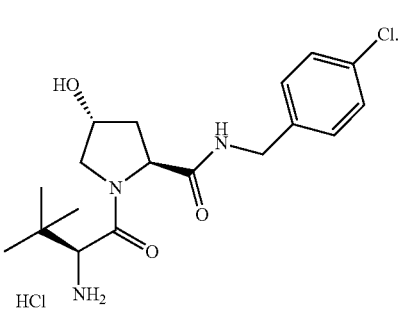

ULM-6 was synthesized according to similar procedure described above for the synthesis of ULM-1, utilizing 4-chlorobenzonitrile as the starting material.

ULM-7: (2S,4R)-1-((S)-2-amino-3,3-dimethylbutanoyl)-N-(4-cyanobenzyl)-4-hydroxypyrrolidine-2-carboxamide Hydrochloride

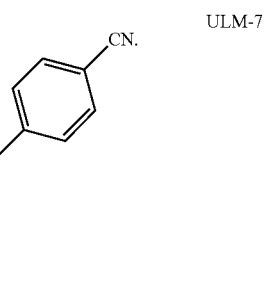
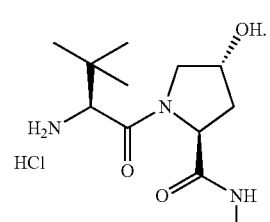
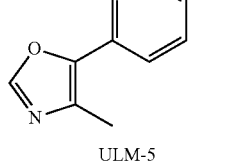

ULM-7 was synthesized according to similar procedure described above for the synthesis of ULM-1, utilizing 4-cyanobenzonitrile as the starting material.

ULM-8: (2S,4R)-1-((S)-2-amino-3-methylbutanoyl)-4-hydroxy-N-(4-(4-methylthiazol-5-yl)benzyl)pyrrolidine-2-carboxamide Hydrochloride

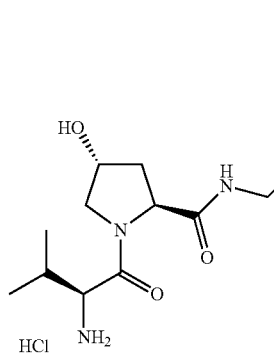

ULM-8 was synthesized according to similar procedure described above for the synthesis of ULM-1, utilizing (S)-2-(tert-butoxycarbonylamino)-3-methylbutanoic acid and 4-methyl-1,3-thiazole (F) as starting materials.

ULM-9: (2S,4R)-1-((S)-2-amino-3-methylbutanoyl)-4-hydroxy-N-(4-(thiazol-5-yl)benzyl)pyrrolidine-2-carboxamide Hydrochloride

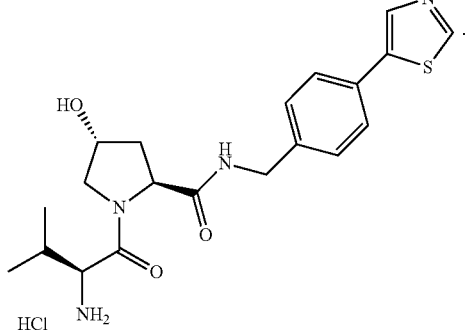

ULM-9 was synthesized according to similar procedure described above for the synthesis of ULM-1, utilizing (S)-2-(tert-butoxycarbonylamino)-3-methylbutanoic acid and 1,3-thiazole as starting materials.

ULM-10: (2S,4R)-1-((S)-2-amino-3-methylbutanoyl)-4-hydroxy-N-(4-(4-methyloxazol-5-yl)benzyl)pyrrolidine-2-carboxamide Hydrochloride

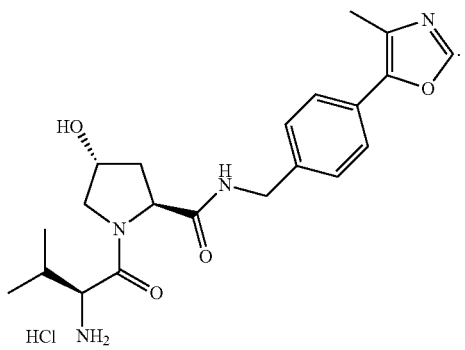

ULM-10 was synthesized according to similar procedure described above for the synthesis of ULM-5, utilizing (S)-2-(tert-butoxycarbonylamino)-3-methylbutanoic acid as starting material.

ULM-11: (2S,4R)-1-((S)-2-amino-3,3-dimethylbutanoyl)-4-hydroxy-N-(4-(1-methyl-1H-pyrazol-5-yl)benzyl)pyrrolidine-2-carboxamide Hydrochloride

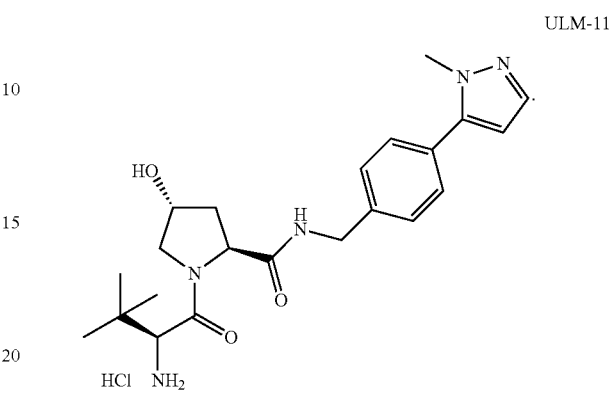

ULM-11 was synthesized according to similar procedure described above for the synthesis of ULM-1, utilizing 1-methylpyrazole as the starting material.

ULM-12: (2S,4R)-4-tert-butoxy-N-(2-hydroxy-4-(4-methylthiazol-5-yl)benzyl)-1-4S)-3-methyl-2-(1-oxoisoindolin-2-yl)butanoyl)pyrrolidine-2-carboxamide

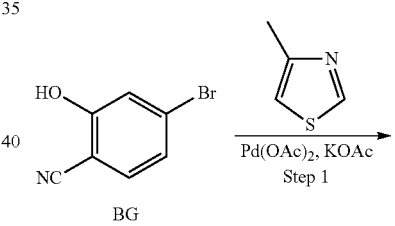

BG

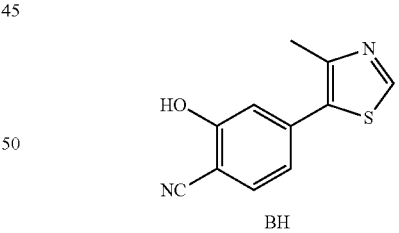

BH

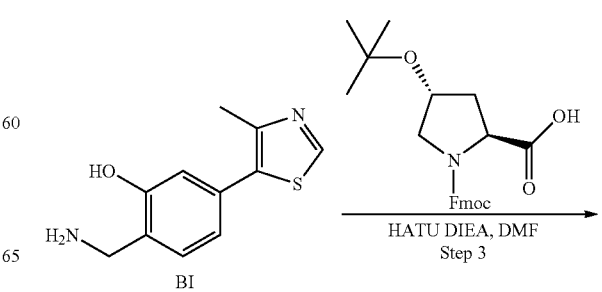

BI

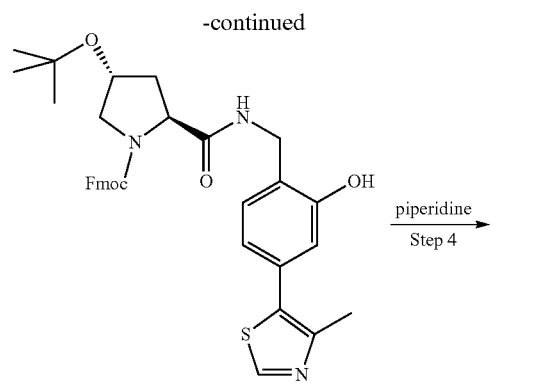

BJ

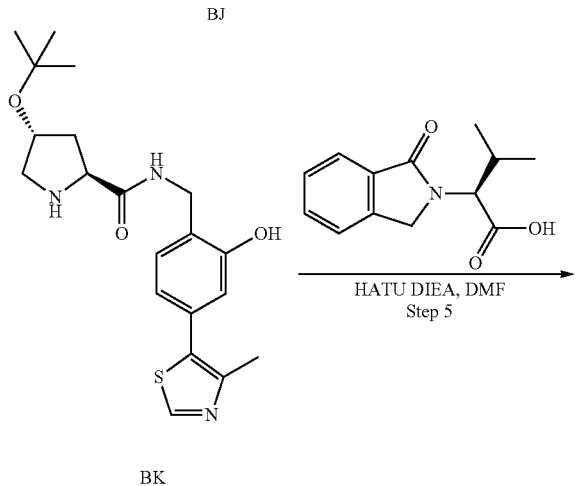

BK

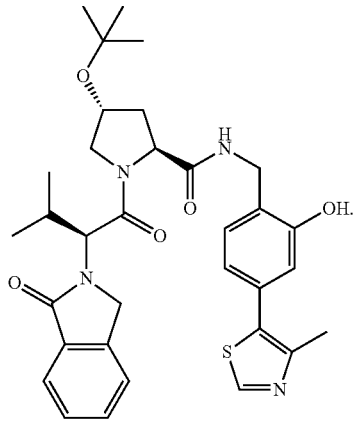

ULM-12

Step 1: Synthesis of 2-hydroxy-4-(4-methyl-1,3-thiazol-5-yl)benzonitrile (BH)

To a stirred solution of 4-bromo-2-hydroxybenzonitrile (BG, 28 g, 141.40 mmol) in DMA (300 mL) was added 4-methyl-1,3-thiazole (28.1 g, 283.40 mmol), potassium acetate (28 g, 285.31 mmol) and palladium (II) acetate (940 mg, 4.19 mol) at rt under an atmosphere of nitrogen. The resulting mixture was then heated to 150° C. and stirred at this temperature for 2.5 h, LC-MS indicated formation of the desired product. The reaction was then cooled to rt, diluted by water (1000 mL) and then extracted with ethyl acetate (500 mL×3). The organic layers were combined, dried over anhydrous sodium sulfate and concentrated under reduced pressure to give a crude residue, which was purified by a flash silica gel chromatography (eluent: ethyl acetate/petroleum ether (v:v=1:1) to give BH (yield: 78%) as a yellow solid. LC-MS (ES$^+$): m/z 216.95 [MH$^+$], $t_R$=1.25 min (2.6 minute run).

Step 1: 2-(aminomethyl)-5-(4-methyl-1,3-thiazol-5-yl)phenol (BI)

To a stirred solution of 2-hydroxy-4-(4-methyl-1,3-thiazol-5-yl)benzonitrile (BH, 15.6 g, 72.14 mmol) in tetrahydrofuran (400 mL) under an atmosphere of nitrogen was added LiAlH$_4$ (11 g, 289.86 mmol) in several portions at 10° C. The resulting mixture was then heated to reflux for 3 h, LC-MS indicated formation of the desired product. The reaction was then cooled to 0° C., quenched by the water (10 mL, added slowly and drop wise), 15% NaOH (aq.) (30 mL) and water (10 mL). The solids precipitated were removed by filtration, the solution phase was concentrated under reduced pressure followed by high vacuum pump to give BI (yield: 65%). LC-MS (ES$^+$): m/z 220.85 [MH$^+$], $t_R$=1.02 min (2.6 minute run).

Step 3. Synthesis of 9H-fluoren-9-ylmethyl(2S,4R)-4-(tert-butoxy)-2-({[2-hydroxy-4-(4-methyl-1,3-thiazol-5-yl)phenyl]methyl}carbamoyl)pyrrolidine-1-carboxylate (BJ)

To a stirred solution of (2S,4R)-4-(tert-butoxy)-1-[(9H-fluoren-9-ylmethoxy)carbonyl]pyrrolidine-2-carboxylic acid (BI, 18.6 g) in N,N-dimethylformamide (250 mL) was added DIEA (7.9 g, 61.24 mmol), HATU (17.3 g, 45.53 mmol) and 2-(aminomethyl)-5-(4-methyl-1,3-thiazol-5-yl)phenol (20 g, 90.79 mmol) at rt. The resulting mixture was stirred overnight at rt, and LC-MS indicated formation of the desired product. The reaction mixture was diluted by water (200 mL) and then extracted with ethyl acetate (300 mL×3). The organic layers were combined, dried over anhydrous sodium sulfate and concentrated under reduced pressure to give a crude residue, which was purified by flash silica gel chromatography (eluent: dichloromethane/methanol (v:v=25:1)) to give BJ (yield: 31%) as a yellow oil. LC-MS (ES$^+$): m/z 611.20 [MH$^+$], $t_R$=1.12 min (2.0 minute run).

Step 4: Synthesis of (2S,4R)-4-(tert-butoxy)-N-{[2-hydroxy-4-(4-methyl-1,3-thiazol-5-yl)phenyl]methyl}pyrrolidine-2-carboxamide (BK)

To a stirred solution of 9H-fluoren-9-ylmethyl(2S,4R)-4-(tert-butoxy)-2-({[2-hydroxy-4-(4-methyl-1,3-thiazol-5-yl)phenyl]methyl}carbamoyl)pyrrolidine-1-carboxylate (BJ, 17.2 g, 28.12 mmol) in dichloromethane (270 mL) was added piperidine (30 mL, 280.00 mmol) at rt. The resulting solution was stirred at rt for 3 h, and LC-MS indicated formation of the desired product. The reaction mixture was concentrated under vacuum to give a crude residue, which was then diluted by dichloromethane (300 mL), washed with water (300 mL×2), dried over anhydrous sodium sulfate and concentrated under reduced pressure to give a crude residue, which was purified by flash silica gel chromatography (eluent: dichloromethane/methanol (v:v=20:1)) to give BK (yield: 71%) as a yellow oil. LC-MS (ES⁺): m/z 389.95 [MH⁺], $t_R$=0.88 min (2.0 minute run).

Step 5: Synthesis of (2S,4R)-4-(tert-butoxy)-N-{[2-hydroxy-4-(4-methyl-1,3-thiazol-5-yl)phenyl]methyl}-1-[(2S)-3-methyl-2-(1-oxo-2,3-dihydro-1H-isoindol-2-yl)butanoyl]pyrrolidine-2-carboxamide ULM-12)

To a stirred solution of (2S)-3-methyl-2-(1-oxo-2,3-dihydro-1H-isoindol-2-yl)butanoic acid (3.6 g, 15.43 mmol) in N,N-dimethylformamide (50 mL) was added DIEA (2.7 g, 20.93 mmol), HATU (5.89 g, 15.49 mmol) and (2S,4R)-4-(tert-butoxy)-N-{[2-hydroxy-4-(4-methyl-1,3-thiazol-5-yl)phenyl]methyl}pyrrolidine-2-carboxamide (BK, 4.0 g, 10.27 mmol) at rt. The resulting solution was stirred overnight at rt, and LC-MS indicated formation of the desired product. The reaction was diluted by the water (100 mL) and extracted with dichloromethane (100 mL×3). The organic layers were combined, dried over anhydrous sodium sulfate and concentrated under reduced pressure to give a crude residue, which was purified by a flash silica gel chromatography (eluent: ethyl acetate/petroleum ether (v:v=2:1)) to give ULM-12 (yield: 43%) as a yellow solid. ¹H NMR (400 MHz, CD₃OD) δ 8.88 (s, 1H), 7.83-7.81 (d, J=7.6 Hz, 1H), 7.66-7.63 (m, 2H), 7.61-7.59 (m, 1H), 7.36-7.34 (d, J=8.0 Hz, 1H), 6.94-6.87 (d, J=6.4 Hz, 1H), 4.88 (s, 1H), 4.56-4.39 (m, 6H), 3.88-3.81 (m, 2H), 2.51 (s, 3H), 2.47-2.45 (m, 1H), 2.15-2.13 (m, 2H), 1.16-1.14 (d, J=6.4 Hz, 3H) 1.02 (s, 9H), 0.89-0.86 (d, J=6.4 Hz, 3H); LC-MS (ES⁺): m/z 605.40 [MH⁺], $t_R$=1.91 min (3.6 minute run).

Unless otherwise noted, the following intermediates and their analogs (for examples, but not limited to, analogs with substitutions such as halogens) were synthesized according to similar procedures described above for the synthesis of ULM-12, by utilizing corresponding starting materials and reagents.

ULM-13: (2S,4R)-4-tert-butoxy-1-((S)-2-(6-fluoro-1-oxoisoindolin-2-yl)-3-methylbutanoyl)-N-(2-hydroxy-4-(4-methylthiazol-5-yl)benzyl)pyrrolidine-2-carboxamide

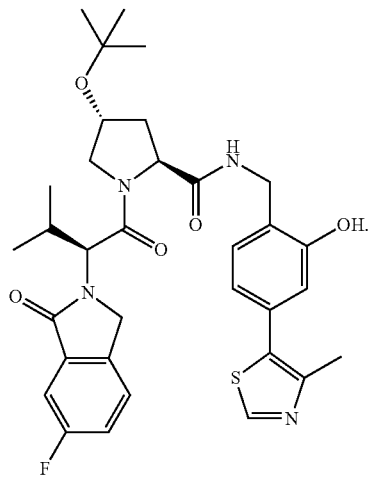

ULM-13

ULM-14: (2S,4R)-4-tert-butoxy-1-((S)-2-(7-cyano-1-oxoisoindolin-2-yl)-3-methylbutanoyl)-N-(2-hydroxy-4-(4-methylthiazol-5-yl)benzyl)pyrrolidine-2-carboxamide

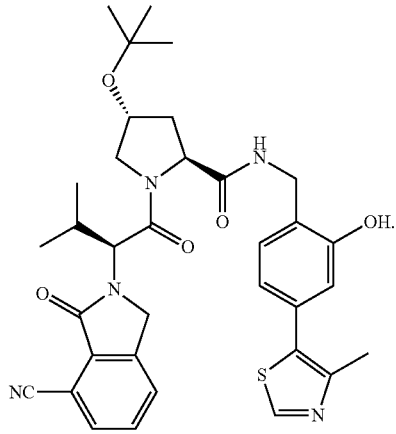

ULM-14

Synthesis of Linker Chemistry, L

L-1: 2-(3-(5-(tosyloxy)pentyloxy)propoxy)acetic Acid

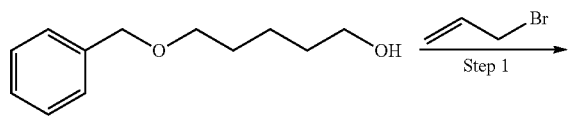

W

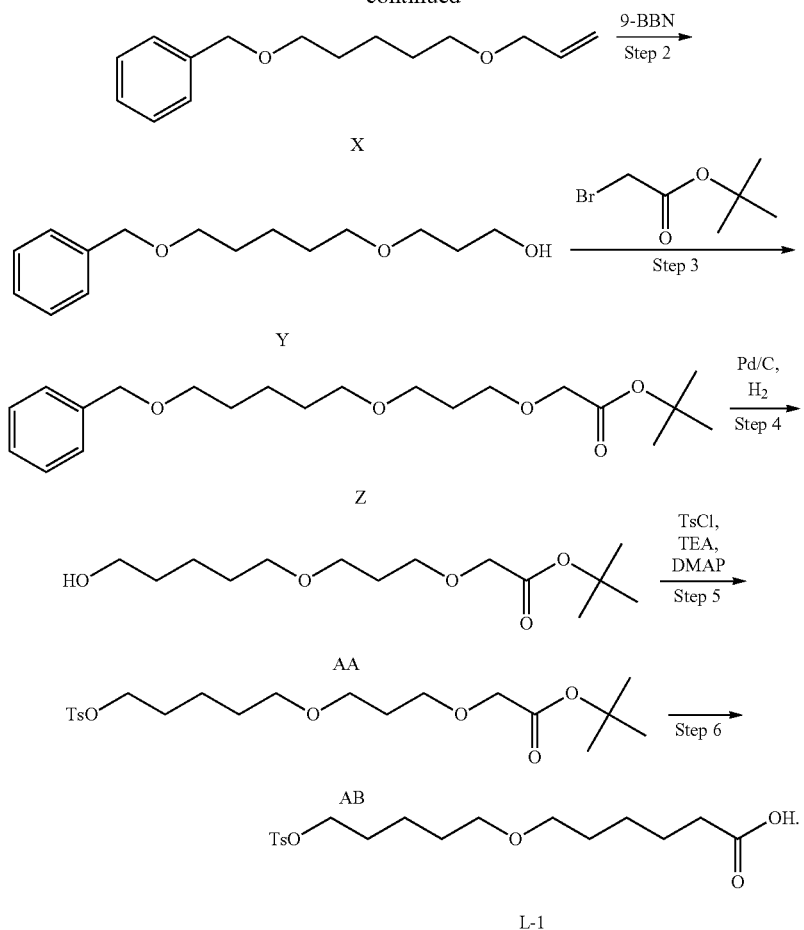

Step 1: Synthesis of ({[5-(prop-2-en-1-yloxy)pentyl]oxy}methyl)benzene

To a stirred solution of 5-(benzyloxy)pentan-1-ol (W, 4.0 g, 20.59 mmol) in N,N-dimethylformamide (50 mL) was added sodium hydride (1.24 g, 51.67 mmol) in portions at 0° C. under an atmosphere of nitrogen. The resulting mixture was then stirred at rt for 1 h. To this mixture was added 3-bromoprop-1-ene (3.71 g, 30.67 mmol), the reaction mixture was stirred overnight at 60° C. in an oil bath. LC-MS indicated formation of the desired product. The reaction mixture was cooled to 0° C. and then quenched by water (100 mL), the resulting mixture was extracted with ethyl acetate (200 mL×2). The organic layers were combined, washed with saturated aqueous solution of sodium chloride (60 mL), dried over anhydrous sodium sulfate and then concentrated under reduced pressure to give a crude residue. The residue was purified by a flash silica gel chromatography (eluent: ethyl acetate/petroleum ether (v:v=1:40)) to give 4.57 g of X. $^1$H NMR (300 MHz, CDCl$_3$): δ 7.36 (s, 4H), 7.32 (m, 1H), 5.98 (m, 1H), 5.33 (m, 1H), 5.21 (m, 1H), 4.53 (s, 2H), 3.99 (m, 2H), 3.53 (m, 4H), 1.72 (m, 4H), 1.52 (m, 2H). LC-MS (ES$^+$): m/z 235.00 [MH$^+$], t$_R$=1.18 min (2.0 minute run).

Step 2: Synthesis of 3-{[5-(benzyloxy)pentyl]oxy}propan-1-ol (Y)

To a 250-mL round-bottom flask with 9-BBN (0.5 M in THF, 77 mL) was added a solution of ({[5-(prop-2-en-1-yloxy)pentyl]oxy}methyl)benzene (X, 3.0 g, 12.80 mmol) in anhydrous tetrahydrofuran (20 mL) with stirring at 0° C. under an atmosphere of nitrogen. The resulting solution was stirred overnight at rt. LC-MS indicated formation of the desired product. Methanol (15 mL, with 30% sodium hydroxide and 30% H$_2$O$_2$) was added to the reaction and the resulting mixture was stirred at rt for 2 h. This mixture was then extracted with ethyl acetate (20 mL×3). The organic layers were combined, washed with saturated aqueous solution of sodium chloride (100 mL), dried over anhydrous sodium sulfate and then concentrated under reduced pressure to give a crude residue. The residue was purified by a flash silica gel chromatography (eluent: ethyl acetate/petroleum ether (v:v=1:1)) to provide 1.96 g of Y as light yellow oil. $^1$H NMR (300 MHz, CDCl$_3$): δ7.34 (m, 5H), 4.49 (s, 2H), 3.75 (m, 2H), 3.59 (m, 2H), 3.49 (m, 4H), 2.65 (bs, 1H), 1.84 (m, 2H), 1.68 (m, 4H), 1.50 (m, 2H). LC-MS (ES$^+$): m/z 253.17 [MH$^+$], t$_R$=1.44 min (2.6 minute run).

Step 3: Synthesis of tert-butyl 2-(3-{[5-(benzyloxy)pentyl]oxy}propoxy)acetate (Z)

To a stirred solution of 3-{[5-(benzyloxy)pentyl]oxy}propan-1-ol (Y, 3.7 g, 14.66 mmol) in dichloromethane (30 mL) was added a solution of NaOH in water (37%, 30 mL) followed by tert-butyl 2-bromoacetate (11.39 g, 58.39 mmol) and TBACl (4.17 g). The resulting mixture was stirred at rt overnight. LC-MS indicated formation of the desired product. The reaction mixture was then extracted with ethyl acetate (50 mL×3). The organic layers were combined, washed with saturated aqueous solution of sodium chloride (60 mL), dried over anhydrous sodium sulfate and then concentrated under reduced pressure to give a crude residue. The residue was purified by a flash silica gel chromatography (eluent: ethyl acetate/petroleum ether (v:v=1:2) to give 3.2 g of Z as a yellow oil. $^1$H NMR (400 MHz, CDCl$_3$): δ7.34 (s, 4H), 7.29 (m, 1H), 4.50 (s, 4H), 4.3 (m, 2H), 3.51 (m, 4H), 3.42 (m, 2H), 1.98 (m, 2H), 1.67 (m, 4H), 1.48 (s, 9H), 1.46 (m, 2H). LC-MS (ES$^+$): m/z 367.25 [MH$^+$], $t_R$=1.28 min (2.0 minute run).

Step 4: Synthesis of tert-butyl 2-[3-[(5-hydroxypentyl)oxy]propoxy]acetate (AA)

To a stirred solution of tert-butyl 2-(3-{[5-(benzyloxy)pentyl]oxy}propoxy)acetate (Z, 3.2 g, 8.73 mmol) in methanol (30 mL) was added AcOH (1.5 mL), palladium on carbon (1.5 g) under an atmosphere of nitrogen. Hydrogen was then introduced to the reaction mixture via a hydrogen balloon, and the reaction was stirred at rt for 3 h. The solid material was removed by filtration, the solution was concentrated under vacuum to provide 2.3 g of AA as light yellow oil, which was used for the next step without any further purifications. LC-MS (ES$^+$): m/z 277.10 [MH$^+$], $t_R$=0.86 min (2.0 minute run).

Step 5: Synthesis of tert-butyl 2-[3-({5-[(4-methylbenzenesulfonyl)oxy]pentyl}oxy)propoxy]acetate (AB)

To a stirred solution of tert-butyl 2-[3-[(5-hydroxypentyl)oxy]propoxy]acetate (AA, 2.3 g, 8.32 mmol) in dichloromethane (30 mL) was added 4-methylbenzene-1-sulfonyl chloride (3.17 g, 16.63 mmol), triethylamine (2.52 g, 24.90 mmol) and 4-dimethylaminopyridine (203 mg, 1.66 mmol) at rt. The resulting mixture was stirred overnight at rt. The resulting mixture was concentrated under reduced pressure to give a crude residue, which was purified by a flash silica gel chromatography (eluent: ethyl acetate/petroleum ether (v:v=1:2) to give 2.6 g of AB as a yellow oil. $^1$H NMR (300 MHz, CDCl$_3$): δ 7.77 (d, J=8.1 Hz, 2H), 7.36 (d, J=8.1 Hz, 2H), 4.51 (s, 2H), 4.31 (m, 2H), 4.13 (m, 2H), 3.52 (m, 4H), 2.05 (s, 3H), 1.97 (m, 2H), 1.69 (m, 4H), 1.48 (s, 9H), 1.46 (m, 2H). LC-MS (ES$^+$): m/z 431.20 [MH$^+$], $t_R$=1.21 min (2.0 minute run).

Step 1: Synthesis of 2-[3-({5-[(4-methylbenzenesulfonyl)oxy]pentyl}oxy)propoxy]acetic Acid (L-1)

To a stirred solution of tert-butyl 2-[3-({5-[(4-methylbenzenesulfonyl)oxy]pentyl}oxy)propoxy]acetate (AB, 1.3 g, 3.02 mmol) in dichloromethane (10 mL) was added trifluoroacetic acid (10 mL) at rt. The resulting solution was stirred at rt for 3 h. The reaction mixture was then concentrated under vacuum to give 1.5 g (crude) of L-1, which was used for next step without any further purification. LC-MS (ES$^+$): m/z 375.34 [MH$^+$], $t_R$=1.39 min (2.6 minute run).

The following Linkers (L) were prepared in a similar manner as for the preparation of L-1.

L-2: 2-(3-(3,3-dimethyl-5-(tosyloxy)pentyloxy)propoxy)acetic Acid

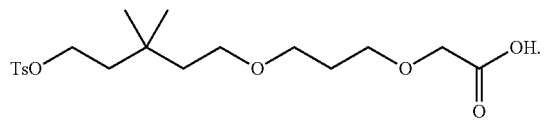

L-3: 2-(3-(3-hydroxy-5-(tosyloxy)pentyloxy)propoxy)acetic Acid

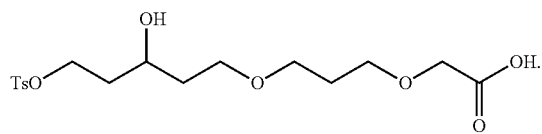

L-4: 2-(2-(2-(2-(tosyloxy)ethoxy)ethoxy)ethoxy)acetic Acid

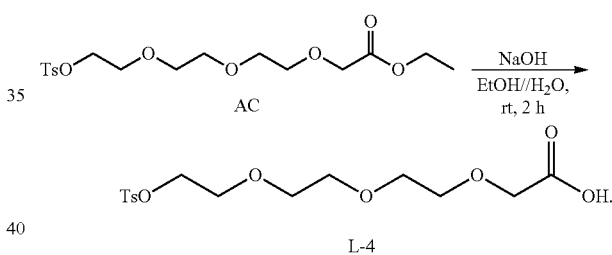

To a stirred solution of ethyl 2-[2-(2-{2-[(4-methylbenzenesulfonyl)oxy]ethoxy}ethoxy)ethoxy]acetate (AC, 2 g, 5.12 mmol, 1.00 equiv) in methanol (20 mL) was added a solution of NaOH (500 mg, 12.50 mmol) in water (4 mL), and the resulting mixture was stirred at rt for 2 h. Aqueous hydrogen chloride (1 M) was then added to the reaction mixture to adjust pH to ~5. Solids precipitated were collected by filtration to give L-4 (yield: 98%). Mass (ES+): m/z 363, [MH+].

The following Linkers (L) were prepared in a similar manner as for the preparation of L-4.

L-5: 2-(2-((2R,3R)-3-(2-(tosyloxy)ethoxy)butan-2-yloxy)ethoxy)acetic Acid

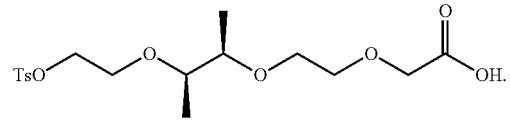

L-6: 2-(2-((2S,3S)-3-(2-(tosyloxy)ethoxy)butan-2-yloxy)ethoxy)acetic Acid

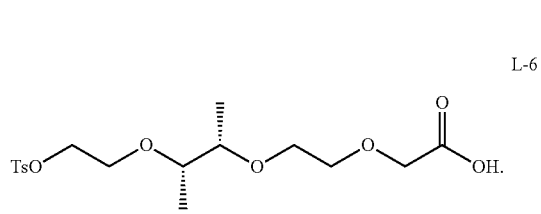 [SMILES: Cc1ccc(S(=O)(=O)OCCO[C@@H](C)[C@H](C)OCCOCC(=O)O)cc1]

L-7: 2-(4-(4-(tosyloxy)butoxy)butoxy)acetic Acid

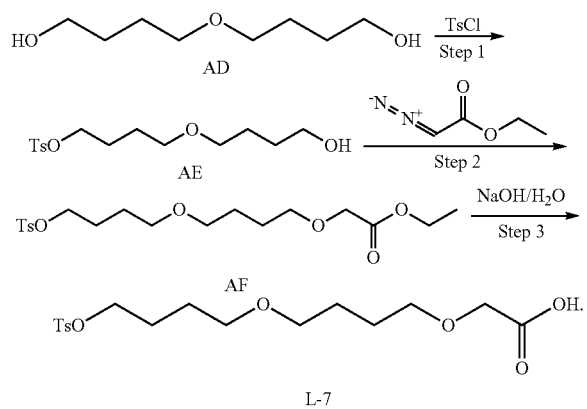

Step 1: Synthesis of 4-{4-[(4-methylbenzenesulfonyl)oxy]butoxy}butan-1-ol (AE)

To a stirred solution of 4-(4-hydroxybutoxy)butan-1-ol (AD, 2 g, 12.33 mmol) in dichloromethane (20 mL) was added Ag$_2$O (4.25 g, 18.49 mmol), KI (409 mg, 2.46 mmol) and TsCl (2.345 g, 12.30 mmol). The resulting mixture was stirred at rt for 12 h. The inorganic salt formed was removed by filtration and the organic solution was concentrated under reduced pressure to give a crude residue. The residue was purified by flash silica gel chromatography (eluent: ethyl acetate/petroleum ether (v:v=1:1)) to give AE (yield: 28%) as a colorless oil.

Step 2: Synthesis of ethyl 2-(4-{4-[(4-methylbenzenesulfonyl)oxy]butoxy}butoxy)acetate (AF)

To a stirred solution of 4-{4-[(4-methylbenzenesulfonyl) oxy]butoxy}butan-1-ol (AE, 1.1 g, 3.48 mmol) in dichloromethane (10 mL) was slowly added BF$_3$.Et$_2$O (49.4 mg, 0.35 mmol) followed by ethyl 2-diazoacetate (794 mg, 6.96 mmol) at 0° C. The resulting mixture was stirred overnight at rt. The reaction was then quenched by water (2.0 mL). The resulting mixture was extracted with dichloromethane (50 mL×3), the organic layers were combined, dried over anhydrous sodium sulfate and then concentrated under reduced pressure to give a crude residue. The residue was purified by flash silica gel chromatography (eluent: ethyl acetate/petroleum ether (v:v=1:4) to give AF (yield: 93 as light yellow oil. Mass (ES$^+$): m/z 403.10 [MH$^+$].

Step 3: Synthesis of 2-(4-{4-[(4-methylbenzenesulfonyl)oxy]butoxy}butoxy)acetic Acid (L-7)

To a stirred solution of ethyl 2-(4-{4-[(4-methylbenzenesulfonyl)oxy]butoxy}butoxy)acetate (AF, 1.3 g, 3.23 mmol) in methanol (25 mL) was added a solution of NaOH (388 mg, 9.70 mmol) in water (6 mL) at rt. The resulting solution was stirred at rt for 4 h. The bulk of organic solvent was removed under reduced pressure, to the resulting mixture was added aqueous hydrogen chloride (1.0 M) to adjust the pH=~5. The solution was then extracted with ethyl acetate (250 mL×3), the organic layers were combined and dried over anhydrous sodium sulfate, concentrated under reduced pressure to give I-7 (yield: 93%) as light yellow oil. Mass (ES$^+$): m/z 375.05 [MH$^+$].

L-8: tert-butyl 2-(3-(4-(tosyloxy)butoxy)propoxy) acetate

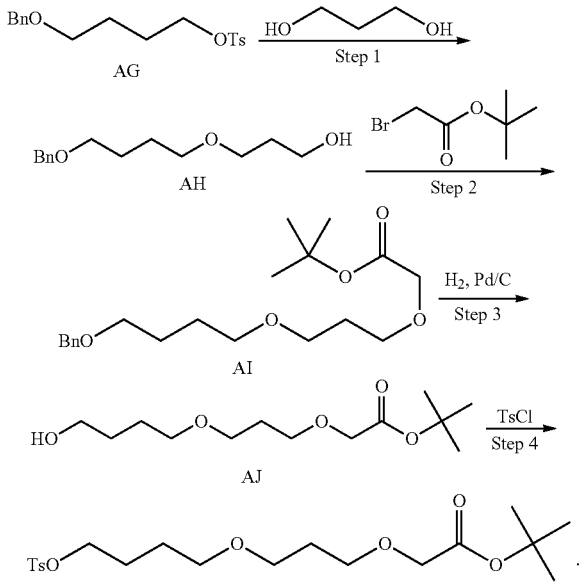

Step 1. Synthesis of 3-[4-(benzyloxy)butoxy]propan-1-ol (AH)

To a stirred solution of propane-1, 3-diol (1.52 g, 19.98 mmol) in N, N-dimethylformamide (20 mL) was added sodium hydride (840 mg, 35.00 mmol) at rt, the resulting mixture was stirred at rt for 30 min. Then to the mixture was added 4-(benzyloxy)butyl 4-methylbenzene-1-sulfonate (AG, 6.68 g, 19.97 mmol) and the reaction was stirred overnight at 50° C. TLC indicated formation of the desired product, at this time the reaction was allowed to cool down to rt. Water (10 mL) was added slowly to quench the reaction; the resulting mixture was then extracted with ethyl acetate (80 mL×2). The organic layers were combined, washed with saturated aqueous solution of sodium chloride (20 mL), dried over anhydrous sodium sulfate and then concentrated under reduced pressure to give a crude residue, which was purified by flash silica gel chromatography (eluent: ethyl acetate/petroleum ether (v:v=1:2)) to give AH (yield: 67%) as a light yellow oil. $^1$H NMR (300 MHz, CDCl$_3$) δ 7.38-7.29 (m, 5H), 4.52 (m, 2H), 3.80 (m, 2H), 3.61 (m, 2H), 3.49-3.46 (m, 4H), 2.04 (m, 2H), 1.82 (m, 2H), 1.68 (m, 2H); Mass (ES$^+$): m/z 239.05 [MH$^+$].

Step 2. Synthesis of tert-butyl 2-[3-[4-(benzyloxy)butoxy]propoxy]acetate (AI)

To a stirred solution of 3-[4-(benzyloxy)butoxy]propan-1-ol (AH, 2.38 g, 9.99 mmol) in dichloromethane (15 mL) was added tert-butyl 2-bromoacetate (7.76 g, 39.78 mmol), TBAC (2.78 g, 10.00 mmol) followed by aqueous sodium hydroxide (37%, 15 mL). The resulting mixture was stirred overnight at rt. The reaction mixture was then extracted with dichloromethane (100 mL×3), the organic layers were combined, washed with saturated aqueous solution of sodium chloride (20 mL), dried over anhydrous sodium sulfate and then concentrated under reduced pressure to give a crude residue. The residue was purified by flash silica gel chromatography (eluent: ethyl acetate/petroleum ether (v:v=1:5)) to give AI (yield 57%) as a yellow oil. Mass (ES$^+$): m/z 353.10 [MH$^+$].

Step 3. Synthesis of tert-butyl 2-[3-(4-hydroxybutoxy)propoxy]acetate (AJ)

To a stirred mixture of tert-butyl 2-[3-[4-(benzyloxy)butoxy]propoxy]acetate (AI, 1 g, 2.84 mmol), palladium on carbon (10%, 200 mg) in methanol (20 mL) was added acetic acid (0.05 mL) under a nitrogen atmosphere. Hydrogen was then introduced to the reaction mixture via a balloon, the reaction was then stirred overnight at rt. The insoluble solids were removed by filtration and the solution phase was concentrated under reduced pressure to give the desired product (yield: 94%) as a yellow oil. Mass (ES$^+$): m/z 263.05 [MH$^+$].

Step 4. Synthesis of tert-butyl 2-(3-{4-[(4-methylbenzenesulfonyl)oxy]butoxy}propoxy)acetate (L-8)

To a stirred solution of tert-butyl 2-[3-(4-hydroxybutoxy)propoxy]acetate (AJ, 700 mg, 2.67 mmol) in dichloromethane (10 mL) was added 4-methylbenzene-1-sulfonyl chloride (558.4 mg, 2.93 mmol), TEA (539.5 mg, 5.33 mmol) and 4-dimethylaminopyridine (32.6 mg, 0.27 mmol). The resulting mixture was stirred overnight at rt. The bulk of solvent was removed under reduced pressure to give a crude residue, which was purified by flash silica gel chromatography (eluent: ethyl acetate/petroleum ether (v:v=1:2)) to give titled product (yield: 52%) as a yellow oil. $^1$H NMR (300 MHz, CDCl$_3$) δ7.79 (d, J=8.4 Hz, 2H), 7.35 (d, J=8.0 Hz, 2H), 4.05 (m, 2H), 3.95 (s, 2H), 3.59 (m, 2H), 3.48 (m, 2H), 3.38 (m, 2H), 2.46 (s, 3H), 1.82 (m, 2H), 1.70 (m, 2H), 1.57 (m, 2H), 1.50 (s, 9H); Mass (ES$^+$): m/z 417.05 [MH$^+$].

L-9: tert-butyl 2-(4-(3-(tosyloxy)propoxy)butoxy)acetate

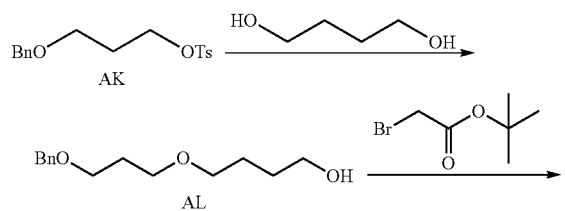

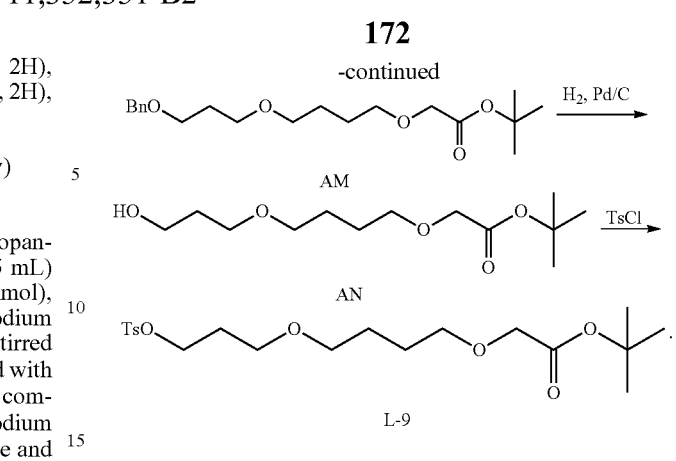

L-9 was prepared in a similar manner as that used to prepare L-8, except that AK was used in place of AG. Mass (ES$^+$): m/z 439.15 [MNa$^+$].

L-10: tert-butyl 2-(6-(tosyloxy)hexa-2,4-diynyloxy)acetate

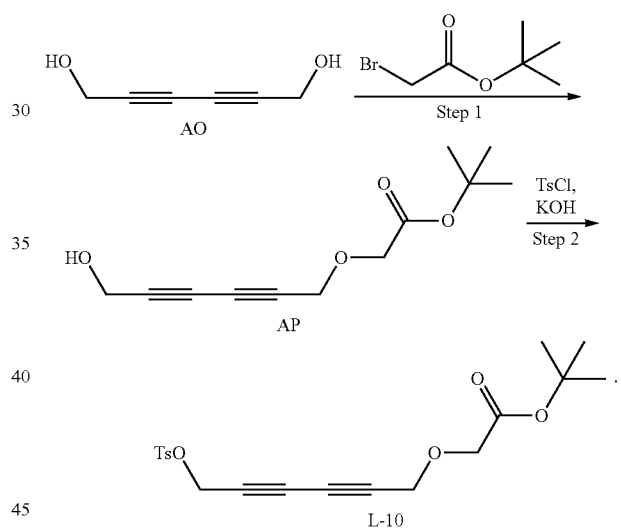

Step 1: Synthesis of tert-butyl 2-[(6-hydroxyhexa-2,4-diyn-1-yl)oxy]acetate (AP)

To a stirred solution of hexa-2, 4-diyne-1, 6-diol (AO, 100 mg, 0.91 mmol) in N, N-dimethylformamide (5 mL) was added sodium hydride (32 mg, 1.33 mmol) at 0° C. The resulting mixture was then warmed up to rt and stirred at rt for 30 min. The reaction mixture was cooled to 0° C. followed by addition of tert-butyl 2-bromoacetate (176 mg, 0.90 mmol), and the resulting mixture was stirred at 0° C. for 2 h. LC-MS indicated formation of the desired product. The reaction was then quenched by water (10 mL, added slowly) at 0° C., and was extracted with ethyl acetate (20×2 mL). The organic layers were combined, dried over anhydrous sodium sulfate and then concentrated under reduced pressure to give a crude residue, which was purified by flash silica gel chromatography (eluent: ethyl acetate/petroleum ether (v:v=1:2)) to give AP (yield: 49%) as a yellow oil.

Step 2. Synthesis of tert-butyl 2-({6-[(4-methylbenzenesulfonyl)oxy]hexa-2,4-diyn-1-yl}oxy)acetate (L-10)

To a stirred solution of tert-butyl 2-[(6-hydroxyhexa-2,4-diyn-1-yl)oxy]acetate (AP, 50 mg, 0.22 mmol) in ether (2 mL) was added 4-toluenesulfonyl chloride (51 mg, 0.27 mmol) at 0° C., followed by potassium hydroxide (125 mg, 2.23 mmol) in several batches at 0° C. The resulting mixture was stirred at 0° C. for 4 h. LC-MS indicated formation of the desired product. Water (10 mL) was added to the reaction, and the resulting mixture was extracted with ethyl acetate (20 mL×2). The organic layers were combined, dried over anhydrous sodium sulfate and then concentrated under reduced pressure to give a crude residue, which was purified by flash silica gel chromatography (eluent: ethyl acetate/petroleum ether (v:v=1:2)) to give L-10 (yield: 71%) as a yellow oil. $^1$H NMR (300 MHz, CDCl$_3$): δ 7.83 (d, J=6.0 Hz, 2H), 7.39 (d, J=6.0 Hz, 2H), 4.79 (s, 2H), 4.37 (s, 2H), 4.05 (s, 2H), 2.48 (s, 3H), 1.51 (s, 9H); LC-MS (ES$^+$): m/z 401.05 [MNa$^+$], $t_R$=1.71 min (2.6 minute run).

The following Linkers (L) were prepared in a similar manner as for the preparation of L-10.

L-11: tert-butyl 3-(6-(tosyloxy)hexa-2,4-diynyloxy)propanoate

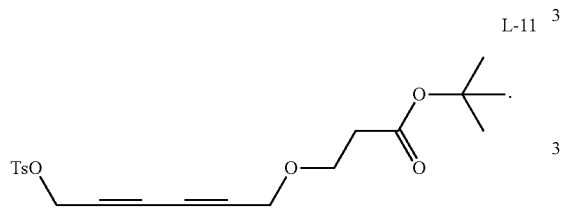

L-12: tert-butyl 4-(6-(tosyloxy)hexa-2,4-diynyloxy)butanoate

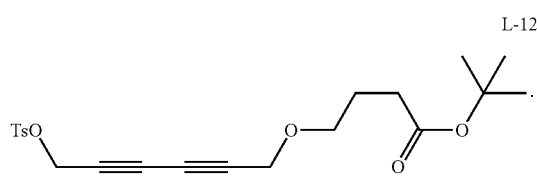 [SMILES: Cc1ccc(S(=O)(=O)OCC#CC#CCOCCCC(=O)OC(C)(C)C)cc1]

L-13: ethyl 2-(2-(2-aminoethoxy)ethoxy)acetate Hydrochloride

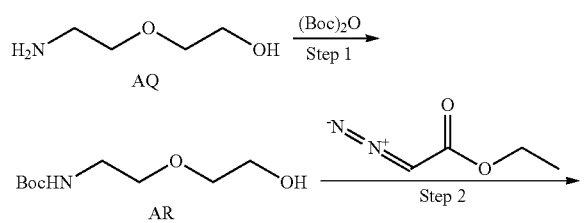

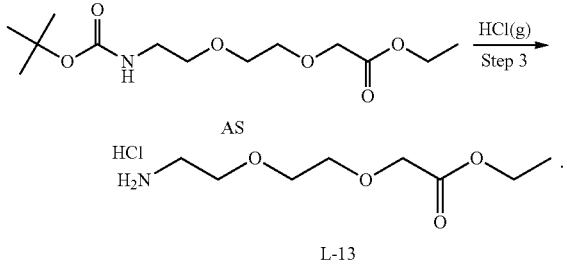

Step 1: Synthesis of tert-butyl N-[2-(2-hydroxyethoxy)ethyl]carbamate (AR)

To a stirred solution of 2-(2-aminoethoxy)ethan-1-ol (AQ, 5.25 g, 49.94 mmol) in tetrahydrofuran (100 mL) was added aqueous solution of sodium bicarbonate (20% (w/w), 40 ml) and (Boc)$_2$O (11.4 g, 52.23 mmol, added in several batches) at 0° C. The resulting mixture was then warmed up slowly to rt and stirred at rt for 5 h. The bulk of organic solvent was removed under reduced pressure and the resulting residue was diluted with water (300 mL), extracted with of ethyl acetate (100 mL×3). The organic layers were combined, washed with saturated aqueous solution of sodium chloride (20 mL×2), dried over anhydrous sodium sulfate and then concentrated under reduced pressure to give AR (yield: 98%) as colorless oil.

Step 2: Synthesis of ethyl 2-[2-(2-{[(tert-butoxy)carbonyl]amino}ethoxy)ethoxy]acetate (AS)

To a stirred solution of tert-butyl N-[2-(2-hydroxyethoxy)ethyl]carbamate (AR, 4.0 g, 19.49 mmol) in dichloromethane (30 mL) was added 1-diazo-3-methoxypropan-2-one (3.34 g, 29.27 mmol) and BF$_3$-Et$_2$O (0.2 mL) at rt. The resulting solution was stirred at rt for 2 h. Water (20 mL) was added to the reaction mixture, organic layer was separated and washed with brine (20 mL), dried over anhydrous sodium sulfate and concentrated under reduced pressure to give a crude residue. The residue was purified by flash silica gel chromatography (eluent: ethyl acetate/petroleum ether (v:v=1:2)) to give AS (yield: 18%) as yellow solid. $^1$H NMR (400 MHz, CDCl$_3$): δ 4.25-4.22 (q, J=7.2 Hz, 2H), 4.14 (s, 2H), 3.74 (b, 2H), 3.72 (b, 1H), 3.67-3.32 (m, 4H), 1.414 (s, 9H), 1.31 (t, J=7.2 Hz, 3H).

Step 3: Synthesis of ethyl 2-[2-(2-aminoethoxy)ethoxy]acetate Hydrochloride (L-13)

To a stirred solution of ethyl 2-[2-(2-{[(tert-butoxy)carbonyl]amino}ethoxy)ethoxy]acetate (AS, 500 mg, 1.72 mmol) in 1,4-dioxane (10 mL) was introduced hydrogen chloride (gas) via bubbling at rt for 2 h. The solvent was then removed under vacuum to give L-13 (yield: 99%). LC-MS (ES$^+$): m/z 192.00 [MH$^+$], $t_R$=0.41 min (2.0 minute run).

L-14: ethyl 2-(5-aminopentyloxy)acetate

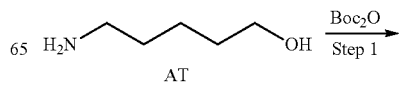

175

-continued

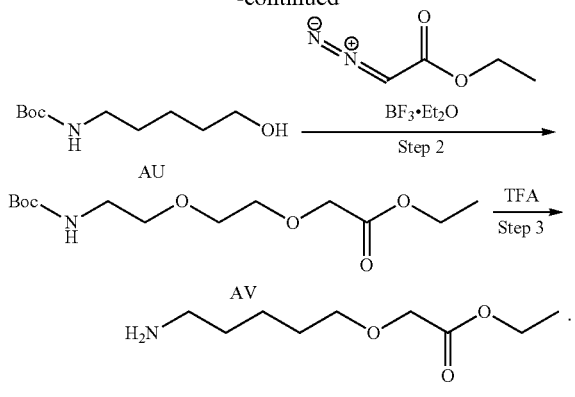

L-14

Step 1: Synthesis of tert-butyl 5-hydroxypentylcarbamate (AU)

To a stirred solution of 5-aminopentan-1-ol (AT, 3.1 g, 30.05 mmol) in dichloromethane (30 mL) was added di-tert-butyl dicarbonate (6.56 g, 30.06 mmol) at 0° C. The resulting mixture was then stirred at rt for 4 h. The solvent was removed under reduced pressure to give a crude residue which was purified by flash silica gel chromatography (eluent: ethyl acetate/petroleum ether (v:v=1:2)) to give AU (yield: 98%) as a colorless oil. LC-MS (ES$^+$): m/z 204.00 [MH$^+$], $t_R$=1.29 min (2.6 minute run).

Step 2: Synthesis of ethyl 2-[(5-{[(tert-butoxy)carbonyl]amino}pentyl)oxy]acetate (AV)

To a stirred solution of tert-butyl N-(5-hydroxypentyl) carbamate (AU, 1.5 g, 7.38 mmol) in dichloromethane (10 mL) was added BF$_3$Et$_2$O (0.1 mL) at 0° C. To this mixture was then added a solution of ethyl 2-diazoacetate (850 mg, 7.45 mmol) in dichloromethane (2 mL) at 0° C. The resulting mixture was allowed to warm up to rt and stirred at rt for 2 h. Saturated aqueous sodium bicarbonate (30 mL) was added to the reaction, the resulting mixture was extracted with ethyl acetate (150 mL×3). The organic layers were combined, dried over anhydrous sodium sulfate and then concentrated under reduced pressure to give a crude residue, which was purified by flash silica gel chromatography (eluent: ethyl acetate/petroleum ether (v:v=1:7)) to give AV (yield: 15%) as a colorless oil. LC-MS (ES$^+$): m/z 290.05 [MH$^+$], $t_R$=1.55 min (2.6 minute run).

Step 3: Synthesis of ethyl 2-(5-aminopentyloxy)acetate (L-14)

To a stirred solution of ethyl ethyl 2-[(5-{[(tert-butoxy) carbonyl]amino}pentyl)oxy]acetate (AV, 400 mg, 1.38 mmol) in dichloromethane (5 mL) was added trifluoroacetic acid (5 mL) and the resulting solution was stirred at rt for 2 h. The reaction mixture was then concentrated under vacuum to give L-14 (yield: 84%) as a yellow oil. LC-MS (ES$^+$): m/z 190.00 [MH$^+$], $t_R$=1.01 min (2.6 minute run).

176

L-15: methyl 2-(2-(2-(methylamino)ethoxy)ethoxy)acetate

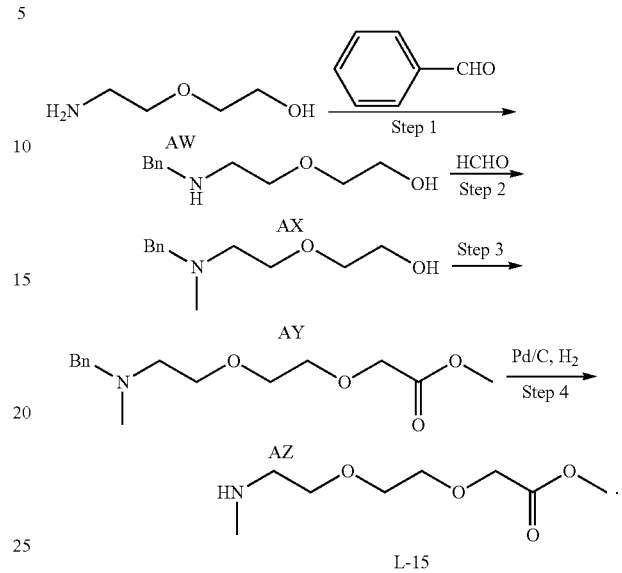

Step 1: Synthesis of 2-[2-(benzylamino)ethoxy]ethan-1-ol (AX)

To a stirred solution of 2-(2-aminoethoxy)ethan-1-ol (AW, 5.0 g) and benzaldehyde (5.0 g) in THF (50 mL) was added sodium triacetoxyborohydride (15.8 g, 74.5 mmol) at 0° C. The resulting solution was then stirred at rt for 4 h. Water (50 mL) was added to the reaction and the resulting mixture was extracted with ethyl acetate (50 mL×2). The organic layers were combined, dried over anhydrous sodium sulfate and then concentrated under reduced pressure to give a crude residue, which was purified by flash silica gel chromatography (eluent: dichloromethane/methanol (v:v=3: 1) to give AX (yield: 85%) as a white solid. LC-MS (ES$^+$): m/z 195.95[MH$^+$], $t_R$=0.22 min (2.0 minute run).

Step 2: Synthesis of 2-{2-[benzyl(methyl)amino] ethoxy}ethan-1-ol (AY)

To a stirred solution of 2-[2-(benzylamino)ethoxy]ethan-1-ol (AX, 10.0 g) in methanol (200 mL) was added formaldehyde (38% in water) (4.9 mL) and triacetoxyborohydride (17.0 g) at rt. The resulting solution was stirred at rt for 2 h. Saturated aq. sodium bicarbonate (100 mL) was added to the reaction, and bulk of organic solvent was then removed under reduced pressure. The resulting mixture was extracted with ethyl acetate (200 mL×3). The organic layers were combined, dried over anhydrous sodium sulfate and then concentrated under reduced pressure followed by high vacuum pump to give AY (yield: 33%) as a yellow oil. LC-MS (ES$^+$): m/z 210.00 [MH$^+$], $t_R$=0.43 min (2.0 minute run).

Step 3: Synthesis of methyl 2-(2-{2-[benzyl (methyl)amino]ethoxy}ethoxy)acetate (AZ)

To a stirred solution of 2-{2-[benzyl(methyl)amino] ethoxy}ethan-1-ol (AY, 2 g) in dichloromethane (20 mL) was added a solution of sodium hydroxide (37%) in water (20 mL) followed by tert-butyl 2-bromoacetate (7.76 g) and TBAC (2.78 g) at rt. The resulting mixture was stirred at rt for 15 h. The aqueous layer was separated, and to which aq. hydrogen chloride (4N) was added to adjust the pH to ~3 before it was concentrated under reduced pressure to give a crude residue. Methanol (20 mL) was then added to this residue and insoluble salts were filtered out. The solution was concentrated under vacuum to give 2-(2-[2-[benzyl (methyl)amino]ethoxy]ethoxy)acetic acid (yield: 78%) as a yellow oil. To a stirred solution of 2-(2-{2-[benzyl(methyl) amino]ethoxy}ethoxy)acetic acid (2 g, 7.48 mmol, 1.00 equiv) prepare above in methanol (50 mL) was slowly added sulfuric acid (2 mL) at rt. The resulting solution was stirred at 70° C. in an oil bath for 3 h. The bulk of solvent was removed under reduced pressure to give a residue, which was diluted with $H_2O$ (30 mL). Sodium carbonate was then added to the mixture to adjust the pH to ~8. The mixture was then extracted with ethyl acetate (50 mL×2), the organic layers were combined, dried over anhydrous sodium sulfate and then concentrated under reduced pressure followed by high vacuum pump to give AZ (yield: 29%) as a yellow oil. LC-MS (ES$^+$): m/z 281.95 [MH$^+$], $t_R$=0.30 min (2.0 minute run).

Step 4: Synthesis of methyl 2-{2-[2-(methylamino) ethoxy]ethoxy}acetate (L-15)

To a stirred mixture of methyl 2-(2-{2-[benzyl(methyl) amino]ethoxy}ethoxy)acetate (AZ, 600 mg, 2.13 mmol) and palladium on carbon (300 mg) in methanol (30 mL) under a nitrogen atmosphere was charged with hydrogen gas via a balloon. The resulting mixture was stirred at rt for 15 h. The solid material was removed by filtration and the solution was concentrated under vacuum to give L-15 (400 mg) as yellow oil, which was used for next step without any further purifications. LC-MS (ES$^+$): m/z 191.95 [MH$^+$], $t_R$=0.31 min (2.0 minute run).

L-16: ethyl 2-(5-(methylamino)pentyloxy)acetate

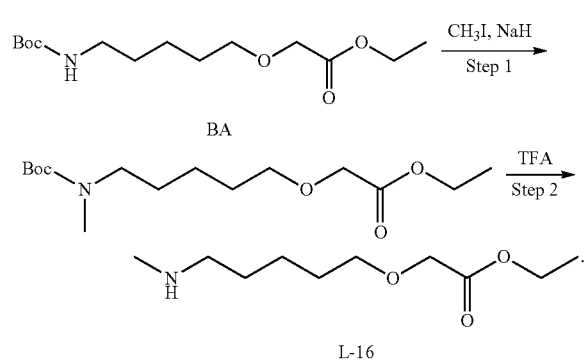

Step 1: Synthesis of ethyl 2-[(5-{[(tert-butoxy)carbonyl](methyl)amino}pentyl)oxy]acetate (BB)

To a stirred solution of ethyl 2-[(5-{[(tert-butoxy)carbonyl]amino}pentyl)oxy]acetate (BA, 1.1 g, 3.8 mmol) in N,N-dimethylformamide (10 mL) was added $CH_3I$ (0.71 mL, 11.4 mmol) at 0° C., followed by sodium hydride (304 mg, 7.60 mmol, 60% in mineral oil) in several portions at 0° C. The resulting mixture was stirred at rt for 16 h. Water (1.0 mL) was added and the resulting mixture was extracted with ethyl acetate (50 mL×2). The organic layers were combined, washed with saturated aqueous solution of sodium chloride (100 mL), dried over anhydrous sodium sulfate and then concentrated under reduced pressure to give a crude residue which was purified by a flash silica gel chromatography (eluent: ethyl acetate/petroleum ether (v:v=1:10)) to give BB (yield: 21%) as a yellow oil. LC-MS (ES$^+$): m/z 326.20 [MNa$^+$], $t_R$=1.55 min (2.6 minute run).

Step 2: Synthesis of ethyl 2-{[5-(methylamino)pentyl]oxy}acetate (L-16)

To a stirred solution of ethyl 2-[(5-{[(tert-butoxy)carbonyl](methyl)amino}pentyl)oxy]acetate (BB, 240 mg, 0.79 mmol) in dichloromethane (5 mL) was added trifluoroacetic acid (0.5 mL). The resulting solution was stirred at rt for 16 h. The solvents were removed under recued pressure followed by high vacuum pump to give L-16 (yield: 99%) as a yellow oil. LC-MS (ES$^+$): m/z 204.20 [MH$^+$], $t_R$=0.56 min (2.0 minute run).

L-17: 2-(3-(2-(tosyloxy)ethoxy)propoxy)acetic Acid

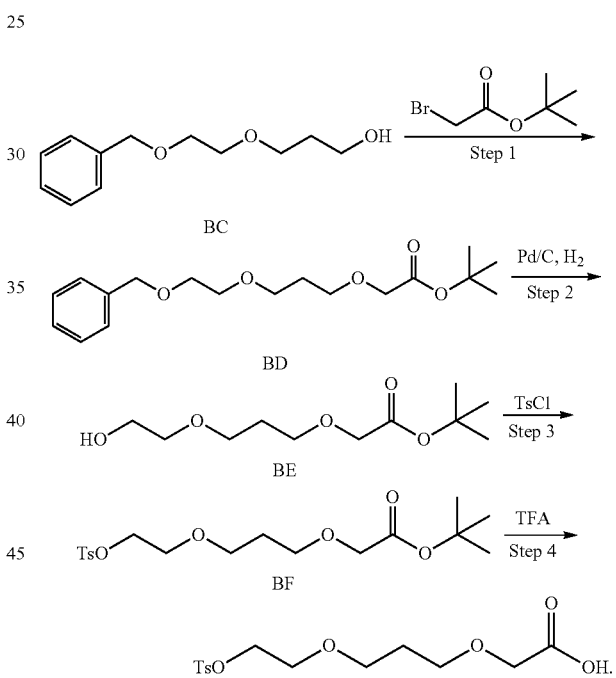

Step 1: Synthesis of tert-butyl 2-{3-[2-(benzyloxy) ethoxy]propoxy}acetate (BD)

To a stirred solution of 3-[2-(benzyloxy)ethoxy]propan-1-ol (BC, 1.8 g, 8.56 mmol) and tert-butyl 2-bromoacetate (6.6 g, 33.84 mmol, 4.00 equiv) in dichloromethane (40 mL) was added TBAC (2.4 g) and aq. Solution of sodium hydroxide (37%, 40 mL). The resulting mixture was stirred at rt overnight. LC-MS indicated formation of the desired product. The reaction mixture was then extracted with ethyl acetate (150×3 mL), the organic layers combined, dried over anhydrous sodium sulfate and concentrated under reduced pressure to give a crude residue, which was purified by a flash silica gel chromatography (eluent: ethyl acetate/petroleum ether (v:v=1:2) to give BD (yield: 90%) as a colorless oil. $^1$H NMR (300 MHz, CDCl$_3$): δ 7.35-7.27 (m, 5H), 4.57 (s, 2H), 3.94 (s, 2H), 3.63-3.57 (m, 8H), 1.96-1.87 (m, 2H), 1.47 (s, 9H); LC-MS (ES$^+$): m/z 347.10 [MNa$^+$], $t_R$=1.72 min (2.6 minute run).

Step 2: Synthesis of tert-butyl 2-[3-(2-hydroxyethoxy)propoxy]acetate (BE)

To a stirred mixture of tert-butyl 2-{3-[2-(benzyloxy) ethoxy]propoxy}acetate (BD, 2.5 g, 7.71 mmol) and palladium on carbon (2.0 g) in methanol (20 mL) under a nitrogen atmosphere was introduced hydrogen gas via a balloon. The resulting mixture was stirred overnight at rt under hydrogen gas atmosphere. LC-MS indicated completion of the reaction. The solids were removed by filtration, the solution was concentrated under vacuum to give BE (yield: 99%) as a colorless oil. LC-MS (ES$^+$): m/z 257.10 [MNa$^+$], $t_R$=1.21 min (2.6 minute run).

Step 3: Synthesis of tert-butyl 2-(3-{2-[(4-methyl-benzenesulfonyl)oxy]ethoxy}propoxy)acetate (BF)

To a stirred solution of tert-butyl 2-[3-(2-hydroxyethoxy) propoxy]acetate (BE, 1.8 g, 7.68 mmol) in dichloromethane (50 mL) was added 4-toluenesulfonyl chloride (2.2 g, 11.54 mmol), triethylamine (2.33 g, 23.03 mmol) and 4-dimethylaminopyridine (95 mg, 0.78 mmol). The resulting mixture was stirred overnight at rt. LC-MS indicated formation of the desired product. The reaction mixture was concentrated under reduced pressure to give a crude residue, which was purified by a flash silica gel chromatography (eluent: ethyl acetate/petroleum ether (v:v=1:2) to give BF (yield: 80%) as a yellow oil. $^1$H NMR (400 MHz, CDCl$_3$): δ 7.80 (d, J=8.0 Hz, 2H), 7.34 (d, J=8.4 Hz, 2H), 4.15 (t, J=3.6 Hz, 2H), 3.93 (s, 2H), 3.61 (t, J=3.6 Hz, 2H), 3.55-3.49 (m, 4H), 2.45 (s, 3H), 1.85-1.78 (m, 2H), 1.48 (s, 9H); LC-MS (ES$^+$): m/z 411.00 [MNa$^+$], $t_R$=1.12 min (2.0 minute run).

Step 4: Synthesis of 2-(3-{2-[(4-methylbenzene-sulfonyl)oxy]ethoxy}propoxy)acetic Acid (L-17)

To a stirred solution of tert-butyl 2-(3-{2-[(4-methylbenzenesulfonyl)oxy]ethoxy}propoxy)acetate (BF, 400 mg, 1.03 mmol) in dichloromethane (3 mL) was added trifluoroacetic acid (1 mL) at rt. The resulting solution was stirred at rt for 1 h. LC-MS indicated completion of the reaction. The reaction mixture was concentrated under reduced pressure to give L-17 (350 mg) as a yellow oil, which was used for next step without further purifications. LC-MS (ES$^+$): m/z 332.90 [MH$^+$], $t_R$=0.81 min (2.0 minute run).

Unless otherwise noted, the following intermediates and their analogs (for examples, but not limited to, analogs with substitutions such as halogens) were synthesized according to similar procedures described above for the synthesis of L-17, by utilizing corresponding starting materials and reagents.

L-18: 2-(2-hydroxyethoxy)ethyl 4-methylbenzenesulfonate

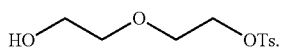

L-19: ethyl 2-(2-(2-(tosyloxy)ethoxy)ethoxy)acetate

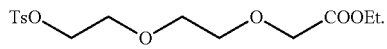 [SMILES: CCOC(=O)COCCOCCOS(=O)(=O)c1ccc(C)cc1]

L-20: ethyl 3-(2-(2-(tosyloxy)ethoxy)ethoxy)propanoate

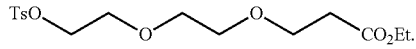

L-21: ethyl 5-(tosyloxy)pentanoate

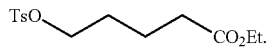

L-22: ethyl 3-(2-(tosyloxy)ethoxy)propanoate

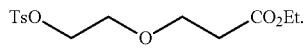

L-23: ethyl 2-(5-(tosyloxy)pentyloxy)acetate

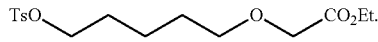 [SMILES: CCOC(=O)COCCCCCOS(=O)(=O)c1ccc(C)cc1]

L-24: ethyl 3-(5-(tosyloxy)pentyloxy)propanoate

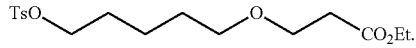

L-25: 5-hydroxypentyl 4-methylbenzenesulfonate

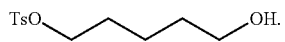 [SMILES: Cc1ccc(S(=O)(=O)OCCCCCO)cc1]

L-26: ethyl 2-(5-(tosyloxy)pentyloxy)acetate

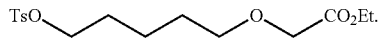 [SMILES: CCOC(=O)COCCCCCOS(=O)(=O)c1ccc(C)cc1]

L-27: ethyl 2-(3-(tosyloxy)propoxy)acetate

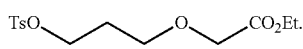

L-28: ethyl 2-(2-(tosyloxy)ethoxy)acetate

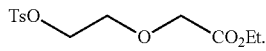

L-29: ethyl 2-(4-(2-(tosyloxy)ethoxy)butoxy)acetate

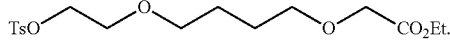

L-30: 2-(2-(2-hydroxyethoxy)ethoxy)ethyl 4-methylbenzenesulfonate

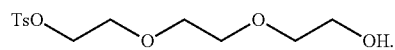 [SMILES: Cc1ccc(S(=O)(=O)OCCOCCOCCO)cc1]

L-31: 2-((2R,3R)-3-(2-hydroxyethoxy)butan-2-yloxy)ethyl 4-methylbenzenesulfonate

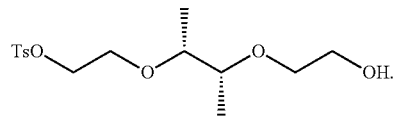 [SMILES: Cc1ccc(S(=O)(=O)OCCO[C@H](C)[C@@H](C)OCCO)cc1]

SYNTHESIS OF EXAMPLES

Example 1

(2S,4R)-1-((S)-2-(2-(3-(5-(4-(3-(4-cyano-3-(trifluoromethyl)phenyl)-5,5-dimethyl-4-oxo-2-thioxoimidazolidin-1-yl)phenoxy)pentyloxy)propoxy)acetamido)-3,3-dimethylbutanoyl)-4-hydroxy-N-(4-(4-methylthiazol-5-yl)benzyl)pyrrolidine-2-carboxamide

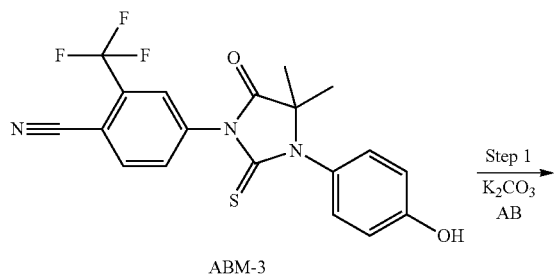

ABM-3

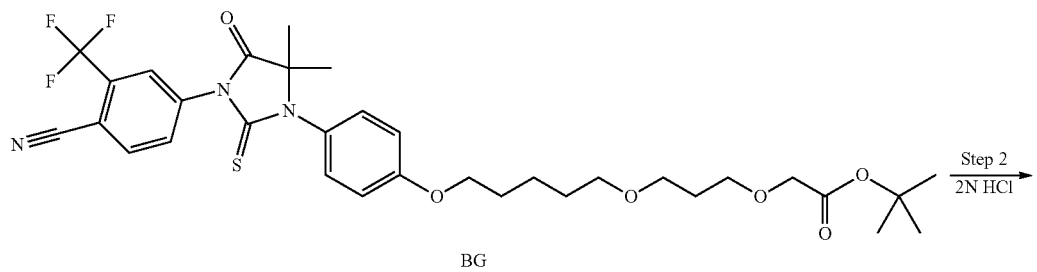

BG

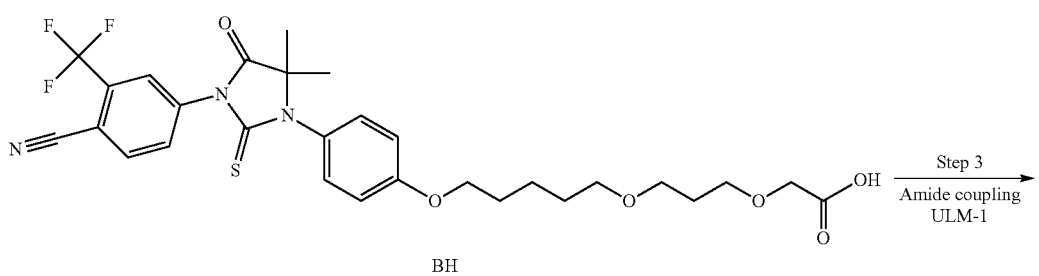

BH

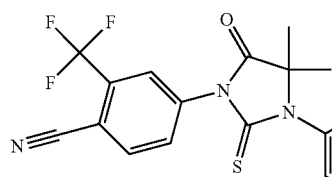
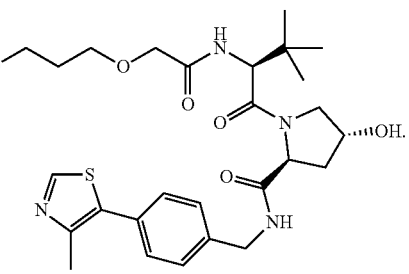

Example 1

Step 1: Synthesis of tert-butyl 2-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propoxy)acetate (BG)

To a stirred solution of tert-butyl 2-[3-[(5-[[(4-methylbenzene)sulfonyl]oxy]pentyl)oxy]propoxy]acetate (AB, 150 mg, 0.35 mmol) in acetonitrile (10 mL) was added 4-[3-(4-hydroxyphenyl)-4,4-dimethyl-5-oxo-2-sulfanylideneimidazolidin-1-yl]-2-(trifluoromethyl)benzonitrile (ABM-3, 141 mg, 0.35 mmol) and potassium carbonate (144 mg, 1.04 mmol). The resulting mixture was stirred overnight at 80° C. in an oil bath. LC-MS indicated formation of the desired product. The reaction mixture was then extracted with ethyl acetate (20 mL×2). The organic layers were combined, washed with saturated aqueous solution of sodium chloride (20 mL), dried over anhydrous sodium sulfate and then concentrated under reduced pressure to give a crude residue, which was purified by flash silica gel chromatography (eluent: ethyl acetate/petroleum ether, v:v=1:1) to give 0.22 g of BG as a yellow oil. $^1$H NMR (400 MHz, CDCl$_3$): δ 7.96 (s, 2H), 7.86 (d, J=8.6 Hz, 1H), 7.19 (d, J=8.8 Hz, 2H), 7.02 (d, J=8.6 Hz, 2H), 4.50 (s, 2H), 4.30 (t, J=6.4 Hz, 2H), 4.02 (t, J=6.4 Hz, 2H), 3.53 (m, 2H), 3.44 (m, 2H), 1.96-1.80 (m, 4H), 1.69-1.53 (m, 2H), 1.49 (s, 6H), 1.48 (s, 9H), 1.44-1.22 (m, 2H); Mass (ES$^+$): m/z 686.35 [MNa$^+$].

Step 2: synthesis of 2-(3-[[5-(4-[3-[4-cyano-3-(trifluoromethyl)phenyl]-5,5-dimethyl-4-oxo-2-sulfanylideneimidazolidin-1-yl]phenoxy)pentyl]oxy]propoxy)acetic Acid (BH)

To a stirred solution of tert-butyl 2-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propoxy)acetate (BG, 220 mg, 0.33 mmol) in dioxane (4.0 mL) was added hydrogen chloride (2N in water, 1.0 mL). The resulting mixture was stirred at 80° C. for 2 h. LC-MS indicated formation of the desired product. The resulting mixture was concentrated under reduced pressure to provide 200 mg of BH as light yellow oil. Mass (ES$^+$): m/z 608.25 [MH$^+$].

Step 3: Synthesis of Example 1

To a stirred solution of 2-(3-[[5-(4-[3-[4-cyano-3-(trifluoromethyl)phenyl]-5,5-dimethyl-4-oxo-2-sulfanylideneimidazolidin-1-yl]phenoxy)pentyl]oxy]propoxy)acetic acid (BH, 160 mg, 0.26 mmol) in N,N-dimethylformamide (5 mL) was added (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1, 182 mg, 0.39 mmol), DIPEA (151 mg, 1.17 mmol), EDCI (101 mg, 0.53 mmol) and HOBt (70 mg, 0.52 mmol). The resulting mixture was stirred at rt for 5 h and LC-MS indicated formation of the desired product. Water (20 mL) was added to the reaction, the resulting mixture was extracted with ethyl acetate (20 mL×2). The organic layers were combined, washed with saturated aqueous solution of sodium chloride (20 mL), dried over anhydrous sodium sulfate and then concentrated under reduced pressure to give a crude residue. The residue was purified by Prep-HPLC to give 60 mg of Example 1 as a white solid. $^1$H NMR (400 MHz, CD$_3$OD): δ 8.88 (s, 1H), 8.16 (d, J=8.0 Hz, 2H), 8.00 (s, 1H), 7.49-7.42 (m, 4H), 7.28 (d, J=8.8 Hz, 2H), 7.06 (m, 2H), 4.87 (s, 1H), 4.59 (m, 3H), 4.37 (m, 1H), 4.05 (m, 4H), 3.88 (m, 2H), 3.65 (m, 2H), 3.58 (m, 2H), 3.50 (m, 2H), 2.48 (s, 3H), 2.25 (m, 1H), 2.10 (m, 1H), 1.90 (m, 2H), 1.80 (m, 2H), 1.66 (m, 2H), 1.56 (s, 8H), 1.04 (s, 9H); LC-MS (ES$^+$): m/z 1020.20 [MH$^+$], t$_R$=2.28 min (3.6 minute run).

Example 2

(2S,4R)-1-((S)-2-(2-(3-(5-(4-(3-(6-cyano-5-(trifluoromethyl)pyridin-3-yl)-5,5-dimethyl-4-oxo-2-thioxoimidazolidin-1-yl)phenoxy)pentyloxy)propoxy)acetamido)-3,3-dimethylbutanoyl)-4-hydroxy-N-(4-(4-methylthiazol-5-yl)benzyl)pyrrolidine-2-carboxamide

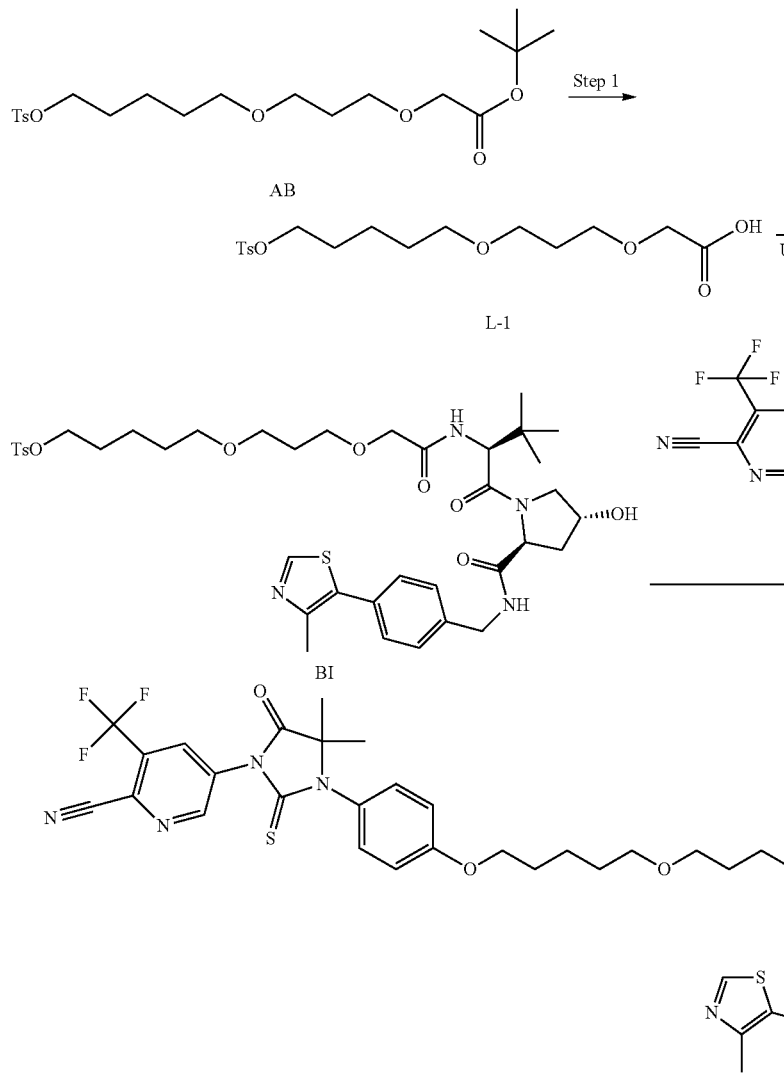

Step 1: Synthesis of 2-[3-({5-[(4-methylbenzenesulfonyl)oxy]pentyl}oxy)propoxy]acetic Acid (L-1)

To a stirred solution of tert-butyl 2-[3-({5-[(4-methylbenzenesulfonyl)oxy]pentyl}oxy)propoxy]acetate (AB, 1.3 g, 3.02 mmol) in dichloromethane (10 mL) was added trifluoroacetic acid (10 mL) at rt. The resulting solution was stirred at rt for 3 h. The reaction mixture was then concentrated under vacuum to give 1.5 g (crude) of L-1, which was used for next step without any further purification. LC-MS (ES⁺): m/z 375.34 [MH⁺], $t_R$=1.39 min (2.6 minute run).

Step 2: Synthesis of (2S,4R)-1-[(2S)-3,3-dimethyl-2-{2-[3-({5-[(4-methylbenzenesulfonyl)oxy]pentyl}oxy)propoxy]acetamido}butanoyl]-4-hydroxy-N-{[4-(4-methyl-1,3-thiazol-5-yl)phenyl]methyl}pyrrolidine-2-carboxamide (BI)

To a stirred solution 2-[3-({5-[(4-methylbenzenesulfonyl)oxy]pentyl}oxy)propoxy]acetic acid (L-1, 1.5 g, 4.01 mmol) in N,N-dimethylformamide (20 mL) was added HATU (1.36 g, 3.58 mmol), DIEA (0.7 mL) and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (ULM-1, 1.3 g, 3.02 mmol) at rt. The resulting mixture was stirred for 2 h at rt. It was then diluted with water (100 mL) and extracted with ethyl acetate (100 mL×3). The organic layers were combined, washed with saturated aqueous solution of sodium chloride (60 mL), dried over anhydrous sodium sulfate and then concentrated under reduced pressure to give a crude residue, which was purified by flash silica gel chromatography (eluent: dichloromethane/methanol (v:v=10:1)) to give 0.5 g of BI. LC-MS (ES⁺): m/z 787.34 [MH⁺], $t_R$=1.87 min (3.0 minute run).

Step 3: Synthesis of (2S,4R)-1-[(2S)-2-[2-(3-{[5-(4-{3-[6-cyano-5-(trifluoromethyl)pyridin-3-yl]-5,5-dimethyl-4-oxo-2-sulfanylideneimidazolidin-1-yl}phenoxy)pentyl]oxy}propoxy)acetamido]-3,3-dimethylbutanoyl]-4-hydroxy-N-{[4-(4-methyl-1,3-thiazol-5-yl)phenyl]methyl}pyrrolidine-2-carboxamide (Example 2)

To a stirred solution of 5-[3-(4-hydroxyphenyl)-4,4-dimethyl-5-oxo-2-sulfanylideneimidazolidin-1-yl]-3-(trifluoromethyl)pyridine-2-carbonitrile (ABM-4, 52 mg, 0.13 mmol), (2S,4R)-1-[(2S)-3,3-dimethyl-2-{2-[3-({5-[(4-methylbenzenesulfonyl)oxy]pentyl}oxy)propoxy]acetamido}butanoyl]-4-hydroxy-N-{[4-(4-methyl-1,3-thiazol-5-yl)phenyl]methyl}pyrrolidine-2-carboxamide (BI, 100 mg, 0.13 mmol) in N,N-dimethylformamide (10 mL) was added potassium carbonate (34 mg, 0.25 mmol) under an atmosphere of nitrogen. The resulting solution was stirred for 2 h at 80° C. The resulting mixture was concentrated under vacuum to give a crude residue, which was purified by Prep-HPLC to give 38.1 mg of Example 2 as a white solid. $^1$H NMR (300 MHz, CD$_3$OD): δ 9.12 (s, 1H), 8.83 (s, 1H), 8.63 (s, 1H), 7.44-7.39 (m, 4H), 7.00 (d, J=9.0 Hz, 2H), 7.20 (d, J=9.0 Hz, 2H), 4.80-4.26 (m, 5H), 4.06-3.65 (m, 6H), 3.62-3.35 (m, 6H), 2.43 (s, 3H), 2.21-2.01 (m, 2H), 1.85-1.65 (m, 4H), 1.60-1.42 (m, 10H), 1.00 (s, 9H): LC-MS (ES$^+$): m/z 1021.12 [MH$^+$], t$_R$=2.36 min (3.6 minute run).

Unless otherwise noted, the following examples were synthesized according to analogous procedures described above for synthesis of examples 1 and 2, utilizing corresponding reagents, intermediates, and starting materials.

When referring to the specific exemplary compounds presented herein, the specification uses the terms "example #." For example, compound 1 (Table 2) is also referred to as Example 1.

TABLE 2

Exemplary Compounds.

| Ex # | Structure | Compound name and Analytical data |
|---|---|---|
| 1 | 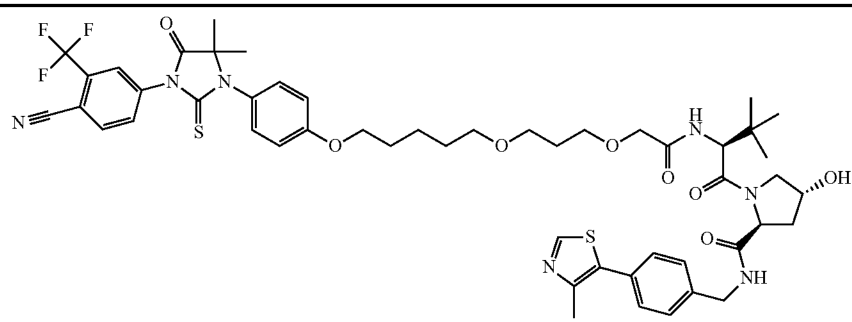 | (2S,4R)-1-((S)-2-(2-(3-(5-(4-(3-(4-cyano-3-(trifluoromethyl)phenyl)-5,5-dimethyl-4-oxo-2-thioxoimidazolidin-1-yl)phenoxy)pentyloxy)propoxy)acetamido)-3,3-dimethylbutanoyl)-4-hydroxy-N-(4-(4-methylthiazol-5-yl)benzyl)pyrrolidine-2-carboxamide<br>1H NMR (400 MHz, CDCl3): δ 7.96 (s, 2H), 7.86 (d, J = 8.6 Hz, 1H), 7.19 (d, J = 8.8 Hz, 2H), 7.02 (d, J = 8.6 Hz, 2H), 4.50 (s, 2H), 4.30 (t, J = 6.4 Hz, 2H), 4.02 (t, J = 6.4 Hz, 2H), 3.53 (m, 2H), 3.44 (m, 2H), 1.96-1.80 (m, 4H), 1.69-1.53 (m, 2H), 1.49 (s, 6H), 1.48 (s, 9H), 1.44-1.22 (m, 2H); Mass (ES+): m/z 686.35 [MNa+] |
| 2 | 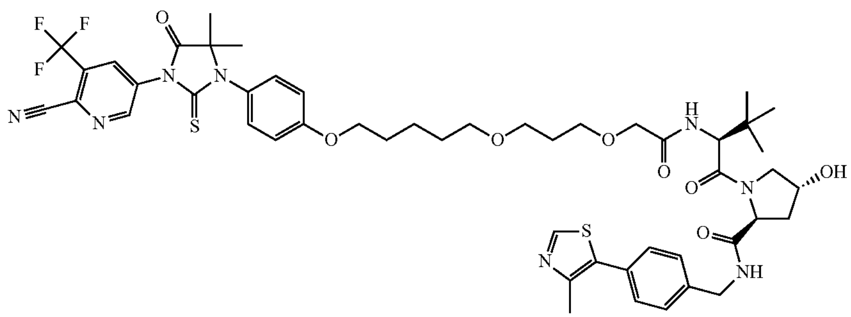 [SMILES: Cc1ncsc1-c1ccc(CNC(=O)[C@@H]2C[C@@H](O)CN2C(=O)[C@@H](NC(=O)COCCCOCCCCCOc2ccc(N3C(=S)N(c4ccc(C#N)c(C(F)(F)F)c4)C(=O)C3(C)C)cc2)C(C)(C)C)cc1] | (2S,4R)-1-((S)-2-(2-(3-(5-(4-(3-(6-cyano-5-(trifluoromethyl)pyridin-3-yl)-5,5-dimethyl-4-oxo-2-thioxoimidazolidin-1-yl)phenoxy)pentyloxy)propoxy)acetamido)-3,3-dimethylbutanoyl)-4-hydroxy-N-(4-(4-methylthiazol-5-yl)benzyl)pyrrolidine-2-carboxamide<br>1H NMR (300 MHz, CD3OD): δ 9.12 (s, 1H), 8.83(s, 1H), 8.63 (s, 1H), 7.44-7.39 (m, 4H), 7.00 (d, J = 9.0 Hz, 2H), 7.20 (d, J = 9.0 Hz, 2H), 4.80-4.26 (m, 5H), 4.06-3.65 (m, 6H), 3.62-3.35 (m, 6H), 2.43 (s, 3H), 2.21-2.01 (m, 2H), 1.85-1.65 (m, 4H), 1.60-1.42 (m, 10H), 1.00 (s, 9H); LC-MS (ES+): m/z 1021.12 [MH+], tR = 2.36 min (3.6 minute run). |

TABLE 2-continued

Exemplary Compounds.

| Ex # | Structure | Compound name and Analytical data |
|---|---|---|
| 3 | 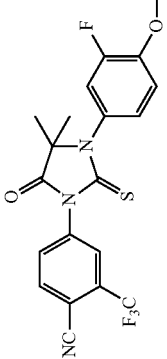 | Prepared from ABM-16, L-1, and ULM-1 (2S,4R)-1-[(2S)-2-[2-(3-{[5-(4-{3-[4-cyano-3-(trifluoromethyl)phenyl]-5,5-dimethyl-4-oxo-2-sulfanylideneimidazolidin-1-yl}-2-fluorophenoxy)pentyl]oxy}propoxy)acetamido]-3,3-dimethylbutanoyl]-4-hydroxy-N-{[4-(4-methyl-1,3-thiazol-5-yl)phenyl]methyl}pyrrolidine-2-carboxamide<br>¹H NMR (300 MHz, CD₃OD): δ 8.84 (s, 1H), 8.01-7.93 (m, 1H), 7.51-7.31 (m, 4H), 7.21-7.01 (m, 3H), 4.70-4.41 (m, 4H), 4.35-4.22 (m, 1H), 4.15-4.03 (m, 2H), 3.95-3.90 (m, 2 H), 3.90-3.73 (m, 2H), 3.61-3.56 (m, 2 H), 3.56-3.51 (m, 2 H), 3.50-3.42 (m, 2 H), 2.45 (s, 3H), 2.21-2.10 (m, 1 H), 2.10-2.12 (m, 1H), 1.92-1.70 (m, 4H), 1.63-1.50 (m, 3 H), 3.50-1.45(m, 7H), 1.04 (s, 9H); LC-MS (ES⁺): m/z 1038.31 [MH⁺], t$_R$ = 2.35 min (3.6 minute run) |

TABLE 2-continued

Exemplary Compounds.

| Ex # | Structure | Compound name and Analytical data |
|---|---|---|
| 4 | 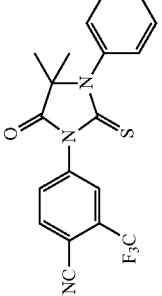 | Prepared from ABM-3, L-1, and ULM-3 (2S,4R)-1-[(2S)-2-{2-(3-{[5-(4-{3-[4-cyano-3-(trifluoromethyl)phenyl]-5,5-dimethyl-4-oxo-2-sulfanylideneimidazolidin-1-yl]phenoxy}pentyl)oxy]phenoxy}pentyl)oxy}propoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide <sup>1</sup>H NMR (300 MHz, CD<sub>3</sub>OD): δ 8.88 (s, 1H), 8.58 (d, J = 7.5 Hz, 1H), 8.16 (m, 2H), 8.00 (m, 1H), 7.53 (d, J = 9.3 Hz, 1H), 7.42 (m, 4H), 7.26 (m, 2H), 7.05 (m, 2H), 5.01 (m, 1H), 4.72 (d, J = 9.3 Hz, 1H), 4.58 (m, 1H), 4.44 (s, 1H), 4.04 (m, 4H), 3.83-3.49 (m, 8H), 2.48 (s, 3H), 2.20 (m, 1H), 1.83 (m, 5H), 1.50 (m, 13H), 1.03 (s, 9H); LC-MS (ES<sup>+</sup>): m/z 518.20 [M + 2]/2, t<sub>R</sub> = 3.67 min, (5.6 minute run) |

TABLE 2-continued

Exemplary Compounds.

| Ex # | Structure | Compound name and Analytical data |
|---|---|---|
| 5 | 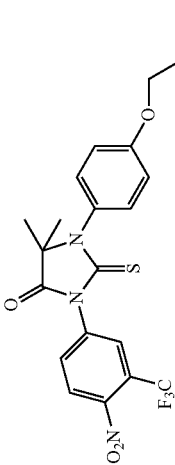 | Prepared from ABM-17, L-1, and ULM-1 (2S,4R)-1-[(2S)-2-[2-(3-{[5-(4-{[5,5-dimethyl-3-[4-nitro-3-(trifluoromethyl)phenyl]-4-oxo-2-sulfanylideneimidazolidin-1-yl}phenoxy)pentyl]oxy}propoxy)acetamido]-3,3-dimethylbutanoyl]-4-hydroxy-N-{[4-(4-methyl-1,3-thiazol-5-yl)phenyl]methyl}pyrrolidine-2-carboxamide ¹H NMR (300 MHz, CD₃OD): δ 8.82 (s, 1H), 8.15-8.13 (m, 2H), 8.01-7.93 (m, 1H), 7.51-7.31 (m, 4H), 7.22-7.22 (m, 2H), 7.22-7.05 (m, 2H), 4.71 (s, 1 H), 4.60-4.35 (m, 3H), 4.32-4.24 (m, 1H), 4.120-3.95 (m, 4H), 3.93-3.75 (m, 2H), 3.62-3.52 (m, 2 H), 3.51-3.41 (m, 2 H), 3.40--3.35 (m, 2H), 2.45 (s, 3H), 2.24-2.10 (m, 1H), 2.09-2.01 (m, 1H), 1.90-1.72 (m, 4H), 1.65-1.52 (m, 3 H), 1.51-1.34(m, 7H), 1.00 (s, 9H); LC-MS (ES⁺): m/z 1040.32 [MH⁺], t_R = 2.52 min (3.6 minute run) |

TABLE 2-continued

Exemplary Compounds.

| Ex # | Structure | Compound name and Analytical data |
|---|---|---|
| 6 | 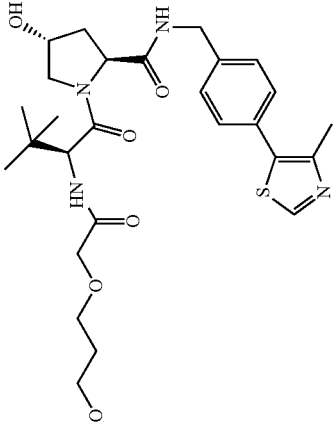 | Prepared from ABM-6, L-1, and ULM-1 (2S,4R)-1-[(2S)-2-(2-{3-[(5-{4-[3-(4-cyano-3-methylphenyl)-5,5-dimethyl-4-oxo-2-sulfanylideneimidazolidin-1-yl]phenoxy]pentyl}oxy)propoxy]acetamido)-3,3-dimethylbutanoyl]-4-hydroxy-N-{[4-(4-methyl-1,3-thiazol-5-yl)phenyl]methyl}pyrrolidine-2-carboxamid <br> $^1$H NMR (400 MHz, CD$_3$OD): δ8.88 (s, 1H), 7.83 (d, J = 8.0 Hz, 1H), 7.53 (m, 6H), 7.28 (d, J = 9.2 Hz, 2H), 7.06 (d, J = 8.8 Hz, 2H), 4.71 (s, 1H), 4.59 (m, 3H), 4.39 (d, J = 15.6 Hz, 1H), 4.05 (m, 4H), 3.88 (m, 2H), 3.68 (m, 4H), 3.52 (m, 2H), 2.61 (s, 3H), 2.50 (s, 3H), 2.25 (m, 1H), 2.10 (m, 1H), 1.93 (m, 4H), 1.68 (m, 10H), 1.06 (s, 9H); LC-MS (ES$^+$): m/z 483.95 [M + 2]/2, t$_R$ = 2.28 min (3.60 minute run). |

TABLE 2-continued

Exemplary Compounds.

| Ex # | Structure | Compound name and Analytical data |
|---|---|---|
| 7 | 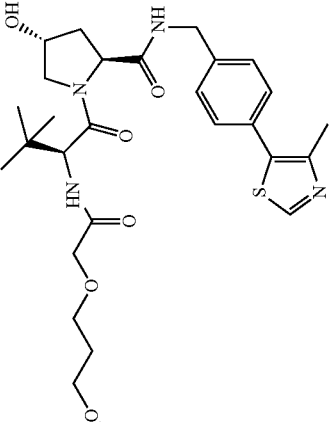 | Prepared from ABM-2, L-1, and ULM-1 (2S,4R)-1-[(2S)-2-(2-{3-[(5-{4-[3-(4-cyano-3-fluorophenyl)-5,5-dimethyl-4-oxo-2-sulfanylideneimidazolidin-1-yl]phenoxy}pentyl)oxy]propoxy}acetamido)-3,3-dimethylbutanoyl]-4-hydroxy-N-{[4-(4-methyl-1,3-thiazol-5-yl)phenyl]methyl}pyrrolidine-2-carboxamide $^{1}$H NMR (300 MHz, CD3OD): δ 8.87 (s, 1H), 7.91 (t, J = 7.8 Hz, 1H), 7.63 (d, J = 8.1 Hz, 1H), 7.54-7.41 (m, 5H), 7.26 (d, J = 8.7, 2H), 7.03 (d, J = 9.0 Hz, 2H), 4.70 (s, 1H), 4.61-4.51 (m, 3H), 4.37-4.32 (m, 1H), 4.04-3.98 (m, 4H), 3.98-3.81 (m, 2H), 3.67-3.63 (m, 2H), 3.57 (t, J = 6.6 Hz, 2H), 3.57 (t, J = 6.6 Hz, 1H), 2.48 (s, 3H), 2.23-2.09 (m, 2H), 1.92-1.79 (m, 4H), 1.67-1.53 (m, 10H), 1.03 (s, 9H); LC-MS (ES$^+$): m/z 970.55 [MH$^+$], t$_R$ = 1.55 min (3.6 minute run) |

TABLE 2-continued

Exemplary Compounds.

| Ex # | Structure | Compound name and Analytical data |
|---|---|---|
| 8 | 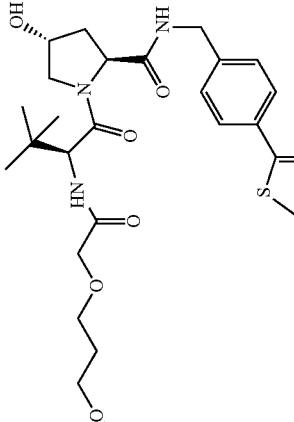 | Prepared from ABM-1, L-1, and ULM-1 2S,4R)-1-[(2S)-2-(2-{3-[(5-{4-[3-(3-chloro-4-cyanophenyl)-5,5-dimethyl-4-oxo-2-sulfanylideneimidazolidin-1-yl]phenoxy}pentyl)oxy]propoxy}acetamido)-3,3-dimethylbutanoyl]-4-hydroxy-N-{[4-(4-methyl-1,3-thiazol-5-yl)phenyl]methyl}pyrrolidine-2-carboxamide $^1$H NMR (400 MHz, CD$_3$OD): δ 9.00 (s, 1H), 7.98 (d, J = 8.4 Hz, 1H), 7.87 (s, 1H), 7.66 (d, J = 10.4 Hz, 1H), 7.50 (m, 4H), 7.29 (d, J = 8.8 Hz, 2H), 7.06 (d, J = 8.8 Hz, 2H), 4.71 (s, 1H), 4.62 (m, 3H), 4.39 (d, J = 15.6 Hz, 1H), 4.05 (m, 4H), 3.89 (m, 2H), 3.68 (m, 4H), 3.52 (m, 2H), 2.50 (s, 3H), 2.25 (m, 1H), 2.10 (m, 1H), 1.93(m, 4H), 1.68 (m, 2H), 1.59 (m, 8H), 1.05 (s, 9H); LC-MS (ES$^+$): m/z 986.25 [MH$^+$], t$_R$ = 3.44 min. (5.00 minute run) |

TABLE 2-continued

Exemplary Compounds.

| Ex # | Structure | Compound name and Analytical data |
|---|---|---|
| 9 | 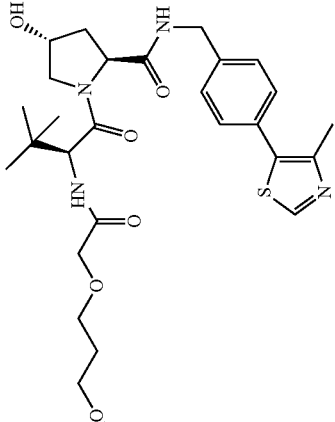 | Prepared from ABM-5, L-1, and ULM-1 (2S,4R)-1-[(2S)-2-(2-{3-[(5-{4-[3-(4-cyano-3-methoxyphenyl)-5,5-dimethyl-4-oxo-2-sulfanylideneimidazolidin-1-yl]phenoxy}pentyl)oxy]propoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.88 (s, 1H), 7.77 (d, J = 8.0 Hz, 1H), 7.49-7.42 (m, 4H), 7.37 (d, J = 1.6 Hz, 1H), 7.18-7.16 (m, 3H), 7.06-7.04 (m, 2H), 4.71 (s, 1H), 4.62-4.54 (m, 3H), 4.39 (d, J = 15.6 Hz, 1H), 4.05-4.00 (m, 7H), 3.91-3.80 (m, 2H), 3.72-3.49 (m, 6H), 2.50 (s, 3H), 2.27-2.07 (m, 2H), 1.93-1.81 (m, 4H), 1.66-1.56 (m, 10H), 1.06 (s, 9H); LC-MS (ES$^+$): m/z 982.55 [MH$^+$], t$_R$ = 2.67 min (5.0 minute run) |

TABLE 2-continued

Exemplary Compounds.

| Ex # | Structure | Compound name and Analytical data |
|---|---|---|
| 10 | 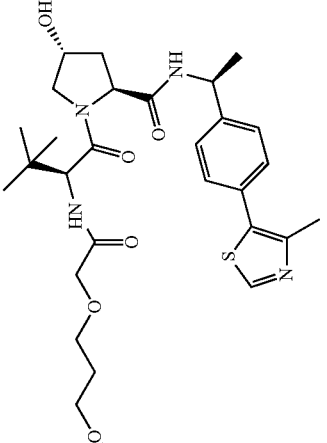 | Prepared from ABM-16, L-1, and ULM-3 (2S,4R)-1-[(2S)-2-[2-(3-{[5-(4-{3-[4-cyano-3-(trifluoromethyl)phenyl]-5,5-dimethyl-4-oxo-2-sulfanylideneimidazolidin-1-yl]-2-fluorophenoxy)pentyl]oxy}propoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (300 MHz, DMSO) δ 8.98 (s, 1H), 8.44-8.40 (m, 2H), 8.27 (s, 1H), 8.08 (d, J = 8.4 Hz, 1H), 7.45-7.28 (m, 7H), 7.17 (d, J = 8.7 Hz, 1H), 5.12 (d, J = 3.3 Hz, 1H), 4.92-4.88 (m, 1H), 4.52-4.45 (m, 2H), 4.28 (s, 1H), 4.12 (t, J = 6.6 Hz, 2H), 3.92 (s, 2H), 3.58-3.38 (m, 8H), 2.45 (s, 3H), 2.08-2.02 (m, 1H), 1.83-1.74 (m, 5H), 1.61-1.46 (m, 11H), 1.38 (d, J = 6.9 Hz, 2H), 0.93 (s, 9H); LC-MS (ES+): m/z 1052.40 [MH+], $t_R$ = 1.79 min |

TABLE 2-continued

Exemplary Compounds.

| Ex # | Structure | Compound name and Analytical data |
|---|---|---|
| 11 | 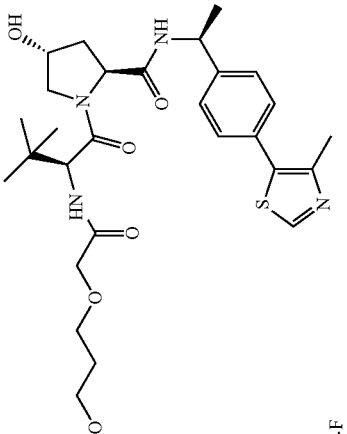 | Prepared from ABM-18, L-1, and ULM-3 (2S,4R)-1-[(2S)-2-[2-(3-{[5-(4-{[5-(4-{3-[4-cyano-3-(trifluoromethyl)phenyl]-5,5-dimethyl-4-oxo-2-sulfanylideneimidazolidin-1-yl}-2,6-difluorophenoxy)pentyl]oxy}propoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide <br> $^1$H NMR (400 MHz, DMSO) δ 8.98 (s, 1H), 8.45-8.39 (m, 2H), 8.26 (s, 1H), 8.07 (d, J = 8.4 Hz, 1H), 7.44-7.28 (m, 7H), 5.12 (d, J = 3.6 Hz, 1H), 4.92-4.88 (m, 1H), 4.55 (d, J = 9.6 Hz, 1H), 4.44 (t, J = 8.0 Hz, 1H), 4.28 (s, 1H), 4.20 (t, J = 6.8 Hz, 2H), 3.91 (s, 2H), 3.57-3.37 (m, 8H), 2.45 (s, 3H), 2.08-2.02 (m, 1H), 1.80-1.71 (m, 5H), 1.61-1.46 (m, 10H), 1.38 (d, J = 6.8 Hz, 3H), 0.93 (s, 9H); Mass (ES$^+$): m/z 1070.50 [MH$^+$] |

TABLE 2-continued

Exemplary Compounds.

| Ex # | Structure | Compound name and Analytical data |
|---|---|---|
| 12 | 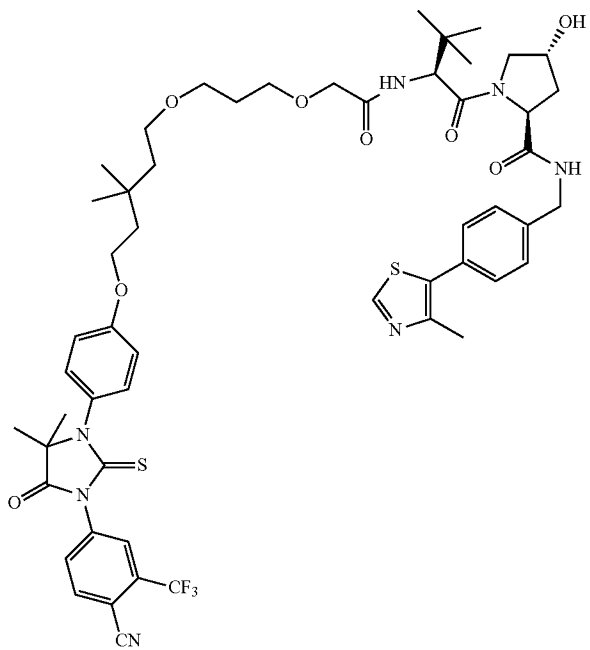 [SMILES: Cc1ncsc1-c1ccc(CNC(=O)[C@@H]2C[C@@H](O)CN2C(=O)[C@@H](NC(=O)COCCCOCCC(C)(C)CCOc2ccc(N3C(=S)N(c4ccc(C#N)c(C(F)(F)F)c4)C(=O)C3(C)C)cc2)C(C)(C)C)cc1] | Prepared from ABM-3, L-2, and ULM-1 (2S,4R)-1-[(2S)-2-[2-[3-[5-(4-{3-[4-cyano-3-(trifluoromethyl)phenyl]-5,5-dimethyl-4-oxo-2-sulfanylideneimidazolidin-1-yl}phenoxy)-3,3-dimethylpentyl]oxy}propoxy]acetamido]-3,3-dimethylbutanoyl]-4-hydroxy-N-{[4-(4-methyl-1,3-thiazol-5-yl)phenyl]methyl}pyrrolidine-2-carboxamide <br> 1H NMR (400 MHz, CD3OD): δ 8.88 (s, 1H), 8.15 (m, 2H), 8.01 (m, 1H), 7.49 (m, 4H), 7.30 (d, J = 9.2 Hz, 2H), 7.06 (d, J = 8.8 Hz, 2H), 4.71 (s, 1H), 4.61 (m, 3H), 4.39 (m, 1H), 4.13 (m, 2H), 3.98 (m, 2H), 3.88 (m, 1H), 3.84 (m, 1H), 3.66 (m, 2H), 3.59 (m, 4H), 2.49 (s, 3H), 2.28 (m, 1H), 2.14 (m, 1H), 1.91 (m, 2H), 1.81 (m, 2H), 1.64 (m, 2H), 1.56 (s, 6H), 1.05 (m, 15H); LC-MS (ES+): m/z 1048.55 [MH+], $t_R$ = 1.86 min (3.0 minute run). |

TABLE 2-continued

Exemplary Compounds.

| Ex # | Structure | Compound name and Analytical data |
|---|---|---|
| 13 | 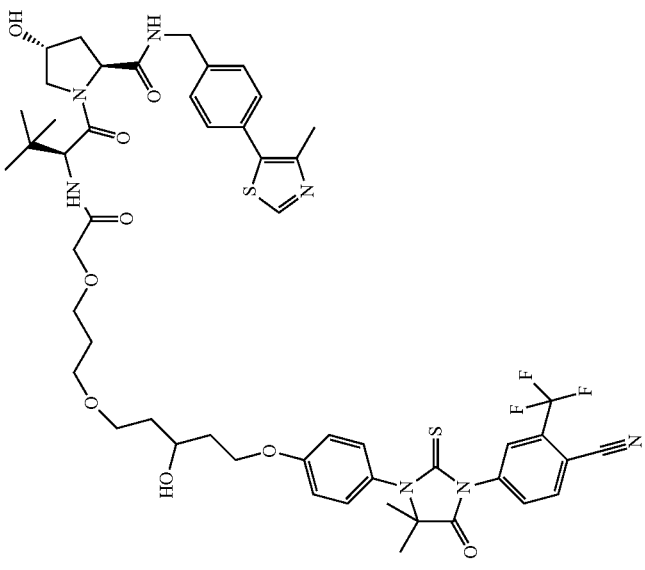 | Prepared from ABM-3, L-3, and ULM-1 (2S,4R)-1-[(2S)-2-[2-(3-{[5-(4-{3-[4-cyano-3-(trifluoromethyl)phenyl]-5,5-dimethyl-4-oxo-2-sulfanylideneimidazolidin-1-yl]phenoxy}-3-hydroxypentyl)oxy}propoxy)acetamido]-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.86 (s, 1H), 8.16-8.13 (d, J = 7.8 Hz, 2H), 8.00-7.96 (d, J = 9.9 Hz, 1H), 7.78-7.40 (m, 4H), 7.29-7.26 (d, J = 9.9 Hz, 2H), 7.07-7.04 (d, J = 8.7 Hz, 2H), 4.70-4.33 (m, 5H), 4.19-4.13 (m, 2H), 4.04-3.81 (m, 5H), 3.65-3.56 (m, 6H), 2.47 (s, 3H), 2.23-1.70 (m, 8H), 1.54 (s, 6H), 1.02 (d, J = 6.0 Hz, 9H). LC-MS (ES$^+$): m/z 1036.35 [MH$^+$], t$_R$ = 1.51 min (3.0 minute run). |

TABLE 2-continued

Exemplary Compounds.

| Ex # | Structure | Compound name and Analytical data |
|---|---|---|
| 14 | 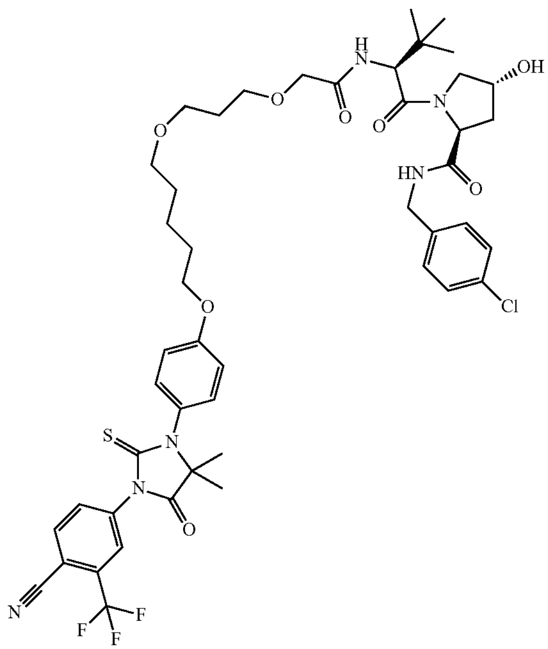 [SMILES: CC(C)(C)[C@H](NC(=O)COCCCOCCCCCOc1ccc(N2C(=S)N(c3ccc(C#N)c(C(F)(F)F)c3)C(=O)C2(C)C)cc1)C(=O)N1C[C@H](O)C[C@H]1C(=O)NCc1ccc(Cl)cc1] | Prepared from ABM-3, L-1, and ULM-6 (2S,4R)-N-[(4-chlorophenyl)methyl]-1-[(2S)-2-[2-(3-{[5-(4-{3-[4-cyano-3-(trifluoromethyl)phenyl]-5,5-dimethyl-4-oxo-2-sulfanylideneimidazolidin-1-yl]phenoxy)pentyl]oxy}propoxy)acetamido]-3,3-dimethylbutanoyl]-4-hydroxypyrrolidine-2-carboxamide NMR (400 MHz, CD$_3$OD) δ 8.13-8.17 (m, 2H), 7.99 (d, J = 7.8 Hz, 1H), 7.32-7.36 (m, 2H), 7.25-7.31 (m, 4H), 7.05 (d, J = 9.0 Hz, 2H), 4.514.57 (m, 2H), 4.47 (d, J = 16.0 Hz, 2H), 4.27 (d, J = 14.9 Hz, 2H), 4.04 (t, J = 6.5 Hz, 1H), 3.99 (d, J = 3.5 Hz, 2H), 3.64-3.68 (m, 2H), 3.56-3.61 (m, 2H), 3.50 (t, J = 6.3 Hz, 2H), 2.17-2.24 (m, 1H), 2.07 (dd, J = 3.9, 13.3 Hz, 1H), 1.89-1.92 (m, 2H), 1.81-1.86 (m, 1H), 1.64-1.70 (m, 1H), 1.57-1.61 (m, 1H), 1.30 (br.s., 6H), 0.99-1.07 (m, 9H), 0.91 (t, J = 6.8 Hz, 4H). LC-MS (ES$^+$): m/z 957.35 [MH$^+$] |

TABLE 2-continued

Exemplary Compounds.

| Ex # | Structure | Compound name and Analytical data |
|---|---|---|
| 15 | 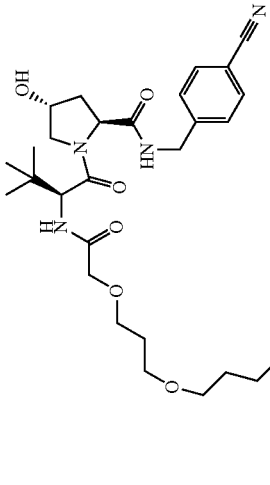 | Prepared from ABM-3, L-1, and ULM-7 (2S,4R)-1-[(2S)-2-[2-(3-{[5-(4-{3-[4-cyano-3-(trifluoromethyl)phenyl]-5,5-dimethyl-4-oxo-2-sulfanylideneimidazolidin-1-yl}phenoxy)pentyl]oxy}propoxy)acetamido]-3,3-dimethylbutanoyl]-N-[(4-cyanophenyl)methyl]-4-hydroxypyrrolidine-2-carboxamide ¹H NMR (400 MHz, CD₃OD) δ 8.11-8.17 (m, 2H), 7.98 (d, J = 8.6 Hz, 1H), 7.64 (d, J = 8.6 Hz, 2H), 7.53 (d, J = 8.2 Hz, 2H), 7.26 (d, J = 9.0 Hz, 2H), 7.03 (d, J = 9.0 Hz, 2H), 4.68 (s, 1H), 4.58 (d, J = 16.0 Hz, 2H), 4.54 (d, J = 9.4 Hz, 1H), 4.48 (br. s., 1H), 4.03 (t, J = 6.3 Hz, 2H), 3.97 (d, J = 2.7 Hz, 1H), 3.84-3.88 (m, 1H), 3.78 (dd, J = 3.5, 11.0 Hz, 1H), 3.61-3.66 (m, 2H), 3.55-3.60 (m, 2H), 3.49 (t, J = 6.3 Hz, 2H), 1.88-1.92 (m, 1H), 1.80-1.85 (m, 2H), 1.63-1.68 (m, 2H), 1.55-1.59 (m, 2H), 1.25-1.33 (m, 6H), 1.00 (br. s., 9H), 0.89 (t, J = 6.8 Hz, 4H). LC-MS (ES⁺): m/z 949.38 [MH⁺]. |

TABLE 2-continued

Exemplary Compounds.

| Ex # | Structure | Compound name and Analytical data |
|---|---|---|
| 16 | 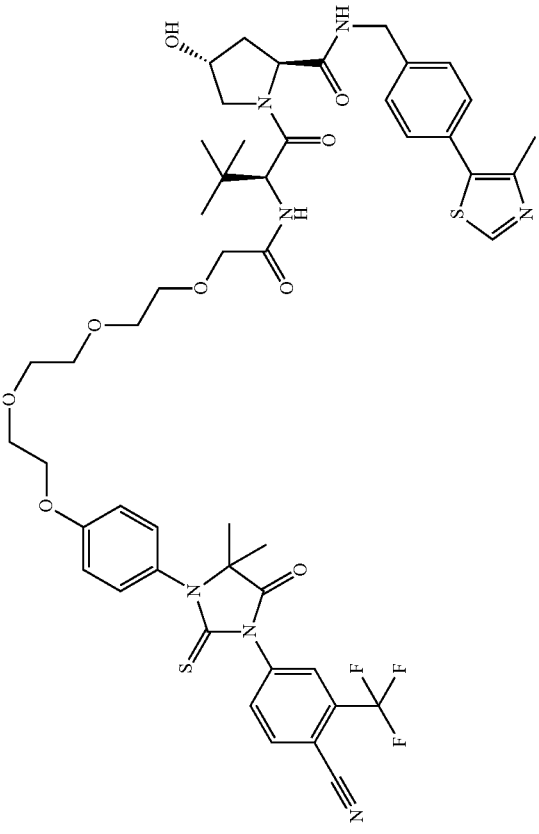 | Prepared from ABM-3, L-4, and ULM-1 (2S,4R)-1-[(2S)-2-[2-(2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.89 (s, 1H), 8.18-8.15 (d, J = 8.4 Hz, 2H), 8.01-7.99 (m, 1H), 7.49-7.42 (m, 4H), 7.31-7.28 (d, J = 10.0 Hz, 2H), 7.10-7.07 (m, 2H), 4.72 (s, 1H), 4.61-4.52 (m, 3H), 4.38-4.34 (m, 1H), 4.19-4.17 (m, 2H), 4.10-4.05 (m, 2H), 3.91-3.80 (m, 4H), 3.77-3.72 (m, 8H), 2.49 (s, 3H), 2.24-2.05 (m, 2H), 1.54 (s, 6H), 1.06 (s, 9H); LC-MS (ES$^+$): m/z 1008.50 [MH$^+$], t$_R$ = 1.49 min (3.0 minute run). |

TABLE 2-continued

Exemplary Compounds.

| Ex # | Structure | Compound name and Analytical data |
|---|---|---|
| 17 | 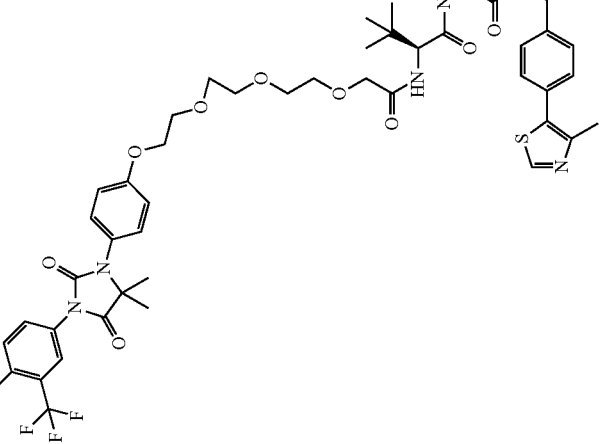 | Prepared from ABM-19, L-4, and ULM-1 (2S,4R)-1-[(2S)-2-[2-(2-{2-[2-(4-{3-[4-cyano-3-(trifluoromethyl)phenyl]-5,5-dimethyl-2,4-dioxoimidazolidin-1-yl}phenoxy)ethoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.84-8.89 (m, 1H), 8.67 (t, J = 5.67 Hz, 1H), 8.25 (s, 1H), 8.08-8.15 (m, 2H), 7.67 (d, J = 9.00 Hz, 1H), 7.43 (q, J = 8.22 Hz, 4H), 7.30 (d, J = 8.22 Hz, 2H), 7.00-7.08 (m, 2H), 4.70 (d, J = 9.78 Hz, 1H), 4.45-4.61 (m, 3H), 4.35 (dd, J = 15.85, 4.89 Hz, 1 H), 4.12-4.17 (m, 2 H), 4.04 (d, J = 3.91 Hz, 2H), 3.77-3.90 (m, 4H), 3.67-3.75 (m, 8H), 2.47 (d, J = 0.78 Hz, 3H), 2.22 (dd, J = 12.91, 8.61 Hz, 1H), 2.03-2.12 (m, 1H), 1.46-1.55 (m, 6H), 0.98-1.10 (m, 9H); Mass (ES$^+$): m/z 992.38 [MH$^+$] |

TABLE 2-continued

Exemplary Compounds.

| Ex # | Structure | Compound name and Analytical data |
|---|---|---|
| 18 | 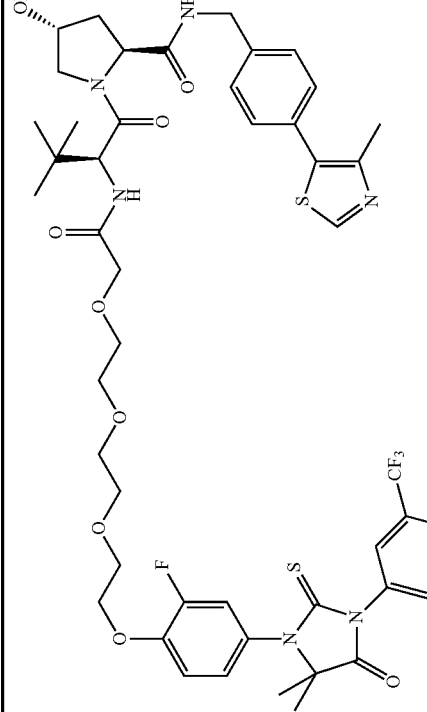 | Prepared from ABM-16, L-4, and ULM-1 (2S,4R)-1-[(2S)-2-[2-(2-{2-[2-(4-{3-[4-cyano-3-(trifluoromethyl)phenyl]-5,5-dimethyl-4-oxo-2-sulfanylideneimidazolidin-1-yl}-2-fluorophenoxy)ethoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD): δ 8.89 (s, 1H), 8.18-8.16 (d, J = 7.2 Hz, 2H), 8.01-7.99 (d, J = 8.4 Hz, 1H), 7.49-7.44 (m, 4H), 7.28-7.21 (m, 2H), 7.16-7.14 (m, 1H), 4.71 (s, 1H), 4.61-4.53 (m, 3H), 4.35-4.31(m, 1H), 4.28-4.26 (m, 2H), 4.10-4.06 (m, 2H), 3.94-3.81 (m, 3H), 3.81-3.80 (m, 1H), 3.80-3.75 (m, 8H), 2.49 (s, 3H), 2.26-2.24 (m, 1H), 2.11-2.09 (m, 1H), 1.57 (s, 6H), 1.03 (s, 9H); LC-MS (ES$^+$): m/z 1026.34 [MH$^+$], t$_R$ = 2.73 min (5.6 minute run). |

TABLE 2-continued

Exemplary Compounds.

| Ex # | Structure | Compound name and Analytical data |
|---|---|---|
| 19 | 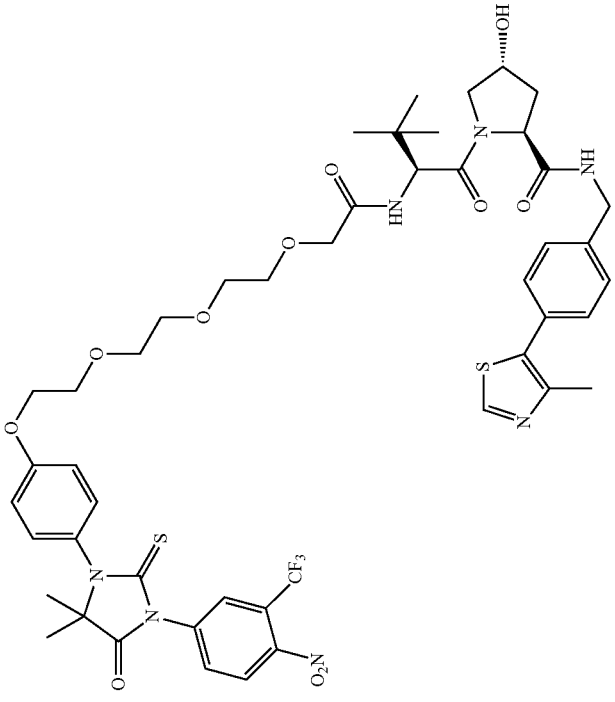 | Prepared from ABM-17, L-4, and ULM-1 (2S,4R)-1-[(2S)-2-[2-[2-(2-[2-[2-(4-{5,5-dimethyl-3-[4-nitro-3-(trifluoromethyl)phenyl]-4-oxo-2-sulfanylideneimidazolidin-1-yl}phenoxy)ethoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide (400 MHz, CD$_3$OD): δ 8.89 (s, 1H), 8.19-8.16 (m, 2H), 8.05-8.02 (m, 1H), 7.49-7.42 (m, 4H), 7.31-7.29 (d, J = 8.8 Hz, 2H), 7.09-7.07 (d, J = 8.8 Hz, 2H), 4.71(s, 1H), 4.61-4.52 (m, 3H), 4.38-4.34 (m, 1H), 4.23-4.17 (m, 2H), 4.06-4.01 (m, 2H), 3.91-3.80 (m, 4H), 3.78-3.68 (m ,8H), 2.49 (s, 3H), 2.27-2.22 (m, 1H), 2.13-2.07 (m, 1H), 1.56 (s, 6H), 1.06 (s, 9H); LC-MS (ES$^+$): m/z 1028.50 [MH$^+$], t$_R$ = 2.62 min (5.0 minute run). |

TABLE 2-continued

Exemplary Compounds.

| Ex # | Structure | Compound name and Analytical data |
|---|---|---|
| 20 | 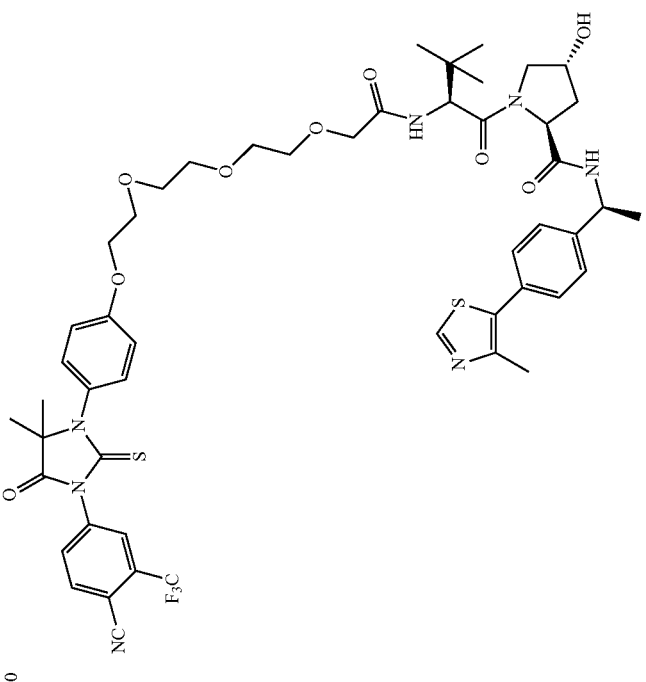 | Prepared from ABM-3, L-4, and ULM-3 (2S,4R)-1-[(2S)-2-{2-[2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (300 MHz, CD$_3$OD): δ 8.90 (s, 1H), 8.16-8.13 (d, J = 8.1 Hz, 2H), 8.00-7.97 (d, J = 8.1 Hz, 1H), 7.45-7.35 (m, 4H), 7.30-7.27 (d, J = 9.0 Hz, 2H), 7.11-7.08 (d, J = 9.0 Hz, 2H), 5.03-5.00(m, 1H), 4.69 (s, 1H), 4.60-4.57(m, 1H), 4.54-4.43 (m, 1H), 4.23-4.22 (m, 2H), 4.12-4.10 (m, 2H), 3.99-3.88 (m, 3H), 3.83-3.71 (m, 9H), 2.54 (s, 3H), 2.24-2.04 (m, 1H), 2.00-1.94 (m, 1H), 1.57 (s, 9H), 1.03 (s, 9H). LC-MS (ES$^+$): m/z 1022.56 [MH$^+$], t$_R$ = 2.07 min (3.6 minute run). |

TABLE 2-continued

Exemplary Compounds.

| Ex # | Structure | Compound name and Analytical data |
|---|---|---|
| 21 | 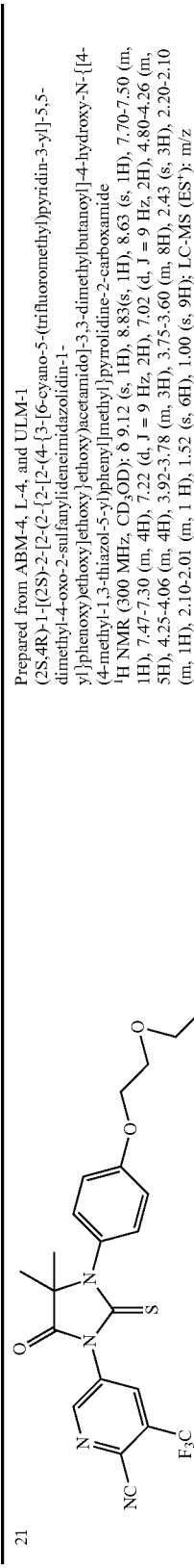 | Prepared from ABM-4, L-4, and ULM-1 (2S,4R)-1-[(2S)-2-[2-[2-[2-[2-(4-{3-[6-cyano-5-(trifluoromethyl)pyridin-3-yl]-5,5-dimethyl-4-oxo-2-sulfanylideneimidazolidin-1-yl]phenoxy]ethoxy]ethoxy]ethoxy]acetamido]-3,3-dimethylbutanoyl]-4-hydroxy-N-{[4-(4-methyl-1,3-thiazol-5-yl)phenyl]methyl}pyrrolidine-2-carboxamide<br>¹H NMR (300 MHz, CD₃OD): δ 9.12 (s, 1H), 8.83(s, 1H), 8.63 (s, 1H), 7.70-7.50 (m, 1H), 7.47-7.30 (m, 4H), 7.22 (d, J = 9 Hz, 2H), 7.02 (d, J = 9 Hz, 2H), 4.80-4.26 (m, 5H), 4.25-4.06 (m, 4H), 3.92-3.78 (m, 3H), 3.75-3.60 (m, 8H), 2.43 (s, 3H), 2.20-2.10 (m, 1H), 2.10-2.01 (m, 1 H), 1.52 (s, 6H), 1.00 (s, 9H); LC-MS (ES⁺); m/z 1009.12 [MH⁺], t_R = 2.16 min (3.6 minute run). |

TABLE 2-continued

Exemplary Compounds.

| Ex # | Structure | Compound name and Analytical data |
|---|---|---|
| 22 | 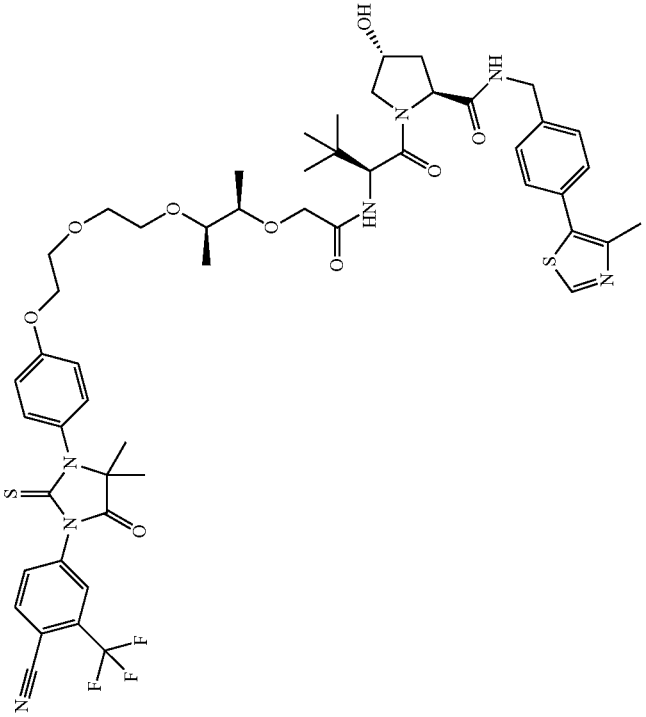 | Prepared from ABM-3, L-5, and ULM-1 (2S,4R)-1-[(2S)-2-(2-{[(2R,3R)-3-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}butan-2-yl]oxy}acetamido)-3,3-dimethylbutanoyl]-4-hydroxy-N-{[4-(4-methyl-1,3-thiazol-5-yl)phenyl]methyl}pyrrolidine-2-carboxamide ¹H NMR (400 MHz, CD₃OD) δ 8.81-8.94 (m, 1H), 8.17 (d, J = 7.43 Hz, 2H), 8.01 (d, J = 8.61 Hz, 1H), 7.73-7.89 (m, 1H), 7.37-7.57 (m, 3H), 7.21-7.36 (m, 2H), 7.01-7.17 (m, 2H), 5.48-5.54 (m, 1H), 3.36-4.88 (m, 20H), 3.20-3.29 (m, 2H), 2.43-2.52 (m, 2H), 2.16-2.30 (m, 1H), 2.03-2.16 (m, 1H), 1.52-1.59 (m, 3H), 1.39 (d, J = 4.30 Hz, 9H), 1.11-1.21 (m, 3H), 1.06 (s, 3H); Mass (ES⁺): m/z 1036.47 [MH⁺] |

TABLE 2-continued

Exemplary Compounds.

| Ex # | Structure | Compound name and Analytical data |
|---|---|---|
| 23 | 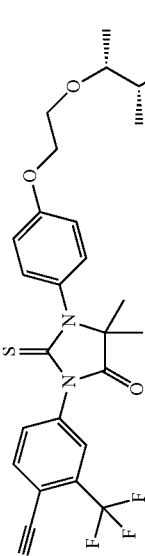 | Prepared from ABM-3, L-6, and ULM-1 (2S,4R)-1-[(2S)-2-[2-(2-{[(2R,3R)-3-[2-(4-{3-[4-cyano-3-(trifluoromethyl)phenyl]-5,5-dimethyl-4-oxo-2-sulfanylideneimidazolidin-1-yl}phenoxy)ethoxy]butan-2-yl]oxy}ethoxy)acetamido]-3,3-dimethylbutanoyl]-4-hydroxy-N-[[4-(4-methyl-1,3-thiazol-5-yl)phenyl]methyl]pyrrolidine-2-carboxamide<br>¹H NMR (400 MHz, CD₃OD) δ 8.86 (s, 1H), 8.12-8.17 (m, 2H), 7.98 (dd, J = 8.22, 1.96 Hz, 1H), 7.39-7.48 (m, 4H), 7.24-7.30 (m, 2H), 7.03-7.08 (m, 2H), 4.70 (s, 1H), 4.58-4.63 (m, 2H), 4.55 (d, J = 15.65 Hz, 2H), 4.50 (br. s., 1H), 4.15 (d, J = 4.30 Hz, 2H), 4.02 (d, J = 7.83 Hz, 1H), 3.88-3.94 (m, 2H), 3.71-3.75 (m, 2H), 3.63-3.68 (m, 2H), 3.56-3.61 (m, 1H), 3.47-3.52 (m, 1H), 2.44-2.50 (m, 3H), 2.19-2.25 (m, 1H), 2.06-2.11 (m, 1H), 1.53 (s, 6H), 1.35 (d, J = 6.65 Hz, 3H), 1.11 (d, J = 6.26 Hz, 6H), 1.01-1.07 (m, 9H); Mass (ES⁺): m/z 1036.47 |

TABLE 2-continued

Exemplary Compounds.

| Ex # | Structure | Compound name and Analytical data |
|---|---|---|
| 24 | 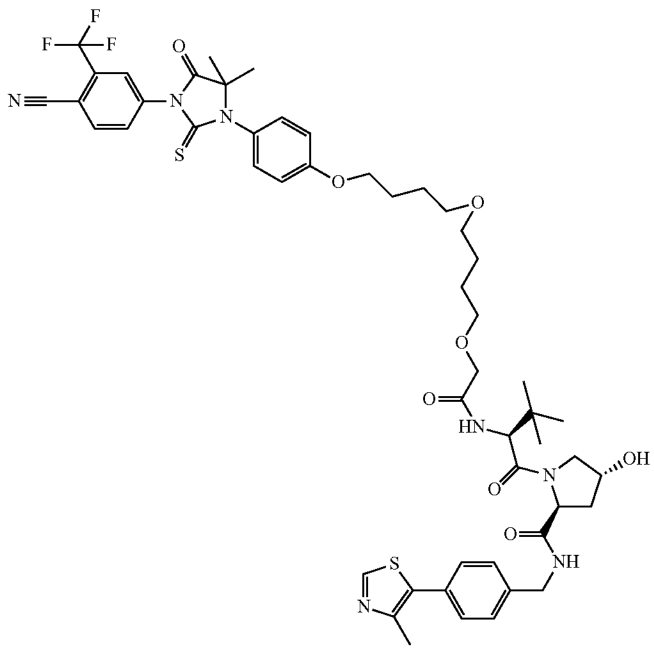 [SMILES: Cc1ncsc1-c1ccc(CNC(=O)[C@@H]2C[C@@H](O)CN2C(=O)[C@@H](NC(=O)COCCCCOCCCCOc2ccc(N3C(=S)N(c4ccc(C#N)c(C(F)(F)F)c4)C(=O)C3(C)C)cc2)C(C)(C)C)cc1] | Prepared from ABM-3, L-7, and ULM-1 (2S,4R)-1-[(2S)-2-(2-{4-[4-(4-{3-[4-cyano-3-(trifluoromethyl)phenyl]-5,5-dimethyl-4-oxo-2-sulfanylideneimidazolidin-1-yl}phenoxy)butoxy]phenoxy}butoxy)acetamido]-3,3-dimethylbutanoyl]-4-hydroxy-N-{[4-(4-methyl-1,3-thiazol-5-yl)phenyl]methyl}pyrrolidine-2-carboxamide<br>¹H NMR (400 MHz, CD₃OD): δ 8.90 (s, 1H), 8.17-8.15 (d, J = 8.4 Hz, 2H), 8.01-8.01 (d, J = 1.6 Hz, 1H), 7.49-7.42 (m, 4H), 7.30-7.27 (d, J = 11.6 Hz, 2H), 7.06-7.04 (d, J = 8.8 Hz, 2H), 4.71 (s, 1H), 4.61-4.54 (m, 3H), 4.38-4.34 (m, 1H), 4.07-4.04 (m, 2H), 3.40-3.95 (m, 2H), 3.91-3.83 (m, 2H), 3.61-3.58 (m, 2H), 3.52-3.50 (m, 4H), 2.50 (s, 3H), 2.05-2.14(m, 1H), 2.20-2.30 (m, 1H), 1.89-1.86 (m, 2H), 1.79-1.723 (m, 6H), 1.56 (s, 6H), 1.06 (s, 9H); LC-MS (ES⁺): m/z 1020.30 [MH⁺], t_R = 4.06 min (5.6 minute run). |

TABLE 2-continued

Exemplary Compounds.

| Ex # | Structure | Compound name and Analytical data |
|---|---|---|
| 25 | (structure) | Prepared from ABM-16, L-7, and ULM-3 (2S,4R)-1-[(2S)-2-(2-{4-[4-(4-{3-[4-cyano-3-(trifluoromethyl)phenyl]-5,5-dimethyl-4-oxo-2-sulfanylideneimidazolidin-1-yl}-2-fluorophenoxy)butoxy]butoxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (300 MHz, CD$_3$OD): δ 8.88 (s, 1H), 8.17-8.14 (d, J = 7.5 Hz, 2H), 8.00-7.97 (d, J = 8.4 Hz, 1H), 7.46-7.39 (m, 4H), 7.27-7.12 (m, 3H), 5.01-4.86 (m, 1H), 4.69 (s, 1H), 4.60-4.55 (t, J = 7.5 Hz, 1H), 4.44 (m, 1H), 4.19-4.17 (t, J = 6.0 Hz, 2H), 3.98-3.97 (d, J = 2.7 Hz, 2H), 3.87-3.76 (m, 2H), 3.61-3.49 (m, 6H), 2.48 (s, 3H), 2.17 (m, 1H), 2.00-1.89 (m, 3H), 1.84-1.75 (m, 2H), 1.74-1.71 (m, 4H), 1.58 (s, 6H), 1.52-1.49 (m, 3H), 1.04 (s, 9H); Mass (ES$^+$): m/z 1052.20 [MH$^+$] |

TABLE 2-continued

Exemplary Compounds.

| Ex # | Structure | Compound name and Analytical data |
|---|---|---|
| 26 | 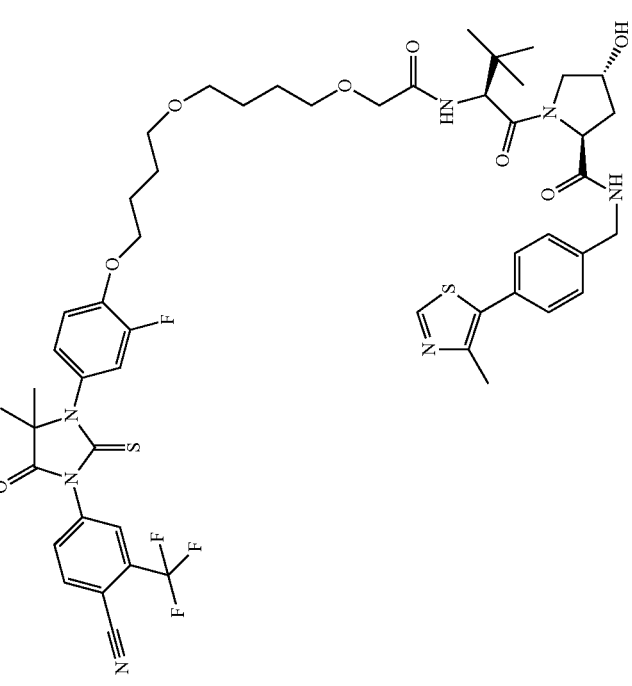 | Prepared from ABM-16, L-7, and ULM-3 (2S,4R)-1-[(2S)-2-(2-{4-[4-(4-{3-[4-(4-cyano-3-(trifluoromethyl)phenyl]-5,5-dimethyl-4-oxo-2-sulfanylideneimidazolidin-1-yl}-2-fluorophenoxy)butoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD): δ 8.88 (s, 1H), 8.17-8.15 (m, 2H), 8.00-7.99 (d, J = 6.4 Hz, 1H), 7.49-7.42 (m, 4H), 7.23-7.13(m, 3H), 4.71 (s, 1H), 4.61-4.52 (m, 3H), 4.38-4.34 (m, 1H), 4.00-3.83 (m, 3H), 3.61-3.49 (m, 6H), 2.49 (s, 3H), 2.30-2.10 (m, 2H), 1.92-1.89(m, 2H), 1.79-1.73 (m, 6H), 1.72 (s, 6H), 1.05(s, 9H); LC-MS (ES$^+$): m/z 1038.50[MH$^+$], t$_R$ = 3.05 min (5.0 minute run). |

TABLE 2-continued

Exemplary Compounds.

| Ex # | Structure | Compound name and Analytical data |
|---|---|---|
| 27 | 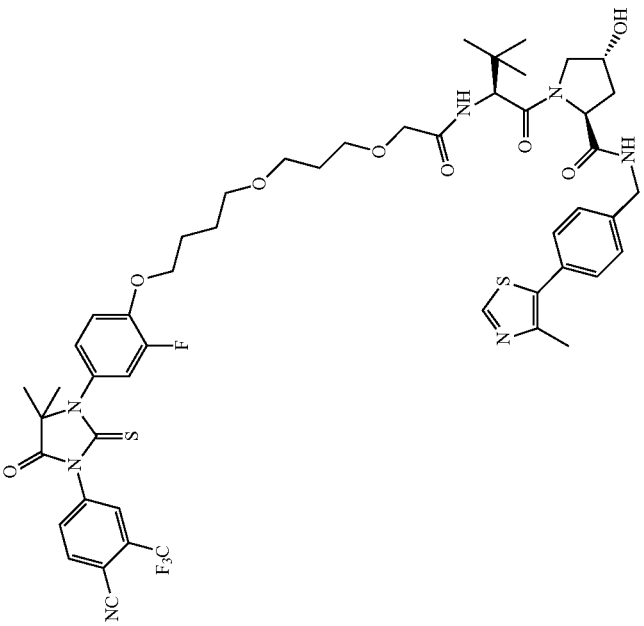 | Prepared from ABM-16, L-8, and ULM-1 (2S,4R)-1-[(2S)-2-(2-{3-[4-(4-{3-[4-cyano-3-(trifluoromethyl)phenyl]-5,5-dimethyl-4-oxo-2-sulfanylideneimidazolidin-1-yl}-2-fluorophenoxy)butoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.87 (s, 1H), 8.10 (d, J = 8.6 Hz, 2H), 7.93 (m, 1H), 7.37 (m, 4H), 7.11 (m, 3H), 4.83-4.48 (m, 5H), 4.12 (m, 2H), 3.94 (m, 2H), 3.78 (m, 2H), 3.50 (m, 6H), 2.44 (s, 3H), 2.05 (m, 2H), 1.73 (m, 6H), 1.52 (s, 6H), 1.00 (s, 9H); LC-MS (ES$^+$): m/z 1024.10 [MH$^+$], t$_R$ = 2.79 min (5.6 minute run). |

TABLE 2-continued

Exemplary Compounds.

| Ex # | Structure | Compound name and Analytical data |
|---|---|---|
| 28 | (structure) | Prepared from ABM-3, L-8, and ULM-1 (2S,4R)-1-[(2S)-2-(2-{3-[4-(4-{3-[4-(4-cyano-3-(trifluoromethyl)phenyl]-5,5-dimethyl-4-oxo-2-sulfanylideneimidazolidin-1-yl]phenoxy}butoxy]phenoxy}propoxy)acetamido)-3,3-dimethylbutanoyl]-4-hydroxy-N-{[4-(4-methyl-1,3-thiazol-5-yl)phenyl]methyl}pyrrolidine-2-carboxamide <br> $^1$H NMR (300 MHz, CD$_3$OD) δ 8.88 (s, 1H), 8.14 (m, 2H), 7.97 (m, 1H), 7.49-7.41 (m, 4H), 7.26 (m, 2H), 7.02 (m, 2H), 4.70 (s, 1H), 4.61-4.52 (m, 3H), 4.38-4.33 (m, 1H), 4.03 (t, J = 6.3 Hz, 2H), 3.98 (s, 2H), 3.86-3.82 (m, 2H), 3.68-3.51 (m, 6H), 2.48 (s, 3H), 2.23-2.09 (m, 2H), 1.93-1.73 (m, 6H), 1.55 (s, 6H), 1.02 (s, 9H); LC-MS (ES$^+$): m/z 1006.50 [MH$^+$], t$_R$ = 2.81 min (5.6 minute run). |

TABLE 2-continued

Exemplary Compounds.

| Ex # | Structure | Compound name and Analytical data |
|---|---|---|
| 29 | 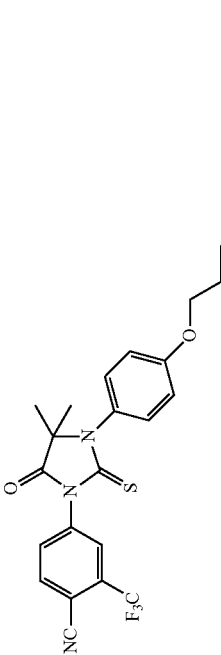 | Prepared from ABM-3, L-8, and ULM-8 (2S,4R)-1-[(2S)-2-(2-{3-[4-(4-{3-[4-(4-cyano-3-(trifluoromethyl)phenyl]-5,5-dimethyl-4-oxo-2-sulfanylideneimidazolidin-1-yl}phenoxy)butoxy]propoxy}acetamido)-3-methylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.88 (s, 1H), 8.17 (d, J = 8.8 Hz, 2H), 8.01 (m, 1H), 7.47 (m, 4H), 7.30 (d, J = 8.8 Hz, 2H), 7.06 (d, J = 8.8 Hz, 2H), 4.66 (m, 1H), 4.61 (m, 1H), 4.54 (m, 2H), 4.42 (m, 1H), 4.08 (m, 2H), 4.01 (m, 2H), 3.85 (m, 2H), 3.67 (m, 2H), 3.61 (m, 2H), 3.56 (m, 2H), 2.50 (s, 3H), 2.25 (m, 1H), 2.16 (m, 2H), 1.93 (m, 4H), 1.78 (m, 2H), 1.56 (s, 6H), 1.03 (m, 3H), 0.96 (m, 3H); LC-MS (ES$^+$); m/z 992.55 [MH$^+$], t$_R$ = 3.39 min (5.6 minute run). |

TABLE 2-continued

Exemplary Compounds.

| Ex # | Structure | Compound name and Analytical data |
|---|---|---|
| 30 | (structure) | Prepared from ABM-4, L-8, and ULM-1 (2S,4R)-1-[(2S)-2-(2-{3-[4-(3-[4-{3-[6-cyano-5-(trifluoromethyl)pyridin-3-yl]-5,5-dimethyl-4-oxo-2-sulfanylideneimidazolidin-1-yl]phenoxy}butoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD) δ 9.15-9.10 (m, 1H), 8.80 (s, 1H), 8.66-8.62 (m, 1H), 7.45-7.36 (m, 4H), 7.25-7.18 (m, 2H), 7.02-6.92 (m, 2H), 4.70-4.62 (m, 1H), 4.60-4.44 (m, 3H), 4.35-4.26 (m, 1H), 4.10-3.90 (m, 4H), 3.89-3.69 (m, 2H), 3.65-3.40 (m, 6H), 2.44 (s, 4H), 2.20-2.01 (m, 2H), 1.88-1.60 (m, 6H), 1.52 (s, 6H), 1.00 (s, 9H); LC-MS (ES$^+$): m/z 1007.30 [MH$^+$], t$_R$ = 1.71 min (3.0 minute run). |

TABLE 2-continued

Exemplary Compounds.

| Ex # | Structure | Compound name and Analytical data |
|---|---|---|
| 31 | (structure) | Prepared from ABM-1, L-8, and ULM-1 (2S,4R)-1-[(2S)-2-[2-[3-(4-{3-[4-[3-(3-chloro-4-cyanophenyl)-5,5-dimethyl-4-oxo-2-sulfanylideneimidazolidin-1-yl]phenoxy}butoxy)propoxy]acetamido]-3,3-dimethylbutanoyl]-4-hydroxy-N-{[4-(4-methyl-1,3-thiazol-5-yl)phenyl]methyl}pyrrolidine-2-carboxamide<br>¹H NMR (300 MHz, CD₃OD) δ 8.87 (s, 1H), 7.87 (s, 1H), 7.66 (m, 1H), 7.49 (m, 4H), 7.28 (m, 2H), 7.05 (m, 2H), 4.71 (s, 1H), 4.59 (m, 3H), 4.38 (m, 1H), 4.07 (m, 4H), 3.987 (m, 2H), 3.68 (m, 6H), 2.48 (s, 3H), 2.27 (m, 2H), 1.93 (m, 6H), 1.54 (s, 6H), 1.03 (s, 9H). LC-MS (ES⁺): m/z 486.40 [M/2H⁺], t_R = 2.21 min (3.6 minute run). |

TABLE 2-continued

Exemplary Compounds.

| Ex # | Structure | Compound name and Analytical data |
|---|---|---|
| 32 | 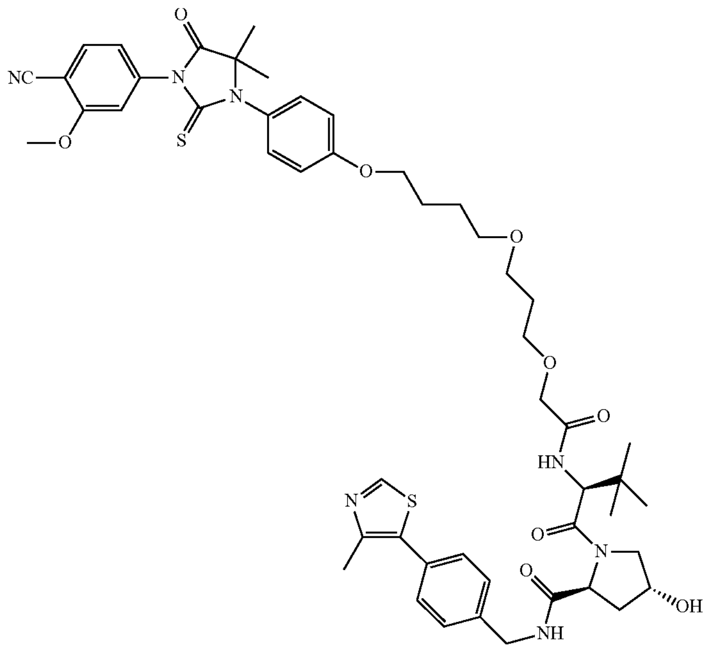 [SMILES: COc1cc(N2C(=O)C(C)(C)N(c3ccc(OCCCCOCCCOCC(=O)N[C@H](C(=O)N4C[C@H](O)C[C@H]4C(=O)NCc4ccc(-c5scnc5C)cc4)C(C)(C)C)cc3)C2=S)ccc1C#N] | Prepared from ABM-5, L-8, and ULM-1<br>(2S,4R)-1-[(2S)-2-{2-[3-(4-{4-[3-(4-cyano-3-methoxyphenyl)-5,5-dimethyl-4-oxo-2-sulfanylideneimidazolidin-1-yl]phenoxy}butoxy)propoxy]acetamido}-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.89 (s, 1H), 7.75 (d, J = 8.4 Hz, 1H), 7.49-7.42 (m, 4H), 7.37 (s, 1H), 7.27 (d, J = 8.8 Hz, 2H), 7.18-7.15 (m, 1H), 7.06-7.04 (m, 2H), 4.88 (s, 1H), 4.59-4.46 (m, 3H), 4.38-4.35 (m, 1H), 4.07-4.00 (m, 2H), 3.99-3.87 (m, 5H), 3.88-3.76 (m, 2H), 3.68-3.60 (m, 2H), 3.59-3.55 (m, 2H), 3.54-3.53 (m, 2H), 2.49 (s, 3H), 2.28-2.19 (m, 1H), 2.14-2.05 (m, 1H), 1.93-1.86 (m, 4H), 1.80-1.78 (m, 2H), 1.54 (s, 6H), 1.04 (s, 9H); LC-MS (ES$^+$): m/z 968.35 [MH$^+$], t$_R$ = 2.57 min (5.6 minute run). |

TABLE 2-continued

Exemplary Compounds.

| Ex # | Structure | Compound name and Analytical data |
|---|---|---|
| 33 | 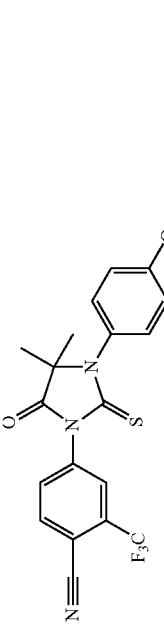 | Prepared from ABM-3, L-8, and ULM-2 (2S,4R)-1-[(2S)-2-(2-{3-[4-(4-{3-[4-cyano-3-(trifluoromethyl)phenyl]-5,5-dimethyl-4-oxo-2-sulfanylideneimidazolidin-1-yl}phenoxy)butoxy]propoxy}acetamido)-3,3-dimethylbutanoyl]-4-hydroxy-N-{[4-(1,3-thiazol-5-yl)phenyl]methyl}pyrrolidine-2-carboxamide<br>¹H NMR (400 MHz, CD₃OD): δ 8.94 (s, 1H), 8.16 (d, J = 8.8 Hz, 3H), 8.00 (d, J = 1.6 Hz, 1H), 7.61 (d, J = 8.0 Hz, 2H), 7.44 (d, J = 8.0 Hz, 2H), 7.28 (d, J = 8.8 Hz, 2H), 7.04 (d, J = 8.8 Hz, 2H), 4.71 (s, 1H), 4.61-4.51 (m, 3H), 4.37-4.33 (m, 1H), 4.07-4.03 (m, 2H), 4.01-3.96 (m, 2H), 3.88-3.82 (m, 1H), 3.81-3.77 (m, 1H), 3.69-3.3.62 (m, 2H), 3.61-3.55 (m, 2H), 3.54-3.53 (m, 2H), 2.28-2.19 (m, 1H), 2.14-2.05 (m, 1H), 1.96-1.84 (m, 4H), 1.80-1.74 (m, 2H), 1.56 (s, 6H), 1.06 (s, 9H); LC-MS (ES⁺): m/z 496.85 [MH/2⁺], t_R = 1.60 min (3.0 minute run). |

TABLE 2-continued

Exemplary Compounds.

| Ex # | Structure | Compound name and Analytical data |
|---|---|---|
| 34 | 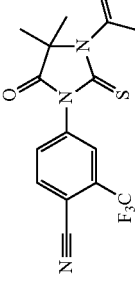 | Prepared from ABM-3, L-8, and ULM-4<br>(2S,4R)-1-[(2S)-2-(2-{3-[4-(4-{3-[4-cyano-3-(trifluoromethyl)phenyl]-5,5-dimethyl-4-oxo-2-sulfanylideneimidazolidin-1-yl}phenoxy)butoxy]propoxy}acetamido)-3,3-dimethylbutanoyl]-4-hydroxy-N-{[4-(1,3-oxazol-5-yl)phenyl]methyl}pyrrolidine-2-carboxamide<br>¹H NMR (400 MHz, CD₃OD) δ 8.24 (s, 1H), 8.17 (d, J = 8.0 Hz, 2H), 8.01 (dd, J = 8.0, 1.6 Hz, 1H), 7.70 (d, J = 8.0 Hz, 2H), 7.49-7.45 (m, 3H), 7.29 (d, J = 8.8 Hz, 2H), 7.06 (d, J = 8.8 Hz, 2H), 4.72 (s, 1H), 4.61-4.51 (m, 3H), 4.37 (m, 1H), 4.08-3.83 (m, 6H), 3.69-3.54 (m, 6H), 2.15-2.05 (m, 2H), 1.93-1.76 (m, 6H), 1.56 (s, 6H), 1.03 (s, 9H); LC-MS (ES⁺): m/z 976.45 [MH⁺], t_R = 1.69 min (3.0 minute run). |

TABLE 2-continued

Exemplary Compounds.

| Ex # | Structure | Compound name and Analytical data |
|---|---|---|
| 35 | 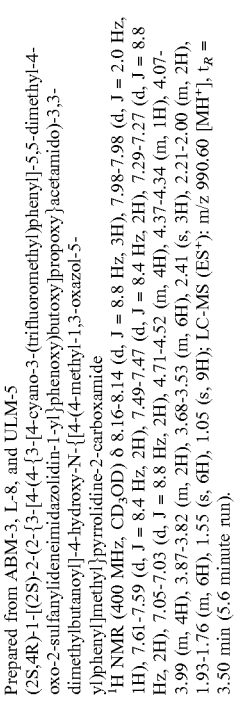 | Prepared from ABM-3, L-8, and ULM-5 (2S,4R)-1-[(2S)-2-(2-{3-[4-(4-{3-[4-(4-cyano-3-(trifluoromethyl)phenyl]-5,5-dimethyl-4-oxo-2-sulfanylideneimidazolidin-1-yl]phenoxy}butoxy]phenoxy)propoxy}acetamido)-3,3-dimethylbutanoyl]-4-hydroxy-N-{[4-(4-methyl-1,3-oxazol-5-yl)phenyl]methyl}pyrrolidine-2-carboxamide ¹H NMR (400 MHz, CD₃OD) δ 8.16-8.14 (d, J = 8.8 Hz, 3H), 7.98-7.98 (d, J = 2.0 Hz, 1H), 7.61-7.59 (d, J = 8.4 Hz, 2H), 7.49-7.47 (d, J = 8.4 Hz, 2H), 7.29-7.27 (d, J = 8.8 Hz, 2H), 7.05-7.03 (d, J = 8.8 Hz, 2H), 4.71-4.52 (m, 4H), 4.37-4.34 (m, 1H), 4.07-3.99 (m, 4H), 3.87-3.82 (m, 2H), 3.68-3.53 (m, 6H), 2.41 (s, 3H), 2.21-2.00 (m, 2H), 1.93-1.76 (m, 6H), 1.55 (s, 6H), 1.05 (s, 9H); LC-MS (ES⁺): m/z 990.60 [MH⁺], t_R = 3.50 min (5.6 minute run). |

TABLE 2-continued

Exemplary Compounds.

| Ex # | Structure | Compound name and Analytical data |
|---|---|---|
| 36 | 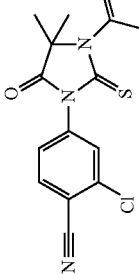 | Prepared from ABM-1, L-8, and ULM-9 (2S,4R)-1-[(2S)-2-[2-[3-(4-{4-[3-(3-chloro-4-cyanophenyl)-5,5-dimethyl-4-oxo-2-sulfanylideneimidazolidin-1-yl]phenoxy}butoxy)propoxy]acetamido]-3-methylbutanoyl]-4-hydroxy-N-{[4-(1,3-thiazol-5-yl)phenyl]methyl}pyrrolidine-2-carboxamide ¹H NMR (400 MHz, CD₃OD): δ 8.89 (s, 1H), 8.12 (s, 1H), 7.90 (d, J = 8.4 Hz, 1H), 7.82 (s, 1H), 7.62-7.56 (m, 3H), 7.40 (d, J = 8.4 Hz, 2H), 7.23 (d, J = 8.4 Hz, 2H), 7.00 (s, 2H), 4.61-4.52 (m, 1H), 4.51-4.40 (m, 2H), 4.394.36 (m, 1H), 4.03-3.95 (m, 4H), 3.78-3.74 (m, 2H), 3.63-3.27 (m, 7H), 2.23-1.98 (m, 3H), 1.89-1.71 (m, 6H), 1.50 (s, 6H), 0.97 (d, J = 6.6 Hz, 3H), 0.89 (d, J = 6.6 Hz, 3H); LC-MS (ES⁺): m/z 944.25 [MH⁺], t_R = 1.51 min (3.0 minute run). |

TABLE 2-continued

Exemplary Compounds.

| Ex # | Structure | Compound name and Analytical data |
|---|---|---|
| 37 | 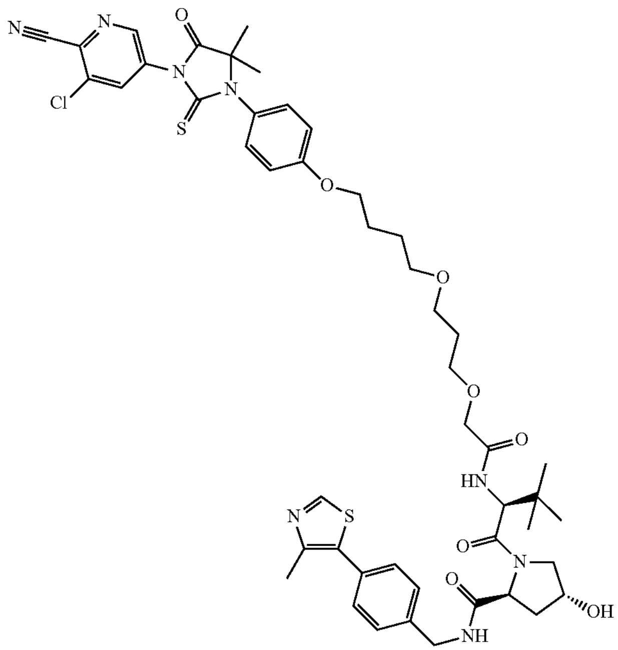 [SMILES: Cc1ncsc1-c1ccc(CNC(=O)[C@@H]2C[C@@H](O)CN2C(=O)[C@@H](NC(=O)COCCCOCCCCOc2ccc(N3C(=S)N(c4cnc(C#N)c(Cl)c4)C(=O)C3(C)C)cc2)C(C)(C)C)cc1] | Prepared from ABM-1, L-8, and ULM-1 (2S,4R)-1-[(2S)-2-{2-[3-(4-{3-[4-[3-(5-chloro-6-cyanopyridin-3-yl)-5,5-dimethyl-4-oxo-2-sulfanylideneimidazolidin-1-yl]phenoxy}butoxy)propoxy]acetamido}-3,3-dimethylbutanoyl]-4-hydroxy-N-{[4-(4-methyl-1,3-thiazol-5-yl)phenyl]methyl}pyrrolidine-2-carboxamide $^1$H NMR (400 MHz, CD$_3$OD): δ 8.87-8.86(m, 2H), 8.44 (s, 1H), 7.49-7.42 (m, 4H), 7.29-7.27 (d, J = 8.8 Hz, 2H), 7.06-7.04 (d, J = 8.8 Hz, 2H), 4.72 (s, 1H), 4.59-4.52 (m, 3H), 4.39-4.35 (m, 1H), 4.08-3.99 (m, 4H), 3.96-3.83 (m, 2H), 3.68-3.59 (m, 6H), 2.50 (s, 3H), 2.15-2.05 (m, 2H), 1.92-1.88 (m, 6H), 1.56 (s, 6H), 1.04 (s, 9H); LC-MS (ES$^+$): m/z 973.30 [MH$^+$], t$_R$ = 1.58 min (3.0 minute run). |

TABLE 2-continued

Exemplary Compounds.

| Ex # | Structure | Compound name and Analytical data |
|---|---|---|
| 38 | 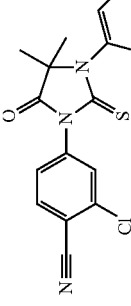 | Prepared from ABM-1, L-8, and ULM-5 (2S,4R)-1-[(2S)-2-{2-[3-(4-{4-[3-(3-chloro-4-cyanophenyl)-5,5-dimethyl-4-oxo-2-sulfanylideneimidazolidin-1-yl]phenoxy}butoxy)propoxy]acetamido}-3,3-dimethylbutanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD) δ 8.20 (s, 1H), 7.97-7.95 (d, J = 8.4 Hz, 1H), 7.87 (s, 1H), 7.66-7.59 (m, 3H), 7.49-7.47 (d, J = 8.4 Hz, 2H), 7.28-7.26 (d, J = 9.2 Hz, 2H), 7.05-7.03 (d, J = 8.8 Hz, 2H), 4.71 (s, 1H), 4.57-4.52 (m, 3H), 4.38-4.34 (m, 1H), 4.07-3.99 (m, 4H), 3.87-3.80 (m, 2H), 3.67-3.53 (m, 6H), 2.42 (s, 1H), 2.20-2.00 (m, 2H), 1.93-1.77 (m, 6H), 1.54 (s, 6H), 1.06 (s, 9H); LC-MS (ES$^+$): m/z 956.30 [MH$^+$], t$_R$ = 1.56 min (3.0 minute run). |

TABLE 2-continued

Exemplary Compounds.

| Ex # | Structure | Compound name and Analytical data |
|---|---|---|
| 39 | 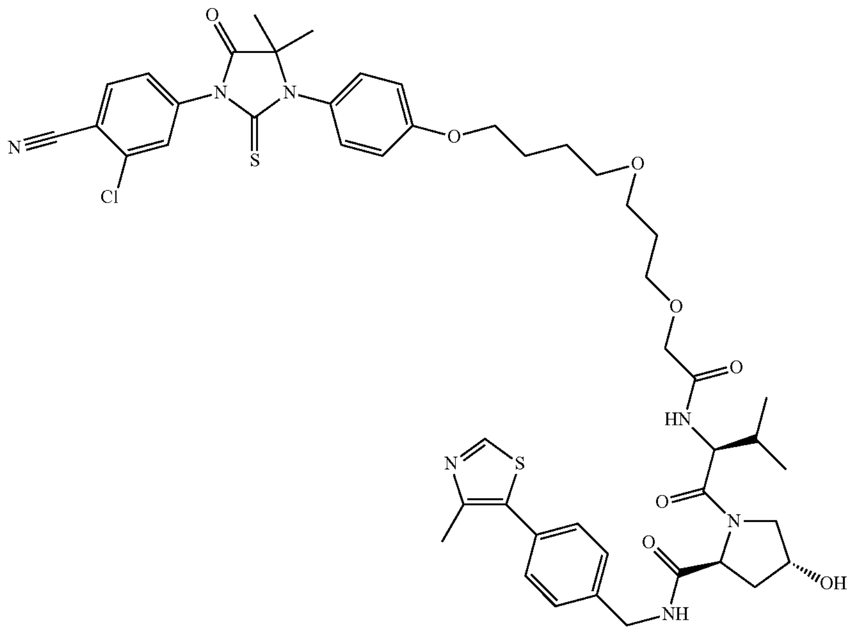 | Prepared from ABM-1, L-8, and ULM-10 (2S,4R)-1-[(2S)-2-{2-[3-(4-{3-[4-[3-(3-chloro-4-cyanophenyl)-5,5-dimethyl-4-oxo-2-sulfanylideneimidazolidin-1-yl]phenoxy}butoxy)propoxy]acetamido}-3-methylbutanoyl]-4-hydroxy-N-{[4-(4-methyl-1,3-oxazol-5-yl)phenyl]methyl}pyrrolidine-2-carboxamide $^1$H NMR (400 MHz, CD$_3$OD) δ 8.15 (s, 1H), 7.97-7.95 (d, J = 8.4 Hz, 1H), 7.87 (s, 1H), 7.66-7.60 (m, 3H), 7.48-7.45 (d, J = 8.4 Hz, 2H), 7.28-7.26 (d, J = 9.2 Hz, 2H), 7.06-7.03 (d, J = 9.2 Hz, 2H), 4.66-4.41 (m, 5H), 4.07-3.99 (m, 4H), 3.85-3.83 (m, 2H), 3.66-3.53 (m, 6H), 2.41 (s, 3H), 2.25-2.00 (m, 3H), 1.93-1.77 (m, 6H), 1.53 (s, 6H), 1.03-1.02 (d, J = 6.8 Hz, 3H), 0.95-0.93(d, J = 6.8 Hz, 3H); LC-MS (ES$^+$): m/z 942.30 [MH$^+$], t$_R$ = 1.50 min (3.0 minute run). |

TABLE 2-continued

Exemplary Compounds.

| Ex # | Structure | Compound name and Analytical data |
|---|---|---|
| 40 | 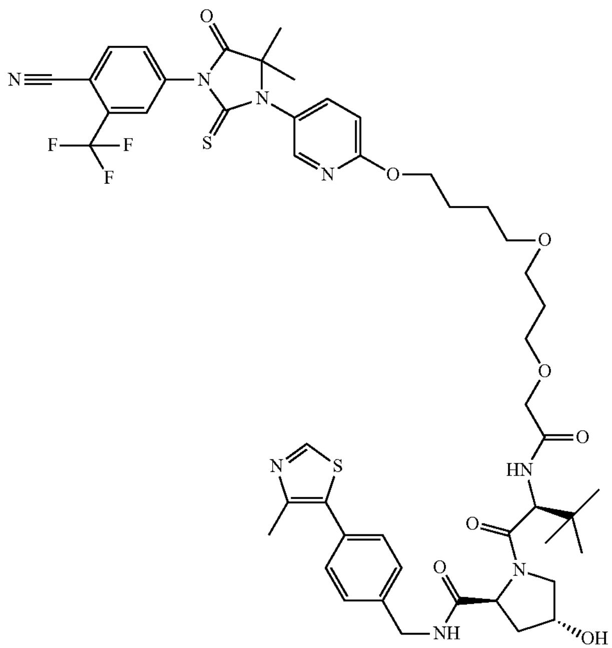 [SMILES: Cc1ncsc1-c1ccc(CNC(=O)[C@@H]2C[C@@H](O)CN2C(=O)[C@@H](NC(=O)COCCCOCCCCOc2ccc(N3C(=S)N(c4ccc(C#N)c(C(F)(F)F)c4)C(=O)C3(C)C)cn2)C(C)(C)C)cc1] | Prepared from ABM-20, L-8, and ULM-1 (2S,4R)-1-[(2S)-2-[2-(3-{4-[(5-{3-[4-(4-cyano-3-(trifluoromethyl)phenyl]-5,5-dimethyl-4-oxo-2-sulfanylideneimidazolidin-1-yl]pyridin-2-yl}oxy]butoxy}propoxy)acetamido]-3,3-dimethylbutanoyl]-4-hydroxy-N-{[4-(4-methyl-1,3-thiazol-5-yl)phenyl]methyl}pyrrolidine-2-carboxamide<br>¹H NMR (300 MHz, CD₃OD): δ8.81 (s, 1H), 8.16-8.03 (m, 3H), 8.00-7.90 (m, 1H), 7.70-7.60 (m, 1H), 7.51-7.30 (m, 4H), 6.91-6.80 (m, 1H), 4.67 (s, 1H), 4.60-4.40 (m, 4H), 4.32-4.21 (m, 3H), 3.89-3.70 (m, 4H), 3.65-3.40 (m, 6H), 2.41 (s, 3H), 2.23-2.01 (m, 2H), 1.90-1.62 (m, 6H), 1.55 (s, 6H), 1.02 (s, 9H); LC-MS (ES⁺): m/z, 1007.35 [MH⁺], t_R = 1.58 min (3.0 minute run). |

TABLE 2-continued

Exemplary Compounds.

| Ex # | Structure | Compound name and Analytical data |
|---|---|---|
| 41 | 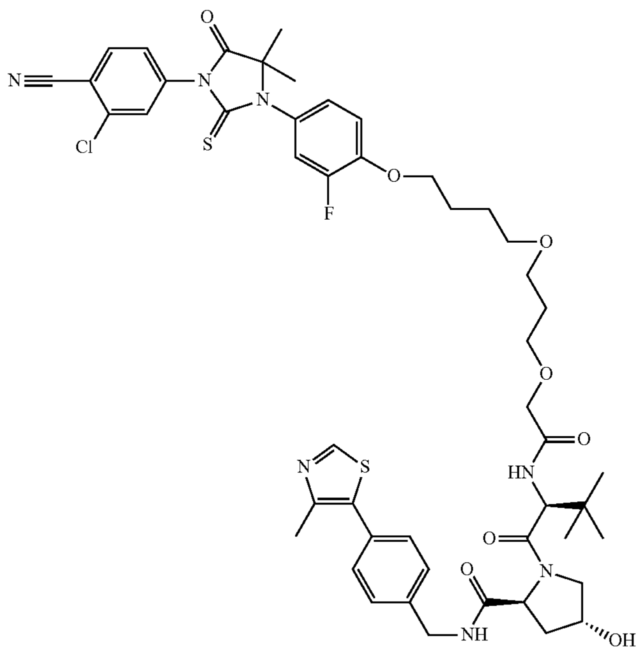 [SMILES: Cc1ncsc1-c1ccc(CNC(=O)[C@@H]2C[C@@H](O)CN2C(=O)[C@@H](NC(=O)COCCCOCCCCOc2ccc(N3C(=S)N(c4ccc(C#N)c(Cl)c4)C(=O)C3(C)C)cc2F)C(C)(C)C)cc1] | Prepared from ABM-21, L-8, and ULM-1 (2S,4R)-1-[(2S)-2-{2-[3-(4-{4-[3-(3-chloro-4-cyanopheny)-5,5-dimethyl-4-oxo-2-sulfanylideneimidazolidin-1-yl]-2-fluorophenoxy}butoxy)propoxy]acetamido}-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.88 (s, 1H), 7.97 (d, J = 8.4 Hz, 1H), 7.88 (s, 1H), 7.66-7.64 (m, 1H), 7.48-7.39 (m, 4H), 7.22-7.19 (m, 2H), 7.14 (s, 1H), 4.71 (s, 1H), 4.59-4.47 (m, 3H), 4.36 (d, J = 15.6 Hz, 1H), 4.14 (t, J = 6.4 Hz, 2H), 4.00 (d, J = 3.6 Hz, 2H), 3.87-3.78 (m, 2H), 3.67-3.54 (m, 6H), 2.45 (s, 3H), 2.26-2.21 (m, 1H), 2.13-2.04 (m, 1H), 1.93-1.89 (m, 4H), 1.83-1.74 (m, 2H), 1.55 (s, 6H), 1.04 (s, 9H); LC-MS (ES$^+$): m/z 990.35 [MH$^+$], t$_R$ = 1.59 min (3.0 minute run). |

TABLE 2-continued

Exemplary Compounds.

| Ex # | Structure | Compound name and Analytical data |
|---|---|---|
| 42 | 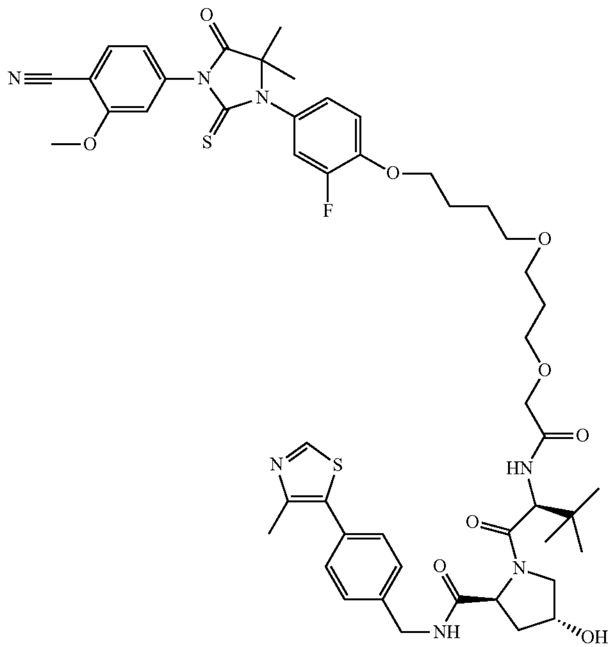 [SMILES: COc1cc(N2C(=O)C(C)(C)N(c3ccc(OCCCCOCCCOCC(=O)N[C@H](C(=O)N4C[C@H](O)C[C@H]4C(=O)NCc4ccc(-c5scnc5C)cc4)C(C)(C)C)c(F)c3)C2=S)ccc1C#N] | Prepared from ABM-22, L-8, and ULM-1 (2S,4R)-1-[(2S)-2-[2-[3-(4-{4-[3-(4-cyano-3-methoxyphenyl)-5,5-dimethyl-4-oxo-2-sulfanylideneimidazolidin-1-yl]-2-fluorophenoxy}butoxy)propoxy]acetamido]-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD) δ 8.98 (s, 1H), 7.77-7.75 (d, J = 8.4 Hz, 2H), 7.49-7.42 (m, 4H), 7.36-7(s, 1H), 7.21-7.14 (m, 4H), 4.71 (s, 1H), 4.59-4.52 (m, 3H), 4.39-4.35(m, 1H), 4.16-4.13 (m, 2H), 4.00-3.98 (m, 5H), 3.99-3.83 (m, 2H), 3.68-3.66 (m, 2H), 2.50 (s, 3H), 2.30-2.10 (m, 2H), 1.93-1.89 (m, 4H), 1.80-1.76 (m, 2H), 1.55 (s, 6H), 1.03 (s, 9H); LC-MS (ES$^+$): m/z 986.45 [MH$^+$], t$_R$ = 1.65 min (3.0 minute run). |

TABLE 2-continued

Exemplary Compounds.

| Ex # | Structure | Compound name and Analytical data |
|---|---|---|
| 43 | 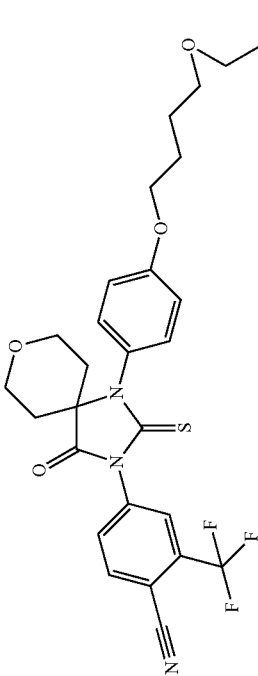 | Prepared from ABM-8, L-8, and ULM-1 (2S,4R)-1-[(2S)-2-(2-{3-[4-(4-{3-[4-cyano-3-(trifluoromethyl)phenyl]-4-oxo-2-sulfanylidene-8-oxa-1,3-diazaspiro[4.5]decan-1-yl}phenoxy)butoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD) δ 8.98-8.83 (s, 1H), 8.18-8.16 (d, J = 8.4 Hz, 2H), 8.01-7.99 (m, 1H), 7.49-7.42 (m, 4H), 7.42-7.24 (d, J = 8.4 Hz, 2H), 7.08-7.06 (d, J = 8.4 Hz, 2H), 4.80 (s, 1H), 4.72 (s, 1H), 4.59-4.34 (m, 3H), 4.20-4.08 (m, 6H), 3.99-3.87 (m, 4H), 3.67-3.56 (m, 6H), 2.49 (s, 3H), 2.21-1.87 (m, 12H), 1.05 (s, 9H); LC-MS (ES$^+$): m/z 1048.45 [MH$^+$], t$_R$ = 1.73 min (3.0 minute run). |

TABLE 2-continued

Exemplary Compounds.

| Ex # | Structure | Compound name and Analytical data |
|---|---|---|
| 44 | 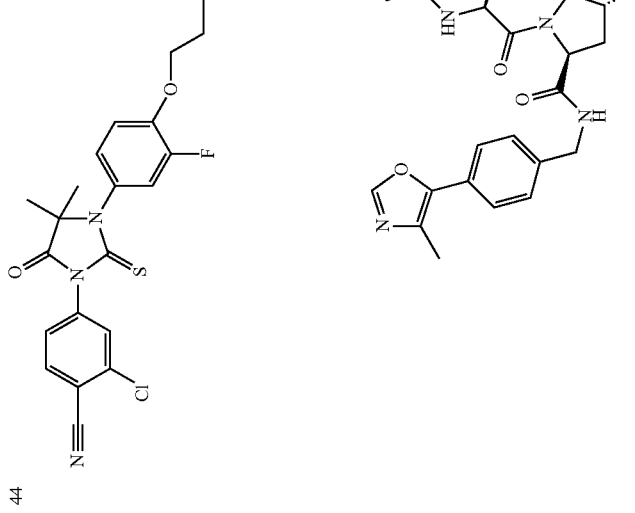 | Prepared from ABM-21, L-8, and ULM-5 (2S,4R)-1-[(2S)-2-{2-[3-(4-{3-[4-[3-(3-chloro-4-cyanophenyl)-5,5-dimethyl-4-oxo-2-sulfanylideneimidazolidin-1-yl]-2-fluorophenoxy}butoxy)propoxy]acetamido}-3,3-dimethylbutanoyl]-4-hydroxy-N-{[4-(4-methyl-1,3-oxazol-5-yl)phenyl]methyl}pyrrolidine-2-carboxamide $^1$H NMR (400 MHz, CD$_3$OD): δ 8.15 (s, 1H), 7.96 (d, J = 8.4 Hz, 1H), 7.87 (s, 1H), 7.66-7.60 (m, 3H), 7.48 (d, J = 8.4 Hz, 2H), 7.24-7.14 (m, 3H), 4.71 (s, 1H), 4.61-4.52 (m, 3H), 4.38-4.33 (m, 1H), 4.14 (m, 2H), 4.00 (d, J = 4.0 Hz, 3H), 3.88-3.82 (m, 2H), 3.68-3.54 (m, 6H), 2.42 (s, 3H), 2.27-2.18 (m, 1H), 2.13-2.04 (m, 1H), 1.93-1.89 (m, 4H), 1.88-1.80 (m, 2H), 1.55 (s, 6H), 1.06 (s, 9H); LC-MS (ES$^+$): m/z 974.25 [MH$^+$], t$_R$ = 1.57 min (3.0 minute run). |

TABLE 2-continued

Exemplary Compounds.

| Ex # | Structure | Compound name and Analytical data |
|---|---|---|
| 45 | 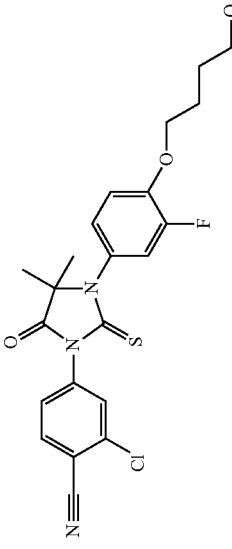 | Prepared from ABM-21, L-8, and ULM-4 (2S,4R)-1-[(2S)-2-{2-[3-(4-{3-[4-[3-(3-chloro-4-cyanophenyl)-5,5-dimethyl-4-oxo-2-sulfanylideneimidazolidin-1-yl]-2-fluorophenoxy}butoxy)propoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, CD$_3$OD): δ 8.24 (s, 1H), 7.96 (d, J = 8.4 Hz, 1H), 7.87 (s, 1H), 7.70-7.64 (m, 3H), 7.49-7.40 (m, 3H), 7.22 (d, J = 8.4 Hz, 2H), 7.14 (d, J = 8.0 Hz, 1H), 4.71 (s, 1H), 4.60-4.51 (m, 3H), 4.38-4.34 (m, 1H), 4.18-4.11 (m, 2H), 4.00-3.96 (m, 2H), 3.92-3.76 (m, 2H), 3.68-3.55 (m, 6H), 2.27-2.21 (m, 1H), 2.18-2.06 (m, 1H), 1.95-1.86 (m, 4H), 1.83-1.72 (m, 2H), 1.55 (s, 6H), 1.06 (s, 9H); LC-MS (ES$^+$): m/z 960.30 [MH$^+$], t$_R$ = 1.54 min (3.0 minute run). |

TABLE 2-continued

Exemplary Compounds.

| Ex # | Structure | Compound name and Analytical data |
|---|---|---|
| 46 | (structure) | Prepared from ABM-21, L-8, and ULM-2 (2S,4R)-1-[(2S)-2-[2-[3-(4-{3-[4-[3-(3-chloro-4-cyanophenyl)-5,5-dimethyl-4-oxo-2-sulfanylideneimidazolidin-1-yl]-2-fluorophenoxy}butoxy)propoxy]acetamido]-3,3-dimethylbutanoyl]-4-hydroxy-N-{[4-(1,3-thiazol-5-yl)phenyl]methyl}pyrrolidine-2-carboxamide<br>$^1$H NMR (400 MHz, CD$_3$OD): δ 8.94 (s, 1H), 8.15 (s, 1H), 7.96 (d, J = 8.4 Hz, 1H), 7.87 (s, 1H), 7.66-7.61 (m, 3H), 7.44 (d, J = 8.4 Hz, 2H), 7.19-7.12 (m, 3H), 4.71 (s, 1H), 4.60-4.51 (m, 3H), 4.38-4.34 (m, 1H), 4.17-4.11 (m, 2H), 3.99-3.94 (m, 2H), 3.88-3.75 (m, 2H), 3.71-3.55 (m, 6H), 2.37-2.20 (m, 1H), 2.13-2.06 (m, 1H), 1.94-1.89 (m, 4H), 1.80-1.77 (m, 2H), 1.55 (s, 6H), 1.03 (s, 9H); LC-MS (ES$^+$): m/z 976.25 [MH$^+$], t$_R$ = 1.57 min (3.0 minute run). |

TABLE 2-continued

Exemplary Compounds.

| Ex # | Structure | Compound name and Analytical data |
|---|---|---|
| 47 | 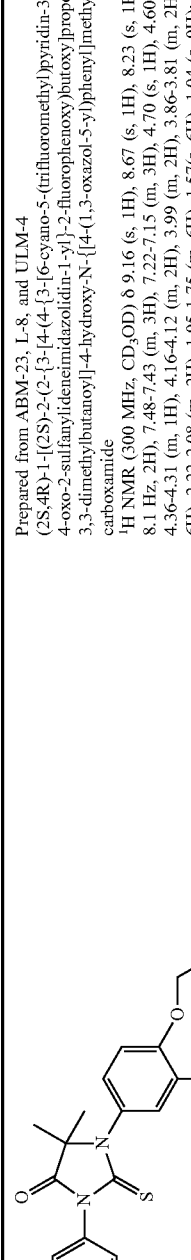 | Prepared from ABM-23, L-8, and ULM-4 (2S,4R)-1-[(2S)-2-(2-{3-[4-{3-[6-cyano-5-(trifluoromethyl)pyridin-3-yl]-5,5-dimethyl-4-oxo-2-sulfanylideneimidazolidin-1-yl}-2-fluorophenoxy)butoxy]propoxy}acetamido)-3,3-dimethylbutanoyl]-4-hydroxy-N-{[4-(1,3-oxazol-5-yl)phenyl]methyl}pyrrolidine-2-carboxamide <br> $^1$H NMR (300 MHz, CD$_3$OD) δ 9.16 (s, 1H), 8.67 (s, 1H), 8.23 (s, 1H), 7.69-7.66 (d, J = 8.1 Hz, 2H), 7.48-7.43 (m, 3H), 7.22-7.15 (m, 3H), 4.70 (s, 1H), 4.60-4.49 (m, 3H), 4.36-4.31 (m, 1H), 4.16-4.12 (m, 2H), 3.99 (m, 2H), 3.86-3.81 (m, 2H), 3.67-3.53 (m, 6H), 2.22-2.08 (m, 2H), 1.95-1.75 (m, 6H), 1.57(s, 6H), 1.04 (s, 9H); LC-MS (ES$^+$): m/z 995.10 [MH$^+$], t$_R$ = 2.26 min (3.6 minute run). |

TABLE 2-continued

Exemplary Compounds.

| Ex # | Structure | Compound name and Analytical data |
|---|---|---|
| 48 | 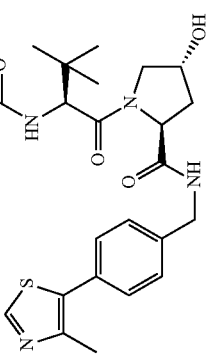 | Prepared from ABM-23, L-8, and ULM-1 (2S,4R)-1-[(2S)-2-(2-{3-[4-(4-{3-[6-cyano-5-(trifluoromethyl)pyridin-3-yl]-5,5-dimethyl-4-oxo-2-sulfanylideneimidazolidin-1-yl}-2-fluorophenoxy)butoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide <sup></sup>1H NMR (300 MHz, CD3OD) δ 9.16 (s, 1H), 8.87 (s, 1H), 8.67(s, 1H), 7.48-7.40 (m, 4H), 7.24-7.12 (m, 3H), 4.70 (s, 1H), 4.62-4.46 (m, 3H), 4.38-4.32 (m, 1H), 4.15-4.09 (m, 2H), 3.99 (s, 2H), 3.90-3.78 (m, 2H), 3.67-3.52 (m, 6H), 2.47 (s, 3H), 2.27-2.17 (m, 1H), 2.16-2.06 (m, 1H), 1.94-1.83 (m, 4H), 1.82-1.71 (m, 2H), 1.57(s, 6H), 1.04 (s, 9H); LC-MS (ES+): m/z 1025.30 [MH+], t$_R$ = 2.27 min, (3.6 minute run) |

TABLE 2-continued

Exemplary Compounds.

| Ex # | Structure | Compound name and Analytical data |
|---|---|---|
| 49 | (structure) | Prepared from ABM-22, L-8, and ULM-4 (2S,4R)-1-[(2S)-2-{2-[3-(4-{3-(4-cyano-3-methoxyphenyl)-5,5-dimethyl-4-oxo-2-sulfanylideneimidazolidin-1-yl]-2-fluorophenoxy}butoxy)propoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, CD$_3$OD) δ 8.25 (s, 1H), 7.77 (d, J = 8.0 Hz, 1H), 7.70(d, J = 8.4 Hz, 2H), 7.50 (m, 3H), 7.36 (m, 1H), 7.24 (m, 4H), 4.71 (s, 1H), 4.60 (m, 3H), 4.37 (m, 1H), 4.16 (m, 2H), 4.01 (m, 5H), 3.88 (m, 1H), 3.83 (m, 1H), 3.69 (m, 6H), 2.28 (m, 1H), 2.14 (m, 1H), 1.94 (m, 4H), 1.81 (m, 2H), 1.56 (s, 6H), 1.06 (m, 9H); LC-MS (ES$^+$): m/z 956.45 [MH$^+$], t$_R$ = 2.17 min (3.6 minute run). |

TABLE 2-continued

Exemplary Compounds.

| Ex # | Structure | Compound name and Analytical data |
|---|---|---|
| 50 | (structure) | Prepared from ABM-21, L-8, and ULM-11 (2S,4R)-1-[(2S)-2-{2-[3-(4-{3-[4-[3-(3-chloro-4-cyanophenyl)-5,5-dimethyl-4-oxo-2-sulfanylideneimidazolidin-1-yl]-2-fluorophenoxy}butoxy)propoxy]acetamido}-3,3-dimethylbutanoyl]-4-hydroxy-N-{[4-(1-methyl-1H-pyrazol-5-yl)phenyl]methyl}pyrrolidine-2-carboxamide $^1$H NMR (300 MHz, CD$_3$OD) δ 7.96-7.93 (d, J = 8.1 Hz, 1H), 7.86 (s, 1H), 7.65-7.61 (d, J = 9.6 Hz, 1H), 7.50-7.41 (m, 5H), 7.23-7.10 (m, 3H), 6.34 (s, 1H), 4.71 (s, 1H), 4.61-4.46 (m, 3H), 4.41-4.34 (m, 1H), 4.18-4.09 (m, 2H), 3.98 (s, 2H), 3.90-3.79 (m, 5H), 3.66-3.51 (m, 6H), 2.28-2.16 (m, 1H), 2.14-2.01 (m, 1H), 1.93-1.83 (m, 4H), 1.81-1.72 (m, 2H), 1.54 (s, 6H), 1.04 (s, 9H); LC-MS (ES$^+$); m/z 973.35 [MH$^+$], t$_R$ = 1.55 min, (3 minute run) |

TABLE 2-continued

Exemplary Compounds.

| Ex # | Structure | Compound name and Analytical data |
|---|---|---|
| 51 | 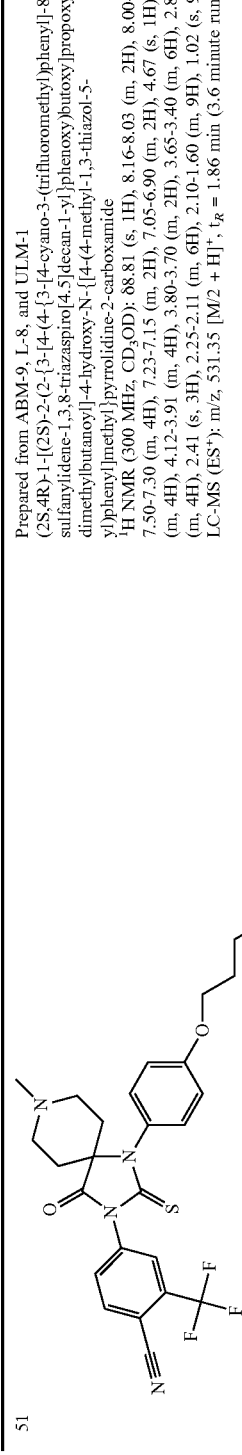 | Prepared from ABM-9, L-8, and ULM-1<br>(2S,4R)-1-[(2S)-2-(2-{3-[4-(4-{3-[4-(4-cyano-3-(trifluoromethyl)phenyl]-8-methyl-4-oxo-2-sulfanylidene-1,3,8-triazaspiro[4.5]decan-1-yl}phenoxy)butoxy]phenoxy}propoxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ8.81 (s, 1H), 8.16-8.03 (m, 2H), 8.00-7.90 (m, 1H), 7.50-7.30 (m, 4H), 7.23-7.15 (m, 2H), 7.05-6.90 (m, 2H), 4.67 (s, 1H), 4.60-4.30 (m, 4H), 4.12-3.91 (m, 4H), 3.80-3.70 (m, 2H), 3.65-3.40 (m, 6H), 2.80-2.61 (m, 4H), 2.41 (s, 3H), 2.25-2.11 (m, 6H), 2.10-1.60 (m, 9H), 1.02 (s, 9H); LC-MS (ES$^+$): m/z, 531.35 [M/2 + H]$^+$, t$_R$ = 1.86 min (3.6 minute run). |

TABLE 2-continued

Exemplary Compounds.

| Ex # | Structure | Compound name and Analytical data |
|---|---|---|
| 52 | (structure) | Prepared from ABM-3, L-9, and ULM-1 (2S,4R)-1-[(2S)-2-(2-{4-[3-(4-{3-[4-cyano-3-(trifluoromethyl)phenyl]-5,5-dimethyl-4-oxo-2-sulfanylideneimidazolidin-1-yl]phenoxy}propoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide <br> $^1$H NMR (300 MHz, CD$_3$OD) δ 8.83 (s, 1H), 8.12-8.10 (m, 2H), 7.96 (d, J = 8.1 Hz, 1H), 7.44-7.37 (m, 4H), 7.25 (d, J = 8.7 Hz, 2H), 7.02 (d, J = 8.7 Hz, 2H), 4.66-4.29 (m, 5H), 4.09-3.78 (m, 6H), 3.60-3.47 (m, 6H), 2.44 (s, 3H), 2.19-1.97 (m, 4H), 1.70-1.63 (m, 4H), 1.50 (s, 6H), 1.00 (s, 9H); LC-MS (ES$^+$): m/z 1006.30 [M H$^+$], t$_R$ = 1.71 min (3.0 minute run). |

TABLE 2-continued

Exemplary Compounds.

| Ex # | Structure | Compound name and Analytical data |
|---|---|---|
| 53 | (structure) | Prepared from ABM-16, L-9, and ULM-1 (2S,4R)-1-[(2S)-2-(2-{4-[3-(4-{3-[4-cyano-3-(trifluoromethyl)phenyl]-5,5-dimethyl-4-oxo-2-sulfanylideneimidazolidin-1-yl}-2-fluorophenoxy)propoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide <br> ¹H NMR (400 MHz, CD₃OD) δ 8.98 (s, 1H), 8.17-8.15 (d, J = 8.4 Hz, 2H), 8.01-7.99 (m, 1H), 7.49-7.42 (m, 4H), 7.42-7.20 (m, 3H), 4.80 (s, 1H), 4.71-4.70 (d, J = 2.8 Hz, 1H), 4.59-4.51 (m, 4H), 4.38-4.20 (m, 4H), 3.99-3.87 (m, 2H), 3.65-3.52 (m, 6H), 2.50 (s, 3H), 2.10-2.05 (m, 4H), 1.72 (m, 4H), 1.56 (s, 6H), 1.03 (s, 9H); LC-MS (ES⁺): m/z 1025.50 [MH⁺], t_R = 3.50 min (5.6 minute run). |

Example 54
(2S,4R)-1-((S)-2-(2-(6-(4-(3-(4-cyano-3-(trifluoromethyl)phenyl)-5,5-dimethyl-4-oxo-2-thioxoimidazolidin-1-yl)phenoxy)hexa-2,4-diynyloxy)acetamido)-3,3-dimethylbutanoyl)-4-hydroxy-N-(4-(4-methylthiazol-5-yl)benzyl)pyrrolidine-2-carboxamide
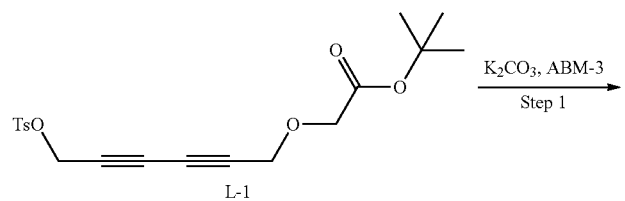
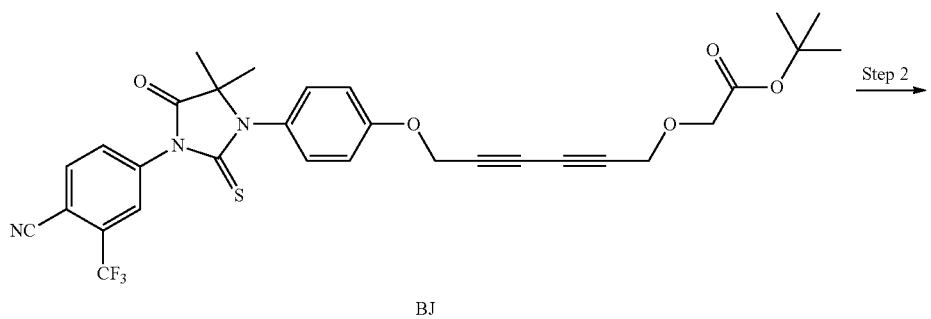
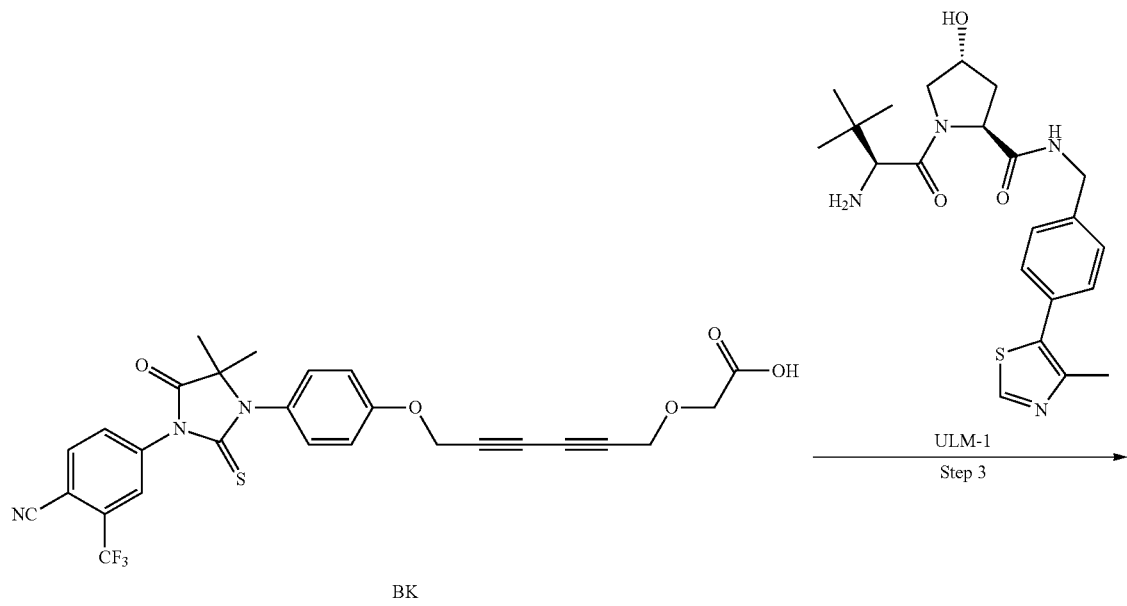

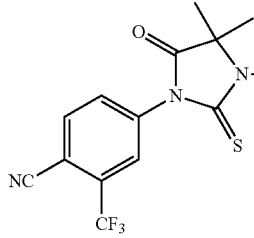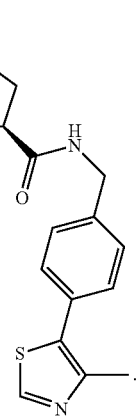

Example 54

Step 1: Synthesis of tert-butyl 2-{[6-(4-{3-[4-cyano-3-(trifluoromethyl)phenyl]-5,5-dimethyl-4-oxo-2-sulfanylideneimidazolidin-1-yl}phenoxy)hexa-2,4-diyn-1-yl]oxy}acetate (BJ)

This material was synthesized according to a similar procedure described in reaction step 1 for the synthesis of Example 1. LC-MS (ES$^+$): m/z 634.05 [MNa$^+$], $t_R$=1.26 min (2.0 minute run).

Step 2: Synthesis of 2-{[6-(4-{3-[4-cyano-3-(trifluoromethyl)phenyl]-5,5-dimethyl-4-oxo-2-sulfanylideneimidazolidin-1-yl}phenoxy)hexa-2,4-diyn-1-yl]oxy}acetic acid (BK)

This material was synthesized according to a similar procedure described in reaction step 2 for the synthesis of example 1. LC-MS (ES$^+$): m/z 556.10 [MH$^+$], $t_R$=1.54 min (2.6 minute run).

Step 3: Synthesis of (2S,4R)-1-[(2S)-2-(2-{[6-(4-{3-[4-cyano-3-(trifluoromethyl)phenyl]-5,5-dimethyl-4-oxo-2-sulfanylideneimidazolidin-1-yl}phenoxy)hexa-2,4-diyn-1-yl]oxy}acetamido)-3,3-dimethylbutanoyl]-4-hydroxy-N-{[4-(4-methyl-1,3-thiazol-5-yl)phenyl]methyl}pyrrolidine-2-carboxamide (Example 54)

This material was synthesized according to a similar procedure described in reaction step 3 for the synthesis of Example 1. $^1$H NMR (400 MHz, CD$_3$OD): δ 8.88 (s, 1H), 8.15 (d, J=8.4 Hz, 2H), 8.00 (d, J=1.6 Hz, 1H), 7.49-7.43 (m, 4H), 7.34 (d, J=8.8 Hz, 2H), 7.14 (d, J=8.8 Hz, 2H), 4.93 (s, 2H), 4.71 (s, 1H), 4.60-4.34 (m, 6H), 4.08 (s, 2H), 3.90-3.80 (m, 2H), 2.49 (s, 3H), 2.25-2.22 (m, 1H), 2.13-2.05 (m, 1H), 1.56 (s, 6H), 1.03 (s, 9H); LC-MS (ES$^+$): m/z 968.45 [MH$^+$], $t_R$=1.67 min (3.0 minute run).

TABLE 3

Exemplary Compounds.

| Ex # | Structure | Compound name and Analytical data |
|---|---|---|
| 55 | 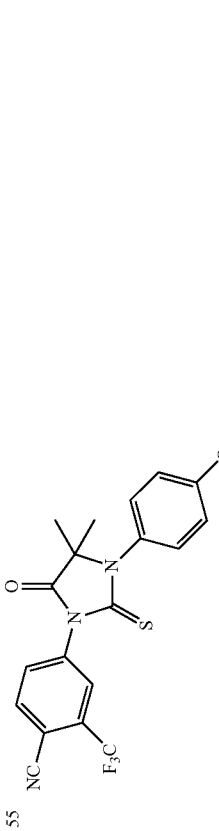 | Prepared from ABM-3, L-11, and ULM-1 (2S,4R)-1-[(2S)-2-(3-{[6-(4-{[3-[4-cyano-3-(trifluoromethyl)phenyl]-5,5-dimethyl-4-oxo-2-sulfanylideneimidazolidin-1-yl]phenoxy}hexa-2,4-diyn-1-yl]oxy}propanamido)-3,3-dimethylbutanoyl]-4-hydroxy-N-{[4-(4-methyl-1,3-thiazol-5-yl)phenyl]methyl}pyrrolidine-2-carboxamide<br>¹H NMR (400 MHz, CD₃OD): δ 8.88 (s, 1H), 8.16 (d, J = 8.8 Hz, 2H), 7.99 (d, J = 1.6 Hz, 1H), 7.49-7.42 (m, 4H), 7.33 (d, J = 8.8 Hz, 2H), 7.14 (d, J = 8.8 Hz, 2H), 4.93 (s, 2H), 4.66 (s, 1H), 4.60-4.38 (m, 3H), 4.38-4.27 (m, 3H), 3.92-3.80 (m, 4H), 2.63-2.59 (m, 1H), 2.58-2.49 (m, 4H), 2.26-2.18 (m, 1H), 2.13-2.05 (m, 1H), 1.56 (s, 6H), 1.03 (s, 9H); LC-MS (ES⁺): m/z 982.40 [MH⁺], t_R = 3.35 min (5.6 minute run). |

TABLE 3-continued

Exemplary Compounds.

| Ex # | Structure | Compound name and Analytical data |
|---|---|---|
| 56 | 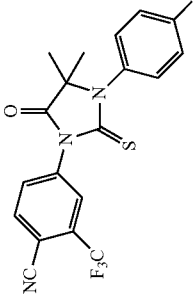 | Prepared from ABM-3, L-12, and ULM-1 (2S,4R)-1-[(2S)-2-(4-{[6-(4-{[3-[4-cyano-3-(trifluoromethyl)phenyl]-5,5-dimethyl-4-oxo-2-sulfanylideneimidazolidin-1-yl]phenoxy}hexa-2,4-diyn-1-yl]oxy}butanamido)-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD): δ 8.88 (s, 1H), 8.16 (d, J = 8.8 Hz, 2H), 7.99 (d, J = 1.6 Hz, 1H), 7.49-7.42 (m, 4H), 7.35 (d, J = 8.8 Hz, 2H), 7.14 (d, J = 8.8 Hz, 2H), 4.93 (s, 2H), 4.63 (s, 1H), 4.59-4.51 (m, 3H), 4.38-4.27 (d, J = 12.4 Hz, 1H), 4.25 (s, 2H), 3.93-3.79 (m, 2H), 3.53 (t, J = 6.0 Hz, 2H), 2.50 (s, 3H), 2.49-2.33 (m, 2H), 2.26-2.18 (m, 1H), 2.13-2.05 (m, 1H), 1.90-1.86 (m, 2H), 1.57 (s, 6H), 1.02 (s, 9H); LC-MS (ES$^+$): m/z 996.40 [MH$^+$], t$_R$ = 3.41 min (5.6 minute run). |

TABLE 3-continued

Exemplary Compounds.

| Ex # | Structure | Compound name and Analytical data |
|---|---|---|
| 57 | 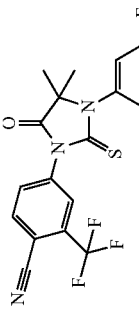 | Prepared from ABM-16, L-10, and ULM-1 (2S,4R)-1-[(2S)-2-(2-{[6-(4-{3-[4-cyano-3-(trifluoromethyl)phenyl]-5,5-dimethyl-4-oxo-2-sulfanylideneimidazolidin-1-yl]-2-fluorophenoxy}hexa-2,4-diyn-1-yl]oxy}acetamido)-3,3-dimethylbutanoyl]-4-hydroxy-N-{[4-(4-methyl-1,3-thiazol-5-yl)phenyl]methyl}pyrrolidine-2-carboxamide ¹H NMR (400 MHz, CD₃OD): δ 8.88 (s, 1H), 8.16 (d, J = 8.0 Hz, 2H), 8.00 (d, J = 1.2 Hz, 1H), 7.49-7.43 (m, 4H), 7.36-7.29 (m, 2H), 7.19 (d, J = 8.0 Hz, 1H), 5.03 (s, 2H), 4.71 (s, 1H), 4.61-4.42 (m, 3H), 4.41-4.33 (m, 3H), 4.09 (s, 2H), 3.90-3.80 (m, 2H), 2.49 (s, 3H), 2.27-2.15 (m, 1H), 2.12-2.06 (m, 1H), 1.56 (s, 6H), 1.03 (s, 9H); LC-MS (ES⁺): m/z 986.30 [MH⁺], t_R = 1.58 min (3.0 minute run). |

TABLE 3-continued

Exemplary Compounds.

| Ex # | Structure | Compound name and Analytical data |
|---|---|---|
| 58 | 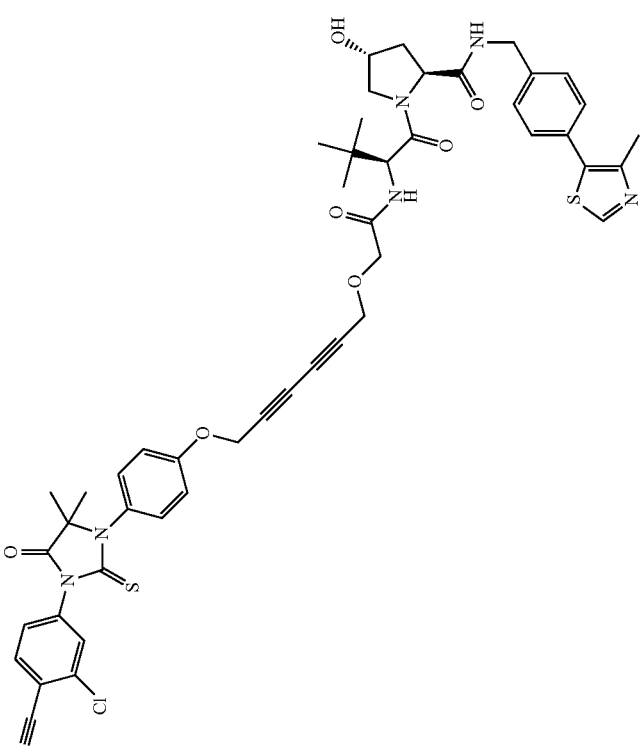 | Prepared from ABM-1, L-10, and ULM-1 (2S,4R)-1-[(2S)-2-{2-[(6-{4-[3-(3-chloro-4-cyanophenyl)-5,5-dimethyl-4-oxo-2-sulfanylideneimidazolidin-1-yl]phenoxy}hexa-2,4-diyn-1-yl)oxy]acetamido}-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.88 (s, 1H), 7.96 (d, J = 8.4 Hz, 1H), 7.87 (s, 1H), 7.66-7.64 (m, 1H), 7.49-7.43 (m, 4H), 7.33 (d, J = 8.8 Hz, 1H), 7.14 (d, J = 9.2 Hz, 1H), 4.94 (s, 2H), 4.71 (s, 1H), 4.61-4.42 (m, 3H), 4.41-4.29 (m, 3H), 4.09 (s, 2H), 3.92-3.86 (m, 1H), 3.82-3.77 (m, 1H), 2.49 (s, 3H), 2.27-2.18 (m, 1H), 2.12-2.06 (m, 1H), 1.52 (s, 6H), 1.01 (s, 9H); LC-MS (ES$^+$): m/z 934.20 [MH$^+$], t$_R$ = 1.54 min (3.0 minute run). |

TABLE 3-continued

Exemplary Compounds.

| Ex # | Structure | Compound name and Analytical data |
|---|---|---|
| 59 | 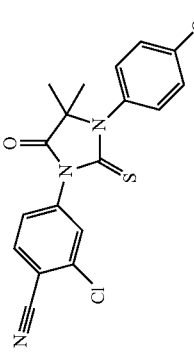 | Prepared from ABM-1, L-10, and ULM-5 (2S,4R)-1-[(2S)-2-{2-[(6-{4-[3-(3-chloro-4-cyanophenyl)-5,5-dimethyl-4-oxo-2-sulfanylideneimidazolidin-1-yl]phenoxy}hexa-2,4-diyn-1-yl)oxy]acetamido}-3,3-dimethylbutanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD): δ 8.15 (s, 1H), 7.95 (d, J = 8.4 Hz, 1H), 7.87 (s, 1H), 7.66-7.58 (m, 3H), 7.49-7.47 (m, 2H), 7.35-7.31 (m, 2H), 7.14 (d, J = 8.8 Hz, 2H), 4.94 (s, 2H), 4.71 (s, 1H), 4.63-4.57 (m, 3H), 4.41-4.28 (m, 3H), 4.09 (s, 2H), 3.90-3.86 (m, 1H), 3.82-3.77 (m, 1H), 2.42 (s, 3H), 2.27-2.20 (m, 1H), 2.12-2.02 (m, 1H), 1.55 (s, 6H), 1.03 (s, 9H); LC-MS (ES$^+$): m/z 918.25 [MH$^+$], t$_R$ = 1.51 min (3.0 minute run). |

TABLE 3-continued

Exemplary Compounds.

| Ex # | Structure | Compound name and Analytical data |
|---|---|---|
| 60 | 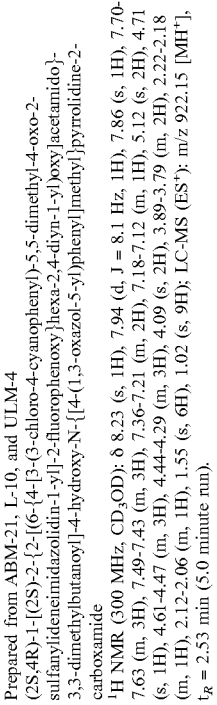 | Prepared from ABM-21, L-10, and ULM-4 (2S,4R)-1-[(2S)-2-{2-[(6-{4-[3-(3-chloro-4-cyanophenyl)-5,5-dimethyl-4-oxo-2-sulfanylideneimidazolidin-1-yl]-2-fluorophenoxy}hexa-2,4-diyn-1-yl)oxy]acetamido}-3,3-dimethylbutanoyl]-4-hydroxy-N-{[4-(1,3-oxazol-5-yl)phenyl]methyl}pyrrolidine-2-carboxamide $^1$H NMR (300 MHz, CD$_3$OD): δ 8.23 (s, 1H), 7.94 (d, J = 8.1 Hz, 1H), 7.86 (s, 1H), 7.70-7.63 (m, 3H), 7.49-7.43 (m, 3H), 7.36-7.21 (m, 2H), 7.18-7.12 (m, 1H), 5.12 (s, 2H), 4.71 (s, 1H), 4.61-4.47 (m, 3H), 4.44-4.29 (m, 3H), 4.09 (s, 2H), 3.89-3.79 (m, 2H), 2.22-2.18 (m, 1H), 2.12-2.06 (m, 1H), 1.55 (s, 6H), 1.02 (s, 9H); LC-MS (ES$^+$): m/z 922.15 [MH$^+$], t$_R$ = 2.53 min (5.0 minute run). |

TABLE 3-continued

Exemplary Compounds.

| Ex # | Structure | Compound name and Analytical data |
|---|---|---|
| 61 | [structure] | Prepared from ABM-16, L-10, and ULM-4 (2S,4R)-1-[(2S)-2-(2-{[6-(4-{3-[4-cyano-3-(trifluoromethyl)phenyl]-5,5-dimethyl-4-oxo-2-sulfanylideneimidazolidin-1-yl]-2-fluorophenoxy)hexa-2,4-diyn-1-yl]oxy}acetamido)-3,3-dimethylbutanoyl]-4-hydroxy-N-{[4-(1,3-oxazol-5-yl)phenyl]methyl}pyrrolidine-2-carboxamide <br> $^1$H NMR (300 MHz, CD$_3$OD): δ 8.23 (s, 1H), 8.15 (d, J = 7.5 Hz, 2H), 7.98 (d, J = 9.0 Hz, 1H), 7.71 (d, J = 7.8 Hz, 2H), 7.49-7.40 (m, 3H), 7.36-7.21 (m, 2H), 7.18-7.12 (m, 1H), 5.02 (s, 2H), 4.71 (s, 1H), 4.59-4.47 (m, 3H), 4.44-4.29 (m, 3H), 4.09 (s, 2H), 3.89-3.74 (m, 2H), 2.22-2.18 (m, 1H), 2.12-2.01 (m, 1H), 1.57 (s, 6H), 1.04 (s, 9H); LC-MS (ES$^+$): m/z 956.20 [MH$^+$], t$_R$ = 2.60 min (5.0 minute run). |

Example 62

(2S,4R)-1-((S)-2-tert-butyl-16-(4-(3-(4-cyano-3-(trifluoromethyl)phenyl)-5,5-dimethyl-4-oxo-2-thioxoimidazolidin-1-yl)phenyl)-4,13-dioxo-6,9-dioxa-3,12-diazahexadecane)-4-hydroxy-N-(4-(4-methylthiazol-5-yl)benzyl)pyrrolidine-2-carboxamide

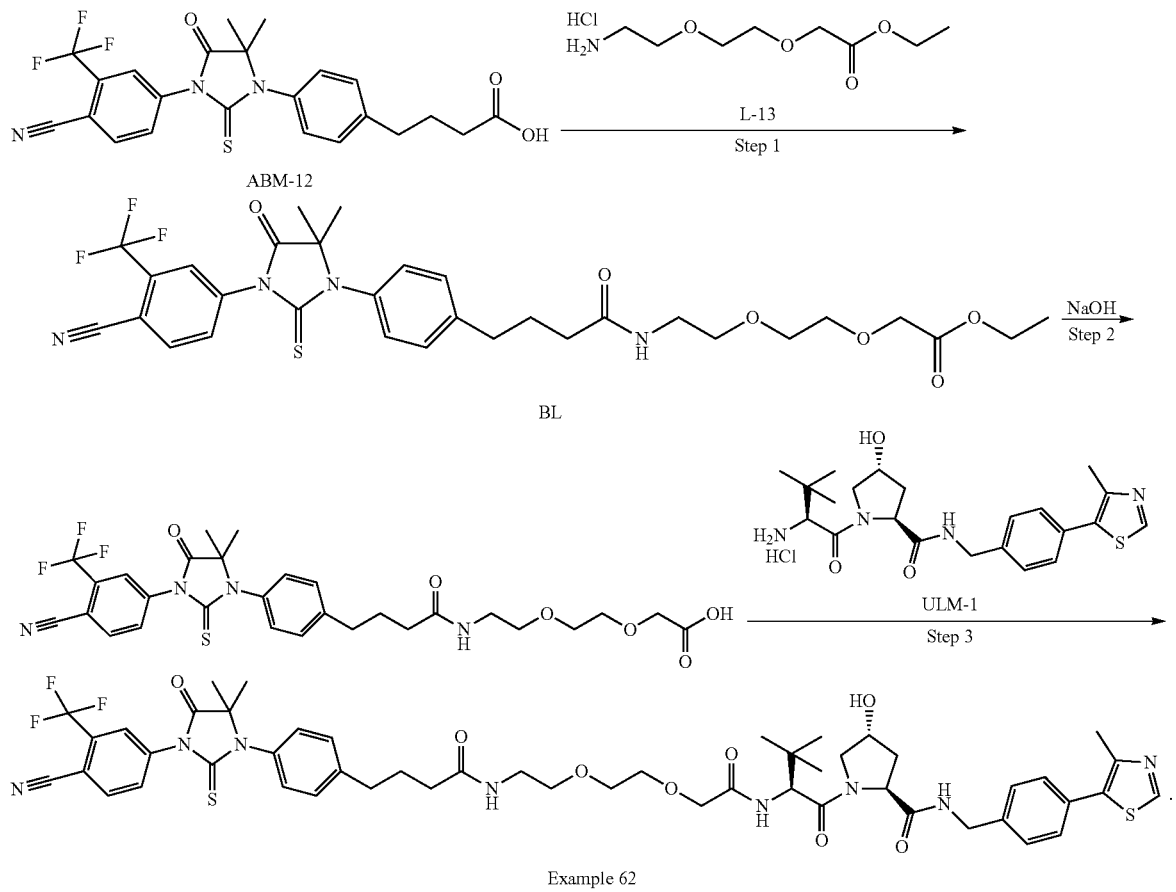

Example 62

Step 1: Synthesis of ethyl 2-(2-{2-[4-(4-{3-[4-cyano-3-(trifluoromethyl)phenyl]-5,5-dimethyl-4-oxo-2-sulfanylideneimidazolidin-1-yl}phenyl)butanamido]ethoxy}ethoxy)acetate (BL)

To a stirred solution of 4-(4-{3-[4-cyano-3-(trifluoromethyl)phenyl]-5,5-dimethyl-4-oxo-2-sulfanylideneimidazolidin-1-yl}phenyl)butanoic acid (ABM-12, 417 mg, 0.88 mmol) in N,N-dimethylformamide (10 mL) was added HATU (669 mg, 1.76 mmol), DIEA (454 mg, 3.51 mmol) and ethyl 2-[2-(2-aminoethoxy)ethoxy]acetate hydrochloride (L-13, 400 mg, 1.76 mmol) at 0° C. The resulting solution was stirred at 0° C. for 30 min, and then it was warmed up to rt and stirred at rt for 15 h. A mixture of water/ice (1:1, 50 mL) was added to the reaction, the resulting mixture was extracted with ethyl acetate (100 mL×3). The organic layers were combined, washed with saturated aqueous solution of sodium chloride (20 mL×2), dried over anhydrous sodium sulfate and then concentrated under reduced pressure to give a crude residue, which was purified by flash silica gel chromatography (eluent: ethyl acetate/petroleum ether (v:v=1:1) to give BL (yield: 35%) as a yellow solid. LC-MS (ES$^+$): m/z 649.15[MH$^+$], t$_R$=1.05 min (2.0 minute run).

Step 2: Synthesis of 2-(2-{2-[4-(4-{3-[4-cyano-3-(trifluoromethyl)phenyl]-5,5-dimethyl-4-oxo-2-sulfanylideneimidazolidin-1-yl}phenyl)butanamido]ethoxy}ethoxy)acetic Acid (BM)

To a stirred solution of ethyl 2-(2-{2-[4-(4-{3-[4-cyano-3-(trifluoromethyl)phenyl]-5,5-dimethyl-4-oxo-2-sulfanylideneimidazolidin-1-yl}phenyl)butanamido]ethoxy}ethoxy)acetate (BL, 200 mg, 0.31 mmol) in methanol (10 mL) was added a solution of NaOH (123 mg, 3.08 mmol) in water (10 mL) at rt. The resulting solution was then heated to 50° C. and stirred at this temperature for 2 h. The bulk of organic solvent was removed under reduced pressure. To the remaining residue was added aqueous hydrogen chloride (1 M) to adjust the pH to ~3. The resulting mixture was extracted with ethyl acetate (50 mL×2), the organic layers were combined, washed with saturated aqueous solution of sodium chloride (20 mL×2), dried over anhydrous sodium sulfate and then concentrated under reduced pressure followed by high vacuum pump to give BM (yield: 78%) as a yellow solid. LC-MS (ES$^+$): m/z 621.20 [MH$^+$], $t_R$=0.96 min (2.0 minute run).

Step 3: Synthesis of (2S,4R)-1-[(2S)-2-[2-(2-{2-[4-(4-{3-[4-cyano-3-(trifluoromethyl)phenyl]-5,5-dimethyl-4-oxo-2-sulfanylideneimidazolidin-1-yl}phenyl)butanamido]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide (Example 62)

To a stirred solution of 2-(2-{2-[4-(4-{3-[4-cyano-3-(trifluoromethyl)phenyl]-5,5-dimethyl-4-oxo-2-sulfanylideneimidazolidin-1-yl}phenyl)butanamido]ethoxy}ethoxy)acetic acid (BM, 200 mg, 0.32 mmol) in N,N-dimethylformamide (20 mL) was added HATU (245 mg, 0.64 mmol), DIEA (166 mg, 1.28 mmol) and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1, 226 mg, 0.48 mmol) at 0° C. The resulting solution was stirred at 0° C. for 30 min, and then it was warmed up to rt and stirred at rt for 15 h. A mixture of water/ice (1:1, 50 mL) was added to the reaction, the resulting mixture was extracted with ethyl acetate (100 mL×3). The organic layers were combined, washed with saturated aqueous solution of sodium chloride (50 mL), dried over anhydrous sodium sulfate and then concentrated under reduced pressure to give a crude residue, which was purified by Prep-HPLC to give Example 62 (yield: 6%) as a yellow solid. $^1$H NMR (400 MHz, CD$_3$OD): δ 8.89 (s, 1H), 8.18-8.16 (d, J=8.4 Hz, 2H), 8.01-7.99 (d, J=8.0 Hz, 1H), 7.47-7.41 (m, 4H), 7.38-7.36 (d, J=8.4 Hz, 2H), 7.30-7.28 (d, J=8.4 Hz, 2H), 4.87 (s, 1H), 4.78-4.60 (m, 3H), 4.39-4.35 (d, J=15.2 Hz, 1H), 4.04-3.98 (m, 2H), 3.98-3.85 (m, 2H), 3.72-3.60 (m, 7H), 3.50-3.49 (m, 1H), 2.71-2.69 (m, 2H), 2.49 (s, 3H), 2.45-2.28 (m, 3H), 2.25-2.10 (m, 1H), 2.10-1.95 (m, 2H), 1.58 (s, 6H), 1.09 (s, 9H); LC-MS (ES$^+$): m/z 1033.50 [MH$^+$], $t_R$=3.06 min (5.6 minute run).

Examples 63-65 were synthesized according to similar procedure described for synthesis of example 62, by using corresponding starting materials and intermediates.

TABLE 4

Exemplary Compounds.

| Ex # | Structure | Compound name and Analytical data |
|---|---|---|
| 63 | (structure) | Prepared from ABM-12, L-14, and ULM-1 (2S,4R)-1-[(2S)-2-[2-({5-[4-(4-{3-[4-cyano-3-(trifluoromethyl)phenyl]-5,5-dimethyl-4-oxo-2-sulfanylideneimidazolidin-1-yl}phenyl)butanamido]pentyl}oxy)acetamido]-3,3-dimethylbutanoyl]-4-hydroxy-N-{[4-(4-methyl-1,3-thiazol-5-yl)phenyl]methyl}pyrrolidine-2-carboxamide $^1$H NMR (400 MHz, DMSO): δ 8.98 (s, 1H), 8.60 (m, 1H), 8.40 (d, J = 8.0 Hz, 1H), 8.30 (s, 1H), 8.10 (d, J = 8.0 Hz, 1H), 7.79 (m, 1H), 7.40 (m, 4H), 7.36 (m, 3H), 7.29 (d, J = 8.0 Hz, 2H), 5.16 (m, 1H), 4.57 (d, J = 9.2 Hz, 1H), 4.45 (m, 4H), 3.92 (m, 2H), 3.66 (m, 2H), 3.48 (m, 2H), 3.07 (m, 2H), 2.64 (m, 2H), 2.51 (m, 3H), 2.14 (m, 3H), 1.90 (m, 3H), 1.57 (m, 2H), 1.50 (s, 6H), 1.44 (m, 2H), 1.36 (m, 2H), 0.94 (s, 9H); LC-MS (ES$^+$); m/z 516.65 [M + 2]/2, t$_R$ = 2.55 min. (5.0 minute run). |

TABLE 4-continued

Exemplary Compounds.

| Ex # | Structure | Compound name and Analytical data |
|---|---|---|
| 64 | 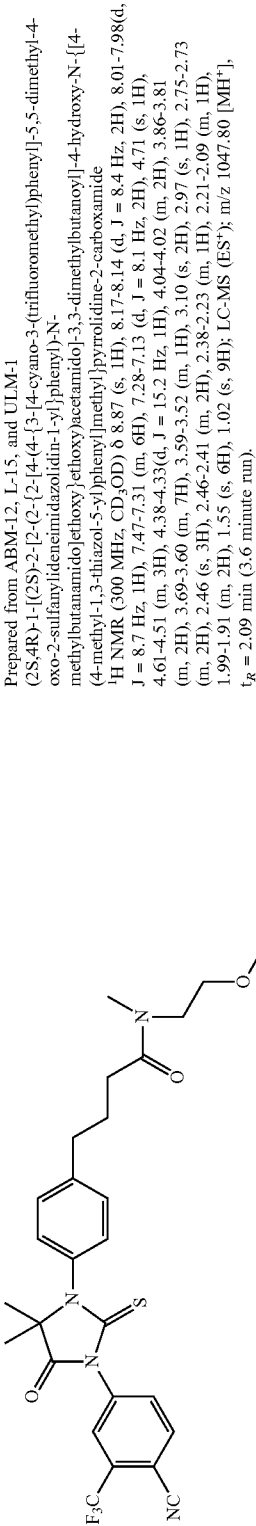 | Prepared from ABM-12, L-15, and ULM-1 (2S,4R)-1-[(2S)-2-[2-(2-{2-[4-(4-{3-[4-cyano-3-(trifluoromethyl)phenyl]-5,5-dimethyl-4-oxo-2-sulfanylideneimidazolidin-1-yl}phenyl)-N-methylbutanamido]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD) δ 8.87 (s, 1H), 8.17-8.14 (d, J = 8.4 Hz, 2H), 8.01-7.98 (d, J = 8.7 Hz, 1H), 7.47-7.31 (m, 6H), 7.28-7.13 (d, J = 8.1 Hz, 2H), 4.71 (s, 1H), 4.61-4.51 (m, 3H), 4.38-4.33 (d, J = 15.2 Hz, 1H), 4.04-4.02 (m, 2H), 3.86-3.81 (m, 2H), 3.69-3.60 (m, 7H), 3.59-3.52 (m, 1H), 3.10 (s, 2H), 2.97 (s, 1H), 2.75-2.73 (m, 2H), 2.46 (s, 3H), 2.46-2.41 (m, 2H), 2.38-2.23 (m, 1H), 2.21-2.09 (m, 1H), 1.99-1.91 (m, 2H), 1.55 (s, 6H), 1.02 (s, 9H); LC-MS (ES$^+$); m/z 1047.80 [MH$^+$], t$_R$ = 2.09 min (3.6 minute run). |

TABLE 4-continued

Exemplary Compounds.

| Ex # | Structure | Compound name and Analytical data |
|---|---|---|
| 65 | (structure shown) | Prepared from ABM-12, L-16, and ULM-1 (2S,4R)-1-{(2S)-2-[2-({5-[4-(4-{3-[4-cyano-3-(trifluoromethyl)phenyl]-5,5-dimethyl-4-oxo-2-sulfanylideneimidazolidin-1-yl}phenyl)-N-methylbutanamido]pentyl}oxy)acetamido]-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, DMSO) δ 8.98 (s, 1H), 8.60 (s, 1H), 8.40 (d, J = 8.0 Hz, 1H), 8.30 (s, 1H), 8.10 (d, J = 8.0 Hz, 1H), 7.46-7.27 (m, 9H), 5.15 (s, 1H), 4.57-4.55 (m, 1H), 4.47-4.23 (m, 4H), 3.92-3.85 (m, 2H), 3.68-3.59 (m, 2H), 3.47 (s, 2H), 3.29-3.20 (m, 2H), 2.91-2.64 (m, 5H), 2.44 (s, 3H), 2.33-2.30 (m, 2H), 2.09-2.03 (m, 1H), 1.95-1.81 (m, 3H), 1.59-1.46 (m, 10H), 1.30-1.24 (m, 2H), 0.94 (s, 9H); Mass (ES$^+$): m/z 1045.40 [MH$^+$] |

Example 66

2-(2-(4'-(3-(4-cyano-3-(trifluoromethyl)phenyl)-5,5-dimethyl-4-oxo-2-thioxoimidazolidin-1-yl)biphenyl-4-yloxy)ethoxy)ethyl(S)-1-(2S,4R)-4-hydroxy-2-(4-(4-methylthiazol-5-yl)benzylcarbamoyl)pyrrolidin-1-yl)-3,3-dimethyl-1-oxobutan-2-ylcarbamate

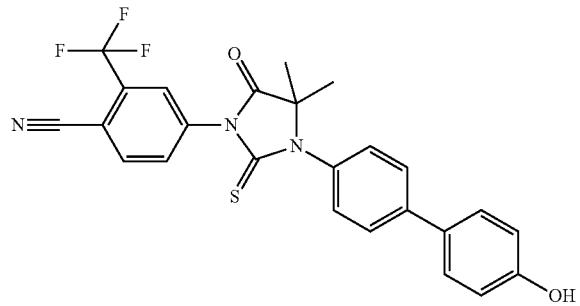

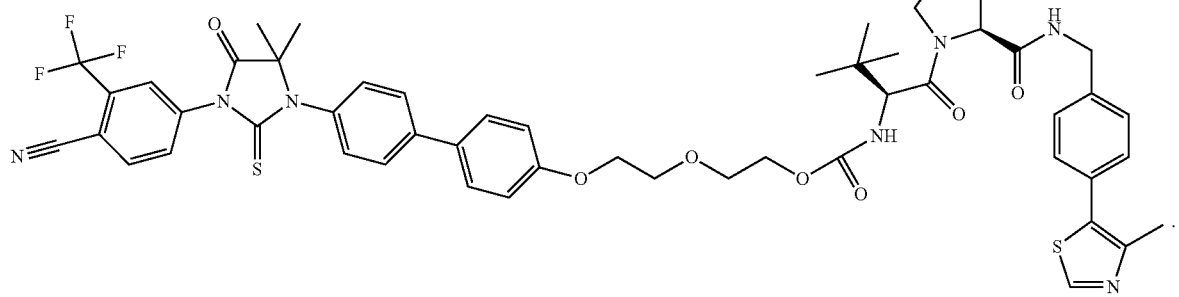

Example 66

Step 1: Synthesis of 4-[3-(4-{4-[2-(2-hydroxyethoxy)ethoxy]phenyl}phenyl)-4,4-dimethyl-5-oxo-2-sulfanylideneimidazolidin-1-yl]-2-(trifluoromethyl)benzonitrile (BN)

To a stirred solution of 4-{3-[4-(4-hydroxyphenyl)phenyl]-4,4-dimethyl-5-oxo-2-sulfanylideneimidazolidin-1-yl}-2-(trifluoromethyl)benzonitrile (ABM-14, 610.5 mg, 1.27 mmol) in N,N-dimethylformamide (10 mL) was added $K_2CO_3$ (318.46 mg, 2.29 mmol) and 2-{2-[(4-methylbenzenesulfonyl)oxy]ethoxy}ethan-1-ol (L-18, 300 mg, 1.15 mmol) at rt. The resulting mixture was then stirred at 80° C. for 2 hours in an oil bath, LC-MS indicated formation of the desired product. The reaction mixture was cooled down to rt, water (20 mL) was added and the resulting mixture was extracted with ethyl acetate (100 mL×2). The organic layers were combined, washed with saturated aqueous solution of sodium chloride (20 mL), dried over anhydrous sodium sulfate and then concentrated under reduced pressure to give a crude residue which was purified by a flash silica gel chromatography (eluent: ethyl acetate/petroleum ether (v:v=7:3) to give BN (yield: 66%) as a light yellow oil. LC-MS (ES$^+$): m/z 570, [MH$^+$], $t_R$=1.60 min (2.0 minute run).

Step 2: synthesis of 2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethyl N-[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamate (Example 66)

To a stirred solution of 4-[3-(4-{4-[2-(2-hydroxyethoxy)ethoxy]phenyl}phenyl)-4,4-dimethyl-5-oxo-2-sulfanylideneimidazolidin-1-yl]-2-(trifluoromethyl)benzonitrile (200 mg, 0.35 mmol) in dichloromethane (10 mL) was added triethylamine (106.5 mg, 1.05 mmol), followed by triphosgene (36.5 mg, 0.12 mmol) which was added slowly in 30 min at 0° C. To this mixture was then added (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1, 196.9 mg, 0.42 mmol) at 0° C. The resulting mixture was then warmed up to rt and stirred at rt for 2 hours. Water (20 mL) was added to the reaction and the resulting mixture was extracted with dichloromethane (50 mL×3). The organic layers were combined, washed with saturated aqueous solution of sodium chloride (20 mL), dried over anhydrous sodium sulfate and then concentrated under reduced pressure to give a crude residue, which was purified by Prep-HPLC to give Example 66 (yield: 6%) as a white solid. $^1$H-NMR (400 MHz, CD$_3$OD): δ 8.88 (s, 1H), 8.20-8.17 (m, 2H), 8.04-8.02 (d, J=8.0 Hz, 1H), 7.77-7.72 (m, 2H), 7.65-7.59 (m, 2H), 7.48-7.42 (m, 6H), 7.08-7.06 (d, J=8.4 Hz, 2H), 4.61-4.53 (m, 1H), 4.47-4.44 (s, 1H), 4.38-4.34 (m, 2H), 4.25-4.20 (m, 4H), 3.92-3.90 (m, 3H), 3.82-3.79 (m, 3H), 2.48 (s, 3H), 2.26-2.21 (m, 1H), 2.13-1.09 (m, 1H), 1.61 (s, 6H), 1.30 (s, 1H), 1.04 (s, 9H); LC-MS (ES$^+$): m/z 1026.40 [MH$^+$], t$_R$=2.23 min (3.0 minute run).

Example 67

(2S,4R)-1-((S)-2-(2-(2-(2-(4'-(3-(4-cyano-3-(trifluoromethyl)phenyl)-5,5-dimethyl-4-oxo-2-thioxoimidazolidin-1-yl)biphenyl-4-yloxy)ethoxy)ethoxy)acetamido)-3,3-dimethylbutanoyl)-4-hydroxy-N-(4-(4-methylthiazol-5-yl)benzyl)pyrrolidine-2-carboxamide

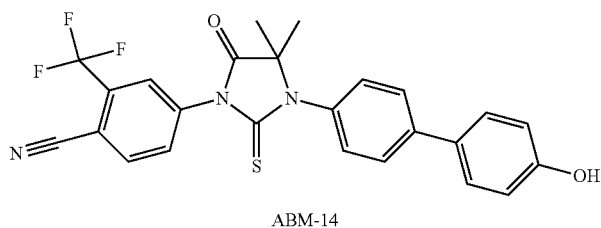

ABM-14

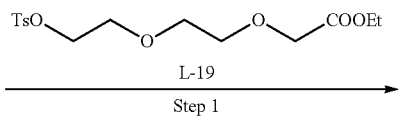

L-19
Step 1

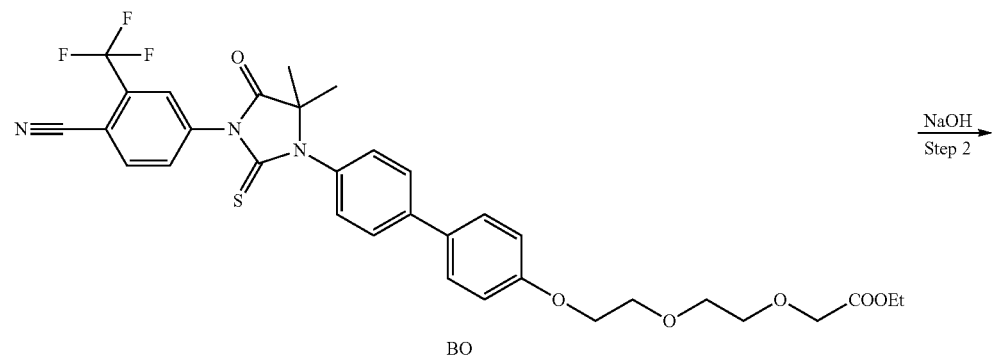

BO

NaOH
Step 2

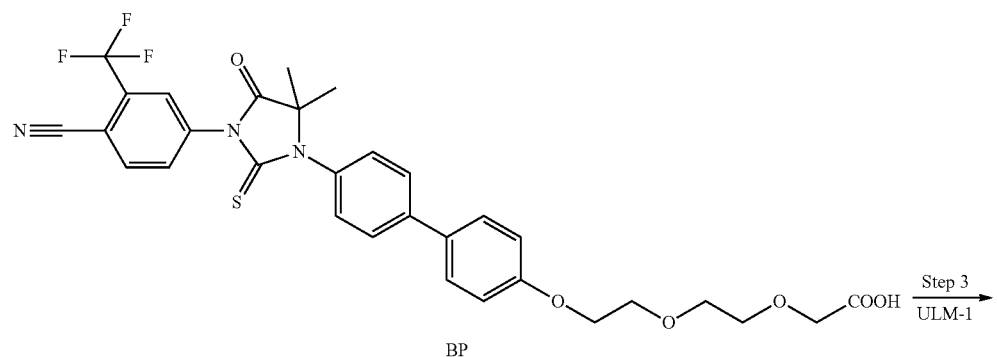

BP

Step 3
ULM-1

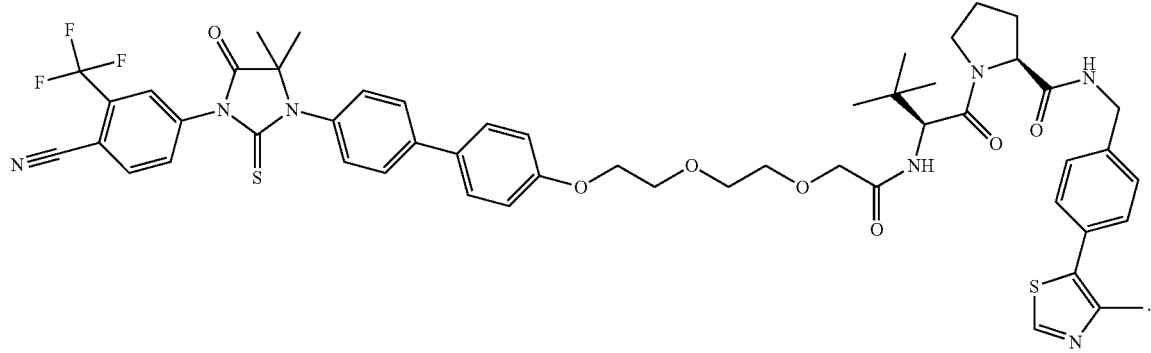

Example 67

Step 1: Synthesis of ethyl 2-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethoxy)acetate (BO)

To a stirred solution of 4-{3-[4-(4-hydroxyphenyl)phenyl]-4,4-dimethyl-5-oxo-2-sulfanylideneimidazolidin-1-yl}-2-(trifluoromethyl)benzonitrile (ABM-14, 300 mg, 0.62 mmol) in N,N-dimethylformamide (10 mL) was added K$_2$CO$_3$ (172 mg, 1.24 mmol) and ethyl 2-(2-{2-[(4-methylbenzene sulfonyl)oxy]ethoxy}ethoxy)acetate (L-19, 237.4 mg, 0.69 mmol). The resulting mixture was stirred at 80° C. in an oil bath for 2 hours. The reaction was cooled down to rt, water (50 mL) was added and the resulting mixture was extracted with ethyl acetate (100 mL×2). The organic layers were combined, washed with saturated aqueous solution of sodium chloride (30 mL×3), dried over anhydrous sodium sulfate and then concentrated under reduced pressure to give a crude residue, which was purified by a flash silica gel chromatography (eluent: ethyl acetate/petroleum ether (v:v=3:7)) to give BO (yield: 48%) as light yellow oil. LC-MS (ES$^+$): m/z 656, [MH$^+$], t$_R$=1.19 min (2.0 minute run).

Step 2: Synthesis of 2-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethoxy)acetic Acid (BP)

To a stirred solution of ethyl 2-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethoxy)acetate (BO, 198 mg, 0.30 mmol) in ethanol (5 mL) was added a solution of sodium hydroxide (36.3 mg, 0.91 mmol) in water (2 mL) at rt. The resulting solution was stirred overnight at rt, the bulk of organic solvent was then removed under reduced pressure. To the remaining aqueous residue was added hydrogen chloride in water (1N) to adjust the pH to ~5.0, and the resulting mixture was extracted with ethyl acetate (250 mL×2). The organic layers were combined, dried over anhydrous sodium sulfate and concentrated under reduced pressure followed by high vacuum pump to give BP (yield: 99%) as a light yellow oil. LC-MS (ES$^+$): m/z 628, [MH$^+$], t$_R$=1.08 min (2.0 minute run).

Step 3: Synthesis of (2S,4R)-1-[(2S)-2-[2-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide (Example 67)

To a stirred solution of 2-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethoxy)acetic acid (BP, 190 mg, 0.30 mmol) in N,N-dimethylformamide (10 mL) was added HATU (149.7 mg, 0.39 mmol), DIEA (156.4 mg, 1.21 mmol) and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride (ULM-1, 183.9 mg, 0.39 mmol). The resulting solution was stirred at rt for 2 hours. Water (50 mL) was added and the resulting mixture was extracted with ethyl acetate (100 mL×2). The organic layers were combined, washed with saturated aqueous solution of sodium chloride (25 mL×3), dried over anhydrous sodium sulfate and then concentrated under reduced pressure to give a crude residue, which was purified Prep-HPLC to give Example 67 (yield: 17%) as a white solid. $^1$H-NMR (400 MHz, CD$_3$OD): δ 8.82 (s, 1H), 8.19-8.16 (d, J=9.0 Hz, 2H), 8.02-8.00 (d, J=8.1 Hz, 1H), 7.72-7.69 (d, J=8.1 Hz, 2H), 7.61-7.55 (m, 2H), 7.46-7.37 (m, 6H), 7.08-7.01 (m, 2H), 4.71 (s, 1H), 4.61-4.51 (m, 1H), 4.47 (s, 2H), 4.38-4.31 (m, 1H), 4.23-4.20 (m, 2H), 4.01 (s, 2H), 3.96-3.78 (m, 4H), 3.63 (s, 4H), 2.43 (s, 3H), 2.27-2.20 (m, 1H), 2.13-2.04 (m, 1H), 1.61 (s, 6H), 1.04 (s, 9H); LC-MS (ES$^+$): m/z 1040.10 [MH$^+$], t$_R$=2.26 min (3.0 minute run).

Examples 74 and 76 were synthesized according to similar procedure described for synthesis of Example 66, by using corresponding starting materials and intermediates. Examples 68-73, 75, 77-79 were synthesized according to similar procedure described for synthesis of Example 67, by using corresponding starting materials and intermediates.

TABLE 5

Exemplary Compounds.

| Ex # | Structure | Compound name and Analytical data |
|---|---|---|
| 68 | 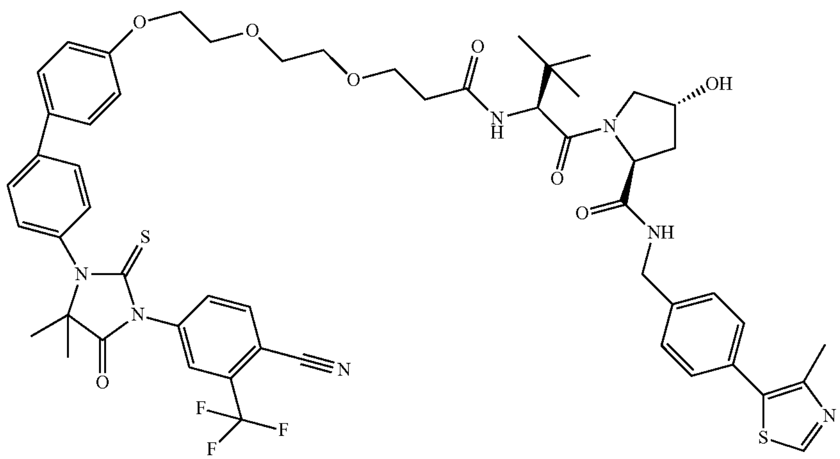 [SMILES: Cc1ncsc1-c1ccc(CNC(=O)[C@@H]2C[C@@H](O)CN2C(=O)[C@@H](NC(=O)CCOCCOCCOc2ccc(-c3ccc(N4C(=S)N(c5ccc(C#N)c(C(F)(F)F)c5)C(=O)C4(C)C)cc3)cc2)C(C)(C)C)cc1] | Prepared from ABM-14, L-20, and ULM-1 (2S,4R)-1-{(2S)-2-[3-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}ethoxy)propanamido]-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD) δ 8.87 (s, 1H), 8.21-8.17 (m, 2H), 8.04 (d, J = 8.0 Hz, 1H), 7.76 (d, J = 8.4 Hz, 2H), 7.63 (d, J = 8.8 Hz, 2H), 7.49-7.41 (m, 6H), 7.07 (d, J = 8.8 Hz, 2H), 4.67 (s, 1H), 4.61-4.51 (m, 3H), 4.37-4.33 (m, 1H), 4.20-4.18 (m, 2H), 3.92-3.66 (m, 10H), 2.62-2.45 (m, 5H), 2.26-2.17 (m, 1H), 2.14-2.05 (m, 1H), 1.61 (s, 6H), 1.05 (s, 9H); LC-MS (ES$^+$): m/z 1054.50 [MH$^+$], t$_R$ = 2.20 min (3.6 minute run). |
| 69 | 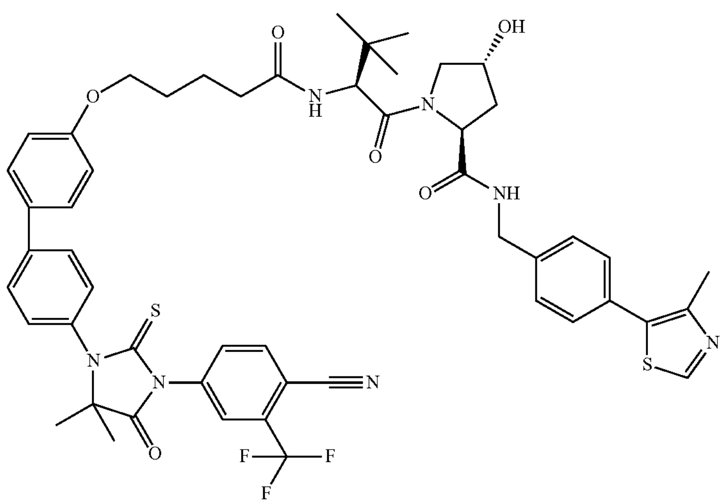 [SMILES: Cc1ncsc1-c1ccc(CNC(=O)[C@@H]2C[C@@H](O)CN2C(=O)[C@@H](NC(=O)CCCCOc2ccc(-c3ccc(N4C(=S)N(c5ccc(C#N)c(C(F)(F)F)c5)C(=O)C4(C)C)cc3)cc2)C(C)(C)C)cc1] | Prepared from ABM-14, L-21, and ULM-1 (2S,4R)-1-{(2S)-2-{5-[4-(4-{3-[4-cyano-3-(trifluoromethyl)phenyl]-5,5-dimethyl-4-oxo-2-sulfanylideneimidazolidin-1-yl}phenyl)phenoxy]pentanamido}-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD): δ 8.90 (s, 1H), 8.20-8.18 (d, J = 8.4 Hz, 2H), 8.04-8.02 (d, J = 7.6 Hz, 1H), 7.77-7.74 (d, J = 8.4 Hz, 2H), 7.63-7.61 (d, J = 8.4 Hz, 2H), 7.50-7.48 (m, 2H), 7.50-7.41 (m, 4H), 7.06-7.04 (d, J = 8.8 Hz, 2H), 4.67(s, 1H), 4.61-4.52 (m, 3H), 4.39-4.35 (m, 1H), 4.08-4.07 (m, 2H), 3.95-3.93 (m, 1H), 3.85-3.81 (m, 1H), 2.48 (s, 3H), 2.41-2.37 (m, 2H), 2.23-2.21 (m, 1H), 2.14-2.10 (m, 1H), 1.86-1.85 (m, 4H), 1.62 (s, 6H), 1.06 (s, 9H); LC-MS (ES$^+$): m/z 994.40 [MH$^+$], t$_R$ = 1.71 min (3.0 minute run). |

TABLE 5-continued

Exemplary Compounds.

| Ex # | Structure | Compound name and Analytical data |
|---|---|---|
| 70 | 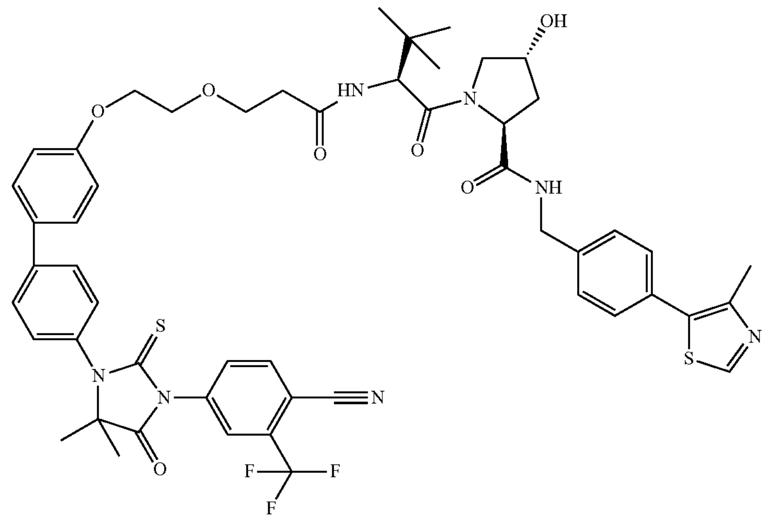 [SMILES: Cc1ncsc1-c1ccc(CNC(=O)[C@@H]2C[C@@H](O)CN2C(=O)[C@@H](NC(=O)CCOCCOc2ccc(-c3ccc(N4C(=S)N(c5ccc(C#N)c(C(F)(F)F)c5)C(=O)C4(C)C)cc3)cc2)C(C)(C)C)cc1] | Prepared from ABM-14, L-22, and ULM-1 (2S,4R)-1-{(2S)-2-(3-{2-[4-(4-{3-[4-cyano-3-(trifluoromethyl)phenyl]-5,5-dimethyl-4-oxo-2-sulfanylideneimidazolidin-1-yl}phenoxy)ethoxy]propanamido)-3,3-dimethylbutanoyl]-4-hydroxy-N-{[4-(4-methyl-1,3-thiazol-5-yl)phenyl]methyl}pyrrolidine-2-carboxamide<br>¹H NMR (400 MHz, CD₃OD) δ 8.85 (s, 1H), 8.21-8.17 (m, 2H), 8.04 (d, J = 8.0 Hz, 1H), 7.74 (d, J = 8.4 Hz, 2H), 7.61 (d, J = 8.4 Hz, 2H), 7.49-7.39 (m, 6H), 7.08 (d, J = 8.8 Hz, 2H), 4.68 (s, 1H), 4.59-4.51 (m, 3H), 4.37 (s, 1H), 4.23-4.20 (m, 2H), 3.93-3.80 (m, 6H), 2.63-2.45 (m, 2H), 2.45 (s, 3H), 2.23-2.06 (m, 2H), 1.62 (s, 6H), 1.05 (s, 9H);<br>LC-MS (ES⁺); m/z 1010.30 [MH⁺], t_R = 1.68 min (3.0 minute run). |
| 71 | 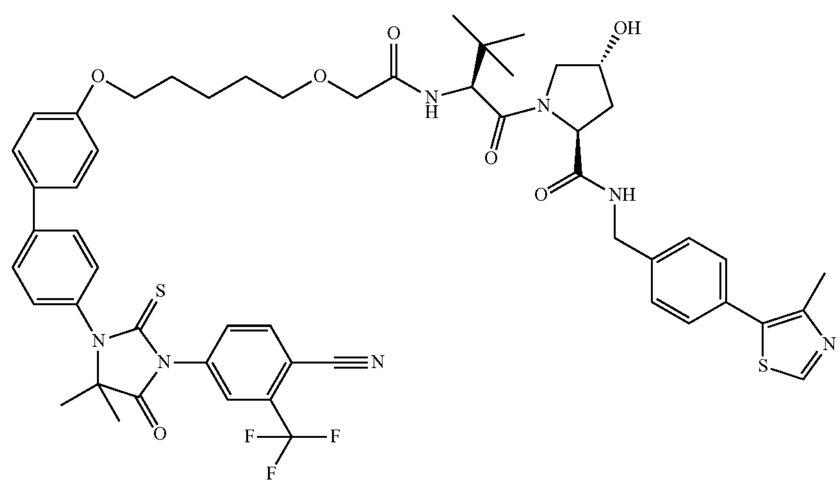 [SMILES: Cc1ncsc1-c1ccc(CNC(=O)[C@@H]2C[C@@H](O)CN2C(=O)[C@@H](NC(=O)COCCCCCOc2ccc(-c3ccc(N4C(=S)N(c5ccc(C#N)c(C(F)(F)F)c5)C(=O)C4(C)C)cc3)cc2)C(C)(C)C)cc1] | Prepared from ABM-14, L-23, and ULM-1 (2S,4R)-1-{(2S)-2-[2-({5-[4-(4-{3-[4-cyano-3-(trifluoromethyl)phenyl]-5,5-dimethyl-4-oxo-2-sulfanylideneimidazolidin-1-yl}phenoxy)pentyl]oxy}acetamido]-3,3-dimethylbutanoyl]-4-hydroxy-N-{[4-(4-methyl-1,3-thiazol-5-yl)phenyl]methyl}pyrrolidine-2-carboxamide<br>¹H NMR (400 MHz, CD₃OD): δ 8.84 (s, 1H), 8.19-8.17 (d, J = 8.4 Hz, 2H), 8.04-8.02 (d, J = 8.4 Hz, 1H), 7.73-7.71 (d, J = 8.4 Hz, 2H), 7.59-7.57 (d, J = 8.4 Hz, 2H), 7.49-7.38 (m, 6H), 7.02-7.00 (d, J = 8.4 Hz, 2H), 4.72 (s, 1H), 4.59-4.46 (m, 3H), 4.37-4.33 (d, J = 10.6 Hz, 1H), 4.08-4.06 (m, 2H), 4.05-4.00 (m, 2H), 3.98-3.83 (m, 2H), 3.64-3.61 (m, 2H), 2.49 (s, 3H), 2.29-2.21 (m, 1H), 2.11-2.01 (m, 1H), 1.90-1.86 (m, 2H), 1.78-1.75 (m, 2H), 1.66-1.62 (m, 2H), 1.61(s, 6H), 1.06 (s, 9H)<br>LC-MS (ES⁺); m/z 1038.38 [MH⁺], t_R = 1.68 min (3.0 minute run). |

TABLE 5-continued

Exemplary Compounds.

| Ex # | Structure | Compound name and Analytical data |
|---|---|---|
| 72 | 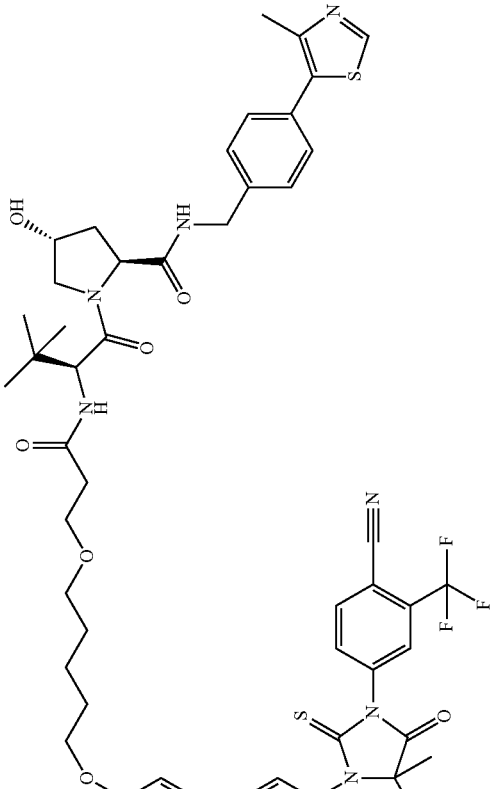 | Prepared from ABM-14, L-24, and ULM-1 (2S,4R)-1-[(2S)-2-[3-[4-(4-{5-[4-({3-[4-cyano-3-(trifluoromethyl)phenyl]-5,5-dimethyl-4-oxo-2-sulfanylideneimidazolidin-1-yl}phenyl)phenoxy]pentyl}oxy)propanamido]-3,3-dimethylbutanoyl]-4-hydroxy-N-{[4-(4-methyl-1,3-thiazol-5-yl)phenyl]methyl}pyrrolidine-2-carboxamide ¹H NMR (400 MHz, CD₃OD): δ 8.84 (s, 1H), 8.19-8.17 (d, J = 8.4 Hz, 2H), 8.04-8.02 (d, J = 8.4 Hz, 1H), 7.73-7.71 (d, J = 8.4 Hz, 2H), 7.59-7.57 (d, J = 8.4 Hz, 2H), 7.49-7.38 (m, 6H), 7.02-7.00 (d, J = 8.4 Hz, 2H), 4.72 (s, 1H), 4.59-4.46 (m, 3H), 4.37-4.33 (d, J = 10.6 Hz, 1H), 4.08-4.06 (m, 2H), 4.05-4.00 (m, 2H), 3.98-3.83 (m, 2H), 3.64-3.61 (m, 2H), 2.49 (s, 3H), 2.29-2.21 (m, 1H), 2.11-2.01 (m, 1H), 1.90-1.86 (m, 2H), 1.78-1.75 (m, 2H), 1.66-1.62 (m, 2H), 1.61(s, 6H), 1.06 (s, 9H); LC-MS (ES⁺); m/z 1052.39 [MH⁺], t_R = 1.81 min (3.0 minute run). |

TABLE 5-continued

Exemplary Compounds.

| Ex # | Structure | Compound name and Analytical data |
|---|---|---|
| 73 | 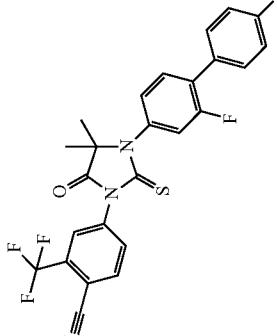 | Prepared from ABM-24, L-29, and ULM-1 (2S,4R)-1-[(2S)-2-[2-(2-{2-[4-(4-{3-[4-cyano-3-(trifluoromethyl)phenyl]-5,5-dimethyl-4-oxo-2-sulfanylideneimidazolidin-1-yl}-2-fluorophenyl)phenoxy]ethoxy}ethoxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.89 (s, 1H), 8.20-8.18 (d, J = 8.4 Hz, 2H), 8.04-8.02 (d, J = 8.4 Hz, 1H), 7.62-7.59 (m, 1H), 7.59-7.57 (m, 2H), 7.49-7.40(m, 2H), 7.40-7.30 (m, 2H), 7.30-7.10 (m, 2H), 7.08-7.06 (d, J = 8.4 Hz, 2H), 4.72 (s, 1H), 4.62-4.60 (m, 3H), 4.37-4.34 (d, J = 15.2 Hz, 1H), 4.25-4.23 (m, 2H), 4.13-4.09 (m, 2H), 3.97-3.92 (m, 4H), 3.89-3.79(m, 4H), 2.46(s, 3H), 2.24-2.22(m, 1H), 2.14-2.12(m, 1H), 1.63 (s, 6H), 1.06 (s, 9H); LC-MS (ES$^+$): m/z 1058.35 [MH$^+$], t$_R$ = 1.47 min (4.6 minute run). |

TABLE 5-continued

Exemplary Compounds.

| Ex # | Structure | Compound name and Analytical data |
|---|---|---|
| 74 | 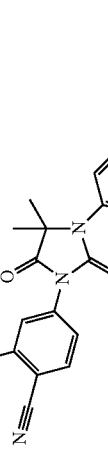 | Prepared from ABM-14, L-25, and ULM-1 5-[4-(4-{3-[4-cyano-3-(trifluoromethyl)phenyl]-5,5-dimethyl-4-oxo-2-sulfanylideneimidazolidin-1-yl}phenyl)phenoxy]pentyl N-[(2S)-1-[(2S,4R)-4-hydroxy-2-{[[4-(4-methyl-1,3-thiazol-5-yl)phenyl]methyl]carbamoyl}pyrrolidin-1-yl]-3,3-dimethyl-1-oxobutan-2-yl]carbamate $^1$H NMR (300 MHz, CD$_3$OD): δ 8.87 (s, 1H), 8.18-8.15 (d, J = 10.2 Hz, 2H), 8.02-8.00 (d, J = 8.1 Hz, 1H), 7.75-7.73 (d, J = 8.4 Hz, 2H), 7.63-7.60 (d, J = 8.4 Hz, 2H), 7.47-7.40 (m, 6H), 7.04-7.01 (d, J = 8.7 Hz, 2H), 4.61-4.51 (m, 3H), 4.37-4.32 (m, 2H), 4.16-4.02 (m, 4H), 3.92-3.78 (m, 2H), 2.47 (s, 3H), 2.26-2.11 (m, 1H), 2.10-2.07 (m, 1H), 1.86-1.80 (m, 2H), 1.76-1.64 (m, 2H), 1.60 (m, 8H), 1.03 (s, 9H); LC-MS (ES$^+$): m/z 1023.82 [MH$^+$], t$_R$ = 2.36 min (3.6 minute run) |

TABLE 5-continued

Exemplary Compounds.

| Ex # | Structure | Compound name and Analytical data |
|---|---|---|
| 75 | 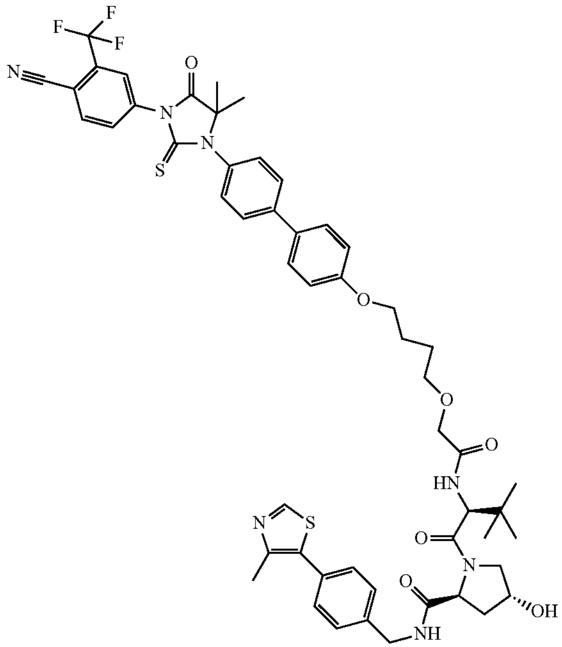 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cc3)cc2)C(C)(C)C)cc1] | Prepared from ABM-14, L-26, and ULM-1 (2S,4R)-1-[(2S)-2-(2-{4-[4-(4-{3-[4-cyano-3-(trifluoromethyl)phenyl]-5,5-dimethyl-4-oxo-2-sulfanylideneimidazolidin-1-yl}phenyl)phenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide <sup>1</sup>H NMR (400 MHz, CD<sub>3</sub>OD): δ 8.83 (s, 1H), 8.19-8.17 (d, J = 8.4 Hz, 2H), 8.04-8.02 (d, J = 9.6 Hz, 1H), 7.75-7.72 (d, J = 8.4 Hz, 2H), 7.60-7.58 (d, J = 8.4 Hz, 2H), 7.59-7.39 (m, 6H), 7.04-7.02 (d, J = 8.8 Hz, 2H), 4.88 (s, 1H), 4.71-4.41 (m, 3H), 4.374.32 (d, J = 15.2 Hz, 1H), 4.11-4.09 (m, 2H), 4.08-4.01(m, 2H), 3.98-3.90 (m, 1H), 3.90-3.83 (m, 1H), 3.69-3.66 (m, 2H), 2.44 (s, 3H), 2.25-2.23 (m, 1H), 2.12-2.10 (m, 1H), 1.98-1.90 (m, 2H), 1.90-1.84 (m, 2H), 1.60 (s, 6H), 1.03 (s, 9H); LC-MS (ES<sup>+</sup>): m/z 1024.10 [MH<sup>+</sup>], t<sub>R</sub> = 2.33 min (4.6 minute run) |

TABLE 5-continued

Exemplary Compounds.

| Ex # | Structure | Compound name and Analytical data |
|---|---|---|
| 76 | 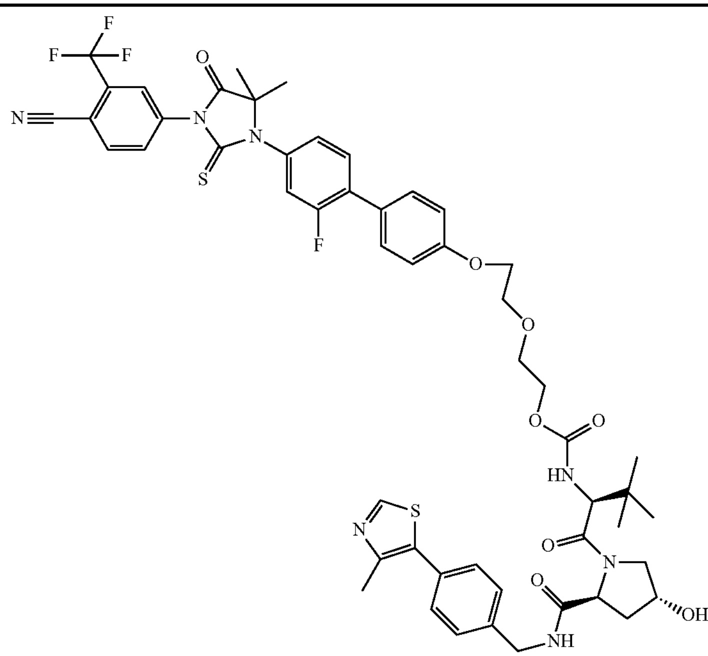 | Prepared from ABM-24, L-18, and ULM-1<br>2-{2-[4-(4-{3-[4-cyano-3-(trifluoromethyl)phenyl]-5,5-dimethyl-4-oxo-2-sulfanylideneimidazolidin-1-yl}-2-fluorophenyl)phenoxy]ethoxy}ethyl N-[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamate<br>¹H NMR (400 MHz, CD₃OD): δ 8.88 (s, 1H), 8.20-8.18 (d, J = 9.6 Hz, 2H), 8.04-8.02 (d, J = 8.4 Hz, 1H), 7.69-7.63 (m, 1H), 7.58-7.56 (d, J = 8.0 Hz, 2H), 7.48-7.42 (m, 4H), 7.34-7.30 (m, 2H), 7.10-7.08 (d, J = 8.8 Hz, 2H), 4.61-4.57 (m, 3H), 4.53-4.47 (m, 2H), 4.38-4.21 (m, 4H), 3.93-3.90 (m, 3H), 3.84-3.78 (m, 3H), 2.48 (s, 3 H), 2.26-2.17 (m, 1H), 2.11-2.07 (m, 1H), 1.63 (s, 6H), 1.02 (s, 9H); LC-MS (ES⁺): m/z 1044.33 [MH⁺], t_R = 2.21 min. (3.6 minute run). |

TABLE 5-continued

Exemplary Compounds.

| Ex # | Structure | Compound name and Analytical data |
|---|---|---|
| 77 | (structure) | Prepared from ABM-14, L-27, and ULM-1 (2S,4R)-1-[(2S)-2-(2-{3-[4-(4-{3-[4-cyano-3-(trifluoromethyl)phenyl]-5,5-dimethyl-4-oxo-2-sulfanylideneimidazolidin-1-yl}phenyl)phenoxy]propoxy}acetamido)-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.83 (s, 1H), 8.19-8.16 (d, J = 9.0 Hz, 2H), 8.03-8.01 (d, J = 8.1 Hz, 1H), 7.75-7.72 (d, J = 8.7 Hz, 2H), 7.72-7.69 (d, J = 8.7 Hz, 2H), 7.63-7.36 (m, 6H), 7.08-7.05 (d, J = 8.7 Hz, 2H), 4.72 (s, 1H), 4.62-4.51 (m, 3H), 4.36-4.31 (d, J = 15.3 Hz, 1H), 4.22-4.19 (m, 2H), 4.04-3.98 (m, 2H), 3.91-3.76 (m, 4H), 2.43 (s, 3H), 2.21-2.10 (m, 4H), 1.60 (s, 6H), 1.02 (s, 9H); Mass (ES$^+$): m/z 1010.30 [MH$^+$] |

TABLE 5-continued

Exemplary Compounds.

| Ex # | Structure | Compound name and Analytical data |
|---|---|---|
| 78 | 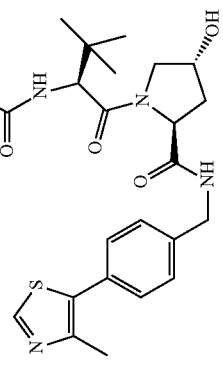 | Prepared from ABM-14, L-28, and ULM-1 (2S,4R)-1-[(2S)-2-(2-{2-[4-(4-{3-[4-cyano-3-(trifluoromethyl)phenyl]-5,5-dimethyl-4-oxo-2-sulfanylideneimidazolidin-1-yl}phenyl)phenoxy]ethoxy}acetamido)-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.79 (s, 1H), 8.71-8.69 (m, 1H), 8.19-8.16 (d, J = 9.0 Hz, 2H), 8.03-8.01 (d, J = 8.4 Hz, 1H), 7.77-7.75 (d, J = 4.8 Hz, 1H), 7.77-7.75 (d, J = 4.8 Hz, 1H), 7.72-7.64 (m, 4H), 7.55-7.45 (m, 4H), 7.17-7.14 (d, J = 8.7 Hz, 2H), 4.784.75 (d, J = 6.6 Hz, 1H), 4.75-4.62 (m, 2H), 4.55-4.52 (m, 1H), 4.28-4.26 (m, 3H), 4.14 (s, 2H), 3.98-3.95 (m, 2H), 3.88-3.84 (m, 2H), 2.38 (s, 3H), 2.29-2.11(m, 1H), 2.11-2.01(m, 1H), 1.60 (s, 6H), 1.04 (s, 9H); LC-MS (ES$^+$): m/z 996.33 [MH$^+$], t$_R$ = 2.92 min (5.0 minute run). |

TABLE 5-continued

Exemplary Compounds.

| Ex # | Structure | Compound name and Analytical data |
|---|---|---|
| 79 | 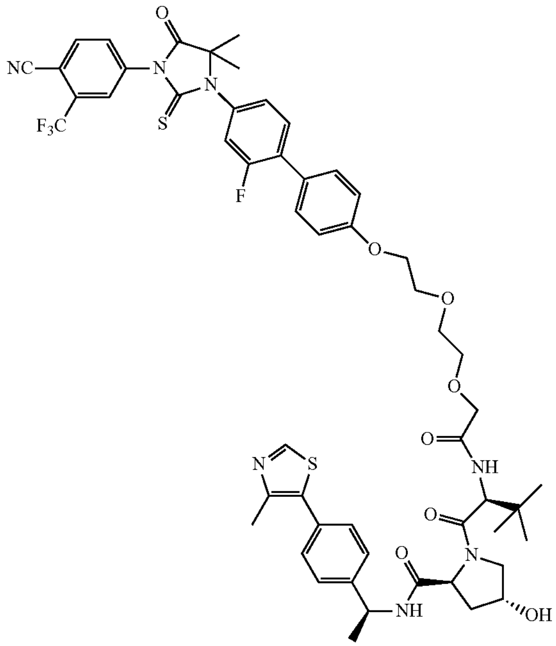 [SMILES: Cc1ncsc1-c1ccc([C@H](C)NC(=O)[C@@H]2C[C@@H](O)CN2C(=O)[C@@H](NC(=O)COCCOCCOc2ccc(-c3ccc(N4C(=S)N(c5ccc(C#N)c(C(F)(F)F)c5)C(=O)C4(C)C)cc3F)cc2)C(C)(C)C)cc1] | Prepared from ABM-24, L-19, and ULM-3 (2S,4R)-1-[(2S)-2-[2-(2-{2-[4-(4-{3-[4-cyano-3-(trifluoromethyl)phenyl]-5,5-dimethyl-4-oxo-2-sulfanylideneimidazolidin-1-yl}-2-fluorophenyl)phenoxy]ethoxy}ethoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, CD$_3$OD): δ 8.76 (s, 1H), 8.08-8.06 (d, J = 9.6 Hz, 2H), 7.91-7.89 (d, J = 7.2 Hz, 1H), 7.56-7.53 (m, 1H), 7.45-7.42 (d, J = 9.2 Hz, 2H), 7.33-7.29 (m, 4H), 7.22-7.20 (m, 2H), 6.99-6.97 (d, J = 8.8 Hz, 2H), 4.95-4.93 (m, 1H), 4.60 (s, 1H), 4.50-4.47 (m, 1H), 4.45-4.34 (m, 1H), 4.16-4.14 (m, 2H), 3.98-3.97 (m, 2H), 3.83-3.81 (m, 2H), 3.77-3.74 (m, 1H), 3.67-3.63 (m, 5H), 2.36 (s, 3H), 2.12-2.10 (m, 1H), 1.89-1.85 (m, 1H), 1.51 (s, 6H), 1.37-1.36 (m, 3H), 0.93 (s, 9H); LC-MS (ES$^+$): m/z 1072.4 [MH$^+$], t$_R$ = 1.46 min (4.6 minute run). |

Example 80

(2S,4R)-1-((S)-2-(2-(3-(2-(4-(4-(3-(4-cyano-3-(trifluoromethyl)phenyl)-5,5-dimethyl-4-oxo-2-thioxoimidazolidin-1-yl)phenyl)piperidin-1-yl)ethoxy)propoxy)acetamido)-3,3-dimethylbutanoyl)-4-hydroxy-N-(4-(4-methylthiazol-5-yl)benzyl)pyrrolidine-2-carboxamide

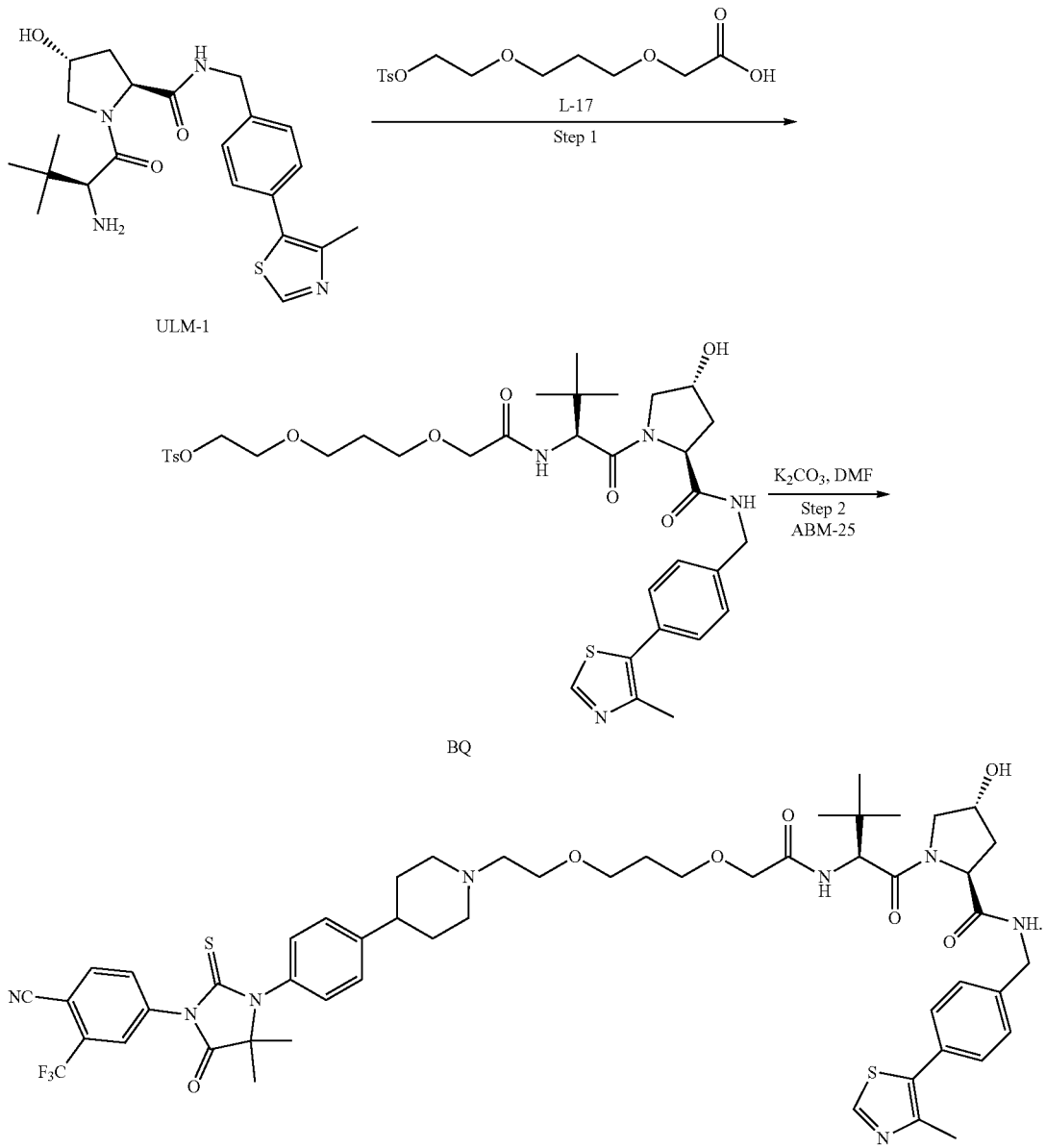

Example 80

Step 1: synthesis of (2S,4R)-1-[(2S)-3,3-dimethyl-2-[2-(3-{2-[(4-methylbenzenesulfonyl)oxy]ethoxy}propoxy)acetamido]butanoyl]-4-hydroxy-N-{[4-(4-methyl-1,3-thiazol-5-yl)phenyl]methyl}pyrrolidine-2-carboxamide (BQ)

To a stirred solution of 2-(3-{2-[(4-methylbenzenesulfonyl)oxy]ethoxy}propoxy)acetic acid (L-17, 300 mg, 0.90 mmol) in N,N-dimethylformamide (5 mL) was added EDCI (350 mg, 1.83 mmol), HOBt (240 mg, 1.78 mmol) and DIEA (350 mg, 2.71 mmol) at rt. The resulting solution was stirred at rt for 10 min. Then to the solution was added (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (ULM-1, 390 mg, 0.91 mmol), and the resulting solution was stirred at rt for 1 h. Water (30 mL) was added and the resulting mixture was extracted with ethyl acetate (30 mL×3). The organic layers were combined, washed with saturated aqueous solution of sodium chloride (30 mL), dried over anhydrous sodium sulfate and then concentrated under reduced pressure to give a crude residue, which was purified by a flash silica gel chromatography (eluent: dichloromethane/methanol (v:v=10:1) to give BQ (yield: 64%) as a yellow solid. LC-MS (ES⁺): m/z 745.35 [MH⁺], $t_R$=0.96 min (2.0 minute run).

Step 2: Synthesis of (2S,4R)-1-[(2S)-2-[2-(3-{2-[4-(4-{3-[4-cyano-3-(trifluoromethyl)phenyl]-5,5-dimethyl-4-oxo-2-sulfanylideneimidazolidin-1-yl}phenyl)piperidin-1-yl]ethoxy}propoxy)acetamido]-3,3-dimethylbutanoyl]-4-hydroxy-N-{[4-(4-methyl-1,3-thiazol-5-yl)phenyl]methyl}pyrrolidine-2-carboxamide (Example 80)

To a stirred solution of 4-{4,4-dimethyl-5-oxo-3-[4-(piperidin-4-yl)phenyl]-2-sulfanylideneimidazolidin-1-yl}-2-(trifluoromethyl)benzonitrile (ABM-25, 150 mg, 0.32 mmol), (2S,4R)-1-[(2S)-3,3-dimethyl-2-[2-(3-{2-[(4-methylbenzenesulfonyl)oxy]ethoxy}propoxy)acetamido]butanoyl]-4-hydroxy-N-{[4-(4-methyl-1,3-thiazol-5-yl)phenyl]methyl}pyrrolidine-2-carboxamide (BQ, 236 mg, 0.32 mmol) in N,N-dimethylformamide (5 mL) was added potassium carbonate (131 mg, 0.95 mmol). The resulting mixture was stirred at 60° C. overnight. The reaction mixture was cooled to rt, water (20 mL) was added and the resulting mixture was extracted with ethyl acetate (30 mL×3). The organic layers were combined, washed with saturated aqueous solution of sodium chloride (20 mL), dried over anhydrous sodium sulfate and then concentrated under reduced pressure to give a crude residue, which was purified by Prep-HPLC to give Example 80 (yield: 7%) as a white solid. $^1$H NMR (300 MHz, CD$_3$OD): δ 8.91 (s, 1H), 8.15 (d, J=4.5 Hz, 2H), 8.02 (d, J=4.5 Hz, 1H), 7.40 (m, 7H), 4.45 (d, J=12.0 Hz, 1H), 4.45 (m, 4H), 4.02 (d, J=3.9 Hz, 2H), 3.70 (m, 10H), 3.38 (m, 2H), 3.11 (m, 3H), 2.48 (s, 3H), 2.26 (m, 8H), 1.54 (s, 6H), 1.03 (s, 9H); LC-MS (ES$^+$): m/z 1045.35 [MH$^+$], t$_R$=2.74 min (5.6 minute run).

Example 81 was synthesized according to similar procedure described for synthesis of Example 80, by using corresponding starting materials and intermediates.

Example 81

(2S,4R)-1-((S)-2-(2-(4-(2-(4-(4-(3-(4-cyano-3-(trifluoromethyl)phenyl)-5,5-dimethyl-4-oxo-2-thioxoimidazolidin-1-yl)phenyl)piperidin-1-yl)ethoxy)butoxy)acetamido)-3,3-dimethylbutanoyl)-4-hydroxy-N-(4-(4-methylthiazol-5-yl)benzyl)pyrrolidine-2-carboxamide

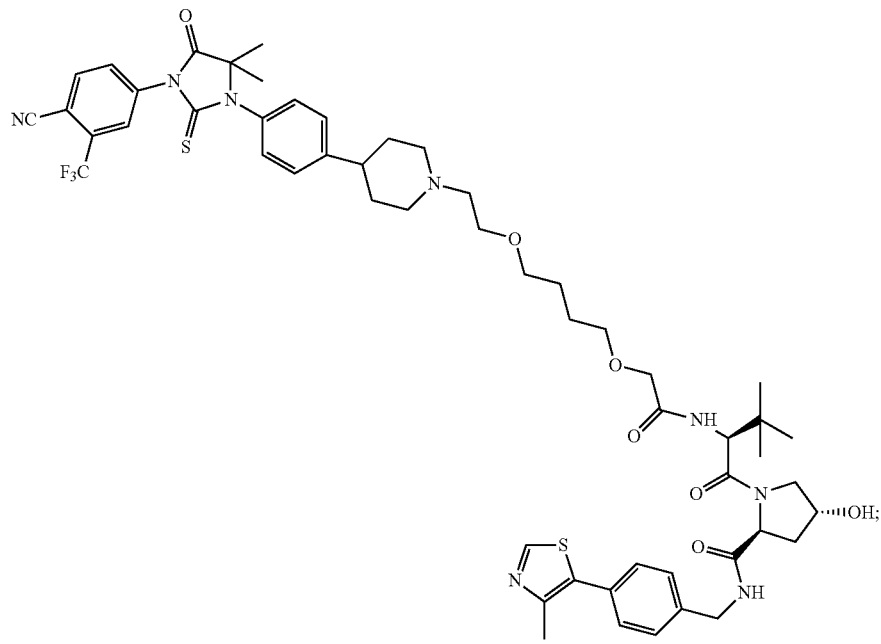 [SMILES: Cc1ncsc1-c1ccc(CNC(=O)[C@@H]2C[C@@H](O)CN2C(=O)[C@@H](NC(=O)COCCCCOCCN2CCC(c3ccc(N4C(=S)N(c5ccc(C#N)c(C(F)(F)F)c5)C(=O)C4(C)C)cc3)CC2)C(C)(C)C)cc1]

$^1$H NMR (300 MHz, DMSO): δ 8.98 (s, 1H), 8.63-8.61 (m, 1H), 8.40-8.37 (m, 1H), 8.37-8.34 (m, 1H), 8.11-8.01 (m, 1H), 7.44-7.40 (m, 3H), 7.37-7.32 (m, 6H), 4.57-4.54 (d, J=9.6 Hz, 1H), 4.47-4.45 (m, 2H), 4.45-4.44 (m, 2H), 4.39-4.37 (m, 1H), 3.92 (s, 2H), 3.71-3.65 (m, 2H), 3.58-3.47 (m, 5H), 3.45-3.40 (m, 4H), 2.99-2.95 (m, 2H), 2.51 (s, 3H), 2.12-2.02 (m, 3H), 1.93-1.90 (m, 1H), 1.90-1.79 (m, 3H), 1.77-1.71 (m, 5H), 1.67-1.61 (m, 6H), 0.94 (s, 9H); Mass (ES$^+$): m/z 1059.44 [MH$^+$].

Example 82
(2S,4R)—N-(2-(2-(2-(2-(4-(3-(4-cyano-3-(trifluoromethyl)phenyl)-5,5-dimethyl-4-oxo-2-thioxoimidazolidin-1-yl)phenoxy)ethoxy)ethoxy)ethoxy)-4-(4-methylthiazol-5-yl)benzyl)-4-hydroxy-1-((S)-3-methyl-2-(1-oxoisoindolin-2-yl)butanoyl)pyrrolidine-2-carboxamide
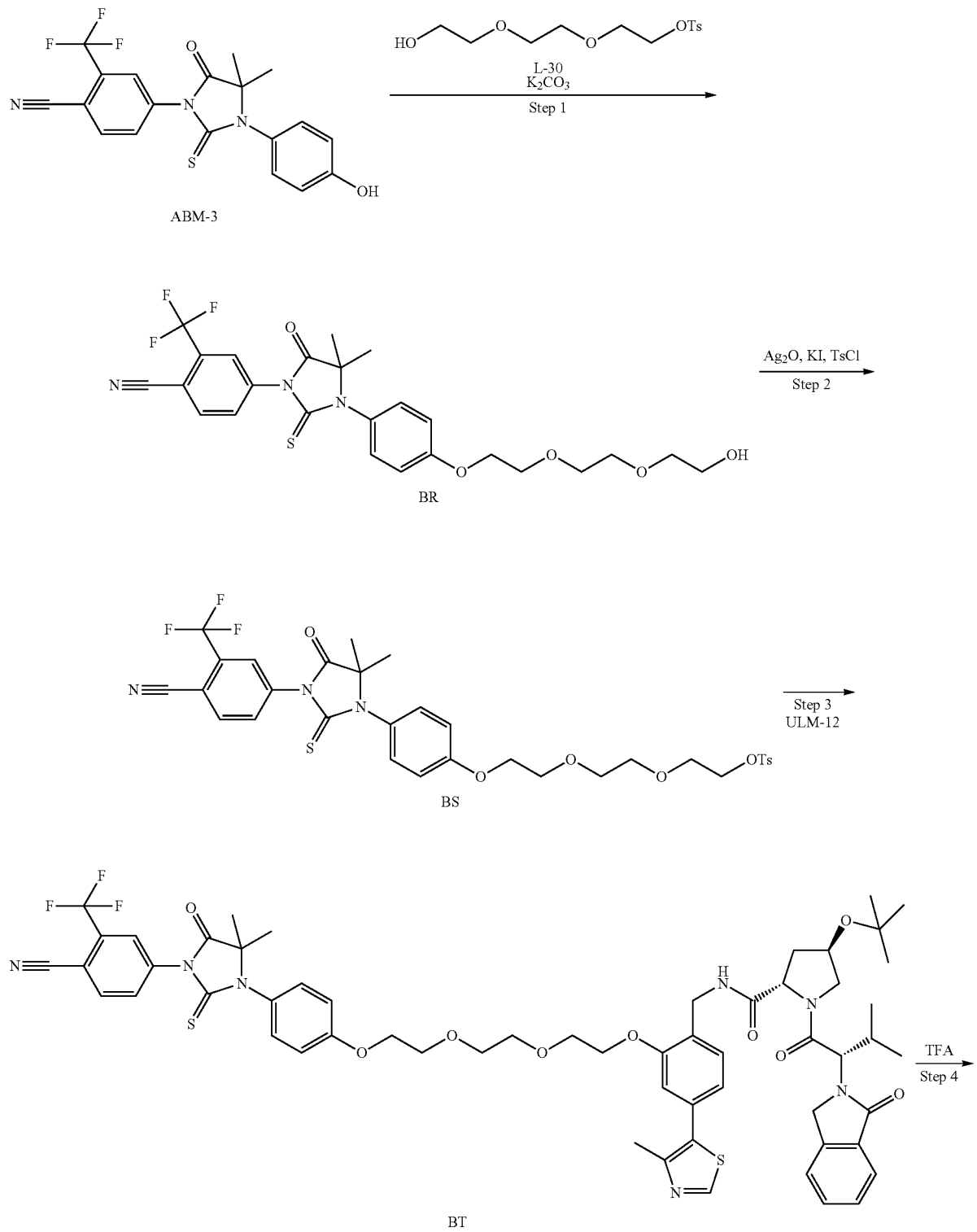

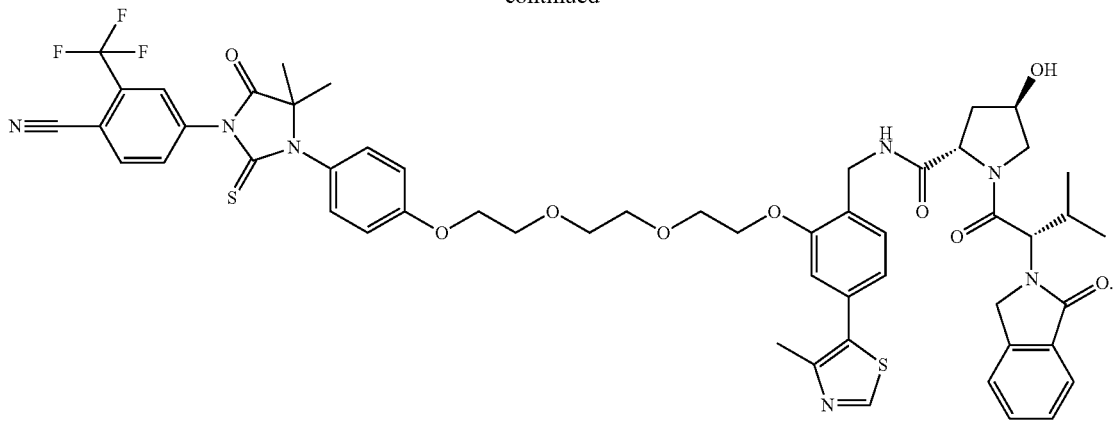

Example 82

Step 1: Synthesis of 4-[3-(4-{2-[2-(2-hydroxy-ethoxy)ethoxy]ethoxy}phenyl)-4,4-dimethyl-5-oxo-2-sulfanylideneimidazolidin-1-yl]-2-(trifluoromethyl)benzonitrile (BR)

To a stirred solution of 4-[3-(4-hydroxyphenyl)-4,4-dimethyl-5-oxo-2-sulfanylideneimidazolidin-1-yl]-2-(trifluoromethyl)benzonitrile (ABM-3, 405 mg, 1.00 mmol) in CH₃CN (20 mL) was added potassium carbonate (276 mg, 1.98 mmol) and 2-(2-{2-[(4-methylbenzenesulfonyl)oxy]ethoxy}ethoxy)ethan-1-ol (L-30, 456 mg, 1.50 mmol) at rt. The resulting mixture was then heated to 80° C. and stirred at this temperature overnight. LC-MS indicated formation of the desired product. The reaction mixture was cooled to rt, concentrated under vacuum to give a crude residue, which was purified by a flash silica gel chromatography (eluent: ethyl acetate/petroleum ether (v:v=1:1)) to give BR (yield: 91%) of as a brown oil.

Step 2: Synthesis of 2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethyl 4-methylbenzene-1-sulfonate (BS)

To a stirred solution of 4-[3-(4-{2-[2-(2-hydroxyethoxy)ethoxy]ethoxy}phenyl)-4,4-dimethyl-5-oxo-2-sulfanylideneimidazolidin-1-yl]-2-(trifluoromethyl)benzonitrile (BR, 490 mg, 0.91 mmol) in dichloromethane (10 mL) was added tosyl chloride (190 mg, 1.00 mmol), potassium iodide (30.2 mg) and silver oxide (314 mg) at rt. The resulting mixture was then stirred at 30° C. for 6 h, LC-MS indicated formation of the desired product. The inorganic salts were removed from the reaction by filtration, the solution phase was concentrated under vacuum to give a crude residue, which was purified by a flash silica gel chromatography (eluent: ethyl acetate/petroleum ether (v:v=1:3)) to give BS (yield: 60%) of as a light yellow solid.

Step 3: Synthesis of (2S,4R)-4-(tert-butoxy)-N-{[2-(2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)-4-(4-methyl-1,3-thiazol-5-yl)phenyl]methyl}-1-[(2S)-3-methyl-2-(1-oxo-2,3-dihydro-1H-isoindol-2-yl)butanoyl]pyrrolidine-2-carboxamide (BT)

To a stirred solution of 2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethyl 4-methylbenzene-1-sulfonate (BS, 207 mg, 0.30 mmol) and (2S,4R)-4-(tert-butoxy)-N-{[2-hydroxy-4-(4-methyl-1,3-thiazol-5-yl)phenyl]methyl}-1-[(2S)-3-methyl-2-(1-oxo-2,3-dihydro-1H-isoindol-2-yl)butanoyl]pyrrolidine-2-carboxamide (ULM-12, 181 mg, 0.30 mmol) in N,N-dimethylformamide (2 mL) was added potassium carbonate (83 mg, 0.60 mmol) at rt. The resulting mixture was then heated to 80° C. and stirred at the same temperature overnight, and LC-MS indicated formation of the desired product. The reaction was then cooled to rt, diluted by water (10 mL) and then extracted with ethyl acetate (20 mL×3). The organic layers were combined, dried over anhydrous sodium sulfate and concentrated under reduced pressure to give a crude residue, which was purified by a flash silica gel chromatography (eluent: ethyl acetate/petroleum ether (v:v=1:1) to give BT (yield: 54%) as a white solid.

Step 4: Synthesis of (2S,4R)—N-{[2-(2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide (Example 82)

To a stirred solution of (2S,4R)-4-(tert-butoxy)-N-{[2-(2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)-4-(4-methyl-1,3-thiazol-5-yl)phenyl]methyl}-1-[(2S)-3-methyl-2-(1-oxo-2,3-dihydro-1H-isoindol-2-yl)butanoyl]pyrrolidine-2-carboxamide (BT, 180 mg, 0.16 mmol) in dichloromethane (5 mL) was added trifluoroacetic acid (0.5 mL) at rt. The resulting solution was stirred rt for 6 h, LC-MS indicated formation of the desired product. Saturated aq. solution of sodium bicarbonate was added to the reaction to neutralize the trifluoroacetic acid. Organic layer was separated, the aqueous layer was extracted with of dichloromethane (10 mL×2). The organic layers combined, dried over anhydrous sodium sulfate and concentrated under reduced pressure to give a crude residue, which was purified by Pre-HPLC to give Example 82 (yield: 31%) as a white solid. ¹H NMR (400 MHz, CD₃OD): δ 8.90 (s, 1H), 8.40-8.38 (d, J=8.0 Hz, 2H), 8.29 (s, 1H), 8.09-8.07 (d, J=8.4 Hz, 1H), 7.72-7.70 (d, J=7.6 Hz, 1H), 7.62-7.61 (d, J=4.0 Hz, 2H), 7.50-7.40 (m, 1H), 7.35-7.33 (d, J=7.6 Hz, 1H), 7.27-7.25 (d, J=8.8 Hz, 2H), 7.10-7.06 (m, 3H), 7.05-7.00 (m, 1H), 5.09 (s, 1H), 4.72-4.69 (d, J=10.8 Hz, 1H), 4.61-4.41 (m, 2H), 4.41-4.31 (m, 2H), 4.31-4.21 (m, 2H), 4.21-4.11 (m, 2H), 4.11-4.01 (m, 2H), 3.82-3.71 (m, 5H), 3.69-3.61 (m, 5H), 2.51 (m, 3H), 2.47-2.25 (m, 1H), 2.10-2.00 (m, 1H), 2.00-1.95 (m, 1H), 1.48 (s, 6H), 0.97-0.96 (d, J=6.4 Hz, 3H), 0.74-0.72 (d, J=6.4 Hz, 3H); LC-MS (ES+): m/z 1068.20 [MH+], $t_R$=1.59 min (3.0 minute run).

Examples 83-85 were synthesized according to similar procedure described for synthesis of Example 82, by using corresponding starting materials and intermediates.

TABLE 6

Exemplary Compounds.

| Ex # | Structure | Compound name and Analytical data |
|---|---|---|
| 83 | (structure) | Prepared from ABM-3, L-30, and ULM-13 (2S,4R)-N-{[2-(2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)-4-(4-methyl-1,3-thiazol-5-yl)phenyl]methyl}-1-[(2S)-2-(6-fluoro-1-oxo-2,3-dihydro-1H-isoindol-2-yl)-3-methylbutanoyl]-4-hydroxypyrrolidine-2-carboxamide<br>$^1$H NMR (400 MHz, CD$_3$OD): δ 8.89 (s, 1H), 8.17-8.15 (d, J = 8.0 Hz, 2H), 8.00-7.98 (d, J = 8.4 Hz, 1H), 7.60-7.56 (m, 1H), 7.49-7.37 (m, 3H), 7.28-7.26 (d, J = 8.8 Hz, 2H), 7.08-7.05 (m, 4H), 4.90-7.83 (m, 1H), 4.59-4.46 (m, 6H), 4.26-4.25 (m, 2H), 417-4.15 (m, 2H), 3.98-3.86 (m, 6H), 3.79-3.77 (m, 4H), 2.51 (s, 3H), 2.50-2.49 (m, 1H), 2.25-2.15 (m, 1H), 2.01-2.00 (m, 1H), 1.54 (s, 6H), 1.07-1.06 (d, J = 6.8 Hz, 3H), 0.85-0.83 (d, J = 6.8 Hz, 3H); LC-MS (ES+): m/z 1086.60 [MH+], $t_R$ = 2.24 min (3.6 minute run). |
| 84 | (structure) | Prepared from ABM-3, L-30, and ULM-14 (2S,4R)-1-[(2S)-2-(7-cyano-1-oxo-2,3-dihydro-1H-isoindol-2-yl)-3-methylbutanoyl]-N-{[2-(2-{2-[2-(4-{3-[4-cyano-3-(trifluoromethyl)phenyl]-5,5-dimethyl-4-oxo-2-sulfanylideneimidazolidin-1-yl}phenoxy)ethoxy]ethoxy}ethoxy)-4-(4-methyl-1,3-thiazol-5-yl)phenyl]methyl}-4-hydroxypyrrolidine-2-carboxamide<br>H NMR (400 MHz, CD$_3$OD): δ 8.89 (s, 1H), 8.17-8.15 (d, J = 7.2 Hz, 2H), 8.01-7.98 (d, J = 8.4 Hz, 1H), 7.98-7.76 (m, 3H), 7.44-7.42 (m, 1H), 7.29-7.25 (m, 2H), 7.08-7.04 (m, 4H), 4.87-7.85 (m, 1H), 4.69-4.41 (m, 6H), 4.25-4.23 (m, 2H), 4.22-4.16 (m, 2H), 4.10-4.00 (m, 1H), 3.94-3.87 (m, 5H), 3.79-3.77 (m, 4H), 2.51 (s, 3H), 2.50-2.49 (m, 1H), 2.23-2.13 (m, 1H), 2.05-2.00 (m, 1H), 1.54 (s, 6H), 1.10-1.07 (d, J = 6.8 Hz, 3H), 0.88-0.86 (d, J = 6.8 Hz, 3H); LC-MS (ES+): m/z 1093.00 [MH+], $t_R$ = 2.22 min (3.6 minute run). |

TABLE 6-continued

Exemplary Compounds.

| Ex # | Structure | Compound name and Analytical data |
|---|---|---|
| 85 | 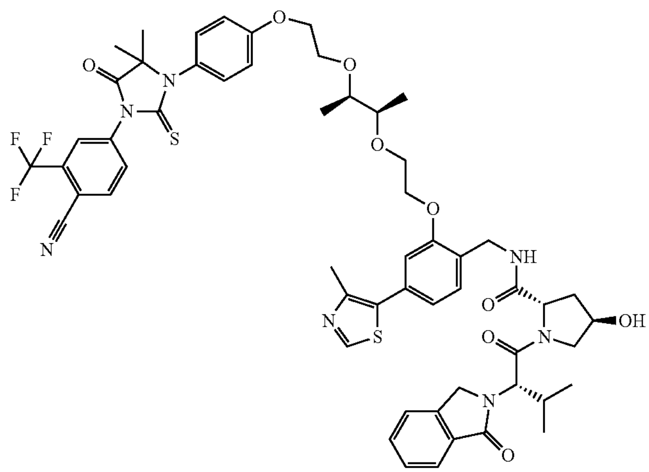 [SMILES: Cc1ncsc1-c1ccc(CNC(=O)[C@@H]2C[C@@H](O)CN2C(=O)[C@H](C(C)C)N2Cc3ccccc3C2=O)c(OCCO[C@H](C)[C@@H](C)OCCOc2ccc(N3C(=S)N(c4ccc(C#N)c(C(F)(F)F)c4)C(=O)C3(C)C)cc2)c1] | Prepared from ABM-3, L-31, and ULM-12 (2S,4R)-N-{[2-(2-{[(2R,3R)-3-[2-(4-{3-[4-cyano-3-(trifluoromethyl)phenyl]-5,5-dimethyl-4-oxo-2-sulfanylideneimidazolidin-1-yl}phenoxy)ethoxy]butan-2-yl]oxy}ethoxy)-4-(4-methyl-1,3-thiazol-5-yl)phenyl]methyl}-4-hydroxy-1-[(2S)-3-methyl-2-(1-oxo-2,3-dihydro-1H-isoindol-2-yl)butanoyl]pyrrolidine-2-carboxamide <sup>1</sup>H NMR (400 MHz, CD<sub>3</sub>OD) δ 0.82 (d, J = 6.65 Hz, 3H), 1.05 (d, J = 6.65 Hz, 3H), 1.15 (t, J = 5.48 Hz, 6H), 1.44-1.56 (m, 6H), 1.98-2.10 (m, 2H), 2.14-2.24 (m, 1H), 2.37-2.52 (m, 4H), 3.52-3.62 (m, 2H), 3.89 (td, J = 10.76, 4.70 Hz, 3H), 3.93-4.01 (m, 3H), 4.09 (br. s., 2H), 4.16-4.24 (m, 2H), 4.44-4.67 (m, 6H), 4.84 (d, J = 10.96 Hz, 1H), 6.95-7.08 (m, 4H), 7.19-7.30 (m, 2H), 7.43 (d, J = 7.43 Hz, 1H), 7.46-7.51 (m, 1H), 7.52-7.63 (m, 2H), 7.78 (d, J = 7.43 Hz, 1H), 7.97 (d, J = 7.83 Hz, 1H), 8.08-8.17 (m, 2H), 8.43 (t, J = 5.87 Hz, 1H), 8.87 (s, 1H); Mass (ES<sup>+</sup>): m/z 1096.37 [MH<sup>+</sup>] |

Synthesis of Example 86

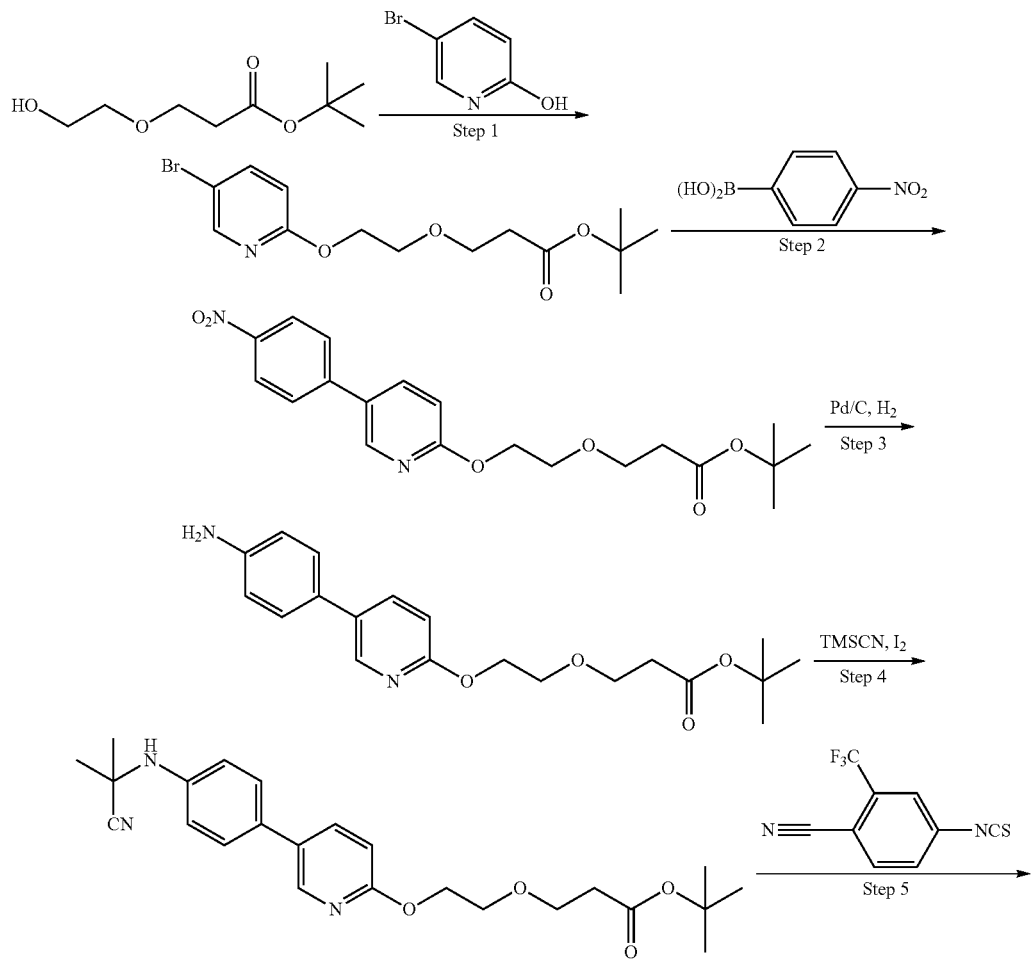

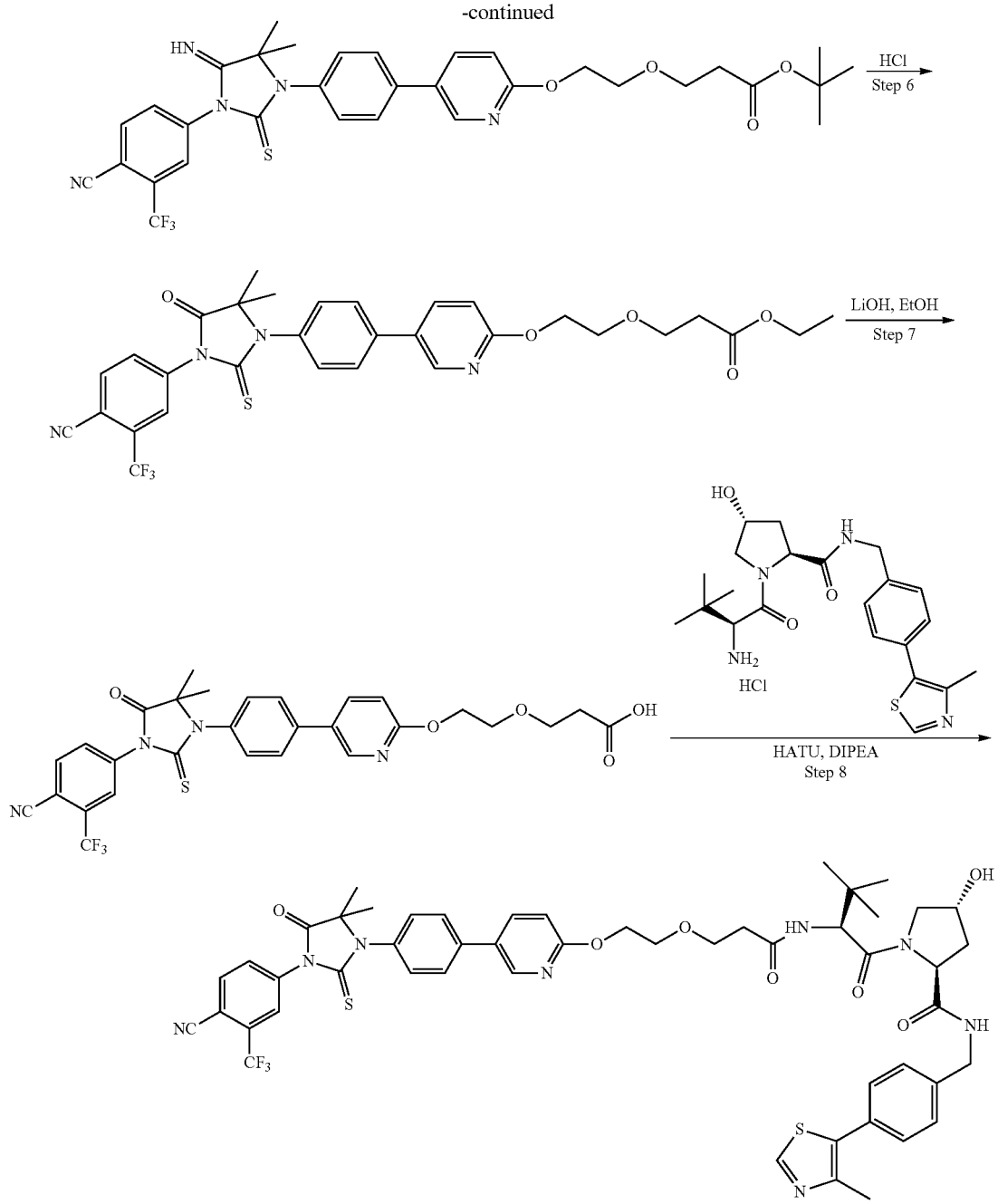

Example 86

Step 1: Synthesis of tert-butyl 3-{2-[(5-bromopyridin-2-yl)oxy]ethoxy}propanoate

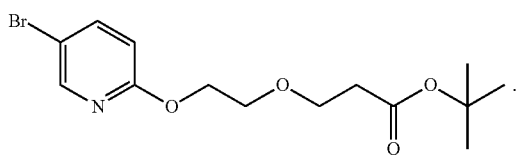 [SMILES: CC(C)(C)OC(=O)CCOCCOc1ccc(Br)cn1]

To a stirred solution of 5-bromopyridin-2-ol (3.0 g, 17.24 mmol), tert-butyl 3-(2-hydroxyethoxy)propanoate (3.3 g, 17.19 mmol) and triphenylphosphine (6.8 g, 25.81 mmol) in tetrahydrofuran (120.0 mL) was added diethyl diazene-1,2-dicarboxylate (4.49 g, 25.78 mmol) dropwise at 0° C. under an atmosphere of nitrogen. The resulting solution was stirred overnight at rt. The reaction mixture was concentrated under reduced pressure to give a crude residue, which was purified by silica gel flash chromatography (eluent: ethyl acetate/petroleum ether, v/v=1/3) to provide the titled product (yield: 50%) as colorless oil.

361

Step 2: Synthesis of tert-butyl 3-(2-{[5-(4-nitrophenyl)pyridin-2-yl]oxy}ethoxy)propanoate

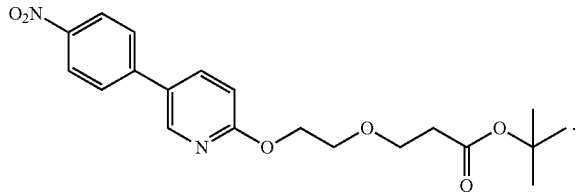 [SMILES: CC(C)(C)OC(=O)CCOCCOc1ccc(-c2ccc([N+](=O)[O-])cc2)cn1]

To a stirred mixture of tert-butyl 3-{2-[(5-bromopyridin-2-yl)oxy]ethoxy}propanoate (3.0 g, 8.67 mmol) and (4-nitrophenyl)boronic acid (1.5 g, 8.87 mmol) in a mixed solvent of dioxane (90.0 mL) and water (9.0 mL) was added potassium carbonate (2.4 g, 17.36 mmol) and Pd(PPh$_3$)$_4$ (450.0 mg, 0.39 mmol) under an atmosphere of nitrogen. The resulting mixture was stirred for 12 h at 100° C. The bulk of solvent was removed under reduced pressure, and the resulting aqueous residue was extracted with ethyl acetate (100 mL×2). The organic layers were combined, washed with brine (70 mL×2), dried over anhydrous sodium sulfate, and concentrated under reduced pressure to give a crude residue which was purified by silica gel flash chromatography (eluent: ethyl acetate/petroleum ether, v/v=1/5) to provide the titled product (yield: 83%) a yellow solid. Mass (ES$^+$): m/z 389.00[MH$^+$].

362

Step 3: Synthesis of tert-butyl 3-(2-{[5-(4-aminophenyl)pyridin-2-yl]oxy}ethoxy)propanoate

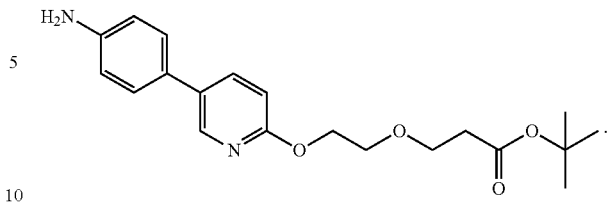

To a stirred solution of tert-butyl 3-(2-{[5-(4-nitrophenyl)pyridin-2-yl]oxy}ethoxy)propanoate (2.8 g, 7.21 mmol) in ethanol (200.0 mL) under an atmosphere of nitrogen was added palladium on carbon (1.5 g) at rt. The reaction mixture was then charge with hydrogen gas and stirred at rt for 12 h. The solids were removed by filtration and the solution phase was concentrated under reduced pressure to give a crude residue which was purified by silica gel flash chromatography (eluent: ethyl acetate/petroleum ether, v/v=1/3) to provide the titled product (yield: 89%) a yellow oil. LC-MS (ES$^+$): m/z 358.97[MH$^+$].

Example 86 was synthesized from tert-butyl 3-(2-{[5-(4-aminophenyl)pyridin-2-yl]oxy}ethoxy)propanoate, according to chemistry highlighted above (steps 4-8), utilizing similar procedures described for the similar chemistry carried out for the synthesis of examples 67, 75, 103, by using corresponding starting materials and intermediates.

Example 90 was synthesized according to similar procedures described for the synthesis of examples 86, by using corresponding starting materials and intermediates.

Examples 88, 91-92 were synthesized according to similar procedures described for the synthesis of examples 80, 75, 103, by using corresponding starting materials and intermediates.

Examples 87, 89, 93-102, 104-134, 136-142, 146-149 were synthesized according to similar procedures described for the synthesis of examples 75, by using corresponding starting materials and intermediates.

TABLE 7

Exemplary Compounds.

| Ex # | Structure | Compound name and Analytical data |
|---|---|---|
| 86 | 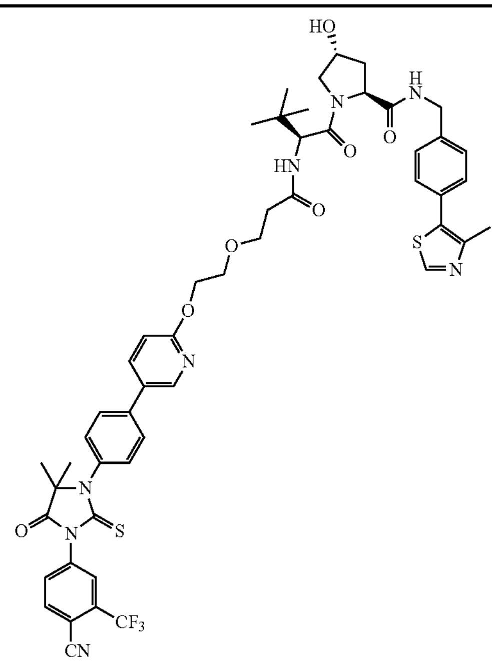 | (2S,4R)-1-[(2S)-2-[3-(2-{[5-(4-{3-[4-cyano-3-(trifluoromethyl)phenyl]-5,5-dimethyl-4-oxo-2-sulfanylidene-imidazolidin-1-yl}phenyl)pyridin-2-yl]oxy}ethoxy)propanamido]-3,3-dimethylbutanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.80 (s, 1H), 8.36-8.30 (m, 1H), 8.17-8.10 (m, 2H), 7.96-7.88 (m, 2H), 7.71-7.65 (m, 2H), 7.46-7.26 (m, 6H), 6.88-6.80 (m, 1H), 4.64-4.35 (m, 6H), 4.30-4.21 (m, 1H), 3.89-3.65 (m, 8H), 3.60-3.35 (m, 5H), 2.23-1.98 (m, 2H), 1.55 (s, 6H), 1.02 (s, 9H); LC-MS (ES$^+$): m/z 1011.20 [MH$^+$] |

TABLE 7-continued

Exemplary Compounds.

| Ex # | Structure | Compound name and Analytical data |
|---|---|---|
| 87 | 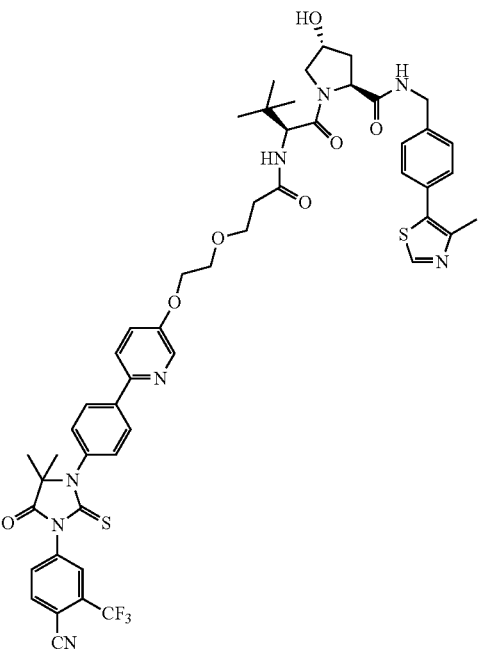 [SMILES: Cc1ncsc1-c1ccc(CNC(=O)[C@@H]2C[C@@H](O)CN2C(=O)[C@@H](NC(=O)CCOCCOc2ccc(-c3ccc(N4C(=S)N(c5ccc(C#N)c(C(F)(F)F)c5)C(=O)C4(C)C)cc3)nc2)C(C)(C)C)cc1] | (2S,4R)-1-[(2S)-2-[3-(2-{[6-(4-{3-[4-cyano-3-(trifluoromethyl)phenyl]-5,5-dimethyl-4-oxo-2-sulfanylidene-imidazolidin-1-yl}phenyl)pyridin-3-yl]oxy}ethoxy)propanamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.80 (s, 1H), 8.36-8.30 (m, 1H), 8.17-8.10 (m, 2H), 8.07-7.92 (m, 3H), 7.81-7.75 (m, 1H), 7.46-7.26 (m, 7H), 4.61 (s, 1H), 4.54-4.50 (m, 1H), 4.49-4.40 (m, 2H), 4.33-4.28 (m, 1H), 4.26-4.15 (m, 2H), 3.89-3.65 (m, 6H), 2.64-2.40 (m, 2H), 2.38 (s, 3H), 2.20-2.10 (m, 1H), 1.19-1.95 (m, 1H), 1.55 (s, 6H), 1.01 (s, 9H); LC-MS (ES$^+$): m/z 1011.20 [MH$^+$] |
| 88 | 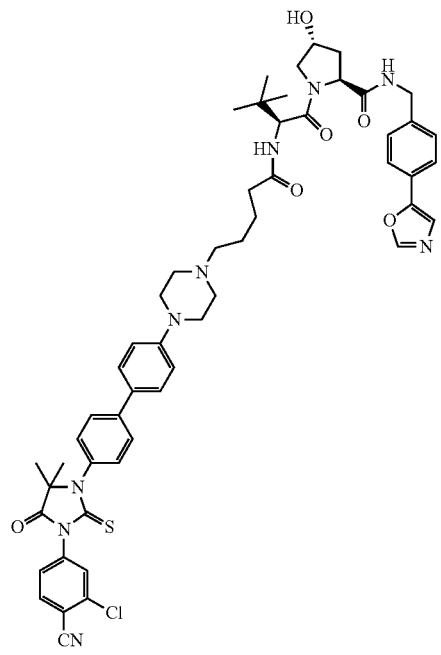 [SMILES: CC(C)(C)[C@H](NC(=O)CCCCN1CCN(c2ccc(-c3ccc(N4C(=S)N(c5ccc(C#N)c(Cl)c5)C(=O)C4(C)C)cc3)cc2)CC1)C(=O)N1C[C@H](O)C[C@H]1C(=O)NCc1ccc(-c2cnco2)cc1] | (2S,4R)-1-[(2S)-2-{5-[4-(4-{4-[3-(3-chloro-4-cyanophenyl)-5,5-dimethyl-4-oxo-2-sulfanylideneimidazolidin-1-yl]phenyl}phenyl)piperazin-1-yl]pentanamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, DMSO): δ 8.51-8.58 (m, 1H), 8.42 (s, 1H), 8.20 (d, J = 8.4 Hz, 1H), 8.05 (s, 1H), 7.87 (d, J = 9.3 Hz, 1H), 7.73-7.79 (m, 3H), 7.60-7.65 (m, 5H), 7.38-7.44 (m, 4H), 7.05 (d, J = 9.0 Hz, 2H), 5.13 (m, 1H), 4.58 (d, J = 9.3 Hz, 1H), 4.36-4.45 (m, 3H), 4.23 (m, 1H), 3.68 (m, 2H), 3.31 (s, 2H), 3.21 (m, 4H), 2.53 (s, 2H), 2.27-2.34 (m, 3H), 2.17-2.19 (m, 1H), 2.07 (m, 1H), 1.89 (m, 1H), 1.52 (m, 10H), 0.96 (s, 9H); LC-MS (ES$^+$): m/z 998.30 [MH$^+$] |

TABLE 7-continued

Exemplary Compounds.

| Ex # | Structure | Compound name and Analytical data |
|---|---|---|
| 89 | 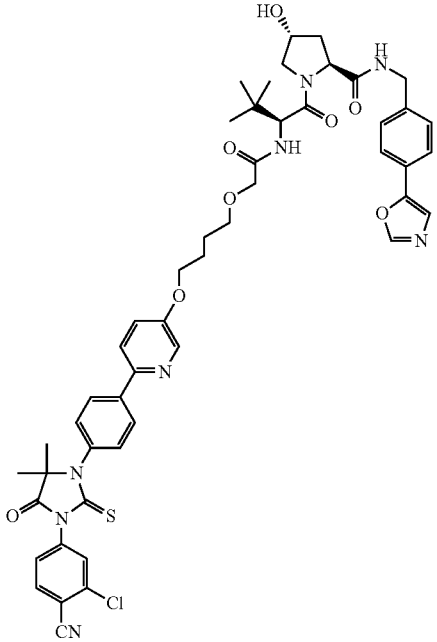 [SMILES: CC(C)(C)[C@H](NC(=O)COCCCCOc1ccc(-c2ccc(N3C(=S)N(c4ccc(C#N)c(Cl)c4)C(=O)C3(C)C)cc2)nc1)C(=O)N1C[C@H](O)C[C@H]1C(=O)NCc1ccc(-c2cnco2)cc1] | (2S,4R)-1-[(2S)-2-(2-{4-[(6-{4-[3-(3-chloro-4-cyanophenyl)-5,5-dimethyl-4-oxo-2-sulfanylideneimidazolidin-1-yl]phenyl}pyridin-3-yl)oxy]biitoxy}acetamido)-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD$_3$OD): δ 8.38 (s, 1H), 8.21 (s, 1H), 8.10-7.95 (m, 3H), 7.90 (s, 1H), 7.89-7.80 (m, 1H), 7.71-7.60 (m, 3H), 7.55-7.40 (m, 6H), 4.70 (m, 1H), 4.63-4.45 (m, 3H), 4.40-4.30 (m, 1H), 4.22-4.13 (m, 2H), 4.10-3.92 (m, 2H), 3.90-3.79 (m, 2H), 3.70-3.60 (m, 2H), 2.30-2.21 (m, 1H), 2.14-2.00 (m, 1H), 2.00-1.90 (m, 2H), 1.90-1.80 (m, 2H), 1.58 (s, 6H), 1.01 (s, 9H); LC-MS (ES$^+$): m/z, 961.20 [MH$^+$] |
| 90 | 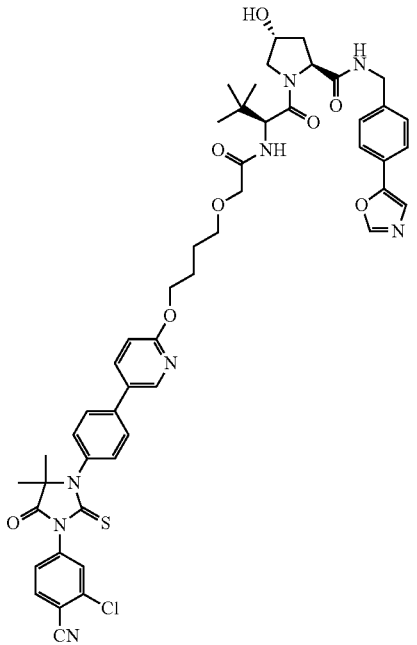 [SMILES: CC(C)(C)[C@H](NC(=O)COCCCCOc1ccc(-c2ccc(N3C(=S)N(c4ccc(C#N)c(Cl)c4)C(=O)C3(C)C)cc2)cn1)C(=O)N1C[C@H](O)C[C@H]1C(=O)NCc1ccc(-c2cnco2)cc1] | (2S,4R)-1-[(2S)-2-(2-{4-[(5-{4-[3-(3-chloro-4-cyanophenyl)-5,5-dimethyl-4-oxo-2-sulfanylideneimidazolidin-1-yl]phenyl}pyridin-2-yl)oxy]butoxy}acetamido)-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD$_3$OD): δ 8.42 (s, 1H), 8.21 (s, 1H), 8.00-7.95 (m, 2H), 7.90 (s, 1H), 7.79-7.71 (m, 2H), 7.70-7.61 (m, 3H), 7.55-7.40 (m, 5H), 6.90 (d, J = 6.6 Hz, 1H), 4.70 (m, 1H), 4.63-4.45 (m, 3H), 4.42-4.30 (m, 3H), 4.10-3.96 (m, 2H), 3.90-3.85 (m, 1H), 3.84-3.76 (m, 1H), 3.70-3.60 (m, 2H), 2.30-2.21 (m, 1H), 2.14-2.00 (m, 1H), 2.00-1.90 (m, 2H), 1.90-1.80 (m, 2H), 1.58 (s, 6H), 1.01 (s, 9H); LC-MS (ES$^+$): m/z, 961.20 [MH$^+$] |

TABLE 7-continued

Exemplary Compounds.

| Ex # | Structure | Compound name and Analytical data |
|---|---|---|
| 91 | 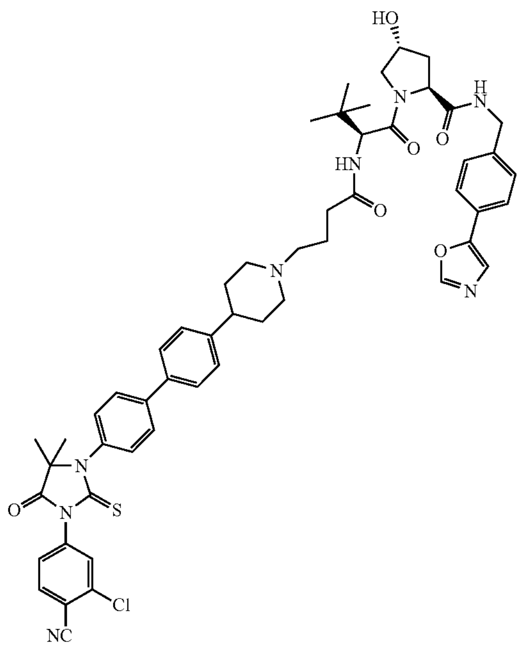 [SMILES: CC(C)(C)[C@H](NC(=O)CCCN1CCC(c2ccc(-c3ccc(N4C(=S)N(c5ccc(C#N)c(Cl)c5)C(=O)C4(C)C)cc3)cc2)CC1)C(=O)N1C[C@H](O)C[C@H]1C(=O)NCc1ccc(-c2cnco2)cc1] | (2S,4R)-1-[(2S)-2-{4-[4-(4-{4-[3-(3-chloro-4-cyanophenyl)-5,5-dimethyl-4-oxo-2-sulfanylideneimidazolidin-1-yl]phenyl}phenyl)piperidin-1-yl]butanamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, CD$_3$OD) δ 8.23 (s, 1H), 7.99 (d, J = 8.0 Hz, 1H), 7.91 (s, 1H), 7.80 (d, J = 8.8 Hz, 2H), 7.69-7.63 (m, 5H), 7.49-7.45 (m, 5H), 7.39 (d, J = 8.4 Hz, 2H), 4.67 (s, 1H), 4.60-4.52 (m, 3H), 4.38 (d, J = 15.6 Hz, 1H), 3.95-3.91 (m, 1H), 3.88-3.81 (m, 1H), 3.17-3.15 (m, 2H), 2.66-2.61 (m, 1H), 2.54-2.45 (m, 2H), 2.38-2.31 (m, 2H), 2.29-2.15 (m, 3H), 2.13-2.06 (m, 1H), 1.88-1.85 (m, 6H), 1.61 (s, 6H), 1.08 (s, 9H); LC-MS (ES$^+$): m/z 983.45 [MH$^+$] |
| 92 | 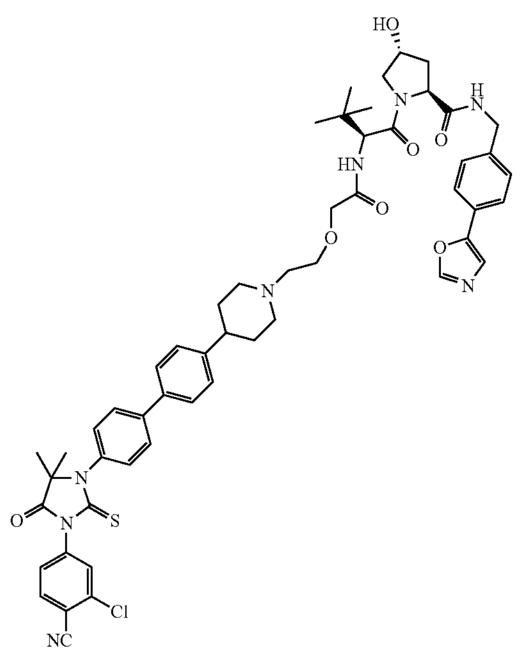 [SMILES: CC(C)(C)[C@H](NC(=O)COCCN1CCC(c2ccc(-c3ccc(N4C(=S)N(c5ccc(C#N)c(Cl)c5)C(=O)C4(C)C)cc3)cc2)CC1)C(=O)N1C[C@H](O)C[C@H]1C(=O)NCc1ccc(-c2cnco2)cc1] | (2S,4R)-1-[(2S)-2-(2-{2-[4-(4-{4-[3-(3-chloro-4-cyanophenyl)-5,5-dimethyl-4-oxo-2-sulfanylidene-imidazolidin-1-yl]phenyl}phenyl)piperidin-1-yl]ethoxy}acetamido)-3,3-dimethylbutanoyl]-4-hydroxy-N-{[4-(1,3-oxazol-5-yl)phenyl]methyl}pyrrolidine-2-carboxamide<br>$^1$H NMR (400 MHz, CD$_3$OD) δ 8.19 (s, 1H), 7.99 (d, J = 8.4 Hz, 1H), 7.91 (s, 1H), 7.77-7.73 (m, 2H), 7.69-7.52 (m, 5H), 7.45-7.43 (m, 5H), 7.36 (d, J = 8.4 Hz, 2H), 4.73 (s, 1H), 4.61-4.49 (m, 3H), 4.36-4.32 (m, 1H), 4.13-4.01 (m, 2H), 3.91-3.77 (m, 4H), 3.21-3.12 (m, 2H), 2.78 (t, J = 5.2 Hz, 2H), 2.68-2.61 (m, 1H), 2.37-2.30 (m, 2H), 2.28-2.19 (m, 1H), 2.14-2.05 (m, 1H), 1.92-1.88 (m, 4H), 1.60 (s, 6H), 1.08 (s, 9H); LC-MS (ES$^+$): m/z 999.65 [MH$^+$] |

TABLE 7-continued

Exemplary Compounds.

| Ex # | Structure | Compound name and Analytical data |
|---|---|---|
| 93 | 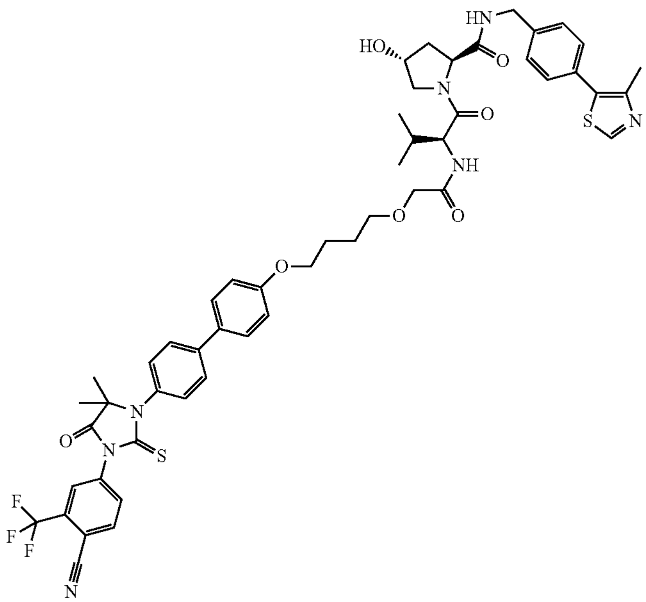 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cc3)cc2)C(C)C)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3-methylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ ppm 8.83 (s, 1 H,) 8.67 (t, J = 6.06 Hz, 1H), 8.18 (d, J = 1.96 Hz, 1H), 8.15 (d, J = 8.22 Hz, 1H), 8.00 (dd, J = 8.22, 1.96 Hz, 1H), 7.69-7.74 (m, 2H), 7.64 (d, J = 9.00 Hz, 1H), 7.54-7.60 (m, 2H), 7.37-7.46 (m, 6H), 6.96-7.02 (m, 2H), 4.63-4.69 (m, 1H), 4.55-4.61 (m, 1H), 4.48-4.55 (m, 2H), 4.34-4.41 (m, 1H), 4.04-4.10 (m, 2H), 3.98-4.03 (m, 2H), 3.83-3.88 (m, 1H), 3.77-3.82 (m, 1H), 3.64 (t, J = 6.26 Hz, 2H), 2.42-2.47 (m, 3H), 2.25 (dd, J = 13.30, 7.83 Hz, 1H), 2.14 (dd, J = 13.30, 6.65 Hz, 1H), 2.07 (ddd, J = 13.30, 9.00, 4.30 Hz, 1H), 1.89-1.97 (m, 2H), 1.81-1.89 (m, 2H), 1.59 (s, 6H), 1.01 (d, J = 6.65 Hz, 3H), 0.91 (d, J = 6.26 Hz, 3H); LC-MS (ES$^+$): m/z 1010.36 [MH$^+$] |
| 94 | 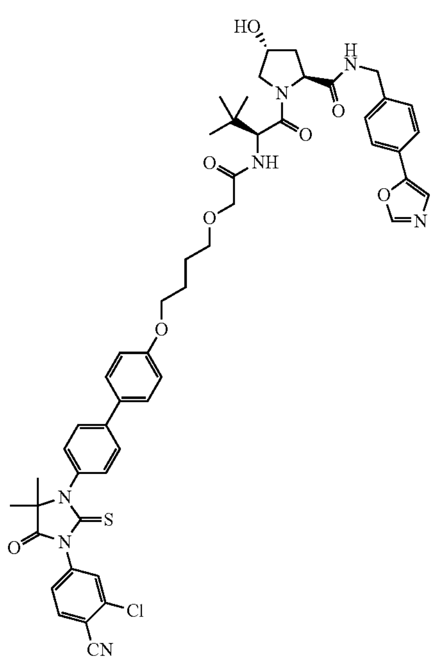 [SMILES: CC(C)(C)[C@H](NC(=O)COCCCCOc1ccc(-c2ccc(N3C(=S)N(c4ccc(C#N)c(Cl)c4)C(=O)C3(C)C)cc2)cc1)C(=O)N1C[C@H](O)C[C@H]1C(=O)NCc1ccc(-c2cnco2)cc1] | (2S,4R)-1-[(2S)-2-{2-[4-(4-{4-[3-(3-chloro-4-cyanophenyl)-5,5-dimethyl-4-oxo-2-sulfanylideneimidazolidin-1-yl]phenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD$_3$OD): δ 8.14 (s, 1H), 8.00-7.91 (m, 1H), 7.90-7.80 (m, 1H), 7.71-7.60 (m, 5H), 7.59-7.51 (m, 2H), 7.45-7.30 (m, 5H), 7.05-6.94 (m, 2H), 4.67 (s, 1H), 4.55-4.50 (m, 1H), 4.49-4.40 (m, 2H), 4.31-3.25 (m, 1H), 4.10-4.00 (m, 2H), 3.99-3.96 (m, 2H), 3.90-3.70 (m, 2H), 3.65-3.55 (m, 2H), 2.22-2.13 (m, 1H), 2.14-2.00 (m, 1H), 2.00-1.72 (m, 4H), 1.56 (s, 6H), 1.01 (s, 9H); LC-MS (ES$^+$): m/z, 960.30 [MH$^+$] |

TABLE 7-continued

Exemplary Compounds.

| Ex # | Structure | Compound name and Analytical data |
|---|---|---|
| 95 | 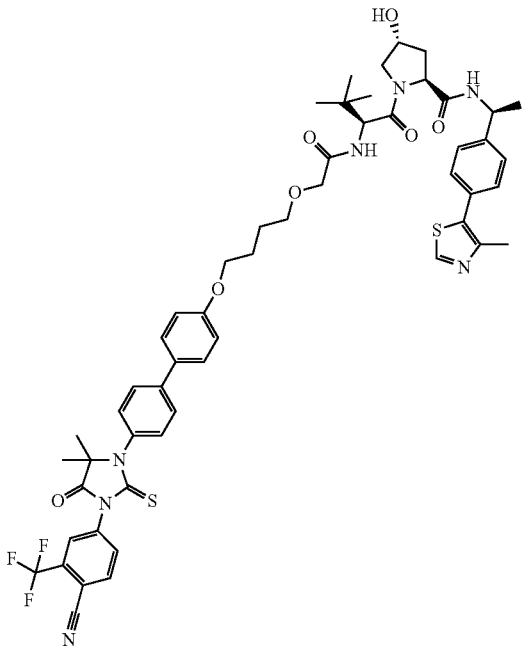 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cc3)cc2)C(C)(C)C)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-[(1S)-1-[4-(4-methyl-1,3-thiazol-5-yl)phenyl]ethyl]pyrrolidine-2-carboxamide<br>$^1$H NMR (300 MHz, CD$_3$OD): δ 8.86 (s, 1H), 8.18-8.15 (d, J = 9.0 Hz, 2H), 8.03-7.99 (m, 1H), 7.76-7.71 (d, J = 14.4 Hz, 2H), 7.64-7.59 (d, J = 15.3 Hz, 2H), 7.45-7.39 (m, 6H), 7.07-7.04 (d, J = 8.7 Hz, 2H), 5.01-4.99 (m, 1H), 4.70 (s, 1H), 4.61-4.55 (m, 1H), 4.45 (s, 1H), 4.13-4.08 (m, 2H), 4.03-3.96 (m, 2H), 3.84-3.80 (m, 1H), 3.78-3.76 (m, 1H), 3.68-3.64 (m, 2H), 2.47 (s, 3H), 2.22-2.15 (m, 1H), 1.99-1.85 (m, 5H), 1.60 (s, 6H), 1.51-1.48 (d, J = 6.9 Hz, 3H), 1.05 (s, 9H); LC-MS (ES$^+$): m/z 1038.50 [MH$^+$] |
| 96 | 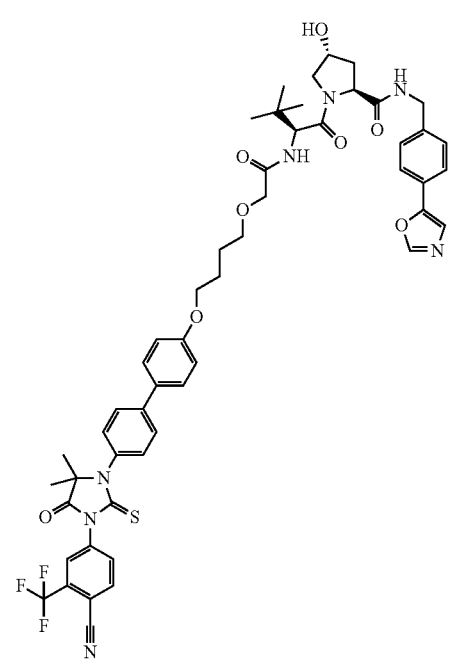 [SMILES: CC(C)(C)[C@H](NC(=O)COCCCCOc1ccc(-c2ccc(N3C(=S)N(c4ccc(C#N)c(C(F)(F)F)c4)C(=O)C3(C)C)cc2)cc1)C(=O)N1C[C@H](O)C[C@H]1C(=O)NCc1ccc(-c2cnco2)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-{[4-(1,3-oxazol-5-yl)phenyl]methyl}pyrrolidine-2-carboxamide<br>$^1$H NMR (300 MHz, CD$_3$OD): δ 8.23-8.15 (m, 3H), 8.03-7.99 (d, J = 9.9 Hz, 1H), 7.73-7.65 (m, 4H), 7.60-7.57 (d, J = 8.7 Hz, 2H), 7.46-7.41 (m, 5H), 7.05-7.00 (d, J = 12.6 Hz, 2H), 4.71 (s, 1H), 4.61-4.50 (m, 3H), 4.36-4.31 (d, J = 15.6 Hz, 1H), 4.10-4.08 (m, 4H), 4.03-3.82 (m, 2H), 3.68-3.64 (t, J = 7.3 Hz, 2H), 2.22-2.10 (m, 1H), 2.10-2.02 (m, 1H), 1.98-1.85 (m, 4H), 1.60 (s, 6H), 1.05 (s, 9H); LC-MS (ES$^+$): m/z 994.65 [MH$^+$] |

TABLE 7-continued

Exemplary Compounds.

| Ex # | Structure | Compound name and Analytical data |
|---|---|---|
| 97 | 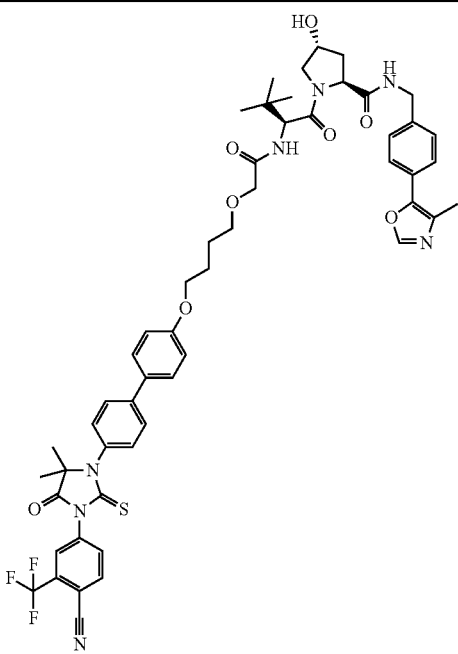 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-{[4-(4-methyl-1,3-oxazol-5-yl)phenyl]methyl}pyrrolidine-2-carboxamide<br>$^1$H NMR (300 MHz, CD$_3$OD): δ 8.18-8.15 (d, J = 9.3 Hz, 2H), 8.08 (s, 1H), 8.03-7.99 (d, J = 9.9 Hz, 1H), 7.73-7.70 (d, J = 8.4 Hz, 2H), 7.61-7.56 (m, 4H), 7.49-7.41 (m, 4H), 7.02-7.00 (d, J = 8.7 Hz, 2H), 4.71 (s, 1H), 4.61-4.52 (m, 3H), 4.37-4.11 (d, J = 15.6 Hz, 2H), 4.11-4.07 (m, 4H), 3.96-3.82 (m, 2H), 3.68-3.64 (t, J = 6.0 Hz, 2H), 2.36 (s, 3H), 2.23-2.14 (m, 1H), 2.14-2.09 (m, 1H), 1.98-1.84 (m, 4H), 1.60 (s, 6H), 1.05 (s, 9H); LC-MS (ES$^+$): m/z 1008.20 [MH$^+$] |
| 98 | 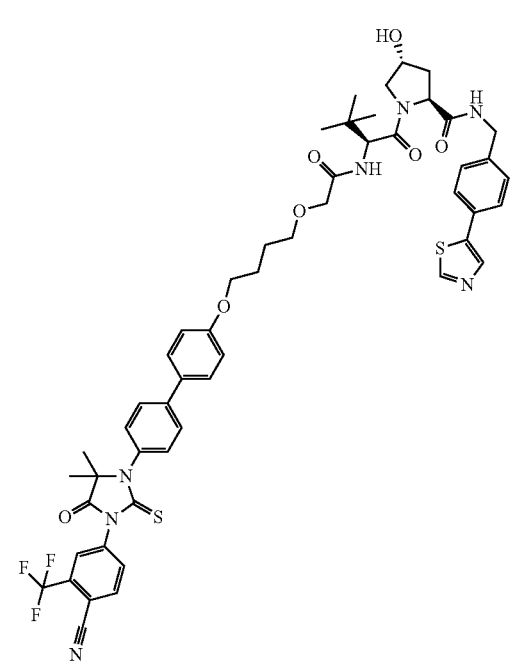 [SMILES: CC(C)(C)[C@H](NC(=O)COCCCCOc1ccc(-c2ccc(N3C(=S)N(c4ccc(C#N)c(C(F)(F)F)c4)C(=O)C3(C)C)cc2)cc1)C(=O)N1C[C@H](O)C[C@H]1C(=O)NCc1ccc(-c2cncs2)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-{[4-(1,3-thiazol-5-yl)phenyl]methyl}pyrrolidine-2-carboxamide<br>$^1$H NMR (300 MHz, CD$_3$OD): δ 8.89 (s, 1H), 8.18-8.15 (d, J = 9.0 Hz, 2H), 8.10 (s, 1H), 8.03-7.99 (d, J = 12.0 Hz, 1H), 7.73-7.70 (d, J = 8.4 Hz, 2H), 7.62-7.56 (m, 4H), 7.44-7.41 (m, 4H), 7.05-7.00 (d, J = 14.1 Hz, 2H), 4.71 (s, 1H), 4.61-4.51 (m, 3H), 4.35-4.30 (m, 1H), 4.12-4.08 (m, 2H), 4.08-4.03 (m, 2H), 3.95-3.82 (m, 2H), 3.68-3.64 (t, J = 6.0 Hz, 2H), 2.22-2.20 (m, 1H), 2.13-2.08 (m, 1H), 1.98-1.84 (m, 4H), 1.60 (s, 6H), 1.04 (s, 9H); LC-MS (ES$^+$): m/z 1010.30 [MH$^+$] |

TABLE 7-continued

Exemplary Compounds.

| Ex # | Structure | Compound name and Analytical data |
|---|---|---|
| 99 | 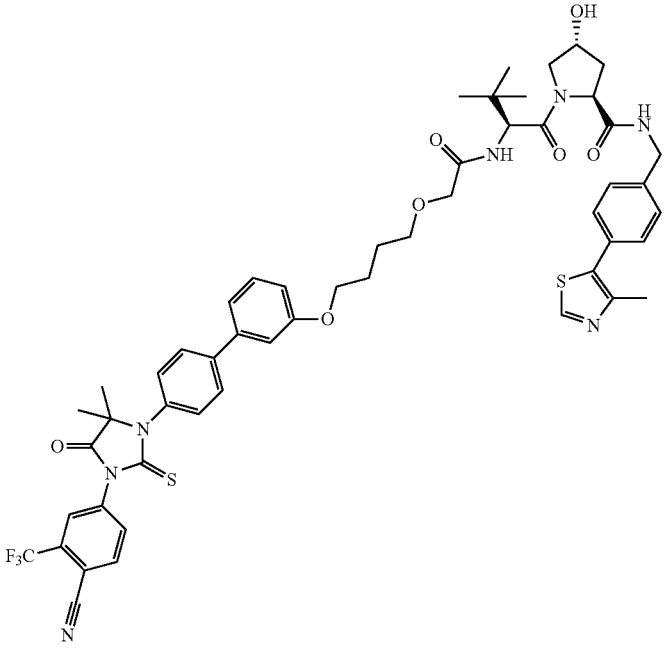 [SMILES: Cc1ncsc1-c1ccc(CNC(=O)[C@@H]2C[C@@H](O)CN2C(=O)[C@@H](NC(=O)COCCCCOc2cccc(-c3ccc(N4C(=S)N(c5ccc(C#N)c(C(F)(F)F)c5)C(=O)C4(C)C)cc3)c2)C(C)(C)C)cc1] | (2S,4R)-1-[(2S)-2-(2-{4-[3-(4-{3-[4-cyano-3-(trifluoromethyl)phenyl]-5,5-dimethyl-4-oxo-2-sulfanylideneimidazolidin-1-yl}phenyl)phenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.82 (s, 1H), 8.20 (d, J = 5.4 Hz, 2H), 8.02 (d, J = 8.0 Hz, 1H), 7.77 (d, J = 5.4 Hz, 2H), 7.52 (m, 4H), 7.44 (m, 3H), 7.24 (d, J = 8.4 Hz, 2H), 6.96 (d, J = 8.4 Hz, 1H), 4.71 (s, 1H), 4.56 (m, 3H), 4.34 (m, 1H), 4.12 (m, 2H), 4.00 (m, 2H), 3.84 (m, 1H), 3.72 (m, 1H), 3.67 (m, 2H), 2.45 (s, 3H), 2.24 (m, 1H), 2.10 (m, 1H), 1.90 (m, 4H), 1.61 (s, 6H), 1.03 (s, 9H); LC-MS (ES$^+$): m/z 1024.35 [MH$^+$] |
| 100 | 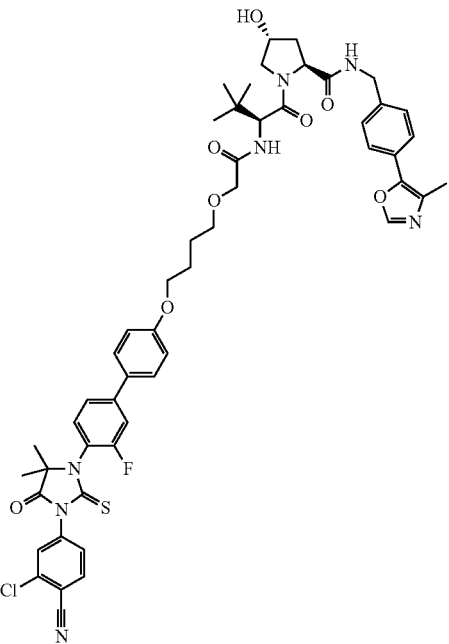 [SMILES: Cc1ncoc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(Cl)c5)C(=O)C4(C)C)c(F)c3)cc2)C(C)(C)C)cc1] | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]-3-fluorophenyl}phenoxy)butoxy]acetamido}-3,3-dimethylbutanoyl]-4-hydroxy-N-{[4-(4-methyl-1,3-oxazol-5-yl)phenyl]methyl}pyrrolidine-2-carboxamide<br>$^1$H NMR (400 MHz, DMSO) δ 8.61 (s, 1H), 8.29 (s, 1H), 8.21 (d, J = 8.4 Hz, 1H), 8.08 (s, 1H), 7.78-7.64 (m, 5H), 7.53-7.42 (m, 6H), 7.04 (m, J = 8.8 Hz, 2H), 5.16 (s, 1H), 4.58 (d, J = 9.6 Hz, 1H), 4.57-4.27 (m, 4H), 4.20 (t, J = 6.8 Hz, 2H), 3.91 (s, 2H), 3.68-3.53 (m, 4H), 2.33 (s, 3H), 2.07 (s, 1H), 1.90-1.72 (m, 5H), 1.60 (s, 3H), 1.48 (s, 3H), 0.95 (s, 9H); LC-MS (ES$^+$): m/z 992.30 [MH$^+$] |

TABLE 7-continued

Exemplary Compounds.

| Ex # | Structure | Compound name and Analytical data |
|---|---|---|
| 101 | 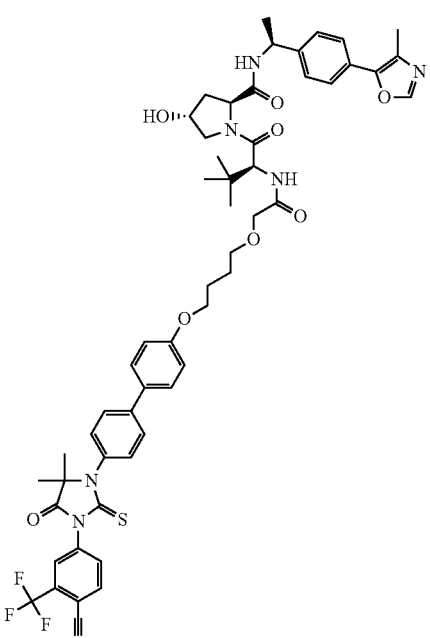 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-[(1S)-1-[4-(4-methyl-1,3-oxazol-5-l)phenyl]ethyl]pyrrolidine-2-carboxamide<br>$^1$H NMR (400 MHz, CD$_3$OD): δ 8.19-8.14 (m, 3H), 8.03-8.01 (d, J = 8.4 Hz, 1H), 7.77-7.73 (d, J = 16.0 Hz, 2H), 7.64-7.60 (m, 4H), 7.45-7.42 (m, 4H), 7.07-7.05 (d, J = 8.4 Hz, 2H), 5.01-5.00 (m, 1H), 4.71 (s, 1H), 4.61-4.56 (m, 1H), 4.45 (s, 1H), 4.13-4.10 (m, 2H), 4.07-4.01 (m, 2H), 3.88-3.85 (m, 1H), 3.78-3.75 (m, 1H), 3.69-3.66 (t, J = 12.0 Hz, 2H), 2.40 (s, 3H), 2.21-2.19 (m, 1H), 2.00-1.86 (m, 5H), 1.61 (s, 6H), 1.51-1.49 (d, J = 7.2 Hz, 3H), 1.06 (s, 9H); LC-MS (ES$^+$): m/z 1022.45 [MH$^+$] |
| 102 | 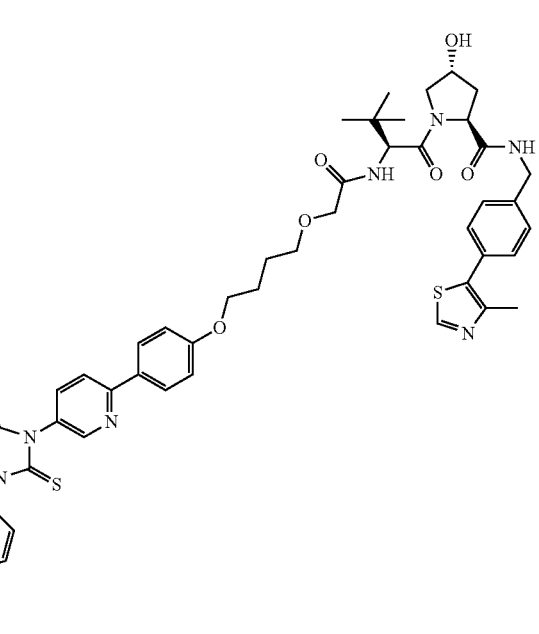 | (2S,4R)-1-[(2S)-2-(2-{4-[4-(5-{3-[4-cyano-3-(trifluoromethyl)phenyl]-5,5-dimethyl-4-oxo-2-sulfanylidene-imidazolidin-1-yl}pyridin-2-yl)phenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.96 (s, 1H), 8.62 (m, 2H), 8.42 (d, J = 8.4 Hz, 1H), 8.33 (s, 1H), 8.12 (m, 4H), 7.89 (m, 1H), 7.44 (m, 5H), 7.07 (d, J = 8.8 Hz, 2H), 5.17 (m, 1H), 4.59 (d, J = 9.6 Hz, 1H), 4.41-4.48 (m, 1H), 4.38 (m, 2H), 4.29 (m, 1H), 4.07-4.10 (m, 2H), 3.97 (m, 2H), 3.55-3.67 (m, 4H), 2.45 (s, 3H), 2.08 (m, 1H), 1.81-1.91 (m, 3H), 1.72-1.77 (m, 2H), 1.58 (s, 6H), 0.95 (s, 9H); LC-MS (ES$^+$): m/z 1025.55 [MH$^+$] |

TABLE 7-continued

Exemplary Compounds.

| Ex # | Structure | Compound name and Analytical data |
|---|---|---|
| 103 | 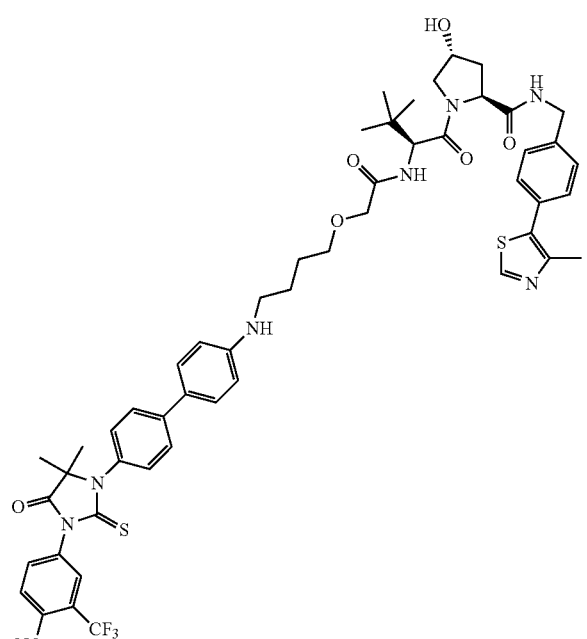 | (2S,4R)-1-[(2S)-2-[2-(4-{[4-(4-{3-[4-cyano-3-(trifluoromethyl)phenyl]-5,5-dimethyl-4-oxo-2-sulfanylidene-imidazolidin-1-yl}phenyl)phenyl]amino}butoxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD) δ 8.71 (s, 1H), 8.18-8.15 (d, J = 8.4 Hz, 2H), 8.03-8.00 (d, J = 7.8 Hz, 1H), 7.68-7.66 (d, J = 8.4 Hz, 2H), 7.47-7.35 (m, 8H), 6.74-6.71 (d, J = 8.7 Hz, 2H), 4.72 (s, 1H), 4.62-4.50 (m, 3H), 4.37-4.32 (d, J = 15.2 Hz, 1H), 4.00-3.98 (m, 2H), 3.94-3.79 (m, 2H), 3.64-3.61 (m, 2H), 3.21-3.11 (m, 2H), 2.48 (s, 3H), 2.28-2.21 (m, 1H), 2.09-2.05 (m, 1H), 1.93-1.89 (m, 4H), 1.59 (s, 6H), 1.01 (s, 9H); LC-MS (ES$^+$): m/z, 1023.30 [MH$^+$] |
| 104 | 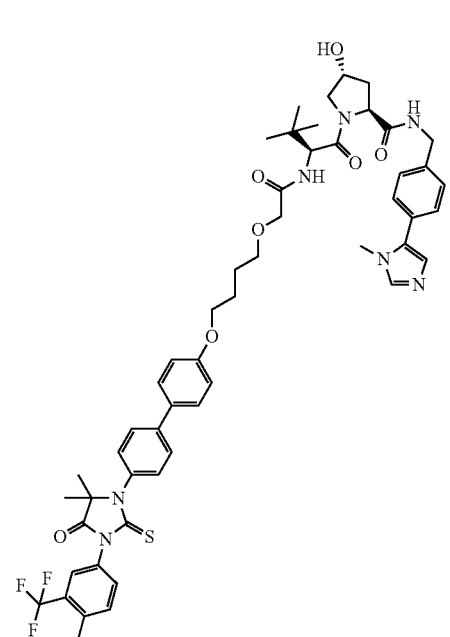 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-{[4-(1-methyl-1H-imidazol-5-yl)phenyl]methyl}pyrrolidine-2-carboxamide<br>$^1$H NMR (300 MHz, CD$_3$OD): δ 8.18-8.15 (d, J = 9.0 Hz, 2H), 8.02-7.99 (d, J = 10.2 Hz, 1H), 7.73-7.70 (d, J = 8.4 Hz, 2H), 7.59-7.56 (d, J = 8.7 Hz, 2H), 7.50-7.39 (m, 7H), 7.03-7.00 (d, J = 8.7 Hz, 2H), 6.30 (s, 1H), 4.71 (s, 1H), 4.62-4.50 (m, 3H), 4.39-4.33 (d, J = 15.2 Hz, 1H), 4.11-4.08 (m, 2H), 4.08-4.00 (m, 2H), 3.87-3.80 (m, 5H), 3.68-3.64 (t, J = 6.0 Hz, 2H), 2.25-2.15 (m, 1H), 2.10-2.00 (m, 1H), 1.97-1.84 (m, 4H), 1.60 (s, 6H), 1.04 (s, 9H); LC-MS (ES$^+$): m/z 1007.50 [MH$^+$] |

TABLE 7-continued

Exemplary Compounds.

| Ex # | Structure | Compound name and Analytical data |
|---|---|---|
| 105 | 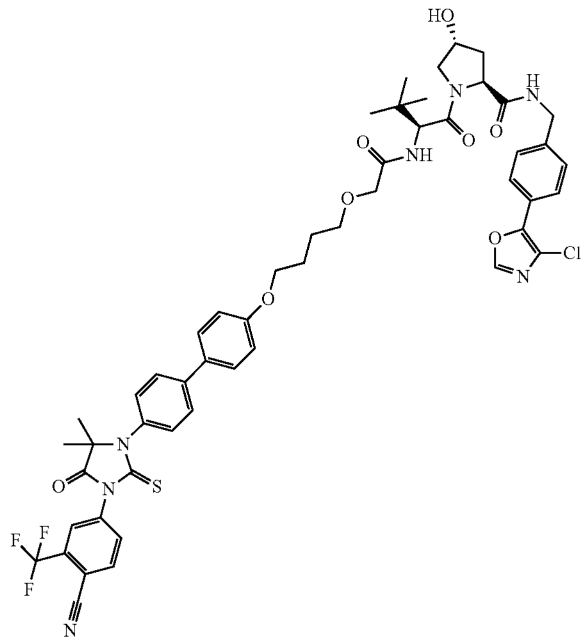 [SMILES: CC(C)(C)[C@H](NC(=O)COCCCCOc1ccc(-c2ccc(N3C(=S)N(c4ccc(C#N)c(C(F)(F)F)c4)C(=O)C3(C)C)cc2)cc1)C(=O)N1C[C@H](O)C[C@H]1C(=O)NCc1ccc(-c2ocnc2Cl)cc1] | (2S,4R)-N-{[4-(4-chloro-1,3-oxazol-5-yl)phenyl]methyl}-1-[(2S)-2-(2-{4-[4-(4-{3-[4-cyano-3-(trifluoromethyl)phenyl]-5,5-dimethyl-4-oxo-2-sulfanylideneimidazolidin-1-yl}phenyl)phenoxy]butoxy}acetamido)-3,3-dimethylbutanoyl]-4-hydroxy-pyrrolidine-2-carboxamide<br>$^1$H NMR (400 MHz, CD$_3$OD): δ 8.63-8.66 (m, 1H), 8.53 (s, 1H), 8.41 (d, J = 8.4 Hz, 1H), 8.32 (s, 1H), 8.12 (d, J = 8.8 Hz, 1H), 7.80 (d, J = 8.0 Hz, 2H), 7.75 (d, J = 8.4 Hz, 2H), 7.67 (d, J = 8.4 Hz, 2H), 7.50 (m, 5H), 7.04 (d, J = 8.8 Hz, 2H), 5.17 (m, 1H), 4.59 (d, J = 8.4 Hz, 1H), 4.48 (m, 2H), 4.39 (m, 1H), 4.32 (m, 1H), 4.08 (m, 2H), 3.97 (m, 2H), 3.55-3.67 (m, 4H), 2.06-2.08 (m, 1H), 1.81-1.91 (m, 3H), 1.72-1.77 (m, 2H), 1.55 (s, 6H), 0.95 (s, 9H); LC-MS (ES$^+$): m/z 1028.50 [MH$^+$] |
| 106 | 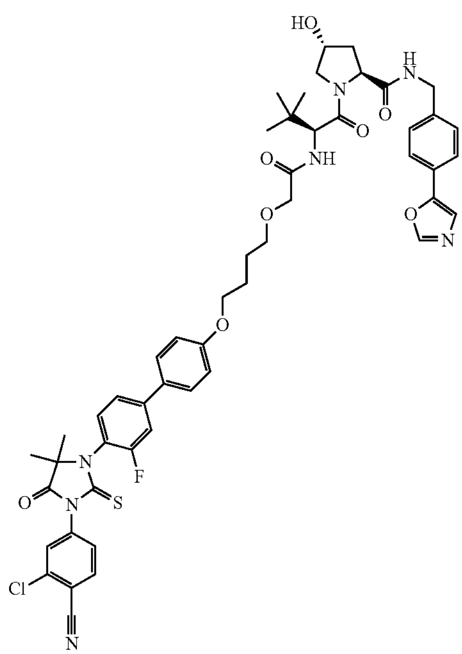 [SMILES: CC(C)(C)[C@H](NC(=O)COCCCCOc1ccc(-c2ccc(N3C(=S)N(c4ccc(C#N)c(Cl)c4)C(=O)C3(C)C)c(F)c2)cc1)C(=O)N1C[C@H](O)C[C@H]1C(=O)NCc1ccc(-c2cnco2)cc1] | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]-3-fluorophenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, CD$_3$OD) δ 8.20 (s, 1H), 8.00 (d, J = 8.4 Hz, 1H), 7.90 (s, 1H), 7.70-7.44 (m, 11H), 7.05 (d, J = 8.8 Hz, 2H), 4.72 (s, 1H), 4.61-4.52 (m, 3H), 4.37-4.33 (m, 1H), 4.14-4.02 (m, 4H), 3.98-3.84 (m, 2H), 3.67 (t, J = 6.4 Hz, 2H), 2.24-2.22 (m, 1H), 2.12-2.09 (m, 1H), 1.99-1.86 (m, 4H), 1.66 (s, 3H), 1.54 (s, 3H), 1.06 (s, 9H); LC-MS (ES$^+$): m/z 978.25 [MH$^+$] |

TABLE 7-continued

Exemplary Compounds.

| Ex # | Structure | Compound name and Analytical data |
|---|---|---|
| 107 | 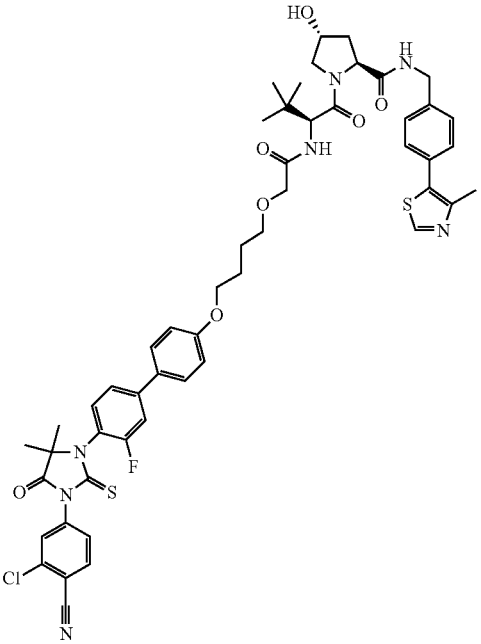 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(Cl)c5)C(=O)C4(C)C)c(F)c3)cc2)C(C)(C)C)cc1] | (2S,4R)-1-[(2S)-2-{2-[4-(4-{4-[3-(3-chloro-4-cyanophenyl)-5,5-dimethyl-4-oxo-2-sulfanylideneimidazolidin-1-yl]-3-fluorophenyl}phenoxy)butoxy]acetamido}-3,3-dimethyl-butanoyl]-4-hydroxy-N-{[4-(4-methyl-1,3-thiazol-5-yl)phenyl]methyl}pyrrolidine-2-carboxamide<br>$^1$H NMR (400 MHz, DMSO) δ 8.96 (s, 1H), 8.61 (m, 1H), 8.20 (d, J = 8.4 Hz, 1H), 8.19 (s, 1H), 7.78-7.64 (m, 5H), 7.70-7.37 (m, 6H), 7.03 (m, J = 8.8 Hz, 2H), 5.16 (s, 1H), 4.57 (d, J = 9.6 Hz, 1H), 4.57-4.27 (m, 4H), 4.08 (t, J = 6.8 Hz, 2H), 3.96 (s, 2H), 3.66-3.55 (m, 4H), 2.43 (s, 3H), 2.16 (m, 1H), 1.92-1.75 (m, 5H), 1.60 (s, 3H), 1.48 (s, 3H), 0.93 (s, 9H); LC-MS (ES$^+$): m/z 1008.50 [MH$^+$] |
| 108 | 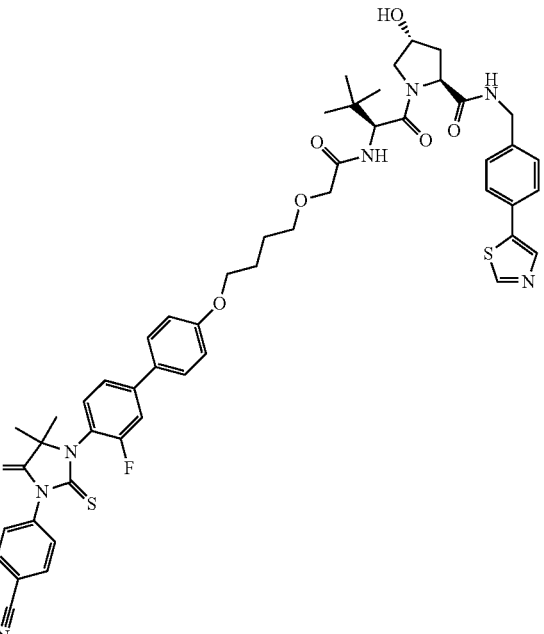 | (2S,4R)-1-[(2S)-2-{2-[4-(4-{4-[3-(3-chloro-4-cyanophenyl)-5,5-dimethyl-4-oxo-2-sulfanylideneimidazolidin-1-yl]-3-fluorophenyl}phenoxy)butoxy]acetamido}-3,3-dimethyl-butanoyl]-4-hydroxy-N-{[4-(1,3-thiazol-5-yl)phenyl]methyl}pyrrolidine-2-carboxamide<br>$^1$H NMR (400 MHz, DMSO) δ 9.04 (s, 1H), 8.61-8.56 (m, 1H), 8.27 (s, 1H), 8.21 (d, J = 8.4 Hz, 1H), 8.08 (s, 1H), 7.78-7.36 (m, 11H), 7.06 (d, J = 8.4 Hz, 2H), 5.16 (s, 1H), 4.58-4.56 (m, 1H), 4.47-4.22 (m, 4H), 4.09-4.06 (m, 2H), 3.96 (s, 2H), 3.66-3.55 (m, 4H), 2.07-2.04 (m, 1H), 1.89-1.72 (m, 5H), 1.60 (s, 3H), 1.48 (s, 3H), 0.95 (s, 9H); LC-MS (ES$^+$): m/z 994.50 [MH$^+$] |

TABLE 7-continued

Exemplary Compounds.

| Ex # | Structure | Compound name and Analytical data |
|---|---|---|
| 109 | 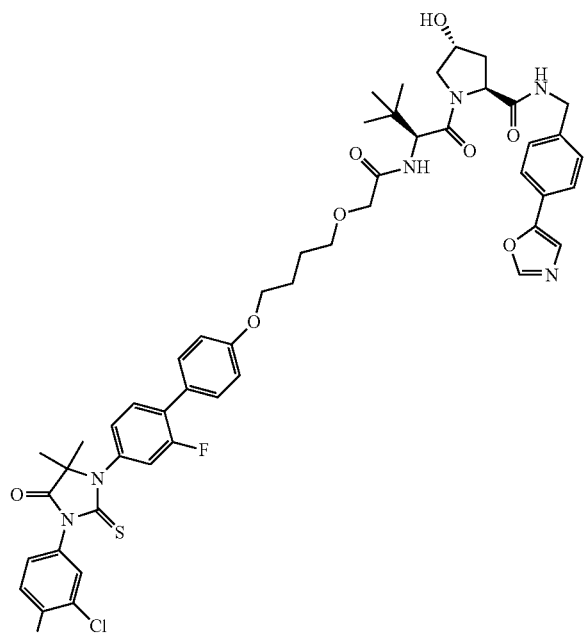 | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]-2-fluorophenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD$_3$OD): δ 8.23 (s, 1H), 8.19-7.99 (d, J = 5.9 Hz, 1H), 7.96 (s, 1H), 7.78-7.61 (m, 4H), 7.58-7.51 (m, 2H), 7.47-7.46 (m, 2H), 7.46-7.41 (m, 3H), 7.31-7.29 (m, 2H), 7.05-7.02 (d, J = 8.7 Hz, 1H), 4.71 (s, 1H), 4.61-4.51 (m, 3H), 4.36-4.31 (d, J = 15.2 Hz, 1H), 4.13-4.11 (m, 2H), 4.09-4.01 (m, 2H), 3.96-3.79 (m, 2H), 3.69-3.65 (t, J = 6.0 Hz, 2H), 2.23-2.20 (m, 1H), 2.13-2.09 (m, 1H), 1.96-1.87 (m, 4H), 1.60 (s, 6H), 1.03 (s, 9H); LC-MS (ES$^+$): m/z 978.25 [MH$^+$] |
| 110 | 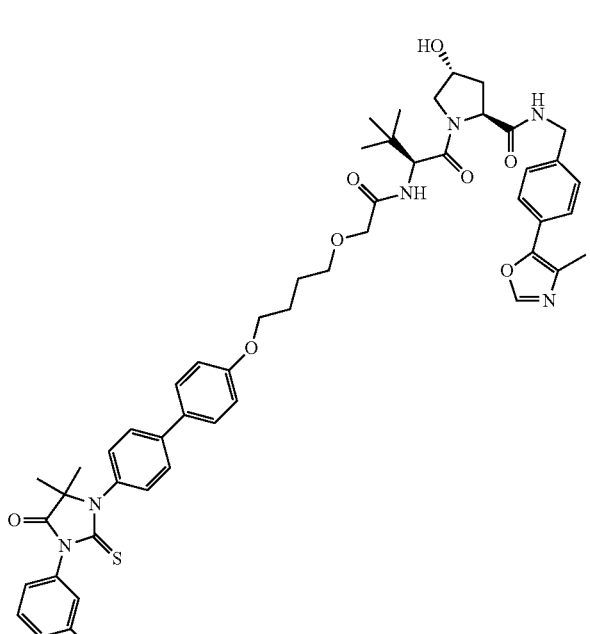 | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]phenyl}phenoxy)butoxy]acetamido}-3,3-dimethyl-butanoyl]-4-hydroxy-N-{[4-(4-methyl-1,3-oxazol-5-yl)phenyl]methyl}pyrrolidine-2-carboxamide<br>$^1$H NMR (300 MHz, CD$_3$OD): δ 8.08 (s, 1H), 7.77-7.72 (m, 3H), 7.69-7.56 (m, 4H), 7.48-7.39 (m, 5H), 7.19-7.17 (d, J = 6.3 Hz, 1H), 7.02-6.99 (d, J = 9.0 Hz, 2H), 4.71 (s, 1H), 4.61-4.52 (m, 3H), 4.36-4.31 (m, 1H), 4.11-4.08 (m, 2H), 4.03-4.01 (m, 5H), 3.95-3.82 (m, 2H), 3.68-3.64 (m, 2H), 2.36 (s, 3H), 2.22-2.09 (m, 1H), 2.09-2.01 (m, 1H), 1.95-1.84 (m, 4H), 1.58 (s, 6H), 1.04 (s, 9H);<br>LC-MS (ES$^+$): m/z 974.30 [MH$^+$] |

TABLE 7-continued

Exemplary Compounds.

| Ex # | Structure | Compound name and Analytical data |
|---|---|---|
| 111 | 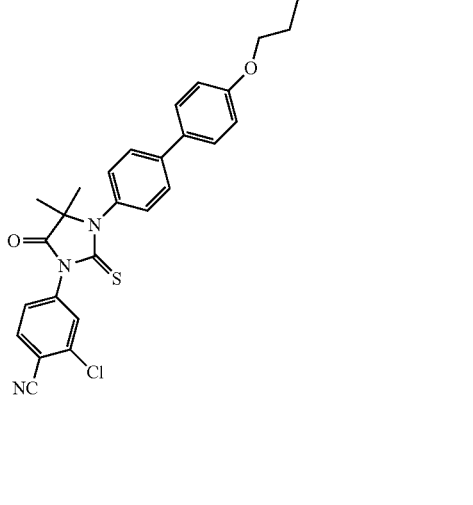 | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]phenyl}phenoxy)butoxy]acetamido}-3,3-dimethyl-butanoyl]-4-hydroxy-N-{[4-(1,3-thiazol-5-yl)phenyl]methyl}pyrrolidine-2-carboxamide<br>$^1$H NMR (300 MHz, CD$_3$OD): δ 8.89 (s, 1H), 8.10 (s, 1H), 7.98-7.95 (d, J = 8.4 Hz, 1H), 7.89-7.88 (d, J = 1.8 Hz, 1H), 7.72-7.56 (m, 7H), 7.44-7.39 (m, 4H), 7.03-7.00 (d, J = 8.7 Hz, 2H), 4.70 (s, 1H), 4.61-4.50 (m, 3H), 4.35-4.30 (d, J = 15.2 Hz, 1H), 4.12-4.03 (m, 2H), 4.01-3.95 (m, 2H), 3.86-3.82 (m, 2H), 3.68-3.64 (m, 2H), 2.22-2.18 (m, 1H), 2.12-2.08 (m, 1H), 1.98-1.85 (m, 4H), 1.58 (s, 6H), 1.04 (s, 9H); LC-MS (ES$^+$): m/z 976.20 [MH$^+$] |
| 112 | 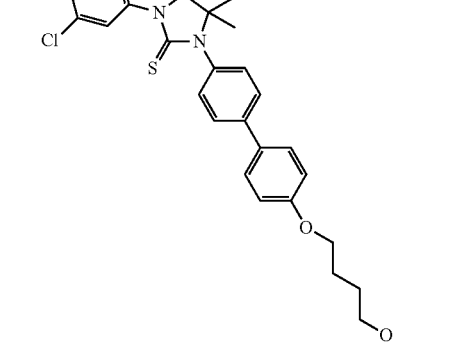 | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]phenyl}phenoxy)butoxy]acetamido}-3,3-dimethyl-butanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.81 (s, 1H), 7.98-7.95 (d, J = 8.4 Hz, 1H), 7.89-7.88 (d, J = 1.8 Hz, 1H), 7.73-7.64 (m, 3H), 7.58-7.56 (d, J = 8.7 Hz, 2H), 7.48-7.38 (m, 6H), 7.02-6.99 (d, J = 8.7 Hz, 2H), 4.71 (s, 1H), 4.62-4.51 (m, 3H), 4.36-4.31 (m, 1H), 4.11-4.07 (m, 2H), 4.02-4.00 (d, J = 5.4 Hz, 2H), 3.87-3.82 (m, 2H), 3.68-3.64 (t, J = 6.0 Hz, 2H), 2.44 (s, 3H), 2.23-2.10 (m, 1H), 2.09-2.00 (m, 1H), 1.97-1.84 (m, 4H), 1.58 (s, 6H), 1.04 (s, 9H): LC-MS (ES$^+$): m/z 990.30 [MH$^+$] |

TABLE 7-continued

Exemplary Compounds.

| Ex # | Structure | Compound name and Analytical data |
|---|---|---|
| 113 | 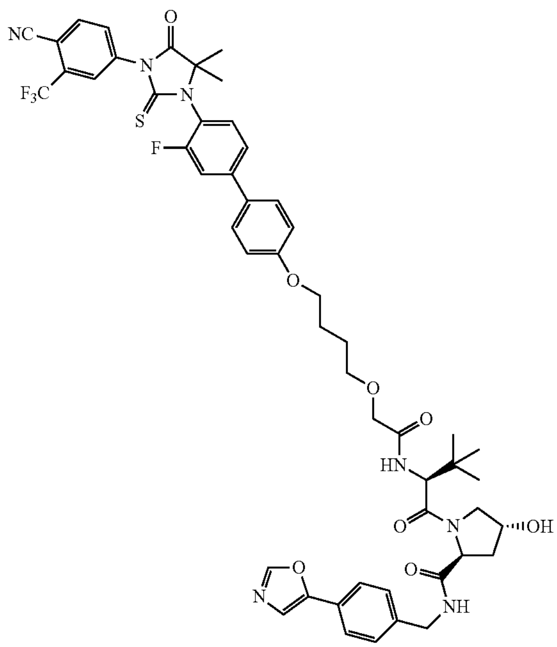 [SMILES: CC(C)(C)[C@H](NC(=O)COCCCCOc1ccc(-c2ccc(N3C(=S)N(c4ccc(C#N)c(C(F)(F)F)c4)C(=O)C3(C)C)c(F)c2)cc1)C(=O)N1C[C@H](O)C[C@H]1C(=O)NCc1ccc(-c2cnco2)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}-3-fluorophenyl)phenoxy]butoxy}acetamido)-3,3-dimethylbutanoyl]-4-hydroxy-N-{[4-(1,3-oxazol-5-yl)phenyl]methyl}pyrrolidine-2-carboxamide<br>$^1$H NMR (300 MHz, DMSO) δ 8.62-8.56 (m, 1H), 8.41 (s, 1H), 8.39 (s, 1H), 8.35 (s, 1H), 8.15 (d, J = 8.4 Hz, 1H), 7.76-7.63 (m, 7H), 7.51-7.38 (m, 4H), 7.06 (d, J = 8.7 Hz, 2H), 5.15 (d, J = 3.3 Hz, 1H), 4.58-4.26 (m, 5H), 4.09-4.05 (m, 2H), 3.96 (s, 2H), 3.66-3.56 (m, 4H), 2.12-2.04 (m, 1H), 1.93-1.73 (m, 5H), 1.60 (s, 3H), 1.50 (s, 3H), 0.95 (s, 9H); LC-MS (ES$^+$): m/z 1012.30 [MH$^+$] |
| 114 | 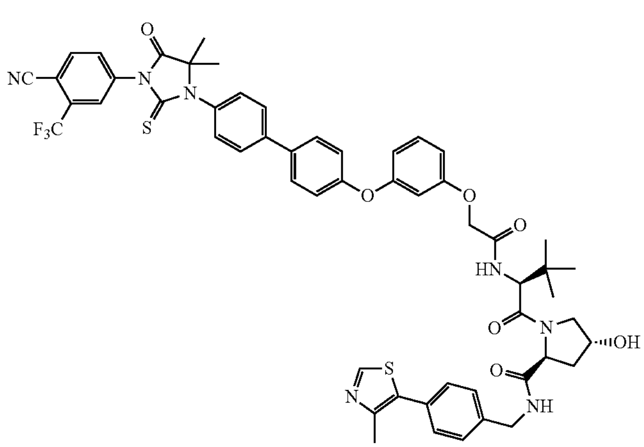 [SMILES: Cc1ncsc1-c1ccc(CNC(=O)[C@@H]2C[C@@H](O)CN2C(=O)[C@@H](NC(=O)COc2cccc(Oc3ccc(-c4ccc(N5C(=S)N(c6ccc(C#N)c(C(F)(F)F)c6)C(=O)C5(C)C)cc4)cc3)c2)C(C)(C)C)cc1] | (2S,4R)-1-[(2S)-2-(2-{3-[4-(4-{3-[4-cyano-3-(trifluoromethyl)phenyl]-5,5-dimethyl-4-oxo-2-sulfanylidene-imidazolidin-1-yl}phenyl)phenoxy]phenoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.81 (s, 1H), 8.14-8.05 (m, 2H), 8.00-7.95 (m, 1H), 7.75-7.69 (m, 2H), 7.65-7.59 (m, 2H), 7.44-7.20 (m, 7H), 7.10-7.00 (m, 2H), 6.80-6.78 (m, 1H), 6.75-6.55 (m, 2H), 4.68 (s, 1H), 4.60-4.40 (m, 5H), 4.30-4.20 (m, 1H), 3.90-3.65 (m, 2H), 2.40 (s, 3H), 2.25-2.21 (m, 1H), 2.14-2.00 (m, 1H), 1.55 (s, 6H), 0.99 (s, 9H): LC-MS (ES$^+$): m/z, 1044.30 [MH$^+$] |

TABLE 7-continued

Exemplary Compounds.

| Ex # | Structure | Compound name and Analytical data |
|---|---|---|
| 115 | 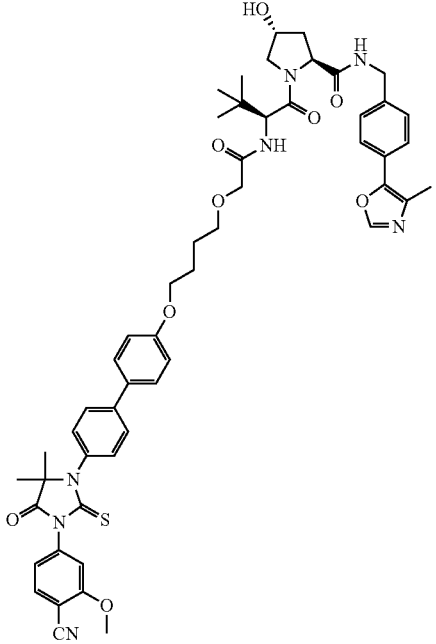 [SMILES: COc1cc(N2C(=O)C(C)(C)N(c3ccc(-c4ccc(OCCCCOCC(=O)N[C@H](C(=O)N5C[C@H](O)C[C@H]5C(=O)NCc5ccc(-c6ocnc6C)cc5)C(C)(C)C)cc4)cc3)C2=S)ccc1C#N] | (2S,4R)-1-[(2S)-2-{2-[4-(4-{4-[3-(4-cyano-3-methoxyphenyl)-5,5-dimethyl-4-oxo-2-sulfanylideneimidazolidin-1-yl]phenyl}phenoxy)butoxy]acetamido}-3,3-dimethylbutanoyl]-4-hydroxy-N-{[4-(4-methyl-1,3-oxazol-5-yl)phenyl]methyl}pyrrolidine-2-carboxamide<br>$^1$H NMR (300 MHz, CD$_3$OD): δ 8.08 (s, 1H), 7.76-7.69 (m, 3H), 7.60-7.55 (d, J = 15.9 Hz, 4H), 7.48-7.37 (m, 5H), 7.19-7.16 (d, J = 9.9 Hz, 1H), 7.02-6.99 (d, J = 8.7 Hz, 2H), 4.71 (s, 1H), 4.61-4.51 (m, 3H), 4.36-4.31 (m, 1H), 4.10-4.00 (m, 7H), 3.98-3.82 (m, 2H), 3.67-3.63 (t, J = 6.0 Hz, 2H), 2.35 (s, 3H), 2.22-2.12 (m, 1H), 2.12-2.09 (m, 1H), 1.97-1.84 (m, 4H), 1.58 (s, 6H), 1.04 (s, 9H); LC-MS (ES$^+$): m/z 971.45 [MH$^+$] |
| 116 | 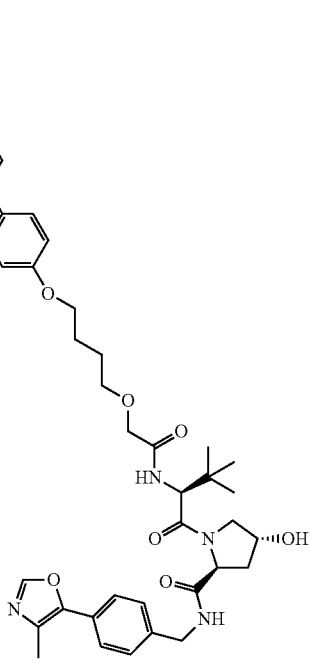 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}-3-fluorophenyl)phenoxy]butoxy}acetamido)-3,3-dimethylbutanoyl]-4-hydroxy-N-{[4-(4-methyl-1,3-oxazol-5-yl)phenyl]methyl}pyrrolidine-2-carboxamide<br>$^1$H NMR (400 MHz, DMSO) δ 8.66-8.61 (m, 1H), 8.42 (d, J = 8.0 Hz, 1H), 8.35 (s, 1H), 8.29 (s, 1H), 8.15 (d, J = 8.4 Hz, 1H), 7.76-7.64 (m, 4H), 7.53-7.40 (m, 6H), 7.05 (d, J = 8.8 Hz, 2H), 5.16 (s, 1H), 4.58-4.27 (m, 5H), 4.09-4.06 (m, 2H), 3.96 (s, 2H), 3.66-3.55 (m, 4H), 2.33 (s, 3H), 2.07-2.02 (m, 1H), 1.94-1.73 (m, 5H), 1.61 (s, 3H), 1.50 (s, 3H), 0.95 (s, 9H); LC-MS (ES$^+$): m/z 1026.30 [MH$^+$] |

TABLE 7-continued

Exemplary Compounds.

| Ex # | Structure | Compound name and Analytical data |
|---|---|---|
| 117 | 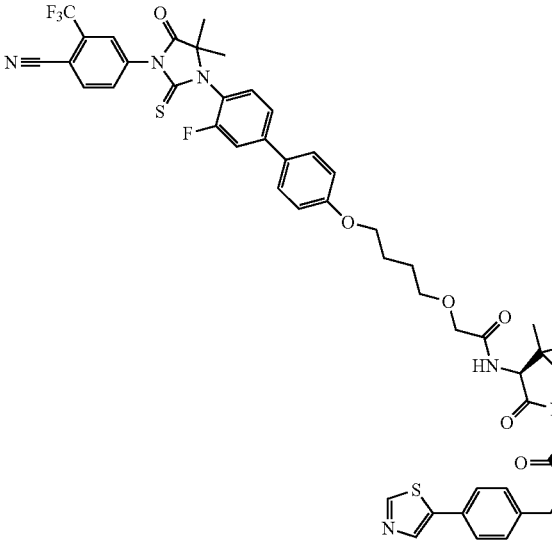 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}-3-fluorophenyl) phenoxy]butoxy}acetamido)-3,3-dimethylbutanoyl]-4-hydroxy-N-{[4-(1,3-thiazol-5-yl)phenyl] methyl}pyrrolidine-2-carboxamide <br> $^1$H NMR (400 MHz, DMSO) δ 9.04 (s, 1H), 8.60 (s, 1H), 8.42-8.35 (m, 2H), 8.27 (s, 1H), 8.14 (d, J = 8.0 Hz, 2H), 7.75-7.67 (m, 3H), 7.66 (d, J = 8.0 Hz, 1H), 7.59 (m, J = 8.4 Hz, 2H), 7.48 (t, J = 8.4 Hz, 1H), 7.41-7.36 (m, 3H), 7.05 (d, J = 8.8 Hz, 2H), 5.19 (s, 1H), 4.57 (d, J = 9.2 Hz, 1H), 4.58-4.44 (m, 1H), 4.42-4.34 (m, 2H), 4.35-4.33 (m, 1H), 4.08 (s, 2H), 3.96 (s, 2H), 3.66-3.55 (m, 4H), 2.10-2.02 (m, 1H), 1.89-1.72 (m, 5H), 1.61 (s, 3H), 1.50 (s, 3H), 0.95 (s, 9H); LC-MS (ES$^+$): m/z 1028.30 [MH$^+$], |
| 118 | 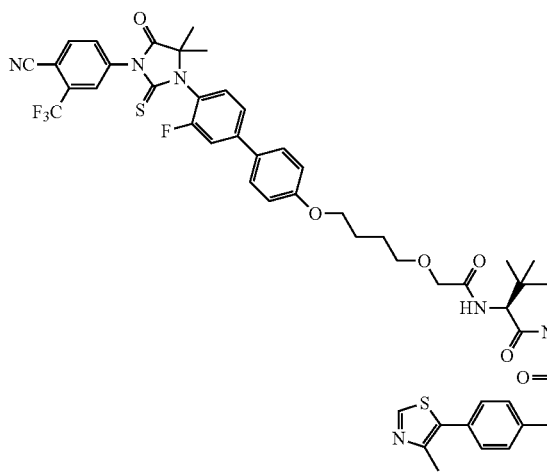 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}-3-fluorophenyl) phenoxy]butoxy}acetamido)-3,3-dimethylbutanoyl]-4-hydroxy-N-{[4-(4-methyl-1,3-thiazol-5-yl)phenyl] methyl}pyrrolidine-2-carboxamide <br> $^1$H NMR (400 MHz, DMSO) δ 8.96 (s, 1H), 8.61 (s, 1H), 8.42-8.35 (m, 2H), 8.15 (d, J = 1.6 Hz, 2H), 7.76-7.64 (m, 4H), 7.51-7.39 (m, 6H), 7.04 (d, J = 8.8 Hz, 2H), 5.17 (s, 1H), 4.57 (d, J = 9.6 Hz, 1H), 4.56-4.38 (m, 3H), 4.36-4.27 (m, 1H), 4.08 (s, 2H), 3.96 (s, 2H), 3.66-3.55 (m, 4H), 2.45 (s, 3H), 2.10-2.02 (m, 1H), 1.93-1.84 (m, 1H), 1.84-1.82 (m, 2H), 1.75-1.73 (m, 2H), 1.61 (s, 3H), 1.50 (s, 3H), 0.94 (s, 9H); LC-MS (ES$^+$): m/z 1042.25 [MH$^+$] |

TABLE 7-continued

Exemplary Compounds.

| Ex # | Structure | Compound name and Analytical data |
|---|---|---|
| 119 | 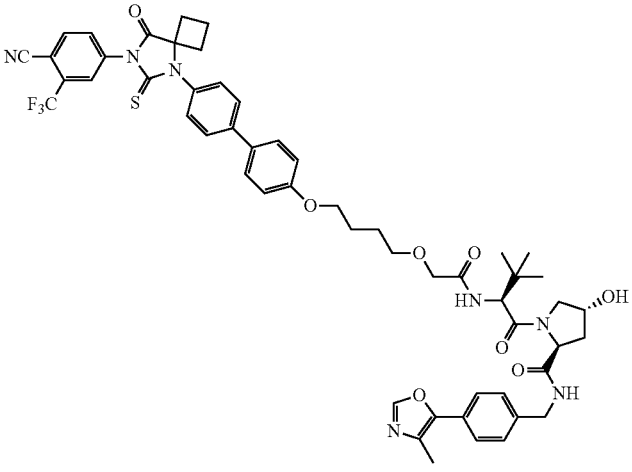 [SMILES: Cc1ncoc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C45CCC5)cc3)cc2)C(C)(C)C)cc1] | (2S,4R)-1-[(2S)-2-(2-{4-[4-(4-{7-[4-cyano-3-(trifluoromethyl)phenyl]-8-oxo-6-sulfanylidene-5,7-diazaspiro[3.4]octan-5-yl}phenyl)phenoxy]butoxy}acetamido)-3,3-dimethyl-butanoyl]-4-hydroxy-N-{[4-(4-methyl-1,3-oxazol-5-yl)phenyl]methyl}pyrrolidine-2-carboxamide<br>$^1$H NMR (300 MHz, CD$_3$OD): δ 8.17-8.15 (d, J = 8.1 Hz, 2H), 8.09 (s, 1H), 8.02-8.00 (d, J = 8.7 Hz, 1H), 7.78-7.75 (d, J = 8.4 Hz, 2H), 7.62-7.57 (m, 4H), 7.49-7.43 (m, 4H), 7.04-7.01 (d, J = 8.7 Hz, 2H), 4.71 (s, 1H), 4.62-4.53 (m, 3H), 4.37-4.32 (d, J = 15.3 Hz, 1H), 4.12-4.11 (m, 2H), 4.09-4.01 (m, 2H), 3.96-3.82 (m, 2H), 3.69-3.65 (m, 2H), 2.80-2.55 (m, 4H), 2.41 (s, 3H), 2.23-2.21 (m, 1H), 2.15-2.10 (m, 2H), 1.98-1.88 (m, 4H), 1.70-1.66 (m, 1H), 1.03 (s, 9H); LC-MS (ES$^+$): m/z 1020.35 [MH$^+$] |
| 120 | 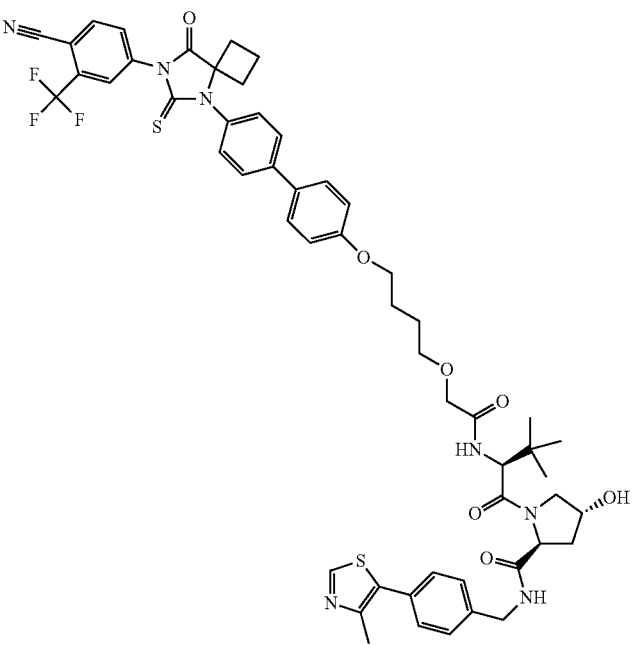 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C45CCC5)cc3)cc2)C(C)(C)C)cc1] | (2S,4R)-1-[(2S)-2-(2-{4-[4-(4-{7-[4-cyano-3-(trifluoromethyl)phenyl]-8-oxo-6-sulfanylidene-5,7-diazaspiro[3.4]octan-5-yl}phenyl)phenoxy]butoxy}acetamido)-3,3-dimethyl-butanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.82 (s, 1H), 8.17-8.15 (d, J = 7.8 Hz, 2H), 8.02-8.00 (d, J = 8.1 Hz, 1H), 7.78-7.75 (d, J = 8.4 Hz, 2H), 7.61-7.59 (d, J = 8.4 Hz, 2H), 7.48-7.42 (m, 6H), 7.04-7.01 (d, J = 8.7 Hz, 2H), 4.71 (s, 1H), 4.62-4.51 (m, 3H), 4.47-4.32 (d, J = 15.9 Hz, 1H), 4.12-4.10 (m, 2H), 4.08-4.01 (m, 2H), 3.96-3.82 (m, 2H), 3.69-3.65 (m, 2H), 2.80-2.55 (m, 4H), 2.48 (s, 3H), 2.23-2.21 (m, 1H), 2.14-2.10 (m, 1H), 1.98-1.89 (m, 4H), 1.70-1.66 (m, 1H), 1.03 (s, 9H); LC-MS (ES$^+$): m/z 1036.25 [MH$^+$] |

TABLE 7-continued

Exemplary Compounds.

| Ex # | Structure | Compound name and Analytical data |
|---|---|---|
| 121 | 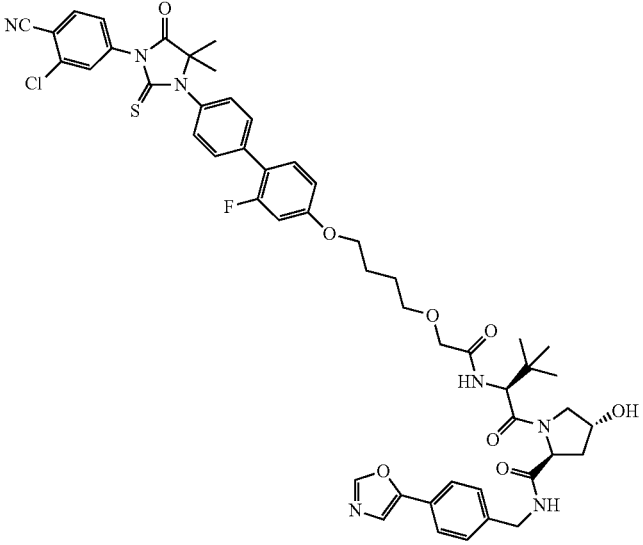 [SMILES: CC(C)(C)[C@H](NC(=O)COCCCCOc1ccc(-c2ccc(N3C(=S)N(c4ccc(C#N)c(Cl)c4)C(=O)C3(C)C)cc2)c(F)c1)C(=O)N1C[C@H](O)C[C@H]1C(=O)NCc1ccc(-c2cnco2)cc1] | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]phenyl}-3-fluorophenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD$_3$OD): δ 8.14 (s, 1H), 8.00-7.91 (m, 1H), 7.90-7.80 (m, 1H), 7.71-7.58 (m, 5H), 7.50-7.41 (m, 6H), 6.90-6.71 (m, 2H), 4.67 (s, 1H), 4.58-4.41 (m, 3H), 4.30-4.22 (m, 1H), 4.12-4.01 (m, 2H), 3.99-3.94 (m, 2H), 3.90-3.70 (m, 2H), 3.65-3.55 (m, 2H), 2.22-2.13 (m, 1H), 2.14-2.00 (m, 1H), 2.00-1.72 (m, 4H), 1.56 (s, 6H), 1.01 (s, 9H); LC-MS (ES$^+$): m/z, 978.30 [MH$^+$] |
| 122 | 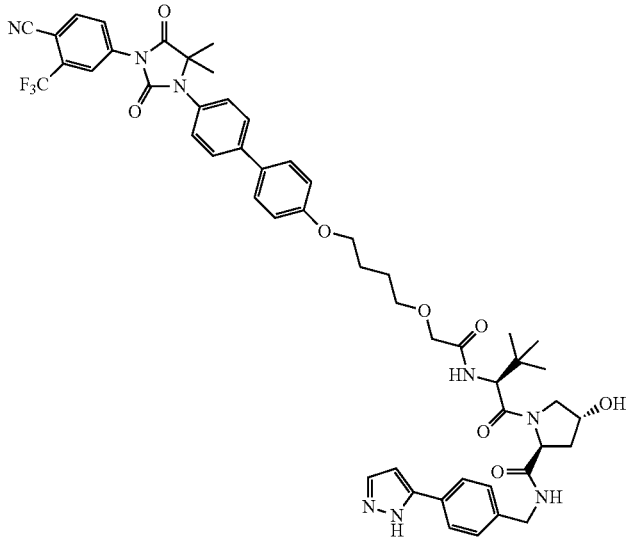 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]butoxy}acetamido)-3,3-dimethyl-butanoyl]-4-hydroxy-N-{[4-(1H-pyrazol-5-yl)phenyl]methyl}pyrrolidine-2-carboxamide<br>$^1$H NMR (400 MHz, CD$_3$OD): δ 8.25-8.15 (m, 2H), 8.05-8.00 (s, 1H), 7.78-7.70 (m, 4H), 7.70-7.58 (m, 3H), 7.48-7.39 (m, 4H), 7.08-7.00 (m, 2H), 6.69-6.60, (s, 1H), 4.95-4.85 (s, 1H), 4.65-4.58 (s, 1H), 4.55-4.49 (m, 2H), 4.40-4.30 (s, 1H), 4.15-4.08 (m, 2H), 4.05-4.00 (m, 2H), 3.90-3.85 (s, 1H), 3.82-3.75 (s, 1H), 3.70-3.60 (m, 2H), 2.28-2.20 (s, 1H), 2.15-2.05 (s, 1H), 1.98-1.89 (m, 4H), 1.63-1.59 (m, 6H) 1.10-1.00 (m, 9H); LC-MS (ES$^+$): m/z 993.35 [MH$^+$] |

TABLE 7-continued

Exemplary Compounds.

| Ex # | Structure | Compound name and Analytical data |
|---|---|---|
| 123 | 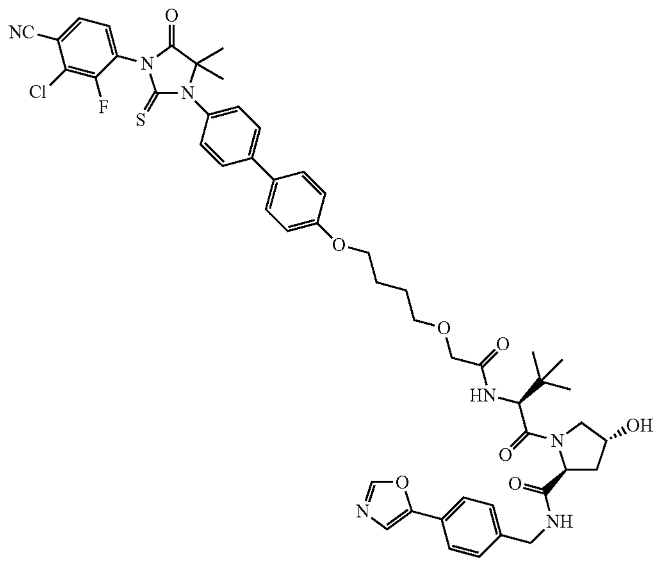 [SMILES: CC(C)(C)[C@H](NC(=O)COCCCCOc1ccc(-c2ccc(N3C(=S)N(c4ccc(C#N)c(Cl)c4F)C(=O)C3(C)C)cc2)cc1)C(=O)N1C[C@H](O)C[C@H]1C(=O)NCc1ccc(-c2cnco2)cc1] | (2S,4R)-1-[(2S)-2-{2-[4-(4-{4-[3-(3-chloro-4-cyano-2-fluorophenyl)-5,5-dimethyl-4-oxo-2-sulfanylidene-imidazolidin-1-yl]phenyl}phenoxy)butoxy]acetamido}-3,3-dimethyl-butanoyl]-4-hydroxy-N-{[4-(1,3-oxazol-5-yl)phenyl]methyl}pyrrolidine-2-carboxamide<br>$^1$H NMR (400 MHz, CD$_3$OD) δ 8.21 (s, 1H), 7.88-7.87 (d, J = 1.6 Hz, 1H), 7.86-7.73 (m, 3H), 7.69-7.67 (d, J = 8.4 Hz, 2H), 7.61-7.59 (d, J = 8.4 Hz, 2H), 7.48-7.43 (m, 5H), 7.05-7.02 (d, J = 8.8 Hz, 2H), 4.88 (s, 1H), 4.73-4.59 (m, 3H), 4.52-4.37 (d, J = 15.2 Hz, 1H), 4.08-4.02 (m, 2H), 3.98-3.82 (m, 2H), 3.89-3.88 (m, 1H), 3.84-3.83 (m, 1H), 3.69-3.66 (t, J = 6.0 Hz, 2H), 2.23-2.20 (m, 1H), 2.13-2.04 (m, 1H), 1.97-1.88 (m, 4H), 1.62 (s, 6H), 1.04 (s, 9H); LC-MS (ES$^+$): m/z 978.26 [MH$^+$] |
| 124 | 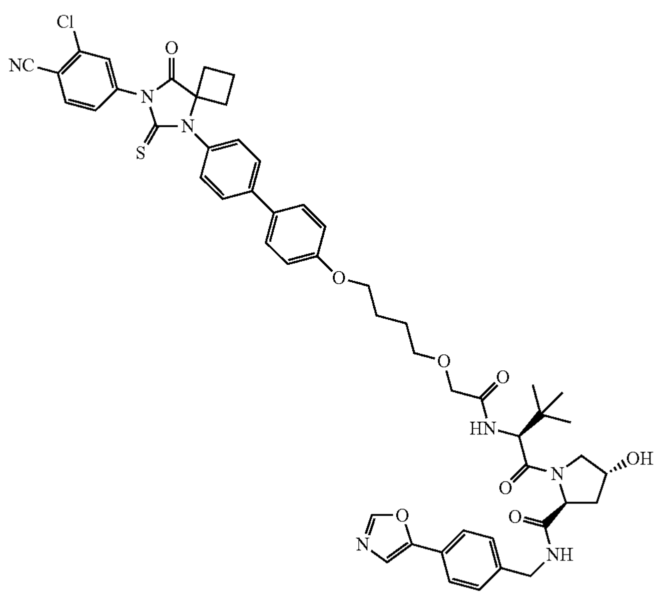 [SMILES: CC(C)(C)[C@H](NC(=O)COCCCCOc1ccc(-c2ccc(N3C(=S)N(c4ccc(C#N)c(Cl)c4)C(=O)C34CCC4)cc2)cc1)C(=O)N1C[C@H](O)C[C@H]1C(=O)NCc1ccc(-c2cnco2)cc1] | (2S,4R)-1-[(2S)-2-{2-[4-(4-{4-[7-(3-chloro-4-cyanophenyl)-8-oxo-6-sulfanylidene-5,7-diazaspiro[3.4]octan-5-yl]phenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, CD$_3$OD) δ 8.18 (s, 1H), 7.99-7.96 (d, J = 8.4 Hz, 1H), 7.89 (s, 1H), 7.79-7.77 (d, J = 8.4 Hz, 2H), 7.67-7.61 (m, 5H), 7.48-7.43 (m, 5H), 7.06-7.04 (d, J = 8.8 Hz, 2H), 4.88 (s, 1H), 4.73-4.59 (m, 3H), 4.52-4.37 (d, J = 15.2 Hz, 1H), 4.14-4.11 (m, 2H), 4.05-4.02 (m, 2H), 3.99-3.83 (m, 2H), 3.70-3.67 (t, J = 6.0 Hz, 2H), 2.66-2.62 (m, 4H), 2.13-2.00 (m, 3H), 1.98-1.88 (m, 4H), 1.80-1.70 (m, 1H), 1.04 (s, 9H); LC-MS (ES$^+$): m/z 972.25 [MH$^+$] |

TABLE 7-continued

Exemplary Compounds.

| Ex # | Structure | Compound name and Analytical data |
|---|---|---|
| 125 | 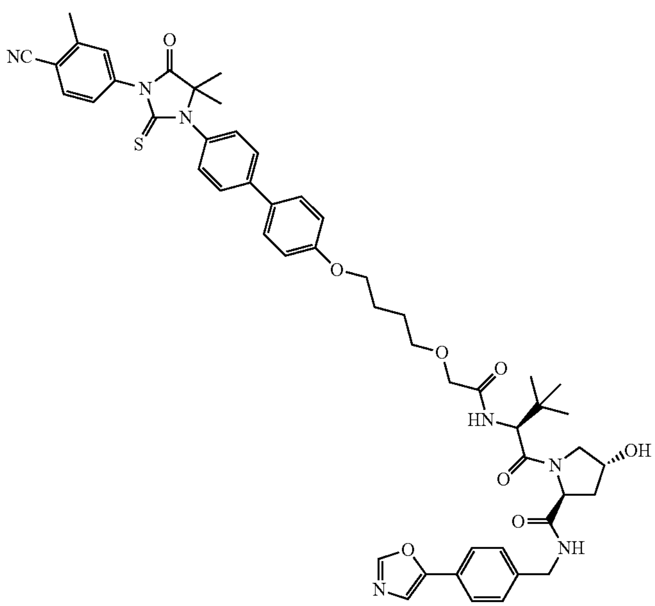 [SMILES: Cc1cc(N2C(=O)C(C)(C)N(c3ccc(-c4ccc(OCCCCOCC(=O)N[C@H](C(=O)N5C[C@H](O)C[C@H]5C(=O)NCc5ccc(-c6cnco6)cc5)C(C)(C)C)cc4)cc3)C2=S)ccc1C#N] | (2S,4R)-1-[(2S)-2-{2-[4-(4-{4-[3-(4-cyano-3-methylphenyl)-5,5-dimethyl-4-oxo-2-sulfanylideneimidazolidin-1-yl]phenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, DMSO) δ 8.60 (t, J = 6.0 Hz, 1H), 8.40 (s, 1H), 7.97 (d, J = 8.0 Hz, 1H), 7.79 (d, J = 8.4 Hz, 2H), 7.67-7.63 (m, 6H), 7.54 (d, J = 8.4 Hz, 1H), 7.44-7.39 (m, 5H), 7.05 (d, J = 8.8 Hz, 2H), 5.16 (s, 1H), 4.58-4.56 (m, 1H), 4.47-4.26 (m, 4H), 4.08-4.05 (m, 2H), 3.97 (s, 2H), 3.66-3.57 (m, 4H), 2.56 (s, 3H), 2.06-2.02 (m, 1H), 1.93-1.72 (m, 5H), 1.52 (s, 6H), 0.93 (s, 9H); LC-MS (ES$^+$): m/z 940.30 [MH$^+$] |
| 126 | 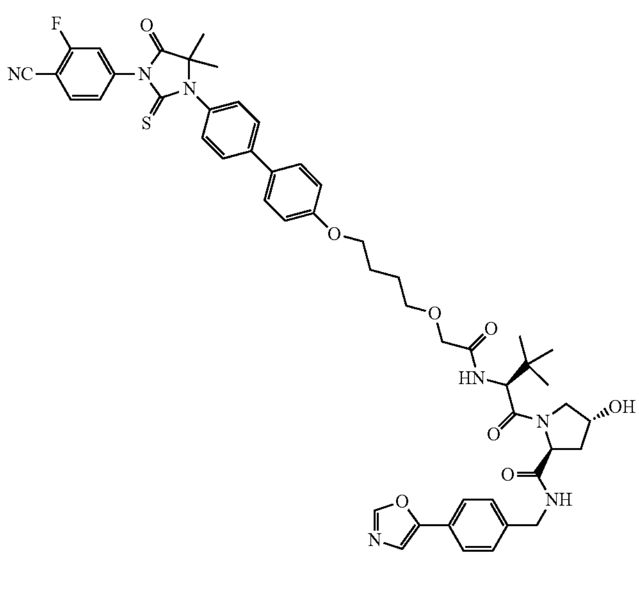 [SMILES: CC(C)(C)[C@H](NC(=O)COCCCCOc1ccc(-c2ccc(N3C(=S)N(c4ccc(C#N)c(F)c4)C(=O)C3(C)C)cc2)cc1)C(=O)N1C[C@H](O)C[C@H]1C(=O)NCc1ccc(-c2cnco2)cc1] | (2S,4R)-1-[(2S)-2-{2-[4-(4-{4-[3-(4-cyano-3-fluorophenyl)-5,5-dimethyl-4-oxo-2-sulfanylideneimidazolidin-1-yl]phenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (400 MHz, DMSO) δ 8.60 (t, J = 6.0 Hz, 1H), 8.40 (s, 1H), 8.15 (d, J = 8.0 Hz, 1H), 7.85-7.78 (m, 3H), 7.67-7.63 (m, 6H), 7.43-7.39 (m, 5H), 7.05 (d, J = 8.8 Hz, 2H), 5.16 (s, 1H), 4.58-4.56 (m, 1H), 4.47-4.26 (m, 4H), 4.08-4.05 (m, 2H), 3.97 (s, 2H), 3.66-3.55 (m, 4H), 2.06-2.02 (m, 1H), 1.93-1.72 (m, 5H), 1.53 (s, 6H), 0.95 (s, 9H); LC-MS (ES$^+$): m/z 944.50 [MH$^+$] |

TABLE 7-continued

Exemplary Compounds.

| Ex # | Structure | Compound name and Analytical data |
|---|---|---|
| 127 | 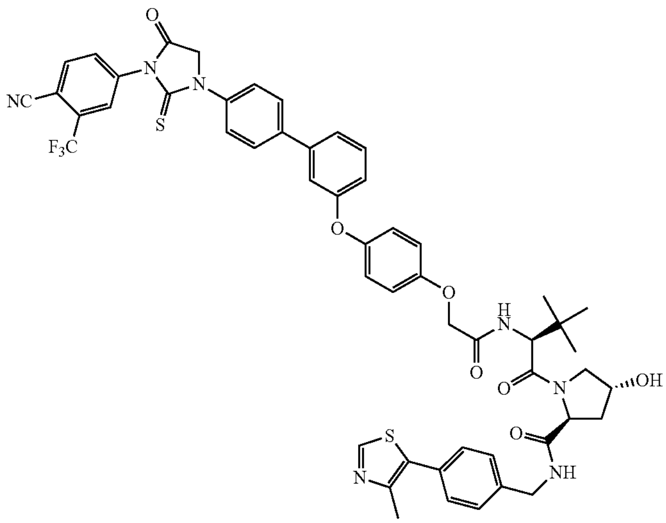 | (2S,4R)-1-[(2S)-2-(2-{4-[3-(4-{3-[4-cyano-3-(trifluoromethyl)phenyl]-5,5-dimethyl-4-oxo-2-sulfanylidene-imidazolidin-1-yl}phenyl)phenoxy]phenoxy}acetamido)-3,3-dimethyl-butanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.81 (s, 1H), 8.14-8.05 (m, 2H), 8.00-7.95 (m, 1H), 7.75-7.69 (m, 2H), 7.55-7.32 (m, 8H), 7.20-7.15 (m, 1H), 7.10-7.00 (m, 4H), 6.99-6.85 (m, 1H), 4.68 (s, 1H), 4.65-4.60 (m, 2H), 4.63-4.55 (m, 1H), 4.50-4.40 (m, 2H), 4.30-4.20 (m, 1H), 3.90-3.80 (m, 1H), 3.75-3.65 (m, 1H), 2.40 (s, 3H), 2.25-2.21 (m, 1H), 2.14-2.00 (m, 1H), 1.55 (s, 6H), 0.99 (s, 9H); LC-MS (ES$^+$): m/z, 1044.30 [MH$^+$] |
| 128 | 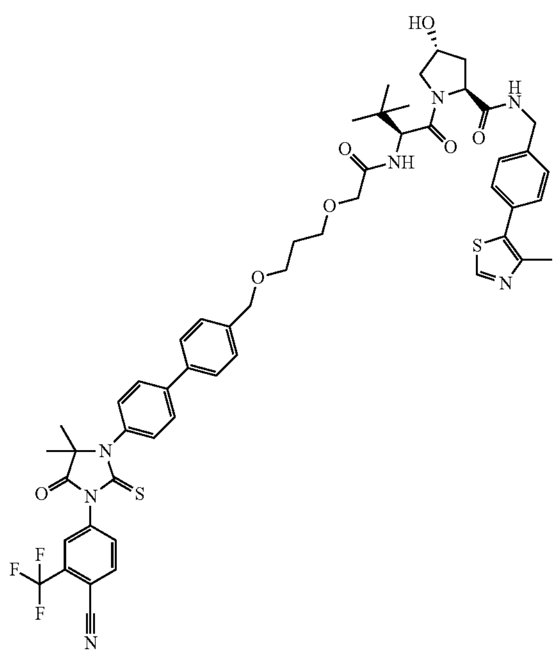 [SMILES: Cc1ncsc1-c1ccc(CNC(=O)[C@@H]2C[C@@H](O)CN2C(=O)[C@@H](NC(=O)COCCCOCc2ccc(-c3ccc(N4C(=S)N(c5ccc(C#N)c(C(F)(F)F)c5)C(=O)C4(C)C)cc3)cc2)C(C)(C)C)cc1] | (2S,4R)-1-[(2S)-2-[2-(3-{[4-(4-{3-[4-cyano-3-(trifluoromethyl)phenyl]-5,5-dimethyl-4-oxo-2-sulfanylidene-imidazolidin-1-yl}phenyl)phenyl]methoxy}propoxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.85 (s, 1H), 8.20 (m, 2H), 8.02 (d, J = 8.4 Hz, 1H), 7.80 (d, J = 7.6 Hz, 2H), 7.66 (d, J = 8.0 Hz, 2H), 7.48 (m, 6H), 7.39 (m, 2H), 4.71 (s, 1H), 4.61 (m, 5H), 4.34 (m, 1H), 4.01 (m, 2H), 3.84 (m, 2H), 3.72 (m, 4H), 2.45 (s, 3H), 2.25 (m, 1H), 2.12 (m, 1H), 1.97 (m, 2H), 1.62 (s, 6H), 1.02 (s, 9H); LC-MS (ES$^+$): m/z 1024.20 [MH$^+$] |

TABLE 7-continued

Exemplary Compounds.

| Ex # | Structure | Compound name and Analytical data |
|---|---|---|
| 129 | 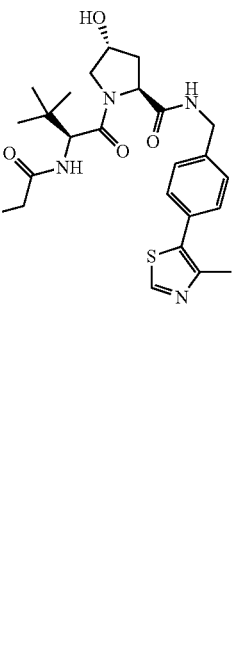 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)phenoxy]-3-hydroxybutoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.82 (s, 1H), 8.20 (m, 2H), 8.03 (m, 1H), 7.74 (m, 2H), 7.60 (m, 2H), 7.48 (m, 6H), 7.07 (m, 2H), 4.74 (m, 1H), 4.60-4.53 (m, 3H), 4.37 (m, 1H), 4.21 (m, 1H), 4.08 (m, 4H), 3.92-3.88 (m, 1H), 3.83-3.75 (m, 3H), 2.49 (s, 3H), 2.26 (m, 1H), 2.14 (m, 2H), 1.87 (m, 1H), 1.62 (s, 6H), 1.03 (s, 9H); LC-MS (ES$^+$): m/z 1040.25 [MH$^+$] |
| 130 | 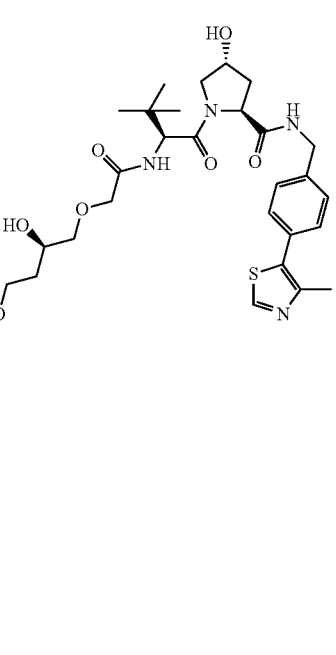 | (2S,4R)-1-[(2S)-2-{2-[(2R)-4-[4-(4-{3-[4-cyano-3-(trifluoromethyl)phenyl]-5,5-dimethyl-4-oxo-2-sulfanylideneimidazolidin-1-yl}phenyl)phenoxy]-2-hydroxybutoxy]acetamido}-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.81 (s, 1H), 8.18 (d, J = 8.4 Hz, 2H), 8.04 (d, J = 8.4 Hz, 1H), 7.71 (s, J = 8.4 Hz, 2H), 7.57 (d, J = 8.8 Hz, 2H), 7.44 (m, 6H), 7.02 (d, J = 8.8 Hz, 2H), 4.71 (s, 1H), 4.56 (m, 3H), 4.33 (m, 1H), 4.17 (m, 2H), 4.05 (m, 3H), 3.75 (m, 2H), 3.65 (m, 2H), 2.44 (s, 3H), 2.22 (m, 1H), 2.08 (m, 2H), 1.90 (m, 1H), 1.60 (s, 6H), 1.05 (s, 9H); LC-MS (ES$^+$): m/z 1040.20 [MH$^+$] |

TABLE 7-continued

Exemplary Compounds.

| Ex # | Structure | Compound name and Analytical data |
|---|---|---|
| 131 | 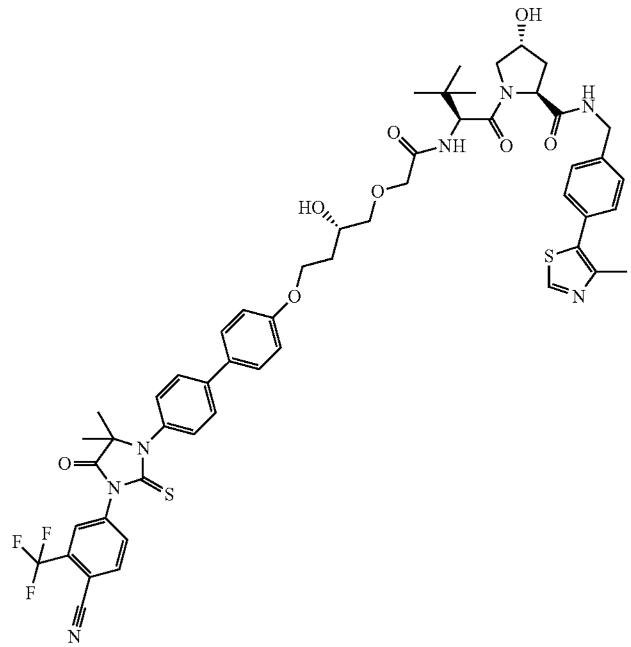 [SMILES: Cc1ncsc1-c1ccc(CNC(=O)[C@@H]2C[C@@H](O)CN2C(=O)[C@@H](NC(=O)COC[C@@H](O)CCOc2ccc(-c3ccc(N4C(=S)N(c5ccc(C#N)c(C(F)(F)F)c5)C(=O)C4(C)C)cc3)cc2)C(C)(C)C)cc1] | (2S,4R)-1-[(2S)-2-{2-[(2S)-4-[4-(4-{3-[4-cyano-3-(trifluoromethyl)phenyl]-5,5-dimethyl-4-oxo-2-sulfanylideneimidazolidin-1-yl}phenyl)phenoxy]-2-hydroxy-butoxy]acetamido}-3,3-dimethyl-butanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.84 (s, 1H), 8.18 (d, J = 8.4 Hz, 2H), 8.04 (d, J = 8.4 Hz, 1H), 7.71 (s, J = 8.4 Hz, 2H), 7.57 (d, J = 8.8 Hz, 2H), 7.44 (m, 6H), 7.02 (d, J = 8.8 Hz, 2H), 4.71 (s, 1H), 4.56 (m, 3H), 4.33 (m, 1H), 4.17 (m, 2H), 4.05 (m, 3H), 3.90 (m, 1H), 3.83 (m, 1H), 3.60 (m, 2H), 2.44 (s, 3H), 2.22 (m, 1H), 2.08 (m, 2H), 1.90 (m, 1H), 1.60 (s, 6H), 1.05 (s, 9H); LC-MS (ES$^+$): m/z 1040.20 [MH$^+$], |
| 132 | 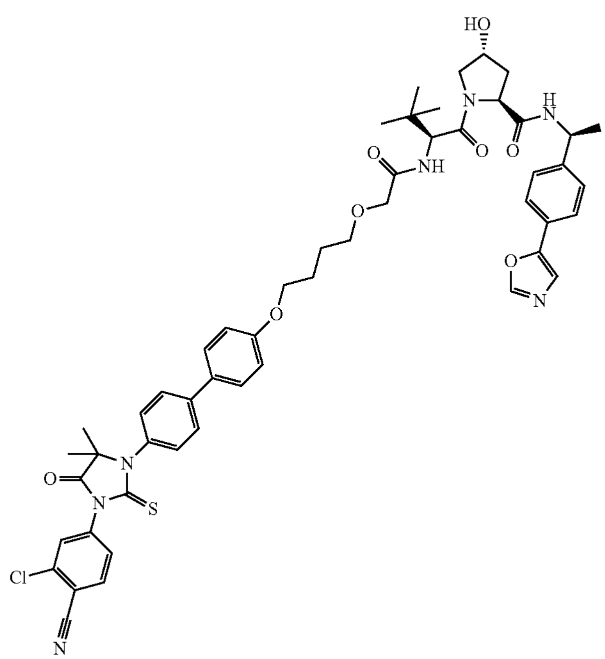 [SMILES: C[C@H](NC(=O)[C@@H]1C[C@@H](O)CN1C(=O)[C@@H](NC(=O)COCCCCOc1ccc(-c2ccc(N3C(=S)N(c4ccc(C#N)c(Cl)c4)C(=O)C3(C)C)cc2)cc1)C(C)(C)C)c1ccc(-c2cnco2)cc1] | (2S,4R)-1-[(2S)-2-{2-[4-(4-{4-[3-(3-chloro-4-cyanophenyl)-5,5-dimethyl-4-oxo-2-sulfanylidene-imidazolidin-1-yl]phenyl}phenoxy)butoxy]acetamido}-3,3-dimethyl-butanoyl]-4-hydroxy-N-[(1S)-1-[4-(1,3-oxazol-5-yl)phenyl]ethyl]pyrrolidine-2-carboxamide<br>$^1$H NMR (300 MHz, CD$_3$OD): δ 8.22 (s, 1H), 7.97-7.95 (d, J = 8.4 Hz, 1H), 7.89-7.88 (d, J = 1.8 Hz, 1H), 7.75-7.58 (m, 7H), 7.47 (s, 1H), 7.43-7.38 (m, 4H), 7.06-7.01 (d, J = 14.1 Hz, 2H), 5.00 (m, 1H), 4.69 (s, 1H), 4.61-4.55 (m, 1H), 4.44 (s, 1H), 4.13-4.09 (t, J = 6.0 Hz, 2H), 4.02-4.00 (d, J = 6.0 Hz, 2H), 3.87-3.76 (m, 2H), 3.68-3.64 (m, 2H), 2.19-2.16 (m, 1H), 2.03-1.84 (m, 5H), 1.58 (s, 6H), 1.49-1.47 (d, J = 6.9 Hz, 3H) 1.04 (s, 9H); LC-MS (ES$^+$): m/z 974.20, 976.20, [MH$^+$] |

TABLE 7-continued

Exemplary Compounds.

| Ex # | Structure | Compound name and Analytical data |
|---|---|---|
| 133 | 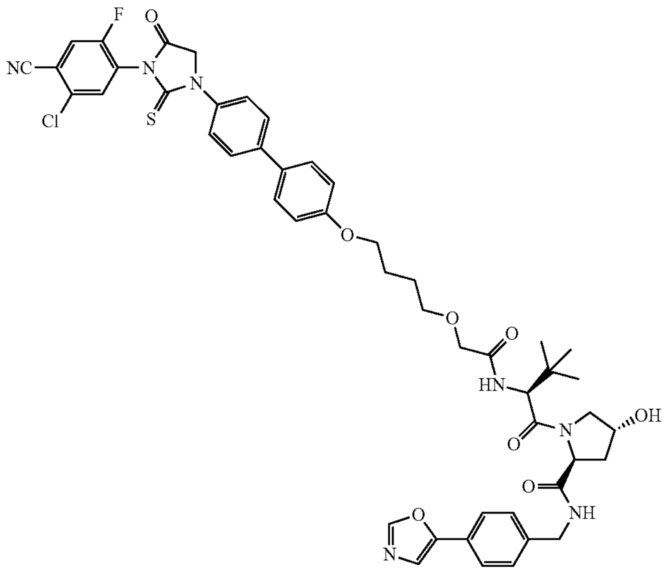 | (2S,4R)-1-[(2S)-2-{2-[4-(4-{4-[3-(5-chloro-4-cyano-2-fluorophenyl)-5,5-dimethyl-4-oxo-2-sulfanylidene-imidazolidin-1-yl]phenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD$_3$OD) δ 8.23 (s, 1H), 8.18-7.94 (m, 2H), 7.74-7.65 (m, 6H), 7.50-7.40 (m, 5H), 7.04-7.01 (d, J = 8.7 Hz, 2H), 4.71 (s, 1H), 4.60-4.56 (m, 3H), 4.53-4.34 (d, J = 15.2 Hz, 1H), 4.12-4.08 (m, 2H), 4.08-4.01 (m, 2H), 3.96-3.82 (m, 2H), 3.69-3.65 (m, 2H), 2.23-2.20 (m, 1H), 2.13-2.04 (m, 1H), 1.98-1.85 (m, 4H), 1.59 (s, 6H), 1.05 (s, 9H); LC-MS (ES$^+$): m/z 978.26 [MH$^+$] |
| 134 | 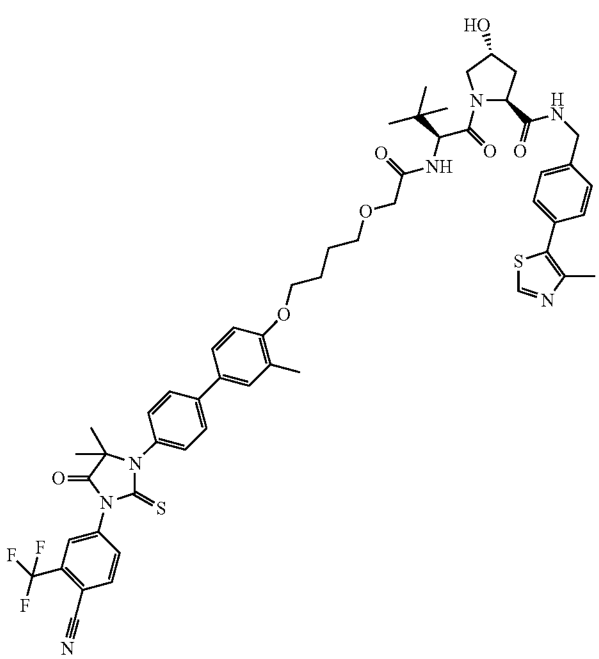 [SMILES: Cc1cc(-c2ccc(N3C(=S)N(c4ccc(C#N)c(C(F)(F)F)c4)C(=O)C3(C)C)cc2)ccc1OCCCCOCC(=O)N[C@H](C(=O)N1C[C@H](O)C[C@H]1C(=O)NCc1ccc(-c2scnc2C)cc1)C(C)(C)C] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)-2-methylphenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, DMSO): δ 8.96 (s, 1H), 8.61 (m, 1H), 8.42 (d, J = 7.6 Hz, 1H), 8.33 (s, 1H), 8.13 (d, J = 8.4 Hz, 1H), 7.50 (d, J = 8.0 Hz, 2H), 7.43 (d, J = 10.4 Hz, 7H), 7.19 (d, J = 8.0 Hz, 1H), 6.83-6.89 (m, 2H), 5.17 (m, 1H), 4.59 (d, J = 9.6 Hz, 1H), 4.40-4.48 (m, 1H), 4.37-4.38 (m, 2H), 4.25-4.29 (m, 1H), 4.02-4.05 (m, 2H), 3.97 (s, 2H), 3.55-3.69 (m, 4H), 2.45 (s, 3H), 2.25 (s, 3H), 2.05-2.10 (m, 1H), 1.91-1.93 (m, 1H), 1.81-1.84 (m, 2H), 1.72-1.75 (m, 2H), 1.55 (s, 6H), 0.95 (s, 9H); LC-MS (ES$^+$): m/z 1038.35 [MH$^+$] |

TABLE 7-continued

Exemplary Compounds.

| Ex # | Structure | Compound name and Analytical data |
|---|---|---|
| 135 | 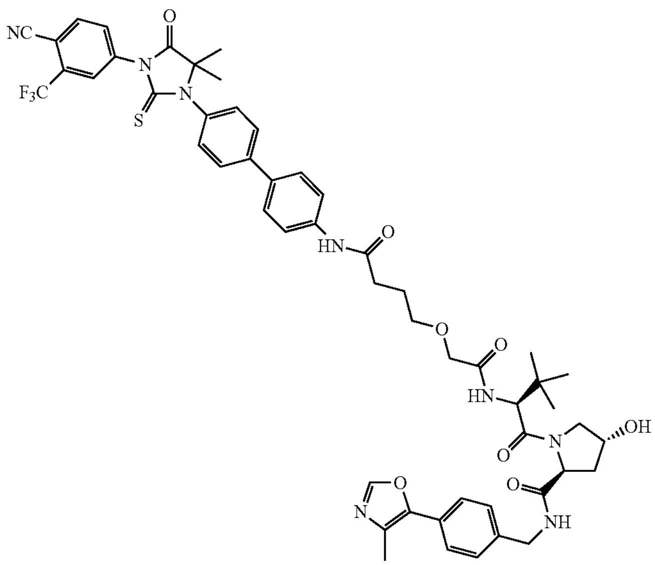 [SMILES: Cc1ncoc1-c1ccc(CNC(=O)[C@@H]2C[C@@H](O)CN2C(=O)[C@@H](NC(=O)COCCCC(=O)Nc2ccc(-c3ccc(N4C(=S)N(c5ccc(C#N)c(C(F)(F)F)c5)C(=O)C4(C)C)cc3)cc2)C(C)(C)C)cc1] | (2S,4R)-1-[(2S)-2-[2-(3-{[4-(4-{3-[4-cyano-3-(trifluoromethyl)phenyl]-5,5-dimethyl-4-oxo-2-sulfanylideneimidazolidin-1-yl}phenyl)phenyl]carbamoyl}propoxy)acetamido]-3,3-dimethylbutanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD) δ 8.19-8.16 (d, J = 12.4 Hz, 2H), 8.13 (s, 1H), 8.04-8.01 (d, J = 10.8 Hz, 1H), 7.78-7.75 (d, J = 11.2 Hz, 2H), 7.75-7.60 (m, 6H), 7.57-7.44 (m, 4H), 4.87 (s, 1H), 4.73-4.57 (m, 3H), 4.52-4.37 (d, J = 15.2 Hz, 1H), 4.10-4.05 (m, 2H), 3.96-3.83 (m, 2H), 3.70-3.66 (m, 2H), 2.59-2.54 (t, J = 9.6 Hz, 2H), 2.36 (s, 3H), 2.24-2.22 (m, 1H), 2.17-2.04 (m, 3H), 1.05 (s, 6H), 1.03 (s, 9H); LC-MS (ES$^+$): m/z 1021.25 [MH$^+$] |
| 136 | 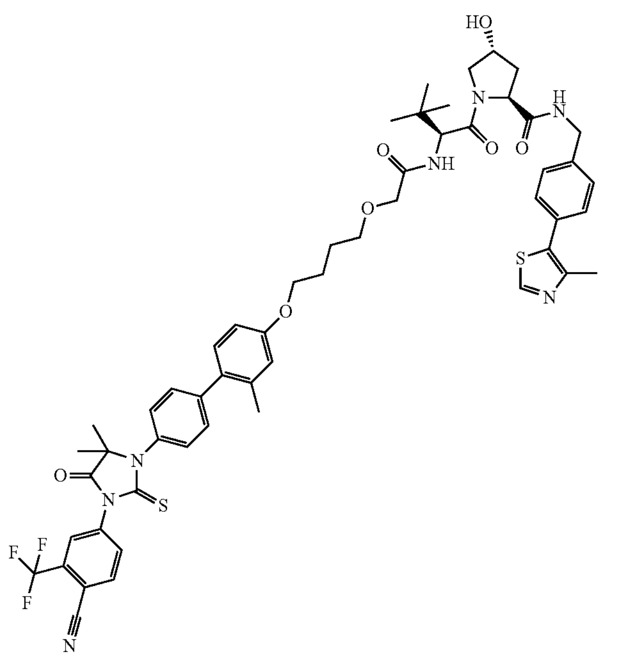 [SMILES: Cc1cc(OCCCCOCC(=O)N[C@H](C(=O)N2C[C@H](O)C[C@H]2C(=O)NCc2ccc(-c3scnc3C)cc2)C(C)(C)C)ccc1-c1ccc(N2C(=S)N(c3ccc(C#N)c(C(F)(F)F)c3)C(=O)C2(C)C)cc1] | (2S,4R)-1-[(2S)-2-(2-{4-[4-(4-{3-[4-cyano-3-(trifluoromethyl)phenyl]-5,5-dimethyl-4-oxo-2-sulfanylideneimidazolidin-1-yl}phenyl)-3-methylphenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 8.80 (s, 1H), 8.15-8.18 (m, 2H), 7.99-8.02 (m, 1H), 7.72 (d, J = 8.4 Hz, 2H), 7.38-7.47 (m, 8H), 6.98 (d, J = 8.8 Hz, 1H), 4.70 (s, 1H), 4.50-4.60 (m, 3H), 4.31-4.34 (m, 1H), 3.96-4.11 (m, 4H), 3.81-3.87 (m, 2H), 3.65-3.68 (m, 2H), 2.43 (s, 3H), 2.26 (m, 4H), 2.09 (m, 1H), 1.87-1.98 (m, 4H), 1.59 (s, 6H), 1.04 (s, 9H); LC-MS (ES$^+$): m/z 1038.40 [MH$^+$] |

TABLE 7-continued

Exemplary Compounds.

| Ex # | Structure | Compound name and Analytical data |
|---|---|---|
| 137 | 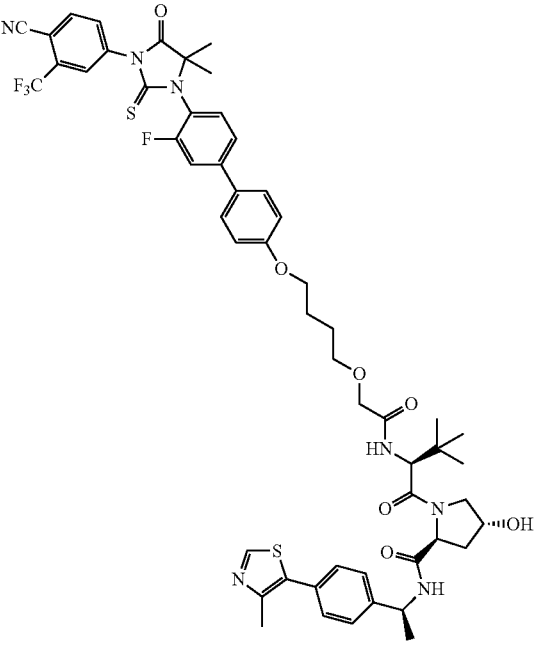 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)c(F)c3)cc2)C(C)(C)C)cc1] | (2S,4R)-1-[(2S)-2-(2-{4-[4-(4-{3-[4-cyano-3-(trifluoromethyl)phenyl]-5,5-dimethyl-4-oxo-2-sulfanylideneimidazolidin-1-yl}-3-fluorophenyl)phenoxy]butoxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, DMSO) δ 8.99 (s, 1H), 8.46-8.40 (m, 2H), 8.36 (s, 1H), 8.15 (d, J = 8.0 Hz, 1H), 7.78-7.67 (m, 4H), 7.45-7.35 (m, 6H), 7.09 (d, J = 8.8 Hz, 2H), 5.15 (s, 1H), 4.93-4.89 (m, 1H), 4.57 (d, J = 9.6 Hz, 1H), 4.46-4.39 (m, 1H), 4.30 (s, 1H), 4.11-4.08 (m, 2H), 3.96 (s, 2H), 3.60-3.56 (m, 4H), 2.46 (s, 3H), 2.07-2.03 (m, 1H), 1.84-1.74 (m, 5H), 1.62 (s, 3H), 1.50 (s, 3H), 1.38 (d, J = 6.8 Hz, 3H), 0.95 (s, 9H); LC-MS (ES$^+$): m/z 1056.30 [MH$^+$] |
| 138 | 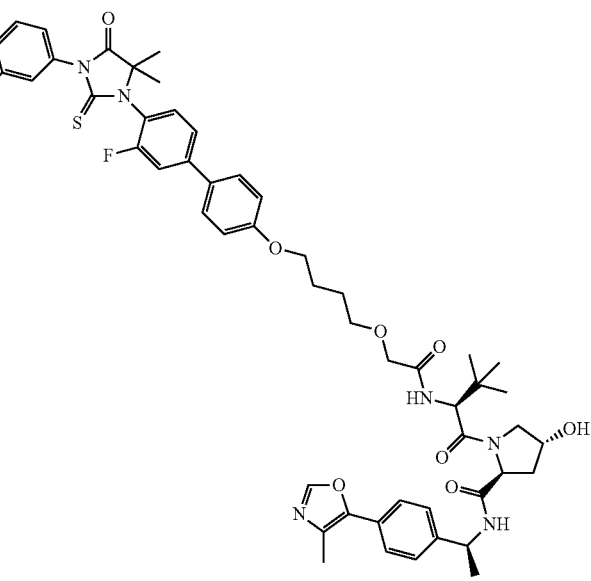 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}-3-fluorophenyl)phenoxy]butoxy}acetamido)-3,3-dimethylbutanoyl]-4-hydroxy-N-[(1S)-1-[4-(4-methyl-1,3-oxazol-5-yl)phenyl]ethyl]pyrrolidine-2-carboxamide<br>$^1$H NMR (400 MHz, DMSO) δ 8.46-8.40 (m, 2H), 8.36 (s, 1H), 8.31 (s, 1H), 8.15 (d, J = 8.4 Hz, 1H), 7.78-7.67 (m, 4H), 7.57-7.48 (m, 3H), 7.40-7.35 (m, 3H), 7.09 (d, J = 8.4 Hz, 2H), 5.15 (s, 1H), 4.93-4.89 (m, 1H), 4.57 (d, J = 9.2 Hz, 1H), 4.46-4.40 (m, 1H), 4.28 (s, 1H), 4.11-4.07 (m, 2H), 3.96 (s, 2H), 3.59-3.56 (m, 4H), 2.35 (s, 3H), 2.07-2.03 (m, 1H), 1.84-1.73 (m, 5H), 1.62 (s, 3H), 1.51 (s, 3H), 1.39 (d, J = 6.4 Hz, 3H), 0.95 (s, 9H); LC-MS (ES$^+$): m/z 1040.25 [MH$^+$] |

TABLE 7-continued

Exemplary Compounds.

| Ex # | Structure | Compound name and Analytical data |
|---|---|---|
| 139 | 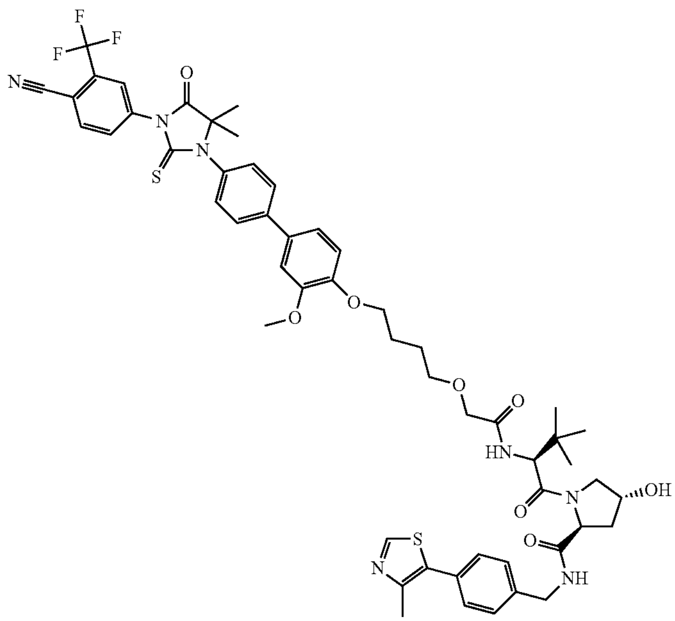 [SMILES: COc1cc(-c2ccc(N3C(=S)N(c4ccc(C#N)c(C(F)(F)F)c4)C(=O)C3(C)C)cc2)ccc1OCCCCOCC(=O)N[C@H](C(=O)N1C[C@H](O)C[C@H]1C(=O)NCc1ccc(-c2scnc2C)cc1)C(C)(C)C] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)-2-methoxyphenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, DMSO) δ 8.96 (s, 1H), 8.61 (s, 1H), 8.41 (d, J = 8.4 Hz, 1H), 8.33 (s, 1H), 8.11 (d, J = 8.0 Hz, 1H), 7.83 (d, J = 8.4 Hz, 2H), 7.45-7.40 (m, 7H), 7.30-7.23 (m, 2H), 7.06 (d, J = 8.4 Hz, 1H), 5.17 (s, 1H), 4.57 (d, J = 9.2 Hz, 1H), 4.46-4.36 (m, 3H), 4.30-4.28 (m, 1H), 4.06-4.03 (m, 2H), 3.96 (s, 2H), 3.86 (s, 3H), 3.67-3.56 (m, 4H), 2.44 (s, 3H), 2.08 (s, 1H), 1.85-1.75 (m, 5H), 1.55 (s, 6H), 0.95 (s, 9H); LC-MS (ES$^+$): m/z 1054.25 [MH$^+$] |
| 140 | 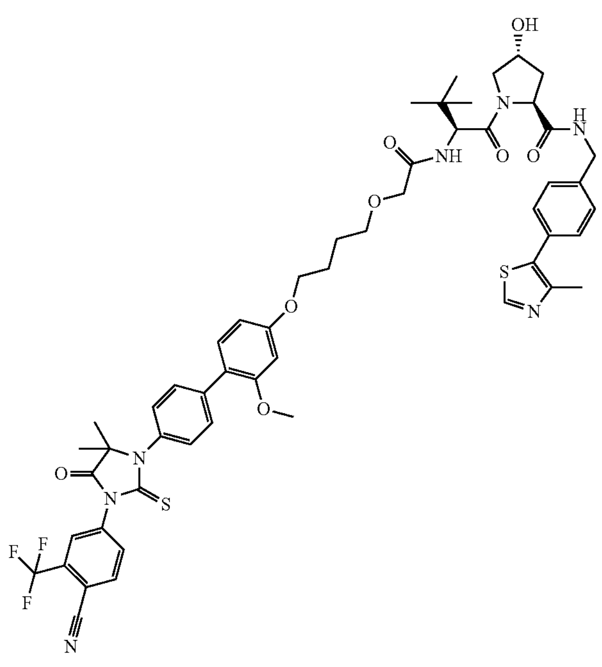 [SMILES: COc1cc(OCCCCOCC(=O)N[C@H](C(=O)N2C[C@H](O)C[C@H]2C(=O)NCc2ccc(-c3scnc3C)cc2)C(C)(C)C)ccc1-c1ccc(N2C(=S)N(c3ccc(C#N)c(C(F)(F)F)c3)C(=O)C2(C)C)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)-3-methoxyphenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, DMSO) δ 8.96 (s, 1H), 8.61 (s, 1H), 8.41 (d, J = 8.4 Hz, 1H), 8.33 (s, 1H), 8.12 (d, J = 1.6 Hz, 1H), 7.64 (d, J = 8.4 Hz, 2H), 7.43-7.37 (m, 7H), 7.28 (d, J = 8.4 Hz, 1H), 6.68-6.61 (m, 2H), 5.17 (s, 1H), 4.57 (d, J = 9.6 Hz, 1H), 4.46-4.36 (m, 3H), 4.30-4.28 (m, 1H), 4.06-4.03 (m, 2H), 3.96 (s, 2H), 3.86 (s, 3H), 3.67-3.56 (m, 4H), 2.44 (s, 3H), 2.08 (s, 1H), 1.85-1.75 (m, 5H), 1.56 (s, 6H), 0.95 (s, 9H); LC-MS (ES$^+$): m/z 1054.25 [MH$^+$] |

TABLE 7-continued

Exemplary Compounds.

| Ex # | Structure | Compound name and Analytical data |
|---|---|---|
| 141, 142 | 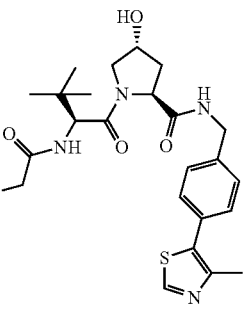 | (2S,4R)-1-[(2S)-2-(2-{[(4S)-4-[4-(4-{3-[4-cyano-3-trifluoromethyl)phenyl]-5,5-dimethyl-4-oxo-2-sulfanylidene-imidazolidin-1-yl}phenyl)phenoxy]pentyl]oxy}acetamido)-3,3-dimethyl-butanoyl]-4-hydroxy-N-{[4-(4-methyl-1,3-thiazol-5-yl)phenyl]methyl}pyrrolidine-2-carboxamide<br>(2S,4R)-1-[(2S)-2-(2-{[(4R)-4-[4-(4-{3-[4-cyano-3-(trifluoromethyl)phenyl]-5,5-dimethyl-4-oxo-2-sulfanylideneimidazolidin-1-yl}phenyl)phenoxy]pentyl]oxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.84 (s, 1H), 8.19-8.17 (d, J = 8.0 Hz, 2H), 8.04-8.02 (d, J = 8.4 Hz, 1H), 7.75-7.73 (d, J = 8.4 Hz, 2H), 7.60-7.58 (d, J = 8.4 Hz, 2H), 7.49-7.41 (m, 6H), 7.03-7.01 (d, J = 8.8 Hz, 2H), 4.87 (s, 1H), 4.73-4.58 (m, 4H), 4.50-4.39 (d, J = 15.2 Hz, 1H), 4.02-4.00 (m, 2H), 3.91-3.88 (m, 1H), 3.84-3.83 (m, 1H), 3.64-3.62 (m, 2H), 2.46 (s, 3H), 2.25-2.23 (m, 1H), 2.13-2.11 (m, 1H), 1.86-1.78 (m, 4H), 1.62 (s, 6H), 1.37-1.34 (m, 3H), 1.12 (s, 9H); LC-MS (ES$^+$): m/z 1038.15 [MH$^+$]<br>$^1$H NMR (400 MHz, CD$_3$OD) δ 8.84 (s, 1H), 8.19-8.17 (d, J = 8.0 Hz, 2H), 8.04-8.02 (d, J = 8.4 Hz, 1H), 7.75-7.73 (d, J = 8.4 Hz, 2H), 7.60-7.58 (d, J = 8.4 Hz, 2H), 7.49-7.41 (m, 6H), 7.03-7.01 (d, J = 8.8 Hz, 2H), 4.87 (s, 1H), 4.73-4.58 (m, 4H), 4.50-4.39 (d, J = 15.2 Hz, 1H), 4.02-4.00 (m, 2H), 3.91-3.88 (m, 1H), 3.84-3.83 (m, 1H), 3.64-3.62 (m, 2H), 2.46 (s, 3H), 2.25-2.23 (m, 1H), 2.13-2.11 (m, 1H), 1.86-1.78 (m, 4H), 1.62 (s, 6H), 1.37-1.34 (m, 3H), 1.12 (s, 9H); LC-MS (ES$^+$): m/z 1038.15 [MH$^+$] |

TABLE 7-continued

Exemplary Compounds.

| Ex # | Structure | Compound name and Analytical data |
|---|---|---|
| 143 | 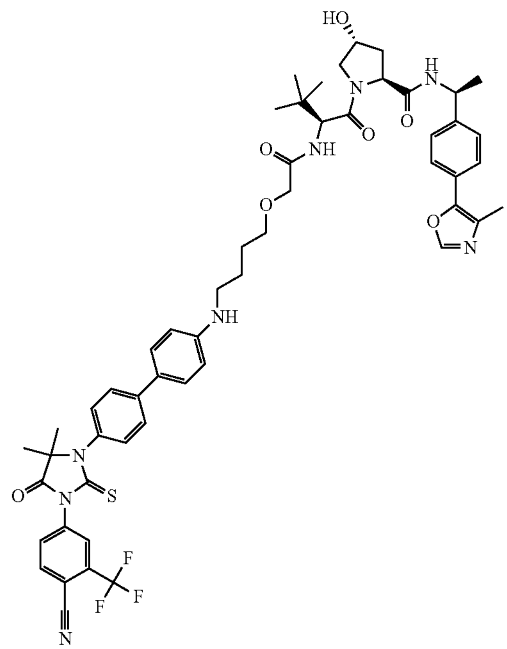 [SMILES: Cc1ncoc1-c1ccc([C@H](C)NC(=O)[C@@H]2C[C@@H](O)CN2C(=O)[C@@H](NC(=O)COCCCCNc2ccc(-c3ccc(N4C(=S)N(c5ccc(C#N)c(C(F)(F)F)c5)C(=O)C4(C)C)cc3)cc2)C(C)(C)C)cc1] | (2S,4R)-1-[(2S)-2-[2-(4-{[4-(4-{3-[4-cyano-3-(trifluoromethyl)phenyl]-5,5-dimethyl-4-oxo-2-sulfanylidene-imidazolidin-1-yl}phenyl]phenyl]amino}butoxy)acetamido]-3,3-dimethylbutanoyl]-4-hydroxy-N-[(1S)-1-[4-(4-methyl-1,3-oxazol-5-yl)phenyl]ethyl]pyrrolidine-2-carboxamide<br>$^1$H NMR (400 MHz, CD$_3$OD) δ 8.20-8.17 (m, 3H), 8.03-8.01 (d, J = 8.1 Hz, 1H), 7.73-7.71 (d, J = 8.4 Hz, 2H), 7.70-7.67 (d, J = 8.4 Hz, 2H), 7.63-7.61 (d, J = 8.4 Hz, 2H), 7.52-7.40 (m, 4H), 6.78-6.76 (d, J = 8.4 Hz, 2H), 5.02-5.00 (m, 1H), 4.87 (s, 1H), 4.62-4.60 (m, 1H), 4.58-4.56 (m, 1H), 4.07-4.00 (m, 2H), 3.88-3.85 (m, 1H), 3.78-3.77 (m, 1H), 3.65-3.63 (m, 2H), 3.23-3.22 (m, 2H), 2.41 (s, 3H), 2.24-2.22 (m, 1H), 1.97-1.96 (m, 1H), 1.80-1.70 (m, 4H), 1.61 (s, 6H), 1.49-1.48 (d, J = 4.4 Hz, 3H), 1.04 (s, 9H); LC-MS (ES$^+$): m/z 1021.25 [MH$^+$] |
| 144 | 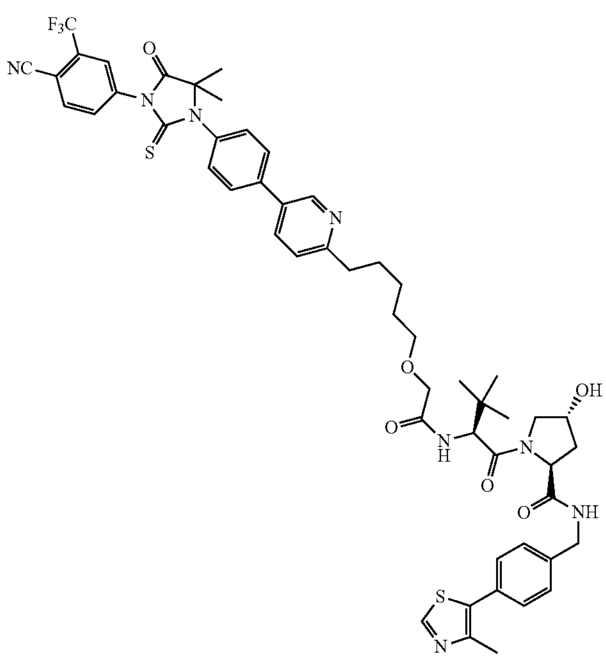 [SMILES: Cc1ncsc1-c1ccc(CNC(=O)[C@@H]2C[C@@H](O)CN2C(=O)[C@@H](NC(=O)COCCCCCc2ccc(-c3ccc(N4C(=S)N(c5ccc(C#N)c(C(F)(F)F)c5)C(=O)C4(C)C)cc3)cn2)C(C)(C)C)cc1] | (2S,4R)-1-[(2S)-2-[2-({5-[5-(4-{3-[4-cyano-3-(trifluoromethyl)phenyl]-5,5-dimethyl-4-oxo-2-sulfanylidene-imidazolidin-1-yl}phenyl)pyridin-2-yl]pentyl}oxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): δ 9.01 (s, 1H), 8.89 (s, 1H), 8.72-8.70 (m, 1H), 8.21-8.18 (m, 2H), 8.04-7.96 (m, 4H), 7.65-7.47 (m, 2H), 7.46-7.38 (m, 4H), 4.73 (s, 1H), 4.63-4.50 (m, 3H), 4.41-4.37 (m, 1H), 4.05-3.99 (m, 2H), 3.89-3.85 (m, 1H), 3.85-3.84m (m, 1H), 3.63-3.60 (m, 2H), 3.14-3.10 (m, 2H), 2.45 (s, 3H), 2.30-2.28 (m, 1H), 2.15-2.03 (m, 1H), 1.94-1.93 (m, 2H), 1.78-1.76 (m, 2H), 1.63-1.59 (m, 8H), 1.01 (s, 9H); LC-MS (ES$^+$): m/z 1023.45 [MH$^+$] |

TABLE 7-continued

Exemplary Compounds.

| Ex # | Structure | Compound name and Analytical data |
|---|---|---|
| 145 | 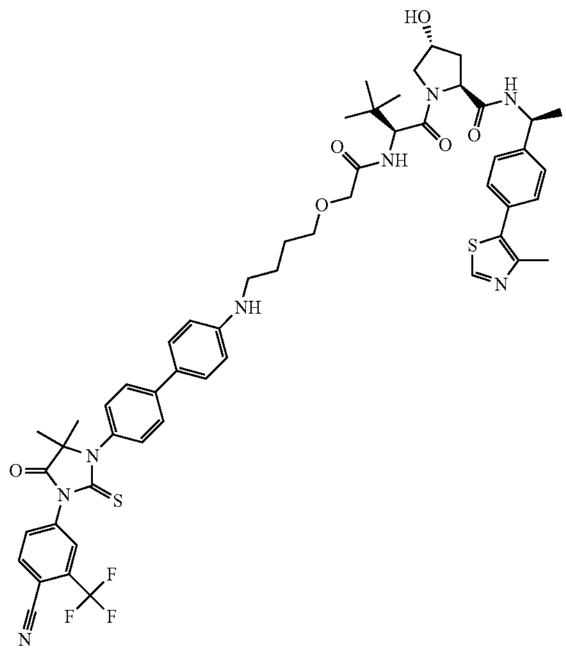 [SMILES: Cc1ncsc1-c1ccc([C@H](C)NC(=O)[C@@H]2C[C@@H](O)CN2C(=O)[C@@H](NC(=O)COCCCCNc2ccc(-c3ccc(N4C(=S)N(c5ccc(C#N)c(C(F)(F)F)c5)C(=O)C4(C)C)cc3)cc2)C(C)(C)C)cc1] | (2S,4R)-1-[(2S)-2-[2-(4-{[4-(4-{3-[4-cyano-3-(trifluoromethyl)phenyl]-5,5-dimethyl-4-oxo-2-sulfanylidene-imidazolidin-1-yl}phenyl)phenyl]amino}butoxy)acetamido]-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (300 MHz, CD$_3$OD) δ 8.95 (s, 1H), 8.19-8.16 (d, J = 8.7 Hz, 2H), 8.03-8.00 (d, J = 8.1 Hz, 1H), 7.87-7.82 (m, 4H), 7.53-7.37 (m, 8H), 5.01-4.99 (m, 1H), 4.87 (s, 1H), 4.70-4.68 (m, 1H), 4.56-4.54 (m, 1H), 4.08-4.05 (m, 2H), 3.83-3.80 (m, 2H), 3.70-3.59 (m, 2H), 3.52-3.47 (m, 2H), 2.48 (s, 3H), 2.24-2.22 (m, 1H), 1.98-1.89 (m, 5H), 1.61 (s, 6H), 1.61-1.60 (m, 1H), 1.56-1.54 (m, 2H), 1.03 (s, 9H); LC-MS (ES$^+$): m/z 1037.10 [MH$^+$] |
| 146 | 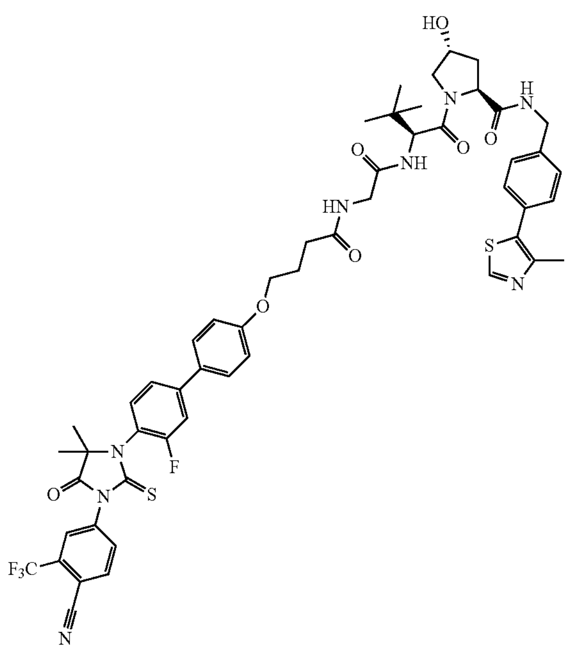 [SMILES: Cc1ncsc1-c1ccc(CNC(=O)[C@@H]2C[C@@H](O)CN2C(=O)[C@@H](NC(=O)CNC(=O)CCCOc2ccc(-c3ccc(N4C(=S)N(c5ccc(C#N)c(C(F)(F)F)c5)C(=O)C4(C)C)c(F)c3)cc2)C(C)(C)C)cc1] | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}-3-fluorophenyl)phenoxy]butanamido}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.87 (s, 1H), 8.19 (m, 2H), 8.05 (m, 1H), 7.64 (d, J = 8.8 Hz, 2H), 7.59 (m, 2H), 7.49 (m, 3H), 7.41 (m, 2H), 7.04 (d, J = 8.8 Hz, 2H), 4.88 (s, 1H), 4.66 (m, 3H), 4.38 (m, 1H), 4.11 (m, 2H), 3.92 (m, 3H), 3.80 (m, 1H), 2.54 (m, 2H), 2.47 (s, 3H), 2.23-2.09 (m, 4H), 1.68 (s, 3H), 1.57 (s, 3H), 1.05 (s, 9H); LC-MS (ES$^+$): m/z 1055.10 [MH$^+$] |

TABLE 7-continued

Exemplary Compounds.

| Ex # | Structure | Compound name and Analytical data |
|---|---|---|
| 147, 148 | | (2S,4R)-1-[(2S)-2-(2-{[(2S)-5-[4-(4-{3-[4-cyano-3-(trifluoromethyl)phenyl]-5,5-dimethyl-4-oxo-2-sulfanylideneimidazolidin-1-yl}phenyl)phenoxy]pentan-2-yl]oxy}acetamido)-3,3-dimethyl-butanoyl]-4-hydroxy-N-{[4-(4-methyl-1,3-thiazol-5-yl)phenyl]methyl}pyrrolidine-2-carboxamide (2S,4R)-1-[(2S)-2-(2-{[(2R)-5-[4-(4-{3-[4-cyano-3-(trifluoromethyl)phenyl]-5,5-dimethyl-4-oxo-2-sulfanylideneimidazolidin-1-yl}phenyl)phenoxy]pentan-2-yl]oxy}acetamido)-3,3-dimethylbutanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD): δ 8.88 (s, 1H), 8.18-8.15 (m, 2H), 8.02-8.00 (d, J = 8.4 Hz, 1H), 7.72-7.70 (d, J = 8.8 Hz, 2H), 7.58-7.55 (d, J = 8.8 Hz, 2H), 7.47-7.38 (m, 6H), 7.01-6.99 (d, J = 4.8 Hz, 2H), 4.86 (s, 1H), 4.58-4.50 (m, 3H), 4.35-4.31 (m, 1H), 4.09-4.05 (m, 3H), 3.86-3.81 (m, 3H), 3.71-3.61 (m, 1H), 2.47 (s, 3H), 2.37-2.23 (m, 1H), 2.11-2.09 (m, 1H), 2.02-1.87 (m, 2H), 1.84-1.68 (m, 2H), 1.59 (s, 6H), 1.26 (s, 3H), 1.02 (s, 9H); LC-MS (ES$^+$): m/z 1038.10 [MH$^+$] <br> $^1$H NMR (400 MHz, CD$_3$OD): δ 8.88 (s, 1H), 8.18-8.15 (m, 2H), 8.02-8.00 (d, J = 8.4 Hz, 1H), 7.72-7.70 (d, J = 8.8 Hz, 2H), 7.58-7.55 (d, J = 8.8 Hz, 2H), 7.47-7.38 (m, 6H), 7.01-6.99 (d, J = 4.8 Hz, 2H), 4.87 (s, 1H), 4.70-4.50 (m, 3H), 4.36-4.32 (m, 1H), 4.09-4.00 (m, 4H), 3.86-3.81 (m, 3H), 2.47 (s, 3H), 2.37-2.23 (m, 1H), 2.11-2.09 (m, 1H), 2.00-1.85 (m, 2H), 1.84-1.68 (m, 2H), 1.58 (s, 6H), 1.23 (s, 3H), 1.01 (s, 9H); LC-MS (ES$^+$): m/z 1038.10 [MH$^+$] |

TABLE 7-continued

Exemplary Compounds.

| Ex # | Structure | Compound name and Analytical data |
|---|---|---|
| 149 | 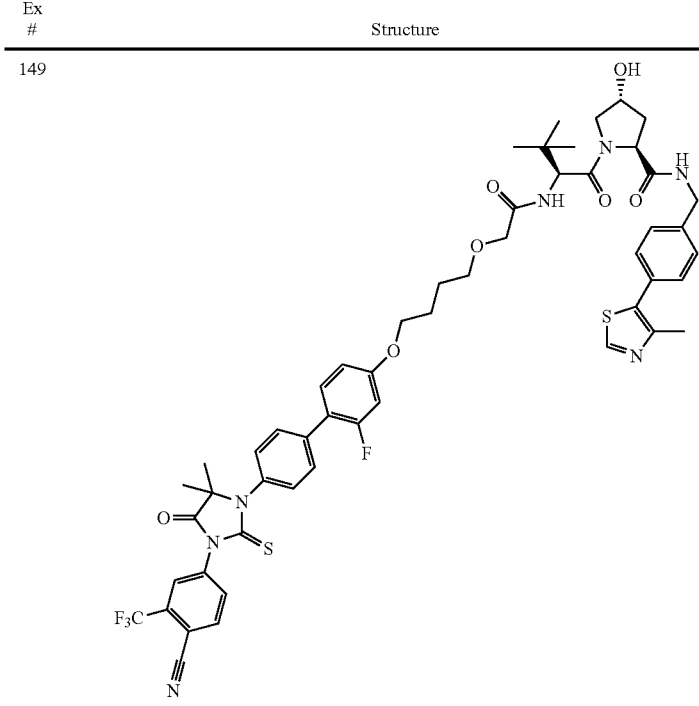 | (2S,4R)-1-[(2S)-2-(2-{4-[4-(4-{3-[4-cyano-3-(trifluoromethyl)phenyl]-5,5-dimethyl-4-oxo-2-sulfanylidene-imidazolidin-1-yl}phenyl)-3-fluorophenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD): 8.80 (s, 1H), 8.18-8.12 (m, 2H), 8.00-7.95 (s, 1H), 7.65-7.60 (m, 2H), 7.45-7.35 (m, 7H), 6.88-6.72 (m, 2H), 4.65 (s, 1H), 4.61-4.52 (s, 1H), 4.50-4.35 (m, 2H), 4.32-4.22 (s, 1H), 4.18-4.02 (m, 2H), 4.00-3.94 (m, 2H), 3.95-3.75 (m, 2H), 3.74-3.55 (m, 2H), 2.40 (m, 3H), 2.28-2.15 (s, 1H), 2.14-2.01 (s, 1H), 2.00-1.72 (m, 4H), 1.68-1.48 (m, 6H), 1.00 (m, 9H); LC-MS (ES$^+$): m/z 1042.05 [MH$^+$] |

Examples 135, 143-145 were synthesized according to similar procedures described for the synthesis of examples 103, by using corresponding starting materials and intermediates.

Synthesis of Example 103

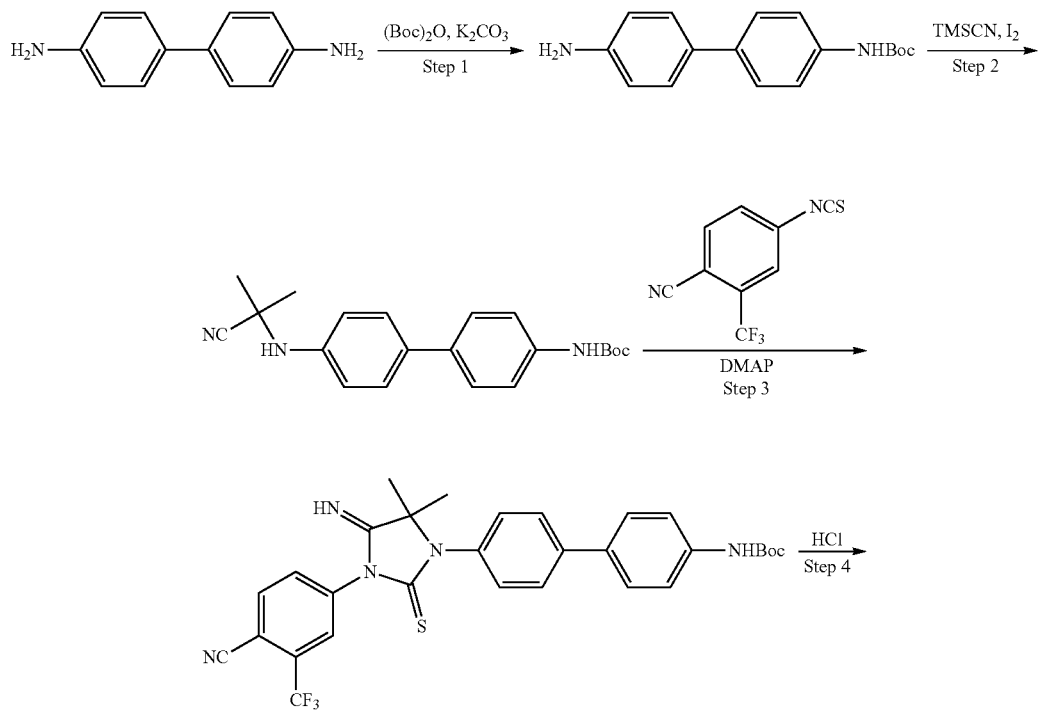

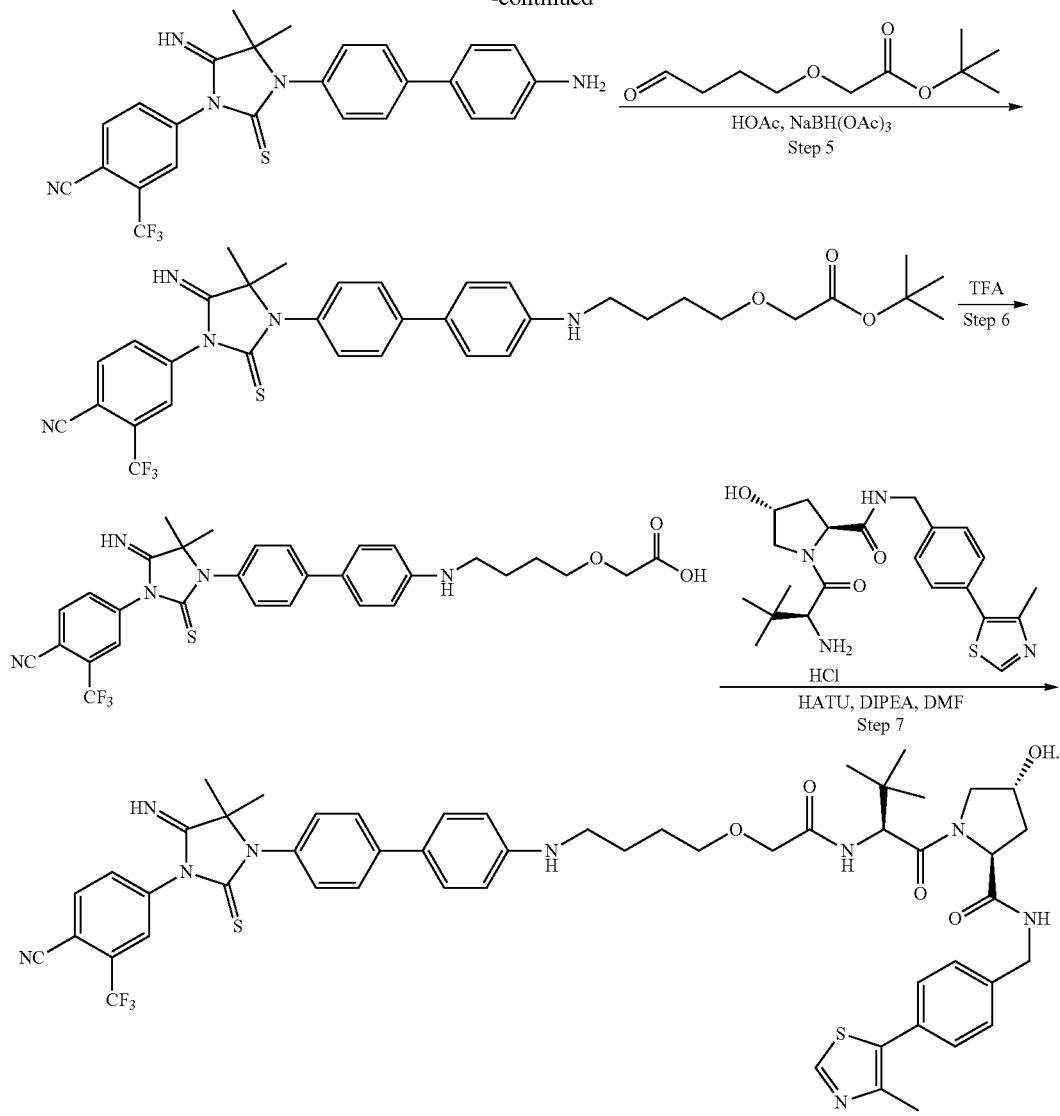

Example 103

Step 1: Synthesis of tert-butyl N-[4-(4-aminophenyl)phenyl]carbamate

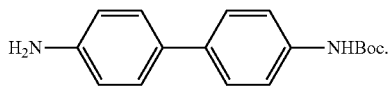

To a stirred solution of 4-(4-aminophenyl)aniline (15.0 g, 81.42 mmol) in a mixed solvent of N,N-dimethylformamide/tetrahydrofuran/water (v/v/v=100/300/50 mL) was added potassium carbonate (9.5 g, 68.74 mmol) and di-tert-butyl dicarbonate (13.67 g, 62.63 mmol) at rt. The resulting mixture was stirred for 5 h at rt. The reaction was then diluted by water (500 mL) and extracted with ethyl acetate (200 mL×3). The organic layers were combined, washed with brine (50 mL×2), dried over anhydrous sodium sulfate, and concentrated under reduced pressure to give a crude residue which was purified by silica gel flash chromatography (eluent: ethyl acetate/petroleum ether, v:v=1:2) to provide the titled product (yield: 97%) as a yellow solid.

Step 2: Synthesis of tert-butyl N-(4-{4-[(1-cyano-1-methylethyl)amino]phenyl}phenyl)carbamate

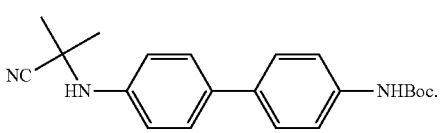 [SMILES: CC(C)(C#N)Nc1ccc(-c2ccc(NC(=O)OC(C)(C)C)cc2)cc1]

To a stirred solution of tert-butyl N-[4-(4-aminophenyl)phenyl]carbamate (7.0 g, 24.62 mmol) in acetone (100 mL) under an atmosphere of nitrogen was added trimethylsilanecarbonitrile (4.9 g, 49.49 mmol) drop wise at 0° C., followed by addition of iodine (630.0 mg, 2.48 mmol) in several batches at 0° C. The resulting mixture was stirred for 15 h at rt. The reaction was then quenched by the addition of water (100 mL), and the resulting solution was extracted with ethyl acetate (100 mL×2). The organic layers were combined, washed with brine (70 mL×2), dried over anhydrous sodium sulfate, and concentrated under reduced pressure to give a crude residue which was purified by silica gel flash chromatography (eluent: ethyl acetate/petroleum ether, v:v=1:3) to provide the titled product (yield: 87%) as a yellow solid. Mass (ES+): m/z 352.20 [MH+].

Step 3: Synthesis of tert-butyl N-[4-(4-{3-[4-cyano-3-(trifluoromethyl)phenyl]-4-imino-5,5-dimethyl-2-sulfanylideneimidazolidin-1-yl}phenyl)phenyl]carbamate

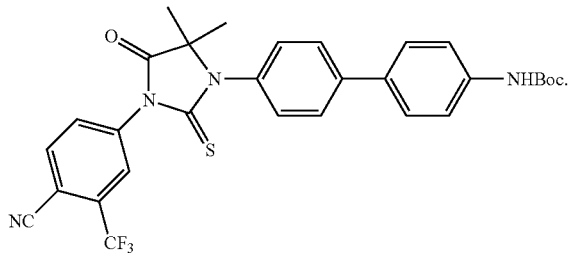 [SMILES: CC(C)(C)OC(=O)Nc1ccc(-c2ccc(N3C(=S)N(c4ccc(C#N)c(C(F)(F)F)c4)C(=O)C3(C)C)cc2)cc1]

To a stirred solution of tert-butyl N-(4-{4-[(1-cyano-1-methylethyl)amino]phenyl}phenyl)carbamate (3.1 g, 8.82 mmol) in toluene (40.0 mL) was added 4-dimethylaminopyridine (1.6 g, 13.10 mmol) and 4-isothiocyanato-2-(trifluoromethyl)benzonitrile (2.0 g, 8.76 mmol) at rt under an atmosphere of nitrogen. The resulting solution was stirred for 12 h at 100° C. in an oil bath. The reaction mixture was then concentrated under reduced pressure to give a crude residue which was purified by silica gel flash chromatography (eluent: ethyl acetate/petroleum ether, v:v=1:1) to provide the titled product (yield: 36%) as a yellow solid. Mass (ES+): m/z 580.30 [MH+].

Step 4: Synthesis of 4-{3-[4-(4-aminophenyl)phenyl]-4,4-dimethyl-5-oxo-2-sulfanylideneimidazolidin-1-yl}-2-(trifluoromethyl)benzonitrile

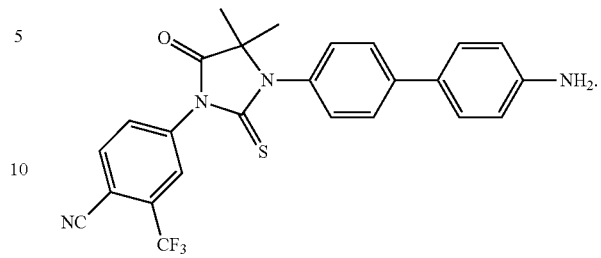

To a stirred solution of tert-butyl N-[4-(4-{3-[4-cyano-3-(trifluoromethyl)phenyl]-4-imino-5,5-dimethyl-2-sulfanylideneimidazolidin-1-yl}phenyl)phenyl]carbamate (2.0 g) in methanol (20 mL) was added hydrogen chloride (3 N solution in water, 5 mL) at rt. The resulting solution was stirred for 2 h at 70° C. in an oil bath. The reaction mixture was then concentrated under reduced pressure to remove the bulk of methanol. To the resulting aqueous mixture was added sodium bicarbonate (sat. aqueous solution) to adjust the pH to ~8, and the resulting mixture was extracted with ethyl acetate (80 mL×3). The organic layers were combined, washed with brine (30 mL×2), dried over anhydrous sodium sulfate, and concentrated under reduced pressure to give a crude residue which was purified by silica gel flash chromatography (eluent: ethyl acetate/petroleum ether, v:v=1:2) to provide the titled product (yield: 45%) as a yellow solid. Mass (ES+): m/z 481.15 [MH+].

Step 5: Synthesis of tert-butyl 2-(4-{[4-(4-{3-[4-cyano-3-(trifluoromethyl)phenyl]-5,5-dimethyl-4-oxo-2-sulfanylideneimidazolidin-1-yl}phenyl)phenyl]amino}butoxy)acetate

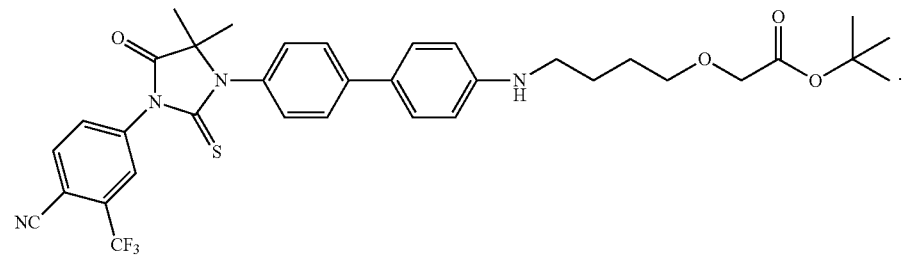 [SMILES: CC(C)(C)OC(=O)COCCCCNc1ccc(-c2ccc(N3C(=S)N(c4ccc(C#N)c(C(F)(F)F)c4)C(=O)C3(C)C)cc2)cc1]

To a stirred solution of 4-{3-[4-(4-aminophenyl)phenyl]-4,4-dimethyl-5-oxo-2-sulfanylideneimidazolidin-1-yl}-2-(trifluoromethyl)benzonitrile (200.0 mg, 0.42 mmol) in dichloromethane (10 mL) was added acetic acid (0.01 mL) and tert-butyl 2-(4-oxobutoxy)acetate (93.0 mg, 0.46 mmol) at rt. The resulting mixture was stirred for 10 min at rt, then to the mixture was added sodium triacetoxyborohydride (124.0 mg, 0.59 mmol). The resulting mixture was stirred overnight at rt. The reaction mixture was diluted by water (30 mL), extracted with dichloromethane (20 mL×3). The organic layers were combined, washed with brine (20 mL×2), dried over anhydrous sodium sulfate, and concentrated under reduced pressure to give a crude residue which was purified by silica gel flash chromatography (eluent: ethyl acetate/petroleum ether, v:v=1:2) to provide the titled product (yield: 36%). Mass (ES+): m/z 667.20[MH+].

Step 6: Synthesis of 2-(4-{[4-(4-{3-[4-cyano-3-(trifluoromethyl)phenyl]-5,5-dimethyl-4-oxo-2-sulfanylideneimidazolidin-1-yl}phenyl)phenyl]amino}butoxy)acetic Acid

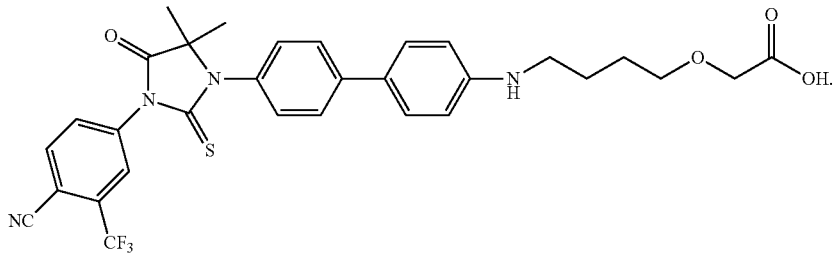 [SMILES: CC1(C)C(=O)N(c2ccc(C#N)c(C(F)(F)F)c2)C(=S)N1c1ccc(-c2ccc(NCCCCOCC(=O)O)cc2)cc1]

To a stirred solution of tert-butyl 2-(4-{[4-(4-{3-[4-cyano-3-(trifluoromethyl)phenyl]-5,5-dimethyl-4-oxo-2-sulfanylideneimidazolidin-1-yl}phenyl)phenyl]amino}butoxy)acetate (100.0 mg, 0.15 mmol) in dichloromethane (10 mL) was added trifluoroacetic acid (2.0 mL) at rt. The resulting solution was stirred for 2 h at rt. The reaction mixture was then concentrated under reduced pressure to give a crude material (yield: 99% based on crude) which was used for next step reaction without any further purification. Mass (ES$^+$): m/z 611.10 [MH$^+$]

Step 7: Synthesis of Example 103

This compound was synthesized from 2-(4-{[4-(4-{3-[4-cyano-3-(trifluoromethyl)phenyl]-5,5-dimethyl-4-oxo-2-sulfanylideneimidazolidin-1-yl}phenyl)phenyl]amino}butoxy)acetic acid and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride, according to similar procedures in the last step (amide coupling) described for the synthesis of example 75.

Synthesis of tert-butyl 2-(4-oxobutoxy)acetate

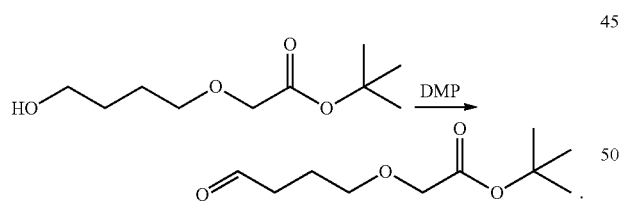

To a stirred solution of tert-butyl 2-(4-hydroxybutoxy)acetate (1.0 g, 4.90 mmol) in dichloromethane (10 mL) was added (1,1,1-triacetoxy)-1,1-dihydro-1,2-benziodoxol-3(1H)-one (2.7 g, 6.37 mmol) at rt. The resulting mixture was stirred for 12 h at rt. The reaction mixture was then diluted with water (20 mL), extracted with ethyl acetate (20 mL×3). The organic layers were combined, washed with brine (20 mL×2), dried over anhydrous sodium sulfate, and concentrated under reduced pressure to give a crude residue which was purified by silica gel flash chromatography (eluent: ethyl acetate/petroleum ether, v/v=1:2) to provide the titled product (yield: 50%) as colorless oil. $^1$H NMR (300 MHz, CD$_3$OD) δ 9.68 (s, 1H), 3.95 (s, 2H), 3.48-3.45 (m, 2H), 2.51-2.50 (m, 2H), 1.81-1.63 (m, 2H), 1.42 (s, 9H).

TABLE 8

Exemplary Compounds.

| Ex # | Structure | Compound name and Analytical data |
|---|---|---|
| 150 | 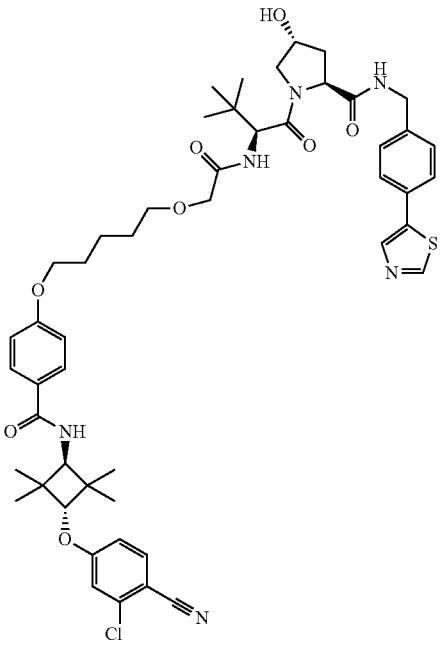 [SMILES: CC(C)(C)[C@H](NC(=O)COCCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2cncs2)cc1] | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl}phenoxy)pentyl]oxy}acetamido)butanoyl]-4-hydroxy-N-{[4-(1,3-thiazol-5-yl)phenyl]methyl}pyrrolidine-2-carboxamide<br>$^1$H NMR (400 MHz, CDCl$_3$): δ 0.95 (s, 9H), 1.22 (s, 6H), 1.27 (s, 6H), 1.56-1.58 (m, 2H), 1.68-1.70 (m, 2H), 1.83-1.86 (m, 2H), 2.11-2.12 (m, 1H), 2.54 (br, 1H), 3.52-3.63 (m, 3H), 3.91-4.16 (m, 7H), 4.28-4.54 (m, 5H), 4.70-4.71 (m, 1H), 6.19 (d, J = 6.8 Hz, 1H), 6.80-6.97 (m, 4H), 7.17 (d, J = 8.4 Hz, 1H), 7.32 (d, J = 6.8 Hz, 2H), 7.48-7.58 (m, 3H), 7.72-7.74 (m, 2H), 8.03-8.10 (m, 2H), 8.78 (br, 1H); LC-MS: (ES$^+$): m/z 941.20 [M + H$^+$] |
| 151 | 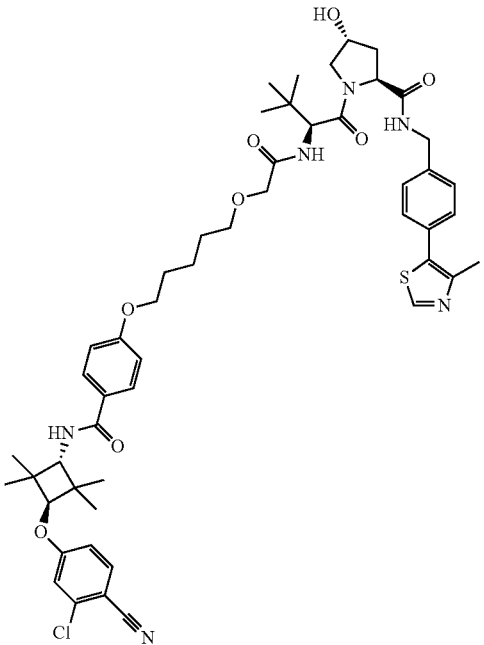 | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl}phenoxy)pentyl]oxy}acetamido)butanoyl]-4-hydroxy-N-{[4-(4-methyl-1,3-thiazol-5-yl)phenyl]methyl}pyrrolidine-2-carboxamide<br>$^1$H NMR (400 MHz, CDCl$_3$) δ 8.67 (s, 1H), 7.72 (d, J = 9.0 Hz, 2H), 7.57 (d, J = 8.6 Hz, 1H), 7.31-7.38 (m, 4H), 7.20 (d, J = 9.0 Hz, 1H), 6.97 (d, J = 2.3 Hz, 1H), 6.92 (d, J = 8.6 Hz, 1H), 6.81 (dd, J = 2.5, 8.8 Hz, 1H), 6.19 (d, J = 8.2 Hz, 1H), 4.72 (t, J = 7.8 Hz, 1H), 4.47-4.58 (m, 3H), 4.31-4.41 (m, 1H), 3.87-4.18 (m, 7H), 3.73 (s, 1H), 3.58 (br. s., 2H), 3.54 (t, J = 6.5 Hz, 2H), 3.48 (s, 1H), 2.46-2.55 (m, 3H), 2.08-2.17 (m, 1H), 1.80-1.88 (m, 2H), 1.65-1.74 (m, 2H), 1.53-1.61 (m, 2H), 1.46 (s, 1H), 1.26 (br. s., 6H), 1.22 (s, 6H), 0.95 (s, 9H). LC-MS (ES$^+$): m/z 955.42 [MH$^+$] |

| Ex # | Structure | Compound name and Analytical data |
|---|---|---|
| 152 | 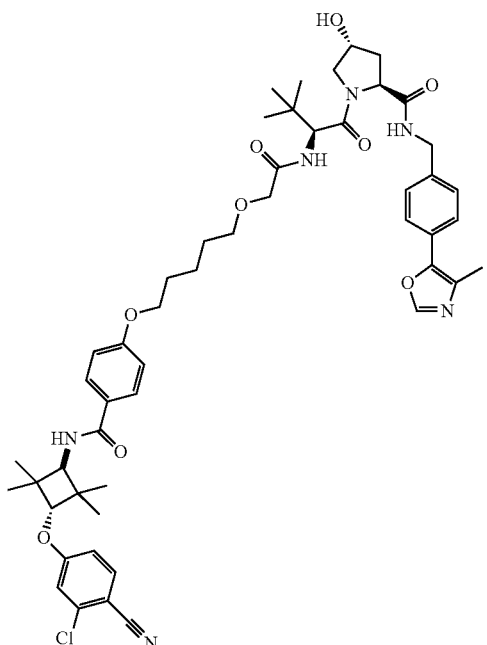 | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl}phenoxy)pentyl]oxy}acetamido)butanoyl]-4-hydroxy-N-{[4-(4-methyl-1,3-oxazol-5-yl)phenyl]methyl}pyrrolidine-2-carboxamide<br>$^1$H NMR (400 MHz, CDCl$_3$) δ 7.85 (s, 1H), 7.72 (d, J = 8.6 Hz, 2H), 7.57 (d, J = 8.6 Hz, 1H), 7.52 (d, J = 8.2 Hz, 2H), 7.35 (d, J = 8.2 Hz, 3H), 7.20 (d, J = 8.6 Hz, 1H), 6.97 (d, J = 2.7 Hz, 1H), 6.92 (d, J = 8.6 Hz, 2H), 6.81 (dd, J = 2.3, 8.6 Hz, 1H), 6.20 (d, J = 7.8 Hz, 1H), 4.70 (t, J = 7.8 Hz, 1H), 4.48-4.56 (m, 3H), 4.34 (dd, J = 5.3, 15.1 Hz, 1H), 4.12-4.16 (m, 1H), 4.04-4.09 (m, 2H), 4.01 (t, J = 6.3 Hz, 2H), 3.85-3.97 (m, 2H), 3.63 (dd, J = 3.3, 11.2 Hz, 1H), 3.53 (t, J = 6.5 Hz, 2H), 2.49 (ddd, J = 4.7, 8.0, 13.1 Hz, 2H), 2.41 (s, 3H), 2.12 (dd, J = 8.2, 13.3 Hz, 1H), 1.80-1.86 (m, 2H), 1.65-1.72 (m, 2H), 1.53-1.60 (m, 2H), 1.26-1.28 (m, 6H), 1.22 (s, 6H), 0.96 (s, 9H). LC-MS (ES$^+$): m/z 940.44 [MH$^+$], |
| 153 | 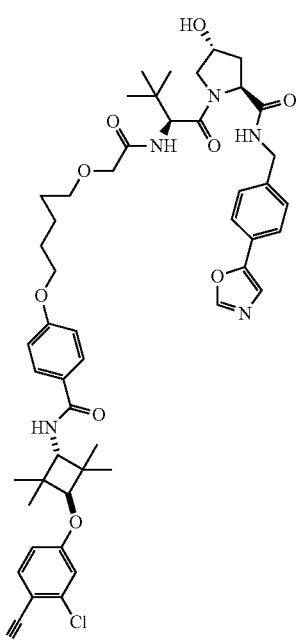 | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl}phenoxy)pentyl]oxy}acetamido)butanoyl]-4-hydroxy-N-{[4-(1,3-oxazol-5-yl)phenyl]methyl}pyrrolidine-2-carboxamide<br>$^1$H NMR (400 MHz, CDCl$_3$) δ 7.91 (s, 1H), 7.72 (d, J = 9.0 Hz, 2H), 7.54-7.57 (m, 2H), 7.34 (s, 3H), 7.21 (d, J = 8.6 Hz, 1H), 6.96 (d, J = 2.3 Hz, 1H), 6.92 (d, J = 9.0 Hz, 2H), 6.81 (dd, J = 2.5, 8.8 Hz, 1H), 6.21 (d, J = 7.8 Hz, 1H), 4.69 (t, J = 8.0 Hz, 1H), 4.48-4.55 (m, 3H), 4.32 (dd, J = 5.3, 15.1 Hz, 1H), 4.15 (d, J = 7.8 Hz, 1H), 3.98-4.08 (m, 4H), 3.84-3.97 (m, 2H), 3.63 (dd, J = 3.5, 11.3 Hz, 1H), 3.53 (t, J = 6.3 Hz, 2H), 2.40-2.57 (m, 4H), 2.11 (dd, J = 8.0, 13.5 Hz, 1H), 1.79-1.88 (m, 2H), 1.64-1.73 (m, 2H), 1.51-1.60 (m, 2H), 1.27 (s, 6H), 1.22 (s, 6H), 0.96 (s, 9H). LC-MS (ES$^+$): m/z 926.42 [MH$^+$] |

TABLE 8-continued

Exemplary Compounds.

| Ex # | Structure | Compound name and Analytical data |
|---|---|---|
| 154 | 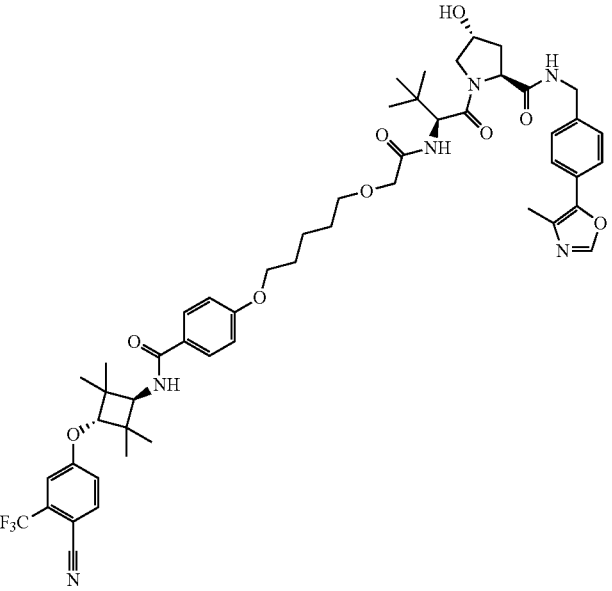 [SMILES: Cc1ncoc1-c1ccc(CNC(=O)[C@@H]2C[C@@H](O)CN2C(=O)[C@@H](NC(=O)COCCCCCOc2ccc(C(=O)N[C@H]3C(C)(C)[C@H](Oc4ccc(C#N)c(C(F)(F)F)c4)C3(C)C)cc2)C(C)(C)C)cc1] | (2S,4R)-1-[(2S)-3,3-dimethyl-2-(2-{[5-(4-{[trans--3-[4-cyano-3-(trifluoromethyl)phenoxy]-2,2,4,4-tetramethylcyclobutyl]carbamoyl}phenoxy)pentyl]oxy}acetamido)butanoyl]-4-hydroxy-N-{[4-(4-methyl-1,3-oxazol-5-yl)phenyl]methyl}pyrrolidine-2-carboxamide<br>$^1$H NMR (300 MHz, CD$_3$OD): δ 8.10 (s, 1H), 7.90-7.83 (m, 1H), 7.80-7.71 (m, 2H), 7.60-7.52 (m, 2H), 7.49-7.541 (m, 2H), 7.32 (s, 1H), 7.23-7.19 (m, 1H), 7.00-6.89 (m, 2H), 4.67 (s, 1H), 4.60-4.40 (m, 3H), 4.35-4.25 (m, 2H), 4.15-4.10 (m, 1H), 1.09-3.98 (m, 2H), 3.97-3.90 (m, 2H), 3.85-3.70 (m, 2H), 3.63-3.49 (m, 2H), 2.40 (s, 3H), 2.25-2.10 (m, 1H), 2.09-2.00 (m, 1H), 1.89-1.79 (m, 2H), 1.80-1.45 (m, 4H), 1.33-1.14 (m, 12H), 1.01 (s, 9 ); LC-MS (ES$^+$): m/z, 973.35 [MH$^+$] |
| 155 | 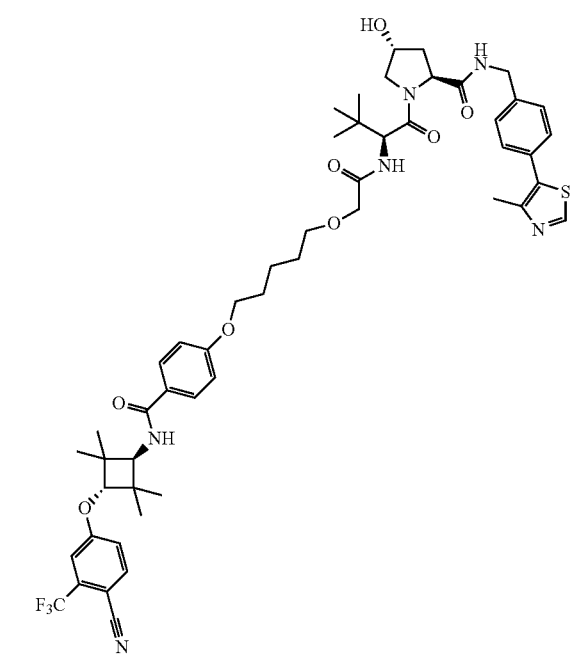 [SMILES: Cc1ncsc1-c1ccc(CNC(=O)[C@@H]2C[C@@H](O)CN2C(=O)[C@@H](NC(=O)COCCCCCOc2ccc(C(=O)N[C@H]3C(C)(C)[C@H](Oc4ccc(C#N)c(C(F)(F)F)c4)C3(C)C)cc2)C(C)(C)C)cc1] | (2S,4R)-1-[(2S)-3,3-dimethyl-2-(2-{[5-(4-{[trans-3-[4-cyano-3-(trifluoromethyl)phenoxy]-2,2,4,4-tetramethylcyclobutyl]carbamoyl}phenoxy)pentyl]oxy}acetamido)butanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.84 (s, 1H), 7.90-7.84 (m, 1H), 7.80-7.70 (m, 2H), 7.45-7.32 (m, 4H), 7.26-7.22 (m, 1H), 7.28-7.20 (m, 1H), 7.00-6.89 (m, 2H), 4.67 (s, 1H), 4.60-4.50 (m, 1H), 4.46-4.40 (m, 1H), 4.27-4.20 (m, 2H), 4.13 (s, 1H), 4.15-4.00 (m, 2H), 3.99-3.95 (m, 2H), 3.90-3.80 (m, 2H), 3.59-3.51 (m, 2H), 2.40 (s, 3H), 2.25-2.10 (m, 1H), 2.11-2.00 (m, 1H), 1.85-1.75 (m, 2H), 1.70-1.50 (m, 4H), 1.33-1.14 (m, 12H), 1.01 (s, 9H); LC-MS (ES$^+$): m/z, 989.30 [MH$^+$] |

TABLE 8-continued

Exemplary Compounds.

| Ex # | Structure | Compound name and Analytical data |
|---|---|---|
| 156 | 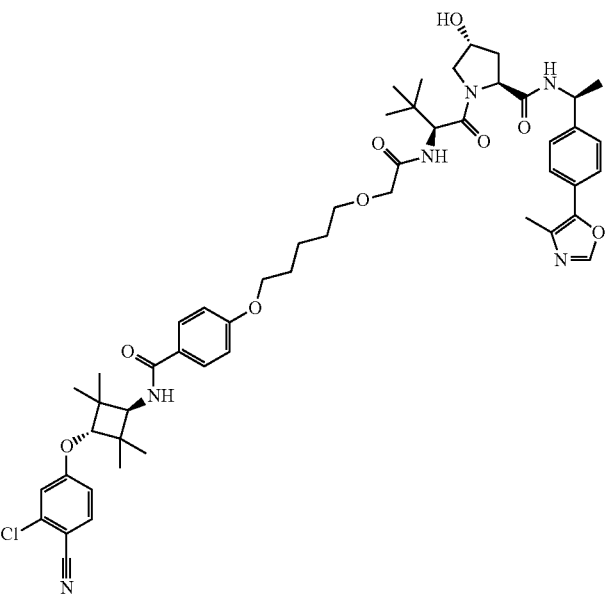 [SMILES: Cc1ncoc1-c1ccc([C@H](C)NC(=O)[C@@H]2C[C@@H](O)CN2C(=O)[C@@H](NC(=O)COCCCCCOc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-(2-{[5-(4-{[trans--3-(3-chloro-4-cyanophenoxy)-2,2,4,4-tetramethylcyclobutyl]carbamoyl}phenoxy)pentyl]oxy}acetamido)butanoyl]-4-hydroxy-N-[(1S)-1-[4-(4-methyl-1,3-oxazol-5-yl)phenyl]ethyl]pyrrolidine-2-carboxamide<br>$^1$H NMR (300 MHz, CD$_3$OD): δ 8.14 (s, H), 7.85-7.80 (m, 2H), 7.78-7.72 (m, 1H), 7.65-7.55 (m, 2H), 7.47-7.40 (m, 2H), 7.15-7.10 (m, 1H), 7.15-6.95 (m, 3H), 5.03-4.94 (m, 1H), 4.67 (s, 1H), 4.60-4.50 (m, 1H), 4.46-4.40 (m, 1H), 4.27-4.25 (m, 1H), 4.15-4.00 (m, 3H), 3.99-3.95 (m, 2H), 3.90-3.80 (m, 1H), 3.79-3.80 (m, 1H), 3.63-3.49 (m, 2H), 2.40 (s, 3H), 2.25-2.10 (m, 1H), 2.09-1.80 (m, 3H), 1.79-1.50 (m, 4H), 1.48-1.46 (m, 3H), 1.33-1.14 (m, 12H), 1.01 (s, 9H); LC-MS (ES$^+$): m/z, 953.35 [MH$^+$] |
| 157 | 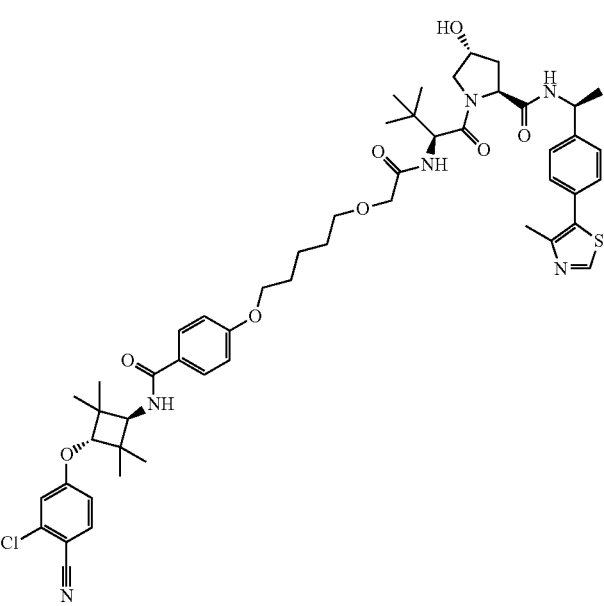 [SMILES: Cc1ncsc1-c1ccc([C@H](C)NC(=O)[C@@H]2C[C@@H](O)CN2C(=O)[C@@H](NC(=O)COCCCCCOc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl}phenoxy)pentyl]oxy}acetamido)butanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, CD$_3$OD): δ 8.90 (s, 1H), 7.85-7.00 (m, 3H), 7.50-7.39 (m, 4H), 7.15-7.10 (s, 1H), 7.05-6.95 (m, 3H), 5.05-4.98 (m, 1H), 4.70 (s, 1H), 4.65-4.52 (m, 1H), 4.48-4.40 (m, 1H), 4.30 (s, 1H), 4.15-4.10 (m, 3H), 4.00 (m, 2H), 4.02-3.70 (m, 2H), 3.70-3.58 (m, 2H), 2.50 (m, 3H), 2.45-2.35 (m, 1H), 2.28-2.15 (m, 1H), 2.08-1.82 (m, 4H), 1.80-1.45 (m, 7H), 1.39-1.20 (m, 12H), l. 10-1.00 (m, 9H); LC-MS (ES$^+$): m/z 969.50 [MH$^+$] |

TABLE 8-continued

Exemplary Compounds.

| Ex # | Structure | Compound name and Analytical data |
|---|---|---|
| 158, 159 | 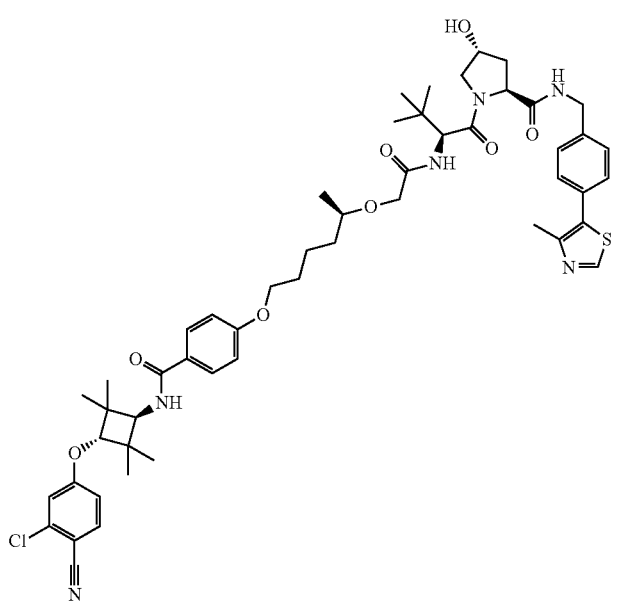 [SMILES: Cc1ncsc1-c1ccc(CNC(=O)[C@@H]2C[C@@H](O)CN2C(=O)[C@@H](NC(=O)CO[C@H](C)CCCCOc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-(2-{[(2R)-6-(4-{[trans-3-(3-chloro-4-cyanophenoxy)-2,2,4,4-tetramethylcyclobutyl]carbamoyl}phenoxy)hexan-2-yl]oxy}acetamido)butanoyl]-4-hydroxy-N-{[4-(4-methyl-1,3-thiazol-5-yl)phenyl]methyl}pyrrolidine-2-carboxamide<br>(2S,4R)-1-[(2S)-3,3-dimethyl-2-(2-{[(2S)-6-(4-{[trans-3-(3-chloro-4-cyanophenoxy)-2,2,4,4-tetramethylcyclobutyl]carbamoyl}phenoxy)hexan-2-yl]oxy}acetamido)butanoyl]-4-hydroxy-N-{[4-(4-methyl-1,3-thiazol-5-yl)phenyl]methyl}pyrrolidine-2-carboxamide |

TABLE 8-continued

Exemplary Compounds.

| Ex # | Structure | Compound name and Analytical data |
|---|---|---|
| 160, 161 | 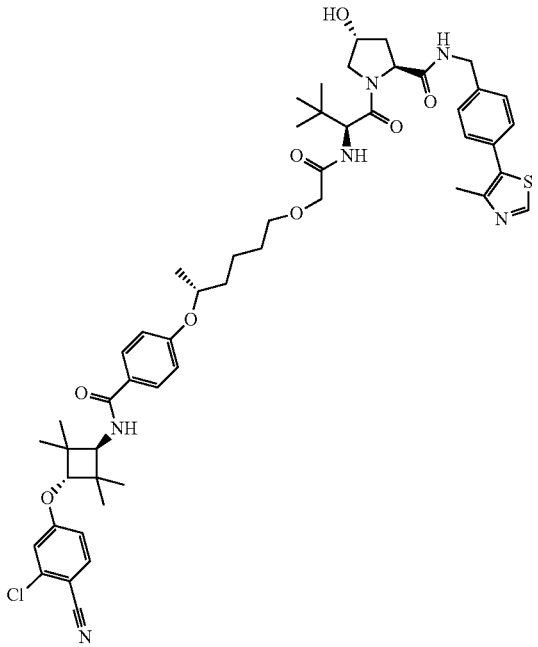 [SMILES: Cc1ncsc1-c1ccc(CNC(=O)[C@@H]2C[C@@H](O)CN2C(=O)[C@@H](NC(=O)COCCCC[C@@H](C)Oc2ccc(C(=O)N[C@H]3C(C)(C)[C@H](Oc4ccc(C#N)c(Cl)c4)C3(C)C)cc2)C(C)(C)C)cc1] 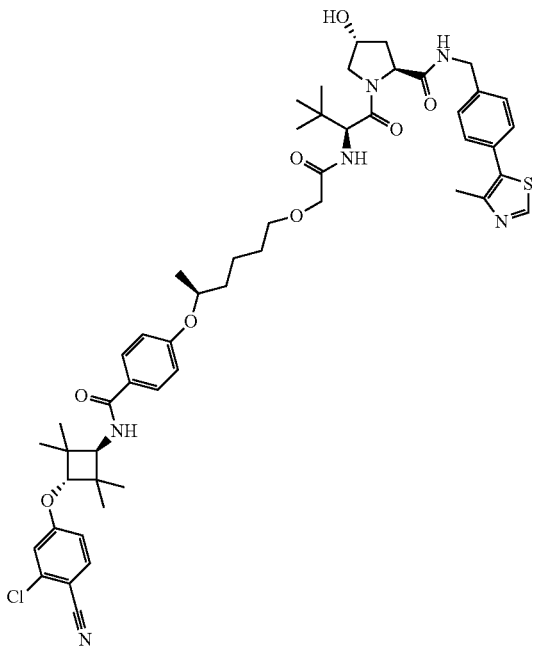 [SMILES: Cc1ncsc1-c1ccc(CNC(=O)[C@@H]2C[C@@H](O)CN2C(=O)[C@@H](NC(=O)COCCCC[C@H](C)Oc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-(2-{[(5S)-5-(4-{[trans-3-(3-chloro-4-cyanophenoxy)-2,2,4,4-tetramethylcyclobutyl]carbamoyl}phenoxy)hexyl]oxy}acetamido)butanoyl]-4-hydroxy-N-{[4-(4-methyl-1,3-thiazol-5-yl)phenyl]methyl}pyrrolidine-2-carboxamide (2S,4R)-1-[(2S)-3,3-dimethyl-2-(2-{[(5R)-5-(4-{[trans-3-(3-chloro-4-cyanophenoxy)-2,2,4,4-tetramethylcyclobutyl]carbamoyl}phenoxy)hexyl]oxy}acetamido)butanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.88 (s, 1H),7.75-7.67 (m, 3H), 7.44-7.36 (m, 4H), 7.09 (s, 1H), 6.96-6.91 (m, 3H), 4.84 (s, 1H), 4.66-4.47 (m, 4H), 4.36-4.31 (m, 1H), 4.26 (s, 1H), 4.24 (s, 1H), 4.10 (s, 1H), 3.93-3.91 (m, 2H), 3.83-5.78 (m, 2H), 3.55-3.51 (m, 2H), 2.43 (s, 3H), 2.12-2.10 (m, 1H), 2.09-1.95 (m, 1H), 1.67-1.62 (m, 6H), 1.30-1.28 (m, 9H), 1.18 (s, 6H), 1.00 (s, 9H); LC-MS (ES$^+$): m/z 969.10 [MH$^+$] $^1$H NMR (300 MHz, CD$_3$OD): δ 8.88 (s, 1H), 7.75-7.67 (m, 3H), 7.44-7.36 (m, 4H), 7.10 (s, 1H), 6.96-6.91 (m, 3H), 4.66 (s, 1H), 4.58-4.48 (m, 4H), 4.35-4.03 (m, 1H), 4.24 (s, 1H), 4.10 (s, 1H), 3.92-3.86 (m, 2H), 3.83-5.55 (m, 2H), 3.53-3.51 (m, 2H), 2.43 (s, 3H), 2.20-2.10 (m, 1H), 2.09-2.01 (m, 1H), 1.67-1.62 (m, 6H), 1.30 (s, 9H), 1.19 (s, 6H), 1.00 (s, 9H); LC-MS (ES$^+$): m/z 969.15 [MH$^+$] |

Synthesis of Example 150
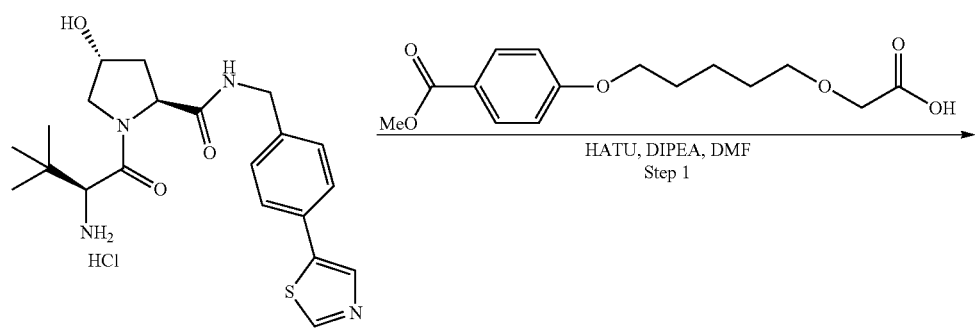
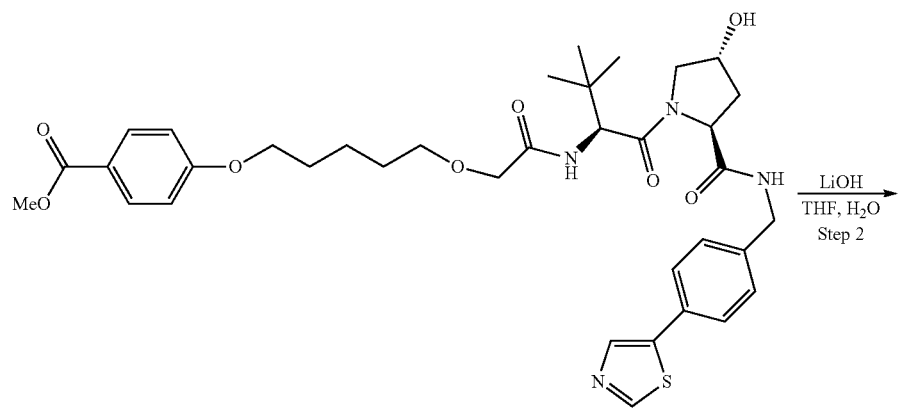
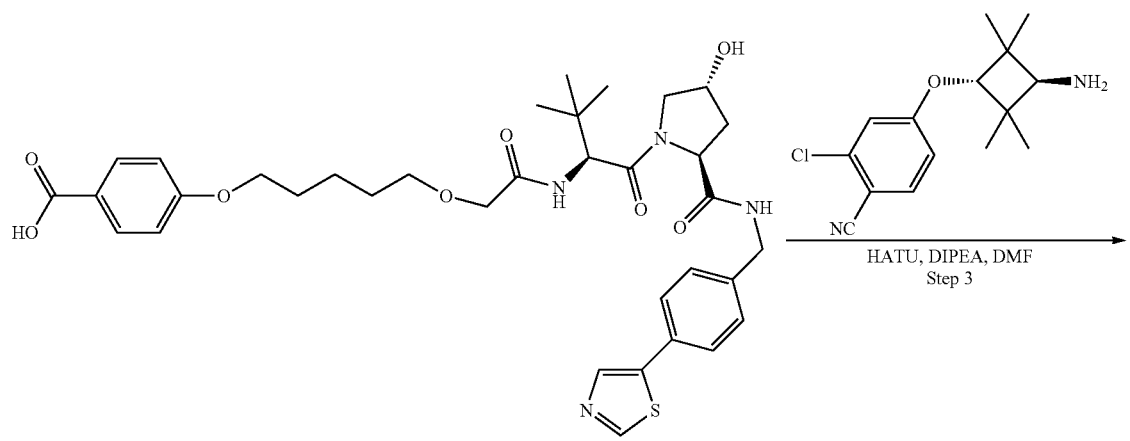
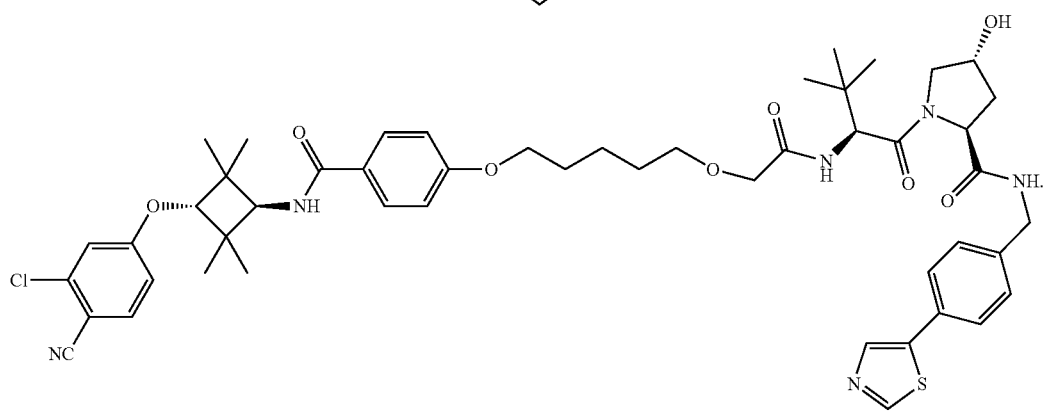
Example 150

Step 1: Synthesis of methyl 4-{[5-({[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoate

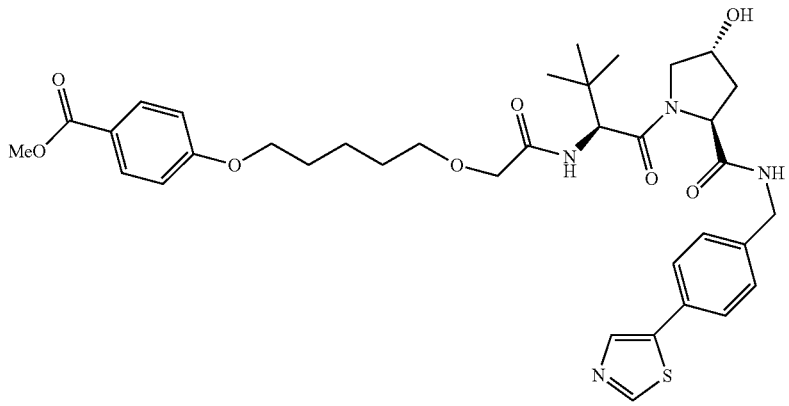 [SMILES: COC(=O)c1ccc(OCCCCCOCC(=O)N[C@H](C(=O)N2C[C@H](O)C[C@H]2C(=O)NCc2ccc(-c3cncs3)cc2)C(C)(C)C)cc1]

To a stirred solution of 2-({5-[4-(methoxycarbonyl)phenoxy]pentyl}oxy)acetic acid (200 mg), (2S,4R)-1-[(2S)-2-amino-3,3-dimethylbutanoyl]-4-hydroxy-N-{[4-(1,3-thiazol-5-yl)phenyl]methyl}pyrrolidine-2-carboxamide hydrogen chloride salt (149 mg, 0.32 mmol), N-ethyl-N-isopropylpropan-2-amine (185 mg, 1.44 mmol) in anhydrous N,N-dimethylformamide (5 mL) was added HATU (2-(7-aza-1H-benzotriazole-1-yl)-1,1,3,3-tetramethyluronium hexafluorophosphate) (203 mg, 0.54 mmol) at 0° C. The resulting mixture was allowed to warm up to rt and stirred at rt for 20 min. TLC and LC-MS showed formation of the desired product. The mixture was partitioned between ethyl acetate (100 mL) and water (50 mL). The organic layer was collected, washed with brine (50 mL), dried over anhydrous sodium sulfate, and concentrated under reduced pressure to give a crude residue which was purified by silica gel flash chromatography (eluent 2% methanol in methylene dichloride) to afford the titled product (yield 25%, 2 steps) as a white solid. Mass: (ES$^+$): m/z 695.30 [M+H$^+$].

Step 2: Synthesis of 4-{[5-({[(2S)-1-[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoic Acid

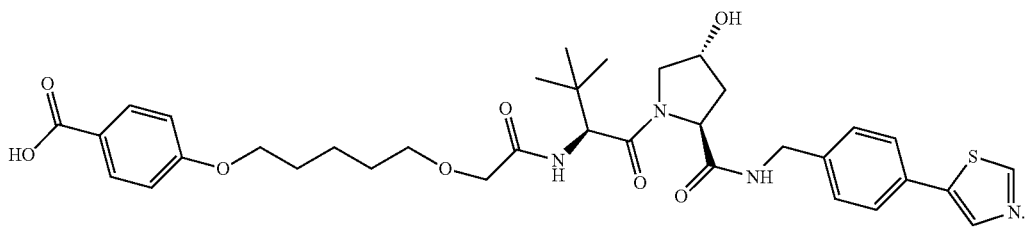 [SMILES: CC(C)(C)[C@H](NC(=O)COCCCCCOc1ccc(C(=O)O)cc1)C(=O)N1C[C@H](O)C[C@H]1C(=O)NCc1ccc(-c2cncs2)cc1]

To a stirred solution of methyl 4-{[5-({[(2S)-1-[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoate (150 mg, 0.22 mmol) in a mixed solvents of tetrahydrofuran (4 mL)-water (2 mL)-methanol (1 ml) was added lithium hydroxide monohydrate (36 mg, 0.86 mmol) at rt. The resulting mixture was stirred at 35° C. overnight. TLC and LC-MS showed formation of the desired product. The reaction mixture was acidified with aqueous HCl (3N) to pH=3-4 and extracted with methylene dichloride (50 mL×2). The organic layers were combined, washed with brine, dried over Na$_2$SO$_4$ and concentrated to afford the titled product (110 mg, crude) as a white solid which was used for next step without further purification. Mass: (ES$^+$): m/z 681.20 [M+H$^+$].

Step 3: Synthesis of Example 150

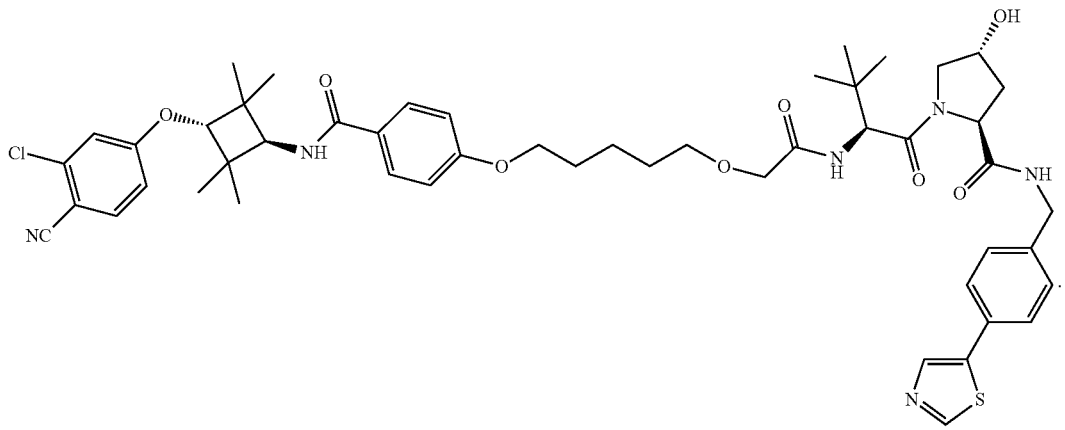 [SMILES: CC(C)(C)[C@H](NC(=O)COCCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2cncs2)cc1]

To a stirred mixture of 4-{[5-({[[(2S)-1-[(2S,4R)-4-hydroxy-2-({[4-(1,3-thiazol-5-yl)phenyl]methyl}carbamoyl)pyrrolidin-1-yl]-3,3-dimethyl-1-oxobutan-2-yl]carbamoyl}methoxy)pentyl]oxy}benzoic acid (110 mg, 0.16 mmol), 2-chloro-4-[trans-3-amino-2,2,4,4-tetramethylcyclobutoxy]benzonitrile hydrogen chloride salt (50 mg, 0.16 mmol), N-ethyl-N-isopropylpropan-2-amine (77 mg, 0.64 mmol) in anhydrous N,N-dimethylformamide (4 mL) was added HATU ((2-(7-Aza-1H-benzotriazole-1-yl)-1,1,3,3-tetramethyluronium hexafluorophosphate)) (68 mg, 0.18 mmol) at 0° C. The resulting mixture was allowed to warm up to rt and stirred at rt for 20 min. TLC and LC-MS showed formation of the desired product. The reaction mixture was partitioned between ethyl acetate (100 mL) and water (40 mL). The organic phase was separated, washed with brine (50 mL), dried over anhydrous sodium sulfate, and concentrated under reduced pressure to give a crude residue which was purified by preparative TLC (eluent: 5% methanol in methylene dichloride) to afford the titled product (yield 25%, 2 steps) as a white solid.

Synthesis of 2-({5-[4-(methoxycarbonyl)phenoxy]pentyl}oxy)acetic Acid

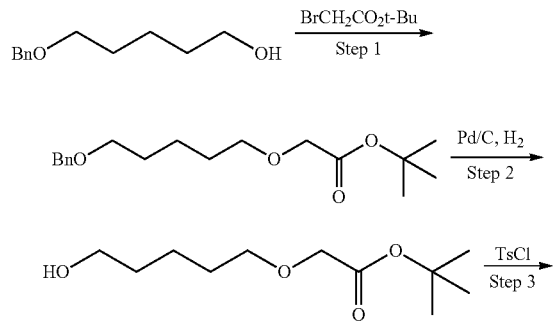

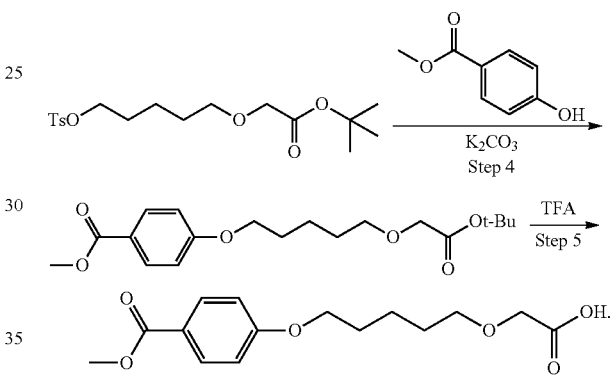

Step 1: Synthesis of tert-butyl 2-{[5-(benzyloxy)pentyl]oxy}acetate

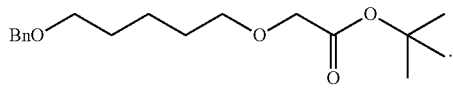

To a stirred mixture of 5-(benzyloxy)pentan-1-ol (10 g, 51.5 mmol), tert-butyl 2-bromoacetate (40.2 g, 206 mmol) and tetrabutyl ammonium chloride (14.2 g, 51.5 mmol) in methylene dichloride (60 mL) was added sodium hydroxide (40 ml, 35% in water) at rt, and the resulting mixture was stirred at rt for 16 h. The reaction mixture was then partitioned between methylene dichloride (200 mL) and water (100 mL). The organic layer was collected and washed with brine (50 mL), dried over anhydrous sodium sulfate, and concentrated under reduced pressure to give a crude residue which was purified by silica gel flash chromatography (eluent: 5% ethyl acetate in hexane) to afford tert-butyl 2-{[5-(benzyloxy)pentyl]oxy}acetate (yield 31.6%) as light yellow oil. LC-MS: (ES$^+$): m/z 331.10 [M+Na$^+$], $^1$H NMR (400 MHz, CDCl$_3$): δ 1.48 (s, 9H), 1.63-1.67 (m, 6H), 3.46-3.53 (m, 4H), 4.10 (s, 2H), 4.50 (s, 2H), 7.28-7.34 (m, 5H).

Step 2: Synthesis of tert-butyl 2-[(5-hydroxypentyl)oxy]acetate

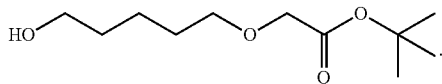

To a stirred solution of tert-butyl 2-{[5-(benzyloxy)pentyl]oxy}acetate (5 g, 16.2 mmol) in ethanol (100 ml) under a nitrogen atmosphere was added palladium on carbon (10%, 600 mg) at rt. The resulting mixture was stirred at 50° C. overnight under hydrogen atmosphere (hydrogen balloon). TLC showed formation of desired product. Palladium on carbon was removed through filtration and washed with ethyl acetate (50 mL). The filtrate was concentrated under reduced pressure to afford tert-butyl 2-[(5-hydroxypentyl)oxy]acetate (2.5 g, crude) as colorless oil which was used in next step without further purification.

Step 3: Synthesis of tert-butyl 2-({5-[(4-methylbenzenesulfonyl)oxy]pentyl}oxy)acetate

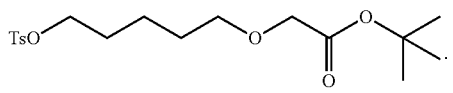 [SMILES: Cc1ccc(S(=O)(=O)OCCCCCOCC(=O)OC(C)(C)C)cc1]

To a stirred solution of tert-butyl 2-[(5-hydroxypentyl)oxy]acetate (2.5 g, crude) and triethylamine (3.5 g, 34.5 mmol) in anhydrous methylene dichloride (50 mL) was added a solution of 4-toluenesulfonyl chloride (2.7 g, 13.8 mmol) in anhydrous methylene dichloride (8 mL) drop wise at 0° C. The reaction mixture was allowed to warm up to rt and stirred at rt overnight. TLC showed formation of desired product. The mixture was quenched with aqueous solution of potassium carbonate (1N, 50 mL) at rt and extracted with ethyl acetate (50 mL×3). The organic layers were combined, washed with brine (50 mL), dried over anhydrous sodium sulfate, and concentrated under reduced pressure to give a crude residue which was purified by silica gel flash chromatography (eluent: 1% methanol in methylene dichloride) to afford tert-butyl 2-({5-[(4-methylbenzenesulfonyl)oxy]pentyl}oxy)acetate (yield 35.1%) as colorless oil. Mass: (ES$^+$): m/z 395.10 [MNa$^+$].

Step 4: Synthesis of methyl 4-({5-[2-(tert-butoxy)-2-oxoethoxy]pentyl}oxy)benzoate

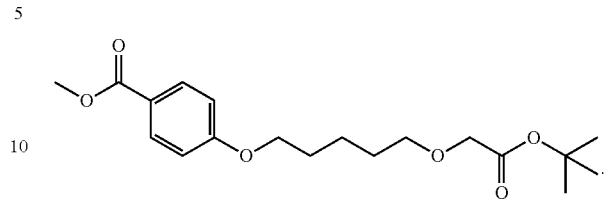

To a stirred mixture of tert-butyl 2-({5-[(4-methylbenzenesulfonyl)oxy]pentyl}oxy)acetate (1.0 g, 2.7 mmol) and potassium carbonate (266 mg, 1.6 mmol) in acetonitrile (15 mL) was added methyl 4-hydroxybenzoate (500 mg, 3.29 mmol) at rt. The resulting mixture was refluxed overnight. TLC showed formation of desired product. The reaction mixture was cooled to rt. and partitioned between ethyl acetate (150 mL) and water (50 mL). The organic layer was washed with washed with brine (50 mL), dried over anhydrous sodium sulfate, and concentrated under reduced pressure to give a crude residue which was purified by silica gel flash chromatography (eluent 10% ethyl acetate in hexane) to afford methyl 4-({5-[2-(tert-butoxy)-2-oxoethoxy]pentyl}oxy)benzoate (yield 33%) as colorless oil. Mass (ES$^+$): m/z 353.10 [M+Na$^+$]; $^1$H NMR (400 MHz, CDCl$_3$): δ 1.48 (s, 9H), 1.55-1.61 (m, 2H), 1.68-1.72 (m, 2H), 1.80-1.87 (m, 2H), 3.55 (t, J=6.4 Hz, 2H), 3.88 (s, 3H), 3.96 (s, 2H), 4.02 (t, J=6.4 Hz, 2H), 6.89 (d, J=9.2 Hz, 2H), 7.97 (d, J=9.2 Hz, 2H).

Step 5: Synthesis of 2-({5-[4-(methoxycarbonyl)phenoxy]pentyl}oxy)acetic Acid

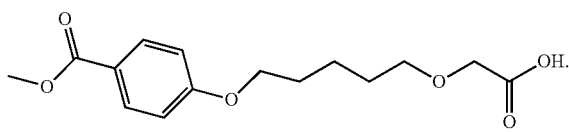 [SMILES: COC(=O)c1ccc(OCCCCCOCC(=O)O)cc1]

To a stirred solution of methyl 4-({5-[2-(tert-butoxy)-2-oxoethoxy]pentyl}oxy)benzoate (300 mg, 0.85 mmol) in DCM (4 mL) was added and TFA (2 ml) at rt, the resulting solution was stirred at room temperature for 1 h. TLC showed formation of the desired product. The solvent was evaporated to afford 2-({5-[4-(methoxycarbonyl)phenoxy]pentyl}oxy)acetic acid (200 mg, crude) as yellow oil which was used in next step without further purification.

Examples 151-157 were synthesized according to similar procedure described for synthesis of example 150, by using corresponding starting materials and intermediates.

TABLE 9

Exemplary Compounds.

| Ex # | Structure | Compound name and Analytical data |
| --- | --- | --- |
| 162 | 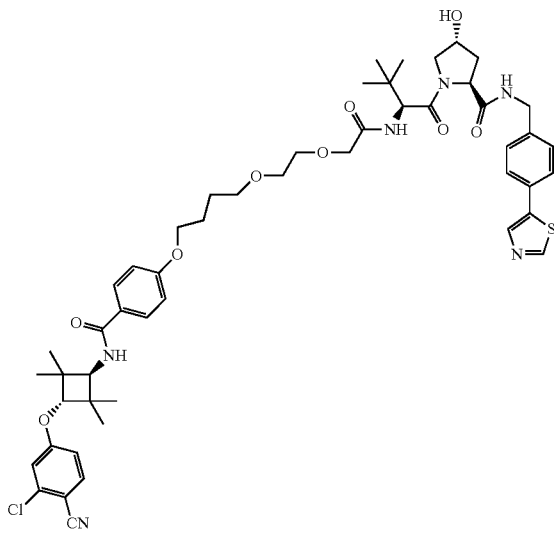 [SMILES: CC(C)(C)[C@H](NC(=O)COCCOCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2cncs2)cc1] | (2S,4R)-1-[(2S)-3,3-dimethyl-2-(2-{2-[4-(4-{[trans-3-(3-chloro-4-cyanophenoxy)-2,2,4,4-tetramethylcyclobutyl]carbamoyl}phenoxy)butoxy]ethoxy}acetamido)butanoyl]-4-hydroxy-N-{[4-(1,3-thiazol-5-yl)phenyl]methyl}pyrrolidine-2-carboxamide <br> $^1$H NMR (400 MHz, CDCl$_3$): δ 0.95 (s, 9H), 1.22 (s, 6H), 1.27 (s, 6H), 1.74-1.80 (m, 4H), 2.09-2.14 (m, 1H), 2.53-2.60 (m, 1H), 3.54-3.69 (m, 8H), 3.99-4.05 (m, 5H), 4.12-4.16 (m, 2H), 4.28-4.33 (m, 1H), 4.46-4.58 (m, 3H), 4.72 (t, J = 8.0 Hz, 1H), 6.20 (d, J = 8.0 Hz, 1H), 6.79-6.97 (m, 4H), 7.26-7.33 (m, 3H), 7.49 (d, J = 8.0 Hz, 2H), 7.57 (d, J = 8.8 Hz, 1H), 7.72 (d, J = 8.4 Hz, 2H), 8.03 (s, 1H), 8.78 (s, 1H). LC-MS: (ES$^+$): m/z 971.20 [M + H$^+$] |
| 163 | 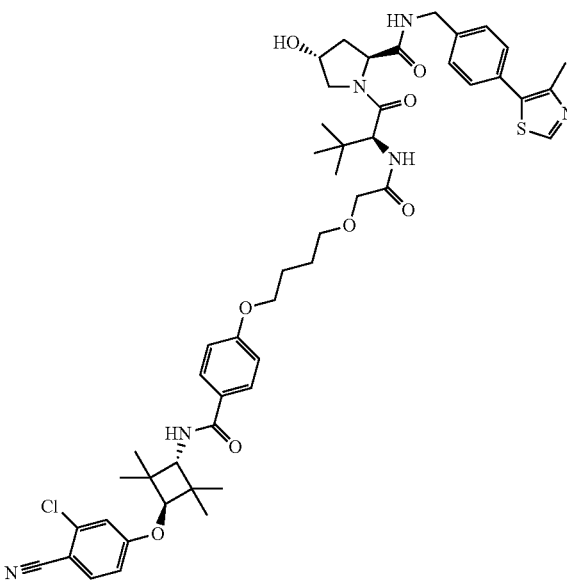 | (2S,4R)-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxy-N-{[4-(4-methyl-1,3-thiazol-5-yl)phenyl]methyl}pyrrolidine-2-carboxamide <br> $^1$H NMR (400 MHz, CD$_3$OD) δ ppm 8.85 (s, 1H), 7.75-7.81 (m, 2H), 7.72 (d, J = 9.00 Hz, 1H), 7.44-7.50 (m, 2H), 7.38-7.43 (m, 2H), 7.13 (d, J = 2.35 Hz, 1H), 6.94-7.02 (m, 3H), 4.70 (s, 1H), 4.54-4.61 (m, 2H), 4.48-4.54 (m, 2H), 4.36 (d, J = 15.65 Hz, 1H), 4.28 (s, 1H), 4.14 (s, 1H), 4.10 (t, J = 6.06 Hz, 2H), 4.01 (d, J = 7.43 Hz, 2H), 3.85-3.90 (m, 1H), 3.77-3.84 (m, 1H), 3.64 (t, J = 6.26 Hz, 2H), 2.45 (s, 3H), 2.24 (dd, J = 13.30, 7.43 Hz, 1H), 2.09 (ddd, J = 13.21, 9.10, 4.30 Hz, 1H), 1.89-1.98 (m, 2H), 1.80-1.88 (m, 2H), 1.28 (s, 6H), 1.22 (s, 6H), 0.99-1.06 (m, 9H); LC-MS (ES$^+$): m/z 941.41 [MH$^+$] |

TABLE 9-continued

Exemplary Compounds.

| Ex # | Structure | Compound name and Analytical data |
|---|---|---|
| 164 | 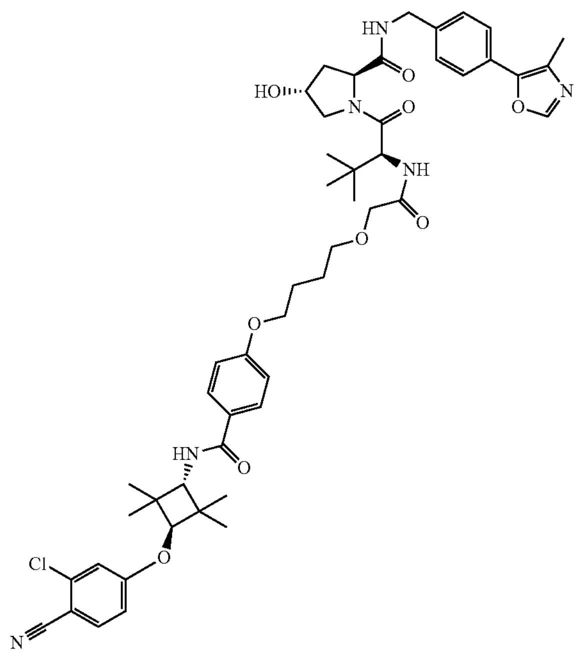 [SMILES: Cc1ncoc1-c1ccc(CNC(=O)[C@@H]2C[C@@H](O)CN2C(=O)[C@@H](NC(=O)COCCCCOc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxy-N-{[4-(4-methyl-1,3-oxazol-5-yl)phenyl]methyl}pyrrolidine-2-carboxmide<br>$^1$H NMR (400 MHz, CD$_3$OD) δ ppm 8.12 (s, 1H), 7.75-7.81 (m, 2H), 7.72 (d, J = 9.00 Hz, 1H), 7.56-7.64 (m, 2H), 7.47 (d, J = 8.61 Hz, 2H), 7.13 (d, J = 2.35 Hz, 1 H), 6.95-7.03 (m, 3H), 4.70 (s, 1H), 4.56-4.61 (m, 1H), 4.55 (s, 1H), 4.46-4.53 (m, 2H), 4.35 (d, J = 15.65 Hz, 1H), 4.28 (s, 1H), 4.12-4.15 (m, 1H), 4.06-4.12 (m, 2H), 3.98-4.03 (m, 2H), 3.85-3.92 (m, 1H), 3.78-3.84 (m, 1H), 3.65 (t, J = 6.06 Hz, 2H), 2.38 (s, 3H), 2.19-2.28 (m, 1H), 2.08 (ddd, J = 13.30, 9.19, 4.50 Hz, 1H), 1.91-1.98 (m, 2H), 1.82-1.89 (m, 2H), 1.28 (s, 6H), 1.22 (s, 6H), 1.04 (s, 9 H); LC-MS (ES$^+$): m/z 925.43 [MH$^+$] |
| 165 | 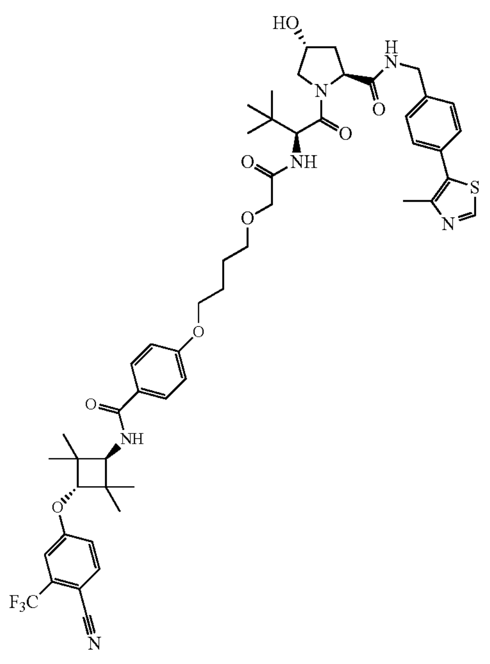 | (2S,4R)-1-[(2S)-3,3-dimethyl-2-{2-[4-(4-{[trans-3-[4-cyano-3-(trifluoromethyl)phenoxy]-2,2,4,4-tetramethylcyclobutyl]carbamoyl}phenoxy)butoxy]acetamido}butanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.88 (s, 1H), 7.75-7.67 (m, 3H), 7.44-7.36 (m, 4H), 7.09 (s, 1H), 6.96-6.91 (m, 3H), 4.84 (s, 1H), 4.66-4.47 (m, 4H), 4.36-4.31 (m, 1 H), 4.26 (s, 1H), 4.24 (s, 1H), 4.10 (s, 1H), 3.93-3.91 (m, 2H), 3.83-5.78 (m, 2H), 3.55-3.51 (m, 2H), 2.43 (s, 3H), 2.12-2.10 (m, 1H), 2.09-1.95 (m, 1H), 1.67-1.62 (m, 6H), 1.30-1.28 (m, 9H), 1.18 (s, 6H), 1.00 (s, 9H); LC-MS (ES$^+$): m/z 969.10 [MH$^+$] |

TABLE 9-continued

Exemplary Compounds.

| Ex # | Structure | Compound name and Analytical data |
|---|---|---|
| 166 | 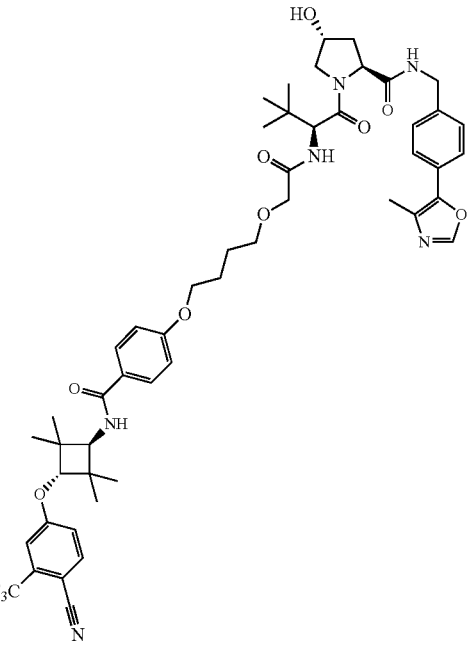 | (2S,4R)-1-[(2S)-3,3-dimethyl-2-{2-[4-(4-{[trans-3-[4-cyano-3-(trifluoromethyl)phenoxy]-2,2,4,4-tetramethylcyclobutyl]carbamoyl}phenoxy)butoxy]acetamido}butanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD): 8.09 (s, 1H), 7.89 (d, 1H), 7.80-7.70 (m, 2H), 7.69-7.50 (m, 2H), 7.49-7.40 (m, 2H), 7.32 (s, 1H), 7.28-7.08 (m, 1H), 7.00-6.82 (m, 2H), 4.72 (s, 1H), 4.60-4.40 (m, 3H), 4.39-4.20 (m, 2H), 4.19-4.00 (m, 3H), 3.99-3.95 (m, 2H), 3.92-3.70 (m, 2H), 3.69-3.53 (m, 2H), 2.40-2.32 (m, 3H), 2.30-2.18 (m, 1H), 2.15-2.01 (m, 1H), 2.00-1.60 (m, 4H), 1.35-1.28 (m, 6H), 1.25-1.15 (m, 6H), 1.03-1.00 (m, 9H); LC-MS (ES$^+$): m/z 959.60 [MH$^+$]. |
| 167 | 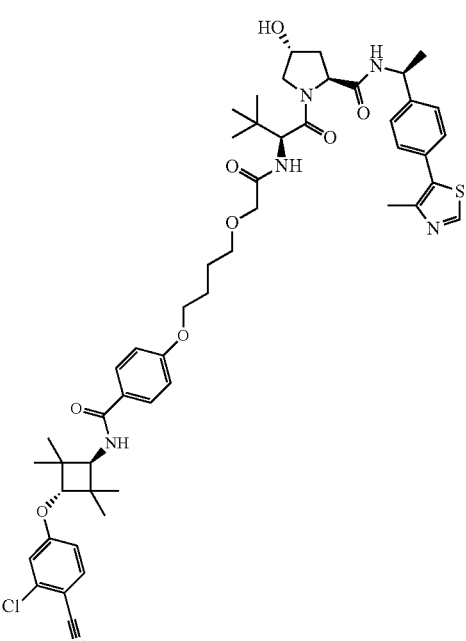 | (2S,4R)-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, CD$_3$OD): 8.82 (s, 1H), 7.81-7.75 (m, 2H), 7.74-7.62 (s, 1H), 7.61-7.53 (m, 2H), 7.49-7.35 (m, 2H), 7.19-7.10 (s, 1H), 7.08-6.80 (m, 3H), 5.08-4.91 (m, 1H), 4.65 (s, 1H), 4.60-4.59 (m, 1H), 4.45-4.36 (m, 1H), 4.22 (s, 1H), 4.11-4.05 (m, 3H), 4.01-3.96 (m, 2H), 3.95-3.70 (m, 2H), 3.69-3.45 (m, 2H), 2.40-2.35 (m, 3H), 2.21-2.04 (s, 1H), 2.00-1.70 (m, 4H), 1.60-1.40 (m, 3H), 1.21-1.12 (m, 12H), 1.00-0.95 (m, 9H); LC-MS (ES$^+$): m/z 478.45 [(M/2)H$^+$] |

TABLE 9-continued

Exemplary Compounds.

| Ex # | Structure | Compound name and Analytical data |
|---|---|---|
| 168 | 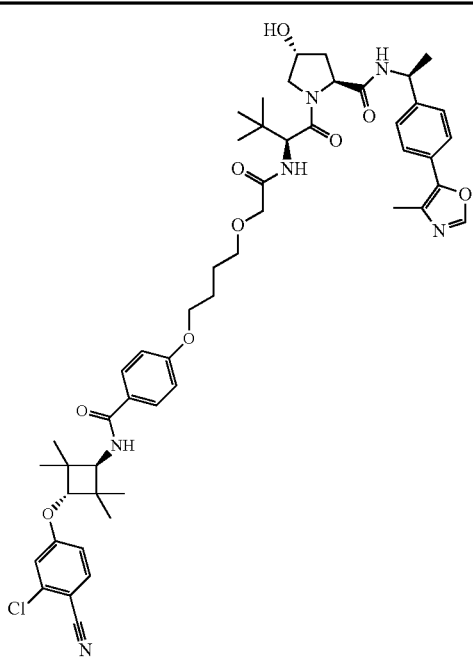 | (2S,4R)-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxy-N-[(1S)-1-[4-(4-methyl-1,3-oxazol-5-yl)phenyl]ethyl]pyrrolidine-2-carboxamide<br>$^1$H NMR (400 MHz, CD$_3$OD): 8.82 (s, 1H), 7.81-7.75 (m, 2H), 7.74-7.62 (s, 1H), 7.61-7.53 (m, 2H), 7.49-7.35 (m, 2H), 7.19-7.10 (s, 1H), 7.08-6.80 (m, 3H), 5.08-4.91 (m, 1H), 4.65 (s, 1H), 4.60-4.59 (m, 1H), 4.45-4.36 (m, 1H), 4.22 (s, 1H), 4.11-4.05 (m, 3H), 4.01-3.96 (m, 2H), 3.95-3.70 (m, 2H), 3.69-3.45 (m, 2H), 2.40-2.35 (m, 3H), 2.21-2.04 (s, 1H), 2.00-1.70 (m, 4H), 1.60-1.40 (m, 3H), 1.21-1.12 (m, 12H), 1.00-0.95 (m, 9H); LC-MS (ES$^+$): m/z 478.45 [MH$^+$] |
| 169 | 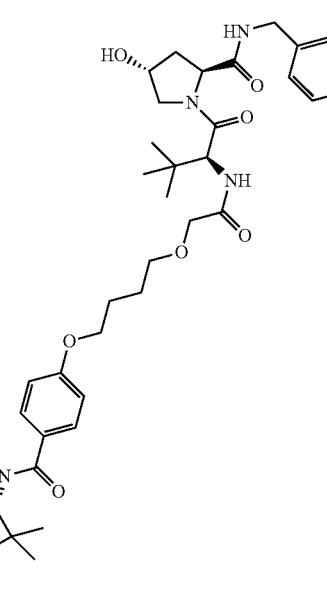 | (2S,4R)-N-[(4-chlorophenyl)methyl]-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxypyrrolidine-2-carboxamide<br>$^1$H NMR (400 MHz, CD$_3$OD) δ ppm 7.80 (d, J = 8.61 Hz, 2H), 7.72 (d, J = 9.00 Hz, 1H), 7.24-7.37 (m, 4H), 7.13 (d, J = 2.35 Hz, 1H), 6.94-7.04 (m, 3H), 4.69 (s, 1H), 4.54 (dd, J = 8.80, 7.63 Hz, 1H), 4.43-4.51 (m, 2H), 4.24-4.32 (m, 2H), 4.08-4.16 (m, 3H), 3.95-4.06 (m, 2H), 3.84-3.90 (m, 1H), 3.76-3.83 (m, 1H), 3.65 (t, J = 6.26 Hz, 2H), 2.21 (dd, J =13.11, 7.63 Hz, 1H), 2.06 (ddd, J = 13.30, 9.19, 4.50 Hz, 1H), 1.90-1.98 (m, 2H), 1.80-1.89 (m, 2H), 1.28 (s, 6H), 1.22 (s, 6H), 0.95-1.15 (m, 9H); LC-MS (ES$^+$): m/z 878.28[MH$^+$] |

TABLE 9-continued

Exemplary Compounds.

| Ex # | Structure | Compound name and Analytical data |
|---|---|---|
| 170 | 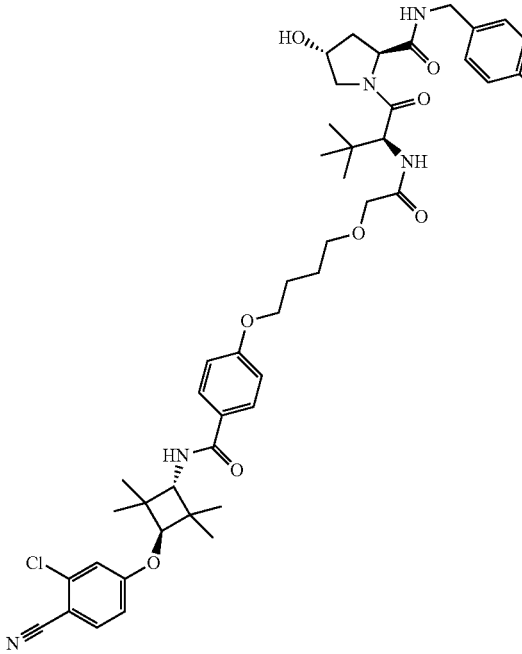 | (2S,4R)-N-[(4-cyanophenyl)methyl]-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxypyrrolidine-2-carboxamide<br>$^1$H NMR (400 MHz, CD$_3$OD) δ ppm 7.80 (d, J = 8.61 Hz, 2H), 7.72 (d, J = 8.61 Hz, 1H), 7.64 (d, J = 8.22 Hz, 2H), 7.54 (d, J = 8.22 Hz, 2H), 7.13 (d, J = 2.35 Hz, 1H), 6.94-7.05 (m, 3H), 4.69 (s, 1H), 4.49-4.62 (m, 4H), 4.34 (d, J = 16.04 Hz, 1H), 4.29 (s, 1H), 4.08-4.17 (m, 3H), 3.95-4.06 (m, 2H), 3.85-3.91 (m, 1H), 3.80 (dd, J = 11.15, 3.72 Hz, 1H), 3.65 (t, J = 6.06 Hz, 2H), 2.23 (dd, J = 13.11, 7.63 Hz, 1H), 2.06 (ddd, J = 13.11, 9.19, 4.30 Hz, 1H), 1.90-1.99 (m, 2H), 1.81-1.90 (m, 2H), 1.28 (s, 6H), 1.22 (s, 6H), 0.92-1.18 (m, 9H); LC-MS (ES$^+$): m/z 869.32 [MH$^+$] |
| 171 | 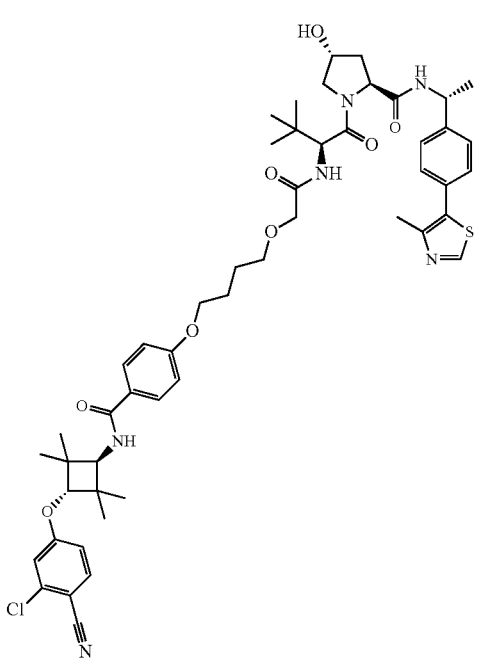 [SMILES: Cc1ncsc1-c1ccc([C@@H](C)NC(=O)[C@@H]2C[C@@H](O)CN2C(=O)[C@@H](NC(=O)COCCCCOc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-{2-[4-(4-{[trans-3-(3-chloro-4-cyanophenoxy)-2,2,4,4-tetramethylcyclobutyl]carbamoyl}phenoxy)butoxy]acetamido}butanoyl]-4-hydroxy-N-[(1R)-1-[4-(4-methyl-1,3-thiazol-5-yl)phenyl]ethyl]pyrrolidine-2-carboxamide<br>$^1$H NMR (400 MHz, CD$_3$OD) δ 8.85 (s, 1H), 7.79 (m, 3H), 7.58 (d, J = 8.4 Hz, 2H), 7.42 (d, J = 8.0 Hz, 2H), 7.15 (s, 1H), 7.01 (m, 3H), 5.00 (m, 1H), 4.69 (m, 2H), 4.53 (s, 1H), 4.30 (s, 1H), 4.16 (s, 1H), 4.13 (m, 2H), 4.01 (s, 2H), 3.91-3.85 (m, 1H), 3.85-3.78 (m, 1H), 3.65 (m, 2H), 2.46 (s, 3H), 2.30-2.19 (m, 1H), 2.18-2.05 (m, 1H), 1.99-1.92 (m, 2H), 1.89-1.82 (m, 2H), 1.53 (m, 3H), 1.30 (s, 6H), 1.24 (s, 6H), 0.92 (s, 9H); Mass (ES$^+$): m/z 955.45 [MH$^+$] |

Synthesis of Example 163
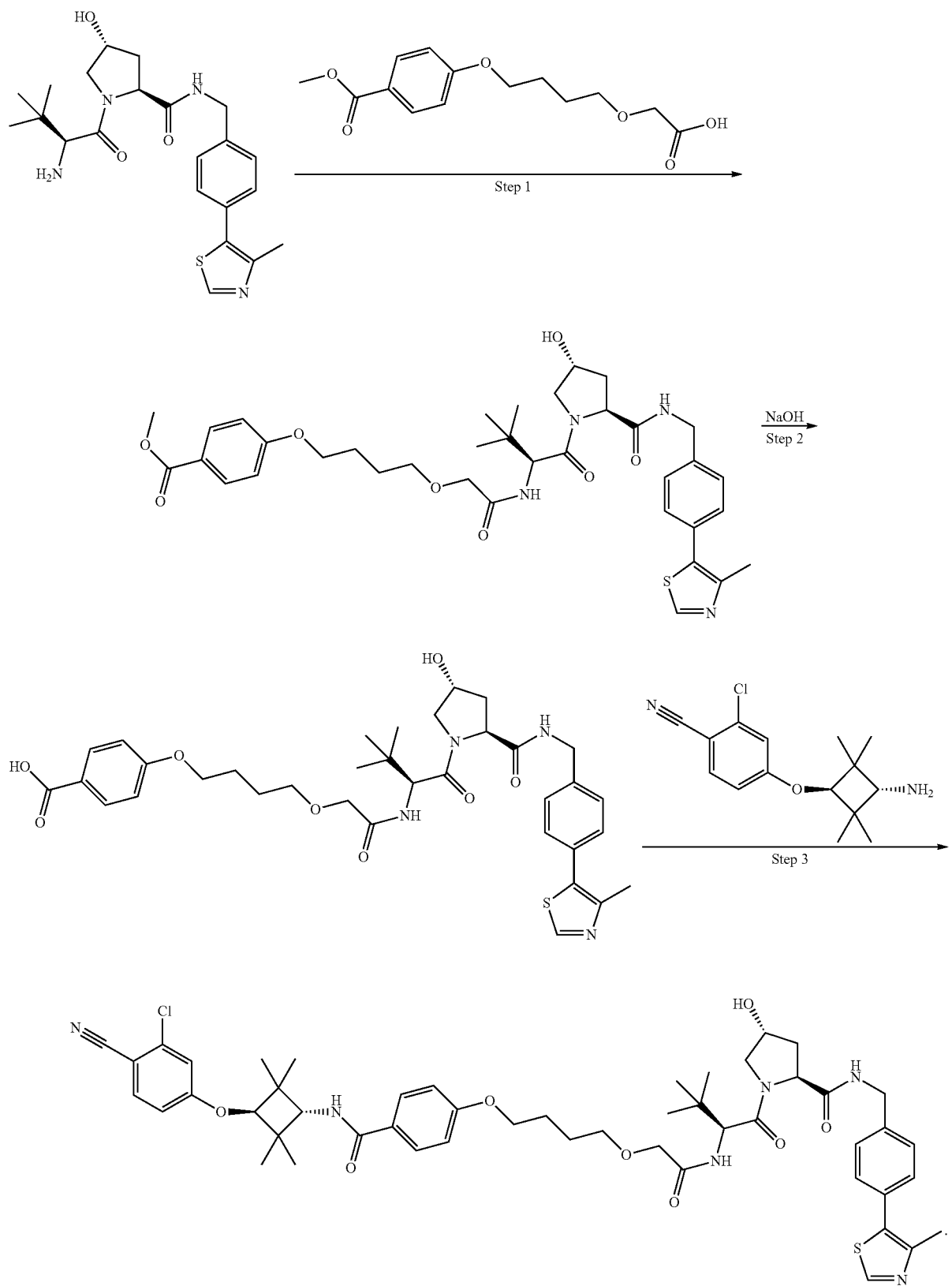
Example 163

Step 1: synthesis of methyl 4-[4-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)butoxy]benzoate

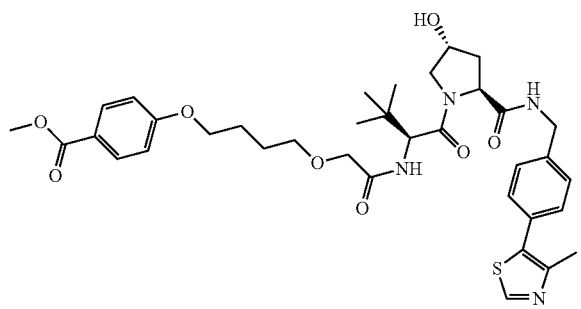

To a stirred solution of 2-{4-[4-(methoxycarbonyl)phenoxy]butoxy}acetic acid (22.0 mg, 77.9 µmol) and (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (36.3 mg, 77.9 µmol) in methylene chloride (2.0 mL) was added O-(benzotriazol-1-yl)-N,N,N',N'-tetramethyluronium tetrafluoroborate (25.0 mg, 77.9 µmol) and diisopropylethylamine (40.5 µL, 233 µmol) at rt. The reaction mixture was stirred at rt for 30 minutes, LC-MS indicated formation of the desired product. The reaction mixture was concentrated under reduced pressure. The crude material was purified by flash silica gel chromatography on a Teledyne Combiflash ISCO (gradient eluent: Heptane/Acetone (v:v=100:0 to 0:100)) to give the titled product (yield: 78%) as a white solid. LC-MS (ES+): m/z 695.3138 [MH+].

Step 2: Synthesis of 4-[4-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)butoxy]benzoic Acid

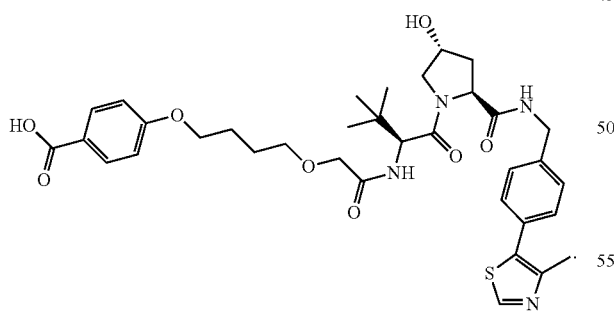

To a stirred solution of methyl 4-[4-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)butoxy]benzoate (42.4 mg, 61.0 µmol) in methanol (2.0 mL) was added 1 M NaOH in water (0.5 mL, 12.5 mmol) at rt. The reaction mixture was stirred at rt for 16 hours. LC-MS indicated formation of the desired product. The reaction mixture was quenched with 1.0 M aqueous HCl and then concentrated under reduced pressure to remove the methanol. The aqueous residue was extracted with EtOAc (15 mL×2). The organic layer was washed with brine (5 mL), dried over Na₂SO₄, filtered and concentrated under reduced pressure to give the titled product (yield: 82%) as a white solid. The material was used in next step without any further purification. Mass (ES+): m/z 681.2986 [MH+].

Step 3: Synthesis of Example 163

To a stirred solution of 2-chloro-4-[trans-3-amino-2,2,4,4-tetramethylcyclobutoxy]benzonitrile (13.9 mg, 50.2 µmol) and 4-[4-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)butoxy]benzoic acid (34.2 mg, 50.2 µmol) in methylene chloride (2.0 mL) was added O-(benzotriazol-1-yl)-N,N,N',N'-tetramethyluronium tetrafluoroborate (16.1 mg, 50.2 µmol) and diisopropylethylamine (26.0 µL, 150 µmol) at rt. The reaction mixture was stirred at rt for 1.5 hours. LC-MS indicated formation of the desired product. The reaction mixture was quenched with water (5 mL) and extracted with DCM (15 mL×3). The organic layers were combined, washed with aqueous NaHCO₃ (5 mL), brine (5 mL), dried over Na₂SO₄, filtered and concentrated under reduced pressure to give a crude material, which was purified by flash silica gel chromatography on a Teledyne Combiflash ISCO (eluent: DCM/MeOH (v:v=90:10)) to give the titled product (yield: 39%) as an off white solid.

Synthesis of 2-{4-[4-(methoxycarbonyl)phenoxy]butoxy}acetic Acid

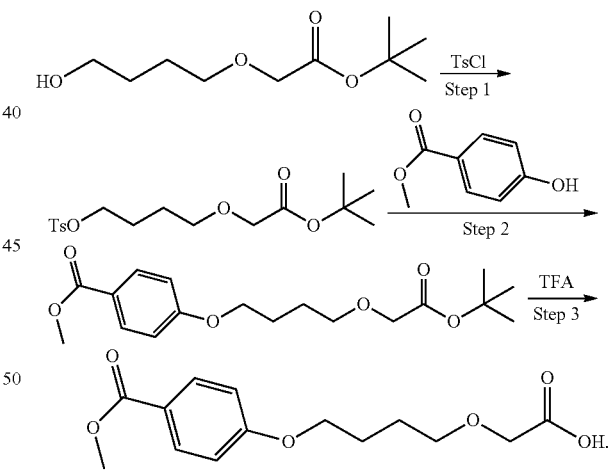

Step 1: synthesis of tert-butyl 2-{4-[(4-methylbenzenesulfonyl)oxy]butoxy}acetate

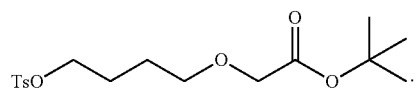 [SMILES: Cc1ccc(S(=O)(=O)OCCCCOCC(=O)OC(C)(C)C)cc1]

This material was synthesized from tert-butyl 2-(4-hydroxybutoxy)acetate and 4-toluenesulfonyl chloride according to similar procedures described above for the synthesis of tert-butyl 2-({5-[(4-methylbenzenesulfonyl)oxy]pentyl}oxy)acetate.

Step 2: synthesis of methyl 4-{4-[2-(tert-butoxy)-2-oxoethoxy]butoxy}benzoate

To a stirred mixture of methyl 4-hydroxybenzoate (27.99 mg, 184.0 μmol) and tert-butyl 2-{4-[(4-methylbenzenesulfonyl)oxy]butoxy}acetate in acetonitrile (2.0 mL) was added potassium carbonate (34.67 mg, 250.9 μmol) at rt. The reaction mixture was then stirred at 80° C. for 16 hours. LC-MS indicated formation of the desired product. The reaction mixture was concentrated under reduced pressure to give a crude residue, which was purified by flash silica gel chromatography on a Teledyne Combiflash ISCO (gradient eluent: heptane/acetone (v:v=100:0 to 50:50)) to give the titled product (yield: 94%) as a clear oil. Mass (ES+): m/z 361.16 [M+Na].

Step 3: Synthesis of Synthesis of 2-{4-[4-(methoxycarbonyl)phenoxy]butoxy}acetic Acid To a stirred solution of methyl 4-{4-[2-(tert-butoxy)-2-oxoethoxy]butoxy}benzoate (53.1 mg, 156 μmol) in dichloromethane (1.0 mL) was added trifluoroacetic acid (1.0 mL, 12.9 mmol) at rt. The reaction mixture was then stirred at rt for 30 minutes. LC-MS indicated formation of the desired product. The reaction mixture was concentrated under reduced pressure to give the titled product (yield: 99% based on crude material) as an off white solid. The crude material was then used in next step without any further purification. Mass (ES+): m/z 305.10.

Examples 162, 164-171 were synthesized according to similar procedure described for synthesis of example 163, by using corresponding starting materials and intermediates.

TABLE 10

Exemplary Compounds.

| Ex# | Structure | Compound name and Analytical data |
|---|---|---|
| 172 | 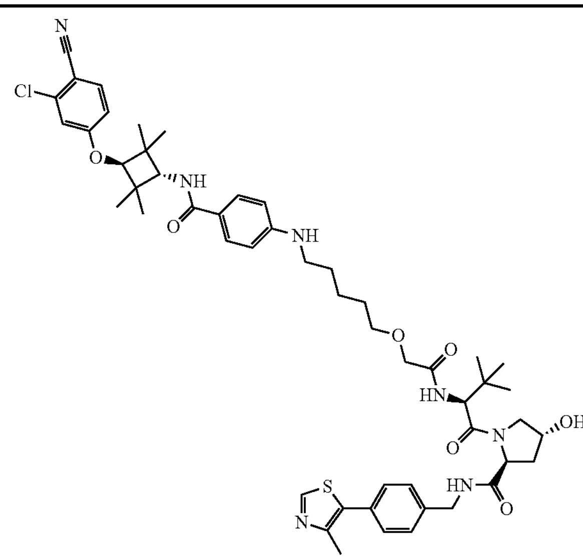 | (2S,4R)-1-[(2S)-3,3-dimethyl-2-[2-({5-[(4-{[trans-3-(3-chloro-4-cyanophenoxy)-2,2,4,4-tetramethylcyclobutyl]carbamoyl}phenyl)amino]pentyl}oxy)acetamido]butanoyl]-4-hydroxy-N-{[4-(4-methyl-1,3-thiazol-5-yl)phenyl]methyl}pyrrolidine-2-carboxamide <br>1H NMR (400 MHz, CDCl3) δ 8.68 (s, 1H), 7.63 (d, J = 8.6 Hz, 2H), 7.57 (d, J = 8.6 Hz, 1H), 7.35 (q, J = 8.5 Hz, 4H), 6.97 (d, J = 2.3 Hz, 1H), 6.81 (dd, J = 2.5, 8.8 Hz, 1H), 6.60 (d, J = 9.0 Hz, 2H), 6.07-6.12 (m, 1H), 4.74 (s, 1H), 4.50-4.59 (m, 3H), 4.37 (d, J = 5.1 Hz, 1H), 4.11-4.17 (m, 2H), 3.64 (dd, J = 3.5, 11.3 Hz, 1H), 3.53 (d, J = 7.0 Hz, 2H), 3.19 (t, J = 7.0 Hz, 2H), 2.55-2.61 (m, 1H), 2.52 (s, 3H), 2.10-2.19 (m, 2H), 1.65-1.71 (m, 4H), 1.50-1.53 (m, 2H), 1.24-1.33 (m, 9H), 1.22 (s, 6H), 0.96 (s, 9H), 0.86-0.91 (m, 3H). LC-MS (ES+): m/z 955.43 [MH+] |
| 173 | 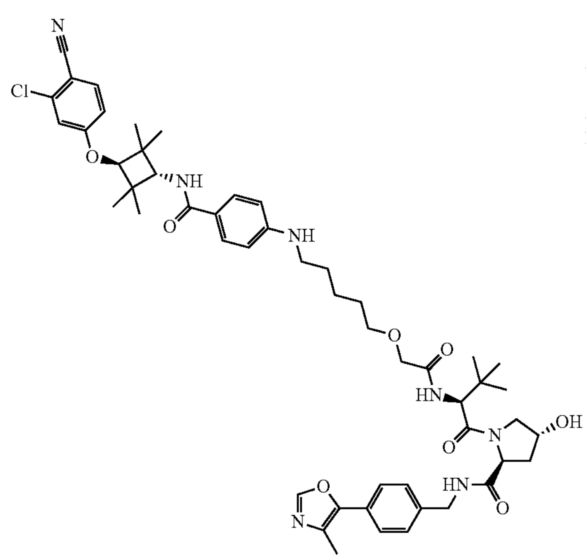 | (2S,4R)-1-[(2S)-3,3-dimethyl-2-[2-({5-[(4-{[trans-3-(3-chloro-4-cyanophenoxy)-2,2,4,4 tetramethylcyclobutyl]carbamoyl}phenyl)amino]pentyl}oxy)acetamido]butanoyl]-4-hydroxy-N-{[4-(4-methyl-1,3-oxazol-5-yl)phenyl]methyl}pyrrolidine-2-carboxamide <br>1H NMR (400 MHz, CDCl3) δ 7.82 (s, 1H), 7.63 (d, J = 8.6 Hz, 2H), 7.53 (d, J = 8.6 Hz, 2H), 7.35 (s, 2H), 7.18-7.21 (m, 1H), 6.97 (d, J = 2.3 Hz, 1H), 6.81 (dd, J = 2.3, 8.6 Hz, 1H), 6.59 (d, J = 8.6 Hz, 2H), 6.08-6.12 (m, 1H), 4.73 (t, J = 8.0 Hz, 1H), 4.49-4.60 (m, 3H), 4.32-4.39 (m, 1H), 4.11-4.17 (m, 2H), 3.63 (dd, J = 3.5, 11.3 Hz, 1H), 3.49-3.57 (m, 2H), 3.18 (t, J = 6.8 Hz, 2H), 2.53-2.61 (m, 1H), 2.42 (s, 3H), 2.08-2.18 (m, 2H), 1.68 (td, J = 7.2, 14.5 Hz, 4H), 1.50-1.53 (m, 2H), 1.26 (d, J = 0.8 Hz, 9H), 1.22 (s, 6H), 0.96 (s, 9H), 0.86-0.91 (m, 3H). LC-MS (ES+): m/z 939.46 [MH+] |

TABLE 10-continued

Exemplary Compounds.

| Ex# | Structure | Compound name and Analytical data |
|---|---|---|
| 174 | 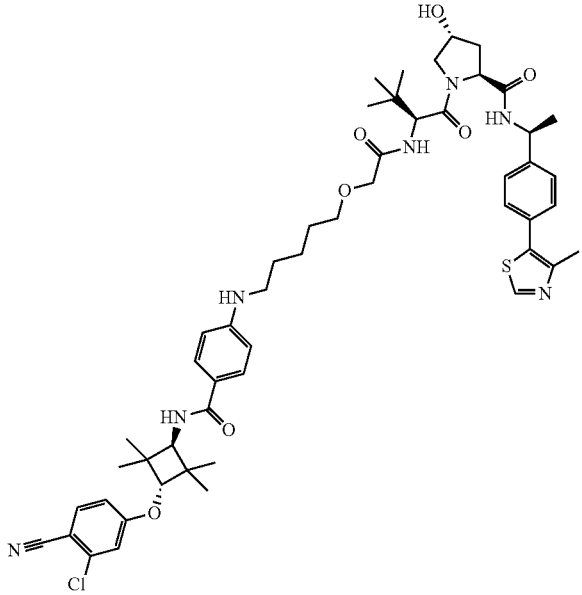 [SMILES: Cc1ncsc1-c1ccc([C@H](C)NC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-[2-({5-[(4-{[trans-3-(3-chloro-4-cyanophenoxy)-2,2,4,4-tetramethylcyclobutyl]carbamoyl}phenyl)amino]pentyl}oxy)acetamido]butanoyl]-4-hydroxy-N-[(1S)-1-[4-(4-methyl-1,3-thiazol-5-yl)phenyl]ethyl]pyrrolidine-2-carboxamide $^1$H NMR (300 MHz, CD$_3$OD): δ 8.88 (s, 1H), 7.80-7.65 (m, 3H), 7.50-7.33 (m, 4H), 7.16 (s, 1H), 7.03-6.93 (m, 1H), 6.54-6.43 (m, 2H), 5.02-4.95 (m, 1H), 4.67 (s, 1H), 4.65-4.50 (m, 1H), 4.46-4.40 (m, 1H), 4.29-4.25 (m, 1H), 4.20-4.15 (m, 1H), 4.04-3.90 (m, 2H), 3.89-3.85 (m, 1H), 3.80-3.73 (m, 1H), 3.66-3.52 (m, 2H), 3.20-3.10 (m, 2H), 2.40 (s, 3H), 2.25-1.95 (m, 1H), 2.02-1.90 (m, 1H), 1.80-1.68 (m, 4H), 1.65-1.50 (m, 2H), 1.49-1.43 (m, 2H), 1.30-1.23 (m, 6H), 1.22-1.15 (m, 6H), 1.01 (s, 9H); LC-MS (ES$^+$): m/z, 968.40 [MH$^+$] |
| 175 | 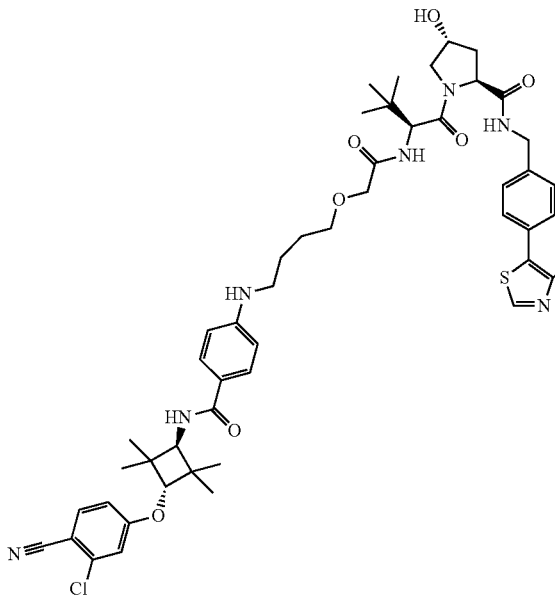 | (2S,4R)-1-[(2S)-3,3-dimethyl-2-(2-{4-[(4-{[trans-3-(3-chloro-4-cyanophenoxy)-2,2,4,4-tetramethylcyclobutyl]carbamoyl}phenyl)amino]butoxy}acetamido)butanoyl]-4-hydroxy-N-{[4-(4-methyl-1,3-thiazol-5-yl)phenyl]methyl}pyrrolidine-2-carboxamide $^1$H NMR (300 MHz, CD$_3$OD): δ 8.88 (s, 1H), 7.750-7.65 (m, 3H), 7.50-7.33 (m, 4H), 7.10-7.05 (m, 1H), 6.99-6.90 (m, 1H), 6.54-6.43 (m, 2H), 4.67 (s, 1H), 4.60-4.50 (m, 3H), 4.48-4.45 (m, 1H), 4.21 (s, 1H), 4.13-4.05 (m, 1H), 3.98-3.90 (m, 2H), 3.88-3.70 (m, 2H), 3.66-3.48 (m, 2H), 3.20-3.03 (m, 2H), 2.40 (s, 3H), 2.25-2.12 (m, 1 H), 2.09-1.99 (m, 1H), 1.80-1.68 (m, 4H), 1.30-1.10 (m, 12H), 1.01 (s, 9H); LC-MS (ES$^+$): m/z, 940.15 [MH$^+$] |

TABLE 10-continued

Exemplary Compounds.

| Ex# | Structure | Compound name and Analytical data |
|---|---|---|
| 176 | 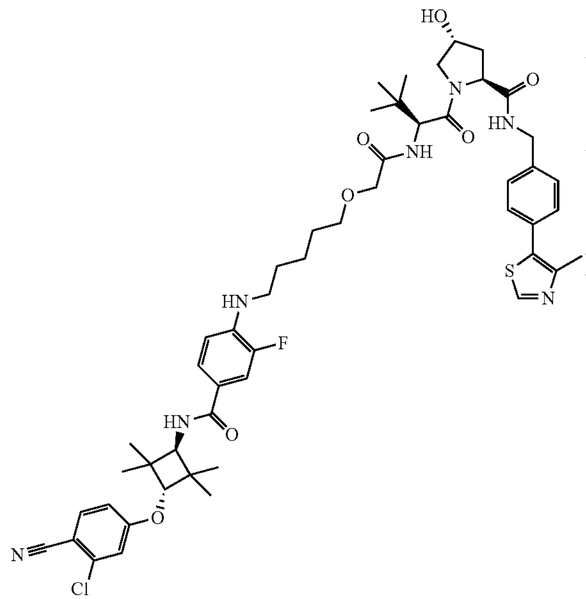 [SMILES: Cc1ncsc1-c1ccc(CNC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2F)C(C)(C)C)cc1] | (2S,4R)-1-[(2S)-2-[2-({5-[(2-fluoro-4-{[trans-3-(3-chloro-4-cyanophenoxy)-2,2,4,4-tetramethylcyclobutyl]carbamoyl}phenyl)amino]pentyl}oxy)acetamido]-3,3-dimethylbutanoyl]-4-hydroxy-N-{[4-(4-methyl-1,3-thiazol-5-yl)phenyl]methyl}pyrrolidine-2-carboxamide<br>$^1$H NMR (300 MHz, CD$_3$OD): δ 8.86 (s, 1H), 7.80-7.70 (m, 1H), 7.60-7.55 (m, 1H), 7.50-7.37 (m, 4H), 7.14 (s, 1H), 7.00-6.93 (m, 1H), 6.80-6.65 (m, 1H), 4.70 (s, 1H), 4.65-4.50 (m, 3H), 4.40-4.30 (m, 1H), 4.29-4.25 (m, 1H), 4.20-4.15 (m, 1H), 4.04-3.90 (m, 2H), 3.89-3.85 (m, 1H), 3.80-3.73 (m, 1H), 3.70-3.65 (m, 1H), 3.60-3.52 (m, 2H), 3.30-3.15 (m, 2H), 2.40 (s, 3H), 2.25-1.95 (m, 1H), 2.02-1.90 (m, 1H), 1.80-1.68 (m, 4H), 1.65-1.50 (m, 2H), 1.30-1.23 (m,6H), 1.22-1.15 (m,6H), 1.01 (s, 9H); LC-MS (ES+): m/z, 972.10 [MH+] |
| 177 | 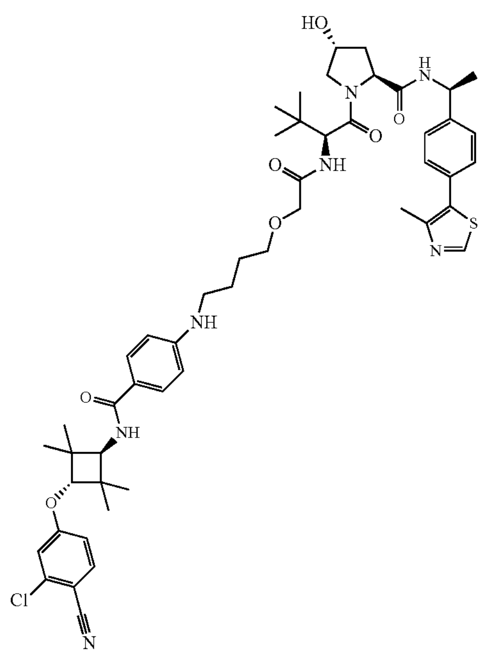 [SMILES: Cc1ncsc1-c1ccc([C@H](C)NC(=O)[C@@H]2C[C@@H](O)CN2C(=O)[C@@H](NC(=O)COCCCCNc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-(2-{4-[(4-{[trans-3-(3-chloro-4-cyanophenoxy)-2,2,4,4-tetramethylcyclobutyl]carbamoyl}phenyl)amino]butoxy}acetamido)butanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, CD3OD) δ 8.86 (s, 1H), 7.72-7.64 (m, 3H), 7.44 (s, 4H), 7.12 (s, 1H), 6.98 (d, J = 2.4 Hz, 1H), 6.64 (d, J = 8.8 Hz, 2H), 5.00 (d, J = 6.8 Hz, 1H), 4.69 (s, 1H), 4.62-4.58 (m, 1H), 4.44 (s, 1H), 4.28 (s, 1H), 4.12 (s, 1H), 4.00-3.93 (m, 2H), 3.87-3.75 (m, 2H), 3.65-3.59 (m, 2H), 3.21 (s, 2H), 2.47 (s, 3H), 2.27-2.15 (m, 1H), 1.95 (m, 1H), 1.76 (s, 4H), 1.58-1.49 (m, 3H), 1.26 (d, J = 9.6 Hz, 12H), 1.02 (s, 9H); Mass (ES$^+$): m/z 955.20 [MH$^+$] |

TABLE 10-continued

Exemplary Compounds.

| Ex# | Structure | Compound name and Analytical data |
|---|---|---|
| 178 | 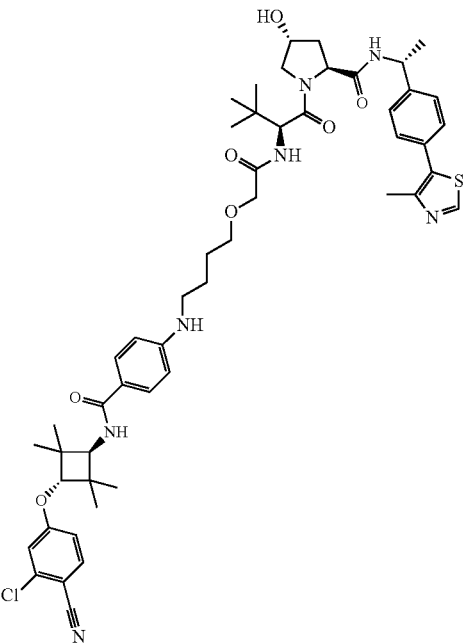 [SMILES: Cc1ncsc1-c1ccc([C@@H](C)NC(=O)[C@@H]2C[C@@H](O)CN2C(=O)[C@@H](NC(=O)COCCCCNc2ccc(C(=O)N[C@H]3C(C)(C)[C@H](Oc4ccc(C#N)c(Cl)c4)C3(C)C)cc2)C(C)(C)C)cc1] | (2S,4R)-1-[(2S)-3,3-dimethyl-2-(2-{4-[(4-{[trans-3-(3-chloro-4-cyanophenoxy)-2,2,4,4-tetramethylcyclobutyl]carbamoyl{phenyl )amino]butoxy}acetamido)butanoyl]-4-hydroxy-N-[(1R)-1-[4-(4-methyl-1,3-thiazol-5-yl)phenyl]ethyl]pyrrolidine-2-carboxamide<br>$^1$H NMR (400 MHz, DMSO) δ 8.96 (s, 1H), 8.49 (d, J = 7.6 Hz, 1H), 7.90 (d, J = 8.8 Hz, 1H), 7. 63 (d, J = 8.4 Hz, 2H), 7.51 (d, J = 8.0 Hz, 2H), 7.42-7.21 (m, 4H), 7.20 (s, 1H), 7.00 (d, J = 8.8 Hz, 1H), 6.55 (d, J = 8.8 Hz, 2H), 6.19 (s, 1H), 5.16 (s, 1H),4.89 (s, 1H), 4.56-4.47 (m, 2H), 4.36-4.40 (m, 2H), 4.03 (d, J= 9.2 Hz, 1H), 3.94 (s, 2H), 3.67-3.57 (m, 2H), 3.56-3.50 (m, 2H), 3.07 (s, 2H), 2.44 (s, 3H), 2.08-2.01 (m, 1H), 1.98-1.92 (m, 1H), 1.64 (m, 4H), 1.38 (d, J = 6.8 Hz, 3H), 1.20 (s,6H), 1.11 (s, 6H), 0.91 (s, 9H); Mass (ES$^+$): m/z 954.15 [MH$^+$]. |

Synthesis of Example 172

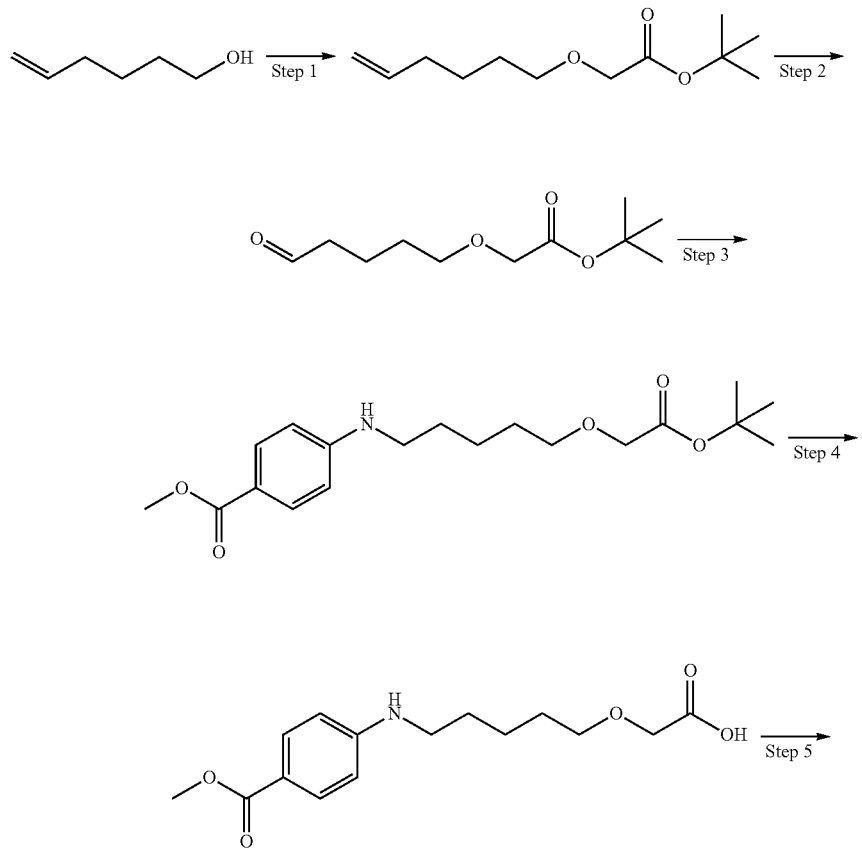

-continued

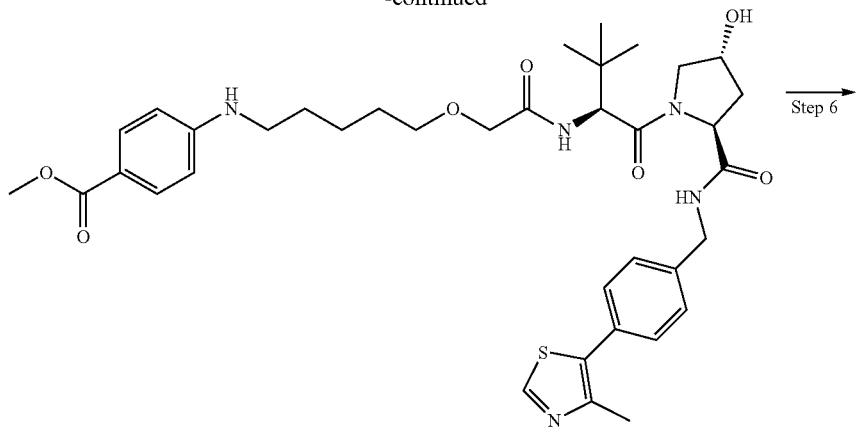

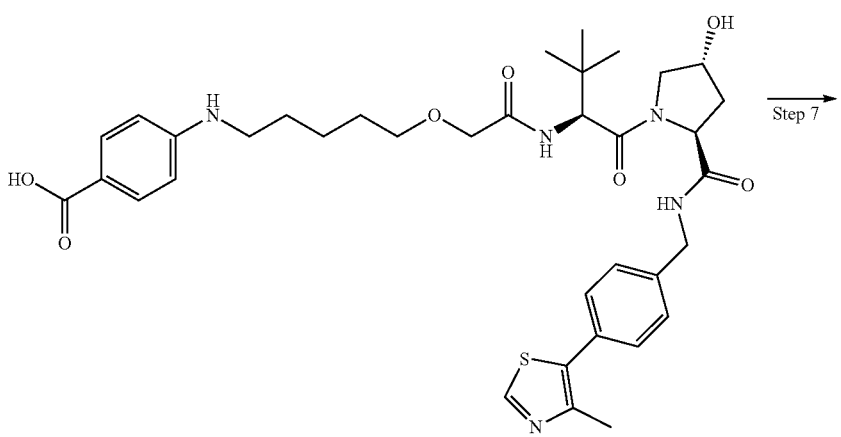

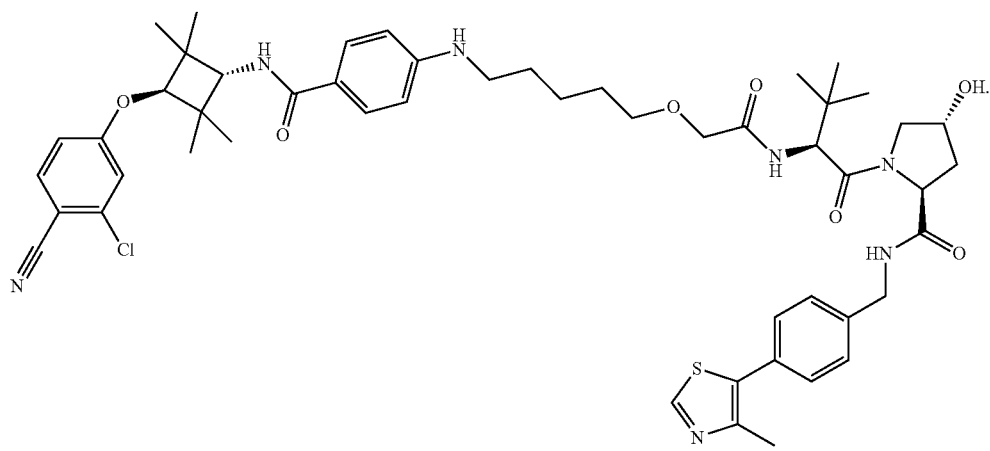

Example 172

Step 7: Synthesis of Example 172

TBTU (21.5 mg, 0.067 mmol) was added to a solution of 4-{[5-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)pentyl]amino}benzoic acid (31 mg, 0.044 mmol), 2-chloro-4-[trans-3-amino-2,2,4,4-tetramethylcyclobutoxy]benzonitrile (12.4 mg, 0.044 mmol) in DMF (3.0 mL) and DIPEA (15.4 μL, 0.089 mmol) at rt. The resulting reaction mixture was stirred at rt for 1 hr. LC-MS indicated formation of the desired product. The reaction mixture was diluted with EtOAc (30 mL), washed with water (15 mL×2), brine (15 mL×1), filtered through a Biotage universal phase separator and then concentrated under reduced pressure to give a crude residue, which was purified by silica gel chromatography on a Teledyne Combiflash ISCO system eluting with MeOH/DCM (v/v=0:100 to 10:90) to yield the desired title product (yield: 41%).

Step 6: Synthesis of 4-{[5-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)pentyl]amino}benzoic Acid

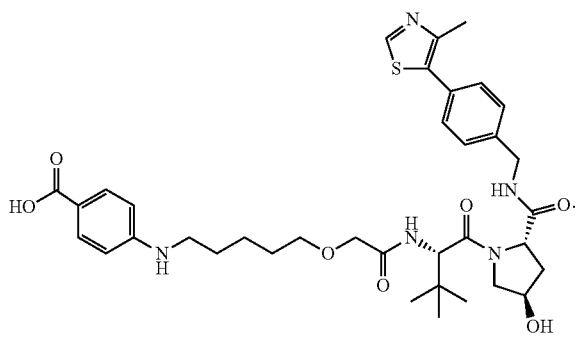 [SMILES: Cc1ncsc1-c1ccc(CNC(=O)[C@@H]2C[C@@H](O)CN2C(=O)[C@@H](NC(=O)COCCCCCNc2ccc(C(=O)O)cc2)C(C)(C)C)cc1]

Lithium hydroxide (9.0 mg, 0.38 mmol) was added to a solution of methyl 4-{[5-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)pentyl]amino}benzoate (96 mg, 0.14 mmol) in a mixed solvent of THF/water/methanol (v/v/v=1/1/1, 2.00 mL) at rt. The resulting mixture was stirred at rt overnight. Aqueous HCl (1 N) was added to the reaction mixture to adjust pH to ~3. The resulting mixture was diluted with EtOAc (30 mL), washed with brine (15 mL×2), dried over sodium sulfate, filtered through a Biotage Universal Phase Separator and then concentrated under reduced pressure to give a crude product, which was used for next step without any further purification. LC-MS (ES$^+$): m/z 694.33[MH$^+$].

Step 5: Synthesis of methyl 4-{[5-({[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl methoxy)pentyl]amino}benzoate TBTU (81.5 mg, 0.25 mmol) was added to a solution of 2-[(5-{[4-(methoxycarbonyl)phenyl]amino}pentyl)oxy]acetic acid (50.0 mg, 0.17 mmol), (2S,4R)-1-[(2S)-2-amino-3,3-dimethylbutanoyl]-4-hydroxy-N-[4-(4-methyl-1,3-thiazol-5-yl)phenyl]methyl}pyrrolidine-2-carboxamide (72.8 mg, 0.17 mmol) in DMF (3.0 mL) and DIPEA (59 µL, 0.34 mmol) at rt. The resulting mixture was stirred at rt for 1 h. The reaction mixture was diluted with EtOAc (30 mL), washed with water (15 mL×2), brine (15 mL×1), dried over sodium sulfate, filtered through a Biotage universal phase separator and then concentrated under reduced pressure to give a crude residue, which was purified by silica gel chromatography on a Teledyne Combiflash ISCO system eluting with MeOH/DCM (v/v=0:100 to 10:90) to yield the titled product (yield: 51%, 2 steps). LC-MS (ES$^+$): m/z 708.35 [MH$^+$].

Step 4: Synthesis of 2-[(5-{[4-(methoxycarbonyl)phenyl]amino}pentyl)oxy]acetic Acid

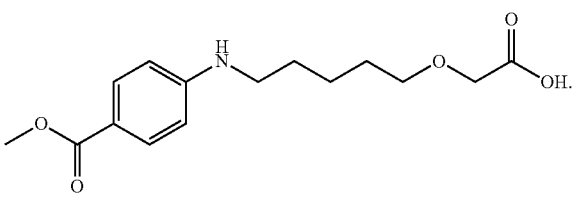 [SMILES: COC(=O)c1ccc(NCCCCCOCC(=O)O)cc1]

Trifluoroacetic acid (2.63 mL, 34.5 mmol) was added to a solution of methyl 4-{[5-(2-methoxy-2-oxoethoxy)pentyl]amino}benzoate (270 mg, 0.7682 mmol) in DCM (3.00 ml) at rt. The resulting mixture was stirred at 45° C. for 2 h. The reaction mixture was then concentrated under reduced pressure to give a crude product, which was used for next step without any further purification. LC-MS (ES$^+$): m/z 296.15 [MH$^+$].

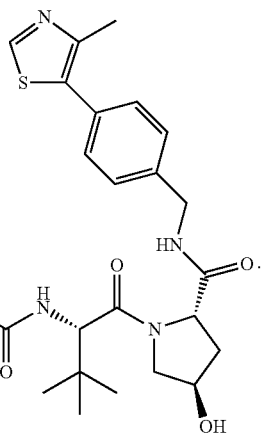

Step 3: Synthesis of methyl 4-({5-[2-(tert-butoxy)-2-oxoethoxy]pentyl}amino)benzoate

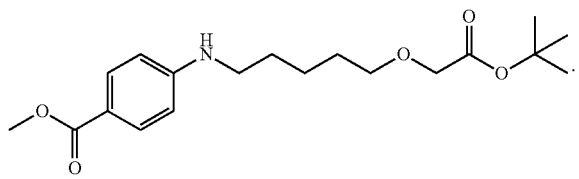 [SMILES: COC(=O)c1ccc(NCCCCCOCC(=O)OC(C)(C)C)cc1]

To a solution of tert-butyl 2-[(5-oxopentyl)oxy]acetate (269 mg, 1.24 mmol) and methyl 4-aminobenzoate (187 mg, 1.24 mmol) in dichloroethane (5.00 mL) was added acetic acid (199 µL, 2.48 mmol) and sodium triacetoxyborohydride (394 mg, 1.86 mmol) at rt. The reaction mixture was stirred at rt for 18 h. NaOH (1N solution in water) was then added to neutralize the acetic acid, the resulting reaction mixture was extracted with DCM (100 mL×3). The organic layers were combined, dried over anhydrous sodium sulfate and concentrated under reduced pressure to give a crude residue, which was purified by silica gel chromatography on a Teledyne Combiflash ISCO system eluting with MeOH/DCM (v/v=0:100 to 15:85) to yield the desired title product (yield: 62%). LC-MS (ES$^+$): m/z 352.21 [MH$^+$]

Step 2: Synthesis of tert-butyl 2-[(5-oxopentyl)oxy]acetate

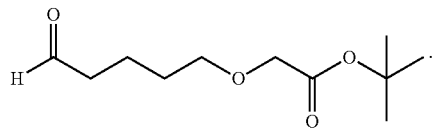

To a solution of tert-butyl 2-(hex-5-en-1-yloxy)acetate (300.0 mg, 1.40 mmol) in acetone (15.00 ml) were added potassium osmate(VI) dihydrate (15.5 mg, 0.042 mmol), follow by NMO (491.9 mg, 4.20 mmol) in water (4.5 ml) at rt. The resulting reaction mixture was stirred for 18 h at rt. The reaction was monitored by TLC (EtOAc/Heptane, v/v=25/75). Sodium periodate (898.2 mg, 4.20 mmol) was then added to the reaction mixture, the reaction was stirred at rt for another 3 h. The reaction mixture was diluted with water (10 mL) and DCM (100 mL). The organic layer was separated and the aqueous layer was extracted with DCM (100 mL×3). The combined organic layers were washed with brine (10 mL×2) and then passed through a Universal Biotage Phase Separator and concentrated under reduced pressure to give a crude residue, which was purified by silica gel chromatography on a Teledyne Combiflash ISCO system eluting with EtOAc/Heptane (v/v=0:100 to 50:50) to yield the titled product (yield 90%). $^1$H NMR (400 MHz, CDCl$_3$) δ 9.75 (t, J=1.8 Hz, 1H), 3.89-3.93 (m, 2H), 3.51 (t, J=6.1 Hz, 2H), 2.47 (dt, J=1.6, 7.2 Hz, 2H), 1.69-1.78 (m, 2H), 1.64 (d, J=8.2 Hz, 2H), 1.46 (s, 9H).

Step 1: Synthesis of tert-butyl 2-(hex-5-en-1-yloxy)acetate

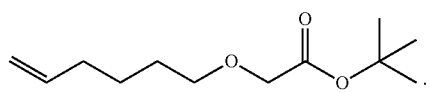

Tetrabutylammonium hydrogen sulfate (677.7 mg, 2.0 mmol) was added to a mixture of sodium hydroxide (23.9 g, 599 mmol) in water (20.0 mL) and toluene (20.00 ml) at 20° C. To this mixture was added hex-5-en-1-ol (2.00 g, 20.0 mmol), the resulting mixture was stirred at 20° C. for 1 h. The reaction was then cooled to 5° C. and tert-butyl 2-bromoacetate (20.0 mmol, 3.89 g) was added slowly while maintaining the internal temperature below 15° C. The reaction mixture was then stirred at rt for additional 16 h. The mixture was diluted with heptane (30 mL) and washed with water (20 mL). The organic phase was dried over anhydrous sodium sulfate, filtered and concentrated under reduced pressure to give a crude residue, which was purified by silica gel chromatography on a Teledyne Combiflash ISCO system (gradient eluent: EtOAc/Heptane, v/v=0/100 to 25/75) to afford the desired product (33%). $^1$H NMR (400 MHz, CDCl$_3$) δ 5.75-5.87 (m, 1H), 4.82-5.10 (m, 2H), 3.95 (s, 2H), 3.52 (t, J=6.7 Hz, 2H), 2.08 (d, J=7.0 Hz, 2H), 1.57-1.69 (m, 2H), 1.45-1.53 (m, 11H). LC-MS (ES$^+$): m/z 237.14 [MNa$^+$]

Examples 173-178 were synthesized according to similar procedure described for synthesis of example 172, by using corresponding starting materials and intermediates.

Alternatively, steps 5-7 of example 174 is synthesized as following:

Step 7: synthesis of (2S,4R)-1-((S)-2-(2-((5-((4-((trans-3-(3-chloro-4-cyanophenoxy)-2,2,4,4-tetramethylcyclobutyl)carbamoyl)phenyl)amino)pentyl)oxy)acetamido)-3,3-dimethylbutanoyl)-4-hydroxy-N—((S)-1-(4-(4-methylthiazol-5-yl)phenyl)ethyl)pyrrolidine-2-carboxamide

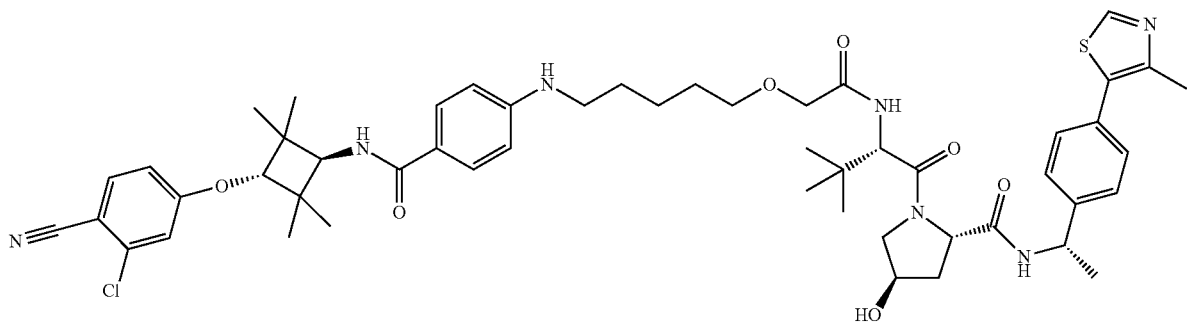 [SMILES: Cc1ncsc1-c1ccc([C@H](C)NC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1]

A solution of 4-((5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentyl)amino)benzoic acid (1.17 g, 1.65 mmol) in methylene chloride (10 mL) was charged with HATU (688 mg, 1.81 mmol) and diisopropylethylamine (859 µL, 4.94 mmol). The reaction mixture was allowed to stir at room temperature for 10 minutes, then 4-(trans-3-amino-2,2,4,4-tetramethylcyclobutoxy)-2-chlorobenzonitrile hydrochloride (545 mg, 1.73 mmol) was added. The reaction mixture was stirred at room temperature for 30 minutes. The reaction mixture was diluted with DCM (30 mL), then washed with water (10 mL), brine (10 mL), dried over Na2SO4, filtered and concentrated under reduced pressure. The crude material was purified by silica gel chromatography on a Teledyne Combiflash ISCO eluting with DCM/MeOH (100:0 to 90:10 to yield the desired product as a white solid (0.86 g, 54%). LC-MS (ES+): m/z 968.42 [MH+].

Step 6: synthesis of 4-((5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentyl)amino)benzoic Acid

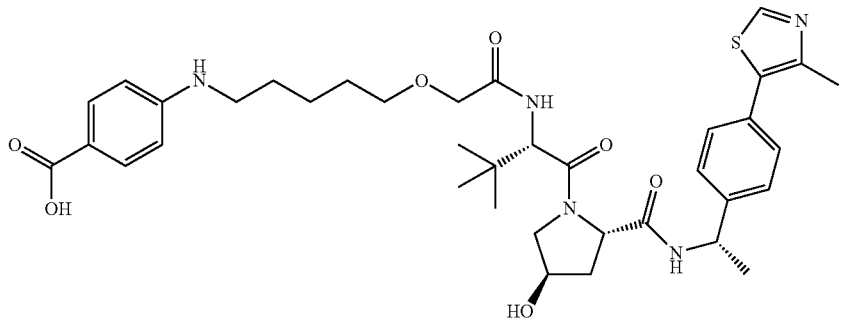 [SMILES: Cc1ncsc1-c1ccc([C@H](C)NC(=O)[C@@H]2C[C@@H](O)CN2C(=O)[C@@H](NC(=O)COCCCCCNc2ccc(C(=O)O)cc2)C(C)(C)C)cc1]

A solution of methyl 4-((5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentyl)amino)benzoate (1.2 g, 1.66 mmol) in methanol (5 mL) was charged with 3 M NaOH (2.0 mL, 50.0 mmol). The reaction mixture was allowed to stir at room temperature for 72 hours. The reaction mixture was quenched with 1.0 M HCl and then concentrated under reduced pressure to remove the methanol. The aqueous was extracted with EtOAc (25 mL×3). The combined organic layers were washed with brine (15 mL), dried over Na2SO4, filtered and concentrated under reduced pressure. The crude material was purified by silica gel chromatography on a Teledyne Combiflash ISCO eluting with DCM/MeOH (100:0 to 90:10) to yield the desired product as a white solid (1.17 g, 100%). LC-MS (ES+): m/z 708.32 [MH+].

Step 5: Synthesis of methyl 4-((5-(2-(((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)amino)-2-oxoethoxy)pentyl)amino)benzoate

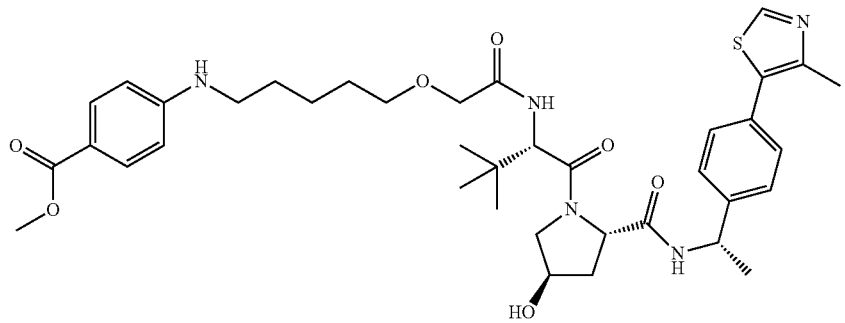 [SMILES: COC(=O)c1ccc(NCCCCCOCC(=O)N[C@H](C(=O)N2C[C@H](O)C[C@H]2C(=O)N[C@@H](C)c2ccc(-c3scnc3C)cc2)C(C)(C)C)cc1]

A solution of 2-((5-((4-(methoxycarbonyl)phenyl)amino)pentyl)oxy)acetic acid (1.68 g, 5.68 mmol) and (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (2.73 g, 5.68 mmol) in methylene chloride (15 mL) was charged with O-(benzotriazol-1-yl)-N,N,N',N'-tetramethyluronium tetrafluoroborate (1.82 g, 5.68 mmol) and diisopropylethylamine (2.95 mL, 17.0 mmol). The reaction mixture was allowed to stir at rt for 30 minutes. The reaction mixture was quenched with water (15 mL) and then extracted with DCM (15 mL). The organic layer was washed with brine (15 mL), dried over Na2SO4, filtered and concentrated under reduced pressure. The crude material was purified by silica gel chromatography on a Teledyne Combiflash ISCO eluting with DCM/MeOH (100:0 to 90:10) to yield the desired product as a white solid (1.2 g, 29%). LC-MS (ES+): m/z 722.34 [MH+].

TABLE 11

Exemplary Compounds.

| Ex# | Structure | Compound name and Analytical data |
|---|---|---|
| 179 | 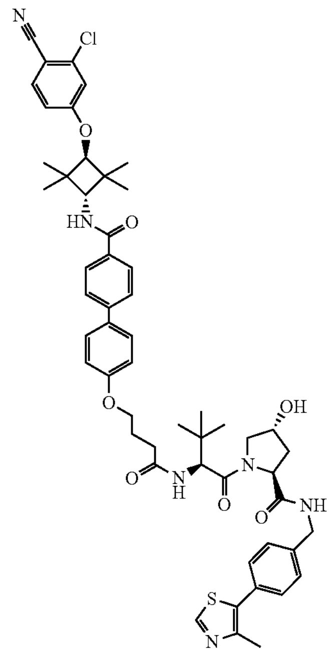 [SMILES: Cc1ncsc1-c1ccc(CNC(=O)[C@@H]2C[C@@H](O)CN2C(=O)[C@@H](NC(=O)CCCOc2ccc(-c3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-{4-[4-(4-{[trans-3-(3-chloro-4-cyanophenoxy)-2,2,4,4-tetramethylcyclobutyl]carbamoyl}phenyl)phenoxy]butanamido}butanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ ppm 8.87 (s, 1H), 7.84-7.90 (m, 2H), 7.73 (d, J = 8.61 Hz, 1H), 7.66-7.71 (m, 2H), 7.58-7.63 (m, 2H), 7.45-7.49 (m, 2H), 7.38-7.43 (m, 2H), 7.14 (d, J = 2.35 Hz, 1H), 7.01-7.06 (m, 2H), 6.99 (dd, J = 8.80, 2.54 Hz, 1H), 4.65 (s, 1H), 4.56-4.60 (m, 1H), 4.52-4.55 (m, 1H), 4.51 (br. s., 1H), 4.35 (d, J = 15.65 Hz, 1H), 4.31 (s, 1H), 4.18 (s, 1H), 4.06 (ddt, J = 9.39, 6.36, 3.28 Hz, 2H), 3.93 (d, J = 10.96 Hz, 1H), 3.81 (dd, J = 10.96, 3.91 Hz, 1H), 2.48-2.57 (m, 2H), 2.42-2.47 (m, 3H), 2.22 (dd, J = 13.11, 7.63 Hz, 1H), 2.06-2.15 (m, 3H), 1.31 (s, 6H), 1.25 (s, 6H), 1.04 (s, 9H); LC-MS (ES$^+$): m/z 973.41 [MH$^+$] |
| 180 | 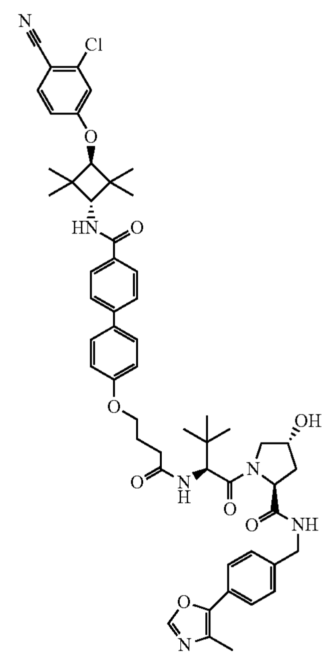 [SMILES: Cc1ncoc1-c1ccc(CNC(=O)[C@@H]2C[C@@H](O)CN2C(=O)[C@@H](NC(=O)CCCOc2ccc(-c3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-{4-[4-(4-{[trans-3-(3-chloro-4-cyanophenoxy)-2,2,4,4-tetramethylcyclobutyl]carbamoyl}phenyl)phenoxy]butanamido}butanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD) δ ppm 8.14 (s, 1H), 7.87 (d, J = 8.22 Hz, 2H), 7.73 (d, J = 8.61 Hz, 1H), 7.67-7.71 (m, 2H), 7.57-7.63 (m, 4H), 7.45-7.51 (m, 2H), 7.14 (d, J = 2.74 Hz, 1H), 7.03 (d, J = 9.00 Hz, 2H), 6.99 (dd, J = 8.80, 2.54 Hz, 1H), 4.65 (s, 1H), 4.55-4.59 (m, 1H), 4.47-4.55 (m, 2H), 4.34 (d, J = 15.65 Hz, 1H), 4.31 (s, 1H), 4.19 (s, 1H), 4.06 (tt, J = 6.16, 3.23 Hz, 2H), 3.93 (d, J = 10.96 Hz, 1H), 3.81 (dd, J = 10.96, 3.91 Hz, 1H), 2.48-2.55 (m, 2H), 2.39 (s, 3H) 2.22 (dd, J = 13.30, 7.43 Hz, 1H), 2.06-2.14 (m, 3H), 1.31 (s, 6H), 1.25 (s, 6H), 1.04 (s, 9H); LC-MS (ES$^+$): m/z 957.44 [MH$^+$] |

TABLE 11-continued

Exemplary Compounds.

| Ex# | Structure | Compound name and Analytical data |
|---|---|---|
| 181 | 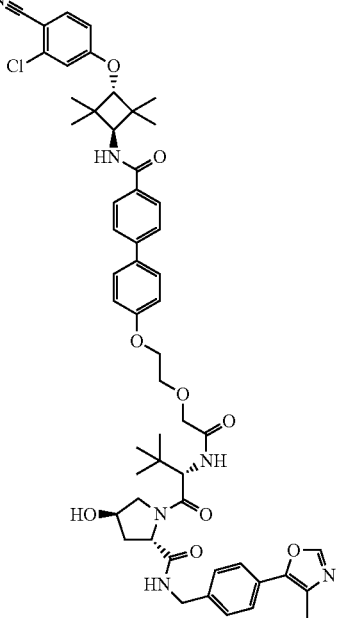 | (2S,4R)-1-[(2S)-3,3-dimethyl-2-(2-{2-[4-(4-{[trans-3-(3-chloro-4-cyanophenoxy)-2,2,4,4-tetramethylcyclobutyl]carbamoyl}phenyl)phenoxy]ethoxy}acetamido)butanoyl]-4-hydroxy-N-{[4-(4-methyl-1,3-oxazol-5-yl)phenyl]methyl}pyrrolidine-2-carboxamide<br>$^1$H NMR (400 MHz, CDCl$_3$) δ ppm 8.05 (s, 1H), 7.81-7.87 (m, 2H), 7.73 (d, J = 9.00 Hz, 1 H), 7.58-7.64 (m, 2H), 7.51-7.58 (m, 4H), 7.43-7.51 (m, 2H), 7.10-7.19 (m, 3H), 6.99 (dd, J = 9.00, 2.35 Hz, 1H), 4.76 (s, 1H), 4.55-4.64 (m, 3H), 4.51 (d, J = 1.96 Hz, 1H), 4.31 (t, J = 7.83 Hz, 2H), 4.25 (q, J = 4.17 Hz, 2H), 4.19 (s, 1H), 4.14 (s, 2H), 3.96 (t, J = 4.30 Hz, 2H), 3.86-3.91 (m, 1H), 3.78-3.86 (m, 1H), 2.26-2.32 (m, 3H), 2.18-2.26 (m, 1H), 2.05-2.13 (m, 1H), 1.31 (s, 6H), 1.25 (s, 6H), 0.99-1.11 (m, 9H); LC-MS (ES$^+$): m/z 973.43 [MH$^+$] |
| 182 | 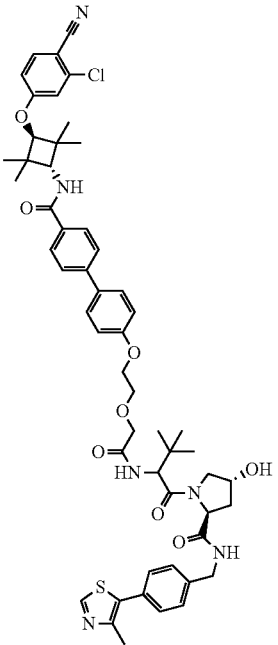 [SMILES: Cc1ncsc1-c1ccc(CNC(=O)[C@@H]2C[C@@H](O)CN2C(=O)C(NC(=O)COCCOc2ccc(-c3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-(2-{2-[4-(4-{[trans-3-(3-chloro-4-cyanophenoxy)-2,2,4,4-tetramethylcyclobutyl]carbamoyl}phenyl)phenoxy]ethoxy}acetamido)butarioyl]-4-hydroxy-N-{[4-(4-methyl-1,3-thiazol-5-yl)phenyl]methyl}pyrrolidine-2-carboxamide<br>$^1$H NMR (400 MHz, CDCl$_3$) δ ppm 8.66 (s, 1H), 7.82 (d, J = 8.22 Hz, 2H), 7.60 (dd, J = 11.54, 8.41 Hz, 3H), 7.53 (d, J = 8.61 Hz, 2H), 7.27-7.41 (m, 6H), 7.04 (d, J = 8.61 Hz, 2 H), 6.99 (d, J = 2.35 Hz, 1H), 6.83 (dd, J = 8.80, 2.15 Hz, 1H), 6.31 (d, J = 8.22 Hz, 1H), 4.75 (t, J = 7.83 Hz, 1H), 4.52-4.64 (m, 2H), 4.50 (d, J = 8.61 Hz, 1H), 4.34 (dd, J = 14.87, 5.48 Hz, 1H), 4.17-4.24 (m, 3H), 4.04-4.17 (m, 4H), 3.88-3.97 (m, 2H), 3.63 (dd, J = 11.35, 3.52 Hz, 1H), 2.61 (ddd, J = 13.30, 7.83, 4.70 Hz, 1H), 2.49 (s, 3H), 2.12 (dd, J = 13.69, 8.22 Hz, 1H), 1.31 (s, 6H), 1.26 (s, 6H), 0.96 (s, 9H); LC-MS (ES$^+$): m/z 989.27 [MH$^+$] |

Examples 179-181 were synthesized according to similar procedure described for synthesis of example 182, by using corresponding starting materials and intermediates.
Synthesis of Example 182
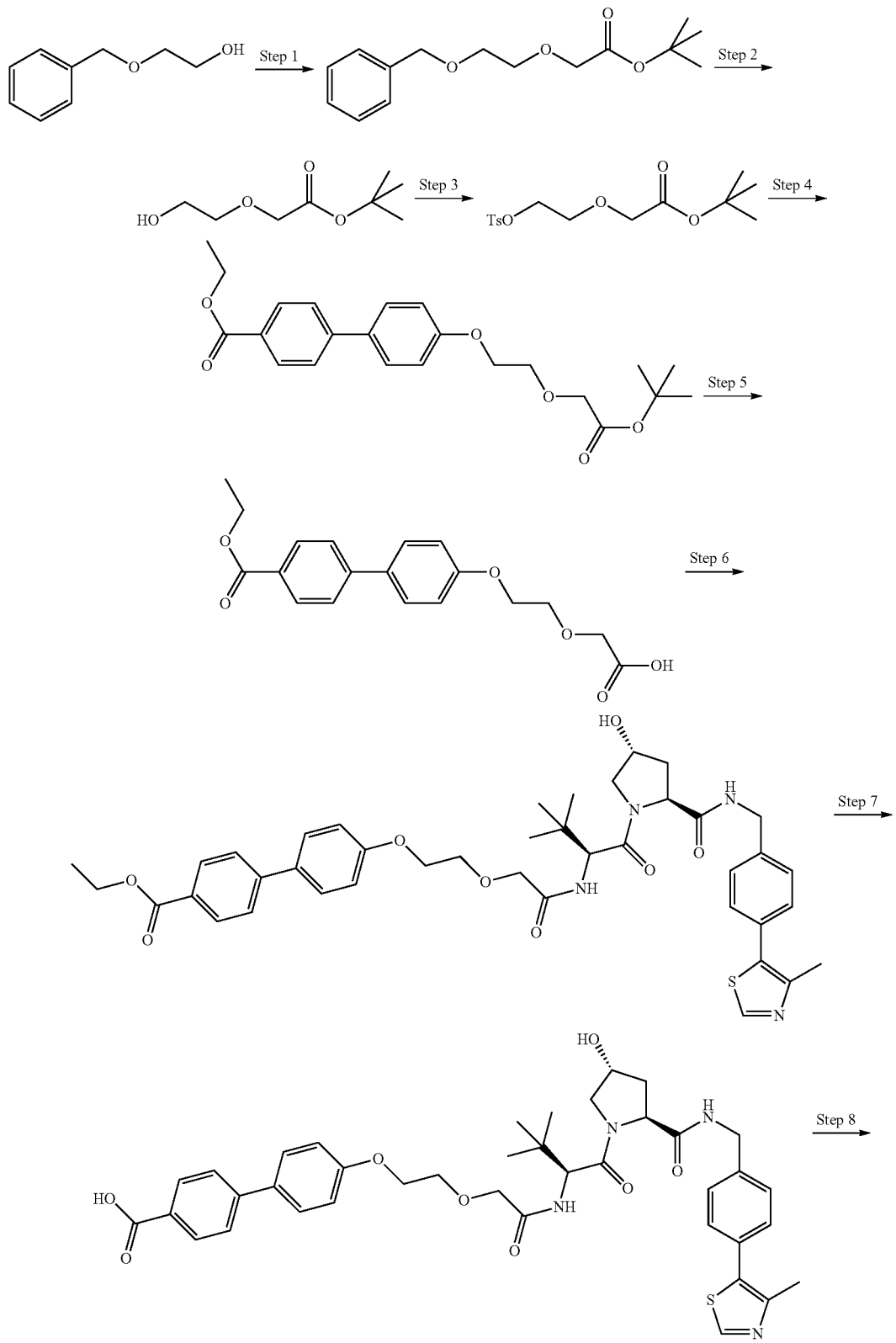

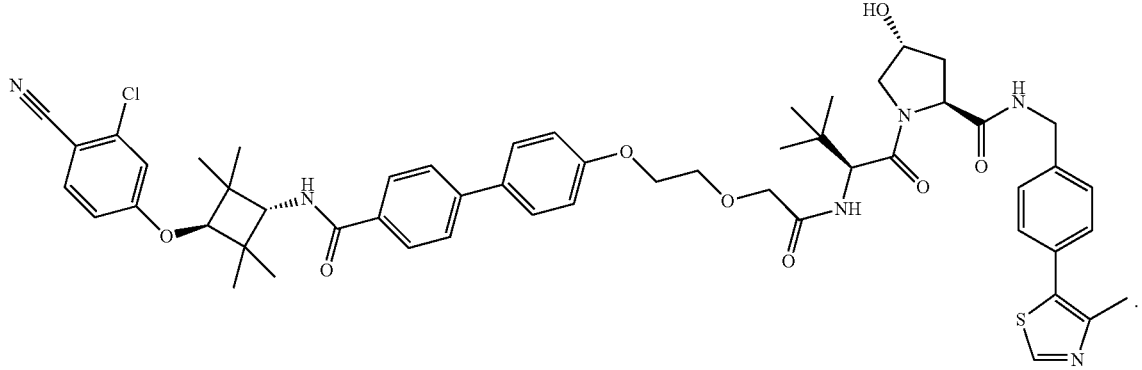

Example 182

Step 8: Synthesis of Example 182

To a stirred solution of 4-{4-[2-({[2S)-1-[(2S,4R)-4-hydroxy-2-({[4-(4-methyl-1,3-thiazol-5-yl)phenyl] methyl}carbamoyl)pyrrolidin-1-yl]-3,3-dimethyl-1-oxobutan-2-yl]carbamoyl}methoxy)ethoxy]phenyl}benzoic acid (89.0 mg, 122 µmol) in methylene chloride (2.0 mL) was added HATU (55.5 mg, 146 µmol) and diisopropylethylamine (63.7 µL, 366 µmol). The reaction mixture was stirred at rt for 10 minutes. The reaction mixture was then charged with 2-chloro-4-[trans-3-amino-2,2,4,4-tetramethylcyclobutoxy]benzonitrile (34.0 mg, 122 µmol). The reaction was stirred at rt for 30 minutes. The reaction was monitored by LC-MS, which indicated completion of reaction. The reaction mixture was quenched with water (5 mL) and then extracted with DCM (25 mL). The organic layer was washed with brine (5 mL), dried over Na$_2$SO$_4$, filtered and concentrated under reduced pressure to give a crude material, which was purified by flash silica gel chromatography on a Teledyne Combiflash ISCO (eluent: DCM/MeOH (v:v=90:10)) to give titled product (yield: 37%) as a white solid.

Step 7: Synthesis of 4-{4-[2-({[(2S)-1-[(2S,4R)-4-hydroxy-24 [4-(4-methyl-1,3-thiazol-5-yl)phenyl] methyl}carbamoyl)pyrrolidin-1-yl]-3,3-dimethyl-1-oxobutan-2-yl]carbamoyl methoxy)ethoxy] phenyl}benzoic Acid

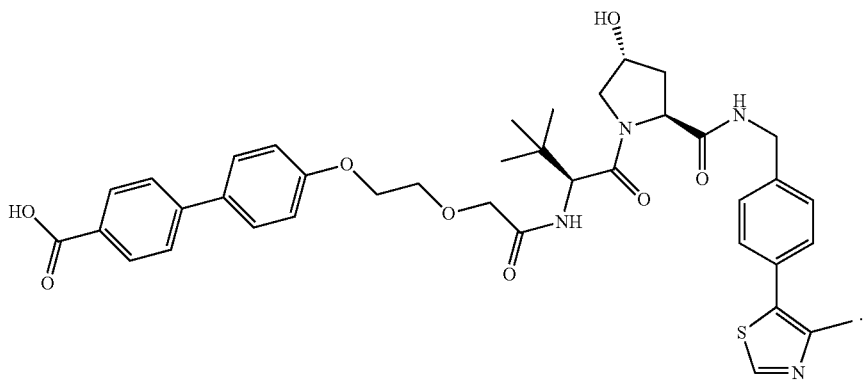 [SMILES: Cc1ncsc1-c1ccc(CNC(=O)[C@@H]2C[C@@H](O)CN2C(=O)[C@@H](NC(=O)COCCOc2ccc(-c3ccc(C(=O)O)cc3)cc2)C(C)(C)C)cc1]

To a stirred solution of ethyl 4-{4-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]phenyl}benzoate (188.4 mg, 248 µmol) in methanol (2.0 mL) was added 1 M NaOH in water (0.5 mL, 12.5 mmol). The reaction mixture was stirred at rt for 16 h. The reaction was monitored by LC-MS, which indicated completion of reaction. The reaction mixture was quenched with 1.0 M HCl in water and then concentrated under reduced pressure to remove the methanol. The aqueous was extracted with EtOAc (25 mL). The organic layer was washed with brine (5 mL), dried over Na$_2$SO$_4$, filtered and concentrated under reduced pressure to give a crude material, which was purified by flash silica gel chromatography on a Teledyne Combiflash ISCO (eluent: DCM/MeOH (v:v=90:10)) to give titled product (yield: 50%) as a white solid. LC-MS (ES$^+$): m/z 729.18 [MH$^+$]

Step 6: Synthesis of ethyl 4-{4-[2-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)ethoxy]phenyl}benzoate

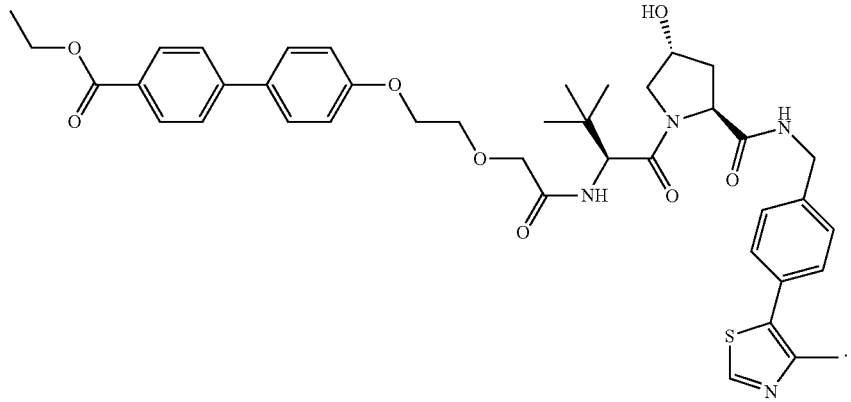 [SMILES: CCOC(=O)c1ccc(-c2ccc(OCCOCC(=O)N[C@H](C(=O)N3C[C@H](O)C[C@H]3C(=O)NCc3ccc(-c4scnc4C)cc3)C(C)(C)C)cc2)cc1]

To a stirred solution of 2-(2-{4-[4-(ethoxycarbonyl)phenyl]phenoxy}ethoxy)acetic acid (100 mg, 290.3 µmol) and (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (135.5 mg, 290.3 µmol) in Dichloromethane (2.0 mL) was added O-(benzotriazol-1-yl)-N,N,N',N'-tetramethyluronium tetrafluoroborate (93.20 mg, 290.3 µmol) and diisopropylethylamine (151.6 µL, 870.9 µmol). The reaction mixture was stirred at rt for 30 minutes. The reaction was monitored by LC-MS, which indicated completion of reaction. The reaction mixture was concentrated under reduced pressure to give a crude material, which was purified by flash silica gel chromatography on a Teledyne Combiflash ISCO (gradient eluent: Heptane/Acetone (v:v=100:0 to 0:100)) to give titled product (yield: 86%) as a white solid. LC-MS (ES$^+$): m/z 757.3283 [MH$^+$].

Step 5: Synthesis of 2-(2-{4-[4-(ethoxycarbonyl)phenyl]phenoxy}ethoxy)acetic Acid

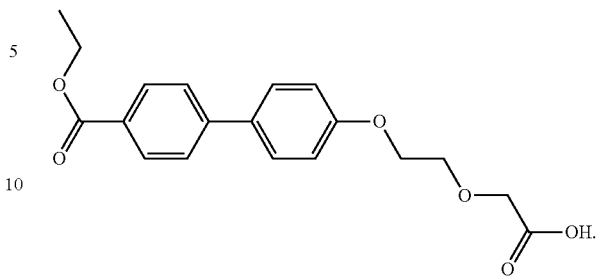

To a stirred solution of ethyl 4-(4-{2-[2-(tert-butoxy)-2-oxoethoxy]ethoxy}phenyl)benzoate (245 mg, 611 µmol) in methylene chloride (1.0 mL) was added trifluoroacetic acid (1.0 mL, 12.9 mmol). The reaction mixture was stirred at rt for 30 minutes. The reaction was monitored by LC-MS, which indicated completion of reaction. The reaction mixture was concentrated under reduced pressure to give titled product (yield: 100% based on crude) as an off white solid. The material was used in next step without any further purification. LC-MS (ES$^+$): m/z 345.1330 [MH$^{-1}$].

Step 4: Synthesis of ethyl 4-(4-{2-[2-(tert-butoxy)-2-oxoethoxy]ethoxy}phenyl)benzoate

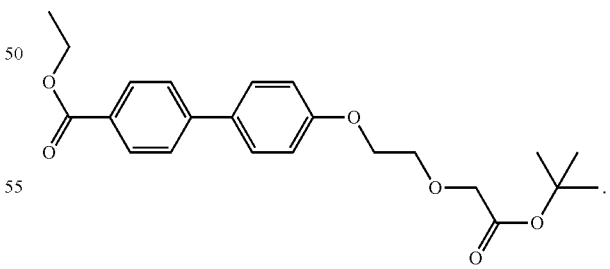

To a stirred mixture of ethyl 4'-hydroxy-[1,1'-biphenyl]-4-carboxylate (146.6 mg, 605.3 µmol) and tert-butyl 2-{2-[(4-methylbenzenesulfonyl)oxy]ethoxy}acetate (200.0 mg, 605.3 µmol) in acetonitrile (2.0 mL) was added potassium carbonate (125.4 mg, 907.9 µmol) at rt. The reaction mixture was then stirred at 80° C. for 16 h. The reaction was monitored by LC-MS, which indicated completion of reaction. The reaction mixture was concentrated under reduced pressure to give a crude material, which was purified by flash silica gel chromatography on a Teledyne Combiflash ISCO (gradient eluent: Heptane/EtOAc (v:v=100:0 to 50:50)) to give titled product (yield: 99%) as a clear oil. LC-MS (ES+): m/z 423.18 [MNa+].

Step 3: synthesis of tert-butyl 2-{2-[(4-methylbenzenesulfonyl)oxy]ethoxy}acetate

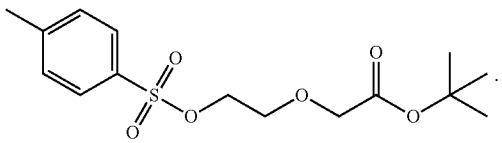 [SMILES: Cc1ccc(S(=O)(=O)OCCOCC(=O)OC(C)(C)C)cc1]

To a stirred solution of tert-butyl 2-(2-hydroxyethoxy) acetate (1.44 g, 0.19 mmol) in methylene chloride (10.0 mL) was added 4-methylbenzene-1-sulfonyl chloride (1.713 g, 0.21 mmol) and triethylamine (1.707 mL, 12.25 mmol) at rt. The reaction mixture was stirred at rt for 16 h. The reaction was monitored by LC-MS, which indicated completion of reaction. The reaction mixture was concentrated under reduced pressure give a crude material, which was purified by flash silica gel chromatography on a Teledyne Combiflash ISCO (gradient eluent: Heptane/Acetone (v:v=100:0 to 0:100)) to give titled product (yield: 69%) as a clear oil. $^1$H NMR (400 MHz, CD$_3$OD) δ ppm 7.77-7.83 (m, 2H), 7.44 (d, J=7.83 Hz, 2H), 4.14-4.19 (m, 2H), 3.93 (s, 2H), 3.68-3.74 (m, 2H), 2.46 (s, 3H), 1.46 (s, 9H); LC-MS (ES+): m/z 353.1053 [MNa+], t$_R$=2.56 min.

Step 2: Synthesis of tert-butyl 2-(2-hydroxyethoxy)acetate

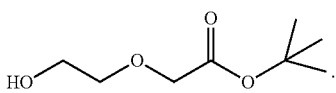

To a stirred solution of tert-butyl 2-[2-(benzyloxy)ethoxy]acetate in Ethanol (10.0 mL) was added palladium on carbon (10% wt.) (1.99 g, 1.87 mmol). The reaction mixture was evacuated and purged with H$_2$ gas (3×). The reaction mixture was stirred at rt under an atmosphere of H$_2$ for 16 h. The reaction was monitored by TLC analysis, which indicated completion of reaction. The reaction mixture was filtered through a pad of celite and the filtrate was concentrated under reduced pressure to give titled product (yield: 87% based on crude) as a clear oil. The crude material was used in next step reaction without any further purification.

Step 1: Synthesis of tert-butyl 2-[2-(benzyloxy)ethoxy]acetate

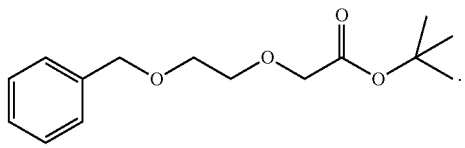 [SMILES: CC(C)(C)OC(=O)COCCOCc1ccccc1]

To a stirred solution of 2-(benzyloxy)ethanol (5.0 g, 32.8 mmol) and tert-butyl 2-bromoacetate (7.02 g, 36.0 mmol) in acetonitrile (10.0 mL) was added potassium carbonate (6.78 g, 49.1 mmol) at rt. The reaction mixture then stirred at 80° C. for 16 h. The reaction was monitored by TLC analysis, which indicated completion of reaction. The reaction mixture was diluted with water (10.0 mL) and extracted with EtOAc (20.0 mL). The organic layer was washed with water (5.0 mL), brine (5.0 mL), dried over Na$_2$SO$_4$, filtered, and concentrated under reduced pressure to give titled product (yield: 100% based on crude) as a yellow oil. This crude material was used in next step reaction without any further purification.

TABLE 12

Exemplary Compounds.

| Ex# | Structure | Compound name and Analytical data |
|---|---|---|
| 183 | 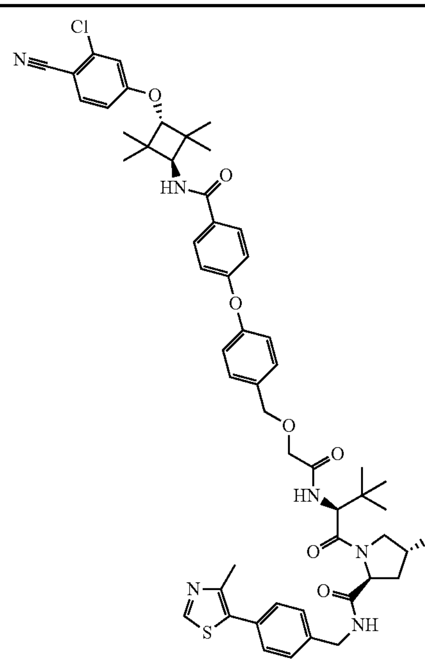 | (2S,4R)-1-[(2S)-3,3-dimethyl-2-(2-{[4-(4-{[trans-3-(3-chloro-4-cyanophenoxy)-2,2,4,4-tetramethylcyclobutyl]carbamoyl}phenoxy)phenyl]methoxy}acetamido)butanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ ppm 8.83-8.90 (m, 1H), 7.79-7.86 (m, 2H), 7.72 (d, J = 8.61 Hz, 1H), 7.43-7.50 (m, 4H), 7.37-7.42 (m, 2H), 7.13 (d, J = 2.35 Hz, 1H), 7.00-7.09 (m, 4 H), 6.98 (dd, J = 9.00, 2.35 Hz, 1H), 4.71 (s, 1H), 4.63 (s, 2H), 4.55-4.61 (m, 2H), 4.47-4.54 (m, 2H), 4.35 (d, J = 15.65 Hz, 1H), 4.28 (s, 1H), 4.15 (s, 1H), 4.00-4.08 (m, 2H), 3.86-3.92 (m, 1H), 3.77-3.84 (m, 1H), 2.44-2.48 (m, 3H), 2.24 (dd, J = 13.30, 7.43 Hz, 1H), 2.09 (ddd, J = 13.21, 9.10, 4.30 Hz, 1H), 1.28 (s, 6H), 1.22 (s, 6H), 1.00-1.09 (m, 9H); LC-MS (ES+): m/z 975.39 [MH+] |

| Ex# | Structure | Compound name and Analytical data |
|---|---|---|
| 184 | 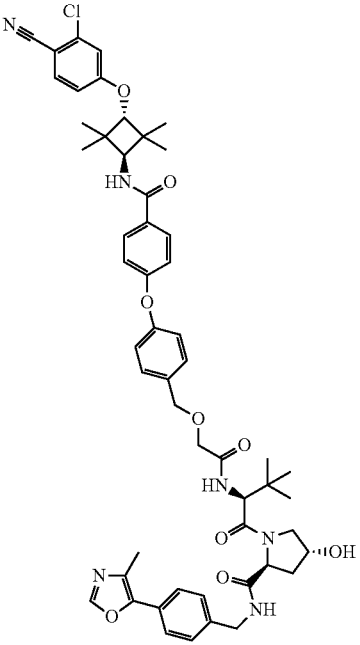 [SMILES: Cc1ncoc1-c1ccc(CNC(=O)[C@@H]2C[C@@H](O)CN2C(=O)[C@@H](NC(=O)COCc2ccc(Oc3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-(2-{[4-(4-{[(1r,3r)-3-(3-chloro-4-cyanophenoxy)-2,2,4,4-tetramethylcyclobutyl]carbamoyl}phenoxy)phenyl]methoxy}acetamido)butanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD) δ ppm 8.10-8.15 (m, 1H), 7.79-7.85 (m, 2H), 7.72 (d, J = 9.00 Hz, 1H), 7.55-7.61 (m, 2H), 7.44-7.51 (m, 4H), 7.12 (d, J = 2.35 Hz, 1H), 7.00-7.09 (m, 4 H), 6.98 (dd, J = 9.00, 2.35 Hz, 1H), 4.71 (s, 1H), 4.63 (s, 2H), 4.55-4.61 (m, 2H), 4.46-4.54 (m, 2H), 4.34 (d, J = 15.26 Hz, 1H), 4.28 (s, 1H), 4.15 (s, 1H), 4.07 (s, 1H), 4.02-4.06 (m, 1 H), 3.85-3.92 (m, 1H), 3.77-3.84 (m, 1H), 2.35-2.42 (m, 3H), 2.23 (dd, J = 13.30, 7.43 Hz, 1H), 2.04-2.12 (m, 1H), 1.28 (s, 6H), 1.22 (s, 6H), 0.97-1.12 (m, 9H); LC-MS (ES$^+$): m/z 959.41 |
| 185 | 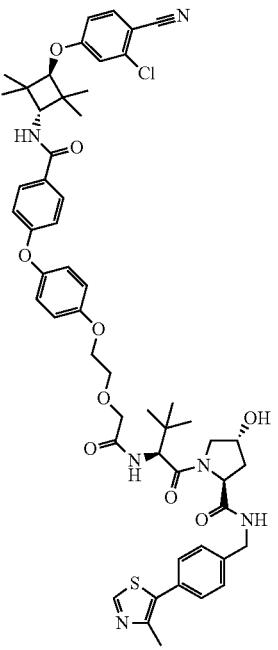 [SMILES: Cc1ncsc1-c1ccc(CNC(=O)[C@@H]2C[C@@H](O)CN2C(=O)[C@@H](NC(=O)COCCOc2ccc(Oc3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-(2-{2-[4-(4-{[trans-3-(3-chloro-4-cyanophenoxy)-2,2,4,4-tetramethylcyclobutyl]carbamoyl}phenoxy)phenoxy]ethoxy}acetamido)butanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ ppm 8.83 (s, 1H), 7.74-7.82 (m, 2H), 7.72 (d, J = 8.61 Hz, 1 H), 7.42-7.49 (m, 2H), 7.33-7.40 (m, 2H), 7.12 (d, J = 2.35 Hz, 1H), 7.06-7.11 (m, 2H), 6.87-7.01 (m, 5H), 4.74 (s, 1H), 4.55-4.61 (m, 2H), 4.49-4.55 (m, 2H), 4.32 (d, J = 15.26 Hz, 1H), 4.28 (s, 1H), 4.17-4.22 (m, 2H), 4.14 (s, 1H), 4.13 (s, 2H), 3.91-3.96 (m, 2H), 3.85-3.90 (m, 1H), 3.79-3.85 (m, 1H), 2.40-2.49 (m, 3H), 2.23 (dd, J = 13.30, 7.83 Hz, 1 H), 2.05-2.14 (m, 1H), 1.28 (d, J = 1.17 Hz, 6H), 1.22 (s, 6H), 1.01-1.09 (m, 9H); LC-MS (ES$^+$): m/z 1005.40 [MH$^+$] |

TABLE 12-continued

Exemplary Compounds.

| Ex# | Structure | Compound name and Analytical data |
|---|---|---|
| 186 | 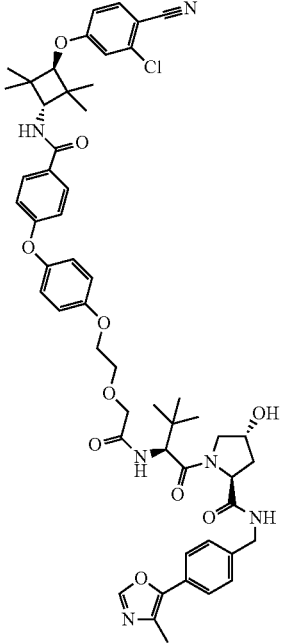 [SMILES: Cc1ncoc1-c1ccc(CNC(=O)[C@@H]2C[C@@H](O)CN2C(=O)[C@@H](NC(=O)COCCOc2ccc(Oc3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-(2-{2-[4-(4-{[trans-3-(3-chloro-4-cyanophenoxy)-2,2,4,4-tetramethylcyclobutyl]carbamoyl}phenoxy)phenoxy]ethoxy}acetamido)butanoyl]-4-hydroxy-N-{[4-(4-methyl-1,3-oxazol-5-yl)phenyl]methyl}pyrrolidine-2-carboxamide<br>$^1$H NMR (400 MHz, CD$_3$OD) δ ppm 8.10 (s, 1H), 7.74-7.83 (m, 2H), 7.72 (d, J = 8.61 Hz, 1 H), 7.52-7.59 (m, 2H), 7.43-7.50 (m, 2H), 7.07-7.15 (m, 3H), 6.86-7.02 (m, 5H), 4.75 (s, 1H), 4.55-4.61 (m, 2H), 4.52 (d, J = 8.61 Hz, 2H), 4.33 (s, 1H), 4.26-4.31 (m, 1H), 4.21 (q, J = 3.78 Hz, 2H), 4.10-4.17 (m, 3H), 3.94 (dd, J = 4.70, 3.91 Hz, 2H), 3.85-3.91 (m, 1H), 3.78-3.85 (m, 1H), 2.33 (s, 3H), 2.23 (dd, J = 13.11, 7.63 Hz, 1H), 2.09 (ddd, J = 13.30, 9.19, 4.50 Hz, 1H), 1.28 (s, 6H), 1.22 (s, 6H), 1.00-1.10 (m, 9H); LC-MS (ES$^+$): m/z 989.44 [MH$^+$] |
| 187 | 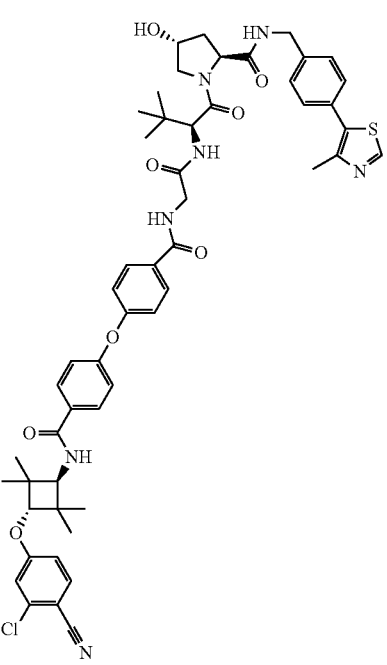 [SMILES: Cc1ncsc1-c1ccc(CNC(=O)[C@@H]2C[C@@H](O)CN2C(=O)[C@@H](NC(=O)CNC(=O)c2ccc(Oc3ccc(C(=O)N[C@H]4C(C)(C)[C@H](Oc5ccc(C#N)c(Cl)c5)C4(C)C)cc3)cc2)C(C)(C)C)cc1] | (2S,4R)-1-[(2S)-3,3-dimethyl-2-(2-{[4-(4-{[trans-3-(3-chloro-4-cyanophenoxy)-2,2,4,4-tetramethylcyclobutyl]carbamoyl}phenoxy)phenyl]formamido}acetamido)butanoyl]-4-hydroxy-N-{[4-(4-methyl-1,3-thiazol-5-yl)phenyl]methyl}pyrrolidine-2-carboxamide<br>Mass (ES$^+$): m/z 988.10 [MH$^+$) |

Examples 184-187 were synthesized according to similar procedure described for synthesis of example 183, by using corresponding starting materials and intermediates.
Synthesis of Example 183
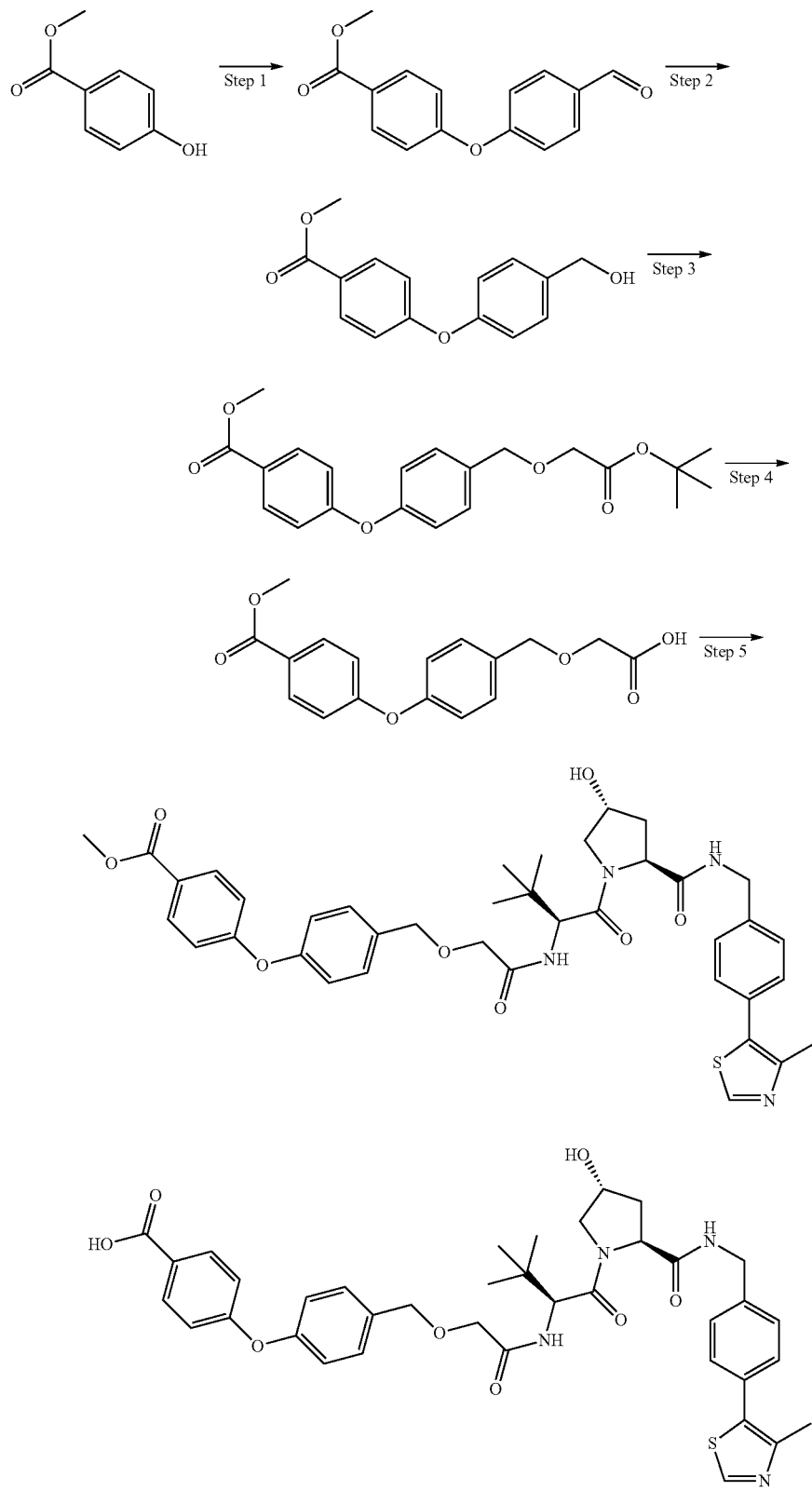

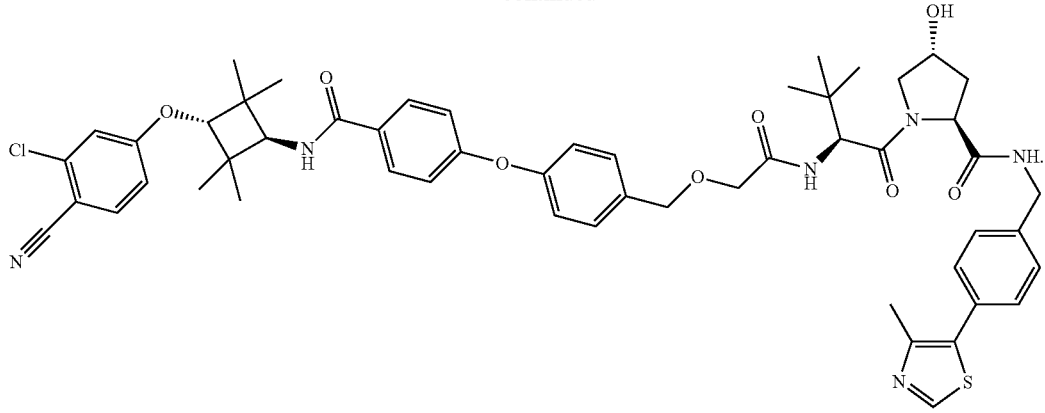

Example 183

Step 7: Synthesis of Example 183

To a stirred solution of 2-chloro-4-[trans-3-amino-2,2,4,4-tetramethylcyclobutoxy]benzonitrile (25.3 mg, 90.9 μmol) and 4-{4-[({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)methyl]phenoxy}benzoic acid (65 mg, 90.9 μmol) in methylene chloride (2.0 mL) was added O-(benzotriazol-1-yl)-N,N,N',N'-tetramethyluronium tetrafluoroborate (29.1 mg, 90.9 μmol) and diisopropylethylamine (47.3 μL, 272 μmol) at rt. The reaction mixture was stirred at rt for 30 minutes. The reaction was monitored by LC-MS, which indicated completion of reaction. The reaction mixture was diluted with water (5 mL) and extracted with DCM (25 mL). The organic layer was separated and washed with brine (5 mL), dried over Na₂SO₄, filtered and concentrated under reduced pressure to give a crude material, which was purified by flash silica gel chromatography on a Teledyne Combiflash ISCO (eluent: DCM/MeOH (v:v=90:10)) to give titled product (yield: 22%) as a white solid.

Step 6: Synthesis of 4-{4-[({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)methyl]phenoxy}benzoic Acid

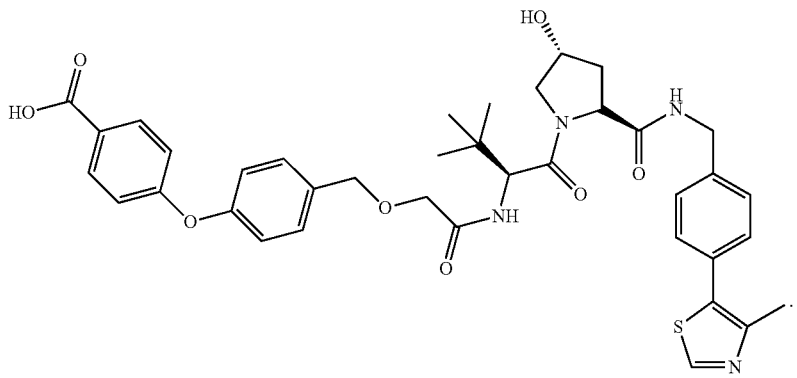

To a stirred solution of methyl 4-{4-[({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)methyl]phenoxy}benzoate (68 mg, 93.2 μmol) in methanol (2.0 mL) was added 1 M NaOH solution in water (0.5 mL, 12.5 mmol) at rt. The reaction mixture was allowed to stir at rt for 16 hours. The reaction was monitored by LC-MS, which indicated completion of reaction. The reaction mixture was quenched with 1.0 M HCl solution in water (0.5 mL) and then concentrated under reduced pressure to remove the methanol. The aqueous was extracted with EtOAc (25 mL). The organic layer was separated, washed with brine (5 mL), dried over Na₂SO₄, filtered and concentrated under reduced pressure to give titled product (yield: 98% based on crude) as a white solid. This material was used in next step reaction without any further purification. LC-MS (ES⁺): m/z 715.28[MH⁺].

Step 5: Synthesis of methyl 4-{4-[({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methoxy)methyl]phenoxy}benzoate

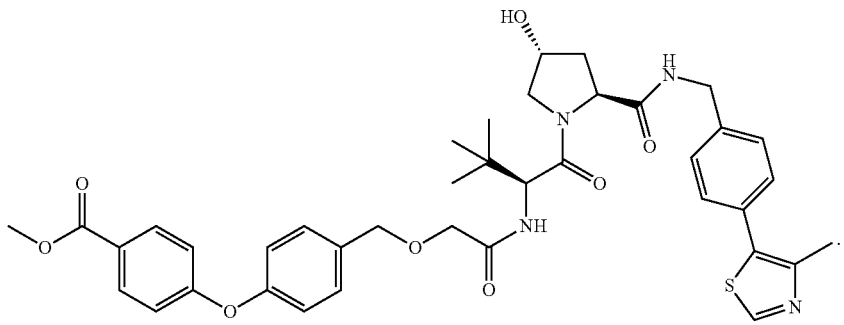

To a stirred solution of 2-({4-[4-(methoxycarbonyl)phenoxy]phenyl}methoxy)acetic acid (30.0 mg, 94.8 μmol) and (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (44.2 mg, 94.8 μmol) in methylene chloride (2.0 mL) was added O-(benzotriazol-1-yl)-N,N,N',N'-tetramethyluronium tetrafluoroborate (30.4 mg, 94.8 μmol) and diisopropylethylamine (49.4 μL, 284 μmol) at rt. The reaction mixture was allowed to stir at rt for 30 minutes. The reaction was monitored by LC-MS, which indicated completion of reaction. The reaction mixture was concentrated under reduced pressure to give a crude material, which was purified by flash silica gel chromatography on a Teledyne Combiflash ISCO (gradient eluent: Heptane/Acetone (v:v=100:0 to 0:100)) to give titled product (yield: 99%) as a white solid. LC-MS (ES⁺): m/z 729.30 [MH⁺].

Step 4: 2-({4-[4-(methoxycarbonyl)phenoxy]phenyl}methoxy)acetic Acid

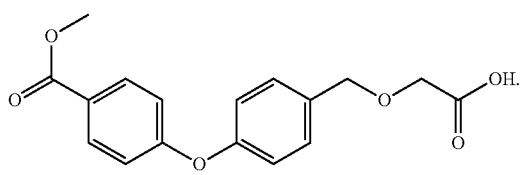 [SMILES: COC(=O)c1ccc(Oc2ccc(COCC(=O)O)cc2)cc1]

A solution of methyl 4-(4-{[2-(tert-butoxy)-2-oxoethoxy]methyl}phenoxy)benzoate (200.0 mg, 537 μmol) in hydrogen chloride solution (4 M in dioxane, 2.0 mL) was stirred at room temperature for 2 h. The reaction was monitored by LC-MS, which indicated completion of reaction. The reaction mixture was concentrated under reduced pressure to give titled product (yield: 95% based on crude) as an off white solid. This material used in next step reaction without any further purification. LC-MS (ES⁺): m/z 339.0858 [MNa⁺].

Step 3: Synthesis of methyl 4-(4-{[2-(tert-butoxy)-2-oxoethoxy]methyl}phenoxy)benzoate

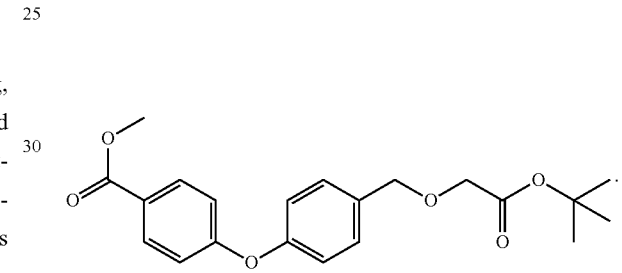

To a stirred mixture of sodium hydroxide (1.16 g, 29 mmol) in water (2.0 mL) and toluene (2.0 mL) at 20° C. was charged with tetrabutylammonium hydrogen sulfate (32.86 mg, 96.79 μmol), followed by methyl 4-[4-(hydroxymethyl)phenoxy]benzoate (250.0 mg, 967.9 μmol), the resulting mixture was stirred at 20° C. for 1 h. The mixture was then cooled to 5° C., tert-butyl 2-bromoacetate (207.5 mg, 1.064 mmol) was added slowly and the internal temperature was maintained below 15° C. Upon the completion of this addition, the reaction mixture was allowed to warm up to rt and stirred for 16 h at rt. The reaction was monitored by LC-MS, which indicated completion of reaction. The mixture was diluted with water (5 mL) and extracted with EtOAc (30 mL). The organic layer was separated, dried over anhydrous sodium sulfate, filtered and concentrated under reduced pressure to a give a crude material, which was purified by flash silica gel chromatography on a Teledyne Combiflash ISCO (eluent (gradient): Heptane/EtOAc (v:v=100:0 to 70:30)) to give titled product (yield: 56%) as a white solid. LC-MS (ES⁺): m/z 395.15 [MNa⁺].

Step 2: Synthesis of methyl 4-[4-(hydroxymethyl)phenoxy]benzoate

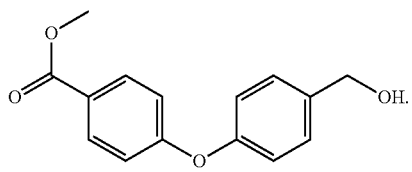 [SMILES: COC(=O)c1ccc(Oc2ccc(CO)cc2)cc1]

To a stirred solution of methyl 4-(4-formylphenoxy)benzoate (750.0 mg, 2.92 mmol) in methanol (2.0 mL) was added sodium borohydride (121 mg, 3.21 mmol) at rt. The reaction mixture was allowed to stir at rt for 30 min. The reaction was monitored by LC-MS, which indicated completion of reaction. The reaction mixture was slowly quenched with 1N HCl (solution in water), concentrated under reduced pressure to remove the bulk of methanol, and then extracted with DCM (30 mL). The organic layer was separated, washed with brine (5 mL), dried over $Na_2SO_4$, filtered and concentrated under reduced pressure to give a crude material, which was purified by flash silica gel chromatography on a Teledyne Combiflash ISCO (eluent (gradient): Heptane/EtOAc (v:v=100:0 to 50:50)) to give titled product (yield: 94%) as a white solid. LC-MS ($ES^+$): m/z 259.10 [$MH^+$].

Step 1: Synthesis of methyl 4-(4-formylphenoxy)benzoate

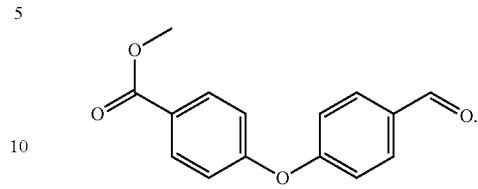

To a stirred mixture of methyl 4-hydroxybenzoate (1.0 g, 6.57 mmol) and potassium carbonate (1.36 g, 9.85 mmol) in dimethylformamide (2.0 mL) was added 4-fluorobenzaldehyde (815 mg, 6.57 mmol) at rt. The reaction mixture was then stirred at 80° C. for 16 h. The reaction was monitored by LC-MS, which indicated completion of reaction. The reaction mixture was cooled to rt, diluted with water (10 mL) and extracted with EtOAc (50 mL×2). The organic layer was separated, washed with brine (10 mL×2), dried over $Na_2SO_4$, filtered and concentrated under reduced pressure to give a crude material, which was purified by flash silica gel chromatography on a Teledyne Combiflash ISCO (eluent (gradient): Heptane/EtOAc (v:v=100:0 to 50:50)) to give titled product (yield: 90%) as a white solid. LC-MS ($ES^+$): m/z 257.08 [$MH^+$].

TABLE 13

Exemplary Compounds.

| Ex# | Structure | Compound name and Analytical data |
|---|---|---|
| 188 | (structure shown) | (2S,4R)-1-[(2S)-3,3-dimethyl-2-(2{[5-(4{[trans-3-(3-chloro-4-canophenoxy)-2,2,4,4-tetramethylcyclobutyl]carbamoyl}phenoxy)pentyl]amino}acetamido)butanoyl]-4-hydroxy-N-{[4-(4-methyl-1,3-oxazol-5-yl)phenyl]methyl}pyrrolidine-2-carboxamide <br> $^1$H NMR (400 MHz, CDCl$_3$) δ 8.68 (s, 1H), 7.63 (d, J = 8.6 Hz, 2H), 7.57 (d, J = 8.6 Hz, 1H), 7.35 (q, J = 8.5 Hz, 4H), 6.97 (d, J = 2.3 Hz, 1H), 6.81 (dd, J = 2.5, 8.8 Hz, 1H), 6.60 (d, J = 9.0 Hz, 2H), 6.07-6.12 (m, 1H), 4.74 (s, 1H), 4.50-4.59 (m, 3H), 4.37 (d, J = 5.1 Hz, 1H), 4.11-4.17 (m, 2H), 3.64 (dd, J = 3.5, 11.3 Hz, 1H), 3.53 (d, J = 7.0 Hz, 2H), 3.19 (t, J = 7.0 Hz, 2H), 2.55-2.61 (m, 1H), 2.52 (s, 3H), 2.10-2.19 (m, 2H), 1.65-1.71 (m, 4H), 1.50-1.53 (m, 2H), 1.24-1.33 (m, 9H), 1.22 (s, 6H), 0.96 (s, 9H), 0.86-0.91 (m, 3H). LC-MS ($ES^+$): m/z 954.43 [$MH^+$] |

TABLE 13-continued

Exemplary Compounds.

| Ex# | Structure | Compound name and Analytical data |
|---|---|---|
| 189 | ![structure] | (2S,4R)-1-[(2S)-3,3-dimethyl-2-(2-{[5-(4-{[trans-3-(3-chloro-4-cyanophenoxy)-2,2,4,4-tetramethylcyclobutyl]carbamoyl}phenoxy)pentyl]amino}acetamido)butanoyl]-4-hydroxy-N-{[4-(4-methyl-1,3-oxazol-5-yl)phenyl]methyl}pyrrolidine-2-carboxamide<br>$^1$H NMR (400 MHz, CDCl$_3$) δ 7.79 (s, 1H), 7.72 (d, J = 8.6 Hz, 2H), 7.54-7.60 (m, 1H), 7.51 (d, J = 8.2 Hz, 2H), 7.34 (d, J = 8.2 Hz, 2H), 6.96 (d, J = 2.3 Hz, 1H), 6.88 (d, J = 9.0 Hz, 2H), 6.81 (dd, J = 2.3, 9.0 Hz, 1H), 4.53-4.67 (m, 2H), 4.40 (br. s., 1H), 4.14 (d, J = 8.2 Hz, 1H), 4.05 (s, 1H), 3.92 (br. s., 2H), 3.74 (br. s., 1H), 3.60 (d, J = 8.6 Hz, 1H), 2.39 (s, 3H), 2.23 (br. s., 2H), 1.71 (br. s., 4H), 1.43 (br. s., 2H), 1.27 (s, 12H), 1.22 (s, 6H), 0.99 (br. s., 8H), 0.86-0.93 (m, 6H). LC-MS (ES$^+$): m/z 938.45 [MH$^+$] |

Example 189 was synthesized according to similar procedure described for synthesis of example 188, by using corresponding starting materials and intermediates.

Synthesis of Example 188

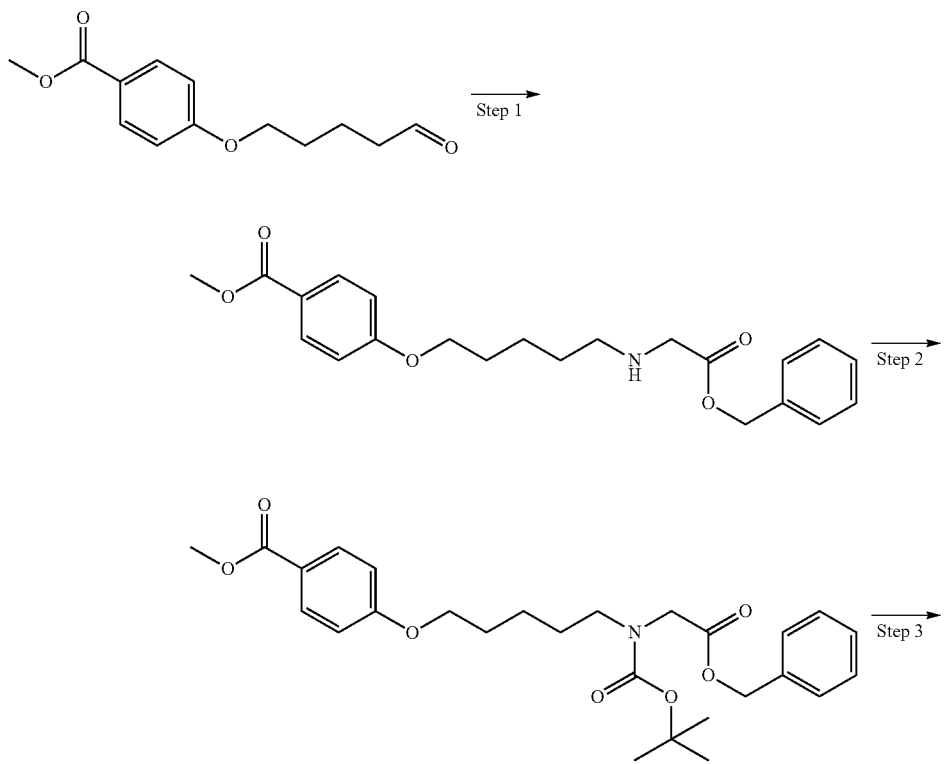

509
510
-continued
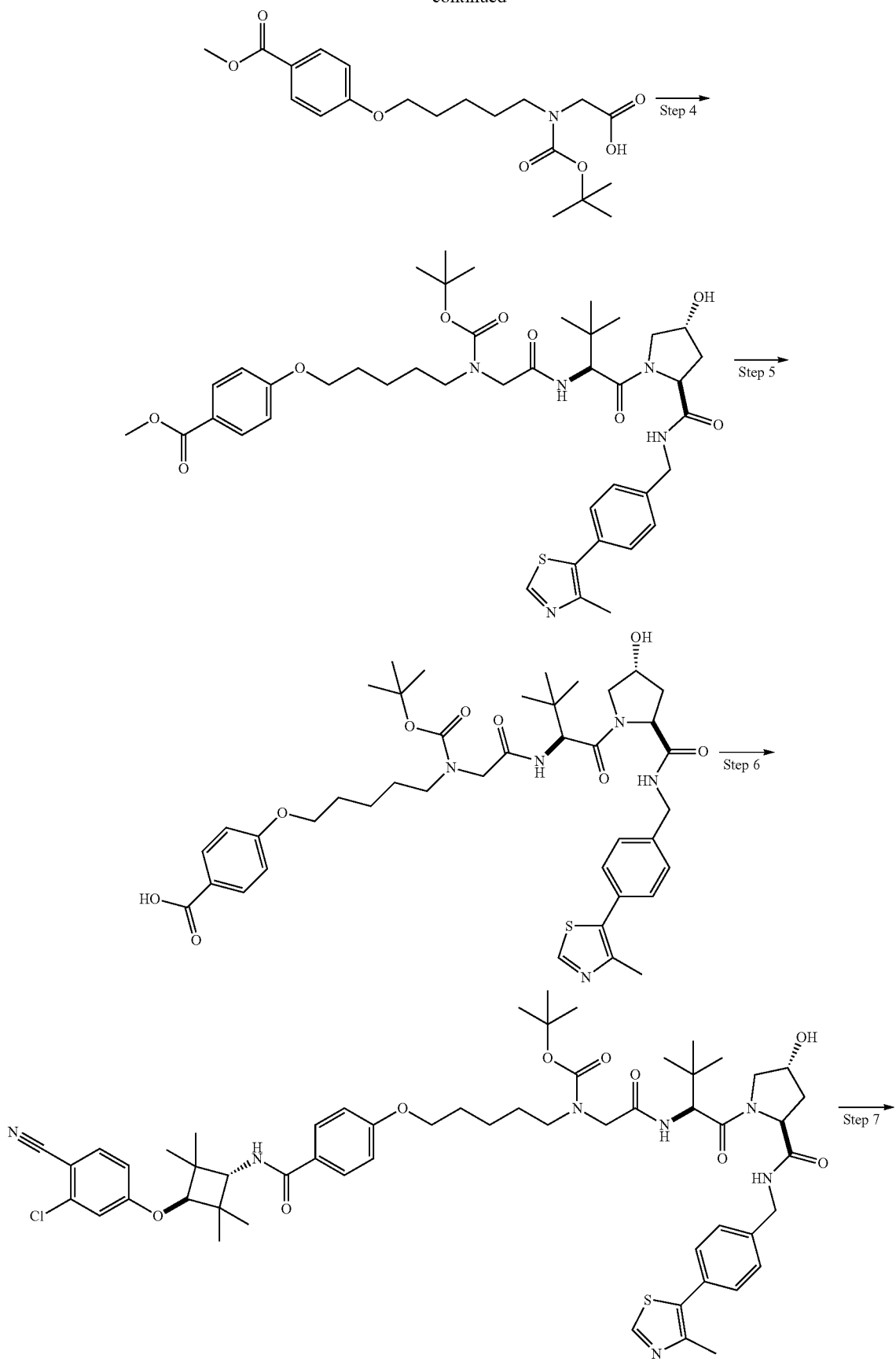

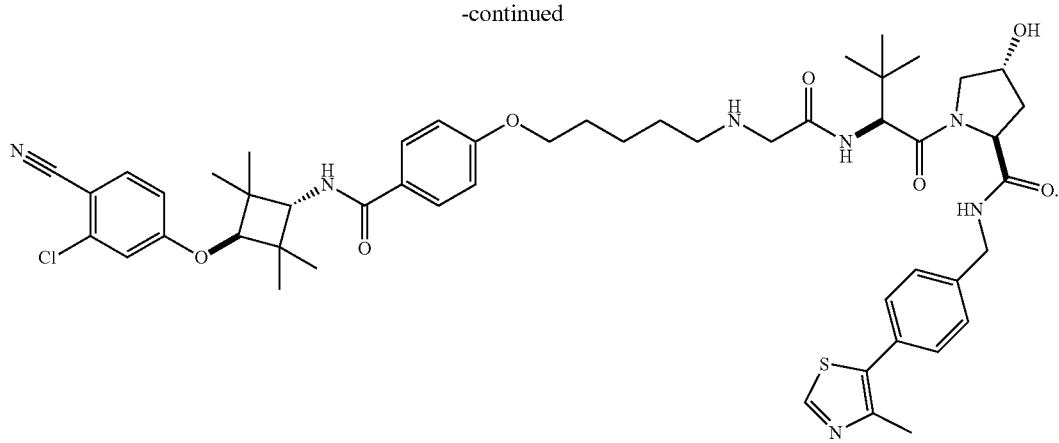

Example 188

Step 7: Synthesis of Example 188

Trifluoroacetic acid (1.12 mL, 14.7 mmol) was added to a stirred solution of tert-butyl N-({[(2S)-1-[(2S,4R)-4-hydroxy-2-({[4-(4-methyl-1,3-oxazol-5-yl)phenyl]methyl}carbamoyl)pyrrolidin-1-yl]-3,3-dimethyl-1-oxobutan-2-yl]carbamoyl}methyl)-N-[5-(4-{[trans-3-(3-chloro-4-cyanophenoxy)-2,2,4,4-tetramethylcyclobutyl]carbamoyl}phenoxy)pentyl]carbamate (34 mg, 0.0327 mmol) in DCM (3.00 ml) at rt. The resulting mixture was stirred at 45° C. for 48 h. The reaction mixture was then concentrated under reduced pressure to give a crude material, which was purified by flash silica gel chromatography on a Teledyne Combiflash ISCO system, eluting with MeOH/DCM (gradient: v:v=0:100 to 10:90) to yield the desired title product (yield: 62%).

Step 6: Synthesis of tert-butyl N-({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methyl)-N-[5-(4-{[trans-3-(3-chloro-4-cyanophenoxy)-2,2,4,4-tetramethylcyclobutyl]carbamoyl}phenoxy)pentyl]carbamate

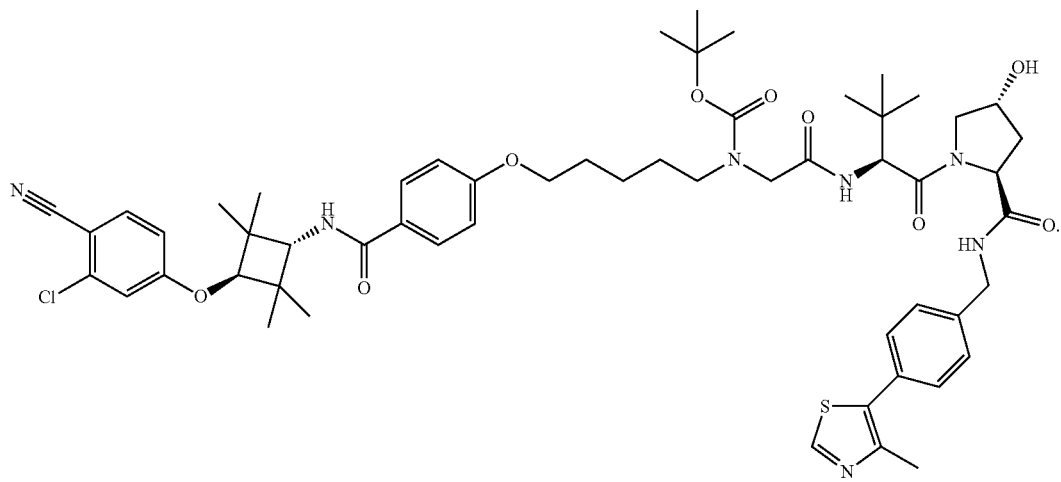 [SMILES: Cc1ncsc1-c1ccc(CNC(=O)[C@@H]2C[C@@H](O)CN2C(=O)[C@@H](NC(=O)CN(CCCCCOc2ccc(C(=O)N[C@H]3C(C)(C)[C@H](Oc4ccc(C#N)c(Cl)c4)C3(C)C)cc2)C(=O)OC(C)(C)C)C(C)(C)C)cc1]

TBTU (23.0 mg, 0.072 mmol) was added to a stirred solution of 4-[(5-{[(tert-butoxy)carbonyl]({[(2S)-1-[(2S,4R)-4-hydroxy-2-([4-(4-methyl-1,3-thiazol-5-yl)phenyl]methyl}carbamoyl)pyrrolidin-1-yl]-3,3-dimethyl-1-oxobutan-2-yl]carbamoyl}methyl)amino}pentyl)oxy]benzoic acid (38 mg, 0.04786 mmol) and 2-chloro-4-[trans-3-amino-2,2,4,4-tetramethylcyclobutoxy]benzonitrile (13.3 mg, 0.04786 mmol) in DMF (3.0 mL) and DIPEA (16.5 tit, 0.095 mmol) at rt. The resulting mixture was stirred at rt for 1 h. The reaction was then diluted with EtOAc (30 mL), washed with brine (5 mL×2), filtered through a Biotage Universal Phase Separator and then concentrated under reduced pressure to give a crude material, which was purified by flash silica gel chromatography on a Teledyne Combiflash ISCO system, eluting with MeOH/DCM (gradient: v:v=0:100 to 10:90) to yield the desired title product (yield: 60%).

Step 5: Synthesis of 4-[(5-{[(tert-butoxy)carbonyl]({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methyl)amino}pentyl)oxy]benzoic Acid

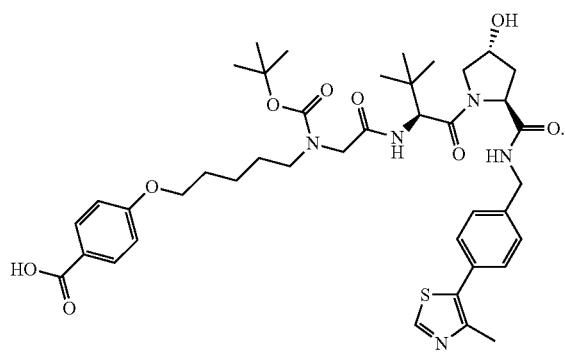 [SMILES: Cc1ncsc1-c1ccc(CNC(=O)[C@@H]2C[C@@H](O)CN2C(=O)[C@@H](NC(=O)CN(CCCCCOc2ccc(C(=O)O)cc2)C(=O)OC(C)(C)C)C(C)(C)C)cc1]

Lithium hydroxide (3.0 mg, 0.128 mmol) was added to a stirred solution of methyl 4-[(5-{[(tert-butoxy)carbonyl]([(2S)-1-[(2S,4R)-4-hydroxy-2-([4-(4-methyl-1,3-thiazol-5-yl)phenyl]methyl}carbamoyl)pyrrolidin-1-yl]-3,3-dimethyl-1-oxobutan-2-yl]carbamoyl methyl)amino pentyl) oxy]benzoate (37 mg, 0.046 mmol) in a mixed solvent of THF/water (v:v=1:1, 2.00 mL) at rt. The resulting reaction mixture was stirred at rt overnight. To the reaction mixture was added 1N HCl (aqueous solution) to adjust pH=~3. The resulting mixture was extracted with EtOAc (20 mL×2), washed with brine (5 mL×2), filtered through a Biotage Universal Phase Separator and then concentrated under reduced pressure to give a crude material (yield: 100% based on crude). This crude product was used for the next step reaction without any further purification.

Step 4: Synthesis of methyl 4-[(5-{[(tert-butoxy)carbonyl]({[(2S)-1-[(2S,4R)-4-hydroxy-2-({[4-(4-methyl-1,3-thiazol-5-yl)phenyl]methyl}carbamoyl)pyrrolidin-1-yl]-3,3-dimethyl-1-oxobutan-2-yl]carbamoyl}methyl)amino}pentyl)oxy]benzoate

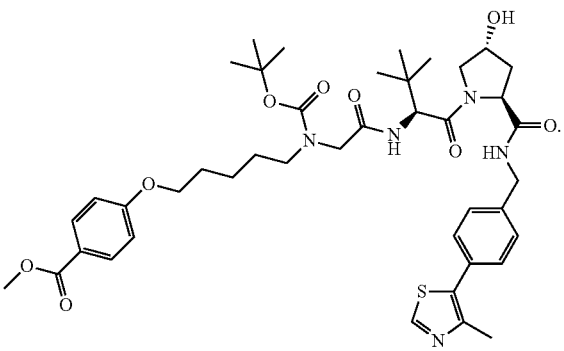 [SMILES: COC(=O)c1ccc(OCCCCCN(CC(=O)N[C@H](C(=O)N2C[C@H](O)C[C@H]2C(=O)NCc2ccc(-c3scnc3C)cc2)C(C)(C)C)C(=O)OC(C)(C)C)cc1]

TBTU (36.6 mg, 0.1142 mmol) was added to a stirred solution of 2-{[(tert-butoxy)carbonyl]({5-[4-(methoxycarbonyl)phenoxy]pentyl})amino}acetic acid (37 mg, 0.076 mmol) and (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide (32.8 mg, 0.076 mmol) in DMF (3.0 mL) and DIPEA (26.4 µL, 0.15 mmol) at rt. The resulting reaction mixture was stirred at rt for 1 hr. The reaction was then diluted with EtOAc (30 mL), washed with brine (10 mL), filtered through a Biotage Universal Phase Separator and then concentrated under reduced pressure to give a crude material, which was purified by flash silica gel chromatography on a Teledyne Combiflash ISCO system, eluting with MeOH/DCM (gradient: v/v=0/100 to 10/90) to yield the desired title product (yield: 64%).

Step 3: Synthesis of 2-{[(tert-butoxy)carbonyl]({5-[4-(methoxycarbonyl)phenoxy]pentyl})amino}acetic Acid

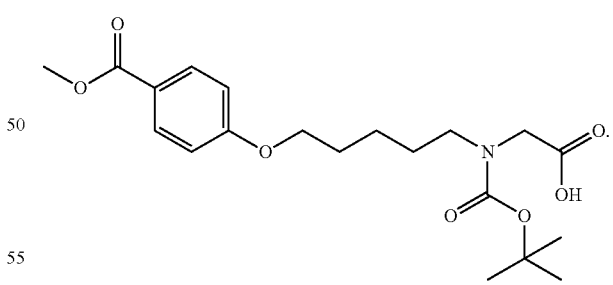

Palladium on carbon (96.8 mg, 0.91 mmol) was added to a stirred solution of methyl 4-[(5-{[2-(benzyloxy)-2-oxoethyl][(tert-butoxy)carbonyl]amino}pentyl)oxy]benzoate (83.0 mg, 0.171 mmol) in ethanol (20 ml) at rt. The reaction mixture was degassed and charged with $H_{(g)}$ and then stirred at rt for 16 h under a hydrogen atmosphere. Solids were then removed by filtration and the solvent was concentrated under reduced pressure to give a crude material (yield: 98% based on crude). This crude product was used for the next step reaction without any further purification.

515

Step 2: Synthesis of methyl 4-[(5-{[2-(benzyloxy)-2-oxoethyl][(tert-butoxy)carbonyl]amino}pentyl)oxy]benzoate

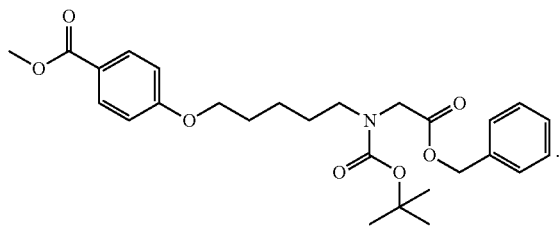 [SMILES: COC(=O)c1ccc(OCCCCCN(CC(=O)OCc2ccccc2)C(=O)OC(C)(C)C)cc1]

Di-tert-butyl dicarbonate (47.7 μL, 0.21 mmol) was added to a stirred solution of methyl 4-[(5-{[2-(benzyloxy)-2-oxoethyl]amino}pentyl)oxy]benzoate (73.0 mg, 0.19 mmol) in THF (5.0 ml) at rt. The reaction mixture was heated to reflux at 80° C. and stirred at 80° C. for 14 h. The reaction was then cooled to rt, diluted with ethyl acetate (20 mL), washed with saturated aq. NaHCO₃ (10 mL). The organic layer was separated and filtered using a Biotage Universal Phase Separator and then concentrated under reduced pressure to give a crude material, which was purified by flash silica gel chromatography on a Teledyne Combiflash ISCO system, eluting with EtOAc/Heptane (gradient v:v=0:100 to 40:60) to yield the desired title product (yield: 95%).

516

Step 1: Synthesis of methyl 4-[(5-{[2-(benzyloxy)-2-oxoethyl]amino}pentyl)oxy]benzoate

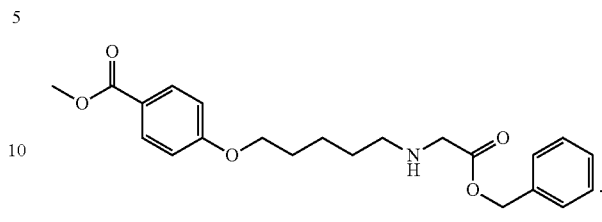

To a stirred mixture of methyl 4[(5-oxopentyl)oxy]benzoate (269 mg, 1.13 mmol) and benzyl 2-aminoacetate hydrochloride (186 mg, 1.13 mmol) in DCE (5.00 mL) was added acetic acid (181 μL, 2.26 mmol) and sodium triacetoxyborohydride (358 mg, 1.69 mmol) at rt. The reaction mixture was stirred at rt for 18 h. To the reaction mixture was added 1N NaOH aqueous solution to adjust pH=~10, the resulting mixture was then extracted with DCM (30 mL×3). The organic layer was separated, washed with brine (10 mL×2), dried over Na₂SO₄, filtered and concentrated under reduced pressure to give a crude material, which was purified by flash silica gel chromatography on a Teledyne Combiflash ISCO, eluting with MeOH/DCM (gradient v:v=0:100 to 15:85) to yield the titled product (17%).

TABLE 14

Exemplary Compounds.

| Ex# | Structure | Compound name and Analytical data |
|---|---|---|
| 190 | (structure shown) | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetamido)-3,3-dimethylbutanoyl]-4-hydroxy-N-{[4-(1,3-oxazol-5-yl)phenyl]methyl}pyrrolidine-2-carboxamide<br>$^1$H NMR (300 MHz, CD₃OD): δ 9.14 (s, 1H), 8.65 (d, J = 2.1 Hz, 1H), 8.21-8.10 (m, 1 H), 7.74-7.50 (m, 6H), 7.47-7.29 (m, 5H), 7.10-6.97 (m, 2H), 4.70-4.22 (m, 5H), 4.15-3.96 (m, 4H), 3.95-3.70 (m, 2H), 3.70-3.50 (m, 2H), 2.24-2.00 (m, 2H), 2.00-1.80 (m, 4H), 1.57 (s, 6H), 1.00 (s, 9H); LC-MS (ES⁺): m/z, 995.20 [MH⁺] |

TABLE 14-continued

Exemplary Compounds.

| Ex# | Structure | Compound name and Analytical data |
|---|---|---|
| 191 | 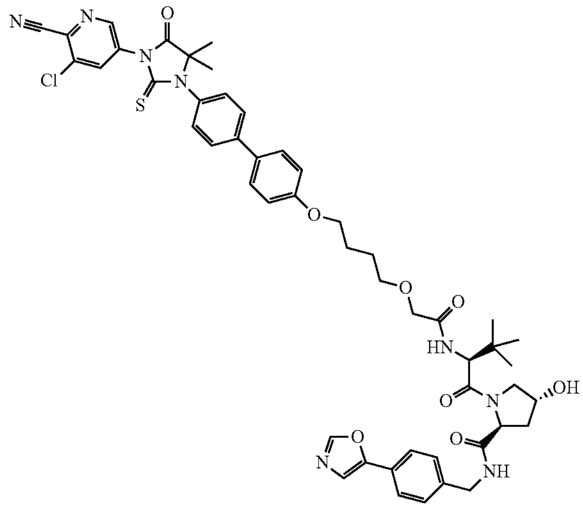 [SMILES: CC(C)(C)[C@H](NC(=O)COCCCCOc1ccc(-c2ccc(N3C(=S)N(c4cnc(C#N)c(Cl)c4)C(=O)C3(C)C)cc2)cc1)C(=O)N1C[C@H](O)C[C@H]1C(=O)NCc1ccc(-c2cnco2)cc1] | (2S,4R)-1-[(2S)-2-{2-[4-(4-{4-[3-(5-chloro-6-cyanopyridin-3-yl)-5,5-dimethyl-4-oxo-2-sulfanylideneimidazolidin-1-yl]phenyl}phenoxy)butoxy]acetamido}-3,3-dimethylbutanoyl]-4-hydroxy-N-{[4-(1,3-oxazol-5-yl)phenyl]methyl}pyrrolidine-2-carboxamide<br>Mass (ES+): m/z 961.20 [MH+] |
| 192 | 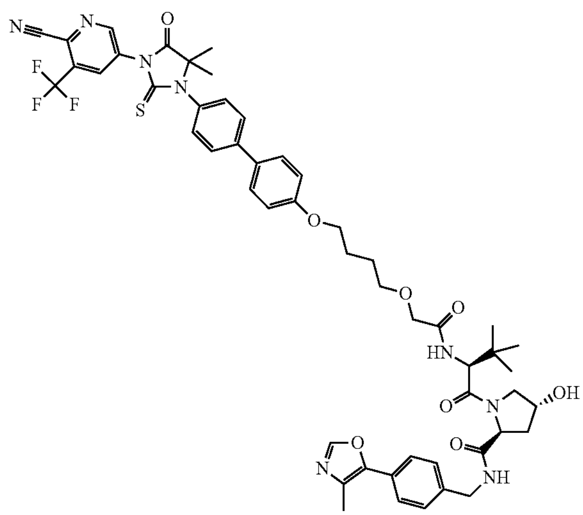 [SMILES: Cc1ncoc1-c1ccc(CNC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C4(C)C)cc3)cc2)C(C)(C)C)cc1] | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetamido)-3,3-dimethylbutanoyl]-4-hydroxy-N-{[4-(4-methyl-1,3-oxazol-5-yl)phenyl]methyl}pyrrolidine-2-carboxamide<br>Mass (ES+): m/z 1009.20 [MH+] |
| 193 | 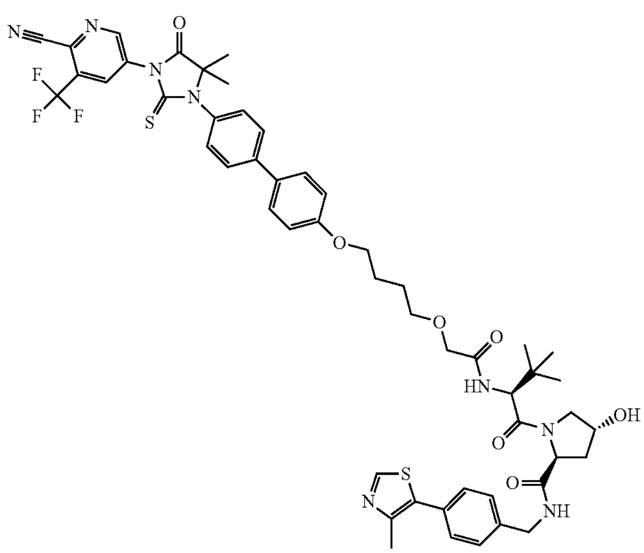 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C4(C)C)cc3)cc2)C(C)(C)C)cc1] | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>Mass (ES+): m/z 1025.45 [MH+] |

| Ex# | Structure | Compound name and Analytical data |
|---|---|---|
| 194 | 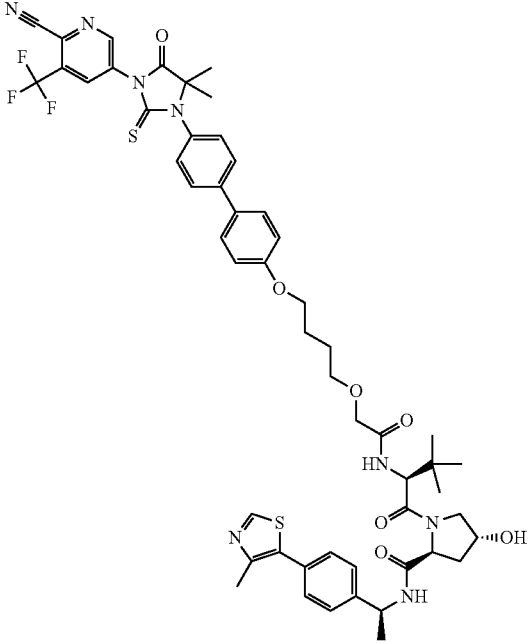 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C4(C)C)cc3)cc2)C(C)(C)C)cc1] | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, CD$_3$OD): δ 9.19 (s, 1H), 8.86 (s, 1H), 8.70 (s, 1H), 7.75 (d, J = 8.8 Hz, 2H), 7.62 (d, J = 8.8 Hz, 2H), 7.40 (m, 6H), 7.05 (d, J = 8.8 Hz, 2H), 5.00 (d, J = 7.2 Hz, 1H), 4.56 (s, 1H), 4.64 (m, 1H), 4.44 (m, 1H), 4.10 (m, 2H), 4.06 (m, 2H), 3.86 (m, 1H), 3.76 (m, 1H), 3.66 (m, 2H), 2.47 (s, 3H), 2.22 (m, 1H), 1.92 (m, 5H), 1.62 (s, 6H), 1.49 (d, J = 6.8 Hz, 3H), 1.02 (s, 9H);<br>LC-MS (ES+): m/z 1039.50 [MH$^+$] |
| 195 | 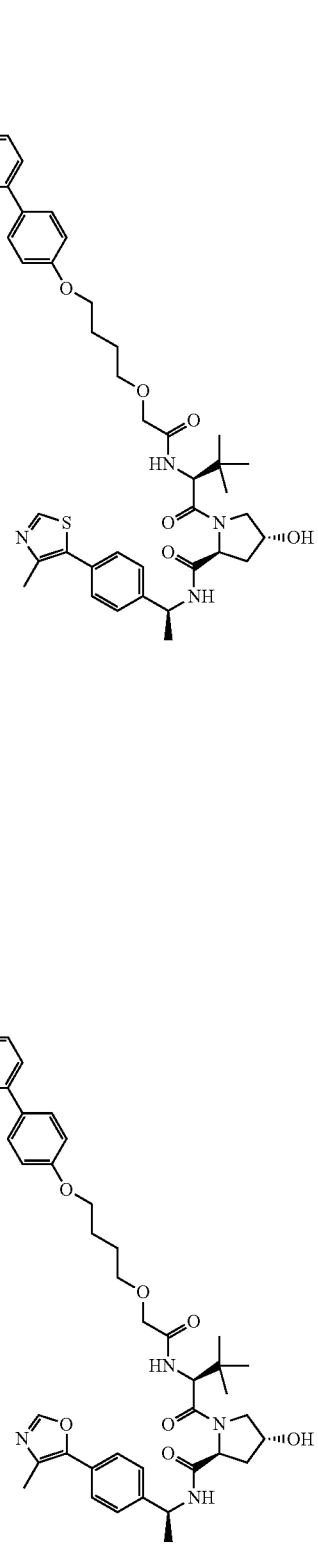 | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetamido)-3,3-dimethylbutanoyl]-4-hydroxy-N-[(1S)-1-[4-(4-methyl-1,3-oxazol-5-yl)phenyl]ethyl]pyrrolidine-2-carboxamide<br>$^1$H NMR (400 MHz, CD$_3$OD): δ 9.19 (s, 1H), 8.70 (s, 1H), 8.12 (s, 1H), 7.75-7.71 (d, J = 8.4 Hz, 2H), 7.61-7.55 (m, 4H), 7.42-7.38 (m, 4H), 7.05-7.01 (d, J = 8.8 Hz, 2H), 5.00-4.96 (d, J = 7.2 Hz, 1H), 4.56 (s, 1H), 4.64-4.62 (m, 1H), 4.44-4.41 (m, 1H), 4.12-4.01 (m, 2H), 4.00-3.98 (m, 2H), 3.86-3.81 (m, 1H), 3.74-3.71 (m, 1H), 3.67-3.65 (m, 2H), 2.38 (s, 3H), 2.22-2.18 (m, 1H), 1.98-1.88(m, 3H), 1.88-1.82 (m, 2H),1.62 (s, 6H), 1.48-1.46 (d, J = 6.8 Hz, 3H), 1.03 (s, 9H);<br>LC-MS (ES+): m/z 1023.50 [MH$^+$] |

TABLE 14-continued

Exemplary Compounds.

| Ex# | Structure | Compound name and Analytical data |
|---|---|---|
| 196 | 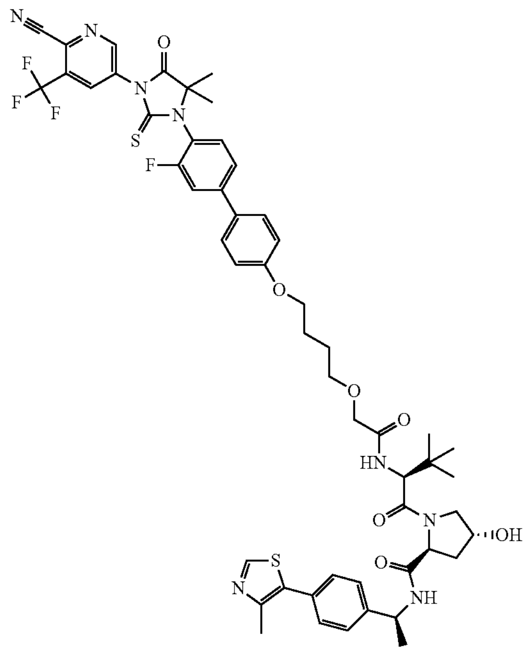 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C4(C)C)c(F)c3)cc2)C(C)(C)C)cc1] | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}-3-fluorophenyl)phenoxy]butoxy}acetamido)-3,3-dimethylbutanoyl]-4-hydroxy-N-[(1S)-1-[4-(4-methyl-1,3-thiazol-5-yl)phenyl]ethyl]pyrrolidine-2-carboxamide<br>Mass (ES+): m/z 1057.15 [MH+] |
| 197 | 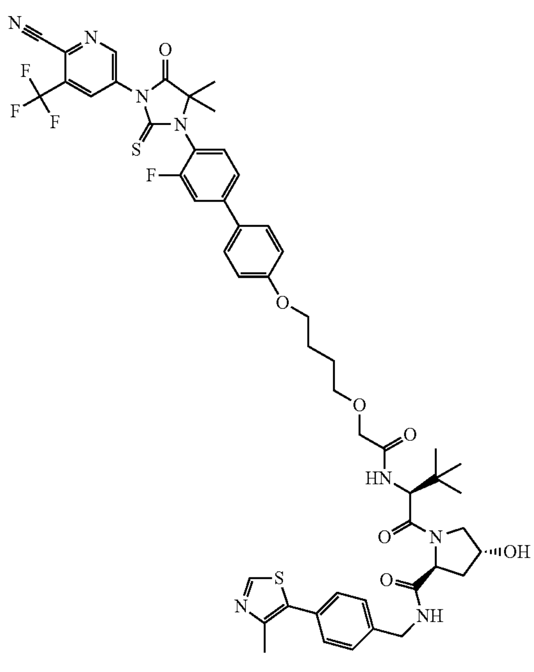 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C4(C)C)c(F)c3)cc2)C(C)(C)C)cc1] | (2S,4R)-1-[(2S)-2-(2-{4-[4-(4-{3-[6-cyano-5-(trifluoromethyl)pyridin-3-yl]-5,5-dimethyl-4-oxo-2-sulfanylideneimidazolidin-1-yl}-3-fluorophenyl)phenoxy]butoxy}acetamido)-3,3-dimethylbutanoyl]-4-hydroxy-N-{[4-(4-methyl-1,3-thiazol-5-yl)phenyl]methyl}pyrrolidine-2-carboxamide<br>Mass (ES+): m/z 1043.20 [MH+] |

TABLE 14-continued

Exemplary Compounds.

| Ex# | Structure | Compound name and Analytical data |
|---|---|---|
| 198 | 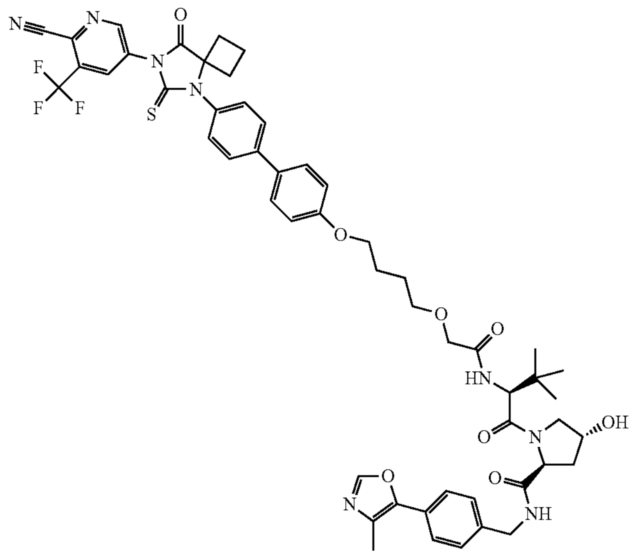 [SMILES: Cc1ncoc1-c1ccc(CNC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C45CCC5)cc3)cc2)C(C)(C)C)cc1] | (2S,4R)-1-[(2S)-2-(2-{4-[4-(4-{7-[6-cyano-5-(trifluoromethyl)pyridin-3-yl]-8-oxo-6-sulfanylidene-5,7-diazaspiro[3.4]octan-5-yl}phenyl)phenoxy]butoxy}acetamido)-3,3-dimethylbutanoyl]-4-hydroxy-N-{[4-(4-methyl-1,3-oxazol-5-yl)phenyl]methyl}pyrrolidine-2-carboxamide <br> $^1$H NMR (400 MHz, CD$_3$OD): δ 9.20 (s, 1H), 8.68 (s, 1H), 8.10 (s, 1H), 7.78-7.75 (d, J = 8.4 Hz, 2H), 7.69-7.60 (m, 4H), 7.48-7.45 (m, 4H), 7.08-7.01 (d, J = 8.8 Hz, 2H), 4.73 (s, 1H), 4.56-4.51 (m, 3H), 4.33-4.30 (m, 1H), 4.17-4.09 (m, 2H), 4.06-4.01 (m, 2H), 3.92-3.85 (m, 2H), 3.83-3.78 (m, 2H), 2.80-2.61 (m, 4H), 2.38 (s, 3H), 2.3-2.02 (m, 3H), 1.99-1.85 (m, 4H), 1.72-1.61 (m, 1H), 1.48-1.39 (m, 2H), 1.05 (s, 9H); LC-MS (ES$^+$): m/z 1021.40 [MH$^+$] |
| 199 | 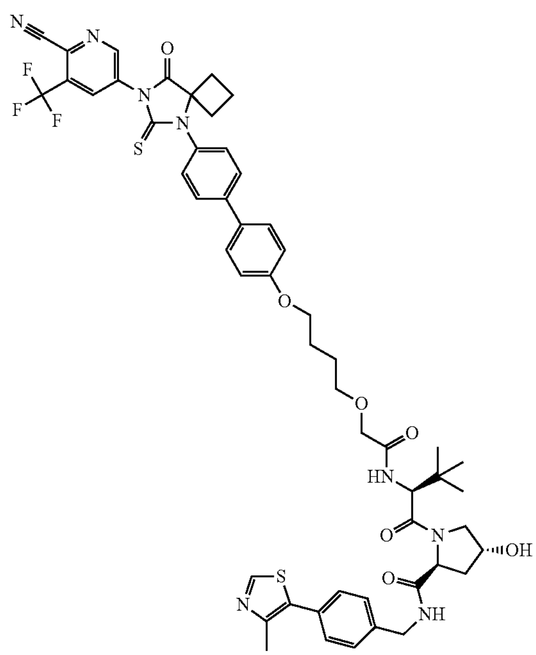 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5cnc(C#N)c(C(F)(F)F)c5)C(=O)C45CCC5)cc3)cc2)C(C)(C)C)cc1] | (2S,4R)-1-[(2S)-2-(2-{4-[4-(4-{7-[6-cyano-5-(trifluoromethyl)pyridin-3-yl]-8-oxo-6-sulfanylidene-5,7-diazaspiro[3.4]octan-5-yl}phenyl)phenoxy]butoxy}acetamido)-3,3-dimethylbutanoyl]-4-hydroxy-N-{[4-(4-methyl-1,3-thiazol-5-yl)phenyl]methyl}pyrrohdine-2-carboxamide <br> $^1$H NMR (400 MHz, CD$_3$OD): δ 9.20 (s, 1H), 8.90 (s, 1H), 8.68 (s, 1H), 7.78 (d, J = 8.4 Hz, 2H), 7.61 (d, J = 8.8 Hz, 2H), 7.52-7.41 (m, 6H), 7.04 (d, J = 8.4 Hz, 2H), 4.73 (s, 1H), 4.60-4.51 (m, 3H), 4.37-4.35 (m, 1H), 4.17-4.11 (m, 2H), 4.05-4.01 (m, 2H), 3.90-3.88 (m, 1H), 3.84-3.78 (m, 1H), 3.68-3.65 (m, 2H), 2.76-2.60 (m, 4H), 2.42 (s, 3H), 2.30-2.05 (m, 3H), 2.01-1.85 (m, 4H), 1.68-1.64 (m, 1H), 1.41-1.29 (m, 3H), 1.05 (s, 9H); LC-MS (ES+): m/z 1037.10 [MH$^+$] |

Examples 191-199 was synthesized according to similar procedure described for synthesis of example 190, by using corresponding starting materials and intermediates.
Synthesis of Example 190
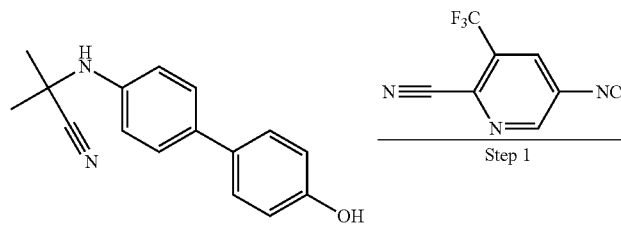
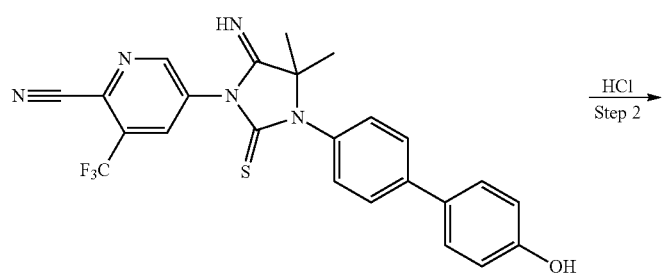
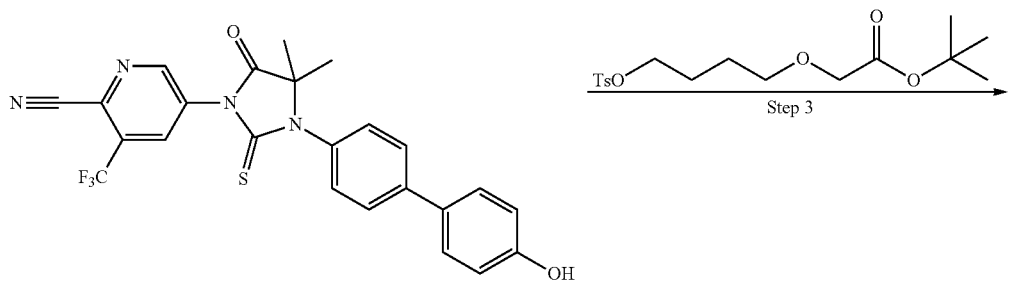
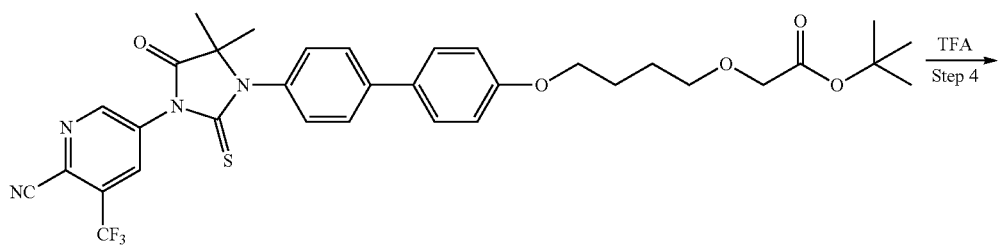
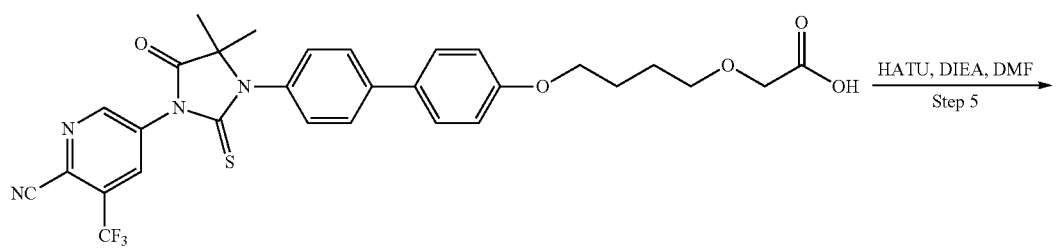

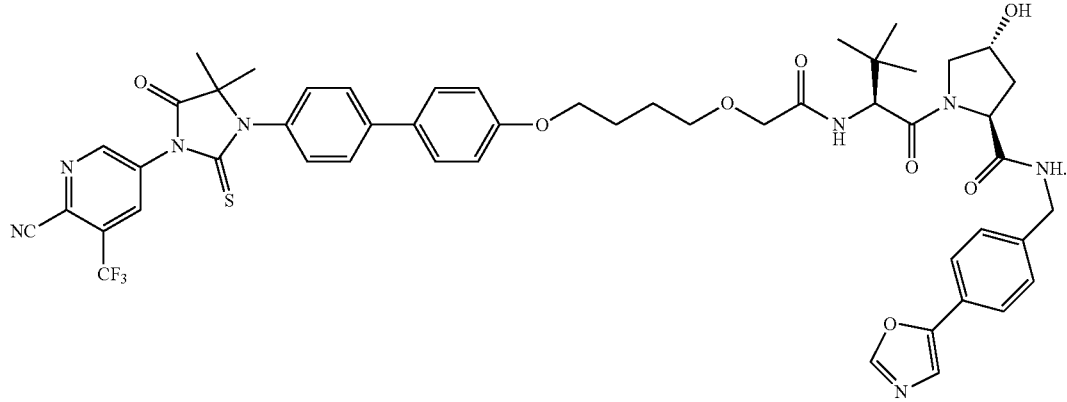

Example 190

Step 1: Synthesis of 5-[3-[4-(4-hydroxyphenyl)phenyl]-5-imino-4,4-dimethyl-2-sulfanylideneimidazolidin-1-yl]-3-(trifluoromethyl)pyridine-2-carbonitrile Step 2: Synthesis of 5-{3-[4-(4-hydroxyphenyl)phenyl]-4,4-dimethyl-5-oxo-2-sulfanylideneimidazolidin-1-yl}-3-(trifluoromethyl)pyridine-2-carbonitrile

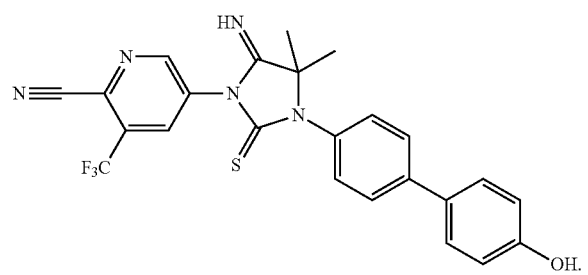 [SMILES: CC1(C)C(=N)N(c2cnc(C#N)c(C(F)(F)F)c2)C(=S)N1c1ccc(-c2ccc(O)cc2)cc1]
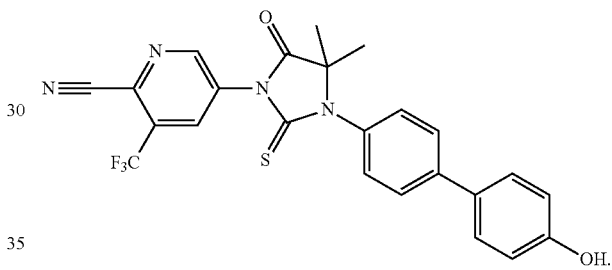

To a stirred solution of 5-isothiocyanato-3-(trifluoromethyl)pyridine-2-carbonitrile (440.0 mg, 1.92 mmol) in N,N-dimethylpyridin-4-amine (322.0 mg, 2.64 mmol) and toluene (10.0 mL) was added 2-[[4-(4-hydroxyphenyl)phenyl]amino]-2-methylpropanenitrile (400.0 mg, 1.59 mmol) under a nitrogen atmosphere at rt. The resulting solution was stirred at 100° C. for 12 h. The reaction mixture was then concentrated under reduced pressure to give a crude material, which was purified by flash silica gel chromatography (eluent: ethyl acetate/petroleum ether, v/v=1/1) to give the titled product (yield: 17%). Mass (ES$^+$): m/z 482.20[MH$^+$].

To a stirred solution of 5-{3-[4-(4-hydroxyphenyl)phenyl]-5-imino-4,4-dimethyl-2-sulfanylideneimidazolidin-1-yl}-3-(trifluoromethyl)pyridine-2-carbonitrile (160.0 mg, 0.33 mmol) in methanol (5.0 mL) was added hydrogen chloride aqueous solution (2N, 2.0 mL) at rt. The resulting solution was then refluxed for 2 h. The reaction was cooled to rt, concentrated under reduced pressure to give a crude material, which was purified by flash silica gel chromatography (eluent: ethyl acetate/petroleum ether, v/v=1/1) to give the titled product (yield: 69%) as a yellow solid. LC-MS (ES$^+$): m/z 481.15[MH$^+$].

Step 3. Synthesis of tert-butyl 2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetate

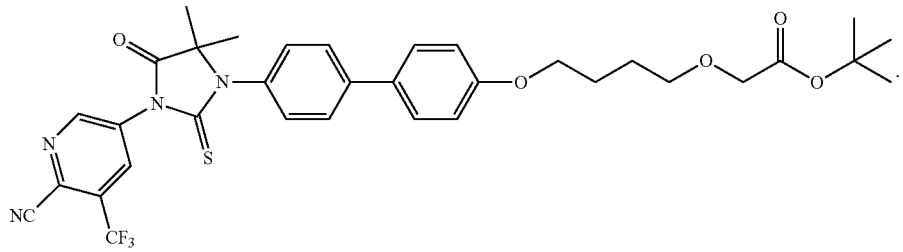 [SMILES: CC(C)(C)OC(=O)COCCCCOc1ccc(-c2ccc(N3C(=S)N(c4cnc(C#N)c(C(F)(F)F)c4)C(=O)C3(C)C)cc2)cc1]

To a stirred solution of 5-{3-[4-(4-hydroxyphenyl)phenyl]-4,4-dimethyl-5-oxo-2-sulfanylideneimidazolidin-1-yl}-3-(trifluoromethyl)pyridine-2-carbonitrile (110.0 mg, 0.23 mmol) and tert-butyl 2-{4-[(4-methylbenzenesulfonyl)oxy]butoxy}acetate (163.0 mg, 0.45 mmol) in N,N-dimethylformamide (3.0 mL) was added potassium carbonate (62.9 mg, 0.46 mmol) at rt. The resulting mixture was stirred at 60° C. for 3 h. The reaction was then cooled to rt, diluted with water (10 mL) and extracted with ethyl acetate (30 mL×3). The organic layers were combined, dried over anhydrous sodium sulfate, concentrated under reduced pressure to give a crude material, which was purified by flash silica gel chromatography (eluent: ethyl acetate/petroleum ether, v/v=1/1) to give the titled product (yield: 98%) as a yellow solid.

Step 4. Synthesis of 2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetic Acid

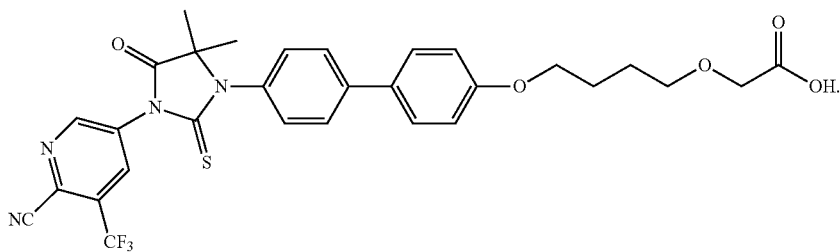 [SMILES: CC1(C)C(=O)N(c2cnc(C#N)c(C(F)(F)F)c2)C(=S)N1c1ccc(-c2ccc(OCCCCOCC(=O)O)cc2)cc1]

To a stirred solution of tert-butyl 2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetate (150.0 mg, 0.22 mmol) in dichloromethane (2.0 mL) was added trifluoroacetic acid (2.0 mL) at rt. The resulting solution was stirred for 2 h at rt. The resulting mixture was concentrated under reduced pressure to give a crude material, which was used for next step reaction without any further purifications. Mass (ES$^+$): m/z 613.00 [MH$^+$].

Step 5. Synthesis of Example 190

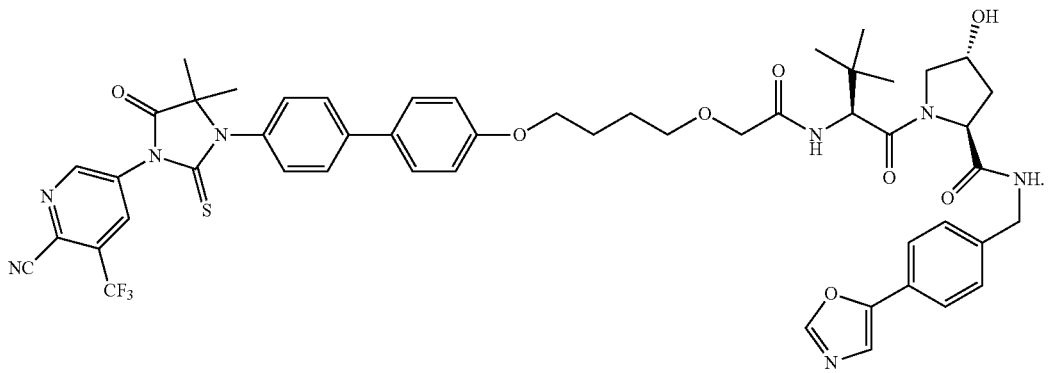 [SMILES: CC(C)(C)[C@H](NC(=O)COCCCCOc1ccc(-c2ccc(N3C(=S)N(c4cnc(C#N)c(C(F)(F)F)c4)C(=O)C3(C)C)cc2)cc1)C(=O)N1C[C@H](O)C[C@H]1C(=O)NCc1ccc(-c2cnco2)cc1]

To a stirred solution of 2-{4-[4-(4-{3-[6-cyano-5-(trifluoromethyl)pyridin-3-yl]-5,5-dimethyl-4-oxo-2-sulfanylideneimidazolidin-1-yl}phenyl)phenoxy]butoxy}acetic acid (80.0 mg, 0.13 mmol) and (2S,4R)-1-[(2S)-2-amino-3,3-dimethylbutanoyl]-4-hydroxy-N-{[4-(1,3-oxazol-5-yl)phenyl]methyl}pyrrolidine-2-carboxamide (53.8 mg, 0.13 mmol) in N,N-dimethylformamide (2.0 mL) was added O-(7-azabenzotriazol-1-yl)-N,N,N,N-tetramethyluronium hexafluorophosphate (51.0 mg, 0.13 mmol) and N-ethyl-N-isopropylpropan-2-amine (43.0 mg, 0.33 mmol) at rt. The resulting solution was stirred for 2 h at rt. LC-MS indicated formation of the desired product. The reaction mixture was diluted with water (10 mL) and extracted with ethyl acetate (50 mL×3). The organic layers were combined, washed with brine (10 mL), dried over anhydrous sodium sulfate and concentrated under reduced pressure to give a crude material, which was purified by a silica gel flash chromatography (eluent: ethyl acetate/petroleum ether, v/v=1/1) to give the titled product as a white solid (yield: 45%).

TABLE 15

Exemplary Compounds.

| Ex# | Structure | Compound name and Analytical data |
|---|---|---|
| 200 | 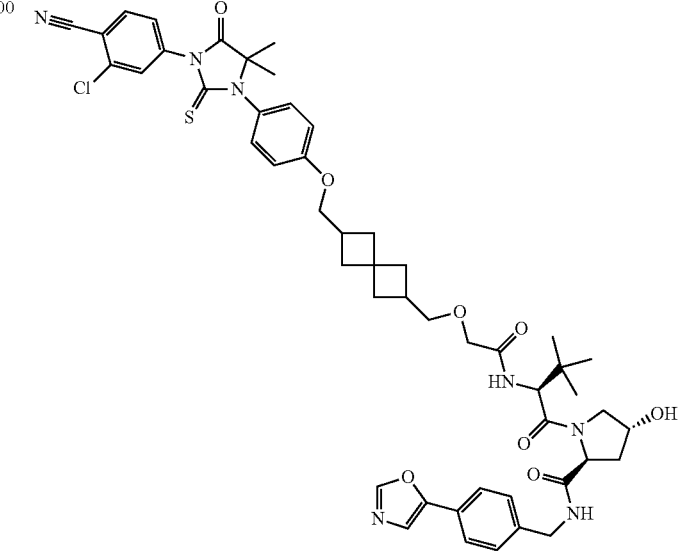 | (2S,4R)-1-[(2S)-2-(2-{[6-({4-[3-(3-chloro-4-cyanophenyl)-5,5-dimethyl-4-oxo-2-sulfanylideneimidazolidin-1-yl]phenoxy}methyl)spiro[3.3]heptan-2-yl]methoxy}acetamido)-3,3-dimethyl-butanoyl]-4-hydroxy-N-{[4-(1,3-oxazol-5-yl)phenyl]methyl}pyrrolidine-2-carboxamide<br>Mass (ES+): m/z 950.50 [MH+] |
| 201 | 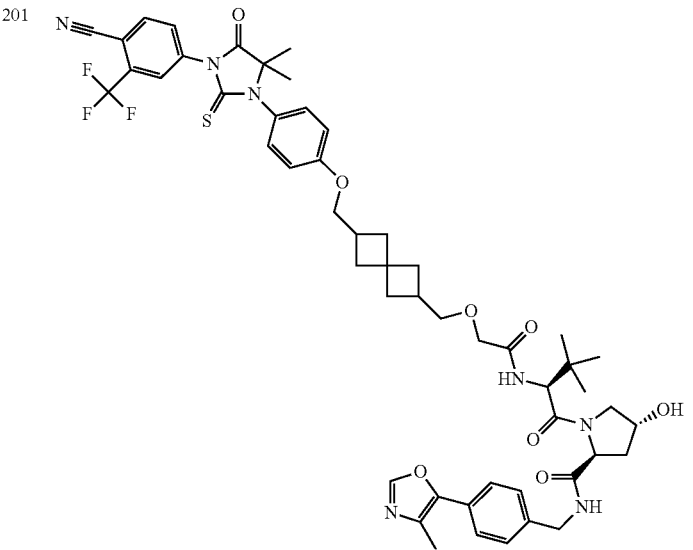 | (2S,4R)-1-[(2S)-2-[2-({6-[(4-{3-[4-cyano-3-(trifluoromethyl)phenyl]-5,5-dimethyl-4-oxo-2-sulfanylideneimidazolidin-1-yl}phenoxy)methyl]spiro[3.3]heptan-2-yl}methoxy)acetamido]-3,3-dimethyl-butanoyl]-4-hydroxy-N-{[4-(4-methyl-1,3-thiazol-5-yl)phenyl]methyl}pyrrolidine-2-carboxamide<br>$^1$H NMR (400 MHz, CD$_3$OD) δ 8.86 (s, 1H), 8.16 (d, J = 8 Hz, 2H), 8.01 (d, J = 8.4 Hz, 1H), 7.51-7.42 (m, 4H), 7.27 (d, J = 8.8 Hz, 2H), 7.07-7.00 (m, 2H), 4.71 (s, 1H), 4.63-4.53 (m, 3H), 4.38-4.33 (m, 1H), 4.04-3.95 (m, 2H), 3.93-3.85 (m, 3H), 3.84-3.80 (m, 1H), 3.53 (s, 2H), 2.63-2.59 (m, 1H), 2.57-2.49 (m, 4H), 2.29-2.19 (m, 3H), 2.18-2.06 (m, 3H), 2.01-1.87 (m, 4H), 1.55 (s, 6H), 1.05 (s, 9H); LC-MS (ES+): m/z 1014.20 [MH+] |

TABLE 15-continued

Exemplary Compounds.

| Ex# | Structure | Compound name and Analytical data |
|---|---|---|
| 202 | 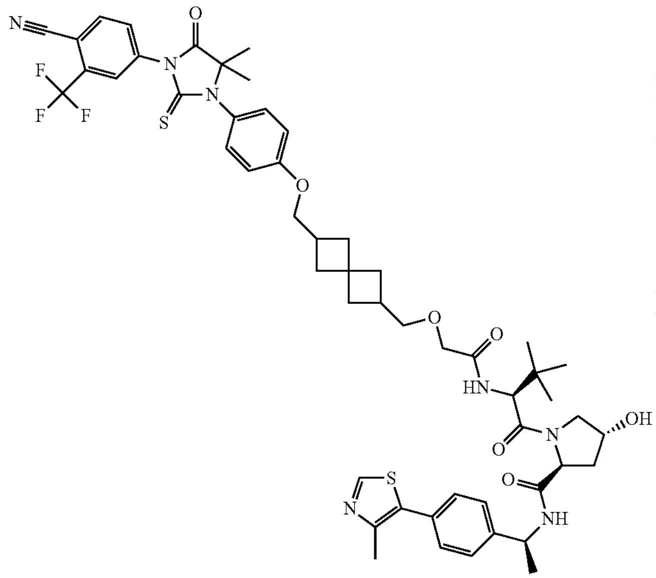 [SMILES: Cc1ncsc1-c1ccc([C@H](C)NC(=O)[C@@H]2C[C@@H](O)CN2C(=O)[C@@H](NC(=O)COCC2CC3(C2)CC(COc2ccc(N4C(=S)N(c5ccc(C#N)c(C(F)(F)F)c5)C(=O)C4(C)C)cc2)C3)C(C)(C)C)cc1] | (2S,4R)-1-[(2S)-2-[2-({6-[(4-{3-[4-cyano-3-(trifluoromethyl)phenyl]-5,5-dimethyl-4-oxo-2-sulfanylideneimidazolidin-1-yl}phenoxy)methyl]spiro[3.3]heptan-2-yl}methoxy)acetamido]-3,3-dimethyl-butanoyl]-4-hydroxy-N-[(1S)-1-[4-(4-methyl-1,3-thiazol-5-yl)phenyl]ethyl]pyrrolidine-2-carboxamide<br>$^1$H NMR (400 MHz, DMSO) δ 8.99 (s, 1H), 8.45 (d, J = 7.6 Hz, 1H), 8.39 (d, J = 8.0 Hz, 1H), 8.29 (s, 1H), 8.08 (d, J = 9.6 Hz, 1H), 7.44 (d, J = 8.4 Hz, 2H), 7.38-7.25 (m, 5H), 7.07 (d, J = 8.8 Hz, 2H), 5.17 (s, 1H), 4.91 (s, 1H), 4.54 (d, J = 9.6 Hz, 1H), 4.45-4.38 (m, 1H), 4.29 (s, 1H), 3.96-3.94 (m, 2H), 3.93-3.90 (m, 2H), 3.60-3.57 (m, 2H), 3.43 (s, 2H), 2.59-2.41 (m, 5H), 2.23-2.04 (m, 5H), 1.93-1.77 (m, 5H), 1.49 (s, 6H), 1.37 (d, J = 7.2 Hz, 3H), 0.95 (s, 9H);<br>LC-MS (ES$^+$): m/z 1028.20 [MH$^+$] |
| 203 | 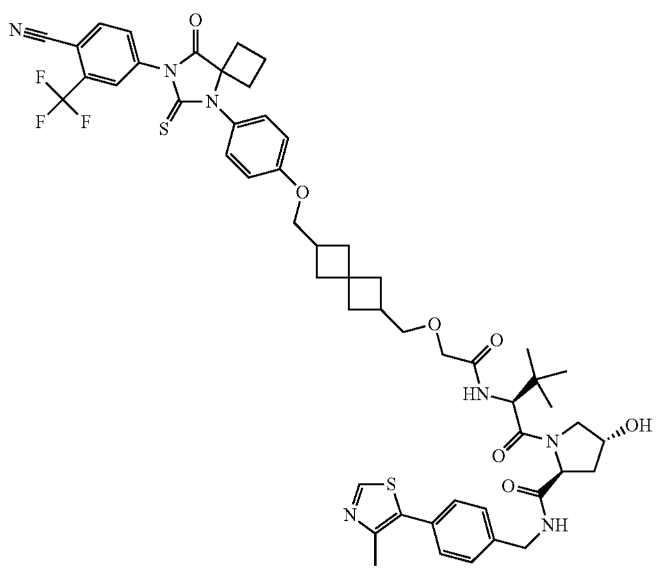 [SMILES: Cc1ncsc1-c1ccc(CNC(=O)[C@@H]2C[C@@H](O)CN2C(=O)[C@@H](NC(=O)COCC2CC3(C2)CC(COc2ccc(N4C(=S)N(c5ccc(C#N)c(C(F)(F)F)c5)C(=O)C45CCC5)cc2)C3)C(C)(C)C)cc1] | (2S,4R)-1-[(2S)-2-[2-({6-[(4-{7-[4-cyano-3-(trifluoromethyl)phenyl]-8-oxo-6-sulfanylidene-5,7-diazaspiro[3.4]octan-5-yl}phenoxy)methyl]spiro[3.3]heptan-2-yl}methoxy)acetamido]-3,3-dimethyl-butanoyl]-4-hydroxy-N-{[4-(4-methyl-1,3-thiazol-5-yl)phenyl]methyl}pyrrolidine-2-carboxamide<br>Mass (ES$^+$): m/z 1026.25 [MH$^+$] |

Example 201 was synthesized according chemistry shown below, utilizing similar procedures used for the synthesis of example 75.

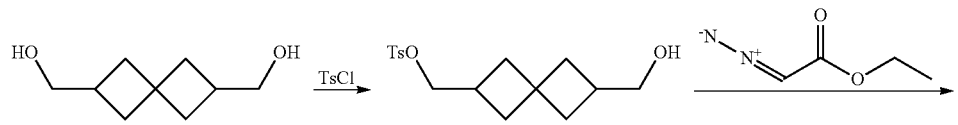

-continued
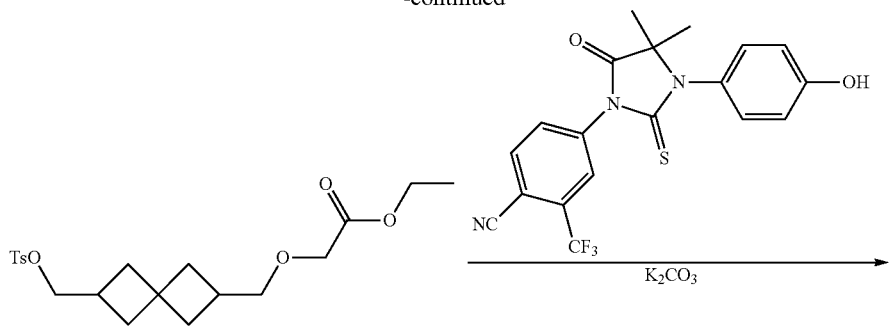
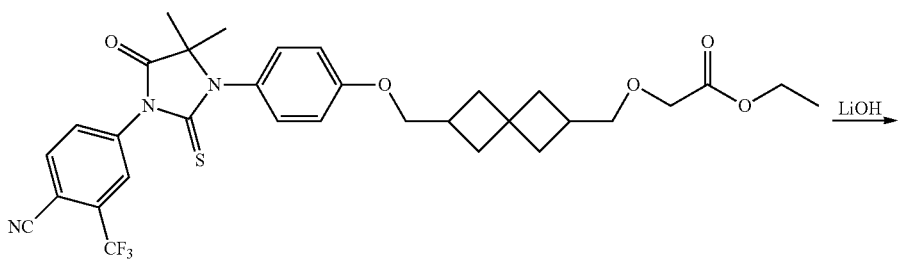
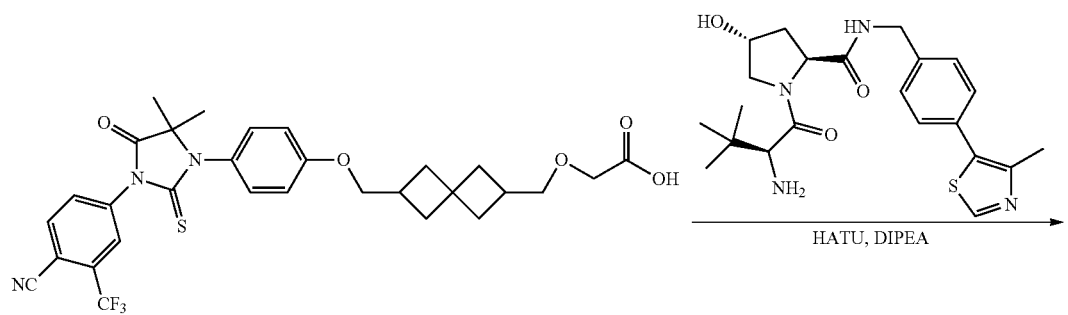
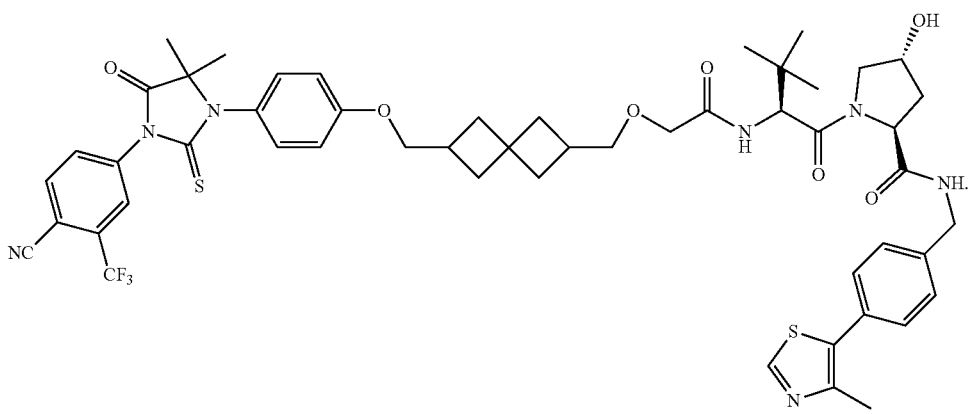
Example 201

Examples 200, 202-203 was synthesized according to similar procedure described for synthesis of example 201, by using corresponding starting materials and intermediates.

TABLE 16

Exemplary Compounds.

| Ex# | Structure | Compound name and Analytical data |
|---|---|---|
| 204 | 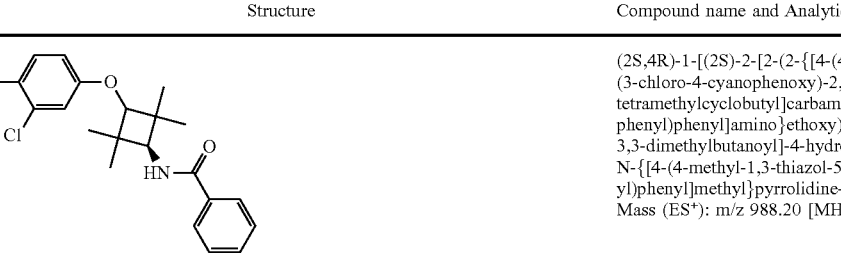 | (2S,4R)-1-[(2S)-2-[2-(2-{[4-(4-{[3-(3-chloro-4-cyanophenoxy)-2,2,4,4-tetramethylcyclobutyl]carbamoyl}phenyl)phenyl]amino}ethoxy)acetamido]-3,3-dimethylbutanoyl]-4-hydroxy-N-{[4-(4-methyl-1,3-thiazol-5-yl)phenyl]methyl}pyrrolidine-2-carboxamide Mass (ES$^+$): m/z 988.20 [MH$^+$] |

TABLE 17

Additional Exemplary Compounds.

| | | Measured Mass Ion Data | |
|---|---|---|---|
| | Structure | MH$^+$ 1 | MH$^+$ 2 |
| 205 | 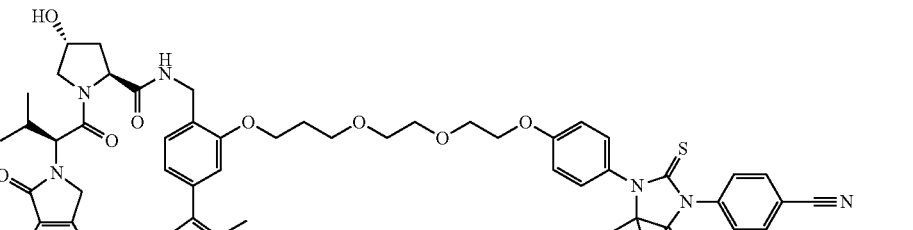 | 1082.37 | |
| 206 | 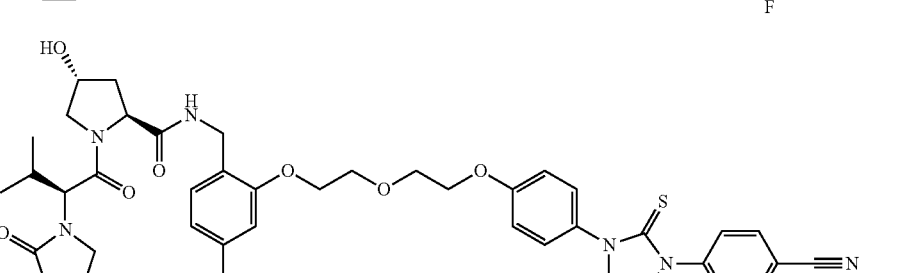 | 1024.33 | |

TABLE 17-continued

Additional Exemplary Compounds.

| Structure | Measured Mass Ion Data | |
|---|---|---|
| | MH+ 1 | MH+ 2 |
| 207 | 1152.45 | |
| 208 | 1096.41 | |
| 209 | 964.33 | |
| 210 | 1112.38 | |

TABLE 17-continued

Additional Exemplary Compounds.

| | Structure | Measured Mass Ion Data | |
|---|---|---|---|
| | | MH+ 1 | MH+ 2 |
| 211 | 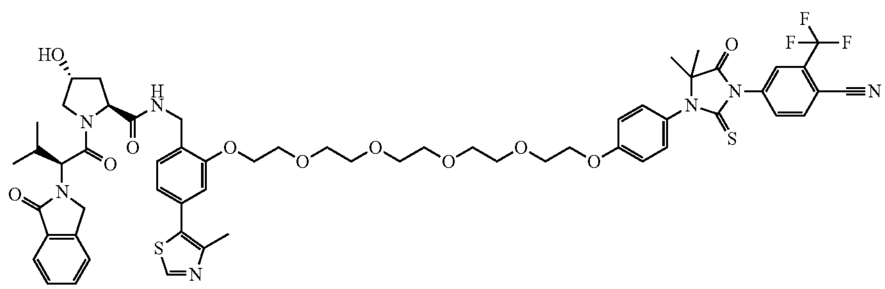 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCOc2ccc(N3C(=S)N(c4ccc(C#N)c(C(F)(F)F)c4)C(=O)C3(C)C)cc2)c1] | 1156.41 | |
| 212 | 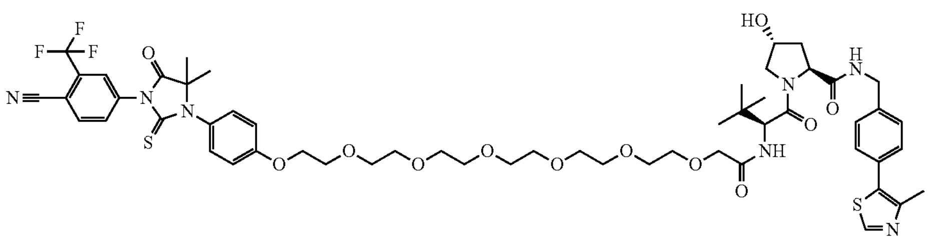 [SMILES: Cc1ncsc1-c1ccc(CNC(=O)[C@@H]2C[C@@H](O)CN2C(=O)[C@@H](NC(=O)COCCOCCOCCOCCOCCOCCOc2ccc(N3C(=S)N(c4ccc(C#N)c(C(F)(F)F)c4)C(=O)C3(C)C)cc2)C(C)(C)C)cc1] | 1140.44 | |
| 213 | 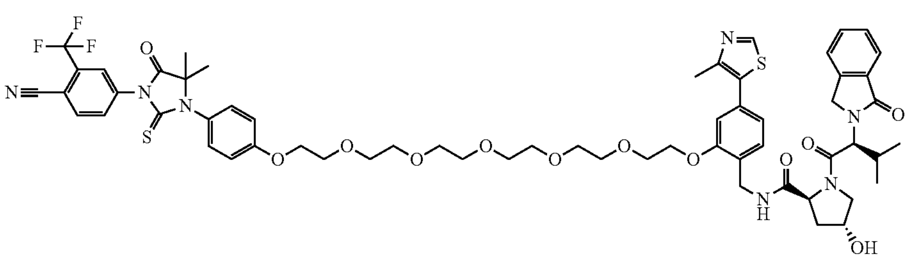 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCOCCOCCOCCOc2ccc(N3C(=S)N(c4ccc(C#N)c(C(F)(F)F)c4)C(=O)C3(C)C)cc2)c1] | 1200.44 | |
| 214 | 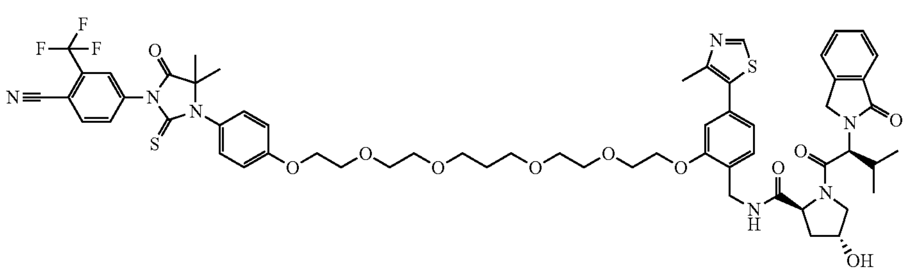 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCOCCOCCOc2ccc(N3C(=S)N(c4ccc(C#N)c(C(F)(F)F)c4)C(=O)C3(C)C)cc2)c1] | 1170.42 | |
| 215 | 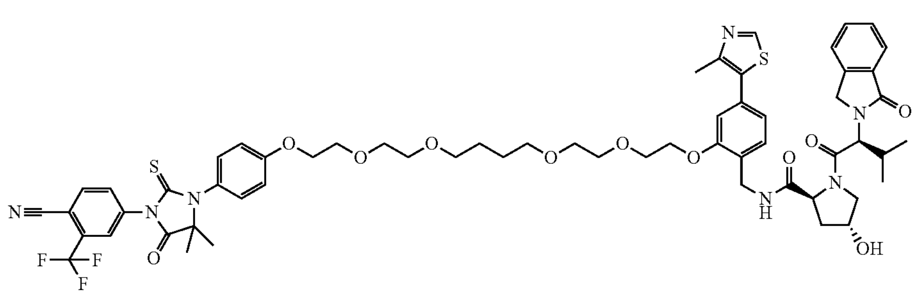 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCCOCCOCCOc2ccc(N3C(=S)N(c4ccc(C#N)c(C(F)(F)F)c4)C(=O)C3(C)C)cc2)c1] | 1184.44 | |

TABLE 17-continued

Additional Exemplary Compounds.

| | Structure | Measured Mass Ion Data | |
|---|---|---|---|
| | | MH+ 1 | MH+ 2 |
| 216 | 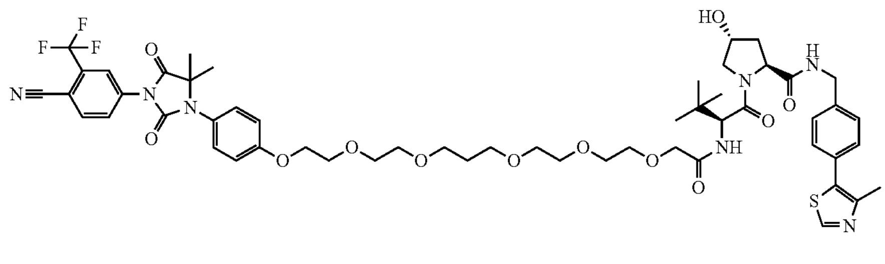 [SMILES: Cc1ncsc1-c1ccc(CNC(=O)[C@@H]2C[C@@H](O)CN2C(=O)[C@@H](NC(=O)COCCOCCOCCCOCCOCCOc2ccc(N3C(=O)N(c4ccc(C#N)c(C(F)(F)F)c4)C(=O)C3(C)C)cc2)C(C)(C)C)cc1] | 1110.43 | |
| 217 | 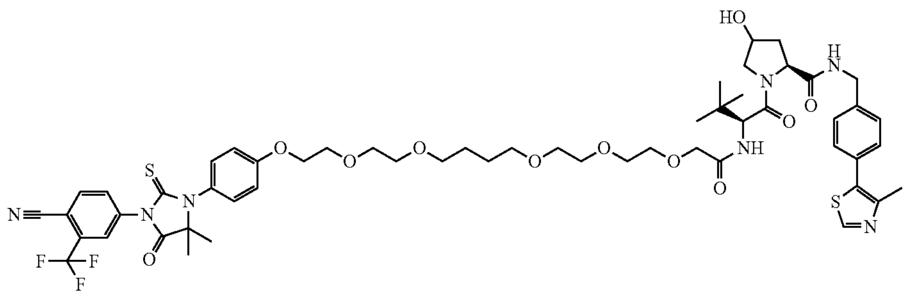 [SMILES: Cc1ncsc1-c1ccc(CNC(=O)[C@@H]2CC(O)CN2C(=O)[C@@H](NC(=O)COCCOCCOCCCCOCCOCCOc2ccc(N3C(=S)N(c4ccc(C#N)c(C(F)(F)F)c4)C(=O)C3(C)C)cc2)C(C)(C)C)cc1] | 1124.44 | |
| 218 | 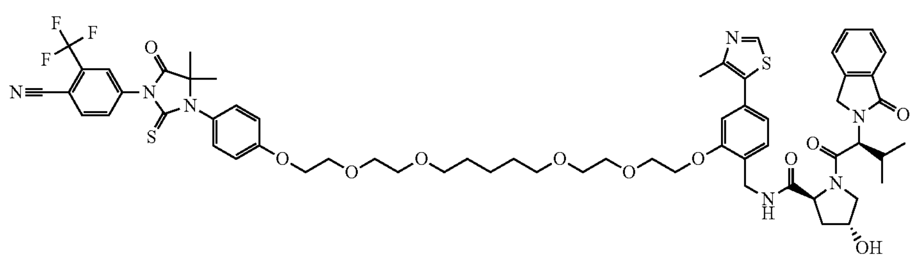 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCCCOCCOCCOc2ccc(N3C(=S)N(c4ccc(C#N)c(C(F)(F)F)c4)C(=O)C3(C)C)cc2)c1] | 1198.46 | |
| 219 | 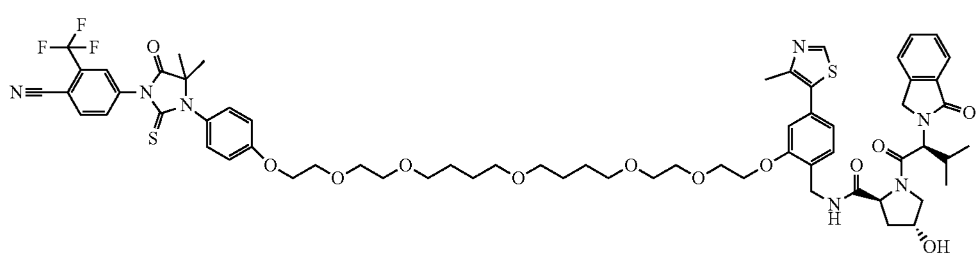 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCCOCCCCOCCOCCOc2ccc(N3C(=S)N(c4ccc(C#N)c(C(F)(F)F)c4)C(=O)C3(C)C)cc2)c1] | 1256.50 | |
| 220 | 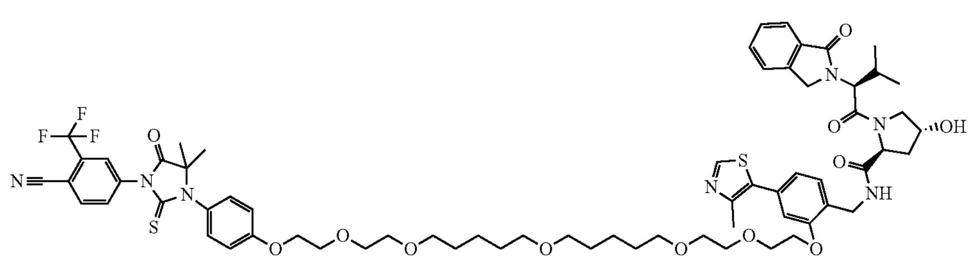 [SMILES: Cc1ncsc1-c1ccc(CNC(=O)[C@@H]2C[C@@H](O)CN2C(=O)[C@H](C(C)C)N2Cc3ccccc3C2=O)c(OCCOCCOCCCCCOCCCCCOCCOCCOc2ccc(N3C(=S)N(c4ccc(C#N)c(C(F)(F)F)c4)C(=O)C3(C)C)cc2)c1] | 1284.53 | |

TABLE 17-continued

Additional Exemplary Compounds.

| Structure | Measured Mass Ion Data | |
|---|---|---|
| | MH⁺ 1 | MH⁺ 2 |
| 221 | 1096.39 | |
| 222 | 1138.46 | |
| 223 | 1152.47 | |
| 224 | 1180.50 | |

TABLE 17-continued

Additional Exemplary Compounds.

| Structure | Measured Mass Ion Data | |
|---|---|---|
| | MH+ 1 | MH+ 2 |
| 225 [structure] | 1050.40 | |
| 226 [structure] | 1090.47 | |

TABLE 17-continued
Additional Exemplary Compounds.
| Structure | Measured Mass Ion Data | |
|---|---|---|
| | MH+ 1 | MH+ 2 |
| 227 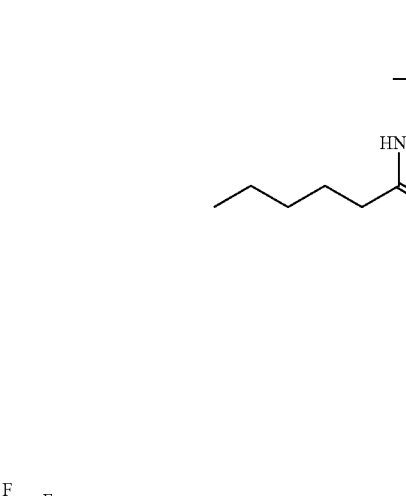 | 1076.46 | |
| 228 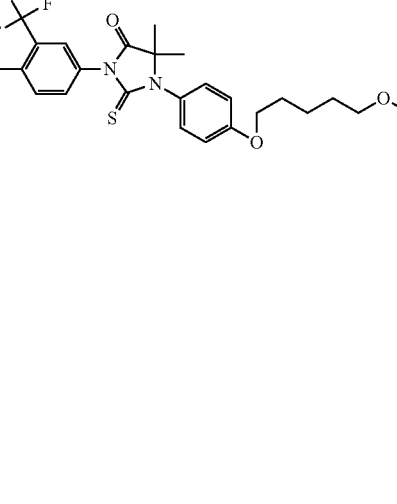 | 1020.40 | |
| 229 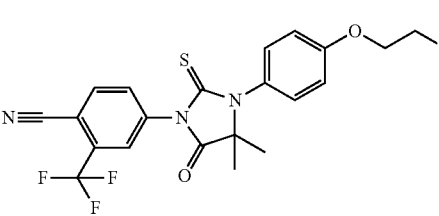 | 1068.36 | |

TABLE 17-continued
Additional Exemplary Compounds.
| Structure | Measured Mass Ion Data | |
|---|---|---|
| | MH+ 1 | MH+ 2 |
| 230 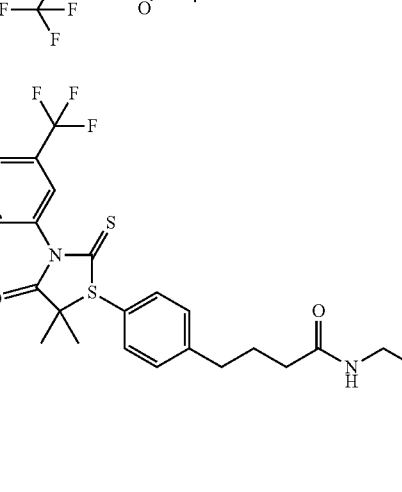 | 1008.36 | |
| 231 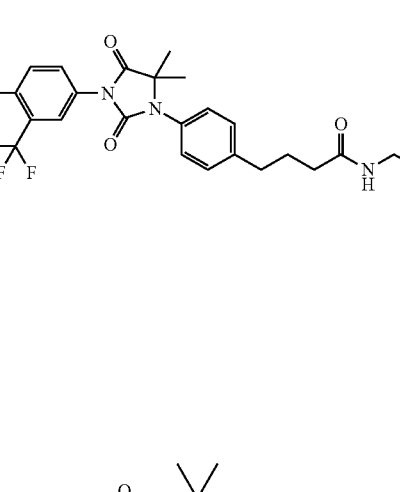 | 959.36 | |
| 232 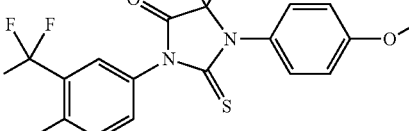 | 1003.38 | |
| 233  | 934.32 | |

TABLE 17-continued

Additional Exemplary Compounds.

| Structure | Measured Mass Ion Data | |
|---|---|---|
| | MH+ 1 | MH+ 2 |
| 234 | 1108.44 | |
| 235 | 1052.37 | |
| 236 | 920.29 | |
| 237 | 904.30 | |

TABLE 17-continued

Additional Exemplary Compounds.

| Structure | Measured Mass Ion Data | |
|---|---|---|
| | MH+ 1 | MH+ 2 |
| 238 | 992.35 | |
| 239 | 1008.34 | |
| 240 | 1022.36 | |
| 241 | 1038.33 | |

TABLE 17-continued

Additional Exemplary Compounds.

| Structure | Measured Mass Ion Data | |
|---|---|---|
| | MH+ 1 | MH+ 2 |
| 242 | 1020.38 | |
| 243 | 978.35 | |
| 244 | 948.34 | |
| 245 | 1037.37 | |

TABLE 17-continued

Additional Exemplary Compounds.

| Structure | Measured Mass Ion Data | |
|---|---|---|
| | MH+ 1 | MH+ 2 |
| 246 | 1004.40 | |
| 247 | 1006.38 | |
| 248 | 1022.35 | |
| 249 | 1040.40 | |

TABLE 17-continued

Additional Exemplary Compounds.

| Structure | Measured Mass Ion Data | |
|---|---|---|
| | MH+ 1 | MH+ 2 |
| 250 | 1052.35 | |
| 251 | 1006.35 | |
| 252 | 1036.36 | |
| 253 | 1022.36 | |

TABLE 17-continued

Additional Exemplary Compounds.

| | Structure | Measured Mass Ion Data | |
|---|---|---|---|
| | | MH+ 1 | MH+ 2 |
| 254 | 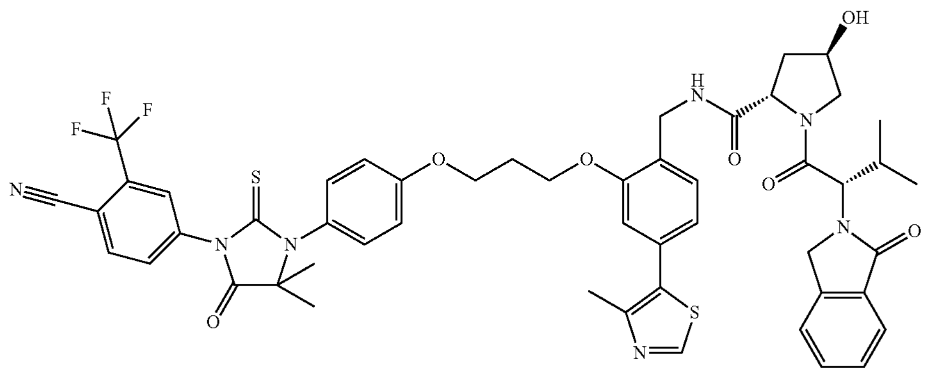 [SMILES: Cc1ncsc1-c1ccc(CNC(=O)[C@@H]2C[C@@H](O)CN2C(=O)[C@H](C(C)C)N2Cc3ccccc3C2=O)c(OCCCOc2ccc(N3C(=S)N(c4ccc(C#N)c(C(F)(F)F)c4)C(=O)C3(C)C)cc2)c1] | 994.31 | |
| 255 | 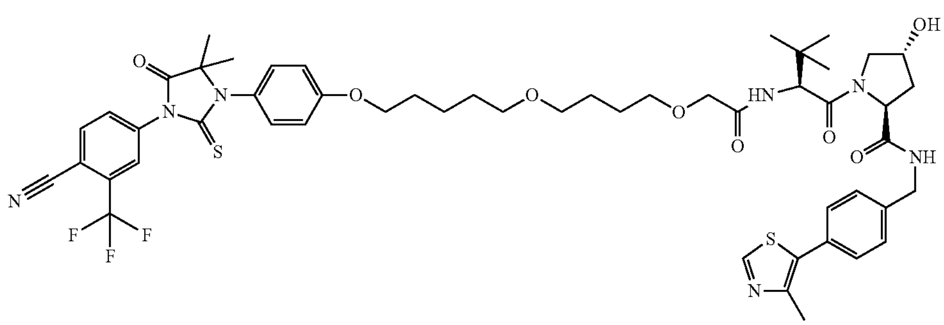 [SMILES: Cc1ncsc1-c1ccc(CNC(=O)[C@@H]2C[C@@H](O)CN2C(=O)[C@@H](NC(=O)COCCCCOCCCCCOc2ccc(N3C(=S)N(c4ccc(C#N)c(C(F)(F)F)c4)C(=O)C3(C)C)cc2)C(C)(C)C)cc1] | 1034.40 | |
| 256 | 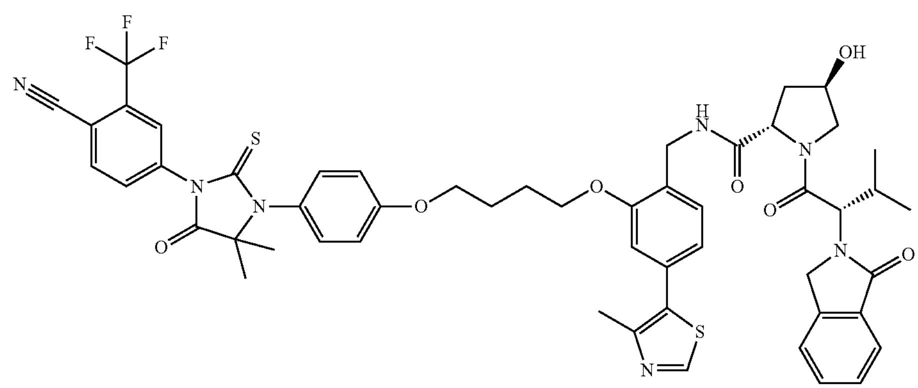 [SMILES: Cc1ncsc1-c1ccc(CNC(=O)[C@@H]2C[C@@H](O)CN2C(=O)[C@H](C(C)C)N2Cc3ccccc3C2=O)c(OCCCCOc2ccc(N3C(=S)N(c4ccc(C#N)c(C(F)(F)F)c4)C(=O)C3(C)C)cc2)c1] | 1008.32 | |
| 257 | 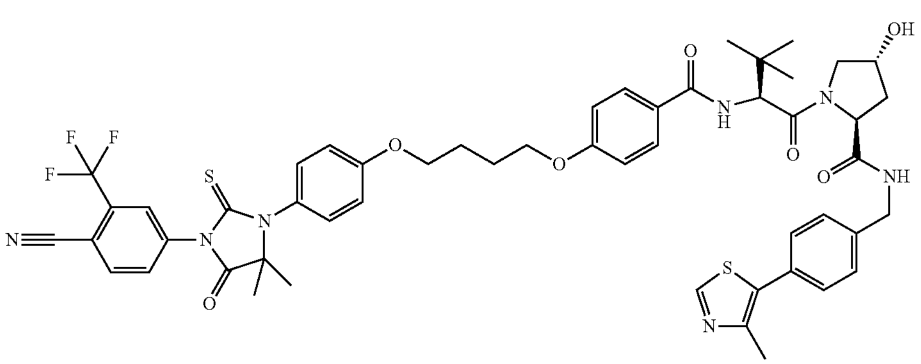 [SMILES: Cc1ncsc1-c1ccc(CNC(=O)[C@@H]2C[C@@H](O)CN2C(=O)[C@@H](NC(=O)c2ccc(OCCCCOc3ccc(N4C(=S)N(c5ccc(C#N)c(C(F)(F)F)c5)C(=O)C4(C)C)cc3)cc2)C(C)(C)C)cc1] | 1010.34 | |

TABLE 17-continued

Additional Exemplary Compounds.

| | Structure | Measured Mass Ion Data | |
|---|---|---|---|
| | | MH+ 1 | MH+ 2 |
| 258 | 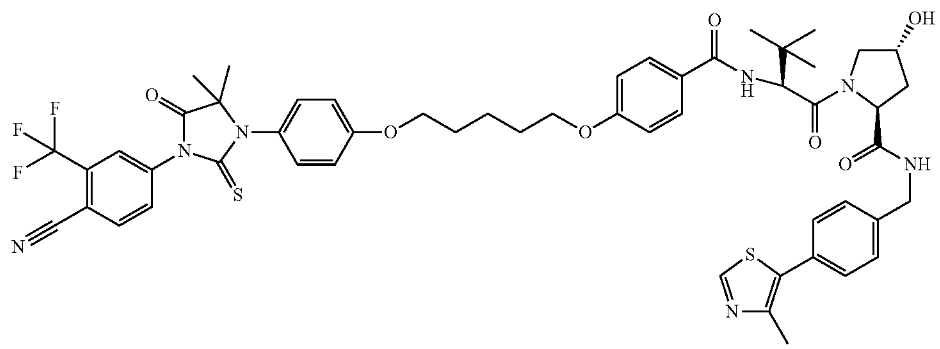 [SMILES: Cc1ncsc1-c1ccc(CNC(=O)[C@@H]2C[C@@H](O)CN2C(=O)[C@@H](NC(=O)c2ccc(OCCCCCOc3ccc(N4C(=S)N(c5ccc(C#N)c(C(F)(F)F)c5)C(=O)C4(C)C)cc3)cc2)C(C)(C)C)cc1] | 1024.35 | |
| 259 | 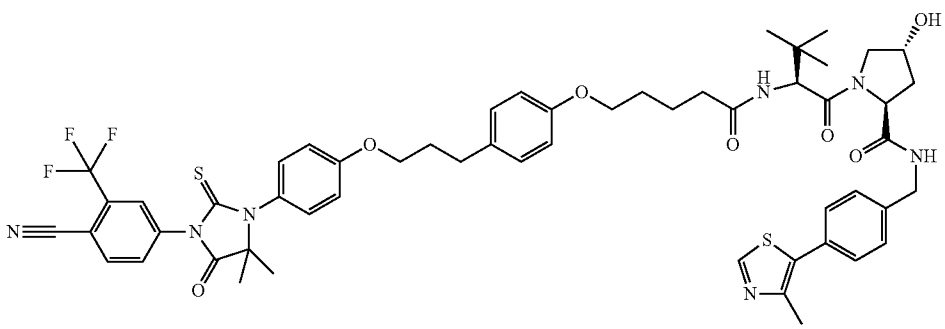 [SMILES: Cc1ncsc1-c1ccc(CNC(=O)[C@@H]2C[C@@H](O)CN2C(=O)[C@@H](NC(=O)CCCCOc2ccc(CCCOc3ccc(N4C(=S)N(c5ccc(C#N)c(C(F)(F)F)c5)C(=O)C4(C)C)cc3)cc2)C(C)(C)C)cc1] | 1052.38 | |
| 260 | 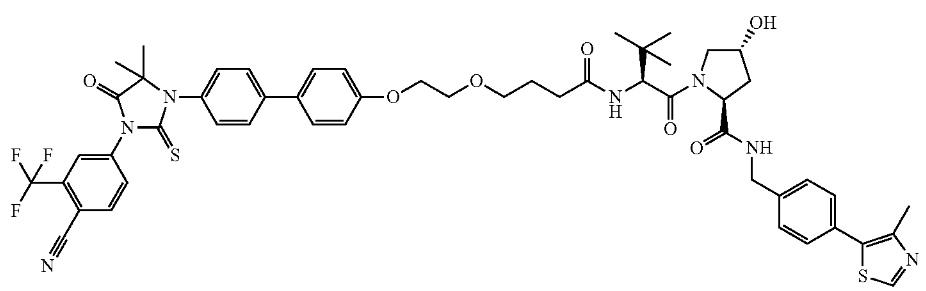 [SMILES: Cc1ncsc1-c1ccc(CNC(=O)[C@@H]2C[C@@H](O)CN2C(=O)[C@@H](NC(=O)CCCOCCOc2ccc(-c3ccc(N4C(=S)N(c5ccc(C#N)c(C(F)(F)F)c5)C(=O)C4(C)C)cc3)cc2)C(C)(C)C)cc1] | 1024.34 | |
| 261 | 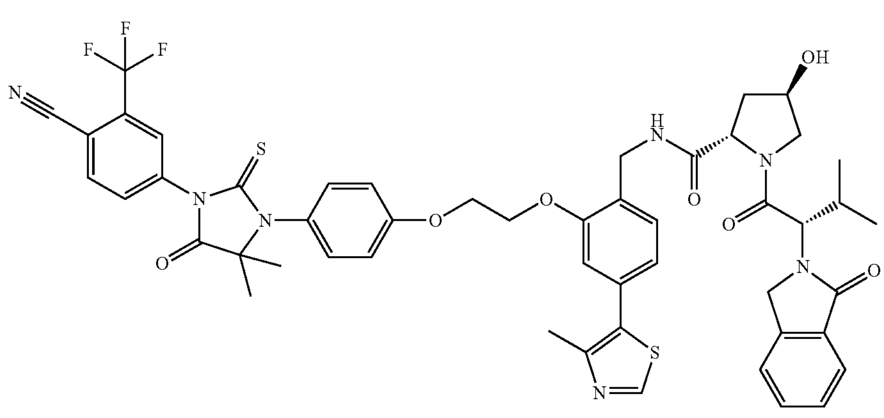 [SMILES: Cc1ncsc1-c1ccc(CNC(=O)[C@@H]2C[C@@H](O)CN2C(=O)[C@H](C(C)C)N2Cc3ccccc3C2=O)c(OCCOc2ccc(N3C(=S)N(c4ccc(C#N)c(C(F)(F)F)c4)C(=O)C3(C)C)cc2)c1] | 980.28 | |

TABLE 17-continued

Additional Exemplary Compounds.

| Structure | Measured Mass Ion Data | |
|---|---|---|
| | MH+ 1 | MH+ 2 |
| 262 | 1036.37 | |
| 263 | 1054.35 | |
| 264 | 1026.32 | |
| 265 | | |

TABLE 17-continued

Additional Exemplary Compounds.

| Structure | Measured Mass Ion Data | |
|---|---|---|
| | MH⁺ 1 | MH⁺ 2 |

266     1008.33

267     1022.35

268     1006.37

269     1036.36

TABLE 17-continued

Additional Exemplary Compounds.

| Structure | Measured Mass Ion Data | |
|---|---|---|
| | MH+ 1 | MH+ 2 |
| 270 | | 1050.38 |
| 271 | | 952.27 |
| 272 | | 966.29 |
| 273 | | 1050.36 |

TABLE 17-continued

Additional Exemplary Compounds.

| Structure | Measured Mass Ion Data | |
|---|---|---|
| | MH+ 1 | MH+ 2 |
| 274 | 1040.34 | |
| 275 | 996.31 | |
| 276 | 1010.33 | |
| 277 | 996.32 | |

TABLE 17-continued

Additional Exemplary Compounds.

| Structure | Measured Mass Ion Data | |
|---|---|---|
| | MH+ 1 | MH+ 2 |
| 278 | 1010.33 | |
| 279 | 1066.36 | |
| 280 | 980.30 | |
| 281 | 994.32 | |

TABLE 17-continued

Additional Exemplary Compounds.

| | Measured Mass Ion Data | |
|---|---|---|
| Structure | MH+ 1 | MH+ 2 |

282

1048.30

283

1026.32

284

1072.34

285

1086.36

TABLE 17-continued

Additional Exemplary Compounds.

| Structure | Measured Mass Ion Data | |
|---|---|---|
| | MH+ 1 | MH+ 2 |
| 286 | 1058.33 | |
| 287 | 1077.41 | |
| 288 | 1054.37 | |
| 289 | 1063.41 | |

TABLE 17-continued

Additional Exemplary Compounds.

| Structure | Measured Mass Ion Data | |
|---|---|---|
| | MH+ 1 | MH+ 2 |
| 290 | 1045.38 | |
| 291 | 1093.38 | |
| 292 | 1024.44 | |

TABLE 17-continued

Additional Exemplary Compounds.

| Structure | Measured Mass Ion Data | |
|---|---|---|
| | MH+ 1 | MH+ 2 |
| 293 | 1059.48 | |
| 294 | 1073.49 | |
| 295 | 1020.46 | |
| 296 | 1054.46 | |

TABLE 17-continued

Additional Exemplary Compounds.

| Structure | Measured Mass Ion Data MH+ 1 | MH+ 2 |
|---|---|---|
| 297 | 1122.49 | |
| 298 | 1054.46 | |
| 299 | 1022.41 | |
| 300 | 1006.44 | |

TABLE 17-continued

Additional Exemplary Compounds.

| | Structure | Measured Mass Ion Data MH+ 1 | MH+ 2 |
|---|---|---|---|
| 301 | | 1020.45 | |
| 302 | | 1024.42 | |
| 303 | | 1010.41 | |
| 304 | | 1108.44 | |

TABLE 17-continued

Additional Exemplary Compounds.

| Structure | Measured Mass Ion Data MH+ 1 | MH+ 2 |
|---|---|---|
| 305 [structure] | 1032.46 | |
| 306 [structure] | 1010.41 | |
| 307 [structure] | 1006.44 | |
| 308 [structure] | 1020.47 | |

TABLE 17-continued
Additional Exemplary Compounds.
| Structure | Measured Mass Ion Data | |
|---|---|---|
| | MH+ 1 | MH+ 2 |
309 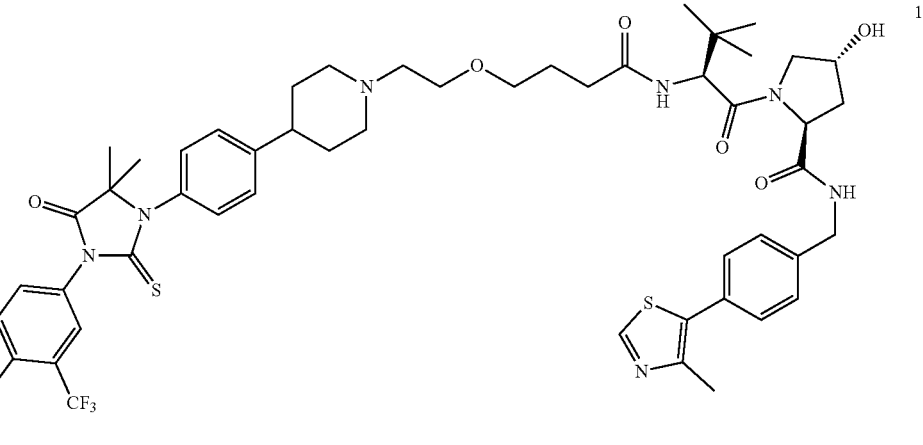 1015.49
310 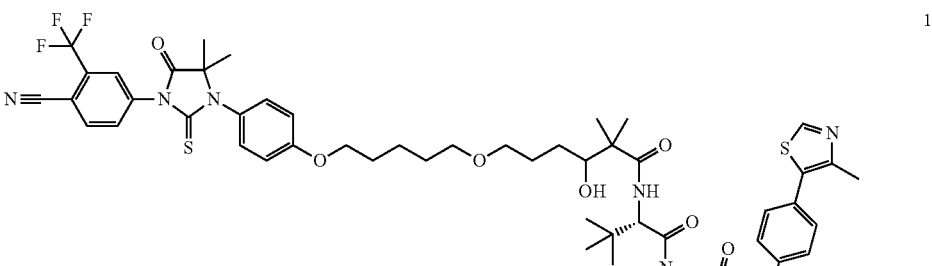 1062.51
311 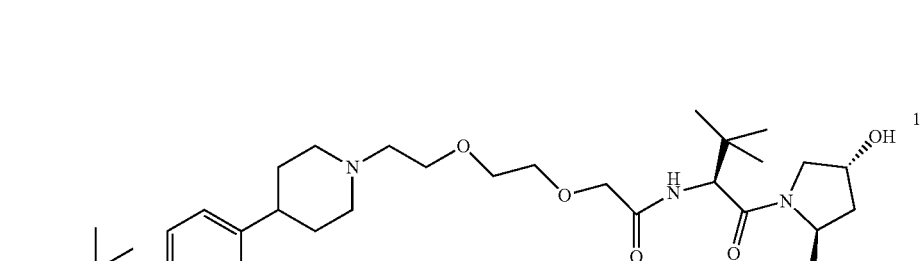 1031.48

TABLE 17-continued

Additional Exemplary Compounds.

| Structure | Measured Mass Ion Data | |
|---|---|---|
| | MH+ 1 | MH+ 2 |
| 312 | 1006.45 | |
| 313 | 1031.48 | |
| 314 | 974.40 | |
| 315 | 1006.46 | |

TABLE 17-continued

Additional Exemplary Compounds.

| | Structure | Measured Mass Ion Data | |
|---|---|---|---|
| | | MH+ 1 | MH+ 2 |
| 316 | 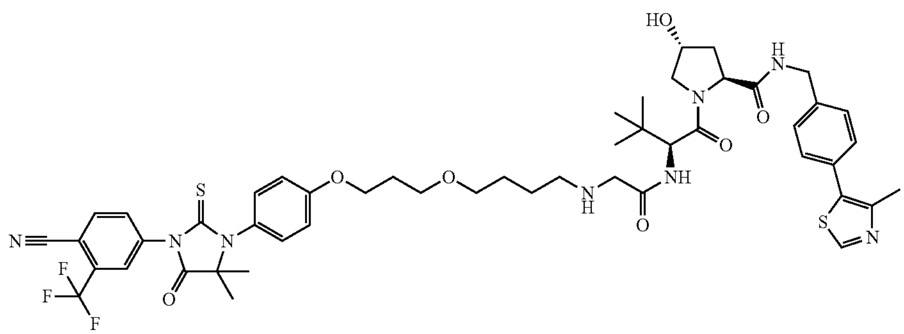 [SMILES: Cc1ncsc1-c1ccc(CNC(=O)[C@@H]2C[C@@H](O)CN2C(=O)[C@@H](NC(=O)CNCCCCOCCCOc2ccc(N3C(=S)N(c4ccc(C#N)c(C(F)(F)F)c4)C(=O)C3(C)C)cc2)C(C)(C)C)cc1] | 1005.48 | |
| 317 | 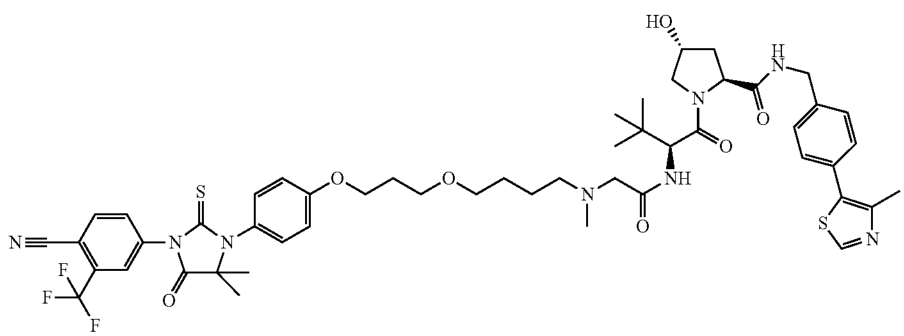 [SMILES: Cc1ncsc1-c1ccc(CNC(=O)[C@@H]2C[C@@H](O)CN2C(=O)[C@@H](NC(=O)CN(C)CCCCOCCCOc2ccc(N3C(=S)N(c4ccc(C#N)c(C(F)(F)F)c4)C(=O)C3(C)C)cc2)C(C)(C)C)cc1] | 1019.50 | |
| 318 | 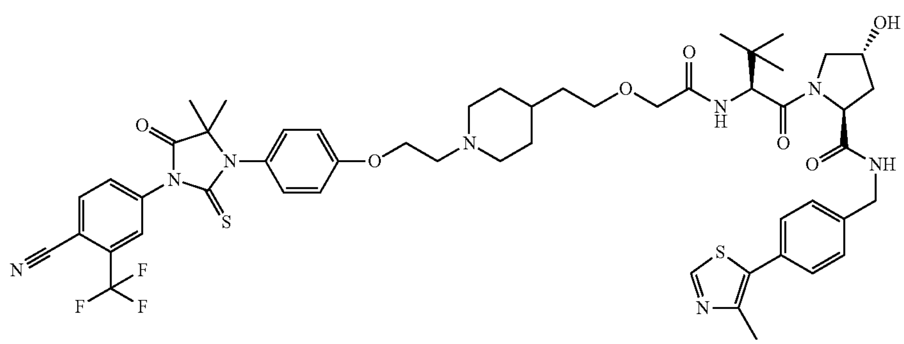 [SMILES: Cc1ncsc1-c1ccc(CNC(=O)[C@@H]2C[C@@H](O)CN2C(=O)[C@@H](NC(=O)COCCC2CCN(CCOc3ccc(N4C(=S)N(c5ccc(C#N)c(C(F)(F)F)c5)C(=O)C4(C)C)cc3)CC2)C(C)(C)C)cc1] | 1031.40 | |
| 319 | 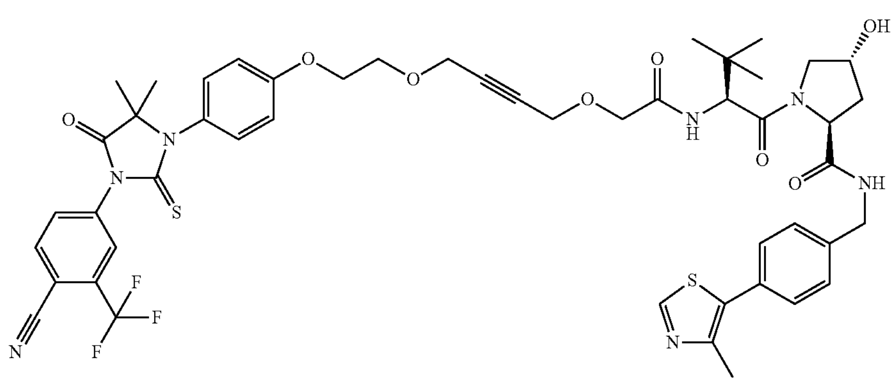 [SMILES: Cc1ncsc1-c1ccc(CNC(=O)[C@@H]2C[C@@H](O)CN2C(=O)[C@@H](NC(=O)COCC#CCOCCOc2ccc(N3C(=S)N(c4ccc(C#N)c(C(F)(F)F)c4)C(=O)C3(C)C)cc2)C(C)(C)C)cc1] | 988.32 | |

TABLE 17-continued

Additional Exemplary Compounds.

| | Structure | Measured Mass Ion Data | |
|---|---|---|---|
| | | MH+ 1 | MH+ 2 |
| 320 | 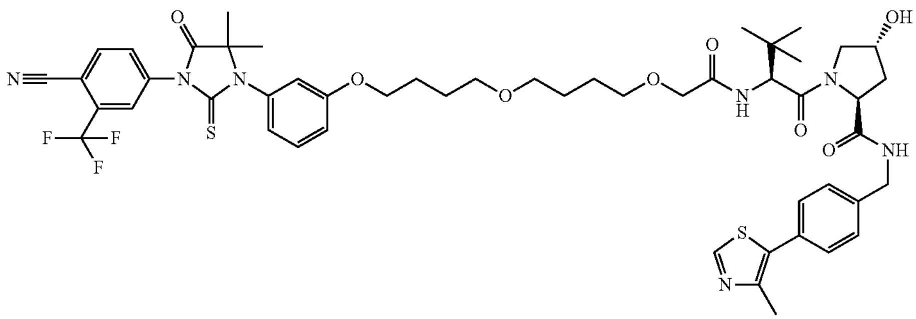 [SMILES: Cc1ncsc1-c1ccc(CNC(=O)[C@@H]2C[C@@H](O)CN2C(=O)[C@@H](NC(=O)COCCCCOCCCCOc2cccc(N3C(=S)N(c4ccc(C#N)c(C(F)(F)F)c4)C(=O)C3(C)C)c2)C(C)(C)C)cc1] | 1020.38 | |
| 321 | 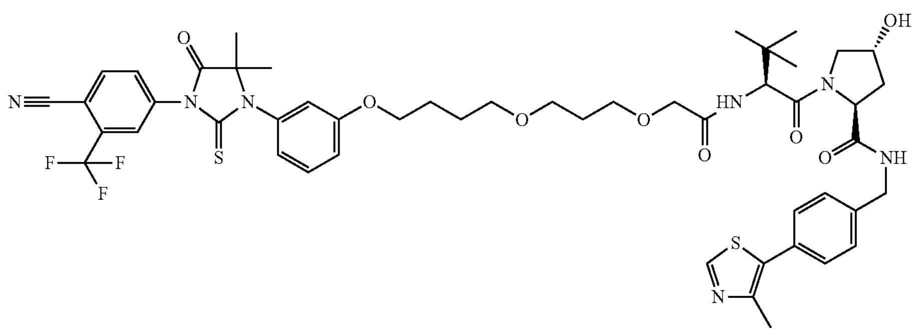 [SMILES: Cc1ncsc1-c1ccc(CNC(=O)[C@@H]2C[C@@H](O)CN2C(=O)[C@@H](NC(=O)COCCCOCCCCOc2cccc(N3C(=S)N(c4ccc(C#N)c(C(F)(F)F)c4)C(=O)C3(C)C)c2)C(C)(C)C)cc1] | 1006.37 | |
| 322 | 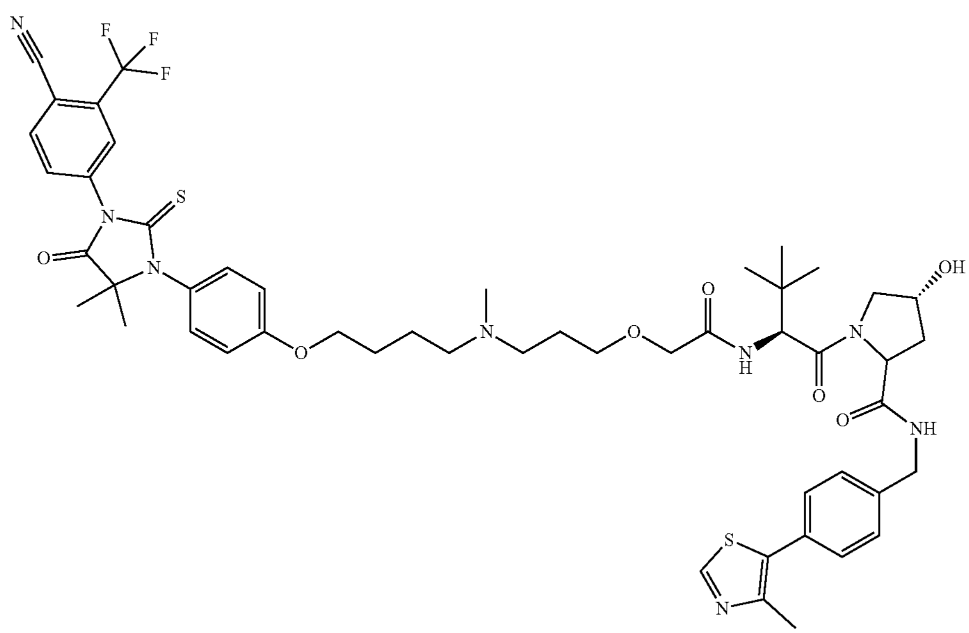 [SMILES: Cc1ncsc1-c1ccc(CNC(=O)C2C[C@@H](O)CN2C(=O)[C@@H](NC(=O)COCCCN(C)CCCCOc2ccc(N3C(=S)N(c4ccc(C#N)c(C(F)(F)F)c4)C(=O)C3(C)C)cc2)C(C)(C)C)cc1] | 1019.40 | |

TABLE 17-continued

Additional Exemplary Compounds.

| Structure | Measured Mass Ion Data MH+ 1 | MH+ 2 |
|---|---|---|
| 323 | 992.34 | |
| 324 | 1017.39 | |
| 325 | 1017.40 | |
| 326 | 1018.20 | |

TABLE 17-continued

Additional Exemplary Compounds.

| | Structure | Measured Mass Ion Data | |
|---|---|---|---|
| | | MH+ 1 | MH+ 2 |
| 327 | 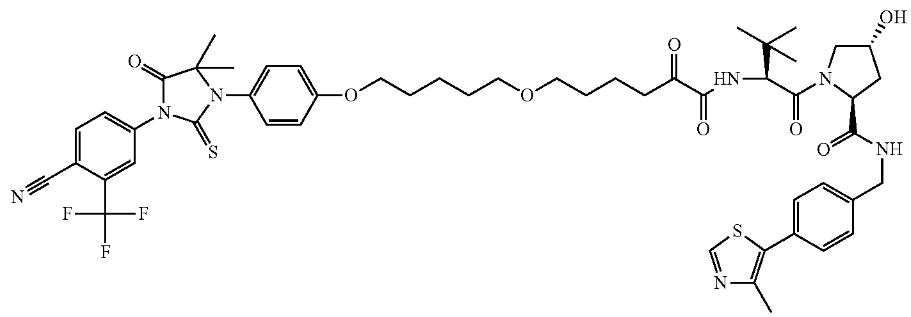 [SMILES: Cc1ncsc1-c1ccc(CNC(=O)[C@@H]2C[C@@H](O)CN2C(=O)[C@@H](NC(=O)C(=O)CCCCOCCCCCOc2ccc(N3C(=S)N(c4ccc(C#N)c(C(F)(F)F)c4)C(=O)C3(C)C)cc2)C(C)(C)C)cc1] | 1032.55 | |
| 328 | 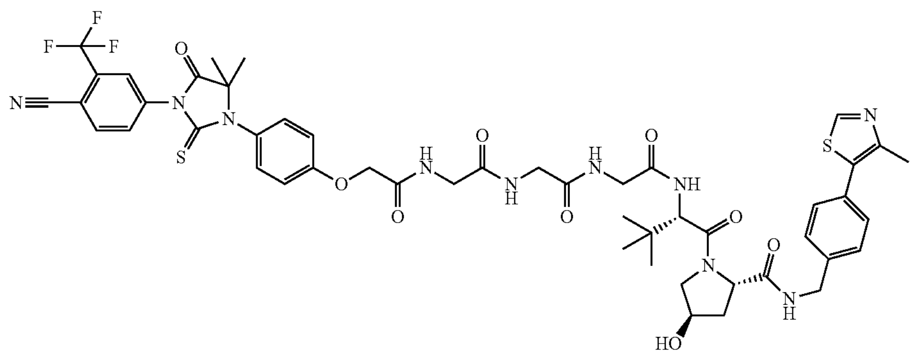 [SMILES: Cc1ncsc1-c1ccc(CNC(=O)[C@@H]2C[C@@H](O)CN2C(=O)[C@@H](NC(=O)CNC(=O)CNC(=O)CNC(=O)COc2ccc(N3C(=S)N(c4ccc(C#N)c(C(F)(F)F)c4)C(=O)C3(C)C)cc2)C(C)(C)C)cc1] | 1047.34 | |
| 329 | 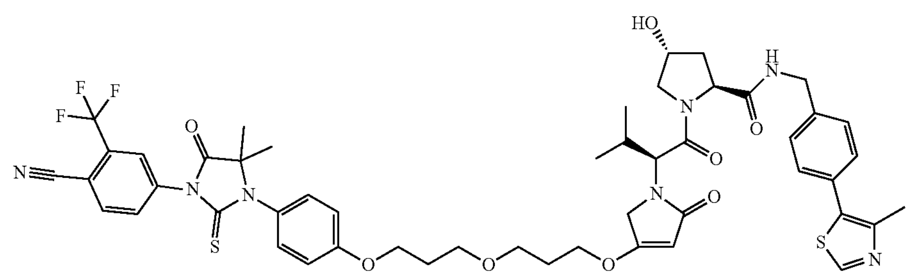 [SMILES: Cc1ncsc1-c1ccc(CNC(=O)[C@@H]2C[C@@H](O)CN2C(=O)[C@H](C(C)C)N2CC(OCCCOCCCOc3ccc(N4C(=S)N(c5ccc(C#N)c(C(F)(F)F)c5)C(=O)C4(C)C)cc3)=CC2=O)cc1] | 1002.10 | |
| 330 | 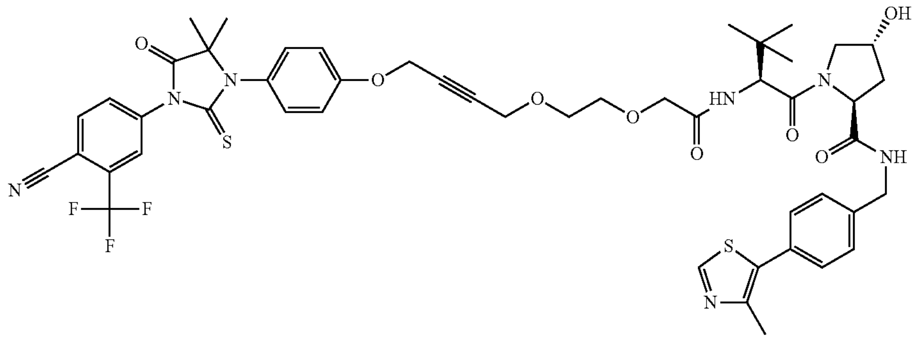 [SMILES: Cc1ncsc1-c1ccc(CNC(=O)[C@@H]2C[C@@H](O)CN2C(=O)[C@@H](NC(=O)COCCOCC#CCOc2ccc(N3C(=S)N(c4ccc(C#N)c(C(F)(F)F)c4)C(=O)C3(C)C)cc2)C(C)(C)C)cc1] | 331.05 | |

TABLE 17-continued

Additional Exemplary Compounds.

| | Measured Mass Ion Data | |
|---|---|---|
| Structure | MH+ 1 | MH+ 2 |="=

| # | | |
|---|---|---|
| 331 | | 1089.39 |
| 332 | | 1167.43 |
| 333 | | 1005.40 |

TABLE 17-continued

Additional Exemplary Compounds.

| Structure | Measured Mass Ion Data | |
|---|---|---|
| | MH+ 1 | MH+ 2 |
| 334 | 1004.40 | |
| 335 | 942.40 | |
| 336 | 960.50 | |
| 337 | 942.40 | |

TABLE 17-continued
Additional Exemplary Compounds.
| Structure | Measured Mass Ion Data | |
|---|---|---|
| | MH+ 1 | MH+ 2 |
| 338 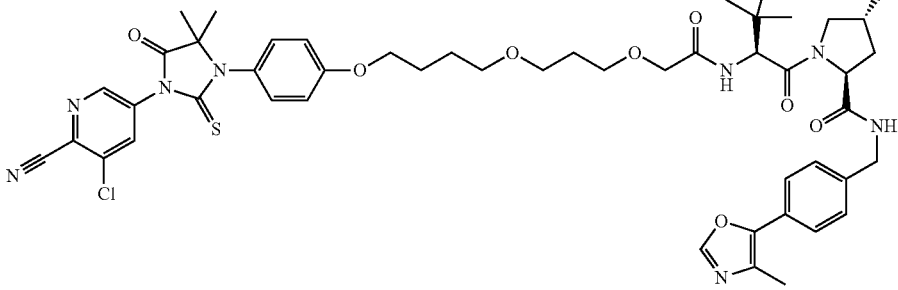 | 957.40 | |
| 339 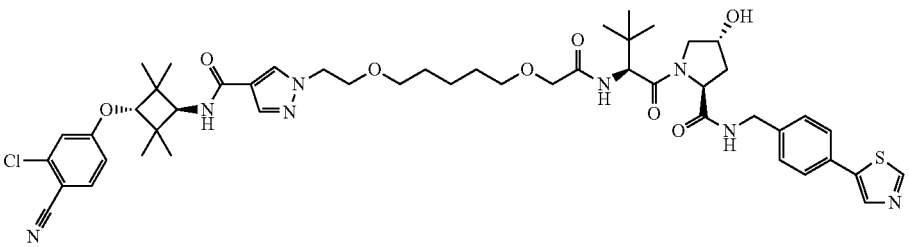 [SMILES: CC(C)(C)[C@H](NC(=O)COCCCCCOCCn1cc(C(=O)N[C@H]2C(C)(C)[C@H](Oc3ccc(C#N)c(Cl)c3)C2(C)C)cn1)C(=O)N1C[C@H](O)C[C@H]1C(=O)NCc1ccc(-c2cncs2)cc1] | 959.20 | |
| 340 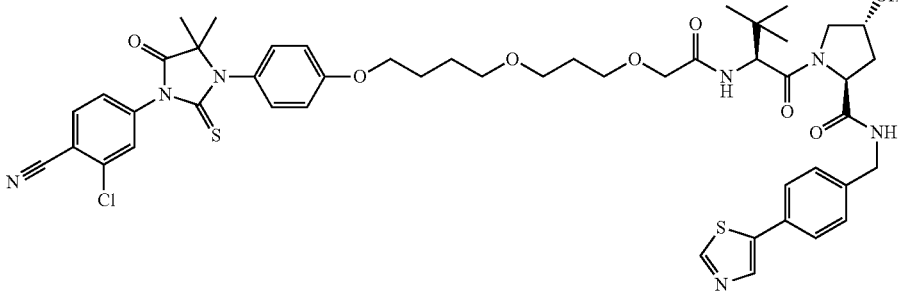 | 1023.40 | |
| 341 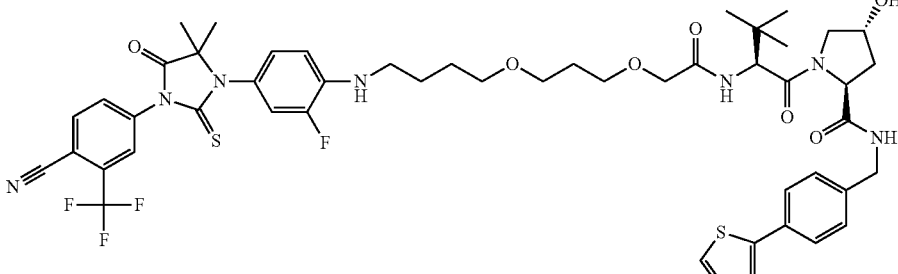 | 978.55 | |

TABLE 17-continued
Additional Exemplary Compounds.
| Structure | Measured Mass Ion Data | |
|---|---|---|
| | MH+ 1 | MH+ 2 |
| 342 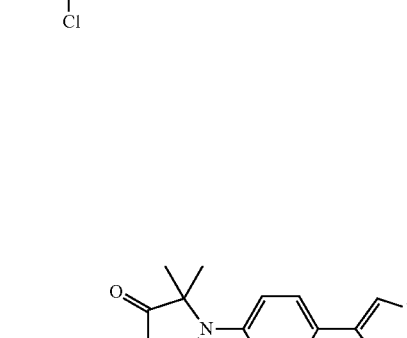 | 934.30 | |
| 343 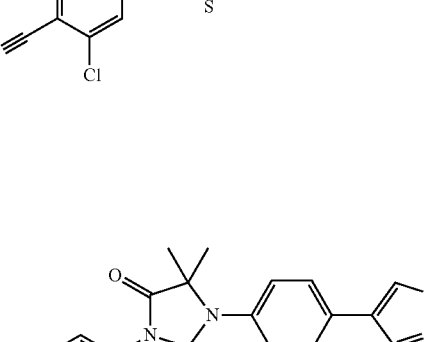 | 920.30 | |
| 344 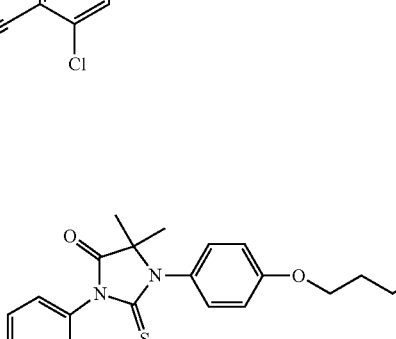 | 956.30 | |
| 345 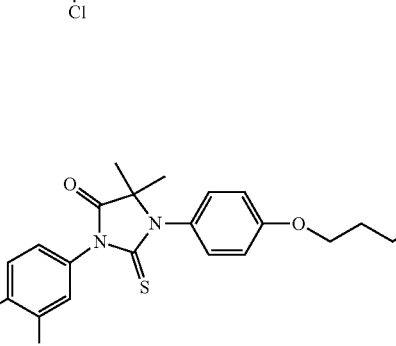 | 956.35 | |

TABLE 17-continued

Additional Exemplary Compounds.

| Structure | Measured Mass Ion Data | |
|---|---|---|
| | MH+ 1 | MH+ 2 |
| 346 | | |
| 347 | 945.40 | |
| 348 | 961.35 | |
| 349 | 972.40 | |

TABLE 17-continued

Additional Exemplary Compounds.

| | Structure | Measured Mass Ion Data | |
|---|---|---|---|
| | | MH+ 1 | MH+ 2 |
| 350 | 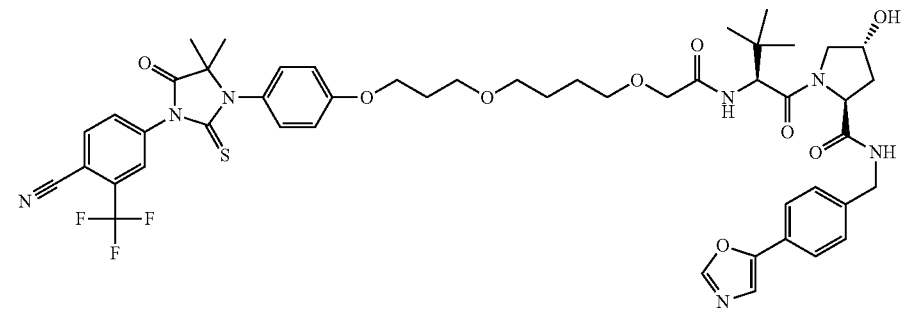 [SMILES: CC(C)(C)[C@H](NC(=O)COCCCCOCCCOc1ccc(N2C(=S)N(c3ccc(C#N)c(C(F)(F)F)c3)C(=O)C2(C)C)cc1)C(=O)N1C[C@H](O)C[C@H]1C(=O)NCc1ccc(-c2cnco2)cc1] | 976.35 | |
| 351 | 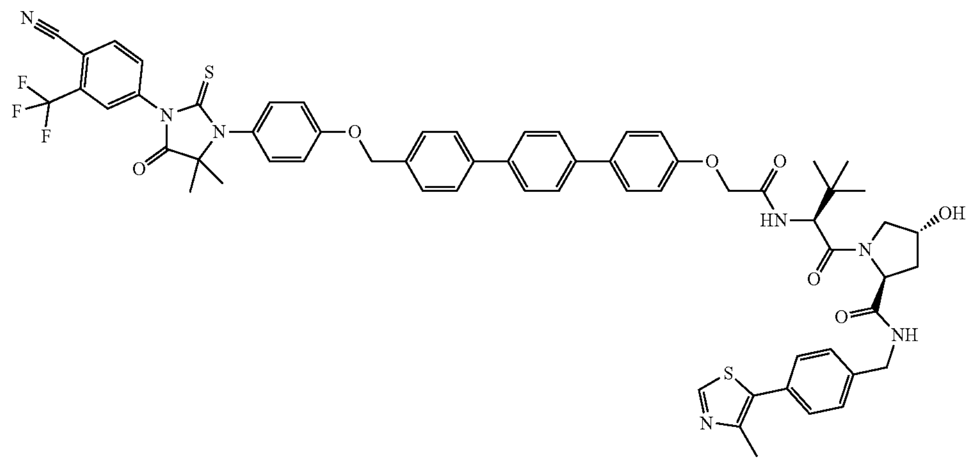 [SMILES: Cc1ncsc1-c1ccc(CNC(=O)[C@@H]2C[C@@H](O)CN2C(=O)[C@@H](NC(=O)COc2ccc(-c3ccc(-c4ccc(COc5ccc(N6C(=S)N(c7ccc(C#N)c(C(F)(F)F)c7)C(=O)C6(C)C)cc5)cc4)cc3)cc2)C(C)(C)C)cc1] | — | |
| 352 | 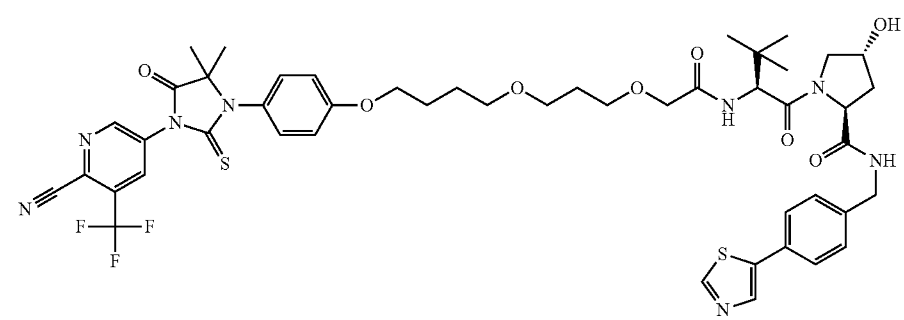 [SMILES: CC(C)(C)[C@H](NC(=O)COCCCOCCCCOc1ccc(N2C(=S)N(c3cnc(C#N)c(C(F)(F)F)c3)C(=O)C2(C)C)cc1)C(=O)N1C[C@H](O)C[C@H]1C(=O)NCc1ccc(-c2cncs2)cc1] | 993.25 | |
| 353 | 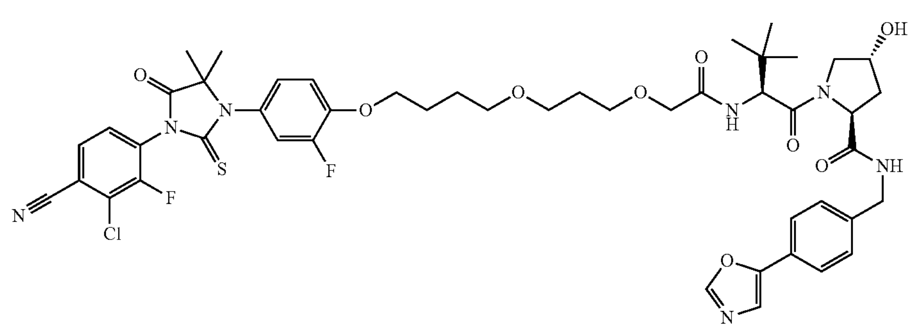 [SMILES: CC(C)(C)[C@H](NC(=O)COCCCOCCCCOc1ccc(N2C(=S)N(c3ccc(C#N)c(Cl)c3F)C(=O)C2(C)C)cc1F)C(=O)N1C[C@H](O)C[C@H]1C(=O)NCc1ccc(-c2cnco2)cc1] | 978.35 | |

TABLE 17-continued
Additional Exemplary Compounds.
| | Structure | Measured Mass Ion Data | |
|---|---|---|---|
| | | MH+ 1 | MH+ 2 |
| 354 | 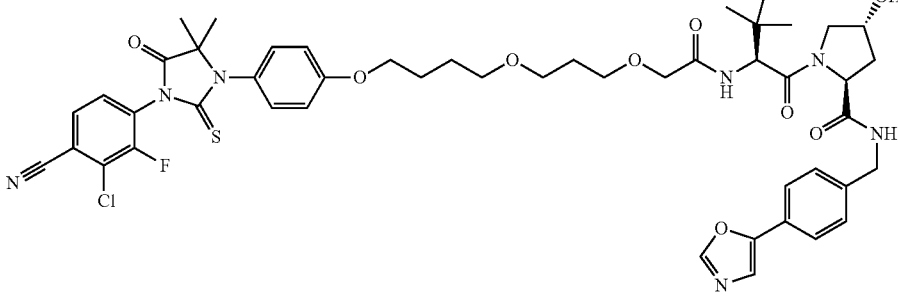 | 960.35 | |
| 355 | 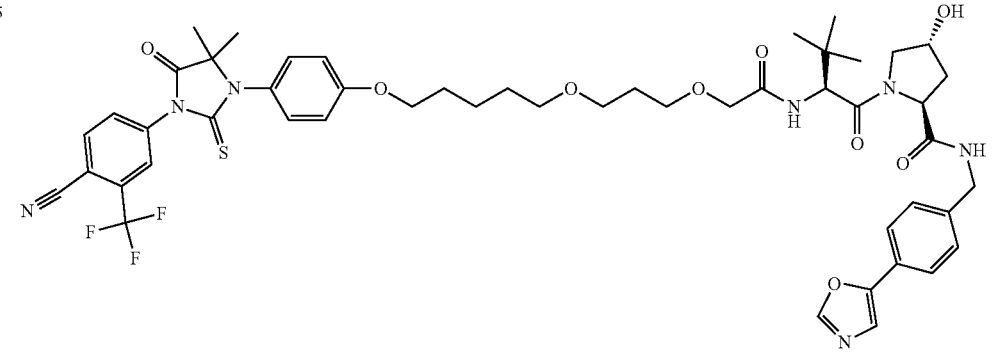 | 990.45 | |
| 356 | 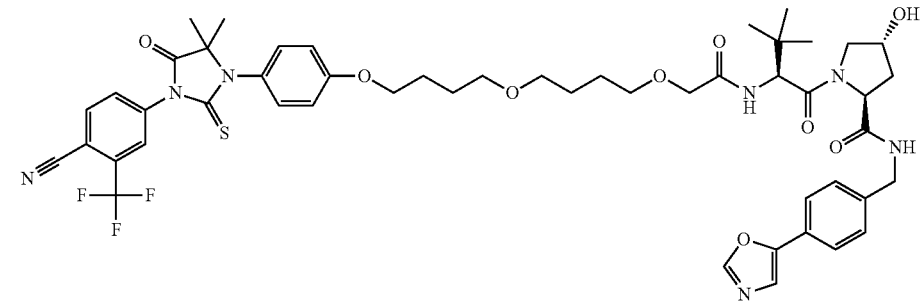 [SMILES: CC(C)(C)[C@H](NC(=O)COCCCCOCCCCOc1ccc(N2C(=S)N(c3ccc(C#N)c(C(F)(F)F)c3)C(=O)C2(C)C)cc1)C(=O)N1C[C@H](O)C[C@H]1C(=O)NCc1ccc(-c2cnco2)cc1] | 990.45 | |
| 357 | 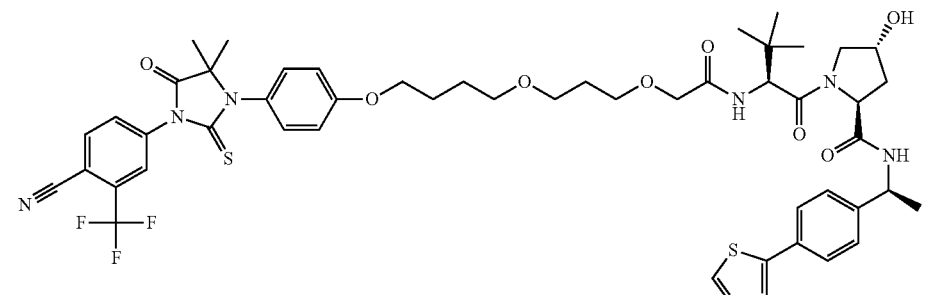 | 1020.40 | |

TABLE 17-continued

Additional Exemplary Compounds.

| | Measured Mass Ion Data | |
|---|---|---|
| Structure | MH⁺ 1 | MH⁺ 2 |

358 — 994.10

359 — 950.20

360 — 978.20

361 — 992.20

362 — 977.25

TABLE 17-continued

Additional Exemplary Compounds.

| | Structure | Measured Mass Ion Data | |
|---|---|---|---|
| | | MH+ 1 | MH+ 2 |
| 363 | 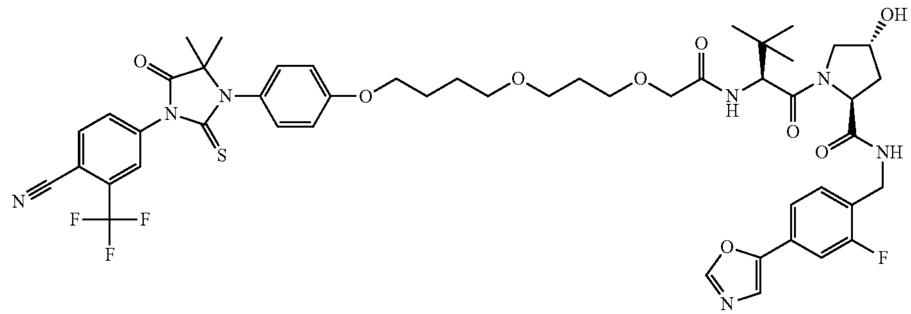 [SMILES: CC(C)(C)[C@H](NC(=O)COCCCOCCCCOc1ccc(N2C(=S)N(c3ccc(C#N)c(C(F)(F)F)c3)C(=O)C2(C)C)cc1)C(=O)N1C[C@H](O)C[C@H]1C(=O)NCc1ccc(-c2cnco2)cc1F] | 994.40 | |
| 364 | 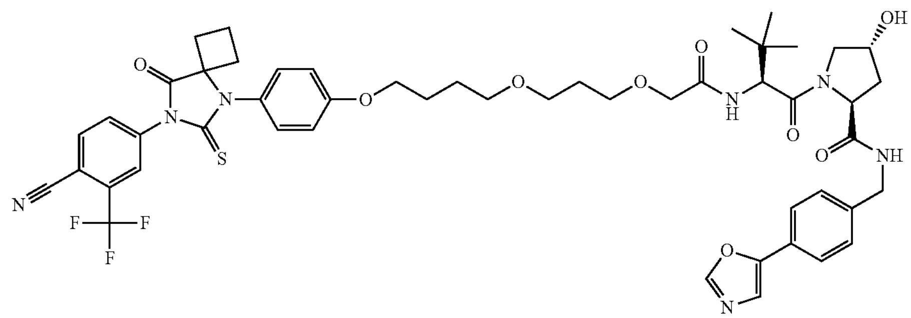 [SMILES: CC(C)(C)[C@H](NC(=O)COCCCOCCCCOc1ccc(N2C(=S)N(c3ccc(C#N)c(C(F)(F)F)c3)C(=O)C23CCC3)cc1)C(=O)N1C[C@H](O)C[C@H]1C(=O)NCc1ccc(-c2cnco2)cc1] | 988.40 | |
| 365 | 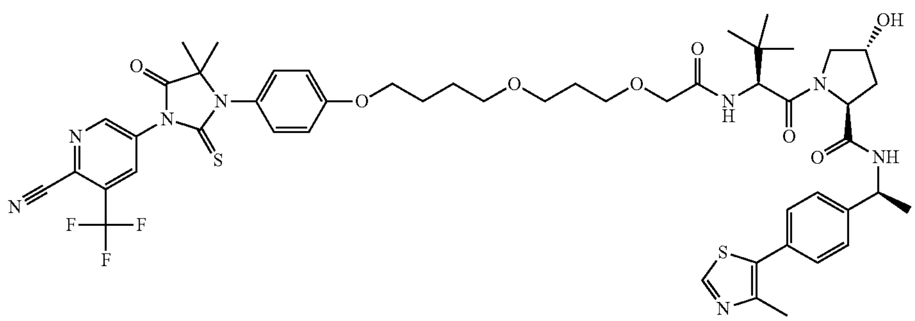 [SMILES: Cc1ncsc1-c1ccc([C@H](C)NC(=O)[C@@H]2C[C@@H](O)CN2C(=O)[C@@H](NC(=O)COCCCOCCCCOc2ccc(N3C(=S)N(c4cnc(C#N)c(C(F)(F)F)c4)C(=O)C3(C)C)cc2)C(C)(C)C)cc1] | 1021.20 | |
| 366 | 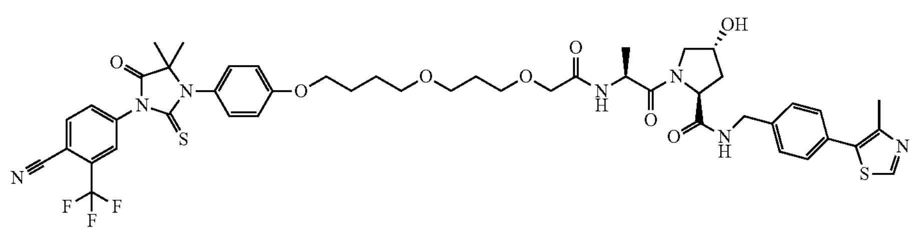 [SMILES: Cc1ncsc1-c1ccc(CNC(=O)[C@@H]2C[C@@H](O)CN2C(=O)[C@H](C)NC(=O)COCCCOCCCCOc2ccc(N3C(=S)N(c4ccc(C#N)c(C(F)(F)F)c4)C(=O)C3(C)C)cc2)cc1] | 964.20 | |
| 367 | 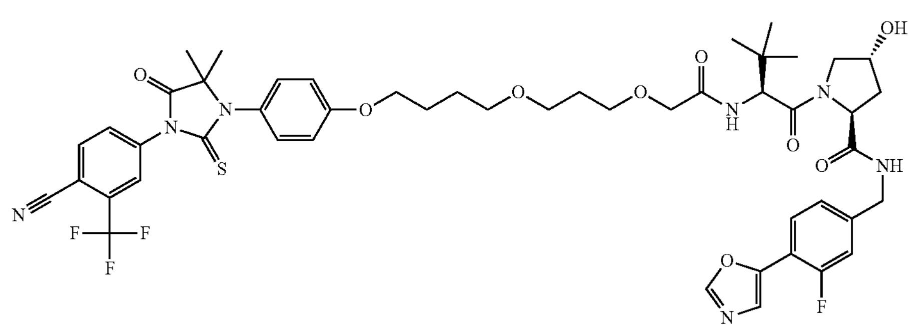 [SMILES: CC(C)(C)[C@H](NC(=O)COCCCOCCCCOc1ccc(N2C(=S)N(c3ccc(C#N)c(C(F)(F)F)c3)C(=O)C2(C)C)cc1)C(=O)N1C[C@H](O)C[C@H]1C(=O)NCc1ccc(-c2cnco2)c(F)c1] | 994.40 | |

TABLE 17-continued

Additional Exemplary Compounds.

| | Structure | Measured Mass Ion Data | |
|---|---|---|---|
| | | MH+ 1 | MH+ 2 |
| 368 | 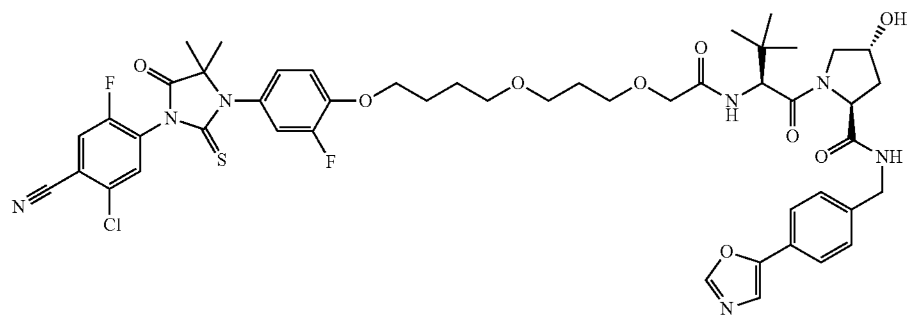 [SMILES: CC(C)(C)[C@H](NC(=O)COCCCOCCCCOc1ccc(N2C(=S)N(c3cc(Cl)c(C#N)cc3F)C(=O)C2(C)C)cc1F)C(=O)N1C[C@H](O)C[C@H]1C(=O)NCc1ccc(-c2cnco2)cc1] | 978.30 | |
| 369 | 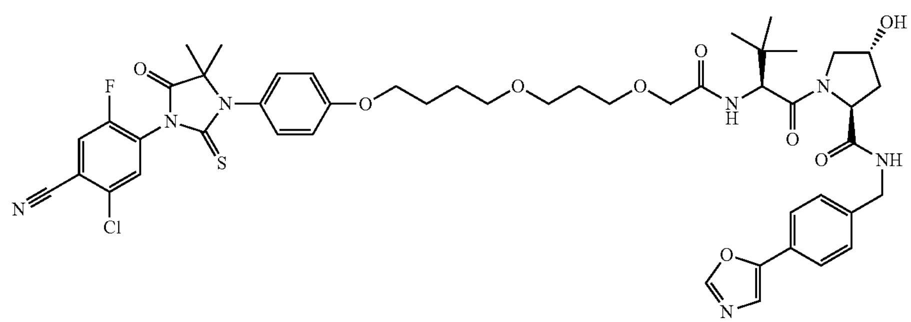 [SMILES: CC(C)(C)[C@H](NC(=O)COCCCOCCCCOc1ccc(N2C(=S)N(c3cc(Cl)c(C#N)cc3F)C(=O)C2(C)C)cc1)C(=O)N1C[C@H](O)C[C@H]1C(=O)NCc1ccc(-c2cnco2)cc1] | 960.30 | |
| 370 | 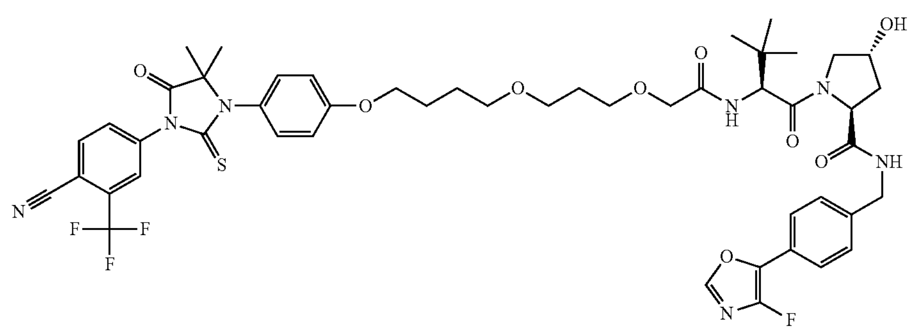 [SMILES: CC(C)(C)[C@H](NC(=O)COCCCOCCCCOc1ccc(N2C(=S)N(c3ccc(C#N)c(C(F)(F)F)c3)C(=O)C2(C)C)cc1)C(=O)N1C[C@H](O)C[C@H]1C(=O)NCc1ccc(-c2ocnc2F)cc1] | 994.40 | |
| 371 | 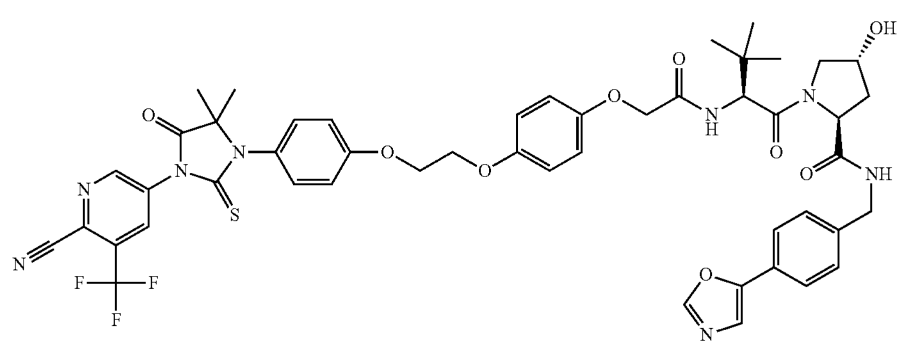 [SMILES: CC(C)(C)[C@H](NC(=O)COc1ccc(OCCOc2ccc(N3C(=S)N(c4cnc(C#N)c(C(F)(F)F)c4)C(=O)C3(C)C)cc2)cc1)C(=O)N1C[C@H](O)C[C@H]1C(=O)NCc1ccc(-c2cnco2)cc1] | 983.30 | |

TABLE 17-continued

Additional Exemplary Compounds.

| | Structure | Measured Mass Ion Data | |
|---|---|---|---|
| | | MH+ 1 | MH+ 2 |
| 372 | 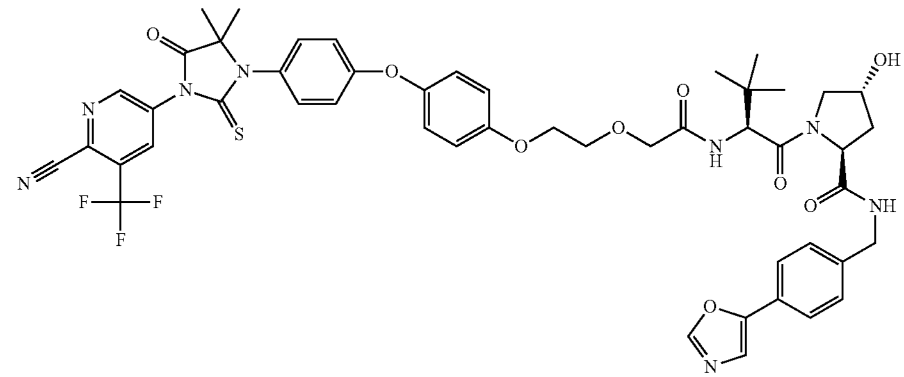 [SMILES: CC(C)(C)[C@H](NC(=O)COCCOc1ccc(Oc2ccc(N3C(=S)N(c4cnc(C#N)c(C(F)(F)F)c4)C(=O)C3(C)C)cc2)cc1)C(=O)N1C[C@H](O)C[C@H]1C(=O)NCc1ccc(-c2cnco2)cc1] | 983.50 | |
| 373 | 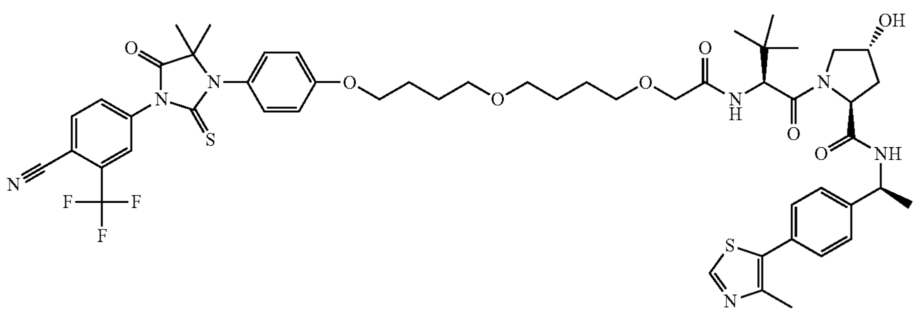 [SMILES: Cc1ncsc1-c1ccc([C@H](C)NC(=O)[C@@H]2C[C@@H](O)CN2C(=O)[C@@H](NC(=O)COCCCCOCCCCOc2ccc(N3C(=S)N(c4ccc(C#N)c(C(F)(F)F)c4)C(=O)C3(C)C)cc2)C(C)(C)C)cc1] | 1034.40 | |
| 374 | 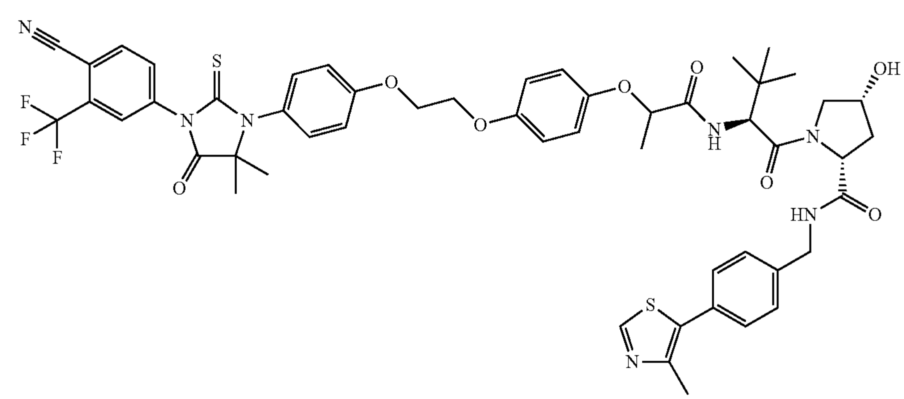 [SMILES: Cc1ncsc1-c1ccc(CNC(=O)[C@H]2C[C@@H](O)CN2C(=O)[C@@H](NC(=O)C(C)Oc2ccc(OCCOc3ccc(N4C(=S)N(c5ccc(C#N)c(C(F)(F)F)c5)C(=O)C4(C)C)cc3)cc2)C(C)(C)C)cc1] | 1026.35 | |

TABLE 17-continued

Additional Exemplary Compounds.

| Structure | Measured Mass Ion Data | |
|---|---|---|
| | MH+ 1 | MH+ 2 |
| 375 | 1059.36 | |
| 376 | 975.30 | |
| 377 | 989.30 | |

TABLE 17-continued

Additional Exemplary Compounds.

| Structure | Measured Mass Ion Data | |
|---|---|---|
| | MH+ 1 | MH+ 2 |
| 378 | 1032.34 | |
| 379 | 1025.37 | |
| 380 | 975.30 | |
| 381 | 1026.16 | |

TABLE 17-continued

Additional Exemplary Compounds.

| Structure | Measured Mass Ion Data | |
|---|---|---|
| | MH+ 1 | MH+ 2 |
| 382 | 1026.16 | |
| 383 | 1025.30 | |
| 384 | 1041.30 | |
| 385 | 991.26 | 993.26 |

TABLE 17-continued

Additional Exemplary Compounds.

| Structure | Measured Mass Ion Data | |
|---|---|---|
| | MH+ 1 | MH+ 2 |
| 386 | 1011.30 | |
| 387 | 927.37 | 929.37 |
| 388 | 951.23 | 953.23 |
| 389 | 1055.10 | |

TABLE 17-continued

Additional Exemplary Compounds.

| | Structure | Measured Mass Ion Data | |
|---|---|---|---|
| | | MH+ 1 | MH+ 2 |
| 390 | 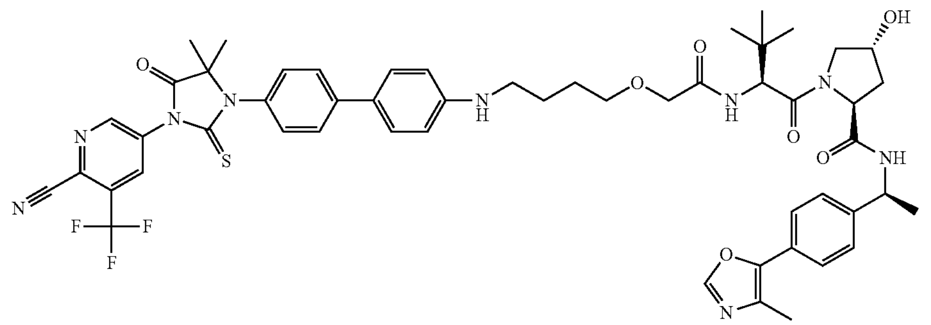 [SMILES: Cc1ncoc1-c1ccc([C@H](C)NC(=O)[C@@H]2C[C@@H](O)CN2C(=O)[C@@H](NC(=O)COCCCCNc2ccc(-c3ccc(N4C(=S)N(c5cnc(C#N)c(C(F)(F)F)c5)C(=O)C4(C)C)cc3)cc2)C(C)(C)C)cc1] | 1022.25 | |
| 391 | 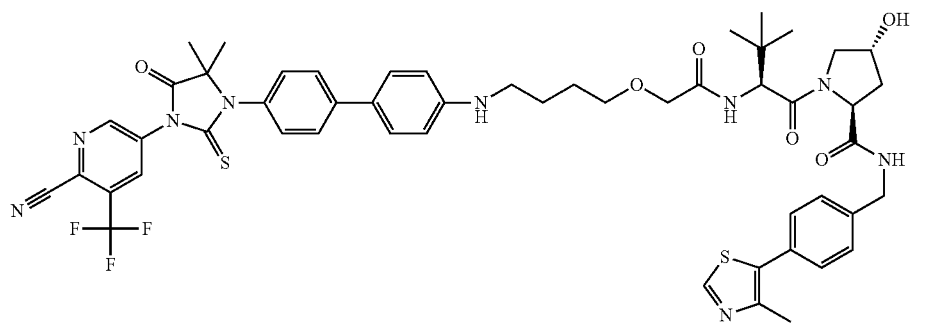 [SMILES: Cc1ncsc1-c1ccc(CNC(=O)[C@@H]2C[C@@H](O)CN2C(=O)[C@@H](NC(=O)COCCCCNc2ccc(-c3ccc(N4C(=S)N(c5cnc(C#N)c(C(F)(F)F)c5)C(=O)C4(C)C)cc3)cc2)C(C)(C)C)cc1] | 1024.15 | |
| 392 | 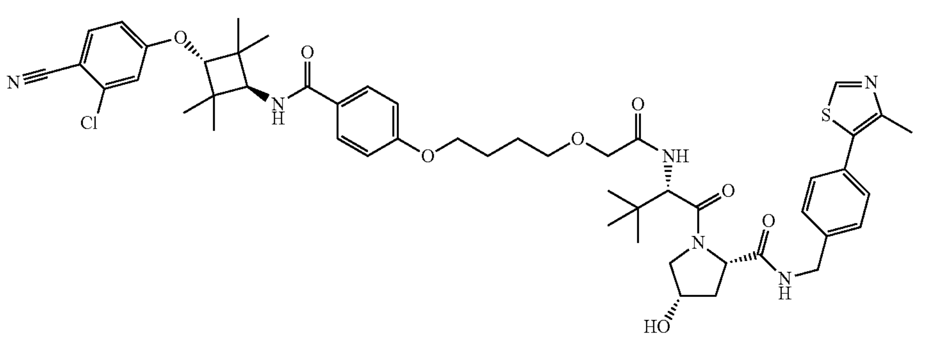 [SMILES: Cc1ncsc1-c1ccc(CNC(=O)[C@@H]2C[C@H](O)CN2C(=O)[C@@H](NC(=O)COCCCCOc2ccc(C(=O)N[C@H]3C(C)(C)[C@H](Oc4ccc(C#N)c(Cl)c4)C3(C)C)cc2)C(C)(C)C)cc1] | 941.39 | 943.39 |
| 393 | 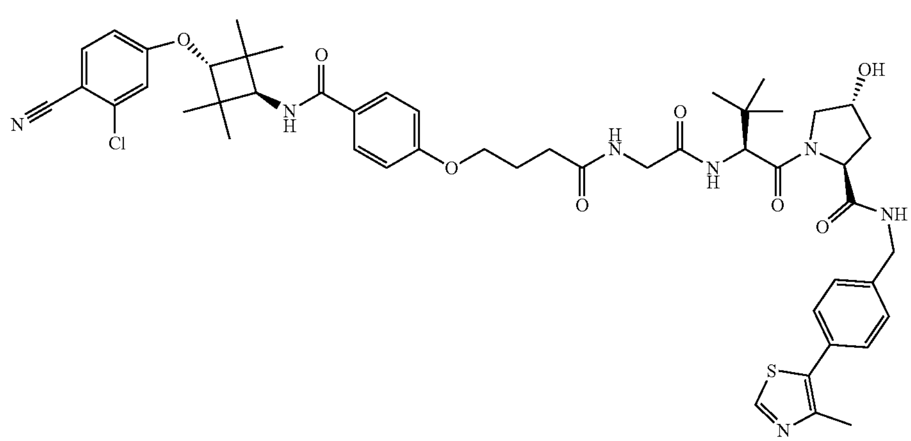 [SMILES: Cc1ncsc1-c1ccc(CNC(=O)[C@@H]2C[C@@H](O)CN2C(=O)[C@@H](NC(=O)CNC(=O)CCCOc2ccc(C(=O)N[C@H]3C(C)(C)[C@H](Oc4ccc(C#N)c(Cl)c4)C3(C)C)cc2)C(C)(C)C)cc1] | 954.31 | 956.31 |

TABLE 17-continued

Additional Exemplary Compounds.

| | Structure | Measured Mass Ion Data | |
|---|---|---|---|
| | | MH+ 1 | MH+ 2 |
| 394 | 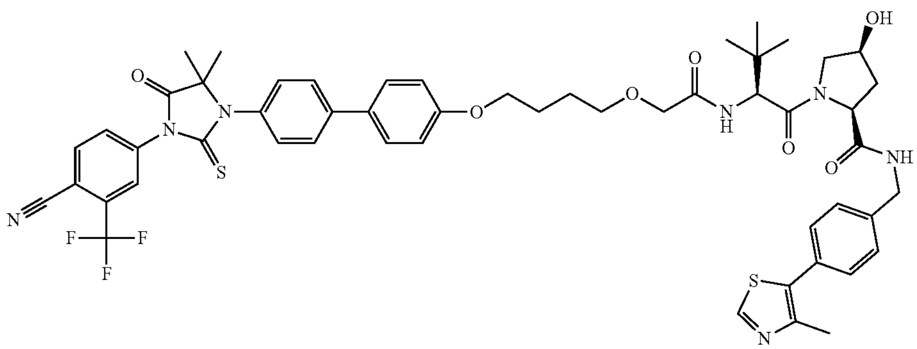 [SMILES: Cc1ncsc1-c1ccc(CNC(=O)[C@@H]2C[C@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cc3)cc2)C(C)(C)C)cc1] | 988.37 | 990.37 |
| 395 | 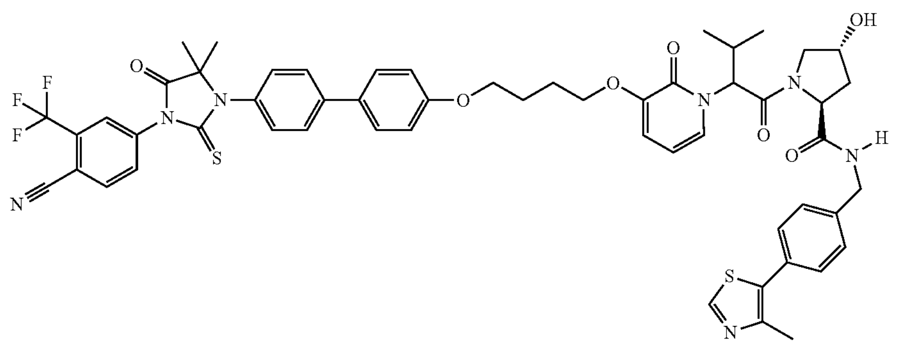 [SMILES: Cc1ncsc1-c1ccc(CNC(=O)[C@@H]2C[C@@H](O)CN2C(=O)C(C(C)C)n2cccc(OCCCCOc3ccc(-c4ccc(N5C(=S)N(c6ccc(C#N)c(C(F)(F)F)c6)C(=O)C5(C)C)cc4)cc3)c2=O)cc1] | 1045.35 | |
| 396 | 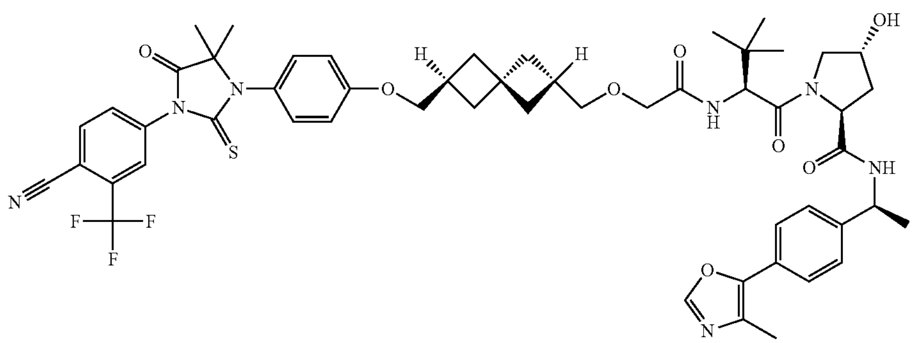 | 1012.15 | |
| 397 | 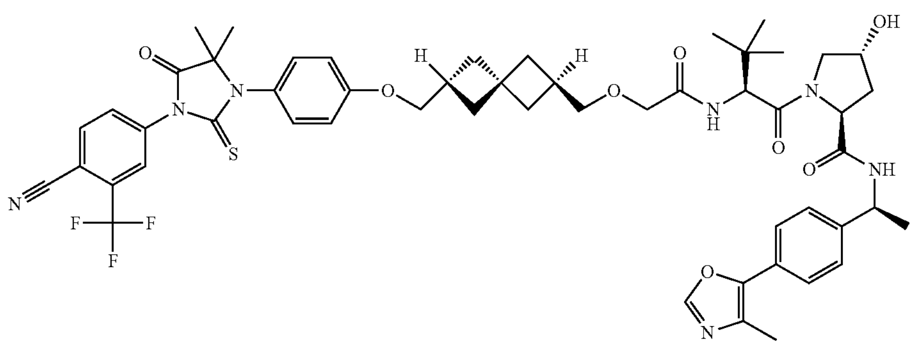 | 1012.15 | |

TABLE 17-continued
Additional Exemplary Compounds.
| | Structure | Measured Mass Ion Data | |
|---|---|---|---|
| | | MH+ 1 | MH+ 2 |
| 398 | 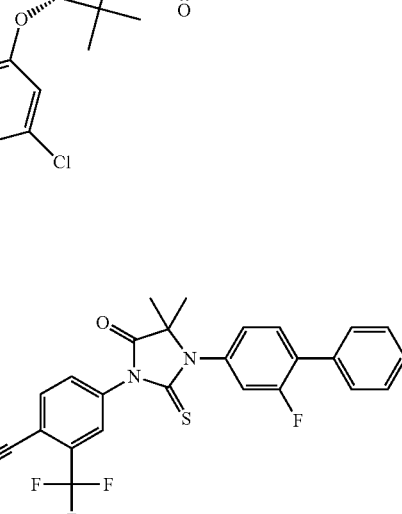 | 968.32 | 970.32 |
| 399 | 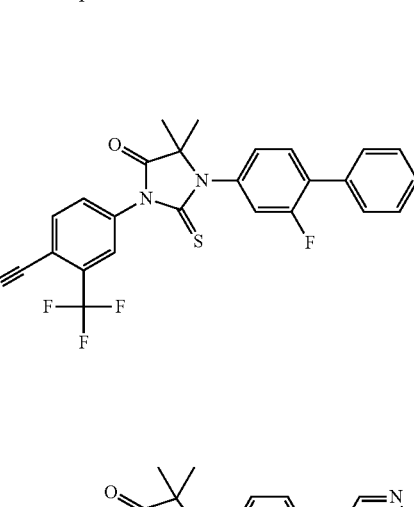 | 1026.15 | |
| 400 | 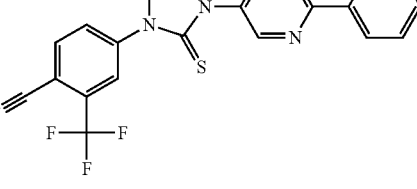 | 1042.20 | |
| 401 | 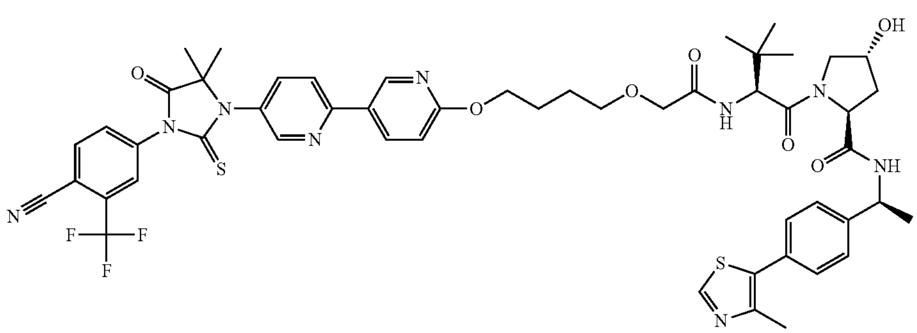 [SMILES: Cc1ncsc1-c1ccc([C@H](C)NC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cn3)cn2)C(C)(C)C)cc1] | 1040.35 | |

TABLE 17-continued

Additional Exemplary Compounds.

| | | Measured Mass Ion Data | |
|---|---|---|---|
| | Structure | MH+ 1 | MH+ 2 |
| 402 | | 1021.20 | |
| 403 | | 1040.15 | |
| 404 | | 980.52 | 982.52 |
| 405 | | 989.40 | 991.40 |

TABLE 17-continued

Additional Exemplary Compounds.

| | | Measured Mass Ion Data | |
|---|---|---|---|
| | Structure | MH+ 1 | MH+ 2 |
| 406 | | 989.40 | 991.40 |
| 407 | | 920.58 | 922.58 |
| 408 | | 1040.10 | |
| 409 | | 954.38 | 956.38 |

TABLE 17-continued

Additional Exemplary Compounds.

| Structure | Measured Mass Ion Data | |
|---|---|---|
| | MH+ 1 | MH+ 2 |
| 410 | 996.37 | 968.41 |
| 411 | 938.44 | 940.44 |
| 412 | 966.42 | 968.42 |

TABLE 17-continued
Additional Exemplary Compounds.
| | Structure | Measured Mass Ion Data | |
|---|---|---|---|
| | | MH+ 1 | MH+ 2 |
| 413 | 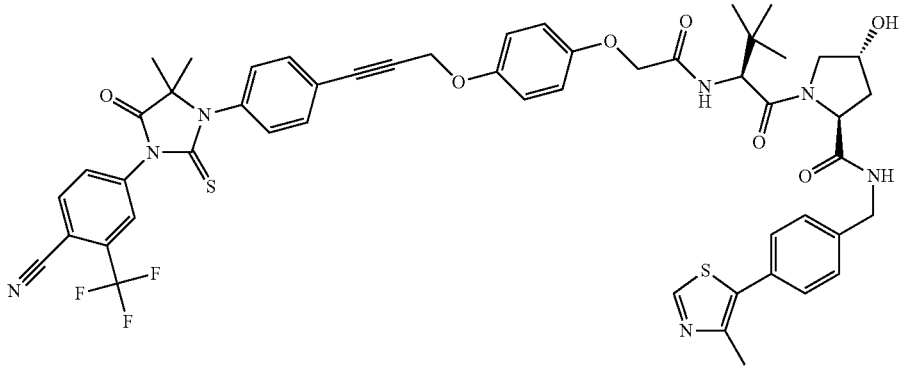 [SMILES: Cc1ncsc1-c1ccc(CNC(=O)[C@@H]2C[C@@H](O)CN2C(=O)[C@@H](NC(=O)COc2ccc(OCC#Cc3ccc(N4C(=S)N(c5ccc(C#N)c(C(F)(F)F)c5)C(=O)C4(C)C)cc3)cc2)C(C)(C)C)cc1] | 1006.30 | |
| 414 | 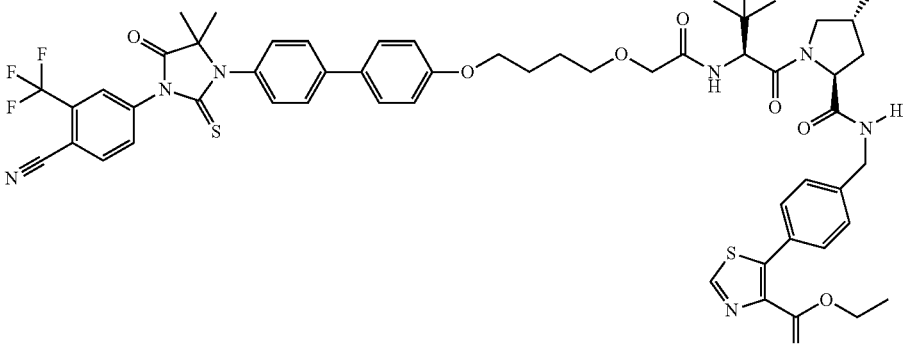 | 1083.34 | |
| 415 | 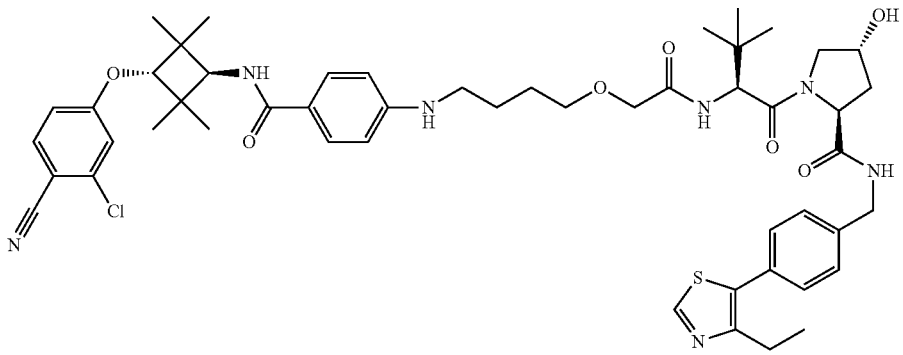 [SMILES: CCc1ncsc1-c1ccc(CNC(=O)[C@@H]2C[C@@H](O)CN2C(=O)[C@@H](NC(=O)COCCCCNc2ccc(C(=O)N[C@H]3C(C)(C)[C@H](Oc4ccc(C#N)c(Cl)c4)C3(C)C)cc2)C(C)(C)C)cc1] | 954.40 | 956.40 |
| 416 | 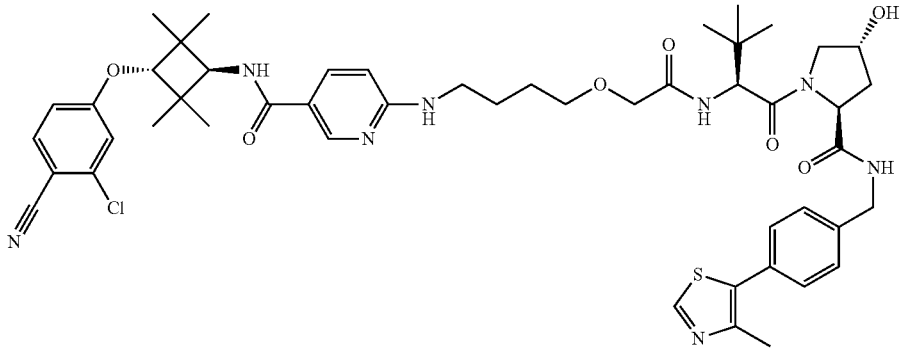 [SMILES: Cc1ncsc1-c1ccc(CNC(=O)[C@@H]2C[C@@H](O)CN2C(=O)[C@@H](NC(=O)COCCCCNc2ccc(C(=O)N[C@H]3C(C)(C)[C@H](Oc4ccc(C#N)c(Cl)c4)C3(C)C)cn2)C(C)(C)C)cc1] | 941.38 | 943.38 |

TABLE 17-continued

Additional Exemplary Compounds.

| Structure | Measured Mass Ion Data | |
|---|---|---|
| | MH+ 1 | MH+ 2 |
| 417 | 1003.39 | 1005.39 |
| 418 | 1045.38 | |
| 419 | 1045.38 | |

TABLE 17-continued

Additional Exemplary Compounds.

| Structure | Measured Mass Ion Data | |
|---|---|---|
| | MH+ 1 | MH+ 2 |
| 420 | 1050.39 | |
| 421 | 1081.38 | |
| 422 | 1042.39 | 1044.39 |

TABLE 17-continued
Additional Exemplary Compounds.
| Structure | Measured Mass Ion Data | |
|---|---|---|
| | MH+ 1 | MH+ 2 |
| 423 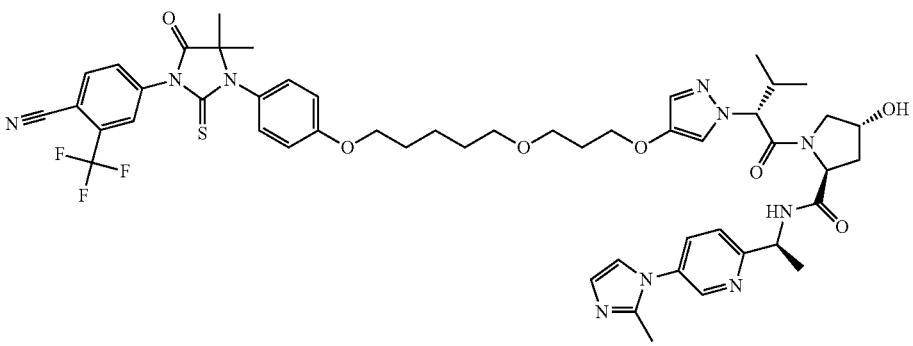 [SMILES: Cc1nccn1-c1ccc([C@H](C)NC(=O)[C@@H]2C[C@@H](O)CN2C(=O)[C@@H](C(C)C)n2cc(OCCCOCCCCCOc3ccc(N4C(=S)N(c5ccc(C#N)c(C(F)(F)F)c5)C(=O)C4(C)C)cc3)cn2)nc1] | 1013.42 | |
| 424 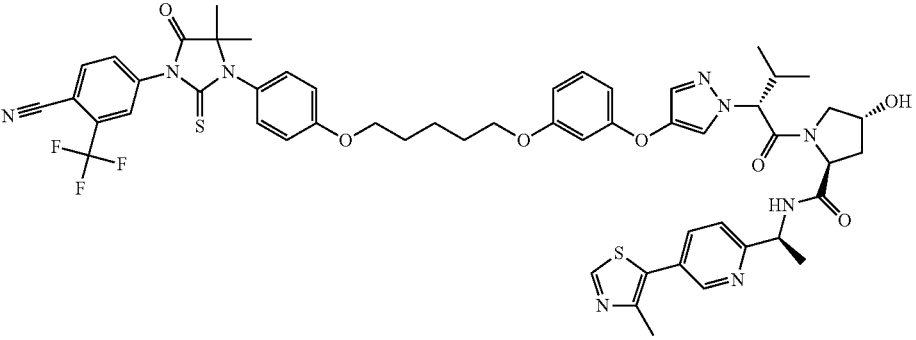 [SMILES: Cc1ncsc1-c1ccc([C@H](C)NC(=O)[C@@H]2C[C@@H](O)CN2C(=O)[C@@H](C(C)C)n2cc(Oc3cccc(OCCCCCOc4ccc(N5C(=S)N(c6ccc(C#N)c(C(F)(F)F)c6)C(=O)C5(C)C)cc4)c3)cn2)nc1] | 1064.36 | |
| 425 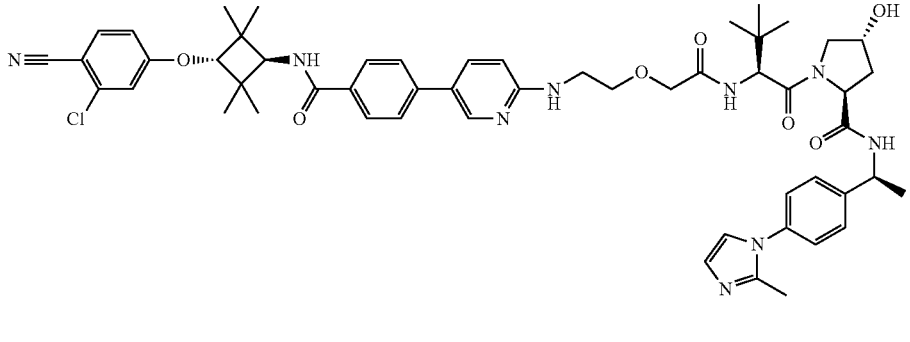 [SMILES: Cc1nccn1-c1ccc([C@H](C)NC(=O)[C@@H]2C[C@@H](O)CN2C(=O)[C@@H](NC(=O)COCCNc2ccc(-c3ccc(C(=O)N[C@H]4C(C)(C)[C@H](Oc5ccc(C#N)c(Cl)c5)C4(C)C)cc3)cn2)C(C)(C)C)cc1] | 986.46 | 988.46 |
| 426 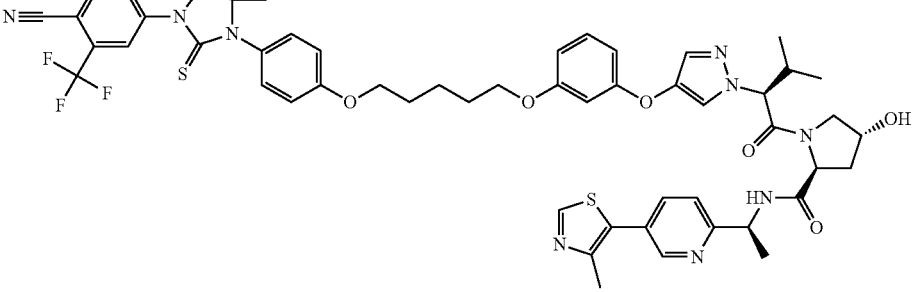 | 1064.37 | |

TABLE 17-continued
Additional Exemplary Compounds.
| Structure | Measured Mass Ion Data | |
|---|---|---|
| | MH+ 1 | MH+ 2 |
| 427 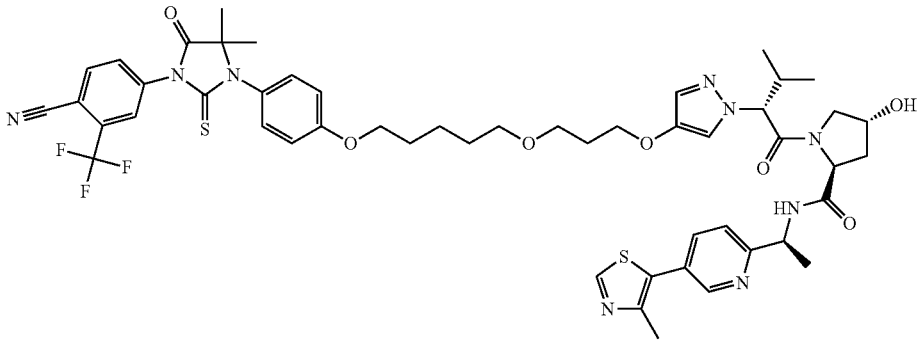 [SMILES: Cc1ncsc1-c1ccc([C@H](C)NC(=O)[C@@H]2C[C@@H](O)CN2C(=O)[C@@H](C(C)C)n2cc(OCCCOCCCCCOc3ccc(N4C(=S)N(c5ccc(C#N)c(C(F)(F)F)c5)C(=O)C4(C)C)cc3)cn2)nc1] | 1030.38 | |
| 428 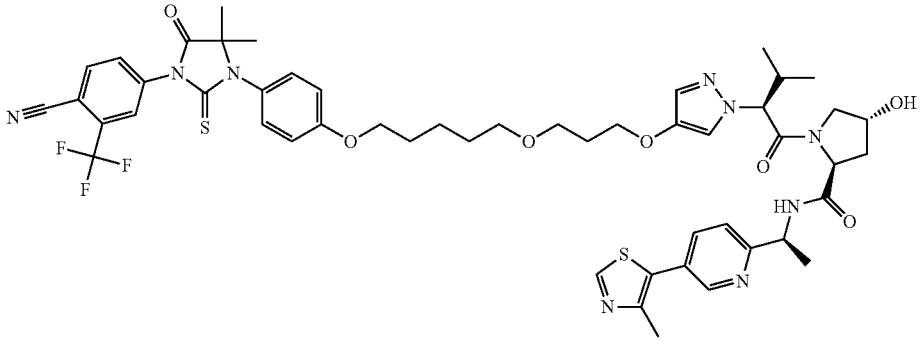 [SMILES: Cc1ncsc1-c1ccc([C@H](C)NC(=O)[C@@H]2C[C@@H](O)CN2C(=O)[C@H](C(C)C)n2cc(OCCCOCCCCCOc3ccc(N4C(=S)N(c5ccc(C#N)c(C(F)(F)F)c5)C(=O)C4(C)C)cc3)cn2)nc1] | 1030.38 | |
| 429 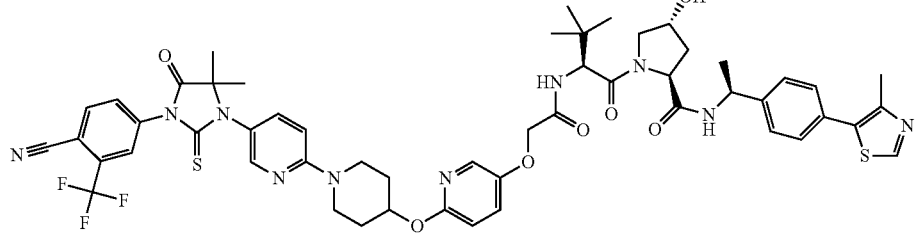 | 1067.38 | |
| 430 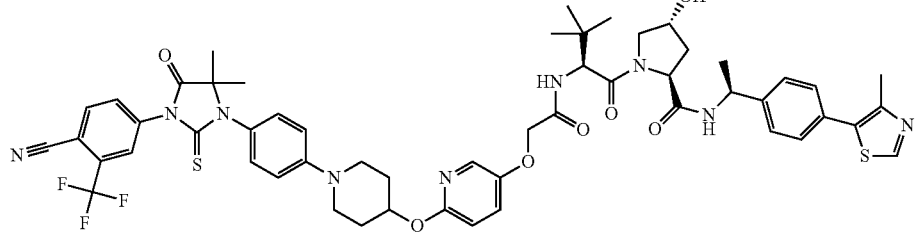 | 1066.38 | |

TABLE 17-continued

Additional Exemplary Compounds.

| | Structure | Measured Mass Ion Data | |
|---|---|---|---|
| | | MH+ 1 | MH+ 2 |
| 431 | | 1016.37 | |
| 432 | | 1004.38 | 1006.38 |
| 433 | | 1074.45 | 1076.45 |
| 434 | | 1029.39 | |
| 435 | | 1029.39 | |

TABLE 17-continued

Additional Exemplary Compounds.

| Structure | Measured Mass Ion Data | |
|---|---|---|
| | MH+ 1 | MH+ 2 |
| 436 | 975.40 | 977.40 |
| 437 | 975.40 | 977.40 |
| 438 | 995.46 | 997.46 |
| 439 | 1036.40 | |

TABLE 17-continued
Additional Exemplary Compounds.
|  | Structure | Measured Mass Ion Data | |
|---|---|---|---|
|  |  | MH+ 1 | MH+ 2 |
| 440 | 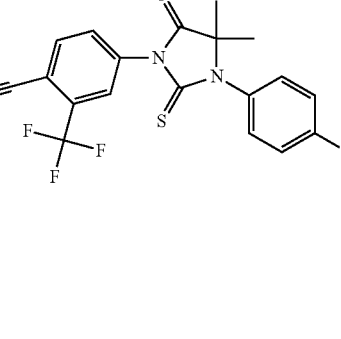 | 1030.38 | |
| 441 | 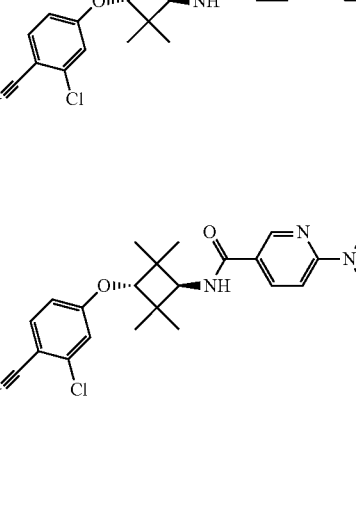 | 1004.30 | 1006.40 |
| 442 | 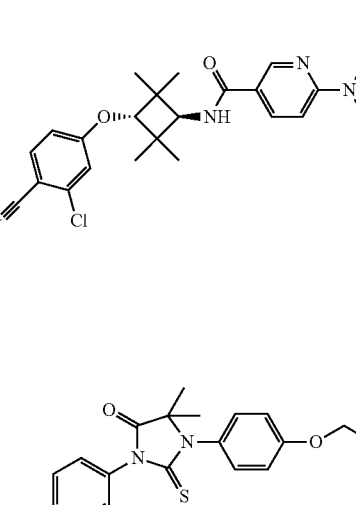 | 981.40 | 983.40 |
| 443 | 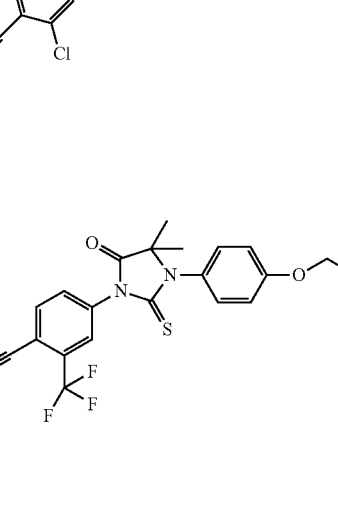 | 1007.42 | |

TABLE 17-continued

Additional Exemplary Compounds.

| | Structure | Measured Mass Ion Data | |
|---|---|---|---|
| | | MH+ 1 | MH+ 2 |
| 444 | 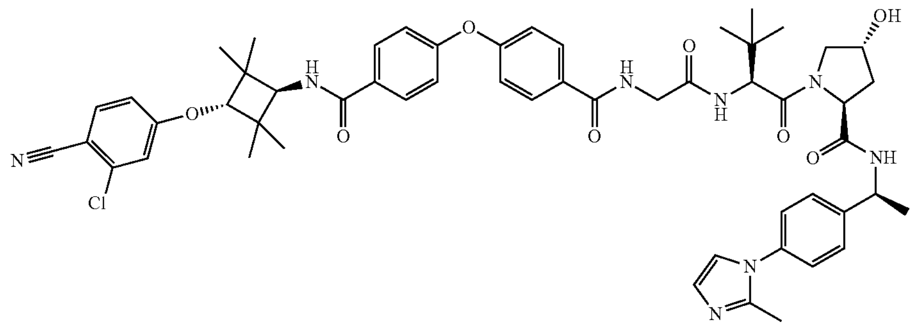 [SMILES: Cc1nccn1-c1ccc([C@H](C)NC(=O)[C@@H]2C[C@@H](O)CN2C(=O)[C@@H](NC(=O)CNC(=O)c2ccc(Oc3ccc(C(=O)N[C@H]4C(C)(C)[C@H](Oc5ccc(C#N)c(Cl)c5)C4(C)C)cc3)cc2)C(C)(C)C)cc1] | 985.43 | 987.43 |
| 445 | 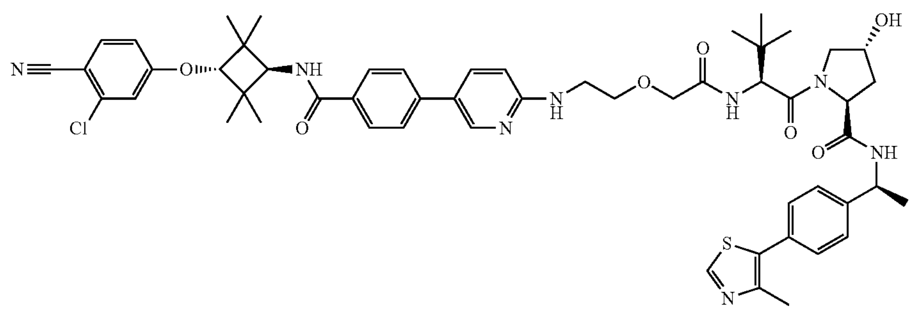 [SMILES: Cc1ncsc1-c1ccc([C@H](C)NC(=O)[C@@H]2C[C@@H](O)CN2C(=O)[C@@H](NC(=O)COCCNc2ccc(-c3ccc(C(=O)N[C@H]4C(C)(C)[C@H](Oc5ccc(C#N)c(Cl)c5)C4(C)C)cc3)cn2)C(C)(C)C)cc1] | 1003.42 | 1005.43 |
| 446 | 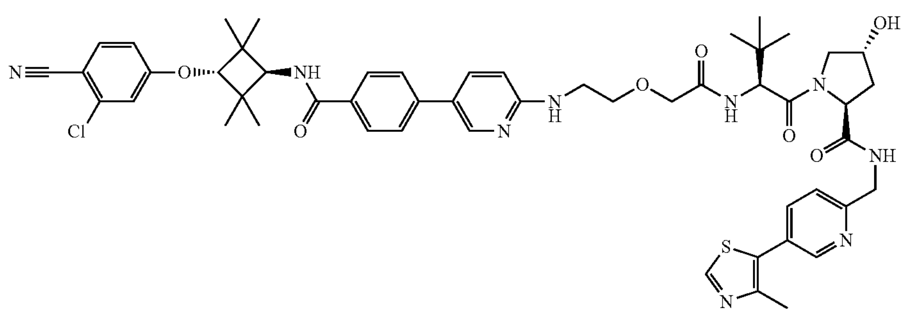 [SMILES: Cc1ncsc1-c1ccc(CNC(=O)[C@@H]2C[C@@H](O)CN2C(=O)[C@@H](NC(=O)COCCNc2ccc(-c3ccc(C(=O)N[C@H]4C(C)(C)[C@H](Oc5ccc(C#N)c(Cl)c5)C4(C)C)cc3)cn2)C(C)(C)C)nc1] | 990.41 | 992.41 |
| 447 | 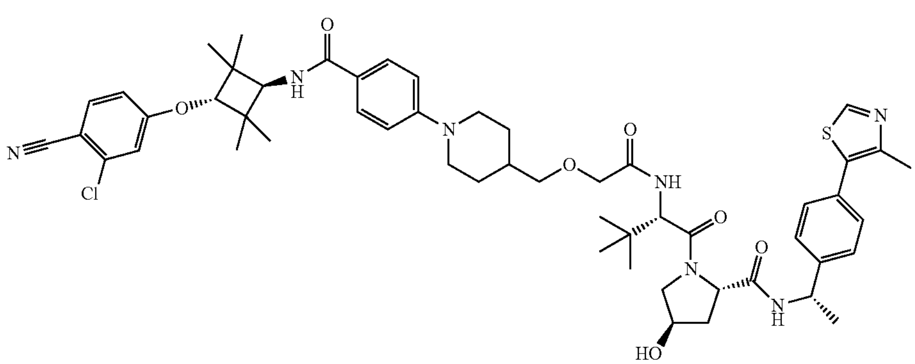 [SMILES: Cc1ncsc1-c1ccc([C@H](C)NC(=O)[C@@H]2C[C@@H](O)CN2C(=O)[C@@H](NC(=O)COCC2CCN(c3ccc(C(=O)N[C@H]4C(C)(C)[C@H](Oc5ccc(C#N)c(Cl)c5)C4(C)C)cc3)CC2)C(C)(C)C)cc1] | 980.45 | 982.45 |
| 448 | 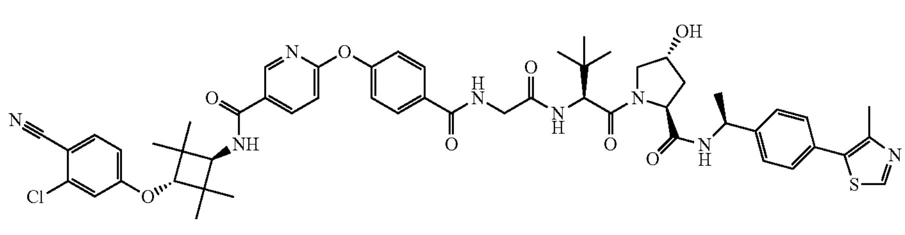 [SMILES: Cc1ncsc1-c1ccc([C@H](C)NC(=O)[C@@H]2C[C@@H](O)CN2C(=O)[C@@H](NC(=O)CNC(=O)c2ccc(Oc3ccc(C(=O)N[C@H]4C(C)(C)[C@H](Oc5ccc(C#N)c(Cl)c5)C4(C)C)cn3)cc2)C(C)(C)C)cc1] | 1003.30 | 1005.40 |

TABLE 17-continued

Additional Exemplary Compounds.

| Structure | Measured Mass Ion Data | |
|---|---|---|
| | MH+ 1 | MH+ 2 |
| 449 | 986.40 | 988.40 |
| 450 | 1003.40 | 1005.40 |
| 451 | 967.43 | |
| 452 | 1017.45 | |

TABLE 17-continued

Additional Exemplary Compounds.

| Structure | Measured Mass Ion Data | |
|---|---|---|
| | MH+ 1 | MH+ 2 |
| 453 | 1021.39 | |
| 454 | 968.45 | 970.45 |
| 455 | 968.45 | 970.45 |
| 456 | 994.55 | 996.45 |

TABLE 17-continued

Additional Exemplary Compounds.

| | Measured Mass Ion Data | |
|---|---|---|
| Structure | MH+ 1 | MH+ 2 |„

| # | MH+ 1 | MH+ 2 |
|---|---|---|
| 457 | 968.35 | 970.35 |
| 458 | 968.35 | 970.35 |
| 459 | 968.35 | 970.35 |
| 460 | 1096.43 | 1098.43 |

TABLE 17-continued
Additional Exemplary Compounds.
| Structure | Measured Mass Ion Data | |
|---|---|---|
| | MH+ 1 | MH+ 2 |
| 461 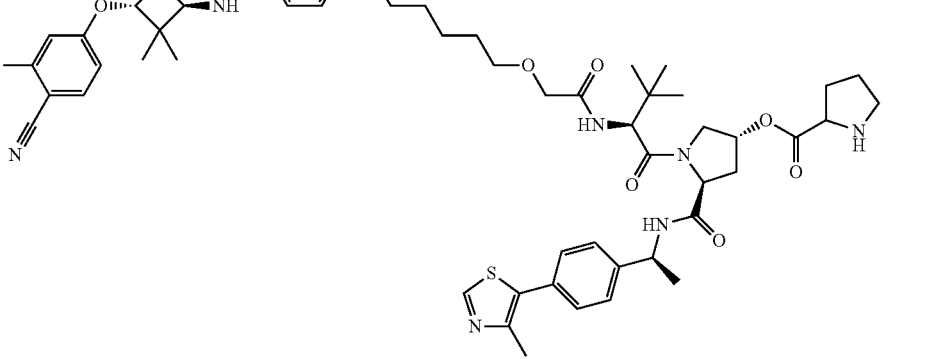 | 1065.38 | 1067.38 |
| 462 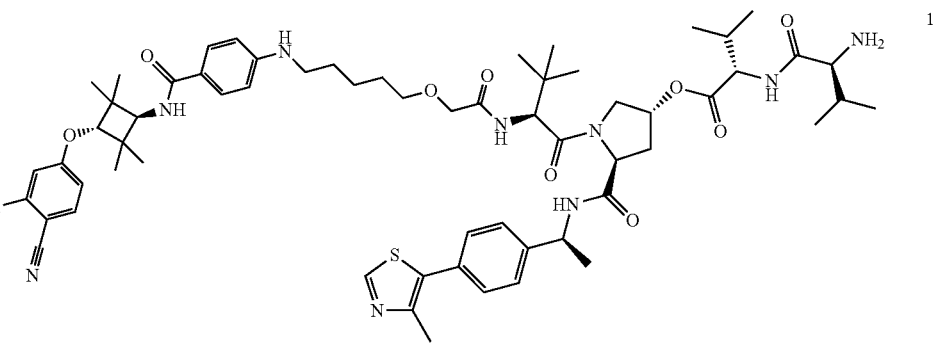 | 1166.46 | 1168.46 |
| 463 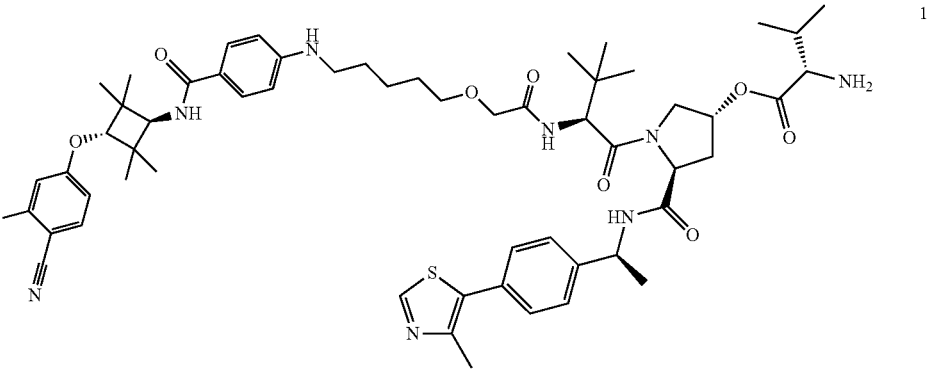 | 1067.40 | 1069.40 |
| 464 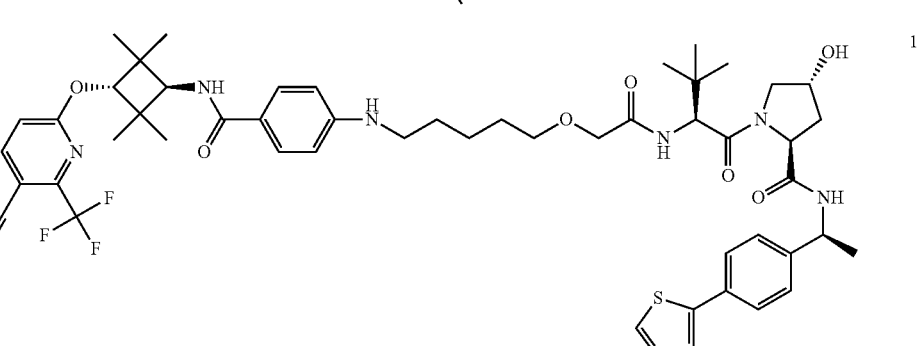 | 1003.50 | |

TABLE 17-continued
Additional Exemplary Compounds.
| Structure | Measured Mass Ion Data | |
|---|---|---|
| | MH+ 1 | MH+ 2 |
| 465 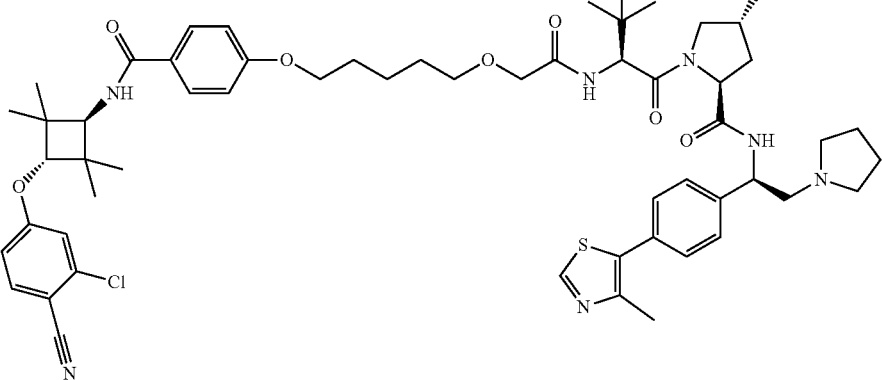 | 1038.50 | 1040.50 |
| 466 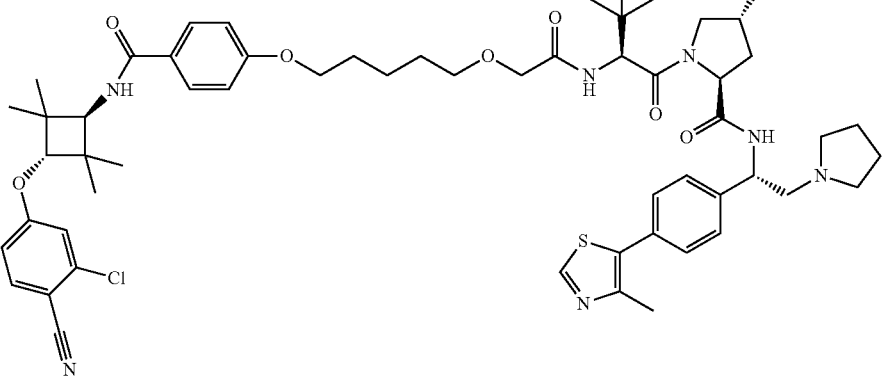 | 1038.55 | 1040.55 |
| 467 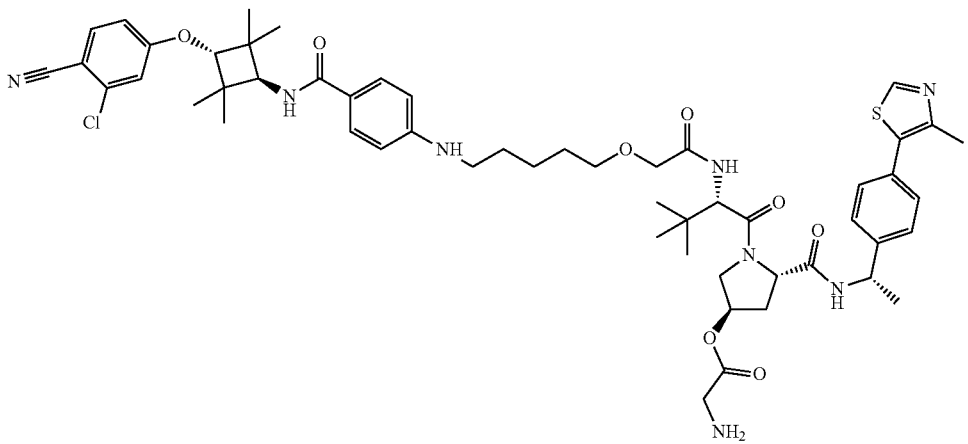 [SMILES: Cc1ncsc1-c1ccc([C@H](C)NC(=O)[C@@H]2C[C@@H](OC(=O)CN)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | 1025.36 | 1027.36 |

TABLE 17-continued

Additional Exemplary Compounds.

| | Structure | Measured Mass Ion Data | |
|---|---|---|---|
| | | MH+ 1 | MH+ 2 |
| 468 | 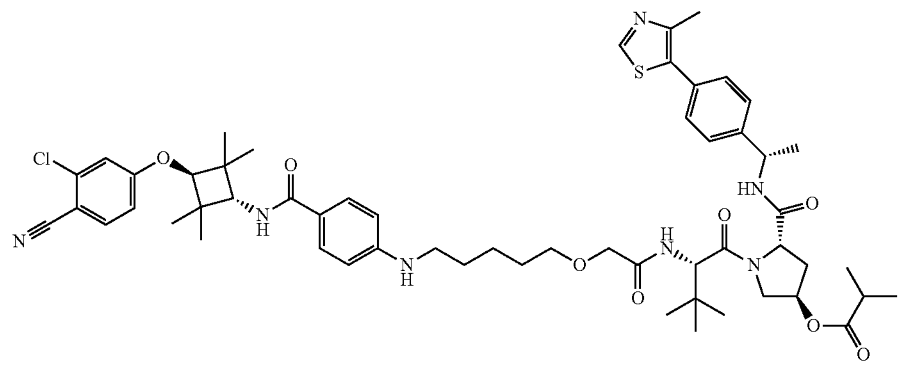 [SMILES: Cc1ncsc1-c1ccc([C@H](C)NC(=O)[C@@H]2C[C@@H](OC(=O)C(C)C)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | 1038.37 | 1040.37 |
| 469 | 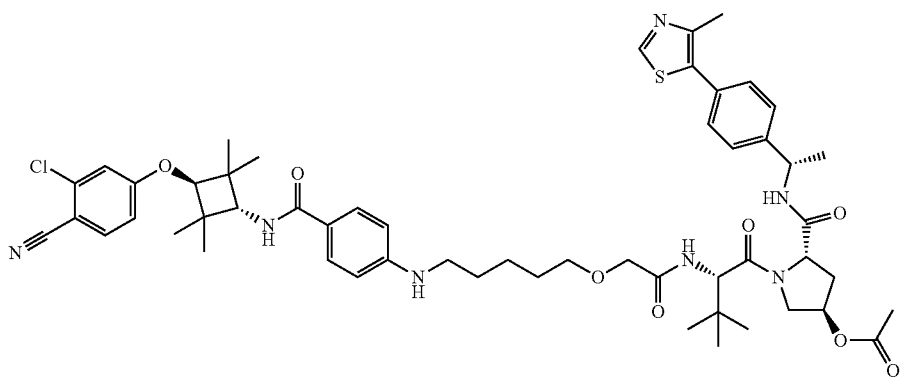 [SMILES: CC(=O)O[C@@H]1C[C@@H](C(=O)N[C@@H](C)c2ccc(-c3scnc3C)cc2)N(C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)C1] | 1010.34 | 1012.35 |
| 470 | 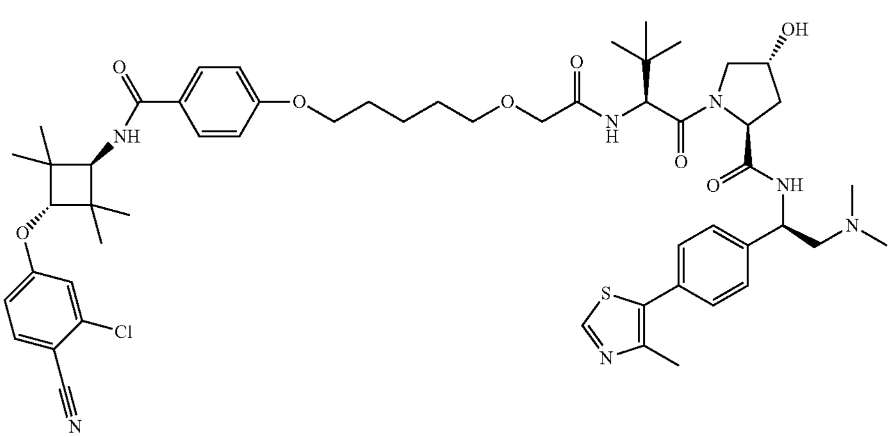 [SMILES: Cc1ncsc1-c1ccc([C@H](CN(C)C)NC(=O)[C@@H]2C[C@@H](O)CN2C(=O)[C@@H](NC(=O)COCCCCCOc2ccc(C(=O)N[C@H]3C(C)(C)[C@H](Oc4ccc(C#N)c(Cl)c4)C3(C)C)cc2)C(C)(C)C)cc1] | 1012.35 | 1014.35 |

TABLE 17-continued
Additional Exemplary Compounds.
| Structure | Measured Mass Ion Data | |
|---|---|---|
| | MH+ 1 | MH+ 2 |
| 471 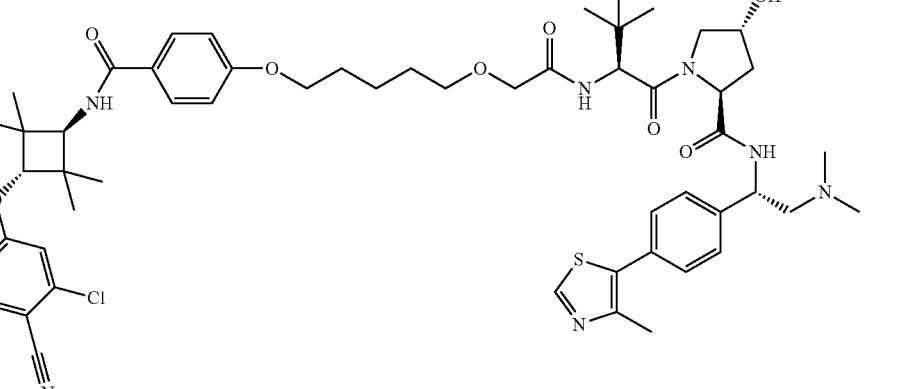 | 1012.35 | 1014.36 |
| 472 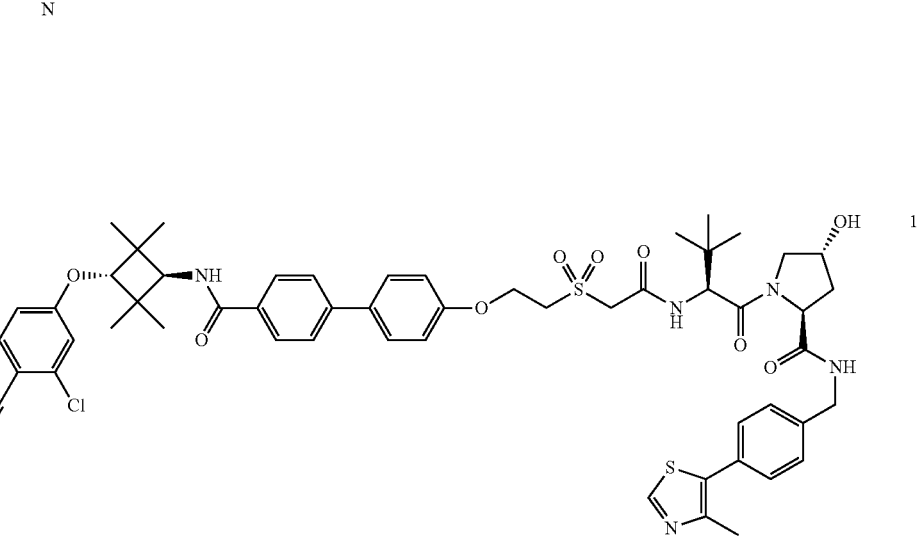 | 1037.25 | 1039.24 |
| 473 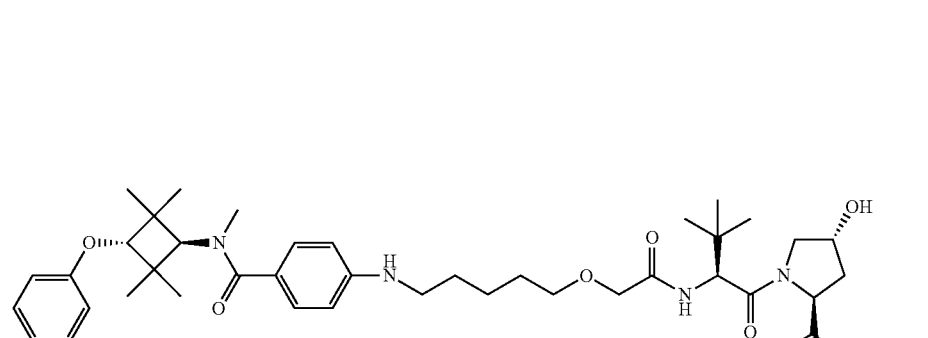 | 982.35 | 984.35 |

TABLE 17-continued
Additional Exemplary Compounds.
| Structure | Measured Mass Ion Data | |
|---|---|---|
| | MH+ 1 | MH+ 2 |
| 474 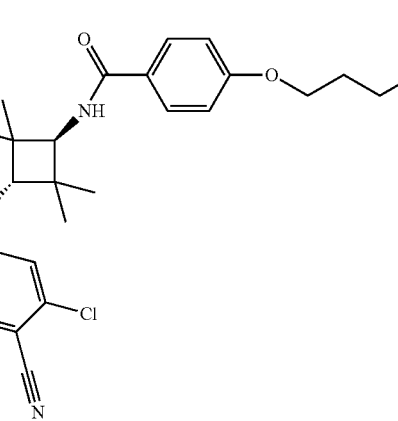 | 984.33 | 986.33 |
| 475 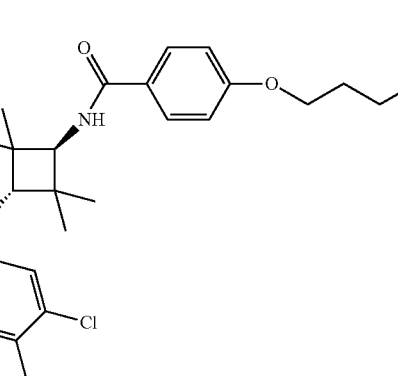 | 984.33 | 986.33 |
| 476 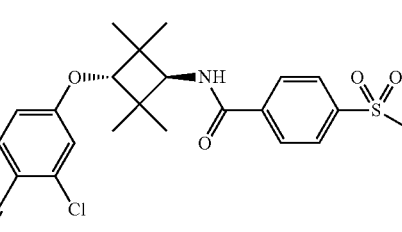 | 1003.26 | 1005.26 |

TABLE 17-continued

Additional Exemplary Compounds.

| | | Measured Mass Ion Data | |
|---|---|---|---|
| | Structure | MH+ 1 | MH+ 2 |
| 477 | | 927.30 | |
| 478 | | 995.30 | 997.30 |
| 479 | | 952.30 | |
| 480 | | 881.34 | 883.34 |

TABLE 17-continued
Additional Exemplary Compounds.
| | | Measured Mass Ion Data | |
|---|---|---|---|
| | Structure | MH+ 1 | MH+ 2 |
| 481 | 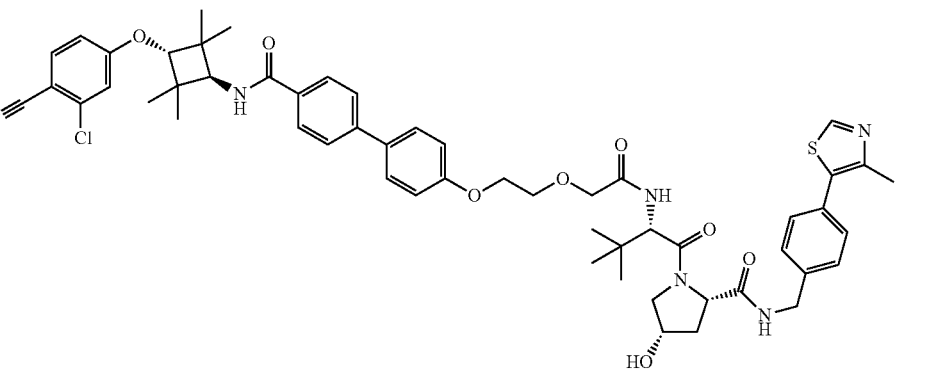 | 989.28 | 991.28 |
| 482 | 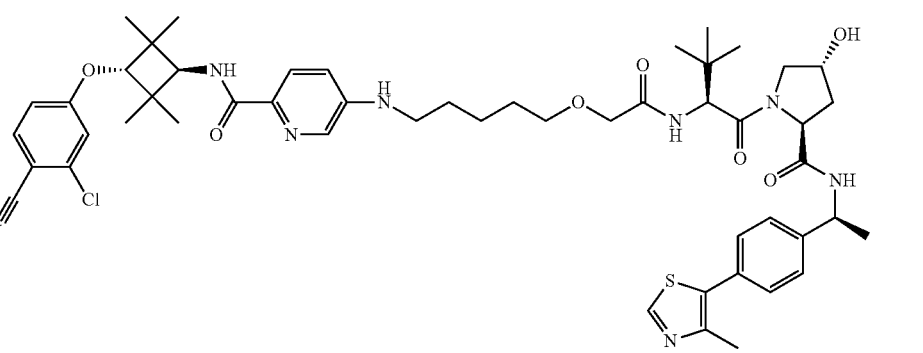 | 969.33 | 971.33 |
| 483 | 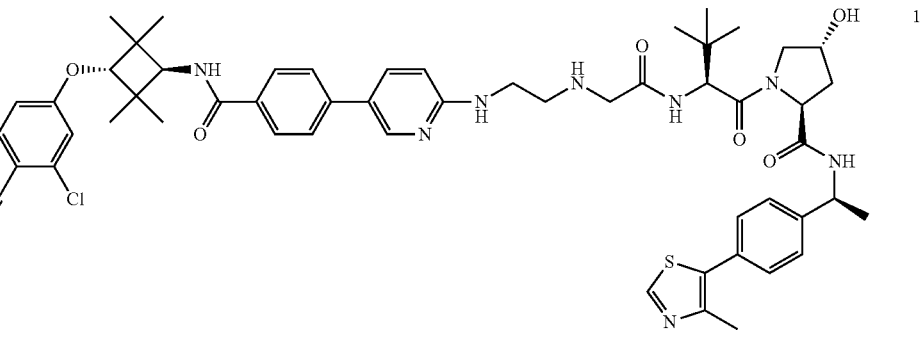 | 1002.33 | 1004.33 |
| 484 | 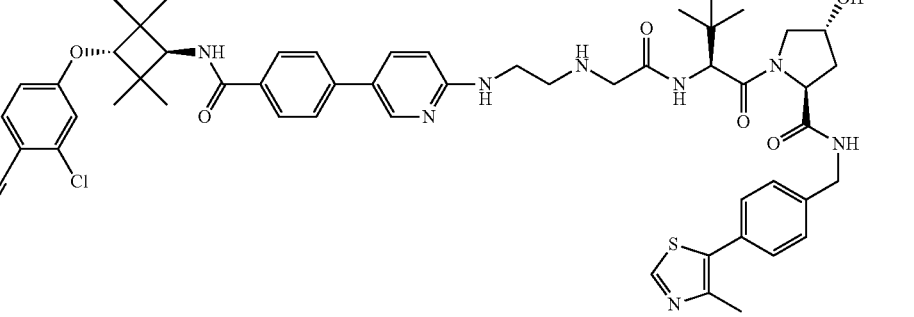 | 988.31 | 990.31 |

TABLE 17-continued

Additional Exemplary Compounds.

| | Structure | Measured Mass Ion Data | |
|---|---|---|---|
| | | MH+ 1 | MH+ 2 |
| 485 | 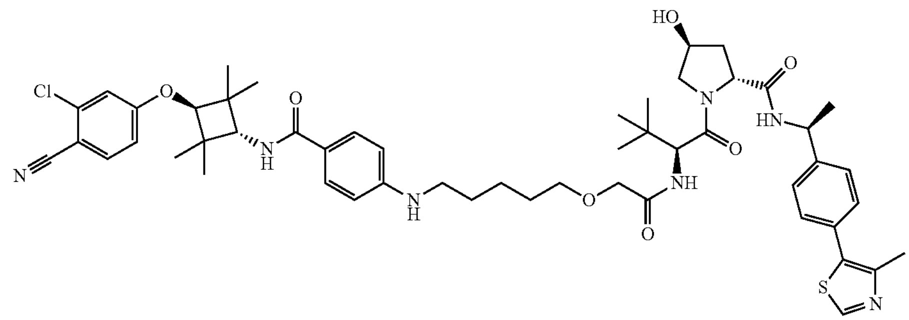 [SMILES: Cc1ncsc1-c1ccc([C@H](C)NC(=O)[C@H]2C[C@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | 968.83 | 970.83 |
| 486 | 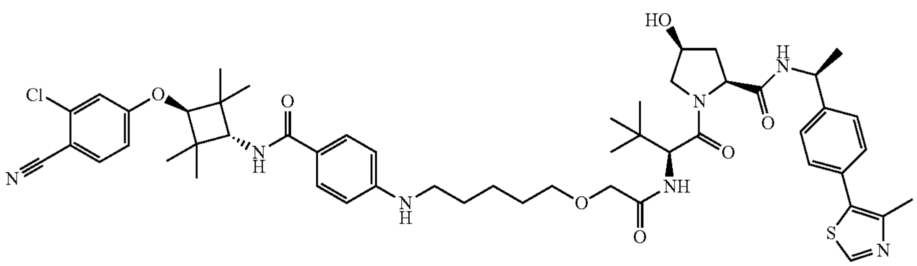 [SMILES: Cc1ncsc1-c1ccc([C@H](C)NC(=O)[C@@H]2C[C@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | 969.33 | 971.33 |
| 487 | 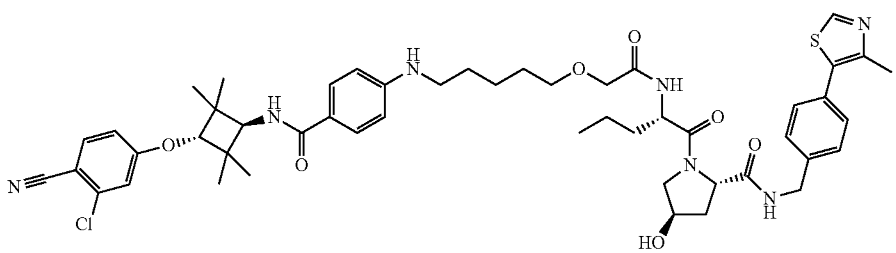 [SMILES: CCC[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2scnc2C)cc1] | 940.30 | |
| 488 | 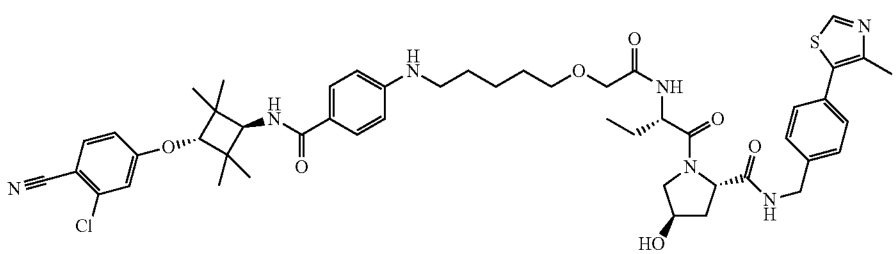 [SMILES: CC[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2scnc2C)cc1] | 926.29 | 928.29 |
| 489 | 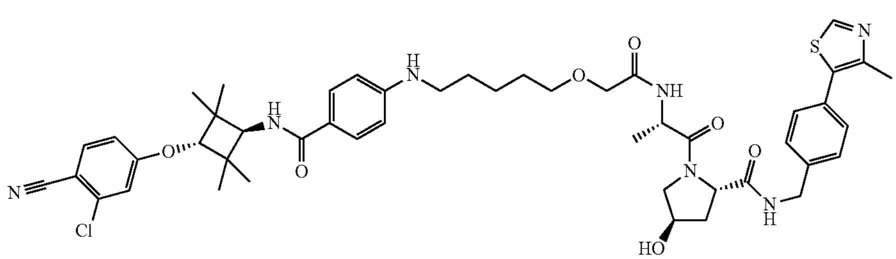 [SMILES: Cc1ncsc1-c1ccc(CNC(=O)[C@@H]2C[C@@H](O)CN2C(=O)[C@H](C)NC(=O)COCCCCCNc2ccc(C(=O)N[C@H]3C(C)(C)[C@H](Oc4ccc(C#N)c(Cl)c4)C3(C)C)cc2)cc1] | 912.23 | 914.23 |

TABLE 17-continued
Additional Exemplary Compounds.
| | Structure | Measured Mass Ion Data | |
|---|---|---|---|
| | | MH+ 1 | MH+ 2 |
| 490 | 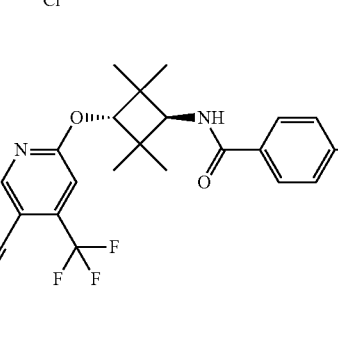 | 898.26 | 900.26 |
| 491 | 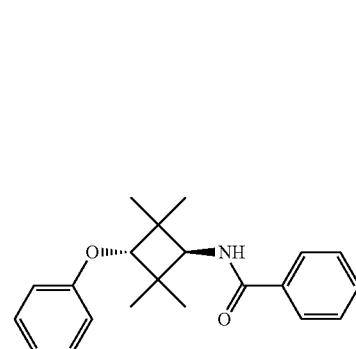 | 1003.60 | |
| 492 | 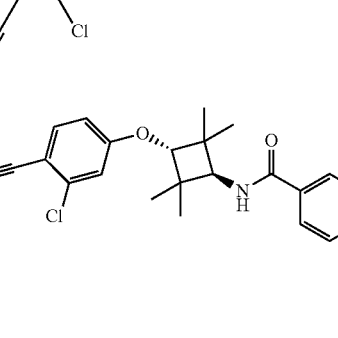 | 882.26 | 884.26 |
| 493 | 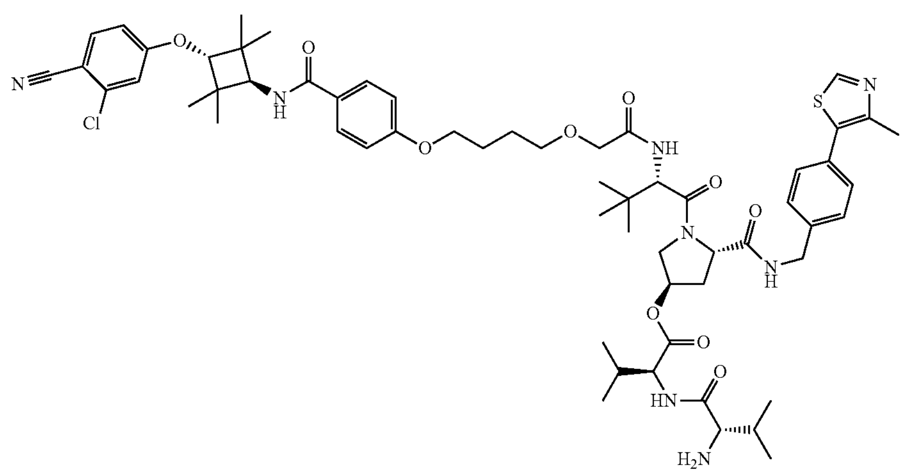 [SMILES: Cc1ncsc1-c1ccc(CNC(=O)[C@@H]2C[C@@H](OC(=O)[C@@H](NC(=O)[C@@H](N)C(C)C)C(C)C)CN2C(=O)[C@@H](NC(=O)COCCCCOc2ccc(C(=O)N[C@H]3C(C)(C)[C@H](Oc4ccc(C#N)c(Cl)c4)C3(C)C)cc2)C(C)(C)C)cc1] | 1139.41 | 1141.41 |

TABLE 17-continued

Additional Exemplary Compounds.

| | Structure | Measured Mass Ion Data | |
|---|---|---|---|
| | | MH+ 1 | MH+ 2 |
| 494 | | 1040.35 | 1042.35 |
| 495 | | 986.32 | 988.32 |
| 496 | | 912.28 | 914.28 |
| 497 | | 1003.45 | |

TABLE 17-continued

Additional Exemplary Compounds.

| Structure | Measured Mass Ion Data | |
|---|---|---|
| | MH+ 1 | MH+ 2 |
| 498 | 897.27 | 899.27 |
| 499 | 938.27 | 940.37 |
| 500 | 916.31 | 918.31 |
| 501 | 916.31 | 918.31 |

TABLE 17-continued

Additional Exemplary Compounds.

| | Structure | Measured Mass Ion Data | |
|---|---|---|---|
| | | MH+ 1 | MH+ 2 |
| 502 | 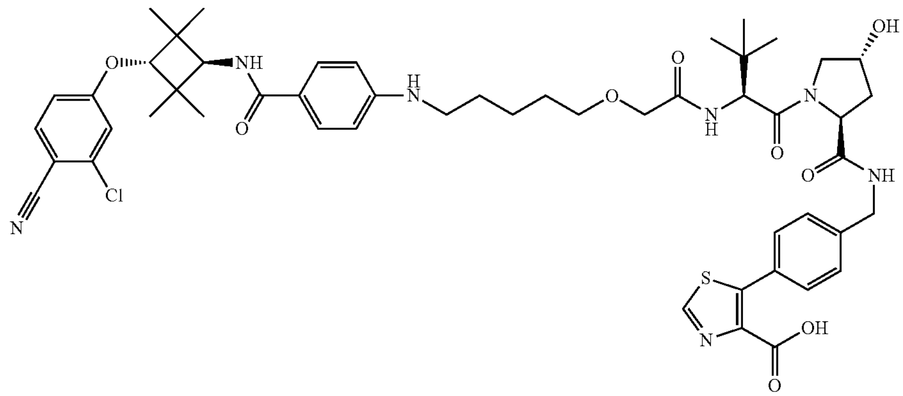 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2scnc2C(=O)O)cc1] | 984.30 | 986.30 |
| 503 | 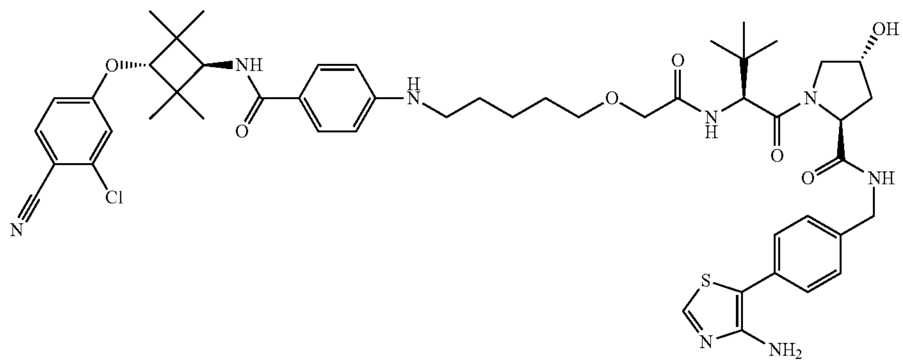 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2scnc2N)cc1] | 955.32 | 957.32 |
| 504 | 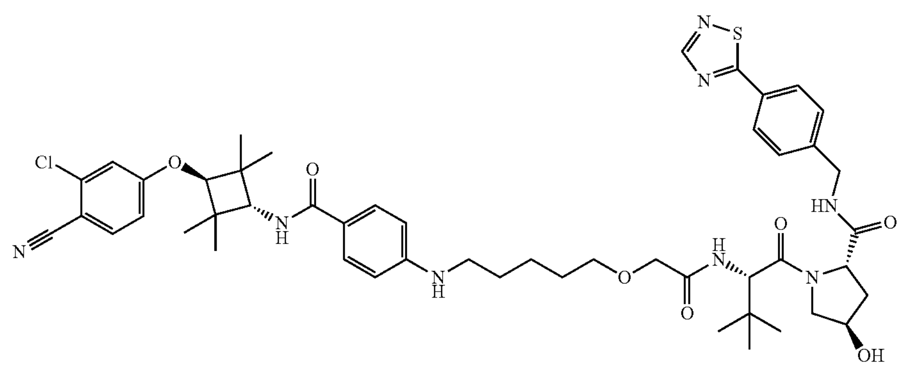 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2ncns2)cc1] | 942.33 | 944.33 |
| 505 | 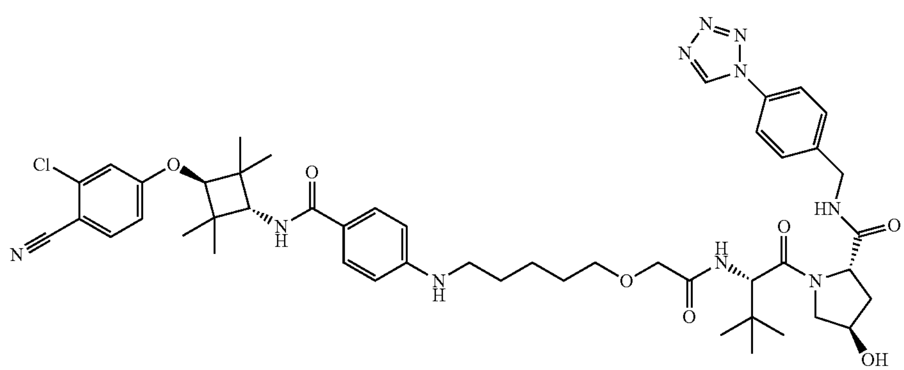 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-n2cnnn2)cc1] | 926.37 | 927.36 |

TABLE 17-continued

Additional Exemplary Compounds.

| | | Measured Mass Ion Data | |
|---|---|---|---|
| | Structure | MH+ 1 | MH+ 2 |
| 506 | | 926.37 | 927.40 |
| 507 | | 782.30 | 784.30 |
| 508 | | 998.36 | 1000.36 |

TABLE 17-continued

Additional Exemplary Compounds.

| Structure | Measured Mass Ion Data | |
|---|---|---|
| | MH+ 1 | MH+ 2 |
| 509 | 769.27 | 771.27 |
| 510 | 912.35 | 914.35 |
| 511 | 914.36 | 916.36 |
| 512 | 901.33 | 903.33 |

TABLE 17-continued

Additional Exemplary Compounds.

| | Structure | Measured Mass Ion Data | |
|---|---|---|---|
| | | MH+ 1 | MH+ 2 |
| 513 | 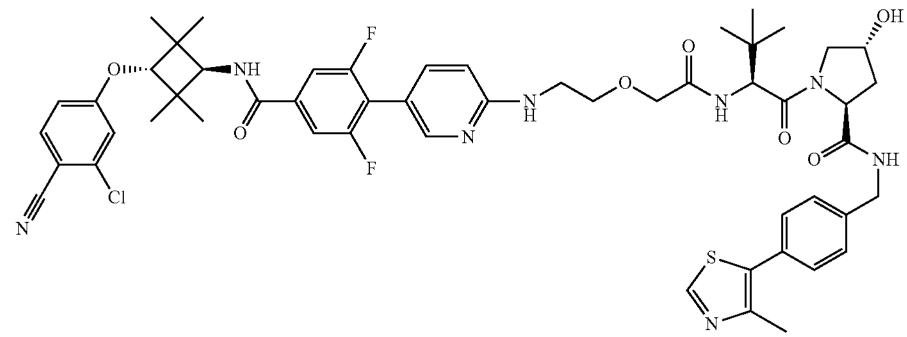 [SMILES: Cc1ncsc1-c1ccc(CNC(=O)[C@@H]2C[C@@H](O)CN2C(=O)[C@@H](NC(=O)COCCNc2ccc(-c3c(F)cc(C(=O)N[C@H]4C(C)(C)[C@H](Oc5ccc(C#N)c(Cl)c5)C4(C)C)cc3F)cn2)C(C)(C)C)cc1] | 1025.29 | 1027.29 |
| 514 | 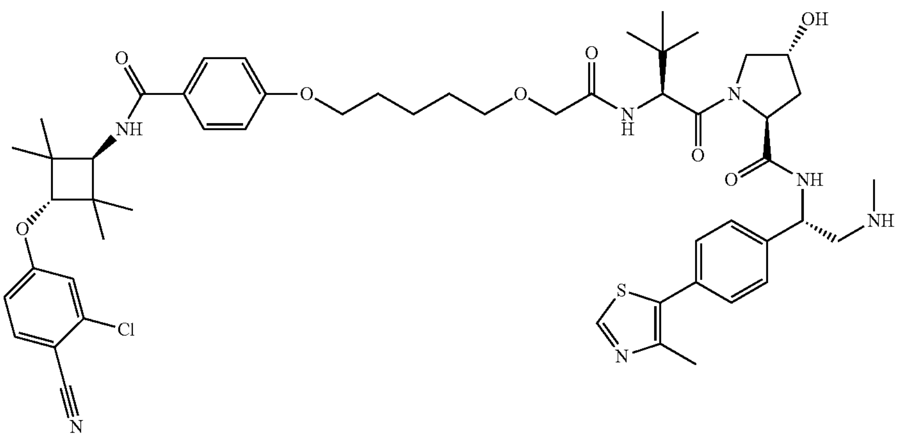 [SMILES: CNC[C@@H](NC(=O)[C@@H]1C[C@@H](O)CN1C(=O)[C@@H](NC(=O)COCCCCCOc1ccc(C(=O)N[C@H]2C(C)(C)[C@H](Oc3ccc(C#N)c(Cl)c3)C2(C)C)cc1)C(C)(C)C)c1ccc(-c2scnc2C)cc1] | 998.34 | 1000.34 |
| 515 | 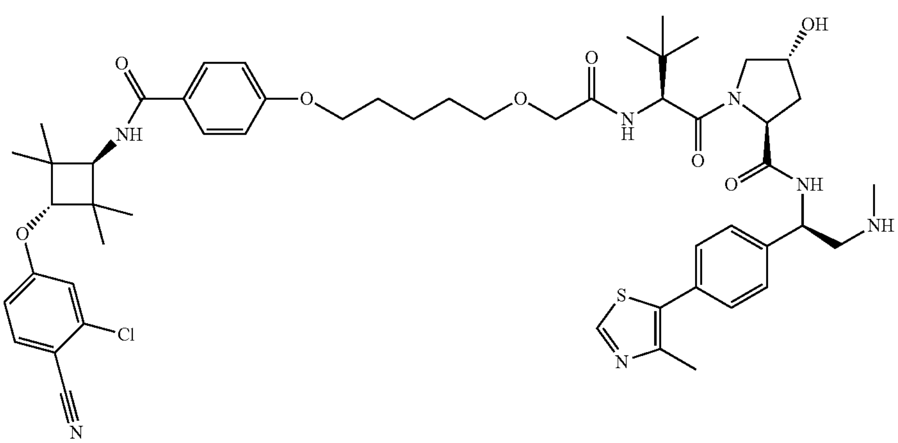 [SMILES: CNC[C@H](NC(=O)[C@@H]1C[C@@H](O)CN1C(=O)[C@@H](NC(=O)COCCCCCOc1ccc(C(=O)N[C@H]2C(C)(C)[C@H](Oc3ccc(C#N)c(Cl)c3)C2(C)C)cc1)C(C)(C)C)c1ccc(-c2scnc2C)cc1] | 998.34 | 1000.34 |

TABLE 17-continued

Additional Exemplary Compounds.

| | Structure | Measured Mass Ion Data | |
|---|---|---|---|
| | | MH+ 1 | MH+ 2 |
| 516 | 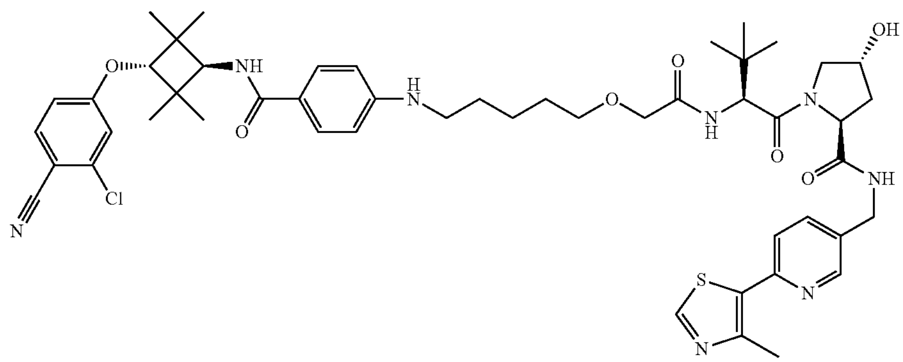 [SMILES: Cc1ncsc1-c1ccc(CNC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cn1] | 955.33 | 957.33 |
| 517 | 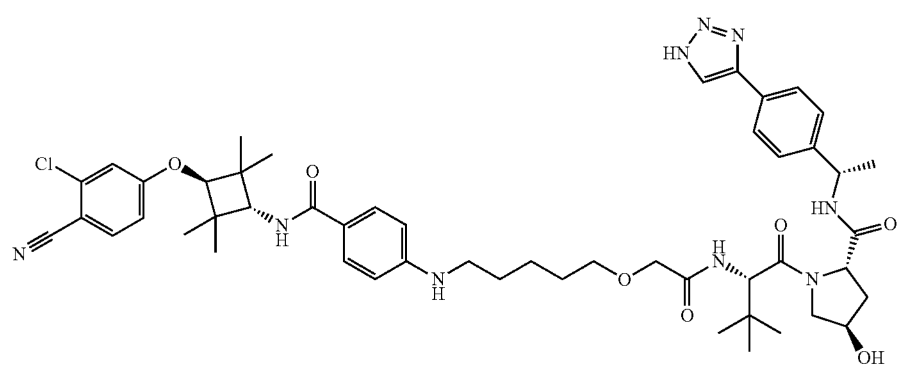 [SMILES: C[C@H](NC(=O)[C@@H]1C[C@@H](O)CN1C(=O)[C@@H](NC(=O)COCCCCCNc1ccc(C(=O)N[C@H]2C(C)(C)[C@H](Oc3ccc(C#N)c(Cl)c3)C2(C)C)cc1)C(C)(C)C)c1ccc(-c2c[nH]nn2)cc1] | 939.45 | 941.45 |
| 518 | 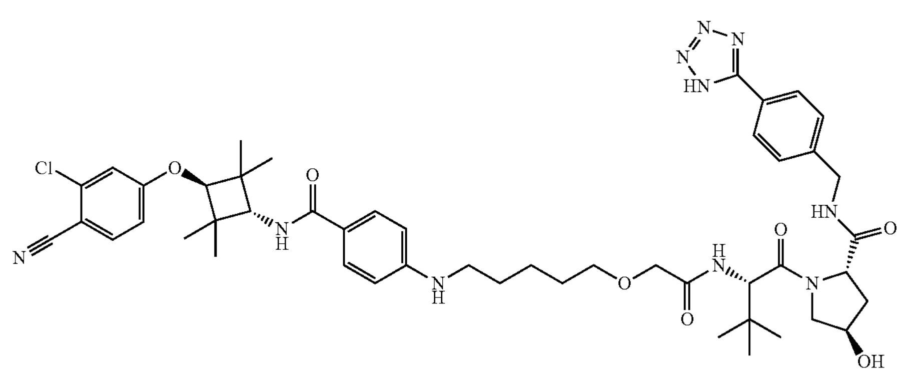 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2nnn[nH]2)cc1] | 926.43 | 928.43 |

TABLE 17-continued

Additional Exemplary Compounds.

| Structure | Measured Mass Ion Data | |
|---|---|---|
| | MH+ 1 | MH+ 2 |
| 519 | 783.30 | 785.30 |
| 520 | 868.34 | 870.34 |
| 521 | 965.34 | 967.34 |
| 522 | 887.37 | 889.37 |

TABLE 17-continued

Additional Exemplary Compounds.

| | | Measured Mass Ion Data | |
|---|---|---|---|
| | Structure | MH+ 1 | MH+ 2 |
| 523 | | 883.35 | 885.35 |
| 524 | | 916.34 | 918.34 |
| 525 | | 980.37 | 982.37 |
| 526 | | 925.43 | 927.43 |

TABLE 17-continued

Additional Exemplary Compounds.

| | Structure | Measured Mass Ion Data | |
|---|---|---|---|
| | | MH+ 1 | MH+ 2 |
| 527 | 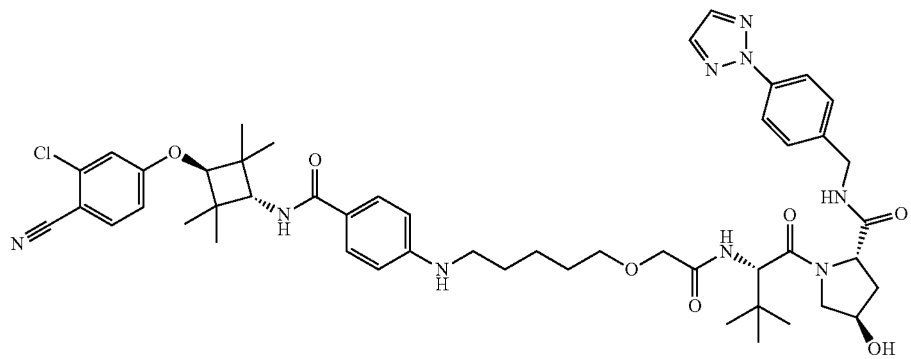 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-n2nccn2)cc1] | 925.44 | 927.43 |
| 528 | 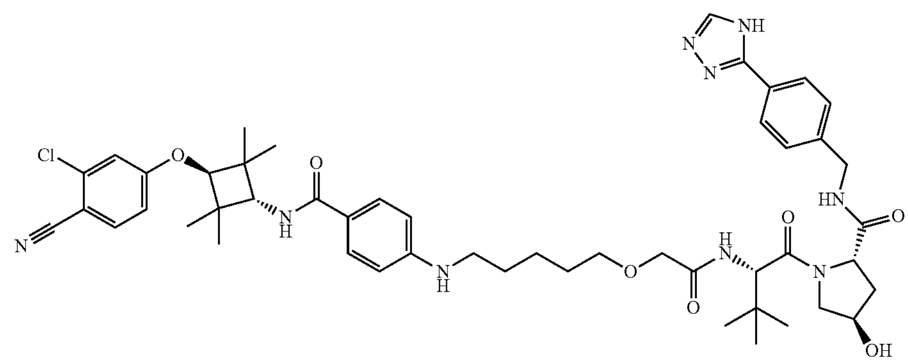 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2nnc[nH]2)cc1] | 925.43 | 927.43 |
| 529 | 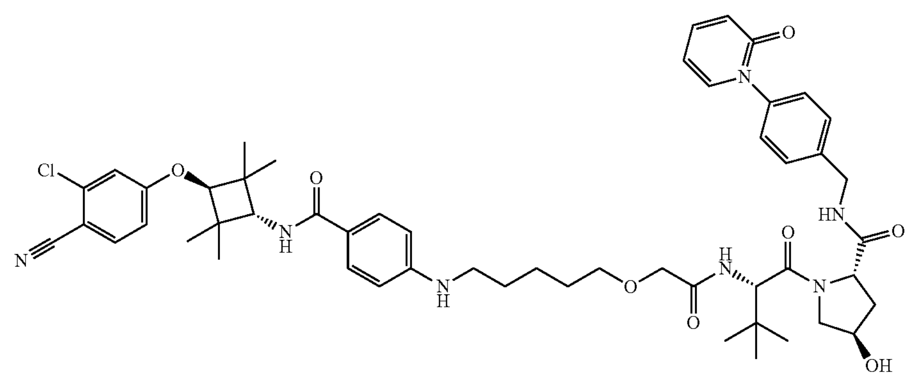 | 951.44 | 953.44 |
| 530 | 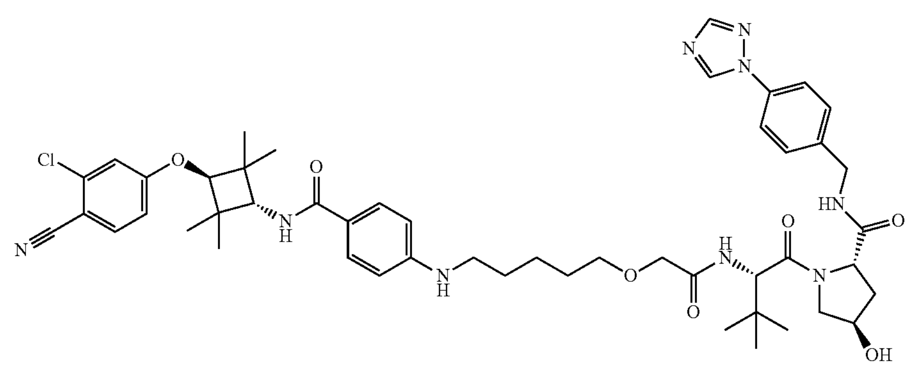 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-n2cncn2)cc1] | 925.44 | 927.43 |

TABLE 17-continued
Additional Exemplary Compounds.
| | Structure | Measured Mass Ion Data | |
|---|---|---|---|
| | | MH+ 1 | MH+ 2 |
| 531 | 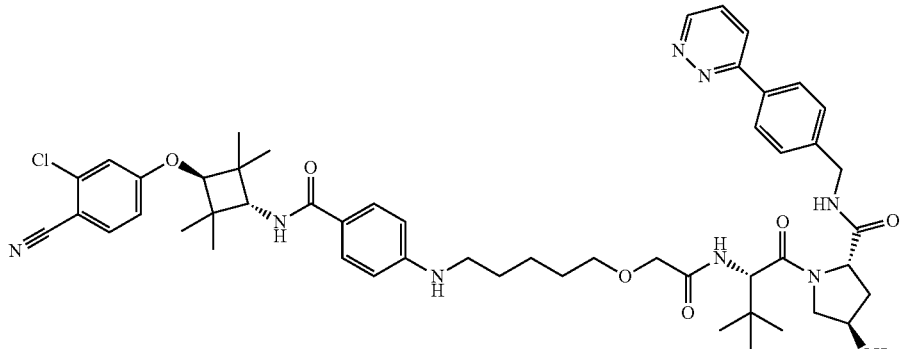 | 936.44 | 938.44 |
| 532 | 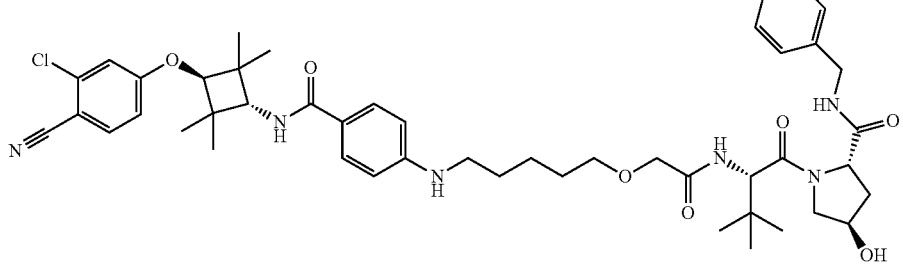 | 936.44 | 938.44 |
| 533 | 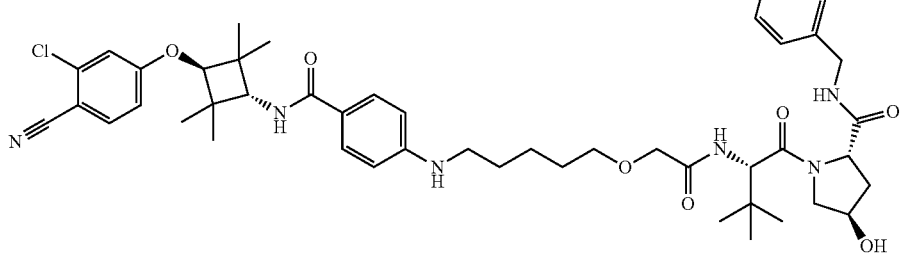 | 936.44 | 938.44 |
| 534 | 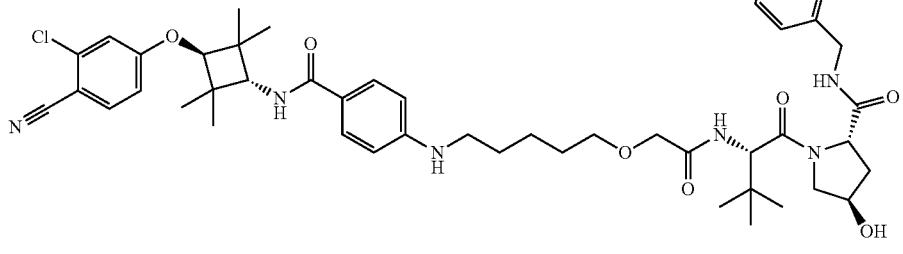 | 936.44 | 938.44 |

US 11,352,351 B2
TABLE 17-continued
Additional Exemplary Compounds.
| | | Measured Mass Ion Data | |
|---|---|---|---|
| | Structure | MH+ 1 | MH+ 2 |
| 535 | 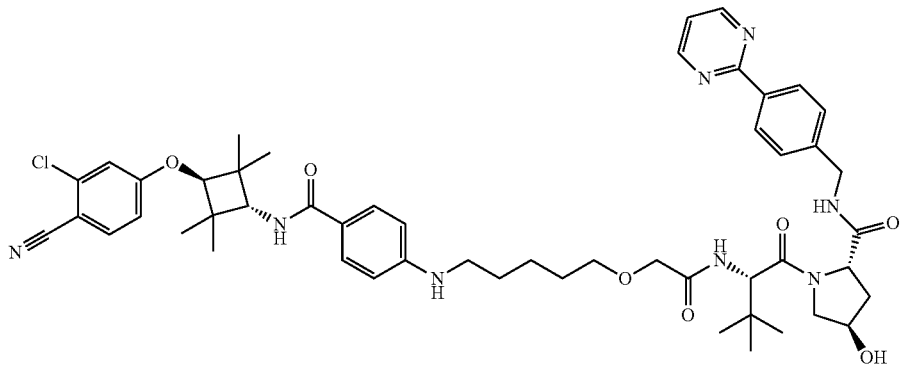 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2ncccn2)cc1] | 936.44 | 938.44 |
| 536 | 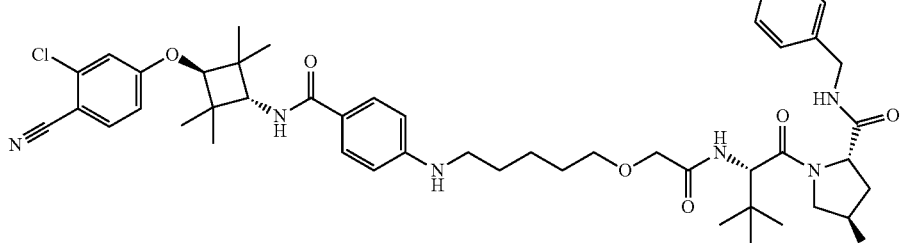 | 935.45 | 937.45 |
| 537 | 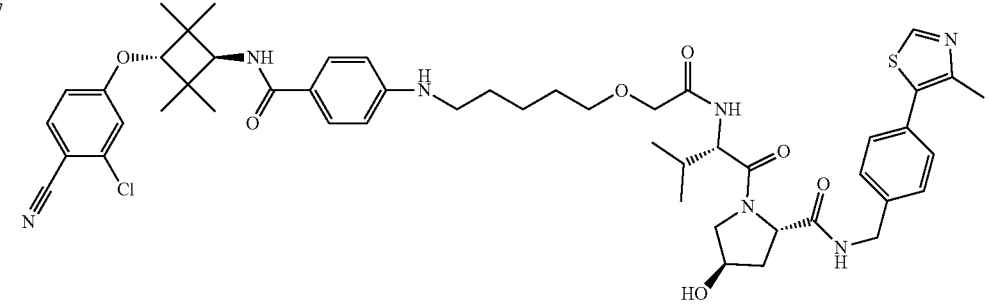 | 940.35 | 942.35 |
| 538 | 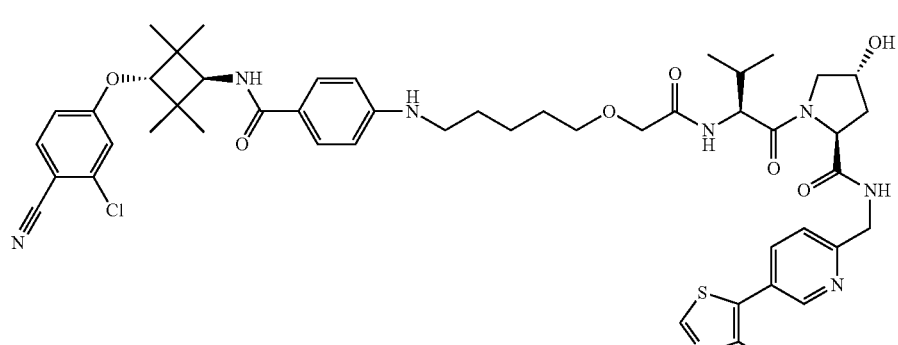 | 955.41 | 957.41 |

TABLE 17-continued

Additional Exemplary Compounds.

| | | Measured Mass Ion Data | |
|---|---|---|---|
| | Structure | MH+ 1 | MH+ 2 |
| 539 | | 883.41 | 885.41 |
| 540 | | 917.39 | 919.39 |
| 541 | | 896.43 | 898.43 |
| 542 | | 882.41 | 884.41 |

TABLE 17-continued

Additional Exemplary Compounds.

| | Structure | Measured Mass Ion Data | |
|---|---|---|---|
| | | MH+ 1 | MH+ 2 |
| 543 | 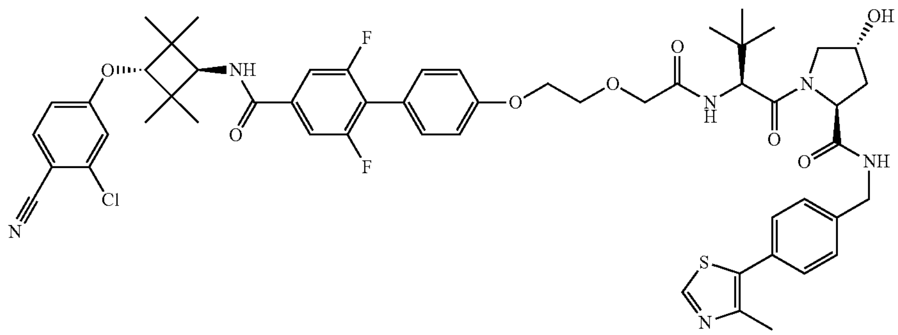 [SMILES: Cc1ncsc1-c1ccc(CNC(=O)[C@@H]2C[C@@H](O)CN2C(=O)[C@@H](NC(=O)COCCOc2ccc(-c3c(F)cc(C(=O)N[C@H]4C(C)(C)[C@H](Oc5ccc(C#N)c(Cl)c5)C4(C)C)cc3F)cc2)C(C)(C)C)cc1] | 1025.38 | 1027.38 |
| 544 | 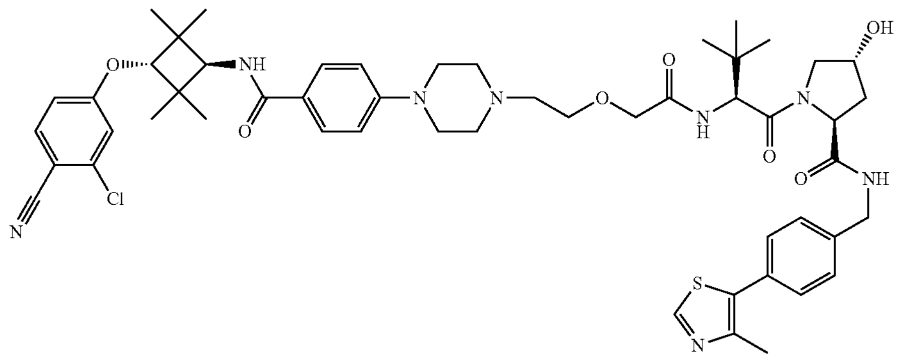 | 981.43 | 983.43 |
| 545 | 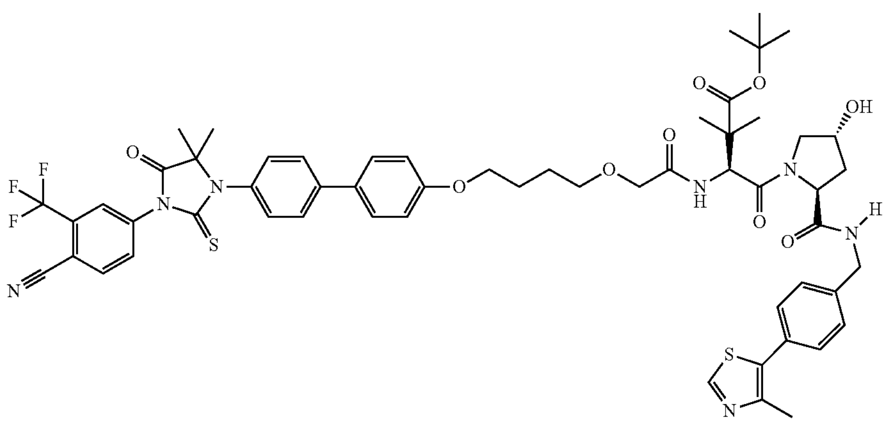 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cc3)cc2)C(C)(C)C(=O)OC(C)(C)C)cc1] | 1110.30 | |
| 546 | 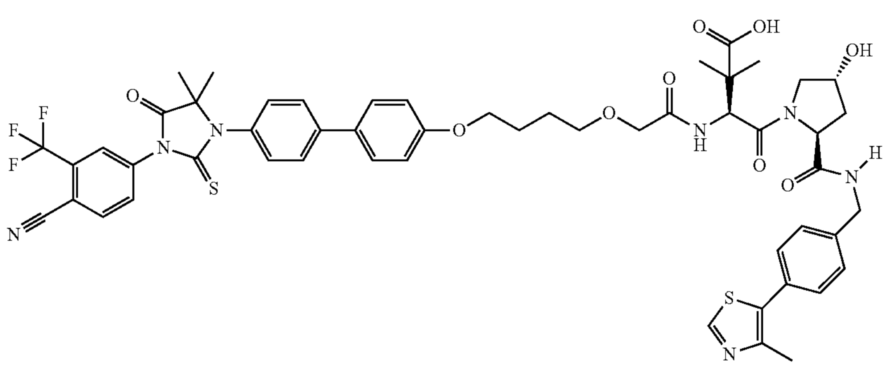 [SMILES: Cc1ncsc1-c1ccc(CNC(=O)[C@@H]2C[C@@H](O)CN2C(=O)[C@@H](NC(=O)COCCCCOc2ccc(-c3ccc(N4C(=S)N(c5ccc(C#N)c(C(F)(F)F)c5)C(=O)C4(C)C)cc3)cc2)C(C)(C)C(=O)O)cc1] | 1055.30 | |

TABLE 17-continued

Additional Exemplary Compounds.

| Structure | Measured Mass Ion Data | |
|---|---|---|
| | MH+ 1 | MH+ 2 |
| 547 | 868.40 | 870.40 |
| 548 | 883.40 | 885.40 |
| 549 | 931.86 | 933.86 |
| 550 | 917.38 | 919.38 |

TABLE 17-continued

Additional Exemplary Compounds.

| | | Measured Mass Ion Data | |
|---|---|---|---|
| | Structure | MH+ 1 | MH+ 2 |
| 551 | | 883.41 | 885.41 |
| 552 | | 891.38 | 893.38 |
| 553 | | 989.40 | 991.40 |
| 554 | | 1024.15 | |

TABLE 17-continued
Additional Exemplary Compounds.
| Structure | Measured Mass Ion Data | |
|---|---|---|
| | MH+ 1 | MH+ 2 |
| 555 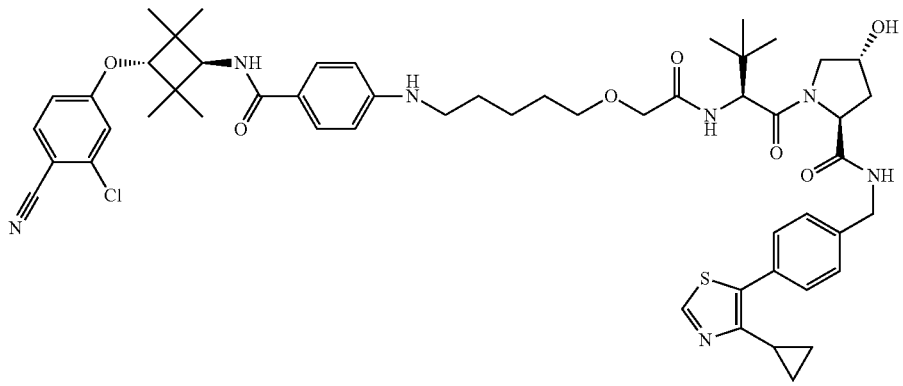 [SMILES: CC(C)(C)[C@H](NC(=O)COCCCCCNc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(-c2scnc2C2CC2)cc1] | 980.43 | 982.43 |
| 556 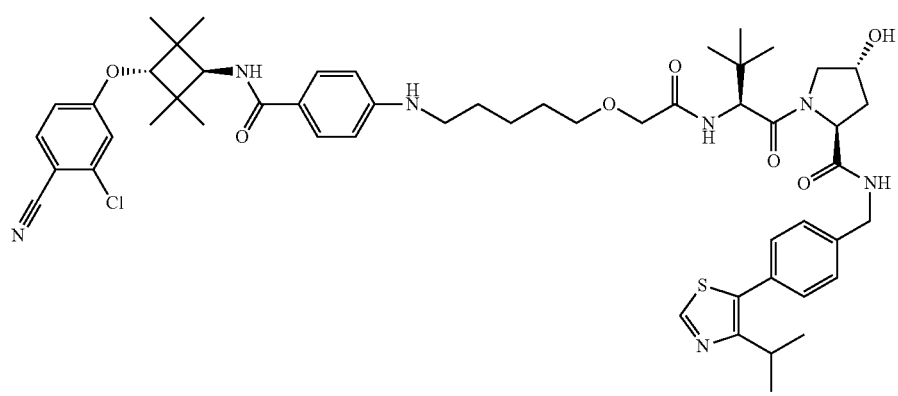 [SMILES: CC(C)c1ncsc1-c1ccc(CNC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | 982.45 | 984.45 |
| 557 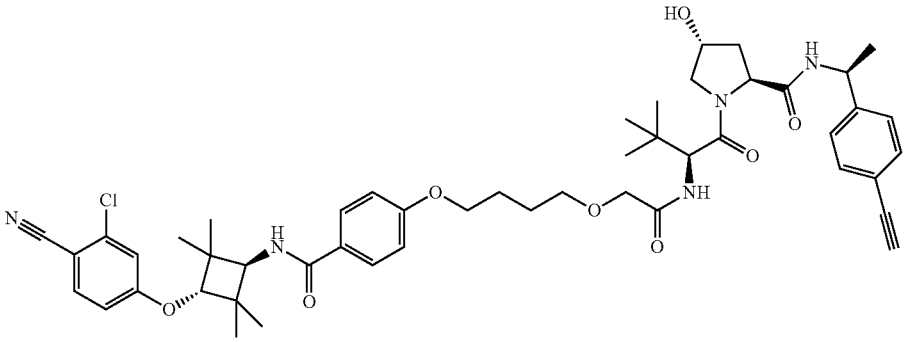 [SMILES: C#Cc1ccc([C@H](C)NC(=O)[C@@H]2C[C@@H](O)CN2C(=O)[C@@H](NC(=O)COCCCCOc2ccc(C(=O)N[C@H]3C(C)(C)[C@H](Oc4ccc(C#N)c(Cl)c4)C3(C)C)cc2)C(C)(C)C)cc1] | 883.39 | 885.39 |
| 558 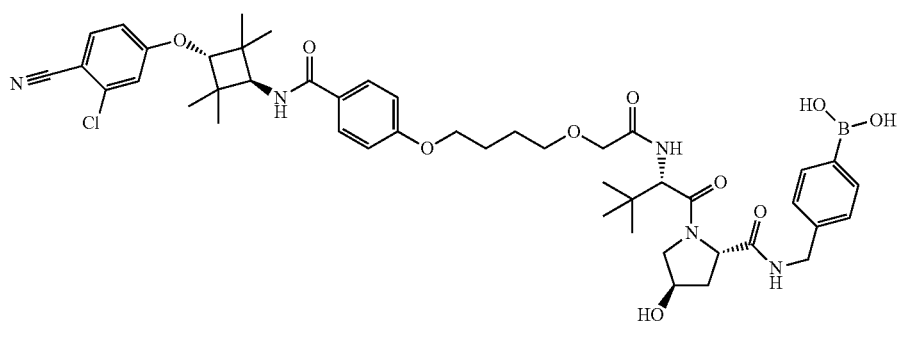 [SMILES: CC(C)(C)[C@H](NC(=O)COCCCCOc1ccc(C(=O)N[C@H]2C(C)(C)[C@H](Oc3ccc(C#N)c(Cl)c3)C2(C)C)cc1)C(=O)N1C[C@H](O)C[C@H]1C(=O)NCc1ccc(B(O)O)cc1] | 888.38 | 890.38 |

TABLE 17-continued

Additional Exemplary Compounds.

| | Structure | Measured Mass Ion Data | |
|---|---|---|---|
| | | MH+ 1 | MH+ 2 |
| 559 | 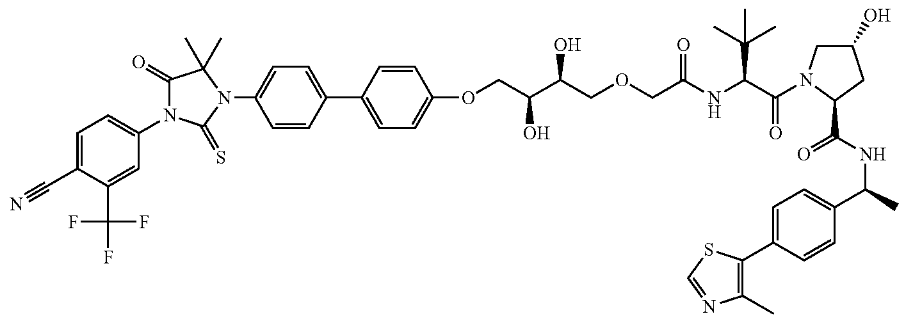 [SMILES: Cc1ncsc1-c1ccc([C@H](C)NC(=O)[C@@H]2C[C@@H](O)CN2C(=O)[C@@H](NC(=O)COC[C@H](O)[C@@H](O)COc2ccc(-c3ccc(N4C(=S)N(c5ccc(C#N)c(C(F)(F)F)c5)C(=O)C4(C)C)cc3)cc2)C(C)(C)C)cc1] | 1070.15 | |
| 560 | 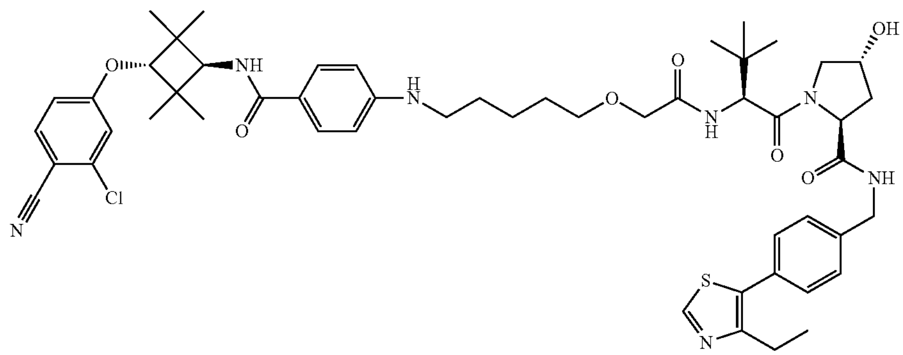 [SMILES: CCc1ncsc1-c1ccc(CNC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cc2)C(C)(C)C)cc1] | 968.41 | 970.41 |
| 561 | 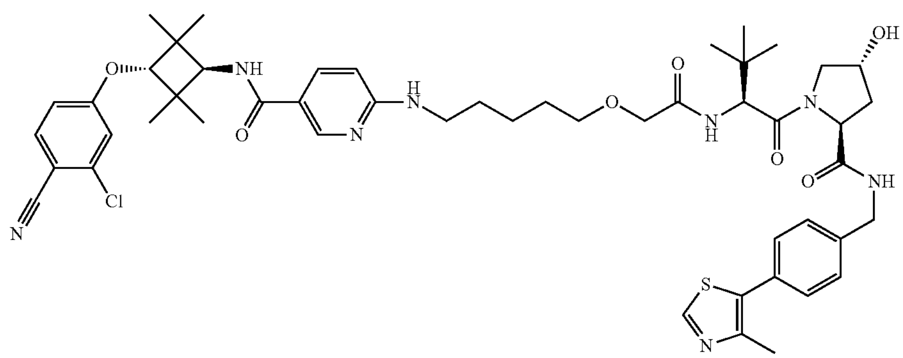 [SMILES: Cc1ncsc1-c1ccc(CNC(=O)[C@@H]2C[C@@H](O)CN2C(=O)[C@@H](NC(=O)COCCCCCNc2ccc(C(=O)N[C@H]3C(C)(C)[C@H](Oc4ccc(C#N)c(Cl)c4)C3(C)C)cn2)C(C)(C)C)cc1] | 955.40 | 957.40 |
| 562 | 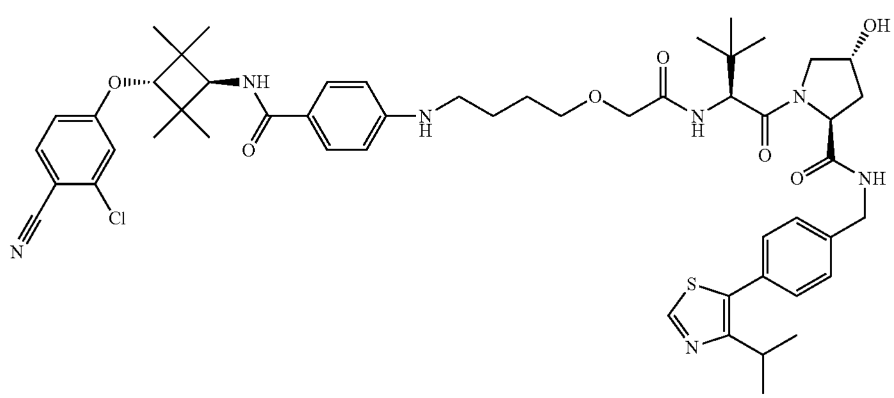 [SMILES: CC(C)c1ncsc1-c1ccc(CNC(=O)[C@@H]2C[C@@H](O)CN2C(=O)[C@@H](NC(=O)COCCCCNc2ccc(C(=O)N[C@H]3C(C)(C)[C@H](Oc4ccc(C#N)c(Cl)c4)C3(C)C)cc2)C(C)(C)C)cc1] | 968.41 | 970.41 |

TABLE 17-continued

Additional Exemplary Compounds.

| | Structure | Measured Mass Ion Data | |
|---|---|---|---|
| | | MH+ 1 | MH+ 2 |
| 563 | 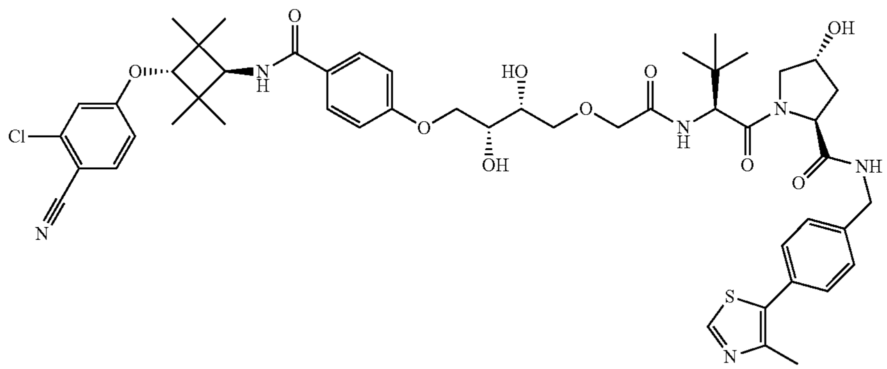 [SMILES: Cc1ncsc1-c1ccc(CNC(=O)[C@@H]2C[C@@H](O)CN2C(=O)[C@@H](NC(=O)COC[C@@H](O)[C@H](O)COc2ccc(C(=O)N[C@H]3C(C)(C)[C@H](Oc4ccc(C#N)c(Cl)c4)C3(C)C)cc2)C(C)(C)C)cc1] | 973.36 | 975.36 |
| 564 | 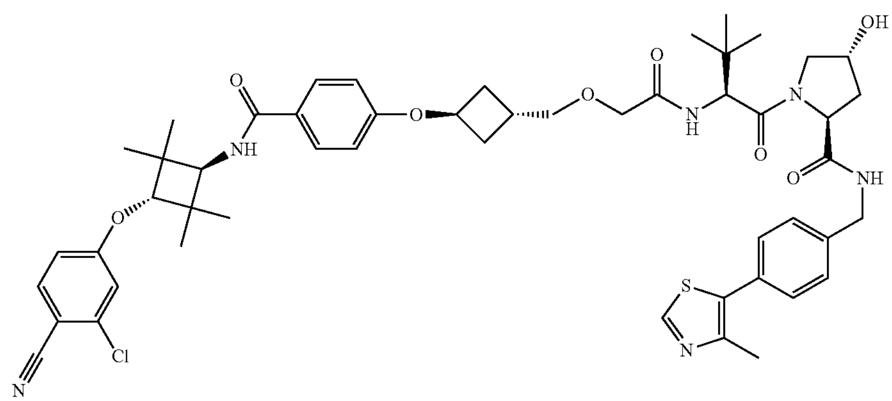 [SMILES: Cc1ncsc1-c1ccc(CNC(=O)[C@@H]2C[C@@H](O)CN2C(=O)[C@@H](NC(=O)COC[C@H]2C[C@H](Oc3ccc(C(=O)N[C@H]4C(C)(C)[C@H](Oc5ccc(C#N)c(Cl)c5)C4(C)C)cc3)C2)C(C)(C)C)cc1] | 953.37 | 955.37 |
| 565 | 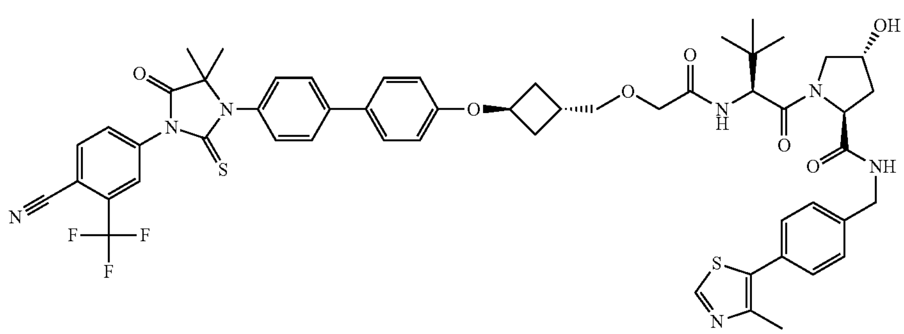 [SMILES: Cc1ncsc1-c1ccc(CNC(=O)[C@@H]2C[C@@H](O)CN2C(=O)[C@@H](NC(=O)COC[C@H]2C[C@H](Oc3ccc(-c4ccc(N5C(=S)N(c6ccc(C#N)c(C(F)(F)F)c6)C(=O)C5(C)C)cc4)cc3)C2)C(C)(C)C)cc1] | 1036.20 | |
| 566 | 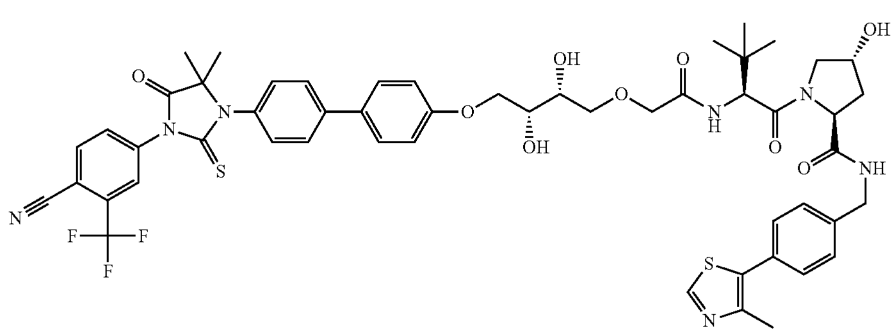 [SMILES: Cc1ncsc1-c1ccc(CNC(=O)[C@@H]2C[C@@H](O)CN2C(=O)[C@@H](NC(=O)COC[C@@H](O)[C@H](O)COc2ccc(-c3ccc(N4C(=S)N(c5ccc(C#N)c(C(F)(F)F)c5)C(=O)C4(C)C)cc3)cc2)C(C)(C)C)cc1] | 1056.15 | |

TABLE 17-continued

Additional Exemplary Compounds.

| Structure | Measured Mass Ion Data | |
|---|---|---|
| | MH+ 1 | MH+ 2 |
| 567 | 1056.15 | |
| 568 | 910.40 | 912.40 |
| 569 | 926.39 | 928.39 |
| 570 | 942.36 | 944.36 |

TABLE 17-continued

Additional Exemplary Compounds.

| Structure | Measured Mass Ion Data | |
|---|---|---|
| | MH+ 1 | MH+ 2 |
| 571 | 953.33 | |
| 572 | 892.35 | 894.35 |
| 573 | 926.34 | 928.34 |
| 574 | 1070.15 | |

TABLE 17-continued

Additional Exemplary Compounds.

| | | Measured Mass Ion Data | |
|---|---|---|---|
| | Structure | MH+ 1 | MH+ 2 |
| 575 | | 1054.00 | |
| 576 | | 1054.20 | |
| 577 | | 973.63 | 975.36 |
| 578 | | | |

TABLE 17-continued
Additional Exemplary Compounds.
| Structure | Measured Mass Ion Data |||
|---|---|---|
| | MH+ 1 | MH+ 2 |
| 579 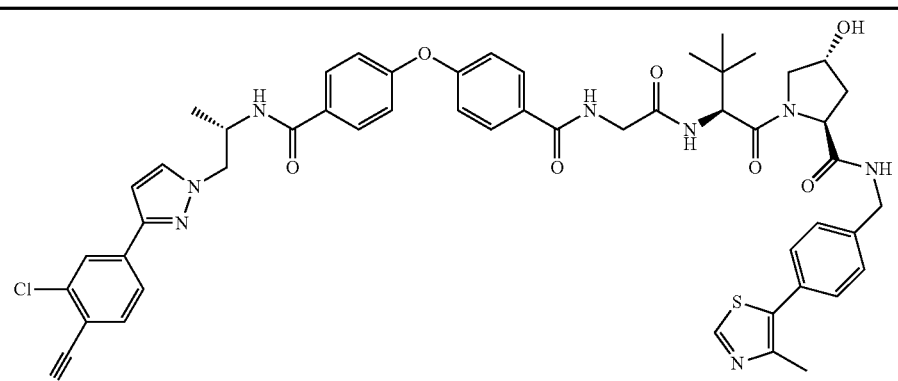 | | |
| 580 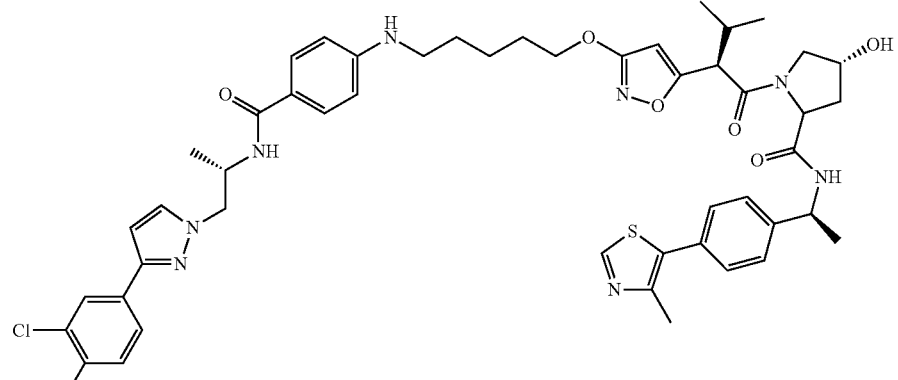 | | |
| 581 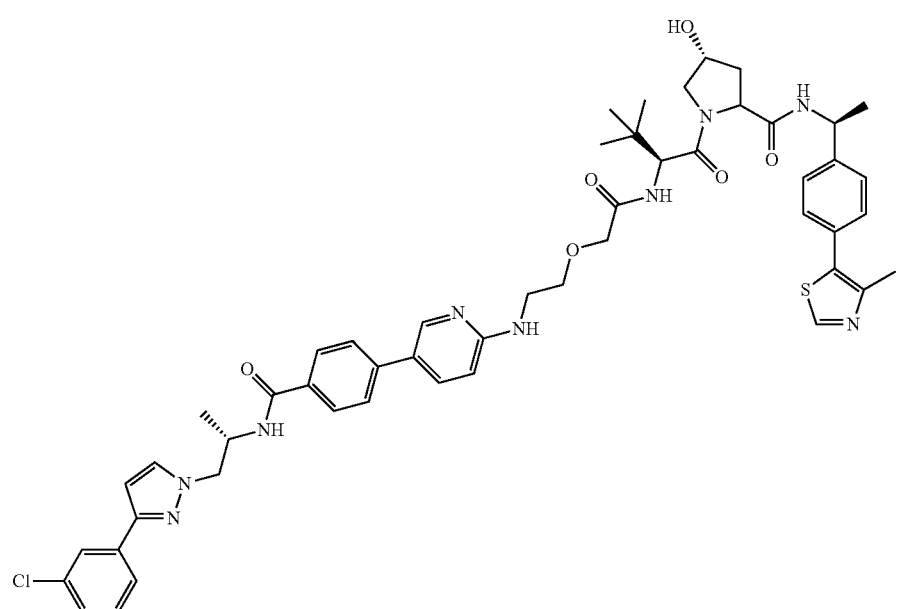 | | |

TABLE 17-continued

Additional Exemplary Compounds.

| Structure | Measured Mass Ion Data | |
|---|---|---|
| | MH+ 1 | MH+ 2 |

582

583

584

TABLE 17-continued

Additional Exemplary Compounds.

| Structure | Measured Mass Ion Data | |
|---|---|---|
| | MH+ 1 | MH+ 2 |

585

586

587

TABLE 17-continued

Additional Exemplary Compounds.

| Structure | Measured Mass Ion Data | |
|---|---|---|
| | MH+ 1 | MH+ 2 |

588

589

590

TABLE 17-continued

Additional Exemplary Compounds.

| | Structure | Measured Mass Ion Data MH+ 1 | MH+ 2 |
|---|---|---|---|
| 591 | 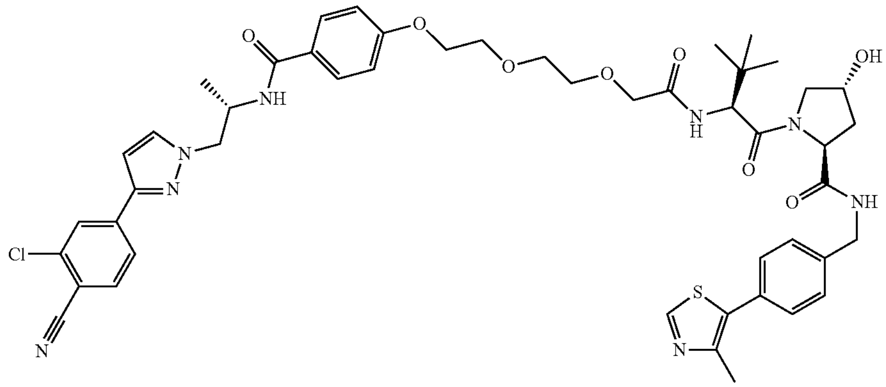 [SMILES: Cc1ncsc1-c1ccc(CNC(=O)[C@@H]2C[C@@H](O)CN2C(=O)[C@@H](NC(=O)COCCOCCOc2ccc(C(=O)N[C@@H](C)Cn3ccc(-c4ccc(C#N)c(Cl)c4)n3)cc2)C(C)(C)C)cc1] | | |
| 592 | 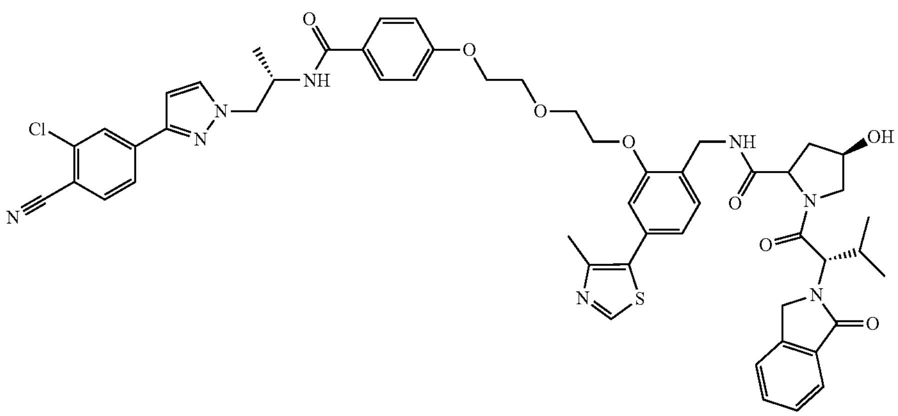 [SMILES: Cc1ncsc1-c1ccc(CNC(=O)C2C[C@@H](O)CN2C(=O)[C@H](C(C)C)N2Cc3ccccc3C2=O)c(OCCOCCOc2ccc(C(=O)N[C@@H](C)Cn3ccc(-c4ccc(C#N)c(Cl)c4)n3)cc2)c1] | | |
| 593 | 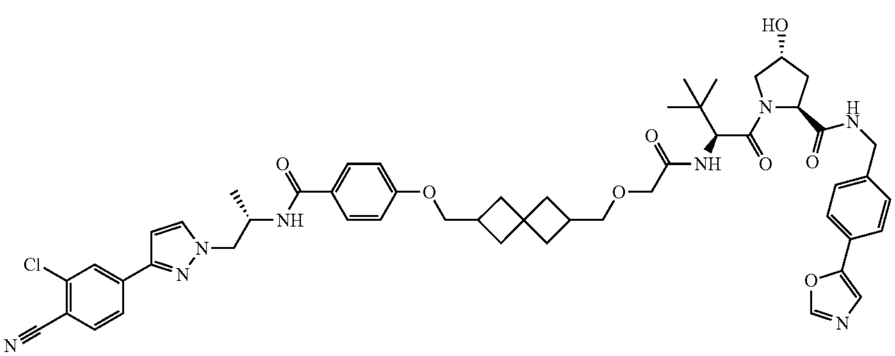 [SMILES: C[C@@H](Cn1ccc(-c2ccc(C#N)c(Cl)c2)n1)NC(=O)c1ccc(OCC2CC3(CC(COCC(=O)N[C@H](C(=O)N4C[C@H](O)C[C@H]4C(=O)NCc4ccc(-c5cnco5)cc4)C(C)(C)C)C3)C2)cc1] | | |

In certain embodiments, the description provides a compound having a structure selected from the group consisting of Examples 1-593 (see Tables 2-17), a salt, a polymorph, and prodrug thereof. In certain additional embodiments, the description provides a composition comprising at least one of the compounds of Examples 1-593, including a salt, polymorph, and prodrug thereof. In still additional embodiments, the description provides a therapeutic composition comprising at least one of the compounds of Examples 1-593, including a salt, a polymorph, and a prodrug thereof, and a pharmaceutically acceptable carrier.

EXAMPLES

In Vitro and In Vivo Assays

The experimental results presented below are made with reference to the Tables and FIGS. 1-7.

1. Androgen Receptor ELISA Assay.

Compounds have been evaluated in this assay in LNCaP and/or VCaP cells utilizing similar protocols. The protocols used with VCaP cells are described below. The androgen receptor ELISA assay was performed using PathScan AR ELISA (Cell Signaling Catalog #12850) according to the following assay steps:

VCaP cells are seeded at 30,000 cells/well at a volume of 200 µL/well in VCaP assay medium [Phenol red free RPMI (Gibco Cat #11835-030); 5% Charcoal Stripped (Dextran treated) FBS (Omega Scientific, Cat #FB-04); Pen/Strep Life Technologies (Gibco Cat #: 10378-016); 0.1 nM R1881 (Sigma, Cat #R0908) is added upon the start of the assay, not during initial plating of the cells) in Corning 3904 plates. The cells are grown for a minimum of 3 days.

First, cells are dosed with compounds diluted in 0.1% DMSO—use a polypropylene plate according to the following protocol: (1)(i) make 1000× stock plate in DMSO; (ii) 20 mM stock diluted 1/6.7 with DMSO (5 µL+28.3 µL DMSO) =3 mM into row H; (iii) perform serial dilutions in ½ log doses (10 µL of PROTAC+20 µL DMSO) from row H towards row B. Reserve row A for DMSO; (iv) 7 doses total (final concentration in this 1000× plate will be 3 mM, 1 mM, 333 µM, 111 µM, etc). (2)(i) Make 10× stock plate in media; (ii) transfer 2.5 µL of the 1000× stock to a new 10× stock plate (use 12 channel pipet, start at A (DMSO control) work thru H. When 247.5 µL of media is added to this plate, it will serve as a 10× stock; (iii) make media+1 nM R1881 for making 10× stock plate; (iv) add 247.5 µL of media with 1 nM R1881 to each well of the 10× stock plate, mix.

Then 22 µL of 10× stock is added to cells and incubated for 24 h. 1× Cell Signaling Cell lysis buffer is made (Catalogue #9803; comes with the kit)—prepare for 50 µL/well. Keep on ice. Media is aspirated, and 50 µL 1× cell lysis buffer/well is added. The cells are placed on ice for 10 minutes. The solution is mixed and transferred to PCR plate, and centrifuged at 4 C for 10 minutes at 4000 rpm.

5 µL is transferred to fresh plate (use immediately or freeze −80 C); 115 µL ELISA Dilutant is added (0.15 ug/ml-0.075 ug/ml; comes with the PathScan ELISA).

Add 100 µL/well AR Elisa; cover and shake, 37 C for 2 hrs; dump, tap, wash 4×200 µL ELISA wash buffer; add 100 µL/well mouse AR detection Ab; cover and shake, 37 C for 1 hr; dump, tap, wash 4×200 µL ELISA wash buffer; add 100 µL/well anti-mouse—HRP conjugated Ab (comes with the kit); cover and shake, 37 C for 30 min; allow TMB reagent to come to RT; dump, tap, wash 4×200 µL Elisa wash buffer; tap; add 100 µL TMB, shake 5 min—while watching color. Add the stop reagent when light blue color develops. Add 100 µL Stop solution; shake and read at 450 nM.

Progression of prostate cancer in patients treated with anti-androgen therapy usually involves one of several mechanisms of enhanced Androgen Receptor (AR) signaling, including increased intratumoral androgen synthesis, increased AR expression and AR mutations. PROTACs (PROteolysis TArgeting Chimera), which uses bi-functional molecules that simultaneously bind a target of choice and an E3 ligase, cause ubiquitination via induced proximity and degradation of the targeted, pathological protein. As opposed to traditional target inhibition, which is a competitive process, degradation is a progressive process. As such, it is less susceptible to increases in endogenous ligand, target expression, or mutations in the target. Thus this technology seems ideal for addressing the mechanisms of AR resistance in patients with prostate cancer.

AR PROTACs degrade AR in LNCaP and VCaP cells, with nM to pM potency, and had a >85% reduction in AR concentration ($D_{max}$). Degradation was rapid, with 50% of AR lost within 15 minutes and maximal degradation observed by 4 hours. The duration of AR knockdown was long-lasting, with no recovery of AR observed over several days. The degradation process in cells was specific, as PROTACs with an inactive epimer for E3 ligase binding did not degrade AR. AR PROTACs induced rapid apoptosis and cell death in VCaP cells. In LNCap and VCaP cell systems, AR PROTACs were anti-proliferative under conditions in which enzalutamide was inactive, such as increasing concentrations of the AR agonist R1881 and cells containing the $AR^{F876L}$ mutation. AR PROTACs typically had $t_{1/2}$ values of several hours and bioavailability of >50% after ip or sc injection. In mice, AR PROTACs have shown in vivo activity, including involution of seminal vesicles, reduction of AR protein levels in the prostate, and regression of VCaP tumors.

The following assay results were generated using the androgen receptor ELISA Assay described above, where compound potencies were characterized in highest percentage of Androgen Receptor degradation ($D_{max}$) observed and compound concentration that caused 50% Androgen Receptor degradation ($DC_{50}$).

TABLE 18

Androgen Receptor degradation ($D_{max}$) observed and compound concentration that caused 50% Androgen Receptor degradation ($DC_{50}$).

| Ex # | LNCaP Dmax (%) | LNCaP $DC_{50}$ (µM) | VCaP Dmax (%) | VCaP $DC_{50}$ (µM) |
|---|---|---|---|---|
| 1 | ++++ | A | | |
| 2 | ++++ | A | | |
| 3 | ++++ | A | | |
| 4 | ++++ | A | | |
| 5 | ++++ | B | | |
| 6 | ++++ | A | | |
| 7 | +++ | A | | |
| 8 | ++++ | A | | |
| 9 | ++++ | A | | |
| 10 | ++++ | A | | |
| 11 | ++++ | A | | |
| 12 | ++++ | B | | |
| 13 | | | ++ | |
| 14 | | | | C |
| 15 | | | ++ | |
| 16 | +++ | A | ++ | |
| 17 | ++ | | | |
| 18 | +++ | B | | |
| 19 | +++ | A | | |
| 20 | ++++ | B | | |
| 21 | ++ | | | |
| 22 | +++ | A | | |
| 23 | ++++ | B | | |
| 24 | ++++ | A | | |
| 25 | ++++ | A | | |
| 26 | | | +++ | A |
| 27 | ++++ | A | | |
| 28 | ++++ | A | | |
| 29 | +++ | B | | |
| 30 | ++++ | A | | |
| 31 | ++++ | A | | |
| 32 | ++++ | A | | |
| 33 | | | +++ | A |
| 34 | | | +++ | A |
| 35 | | | +++ | A |
| 36 | | | ++ | B |
| 37 | | | ++++ | A |
| 38 | | | +++ | A |
| 39 | | | ++ | A |
| 40 | | | +++ | A |
| 41 | | | ++++ | A |
| 42 | | | +++ | A |
| 43 | | | +++ | A |
| 44 | | | ++++ | A |
| 45 | | | ++++ | A |
| 46 | | | ++++ | A |
| 47 | | | +++ | A |
| 48 | | | ++++ | A |
| 49 | | | +++ | A |
| 50 | | | ++++ | A |
| 51 | | | ++ | A |
| 52 | ++++ | A | | |

TABLE 18-continued

Androgen Receptor degradation ($D_{max}$) observed and compound concentration that caused 50% Androgen Receptor degradation ($DC_{50}$).

| Ex # | $D_{max}$ | $DC_{50}$ |
|---|---|---|
| 53 | ++++ | A |
| 54 | ++++ | A |
| 55 | ++ | |
| 56 | ++ | |
| 57 | | |
| 58 | | |
| 59 | | |
| 60 | +++ | B |
| 61 | +++ | B |
| 62 | +++ | C |
| 63 | ++++ | B |
| 64 | +++ | B |
| 65 | +++ | B |
| 66 | +++ | B |
| 67 | 72.1 | A |
| 68 | ++ | B |
| 69 | ++++ | B |
| 70 | ++++ | A |
| 71 | ++++ | A |
| 72 | ++++ | B |
| 73 | ++++ | A |
| 74 | ++++ | A |
| 75 | ++++ | A |
| 76 | +++ | A |
| 77 | ++++ | A |
| 78 | ++++ | A |
| 79 | ++++ | A |
| 80 | +++ | C |
| 81 | +++ | C |
| 82 | +++ | B |
| 83 | +++ | B |
| 84 | +++ | B |
| 85 | +++ | C |

| Ex # | VCaP Dmax (%) | VCaP $DC_{50}$ (μM) |
|---|---|---|
| 86 | ++ | |
| 87 | ++ | |
| 88 | | |
| 89 | ++++ | A |
| 93 | | |
| 94 | ++++ | A |
| 95 | ++++ | A |
| 96 | +++ | A |
| 99 | +++ | A |
| 100 | ++++ | A |
| 101 | ++++ | A |
| 102 | ++++ | A |
| 103 | ++++ | A |
| 104 | ++++ | A |
| 105 | +++ | B |
| 106 | ++++ | A |
| 107 | ++++ | A |
| 108 | ++++ | A |
| 109 | ++++ | A |
| 110 | ++++ | A |
| 111 | ++++ | A |
| 112 | ++++ | B |
| 114 | +++ | A |
| 115 | ++++ | A |
| 116 | ++++ | A |
| 117 | ++++ | A |
| 118 | ++++ | A |
| 119 | +++ | A |
| 120 | ++++ | A |
| 121 | ++++ | A |
| 122 | ++++ | A |
| 123 | ++++ | A |
| 124 | +++ | A |
| 125 | ++++ | A |
| 126 | +++ | A |
| 127 | ++++ | A |
| 128 | +++ | A |
| 129 | +++ | A |
| 130 | +++ | A |
| 131 | +++ | A |
| 132 | ++++ | A |
| 133 | + | |
| 134 | ++++ | A |
| 135 | +++ | A |
| 136 | ++++ | A |
| 137 | ++++ | A |
| 138 | ++++ | A |
| 139 | ++++ | A |
| 140 | ++++ | A |
| 141 | ++++ | A |
| 142 | ++++ | A |
| 145 | ++++ | A |
| 147 | ++++ | A |
| 148 | ++++ | A |
| 150 | ++++ | A |
| 151 | ++++ | A |
| 152 | ++++ | A |
| 153 | ++++ | A |
| 154 | ++++ | A |
| 155 | ++++ | A |
| 156 | ++++ | A |
| 157 | ++++ | A |
| 158 | ++++ | A |
| 159 | ++++ | A |
| 162 | ++++ | A |
| 163 | ++++ | A |
| 164 | ++++ | A |
| 165 | ++++ | A |
| 166 | +++ | A |
| 172 | ++++ | A |
| 173 | ++++ | A |
| 174 | +++ | A |
| 175 | +++ | A |
| 180 | ++++ | A |
| 181 | ++++ | A |
| 182 | ++++ | A |
| 183 | ++++ | A |
| 184 | ++++ | A |
| 185 | ++++ | A |
| 186 | ++++ | A |
| 188 | ++++ | A |
| 189 | +++ | A |
| 418 | +++ | C |
| 419 | ++ | C |
| 420 | ++++ | A |
| 421 | ++++ | A |
| 422 | ++++ | A |
| 423 | + | C |
| 424 | + | C |
| 425 | ++++ | A |
| 426 | + | C |
| 427 | + | C |
| 428 | + | C |
| 429 | ++ | C |
| 430 | + | C |
| 431 | + | C |
| 432 | + | C |
| 433 | +++ | A |
| 434 | + | C |
| 435 | + | C |
| 436 | +++ | |
| 437 | + | C |
| 438 | ++++ | A |
| 439 | | |
| 440 | | |
| 441 | | |
| 442 | ++++ | A |
| 443 | | |
| 444 | ++++ | A |
| 445 | ++++ | A |
| 446 | ++ | C |
| 447 | ++++ | A |
| 448 | ++++ | A |
| 449 | ++++ | A |
| 450 | ++++ | A |

TABLE 18-continued

Androgen Receptor degradation ($D_{max}$) observed and compound concentration that caused 50% Androgen Receptor degradation ($DC_{50}$).

| | | |
|---|---|---|
| 451 | + | C |
| 452 | + | C |
| 453 | + | C |
| 454 | ++++ | A |
| 455 | ++ | C |
| 456 | +++ | C |
| 457 | ++++ | A |
| 458 | + | C |
| 459 | + | C |
| 460 | ++ | C |
| 461 | | |
| 462 | ++++ | A |
| 463 | | |
| 464 | | |
| 465 | ++++ | C |
| 466 | ++++ | A |
| 467 | ++++ | B |
| 468 | | |
| 469 | ++++ | A |
| 470 | ++++ | A |
| 471 | ++++ | A |
| 472 | ++ | C |
| 473 | ++++ | A |
| 474 | ++ | A |
| 475 | ++ | B |
| 476 | ++++ | A |
| 477 | ++++ | A |
| 478 | + | C |
| 479 | ++ | C |
| 480 | ++ | C |
| 481 | ++ | C |
| 482 | + | C |
| 483 | ++++ | A |
| 484 | ++++ | A |
| 485 | +++ | A |
| 486 | | |
| 487 | | |
| 488 | | |
| 489 | | |
| 490 | | |
| 491 | | |
| 492 | | |
| 493 | | |
| 494 | | |
| 495 | | |
| 496 | ++++ | A |
| 497 | +++ | A |
| 498 | +++ | A |
| 499 | ++++ | A |
| 500 | ++ | C |
| 501 | ++ | C |
| 502 | +++ | A |
| 503 | ++ | B |
| 504 | ++++ | A |
| 505 | +++ | A |
| 506 | ++ | C |
| 507 | +++ | A |
| 508 | ++ | C |
| 509 | ++++ | A |
| 510 | ++ | C |
| 511 | +++ | A |
| 512 | +++ | A |
| 513 | +++ | B |
| 514 | ++++ | A |
| 515 | ++ | C |
| 516 | ++++ | A |
| 517 | +++ | A |
| 518 | ++++ | A |
| 519 | + | C |
| 520 | ++ | C |
| 521 | ++ | C |
| 522 | +++ | A |
| 523 | +++ | A |
| 524 | +++ | A |
| 525 | +++ | A |
| 526 | ++++ | A |
| 527 | +++ | A |
| 528 | ++ | C |
| 529 | +++ | A |
| 530 | + | C |
| 531 | ++++ | A |
| 532 | ++ | C |
| 533 | +++ | A |
| 534 | ++ | C |
| 535 | +++ | A |
| 536 | ++ | C |
| 537 | ++ | C |
| 538 | ++ | C |
| 539 | +++ | A |
| 540 | ++ | C |
| 541 | ++++ | A |
| 542 | ++++ | A |
| 543 | ++++ | A |
| 544 | ++++ | A |
| 545 | ++++ | A |
| 546 | +++ | A |
| 547 | + | C |
| 548 | +++ | A |
| 549 | ++++ | A |
| 550 | ++++ | A |
| 551 | ++++ | A |
| 552 | +++ | A |
| 553 | +++ | A |
| 554 | ++++ | A |
| 555 | +++ | A |
| 556 | ++++ | A |
| 557 | ++++ | A |
| 558 | | |
| 559 | | |
| 560 | ++++ | A |
| 561 | | |
| 562 | | |
| 563 | | |
| 564 | +++ | A |
| 565 | ++++ | A |
| 566 | ++++ | A |
| 567 | +++ | A |
| 568 | ++++ | A |
| 569 | ++++ | A |
| 570 | ++++ | A |
| 571 | ++++ | A |
| 572 | ++++ | A |
| 573 | ++++ | A |
| 574 | ++++ | A |
| 575 | ++++ | A |
| 576 | ++++ | A |
| 577 | ++++ | A |
| 578 | ++++ | A |

$D_{max}$: + ($D_{max} \leq 25\%$); ++ ($26\% \leq D_{max} \leq 50\%$); +++ ($51\% \leq D_{max} \leq 70\%$); ++++ ($71\% \leq D_{max}$); $DC_{50}$: A ($D_{max} \leq 50$ nM); B ($51$ nM $\leq DC_{50} \leq 500$ nM); C ($501$ nM $\leq DC_{50}$).

2. VCaP Cell Proliferation Assay.

VCaP cells are plated 7,500/well 200 µL/well in VCaP assay medium [Phenol red free RPMI (Gibco Cat #11835-030); 5% Charcoal Stripped (Dextran treated) FBS (Omega Scientific, Cat #FB-04); Pen/Strep Life Technologies (Gibco Cat #: 10378-016); 0.1 nM R1881 (Sigma, Cat #R0908) is added upon the start of the assay, not during initial plating of the cells).

The assay was performed as follows: the cells are grown for a minimum of 3 days to deplete androgens; dosing of PROTACs and R1881 is performed as for AR ELISA; the baseline reading of Cell Titer Glo can be performed on day of dosing.

VCaP cells with 0.1 nM R1881 will double once in 4 days. Gently draw off 110 µL of media so as not to disturb the adherent cells; add 110 µL of CTG; incubate with slow shaking for 20 minutes; and read luminescence on a plate reader.

VCaP Anti-Proliferation Data:

GI$_{50}$ definition: A (GI$_{50}$≤50 nM); B (51 nM≤GI$_{50}$≤250 nM); C (251 nM≤GI$_{50}$)

TABLE 19

Inhibition of VCaP Proliferation.

| Ex # | GI$_{50}$ |
| --- | --- |
| 75 | B |
| 131 | B |
| 134 | B |
| 150 | A |
| 156 | A |
| 157 | A |
| 163 | A |
| 169 | B |
| 170 | A |
| 172 | A |
| 174 | A |
| 182 | A |
| 183 | A |
| 194 | B |
| 195 | B |
| 197 | B |
| 201 | B |
| 202 | B |
| 204 | A |

Mass Data

| Ex # | Observed Mass 1: MH+ | Observed Mass 2: MH+ | GI$_{50}$ |
| --- | --- | --- | --- |
| ABM-26 | 279.11 | 281.11 | B |
| ABM-27 | 279.30 | 281.30 | C |
| ABM-28 | 400.14 | 402.14 | |
| ABM-29 | 379.17 | 381.16 | B |
| ABM-30 | 398.13 | 400.12 | A |
| ABM-31 | 400.14 | 402.14 | B |
| ABM-32 | 400.14 | 402.14 | |
| ABM-33 | 413.20 | 415.20 | B |
| ABM-34 | 417.16 | 419.16 | C |
| ABM-35 | 399.15 | 401.15 | |
| ABM-36 | 484.16 | 486.16 | A |
| ABM-37 | 598.29 | 600.29 | A |

These results support that both the difunctional compounds (ABM-L-ULM) and androgen receptor binding moieties (ABM-e) inhibit VCaP Proliferation.

3. Apoptosis in VCaP Cells.

Figure 2:
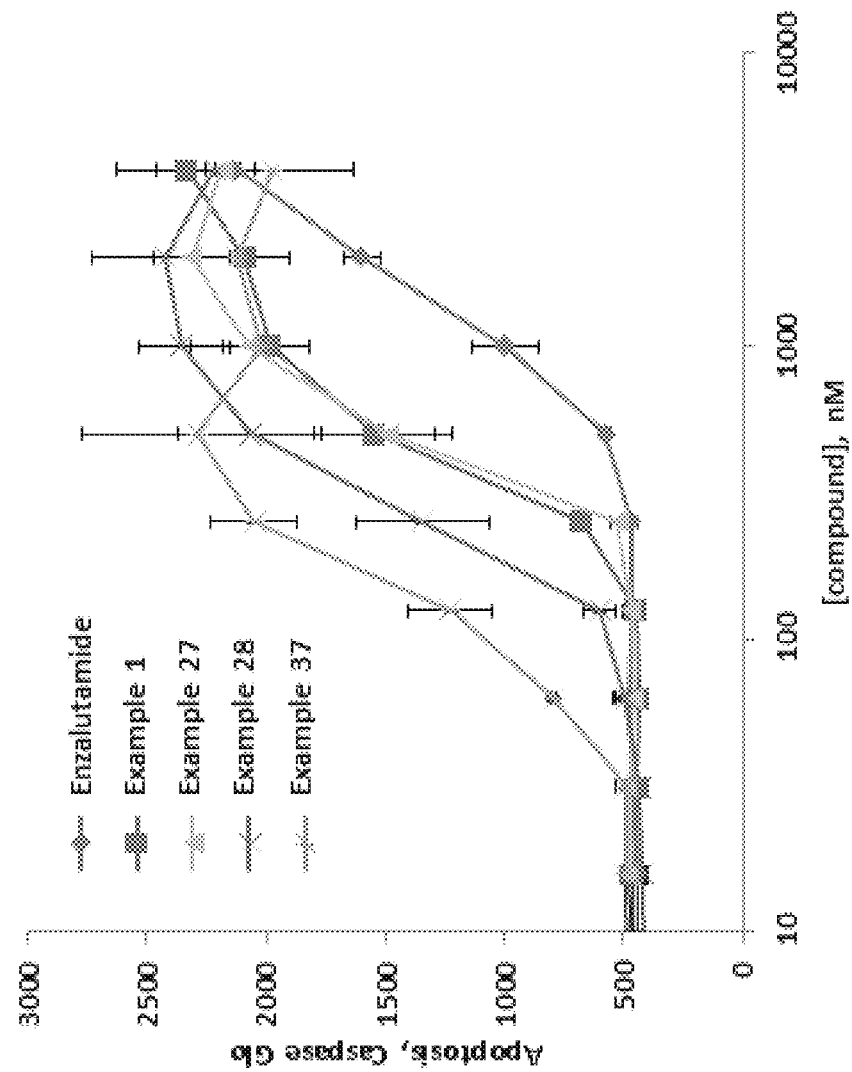
FIG. 2. Apoptosis in VCaP cells. VCaP cells were cultured in Charcoal Stripped Serum containing media supplemented with 0.1 nM R1881 for 48 hrs. The degree of apoptosis was ascertained with CaspaseGlo assay (Promega). These results demonstrated that PROTACs are much more potent in inducing apoptosis than an AR antagonist enzalutamide. Further, the degree of AR degradation correlates with their ability to induce apoptosis in VCaP cells.

FIG. 2 illustrates that compounds as described herein induce apoptosis in VCaP cells. VCaP cells were cultured in Charcoal Stripped Serum containing media supplemented with 0.1 nM R1881 for 48 hrs. The degree of apoptosis was ascertained with CaspaseGlo assay (Promega). These results demonstrated that PROTACs are much more potent in inducing apoptosis than an AR antagonist enzalutamide. Further, the degree of AR degradation correlates with their ability to induce apoptosis in VCaP cells.

4. Anti-Proliferation in LNCaP F876L.

Figure 3:
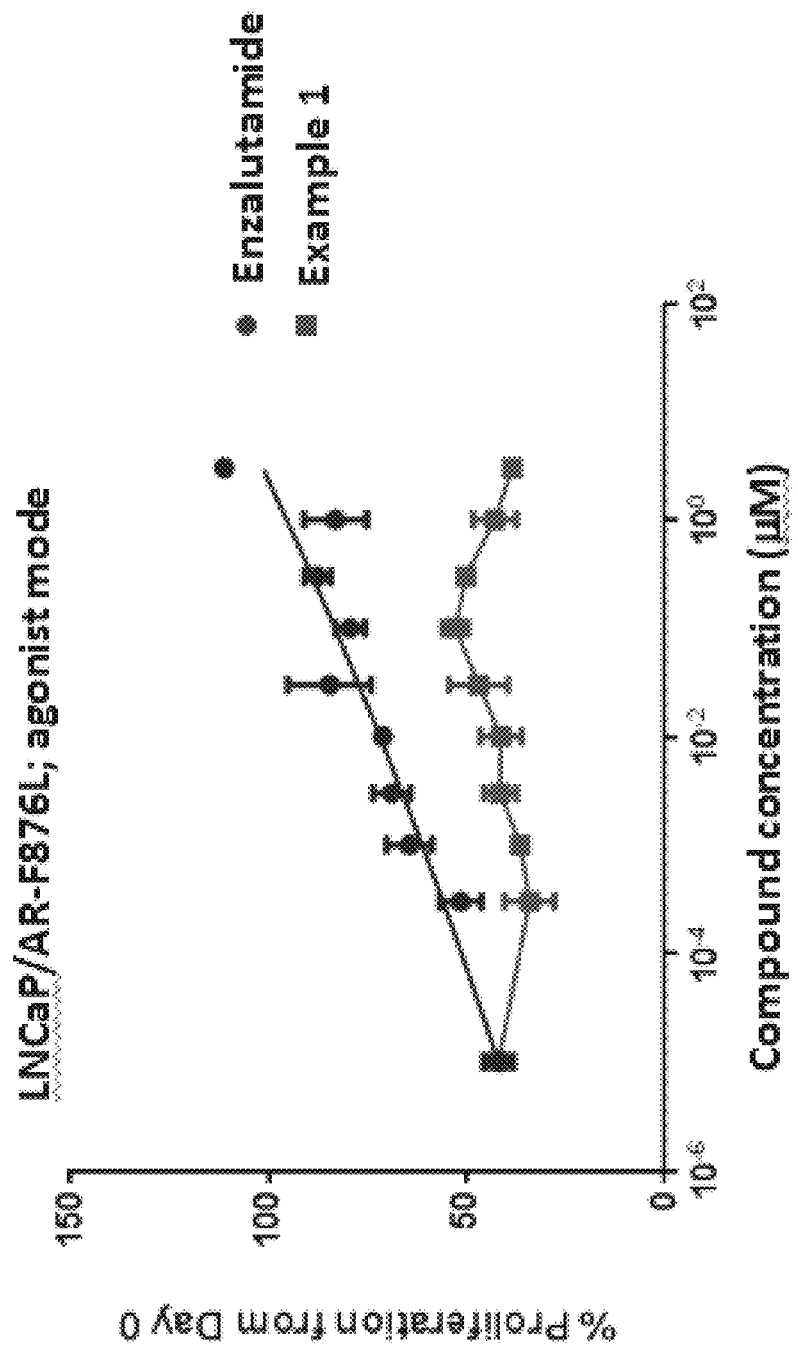
FIG. 3. Anti-proliferation in LNCaP F876L. Anti-proliferation in LNCaP F876L cells observed with treatment with Example 1 as compared to enzalutamide. LNCaP cells transduced with AR F876L construct were cultured in Charcoal Stripped Serum containing media.

FIG. 3 demonstrates the anti-proliferation in LNCaP F876L cells observed with treatment with a compounds as described herein. LNCaP cells transduced with AR F876L construct were cultured in Charcoal Stripped Serum containing media. Indicated doses of enzalutamide or Example 1 were added for 7 days. CellTiterGlo reagent (Promega) was employed to assess proliferation. As shown, LNCaP cells expressing F876L construct proliferate in response to increasing doses of enzalutamide, whereas Example 1 did not exhibit agonist activity. These results demonstrated that AR PROTACs do not possess agonist activity.

5. PSA Suppression in LNCaP F876L

Figure 4:
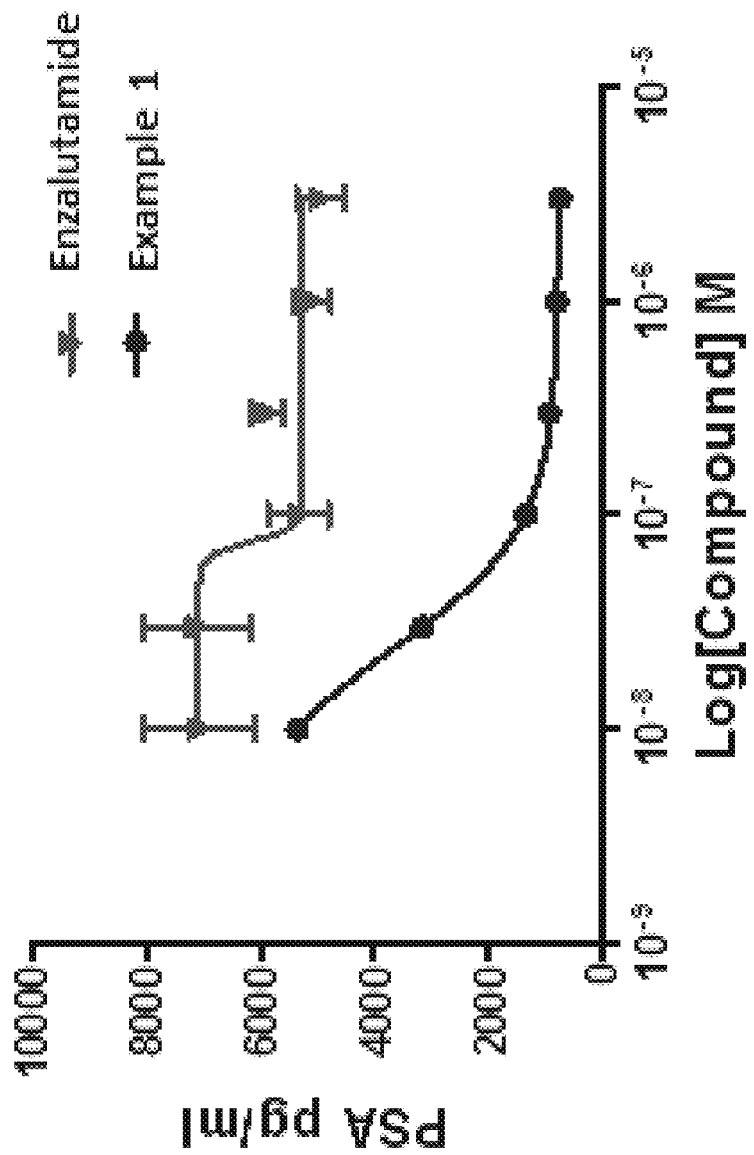
FIG. 4. PSA suppression in LNCaP F876L. LNCaP cells transduced with AR F876L construct were cultured in Charcoal Stripped Serum containing media supplemented with 0.1 nM R1881 for 7 days. The results demonstrated that AR PROTAC is able to suppress the transcriptional activity of AR in F876L containing cells.

Compounds as described herein also suppress PSA in LNCaP F876L cells (See FIG. 4). LNCaP cells transduced with AR F876L construct were cultured in Charcoal Stripped Serum containing media supplemented with 0.1 nM R1881 for 7 days. Secreted PSA in the media was detected by PSA ELISA (Sigma). These results demonstrated that AR PROTAC is able to suppress the transcriptional activity of AR in F876L containing cells.

6. Prostate Involution in C57B6 Mouse Model.

Figure 5:
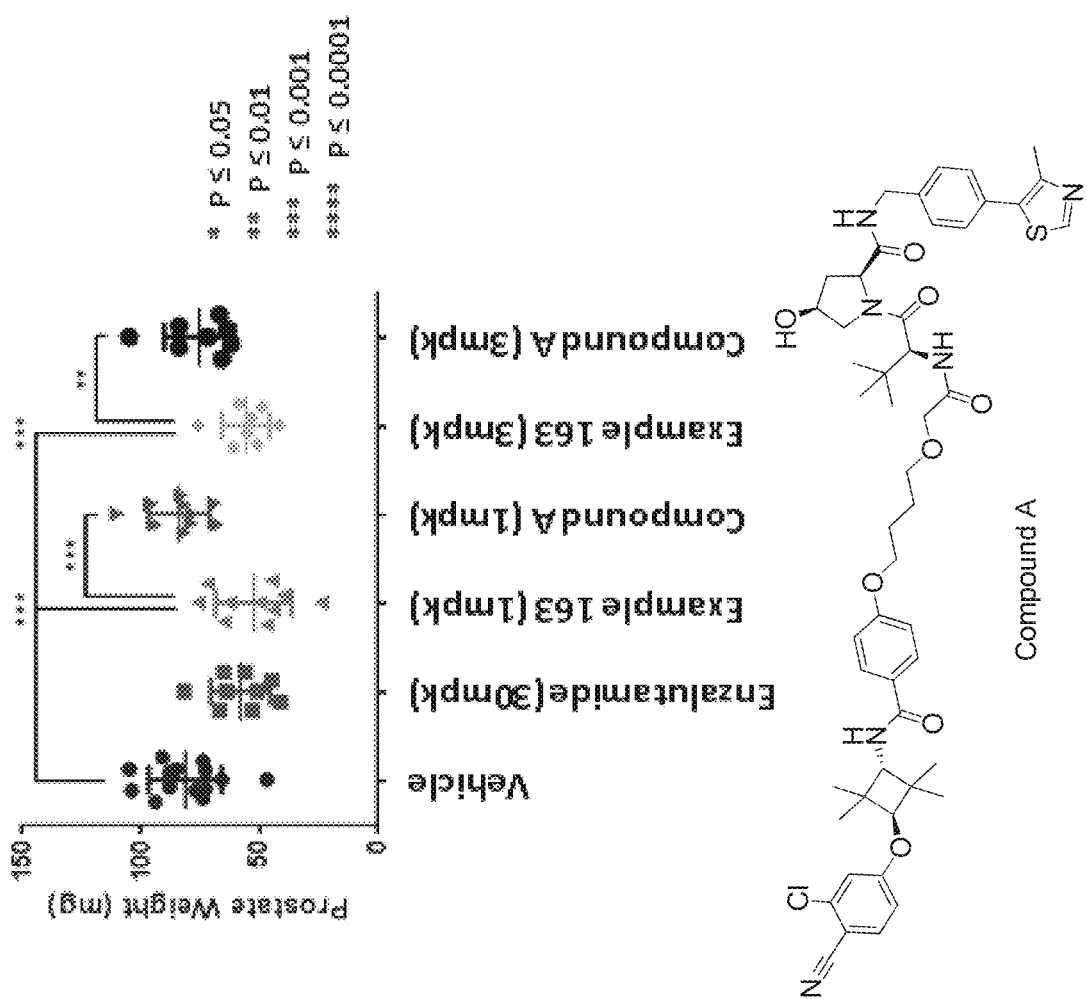
FIG. 5. Prostate involution in C57B6 mouse model. 12-week old male C57BL/6 mice were treated with AR PROTAC Example 163 and its inactive epimer analog Compound A which is unable to bind to VHL E3 ligase. Enzalutamide (PO, QD, 30 mpk), Example 163 (IP, QD, 1 and 3 mpk) and Compound A (IP, QD, 1 and 3 mpk) were administered for 10 days, upon which the prostates were isolated and weighed. These results demonstrated that the ability of PROTAC Example 163 to degrade AR leads to significant prostate involution in mice at very low doses.

FIG. 5 demonstrates that compounds as described herein induce prostate involution in C57B6 mouse model. 12-week old male C57BL/6 mice were treated with AR PROTAC Example 163 and its inactive epimer analog Compound A which is unable to bind to VHL E3 ligase. Enzalutamide (PO, QD, 30 mpk), Example 163 (IP, QD, 1 and 3 mpk) and Compound A (IP, QD, 1 and 3 mpk) were administered for 10 days, upon which the prostates were isolated and weighed. PROTAC Example 163 demonstrated a significant reduction in prostate weights, whereas Compound A showed no significant activity. These results demonstrated that the ability of PROTAC Example 163 to degrade AR leads to significant prostate involution in mice at very low doses.

7. Tumor Growth Inhibition in VCaP Xenograft Model.

Figure 6:
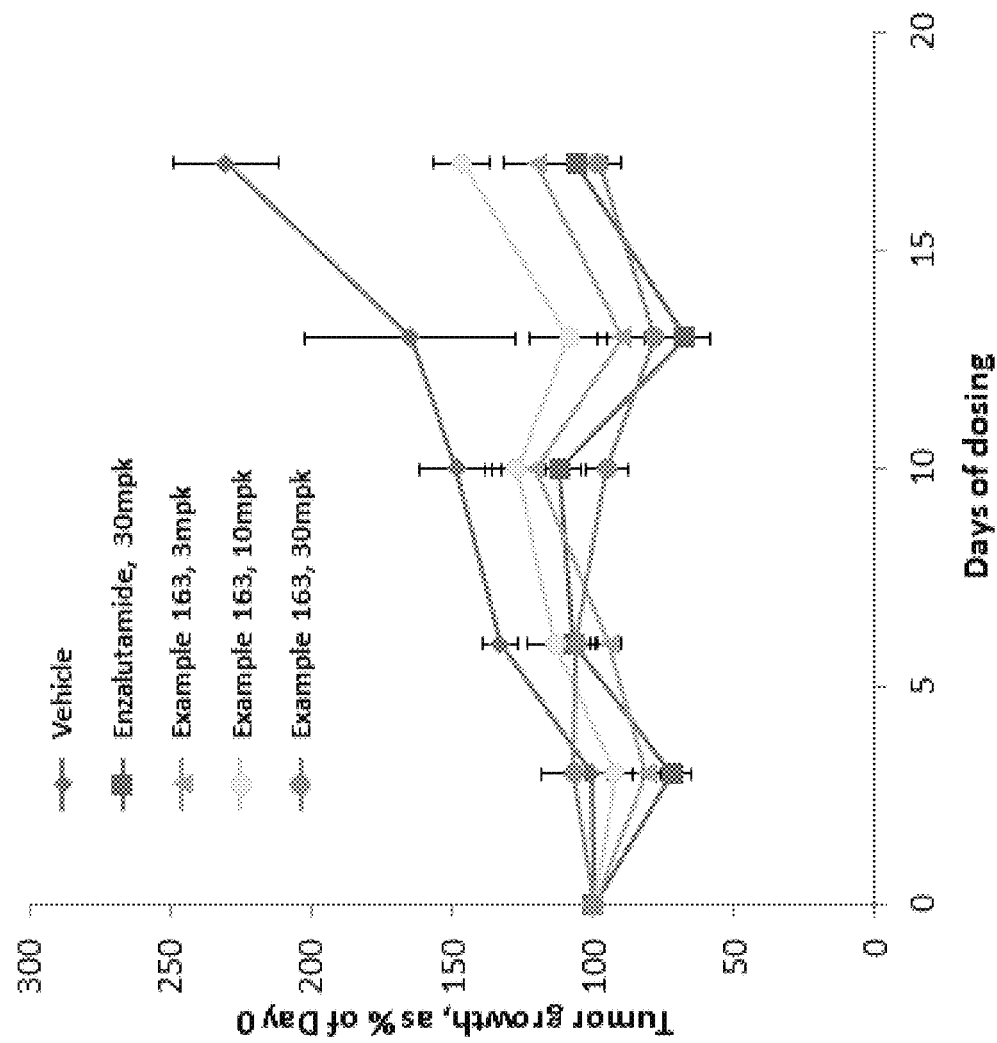
FIG. 6. Tumor growth inhibition in VCaP xenograft model. VCaP cells were implanted into CB17 scid mice subcutaneously. Once the tumors were palpable, the mice were castrated, leading to temporary tumor stasis. Upon regrowth of tumors, the mice were dosed with enzalutamide (PO, QD, 30 mpk) or AR PROTAC Example 163 (IP, QD, at 30, 10 and 3 mpk) as indicated. Tumor growth inhibition was observed in all treatment arms.

FIG. 6 illustrates tumor growth inhibition in a VCaP xenograft model, which was achieved with compounds as described herein. VCaP cells were implanted into CB17 scid mice subcutaneously. Once the tumors were palpable, the mice were castrated, leading to temporary tumor stasis. Upon regrowth of tumors, the mice were dosed with enzalutamide (PO, QD, 30 mpk) or AR PROTAC Example 163 (IP, QD, at 30, 10 and 3 mpk) as indicated. Tumor growth inhibition was observed in all treatment arms.

8. AR Degradation of PROTAC is E3 Ligase Dependent.

Figure 7A:
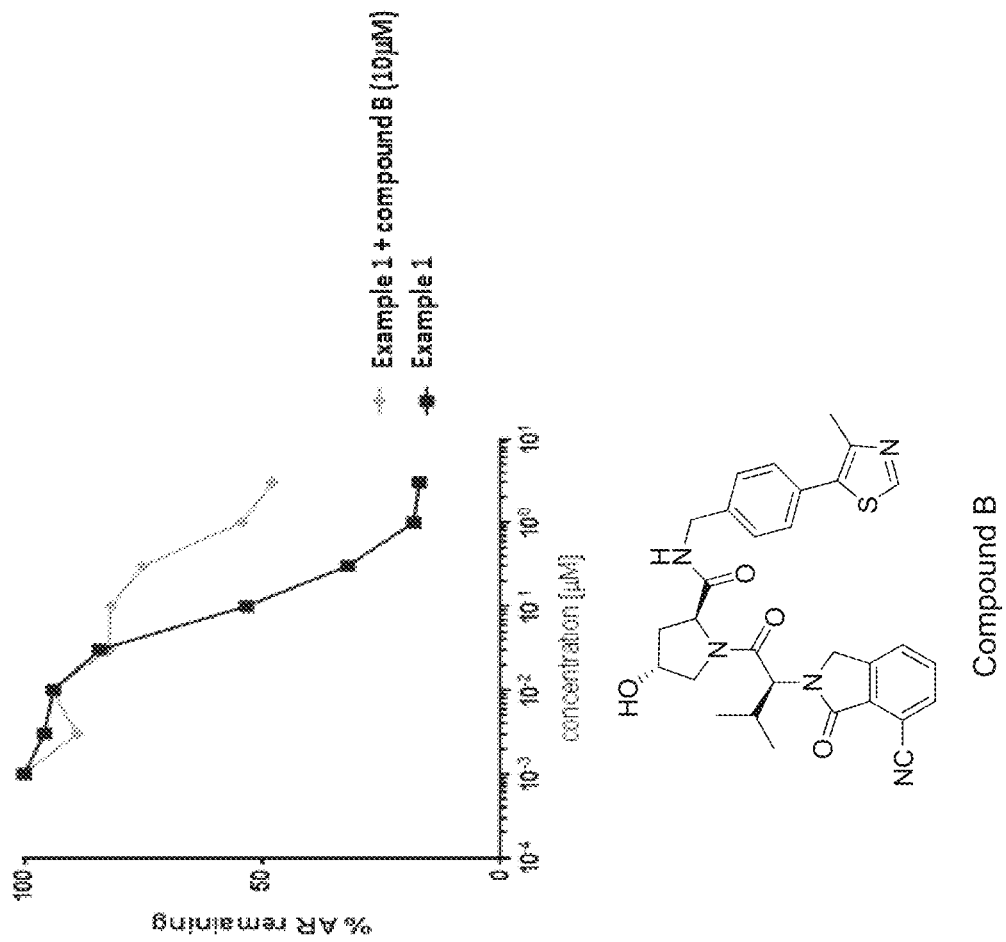
FIG. 7A and FIG. 7B. AR degradation of PROTAC is E3 ligase dependent.
Figure 7B:
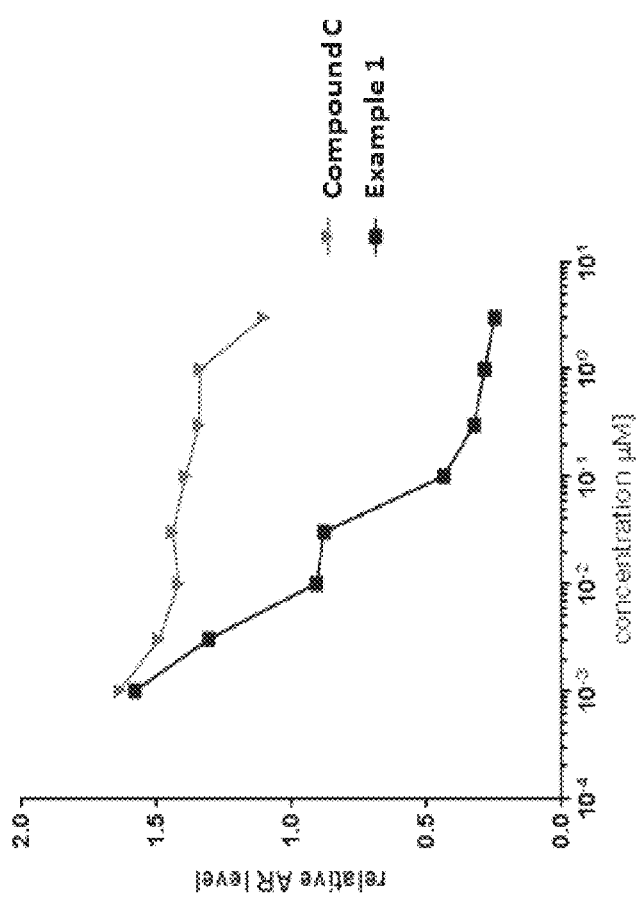
Figure 7B:
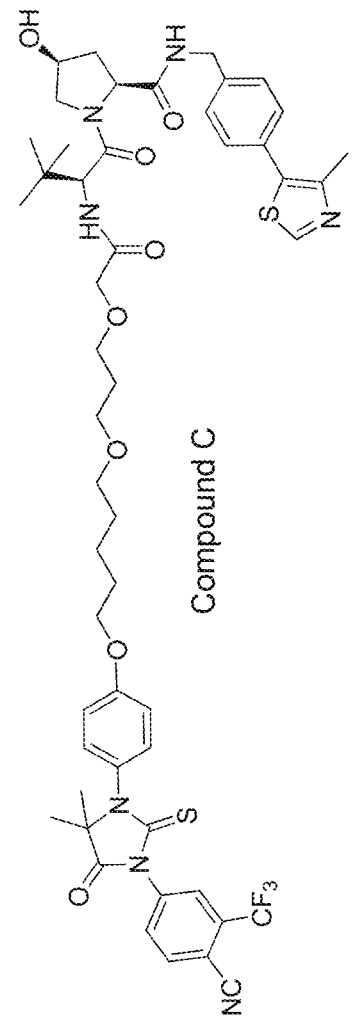

FIG. 7A and FIG. 7B demonstrates that AR degration achieved with compounds as described herein is E3 ligase dependent. For example, in FIG. 7A, AR PROTAC Example 1 was added to LNCaP cells at indicated concentrations for 24 hours in the presence or absence of 10 uM VHL E3 ligase ligand compound B. The presence of compound B competes with AR PROTAC Example 1 in VHL E3 ligase binding and greatly diminishes the AR degradation activity of AR PROTAC Example 1. In FIG. 7B, LNCaP cells were treated with AR PROTAC Example 1 and its inactive epimer analog compound C which is unable to bind to VHL E3 ligase. While AR PROTAC Example 1 led to significant degradation of AR, compound C did not. These results demonstrated that AR PROTAC activity in AR degradation is VHL E3 ligase dependent."

9. PROTAC Prodrug Oral Pharmacokinetics and PROTAC Subcutaneous Pharmacokinetics.

Representative Pharmacokinetic Procedure

Male CD-1 mice (6-8 weeks old, weighing 20-30 g, 3 per study) with free access to food and water were administered with the test article at 10 mg/kg either by oral gavage or sub-cutaneous injection in the formulation specified in tables 20 and 21, at 10 mL/kg.

Approximately 0.04 mL blood samples were collected from the dorsal metatarsal vein serially at 0.25, 0.5, 1, 2, 4, 8 and 24 h timepoints; heparin was used as the anticoagulant. The samples were centrifuged at 4000 g for 5 min at 4° C. then stored at −75° C. prior to analysis.

The plasma samples were analysed via an LC/MS/MS method quantitating for unchanged, administered test article, and/or a derivative species as appropriate. WinNonlin (Phoenix™) was used for the pharmacokinetic calculations and modeling, to generate parameters such as C$_{max}$ and AUC.

TABLE 20

Examples of PROTAC prodrug pharmacokinetics (ESP-4: 5% EtOH, 5% solutol HS15 in PBS; ESD-4 5% EtOH, 15% solutol in D5W).

| | | | Plasma Exposure | | | |
|---|---|---|---|---|---|---|
| | | | Prodrug | | Derivative | |
| Ex # | Dose/Route | Vehicle | $C_{max}$ (ng/mL) | AUC (ng · h/mL) | $C_{max}$ (ng/mL) | AUC (ng · h/mL) |
| 464 | 10 mpk PO | ESP-4 | 48 | 118 | 157 | 571 |
| 463 | 10 mpk PO | ESP-4 | 12 | 49 | 15 | 42 |
| 462 | 10 mpk PO | ESP-4 | 0 | 0 | 178 | 1479 |
| 461 | 10 mpk PO | ESP-4 | 0 | 0 | 524 | 2412 |
| 468 | 10 mpk PO | ESP-4 | 0 | 0 | 209 | 616 |
| 470 | 10 mpk PO | ESP-4 | 346 | 469 | 565 | 1600 |
| 469 | 10 mpk PO | ESD-4 | 181 | 353 | 528 | 4279 |

TABLE 21

Examples of PROTAC Subcutaneous pharmacokinetics (ELP-1: 5% EtOH, 20% labrasol in PBS; ESD-2: 5% EtOH, 20% solutol in D5W).

| | | CD-1 Mouse Plasma Exposure following a 10 mg/kg SC dose | |
|---|---|---|---|
| Vehicle | Ex # | $C_{max}$ (ug/mL) | $AUC_{0-24}$ (ng · h/mL) |
| ESD-1 | 1 | 1.15 | 15600 |
| ELP-1 | 80 | 0.18 | 2530 |
| ESD-1 | 150 | 2.75 | 40200 |
| ELP-1 | 182 | 1.53 | 29162 |
| ESD-1 | 174 | 1.9 | 35065 |

In summary, PROTACs designed to degrade AR are potent (low nM to pM), specific, rapid (within 2-4 hrs); long-lasting (days); active in vitro and in vivo, and have cellular efficacy superior to enzalutamide. AR PROTACs have efficacy in cell systems and work in vivo (AR degradation in prostate; prostate involution in prostate and seminal vesicle; tumor xenograft models). Thus, targeted degradation of AR may provide a novel mechanism for providing efficacious therapy for patients with prostate cancer for whom current therapies have failed.

The invention claimed is:

1. A bifunctional compound that is represented by the chemical structure:

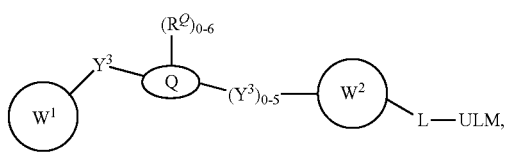

wherein:

ULM is an E3 ubiquitin ligase binding moiety that is represented by the chemical structure:

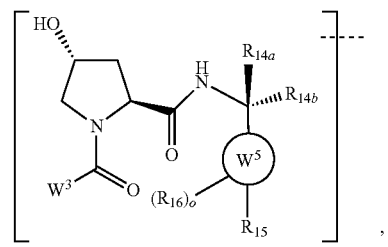

wherein:

$W^3$ is optionally substituted aryl, optionally substituted heteroaryl, or

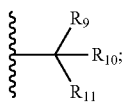

each of $R_9$ and $R_{10}$ is independently hydrogen, optionally substituted alkyl, optionally substituted cycloalkyl, optionally substituted hydroxyalkyl, optionally substituted heteroaryl, or haloalkyl; or $R_9$, $R_{10}$, and the carbon atom to which they are attached form an optionally substituted cycloalkyl;

$R_{11}$ is optionally substituted heterocyclic, optionally substituted alkoxy, optionally substituted heteroaryl, optionally substituted aryl,

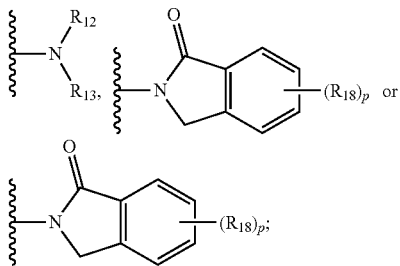

$R_{12}$ is H or optionally substituted alkyl;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$ and $R_{14b}$ are each independently H, haloalkyl, or optionally substituted alkyl;

$W^5$ is a phenyl or a 5-10 membered heteroaryl;

$R_{15}$ is H, halogen, CN, OH, $NO_2$, $NR_{14a}R_{14b}$, $OR_{14a}$, $CONR_{14a}R_{14b}$, $NR_{14a}COR_{14b}$, $SO_2NR_{14a}R_{14b}$, $NR_{14a}SO_2R_{14b}$, optionally substituted alkyl, optionally substituted haloalkyl, optionally substituted haloalkoxy, aryl, heteroaryl, cycloalkyl, cycloheteroalkyl, or

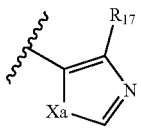

wherein $R_{17}$ is H, halogen, optionally substituted $C_{3-6}$cycloalkyl, optionally substituted $C_{1-6}$alkyl, optionally substituted $C_{1-6}$alkenyl, or $C_{1-6}$haloalkyl, and Xa is S or O;

each $R_{16}$ is independently halogen, optionally substituted alkyl, optionally substituted haloalkyl, hydroxy, or optionally substituted haloalkoxy o is 0, 1, 2, 3, or 4;

each $R_{18}$ is independently halogen, optionally substituted alkoxy, cyano, optionally substituted alkyl, haloalkyl, haloalkoxy, or a point of attachment of L; and p is 0, 1, 2, 3, or 4, L is a bond or a chemical linker, and $W^1$ is aryl or heteroaryl, independently substituted by 1 or more halogen, hydroxyl, nitro, CN, C≡CH, $C_{2-6}$ alkenyl, $C_{2-6}$ alkynyl, linear or branched $C_{1-6}$ alkyl optionally substituted by 1 or more halogen or $C_{1-6}$ alkoxyl, or linear or branched $C_{1-6}$ alkoxyl optionally substituted by 1 or more halogen;

$Y^3$ are each independently a bond, O, $NR^{Y2}$, $CR^{Y1}R^{Y2}$, C=O, C=S, SO, or $SO_2$;

Q is a 3-6 membered alicyclic ring with 0-4 heteroatoms, optionally substituted with 0-6 $R^Q$, each $R^Q$ is independently H, linear or branched $C_{1-6}$ alkyl optionally substituted by 1 or more halogen or $C_{1-6}$ alkoxyl;

$R^{Y1}$, and $R^{Y2}$ are each independently H, linear or branched $C_{1-6}$ alkyl optionally substituted by 1 or more halogen or $C_{1-6}$ alkoxyl;

$W^2$ is a bond, $C_{1-6}$ alkyl, $C_{1-6}$ alicyclic, heterocyclic, aryl, or heteroaryl, each optionally substituted by 1, 2 or 3 $R^{W2}$; and each $R^{W2}$ is independently H, halogen, OH, $NH_2$, $NR^{Y1}R^{Y2}$, CN, $C_{1-6}$ alkyl optionally substituted by 1 or more F, or $OC_{1-3}$alkyl optionally substituted by 1 or more F.

2. The bifunctional compound of claim 1, wherein the bifunctional compound is represented by the structure:

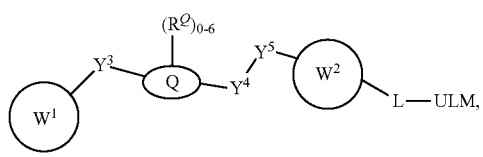

wherein:

$Y^4$ and $Y^5$ are each independently a bond, O, $NR^{Y2}$, $CR^{Y1}R^{Y2}$, C=O, C=S, SO, or $SO_2$; and Q is a 4 membered alicyclic ring with 0-2 heteroatoms, optionally substituted with 1-6 $R^Q$, each $R^Q$ is independently linear or branched $C_{1-6}$ alkyl optionally substituted by 1 or more halogen or $C_{1-6}$ alkoxyl.

3. The bifunctional compound of claim 1, wherein the ULM is represented by the structure:

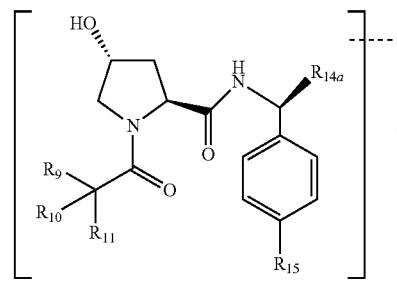

wherein:

$R_9$ is H;

$R_{10}$ is isopropyl, tert-butyl, sec-butyl, cyclopentyl, or cyclohexyl;

$R_{11}$ is

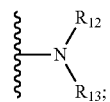

$R_{12}$ is H;

$R_{13}$ is H, optionally substituted alkyl, optionally substituted alkylcarbonyl, optionally substituted (cycloalkyl)alkylcarbonyl, optionally substituted aralkylcarbonyl, optionally substituted arylcarbonyl, optionally substituted (heterocyclyl)carbonyl, or optionally substituted aralkyl;

$R_{14a}$ is H, haloalkyl, or optionally substituted methyl, ethyl, isopropyl, or cyclopropyl; and $R_{15}$ is

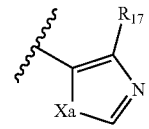

wherein $R_{17}$ is H, halogen, optionally substituted $C_{3-6}$cycloalkyl, optionally substituted $C_{1-6}$alkyl, optionally substituted $C_{1-6}$alkenyl, or $C_{1-6}$haloalkyl; and Xa is S or O.

4. The bifunctional compound of claim 1, wherein ULM is selected from the group consisting of:

(2S,4R)-1-((S)-2-amino-3,3-dimethylbutanoyl)-4-hydroxy-N-(4-(4-methylthiazol-5-yl)benzyl)pyrrolidine-2-carboxamide;

(2S,4R)-1-((S)-2-amino-3,3-dimethylbutanoyl)-4-hydroxy-N-(4-(thiazol-5-yl)benzyl)pyrrolidine-2-carboxamide;

(2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide;

(2S,4R)-1-((S)-2-amino-3,3-dimethylbutanoyl)-4-hydroxy-N-(4-(oxazol-5-yl)benzyl)pyrrolidine-2-carboxamide;

(2S,4R)-1-((S)-2-amino-3,3-dimethylbutanoyl)-4-hydroxy-N-(4-(4-methyloxazol-5-yl)benzyl)pyrrolidine-2-carboxamide;

(2S,4R)-1-((S)-2-amino-3,3-dimethylbutanoyl)-N-(4-chlorobenzyl)-4-hydroxypyrrolidine-2-carboxamide;

(2S,4R)-1-((S)-2-amino-3,3-dimethylbutanoyl)-N-(4-cyanobenzyl)-4-hydroxypyrrolidine-2-carboxamide;

(2S,4R)-1-((S)-2-amino-3-methylbutanoyl)-4-hydroxy-N-(4-(4-methylthiazol-5-yl)benzyl)pyrrolidine-2-carboxamide;

(2S,4R)-1-((S)-2-amino-3-methylbutanoyl)-4-hydroxy-N-(4-(thiazol-5-yl)benzyl)pyrrolidine-2-carboxamide;

(2S,4R)-1-((S)-2-amino-3-methylbutanoyl)-4-hydroxy-N-(4-(4-methyloxazol-5-yl)benzyl)pyrrolidine-2-carboxamide; and (2S,4R)-1-((S)-2-amino-3,3-dimethylbutanoyl)-4-hydroxy-N-(4-(1-methyl-1H-pyrazol-5-yl)benzyl)pyrrolidine-2-carboxamide.

5. The bifunctional compound of claim 1, wherein the chemical linker is represented by the formula:

$-(A)_q-$, wherein:

q is an integer greater than 1; and

A is independently selected from the group consisting of $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}=CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(NCN)$, $NR^{L3}C(=CNO_2)NR^{L4}$, $C_{3-11}$cycloalkyl optionally substituted with 1-6 $R^{L1}$ and/or $R^{L2}$ groups, $C_{3-11}$heteocyclyl optionally substituted with 1-6 $R^{L1}$ and/or $R^{L2}$ groups, aryl optionally substituted with 1-6 $R^{L1}$ and/or $R^{L2}$ groups, and heteroaryl optionally substituted with 1-6 $R^{L1}$ and/or $R^{L2}$ groups; wherein $R^{L1}$, $R^{L2}$, $R^{L3}$, $R^{L4}$ and $R^{L5}$ are each, independently, selected from the group consisting of H, $C_{1-8}$alkyl, $OC_{1-8}$alkyl, $SC_{1-8}$alkyl, $NHC_{1-8}$alkyl, $N(C_{1-8}$alkyl$)_2$, $C_{3-11}$cycloalkyl, aryl, heteroaryl, $C_{3-11}$heterocyclyl, $OC_{3-8}$cycloalkyl, $SC_{1-8}$cycloalkyl, $NHC_{3-8}$ cycloalkyl, $N(C_{3-8}$cycloalkyl$)_2$, $N(C_{3-8}$cycloalkyl)($C_{1-8}$alkyl), OH, $NH_2$, SH, $SO_2C_{1-8}$alkyl, $P(O)(OC_{1-8}$alkyl)($C_{1-8}$alkyl), $P(O)(OC_{1-8}$alkyl$)_2$, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C($C_{1-8}$alkyl$)_2$, $Si(OH)_3$, $Si(C_{1-8}$ alkyl$)_3$, $Si(OH)(C_{1-8}$alkyl$)_2$, $COC_{1-8}$alkyl, $CO_2H$, halogen, CN, $CF_3$, $CHF_2$, $CH_2F$, $NO_2$, $SF_5$, $SO_2NHC_{1-8}$alkyl, $SO_2N(C_{1-8}$alkyl$)_2$, $SONHC_{1-8}$alkyl, $SON(C_{1-8}$alkyl$)_2$, $CONHC_{1-8}$alkyl, $CON(C_{1-8}$alkyl$)_2$, $N(C_{1-8}$alkyl)CONH($C_{1-8}$alkyl), $N(C_{1-8}$alkyl)CON($C_{1-8}$alkyl$)_2$, NHCONH($C_{1-8}$alkyl), NHCON($C_{1-8}$alkyl$)_2$, $NHCONH_2$, $N(C_{1-8}$alkyl)$SO_2NH(C_{1-8}$alkyl), $N(C_{1-8}$alkyl)$SO_2N(C_{1-8}$alkyl$)_2$, NH $SO_2NH(C_{1-8}$alkyl), NH $SO_2N(C_{1-8}$alkyl$)_2$, and NH $SO_2NH_2$; and wherein $R^{L1}$ or $R^{L2}$ each, independently, can be linked to another A group to form cycloalkyl and/or heterocyclyl moiety that can be further substituted with 1-4 $R^{L5}$ groups.

6. The bifunctional compound of claim 1, wherein the compound is a member selected from the group consisting of:

(151)
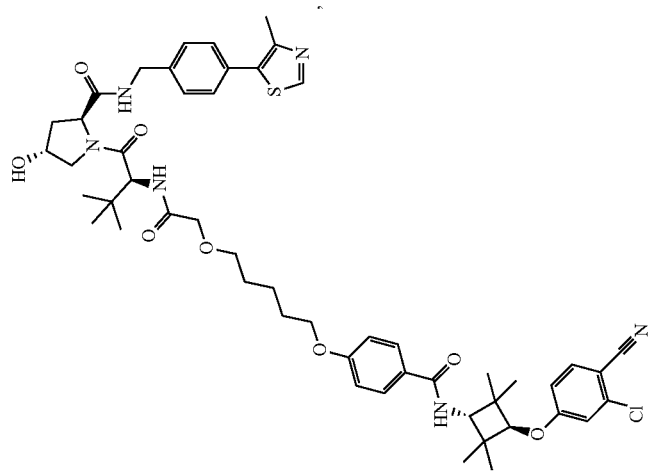
(150)
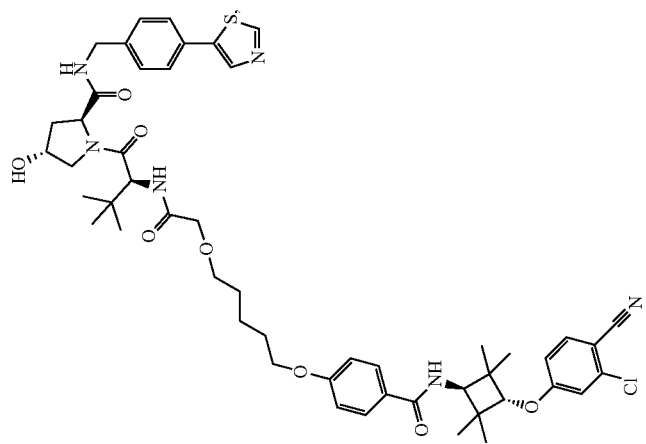

(153)
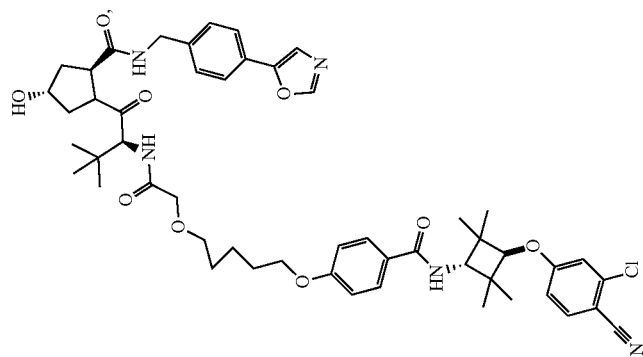
(152)
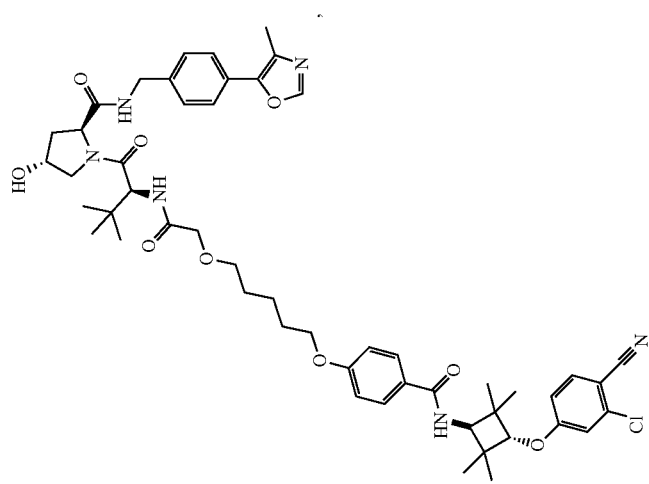

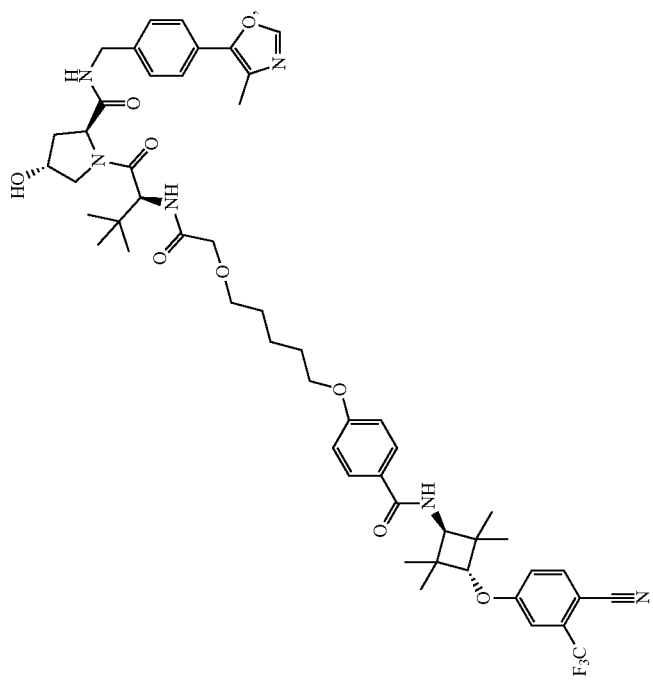
(154)
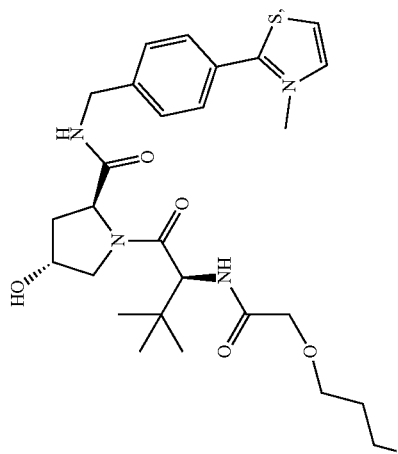
(155)

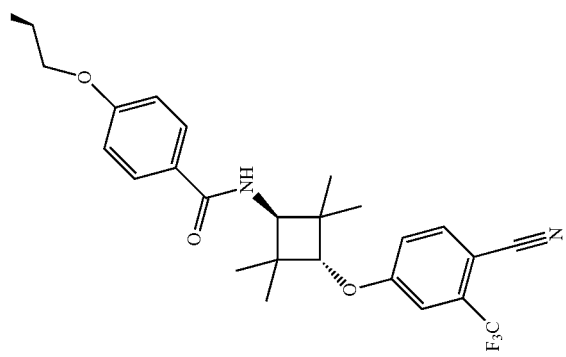

(156)
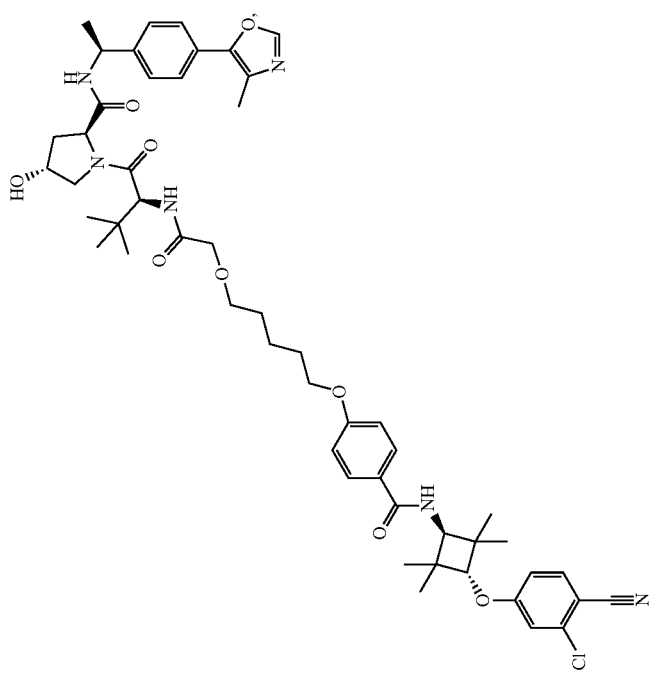

-continued
(158)
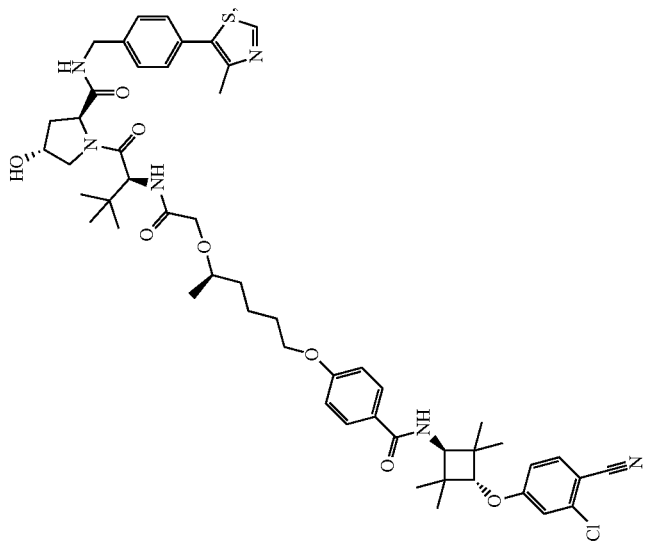
(157)
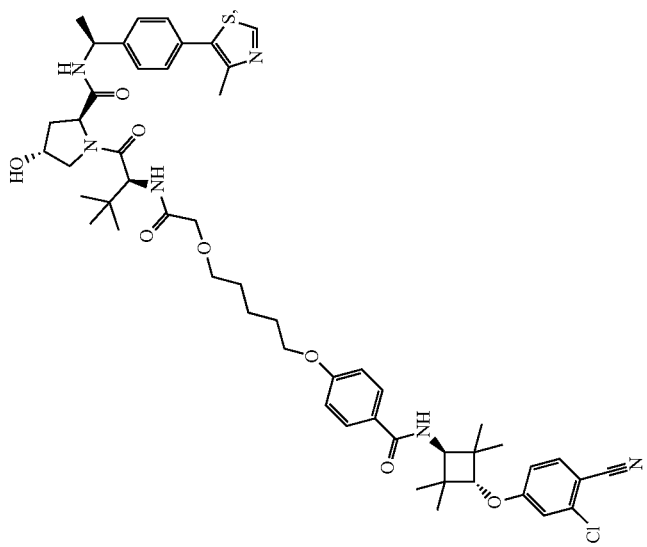

(160)
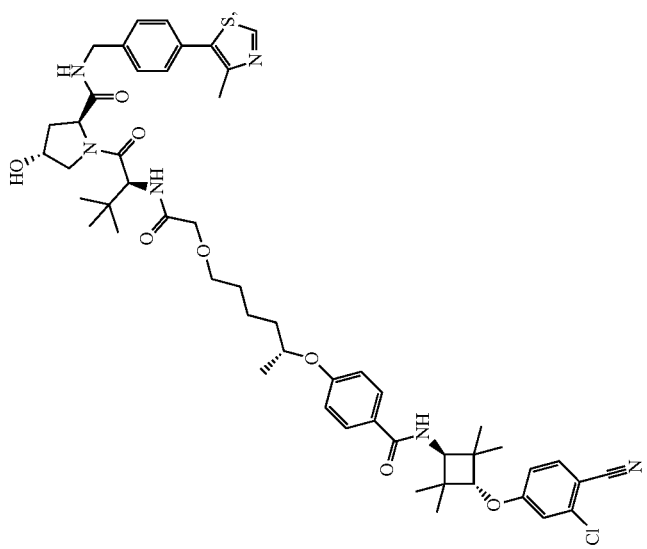
(159)
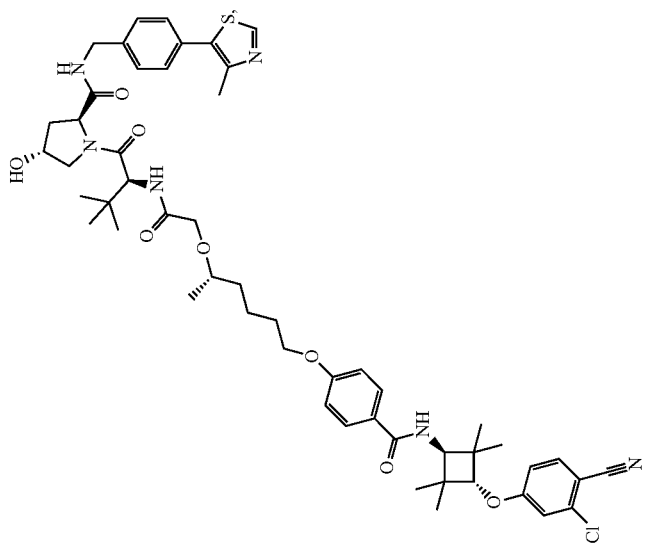

-continued
(162)
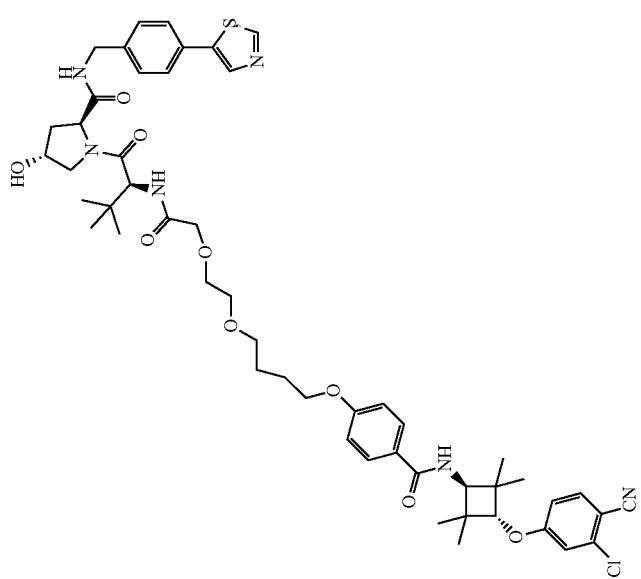
(161)
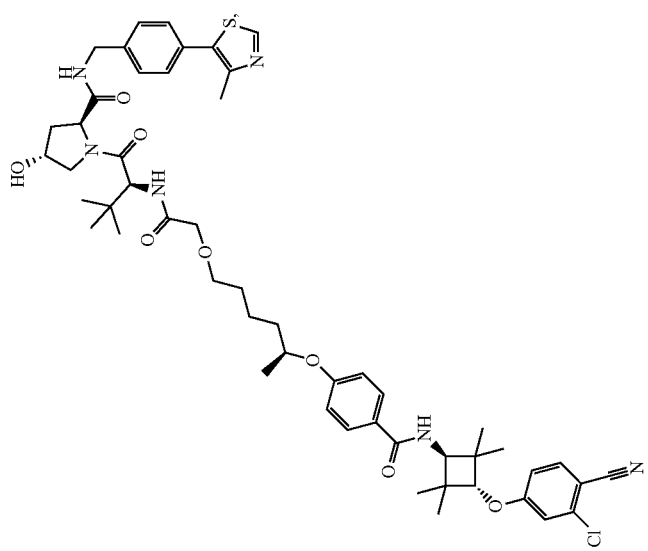

(163)
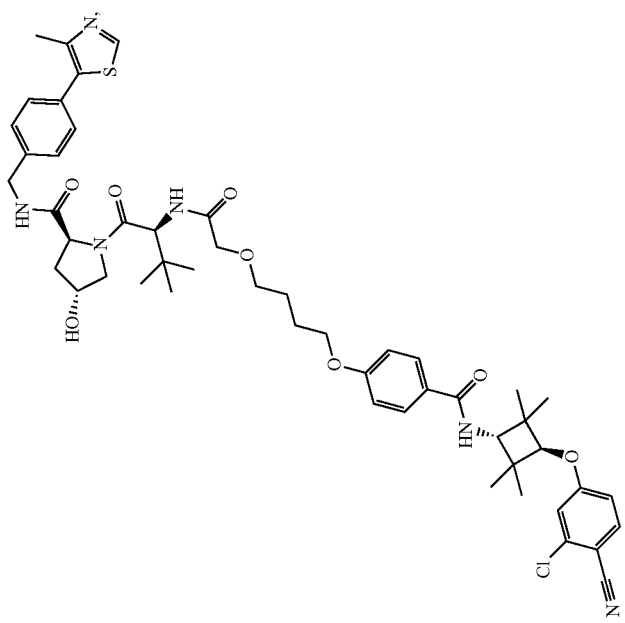

-continued
(164)
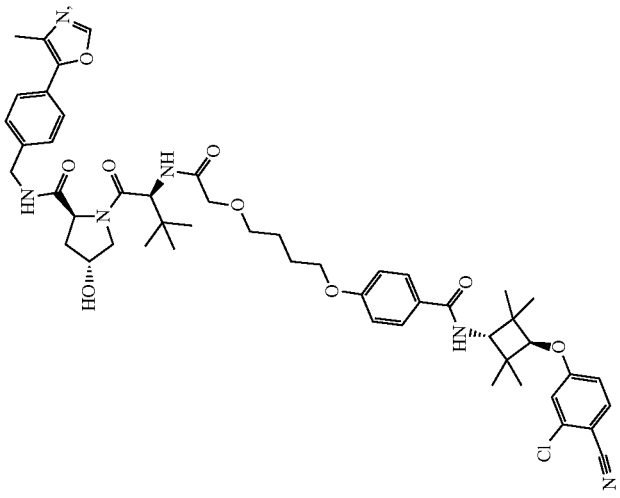
(165)

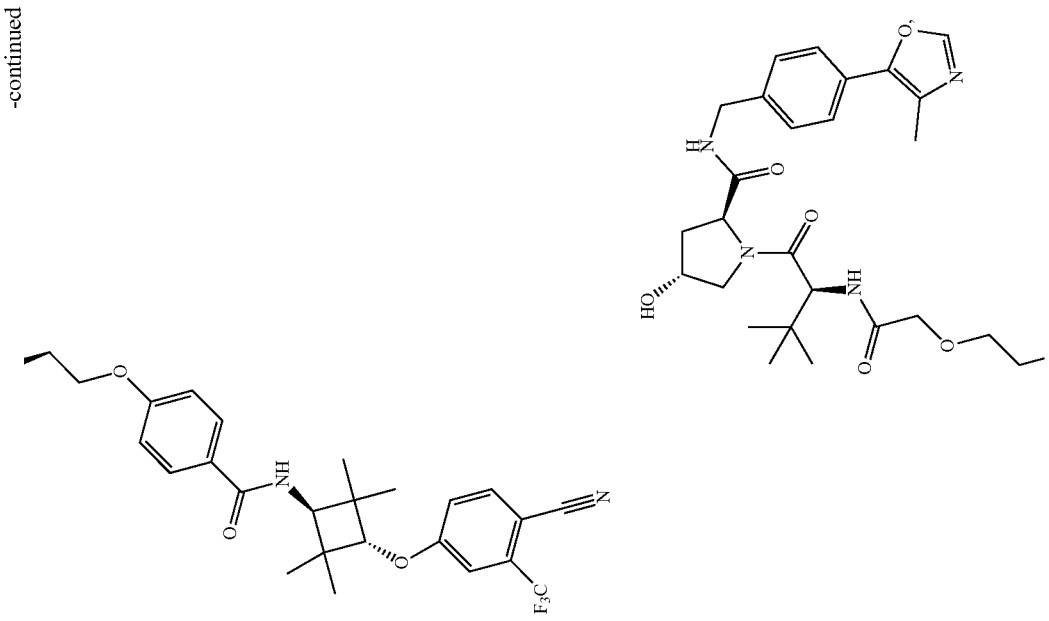
(166)

-continued
(167)
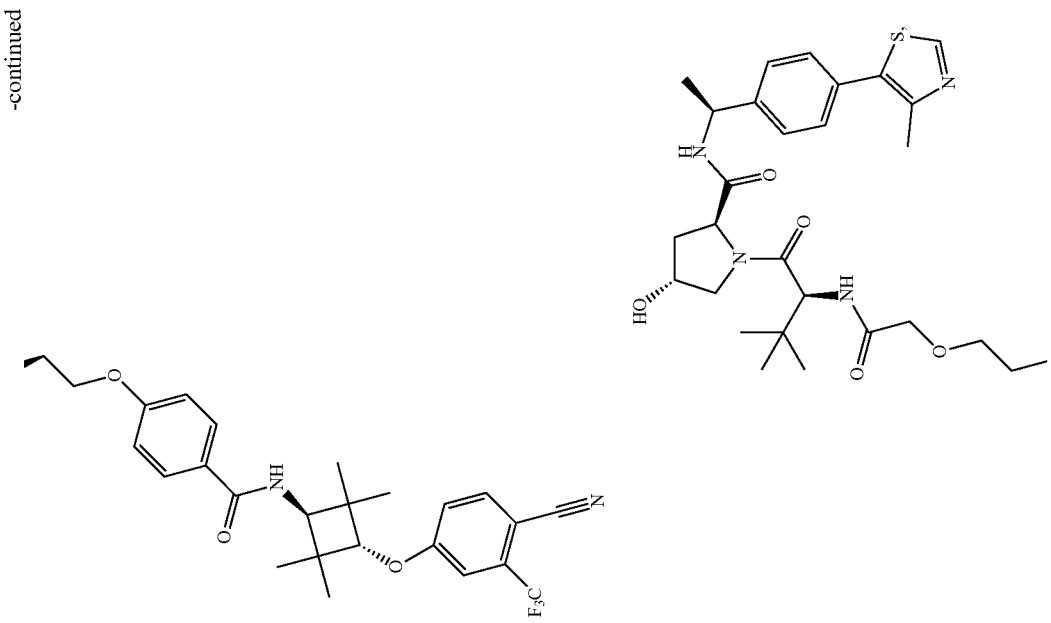

(168)
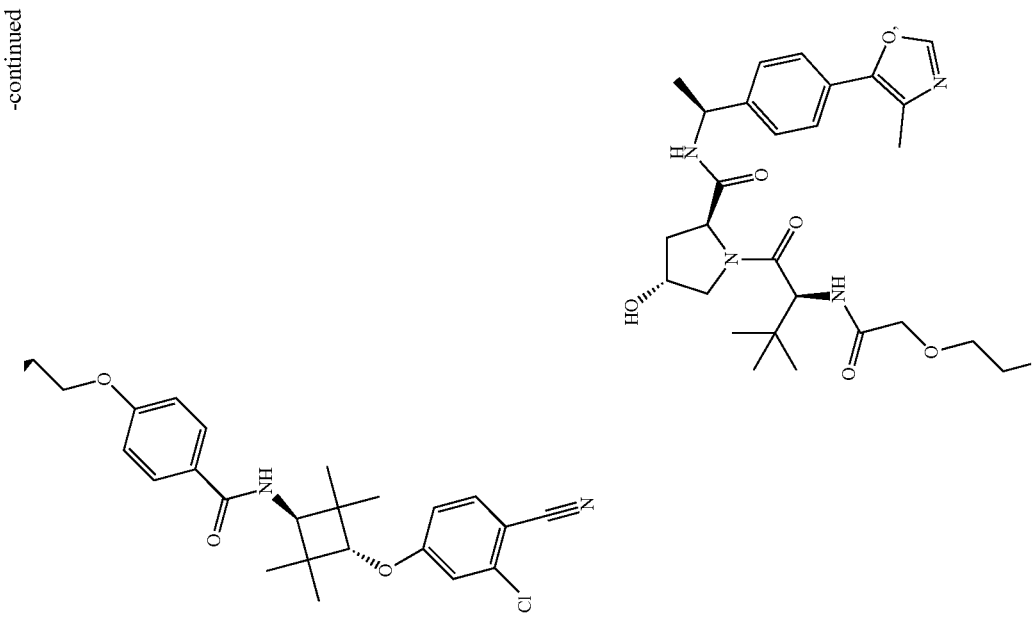

-continued
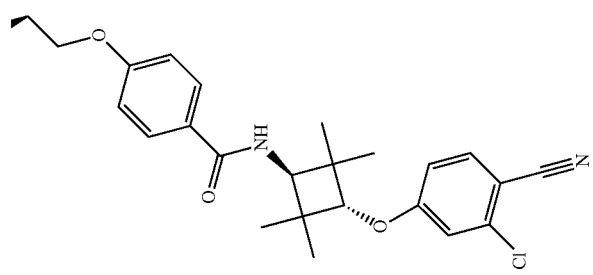

(169)
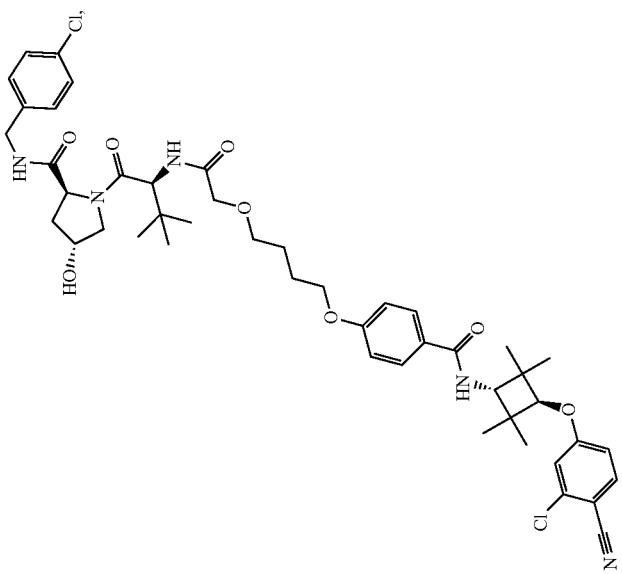

(170)
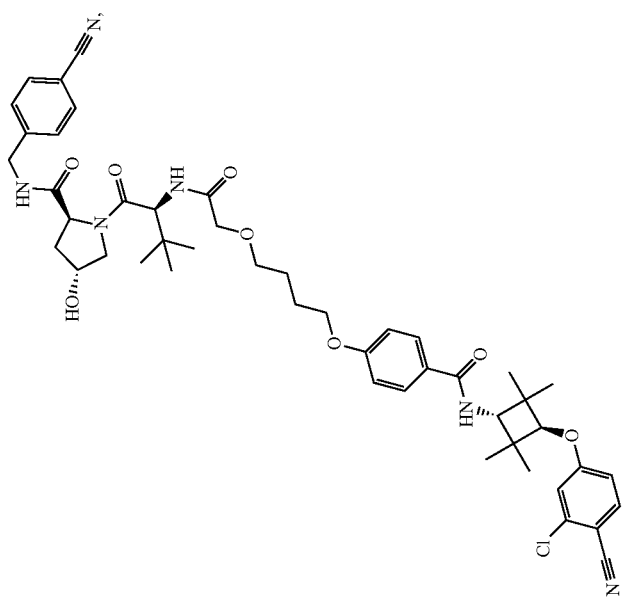

(171)
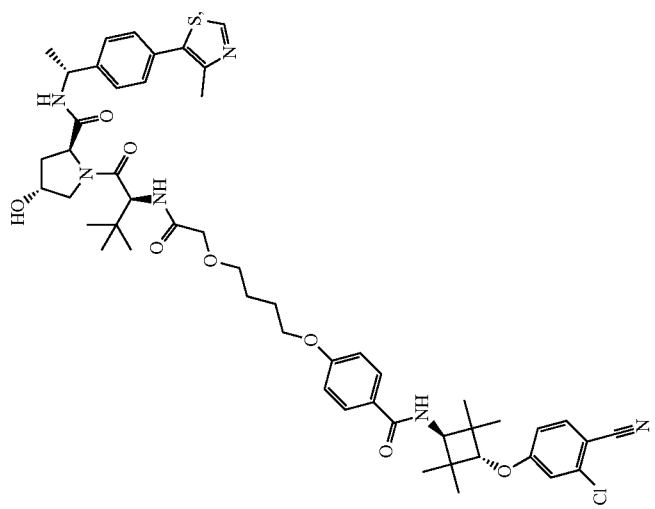

(172)
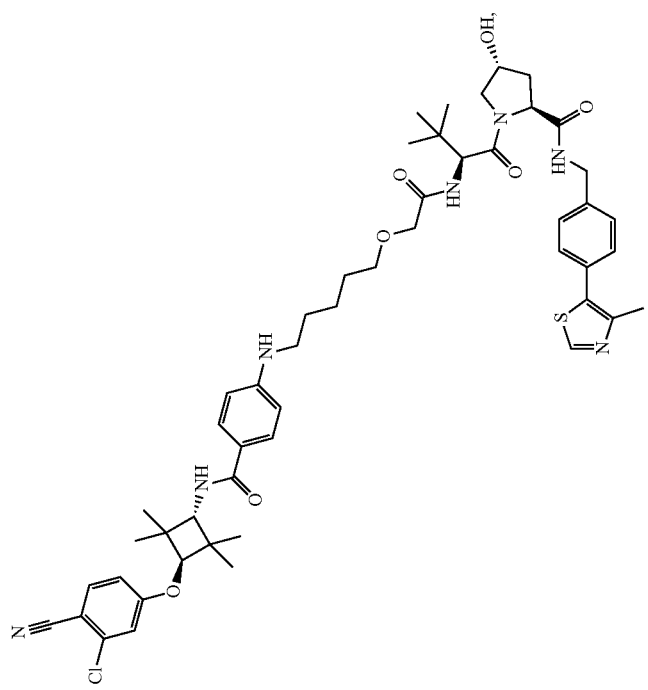

(173)
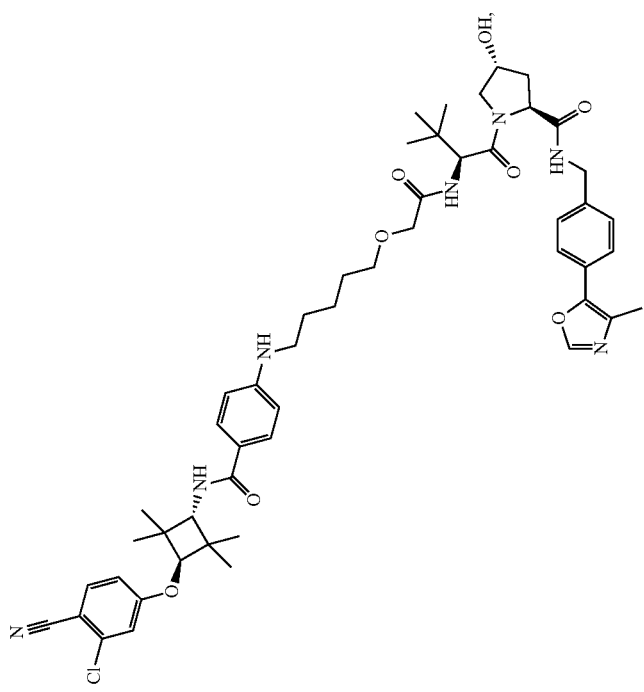

(174)
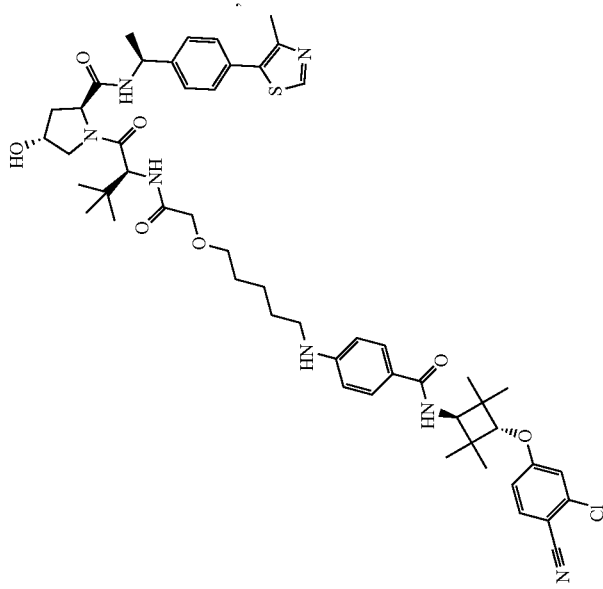

(175)
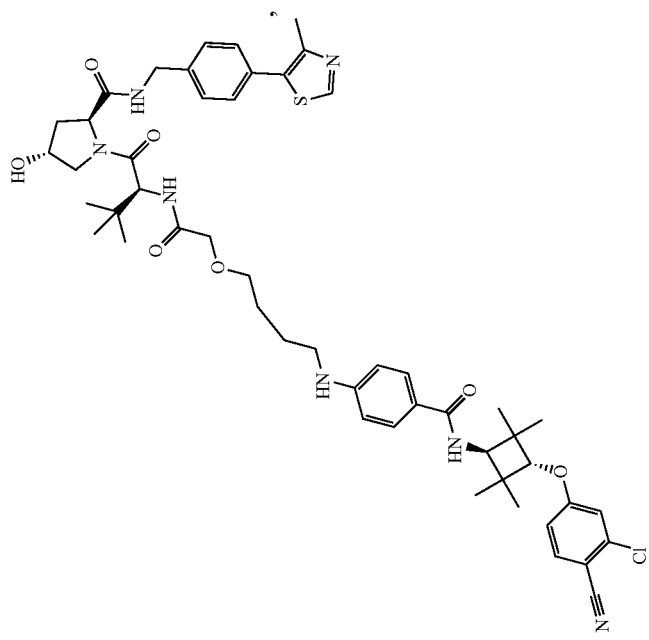

(176)
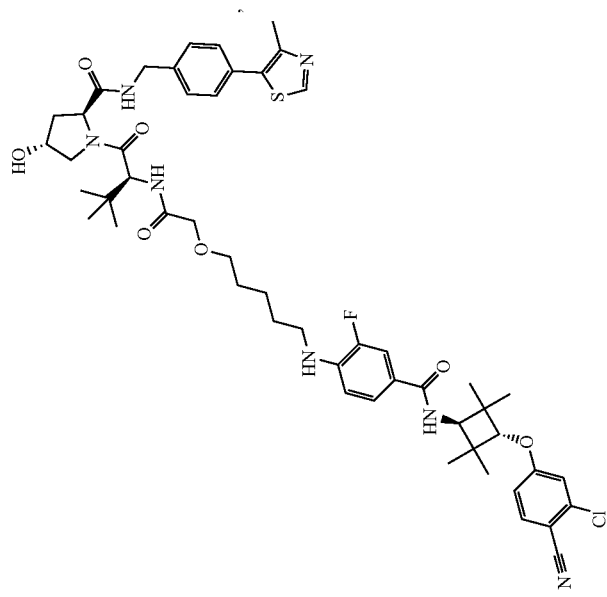

(177)
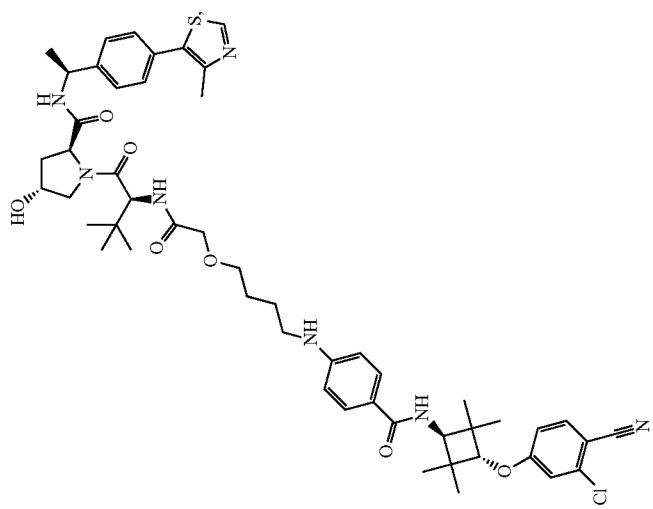

(178)
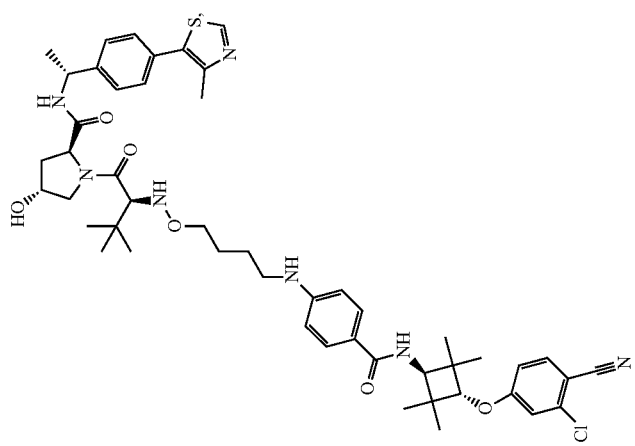

(179)
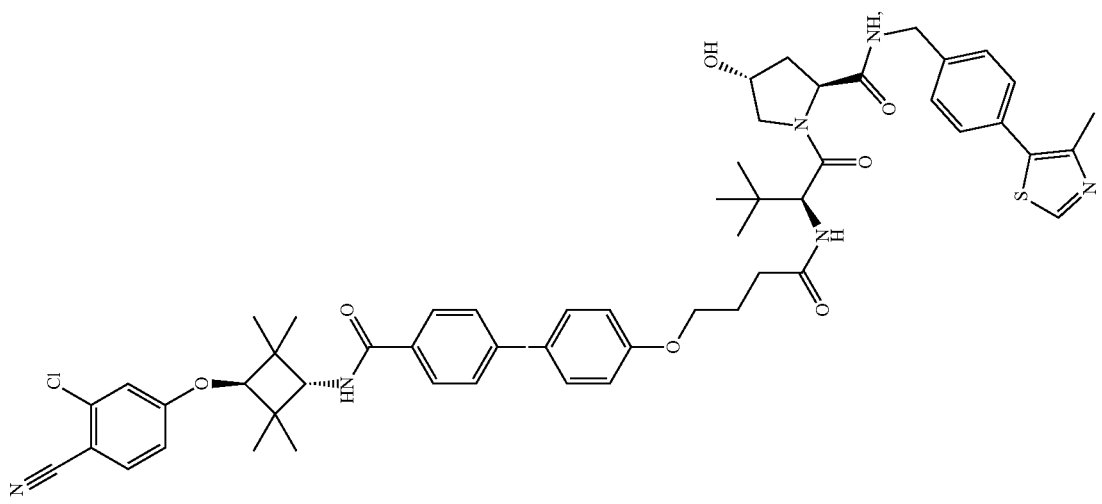

(180)
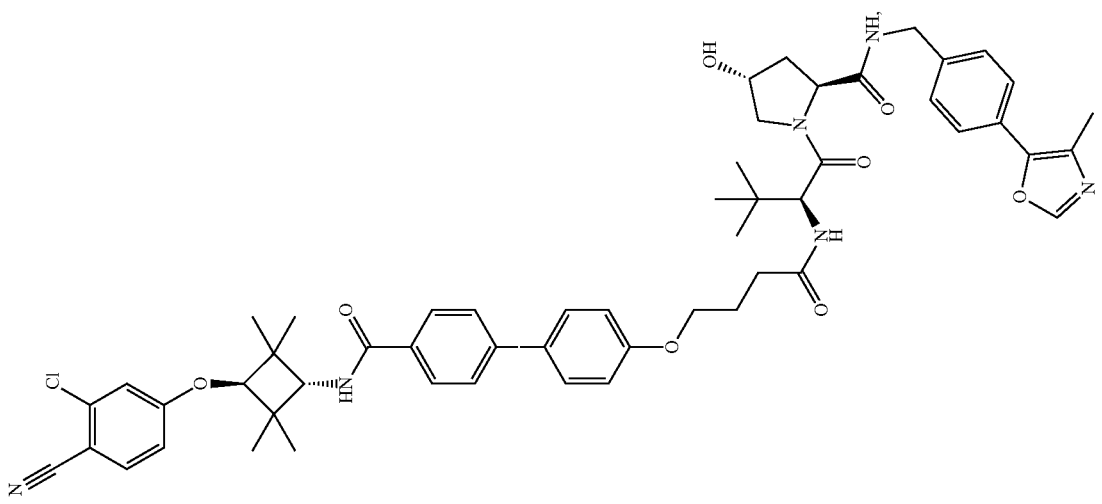

(181)
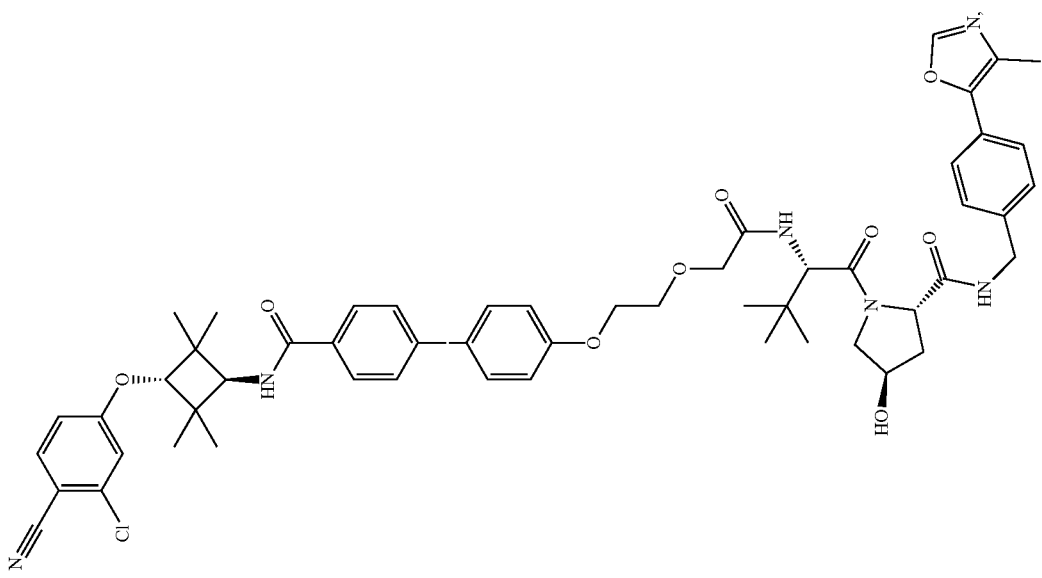

(182)
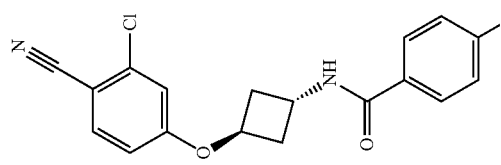

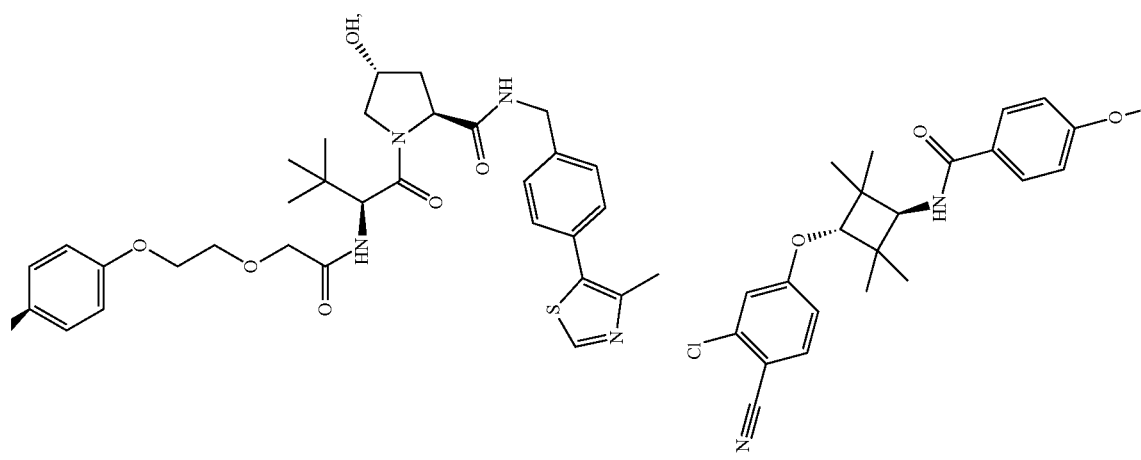
(183)

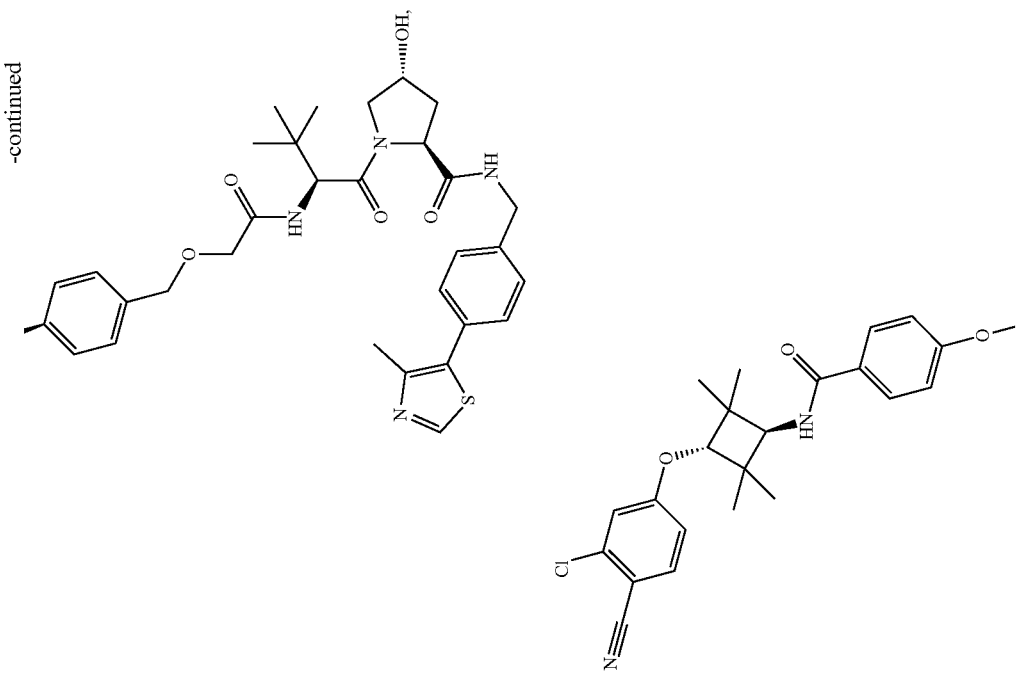
(184)

(185)
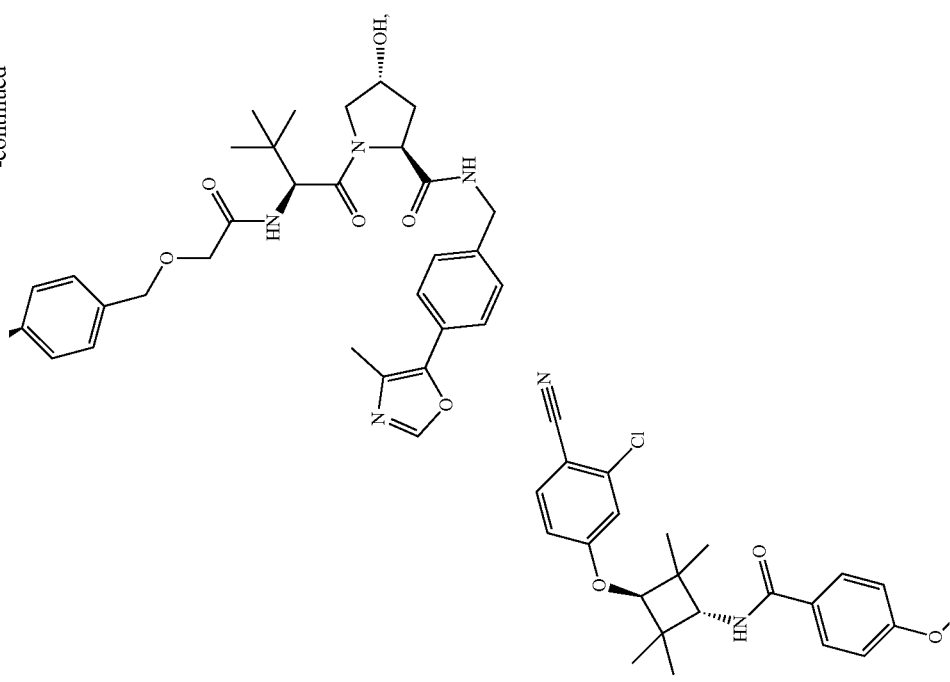

(186)
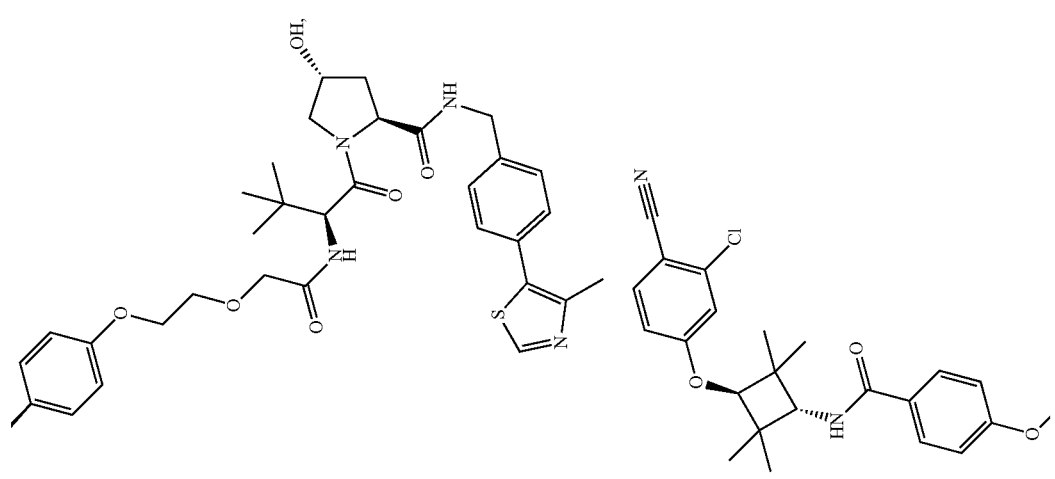

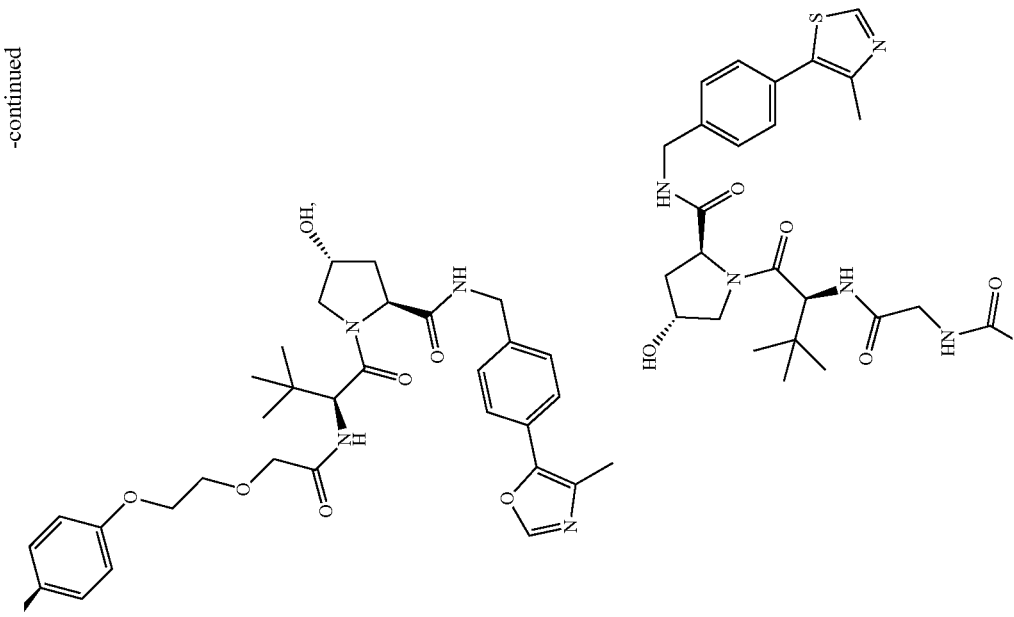
(187)

(188)
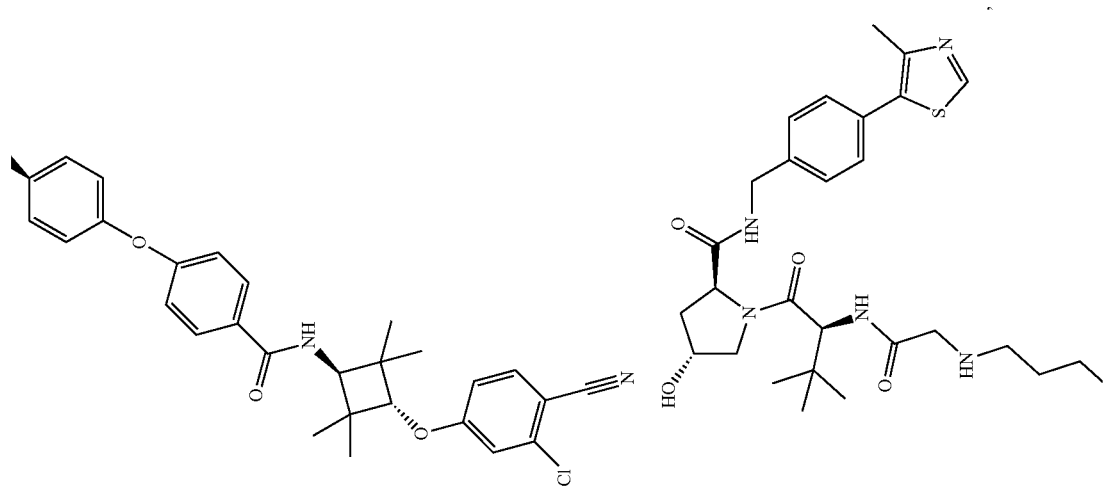

(189)
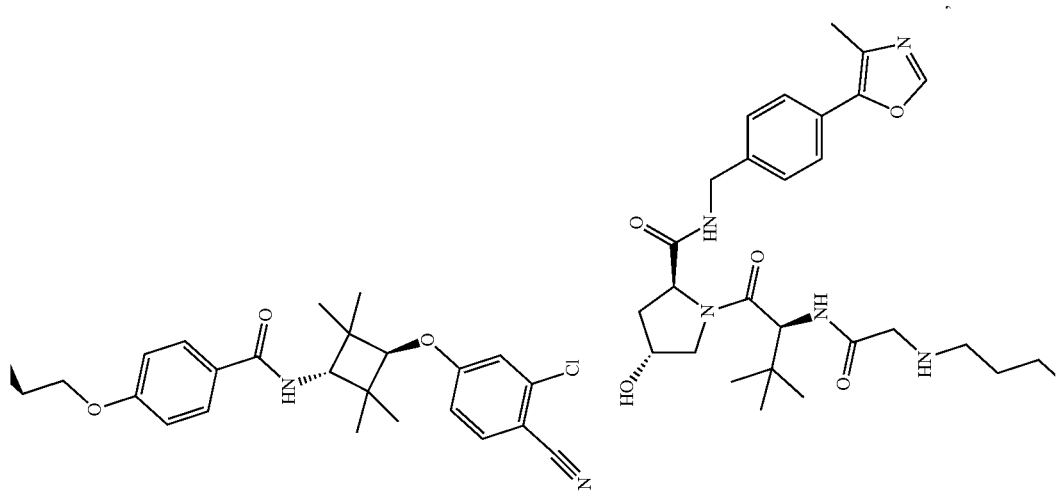

-continued
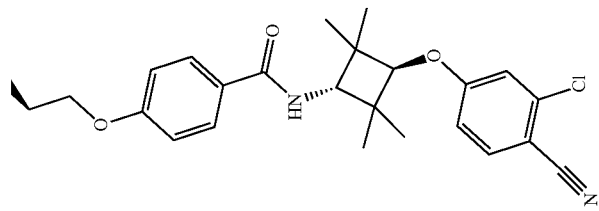

(204)
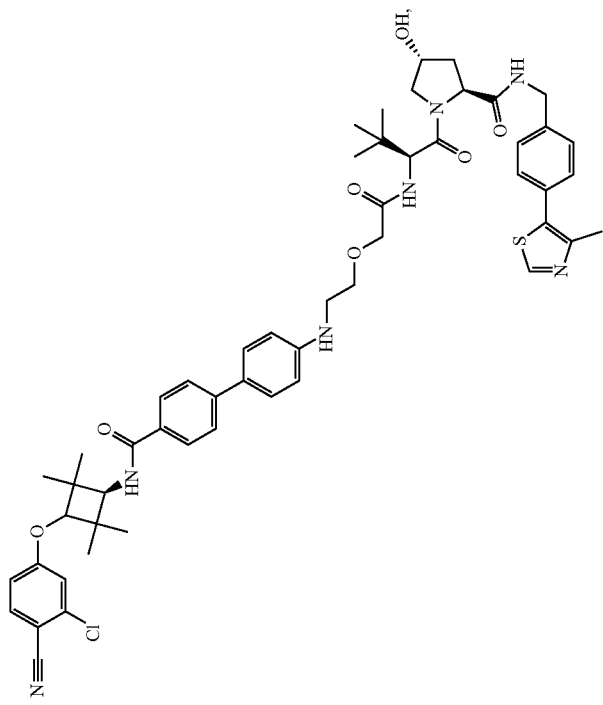
(339)
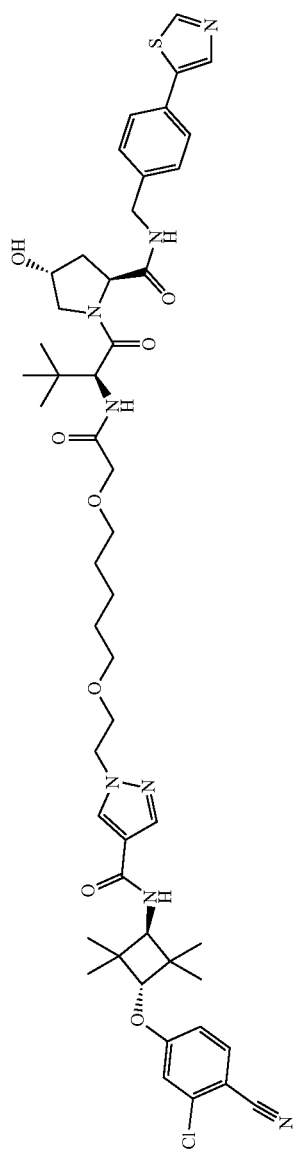

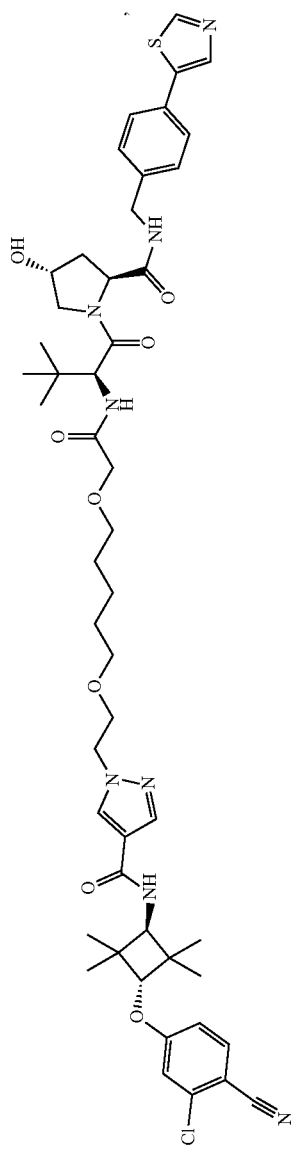
(347)
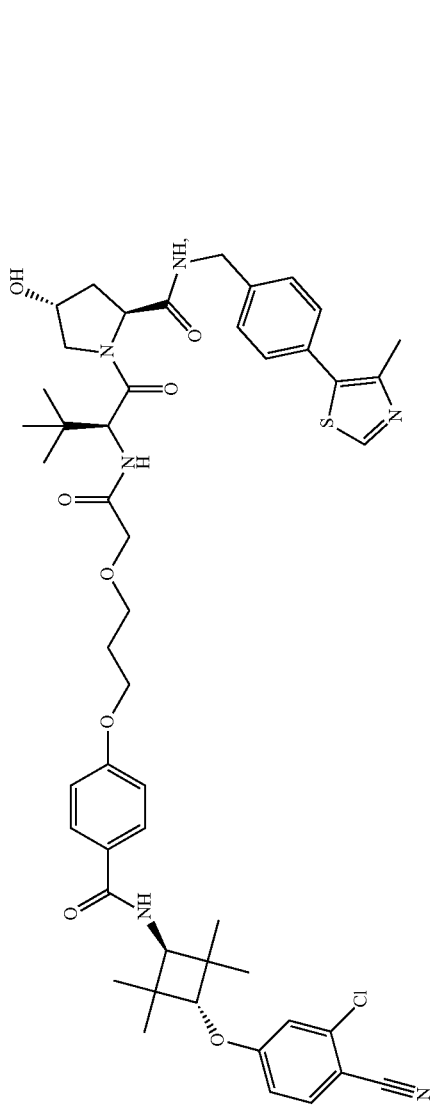
(387)

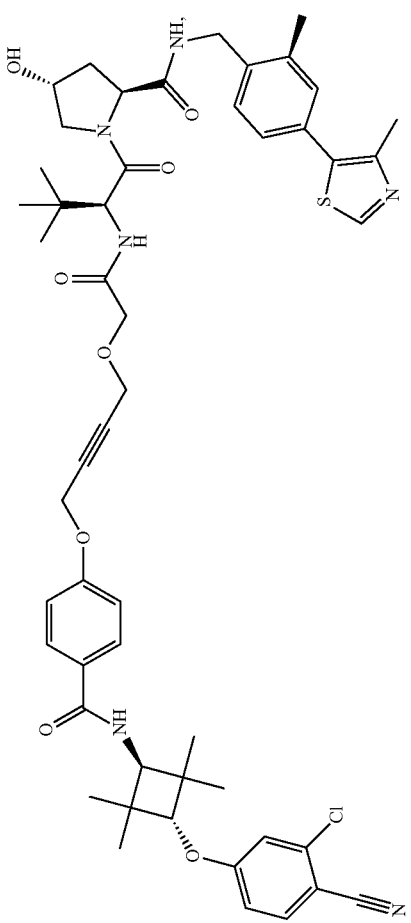
(388)
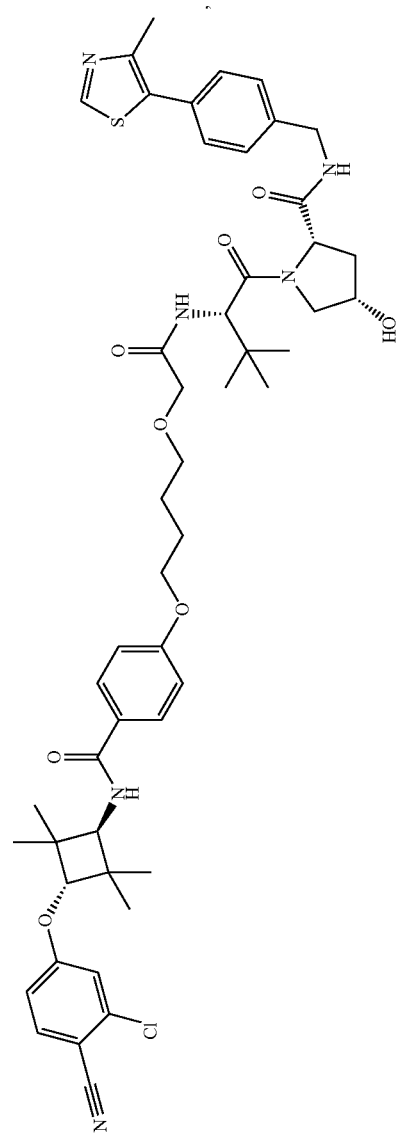
(392)

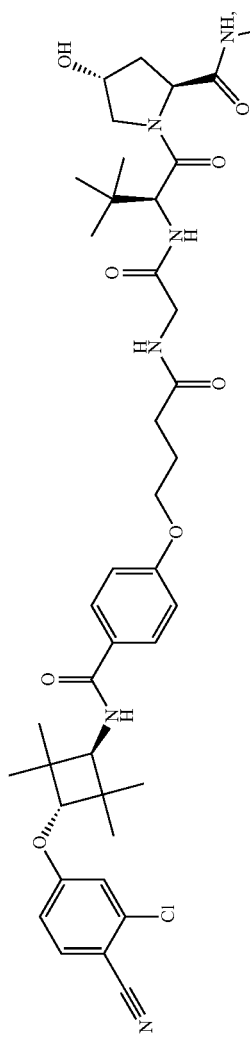
(393)
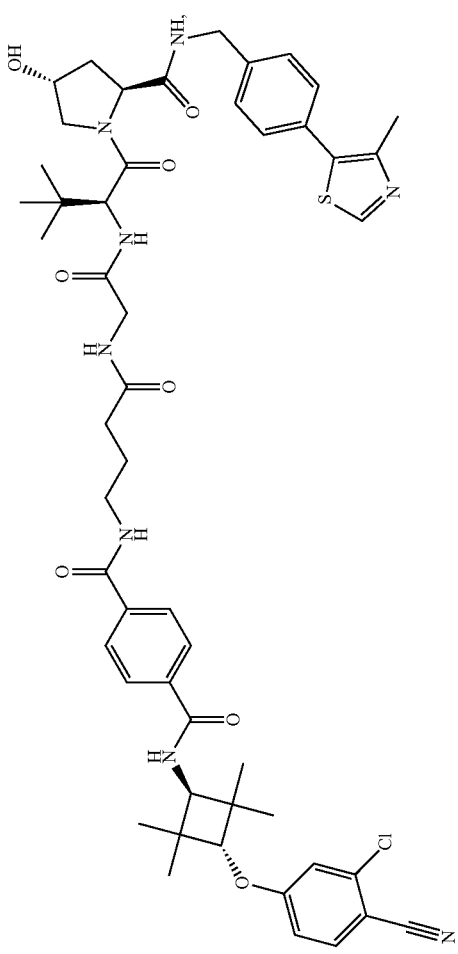
(398)

(404)
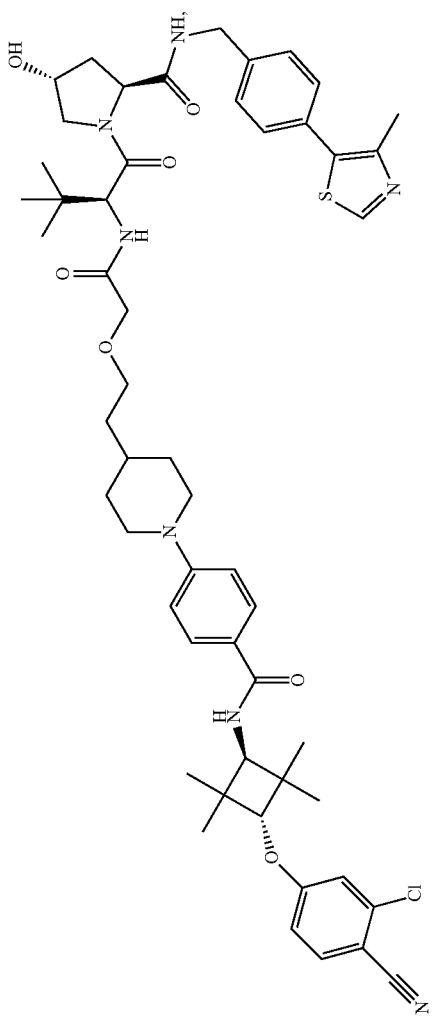
(405)
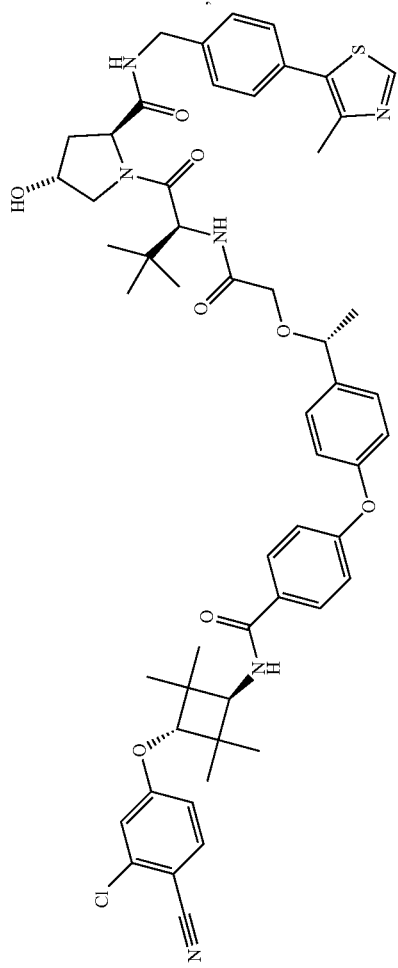

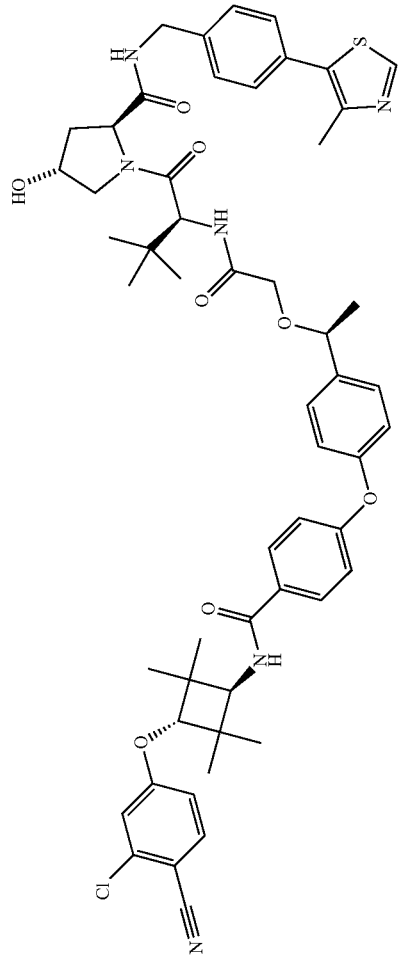
(406)
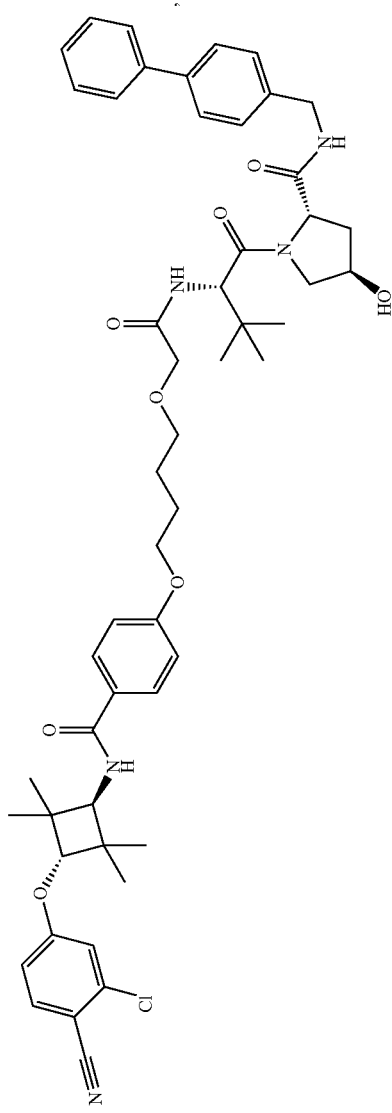
(407)

(409)
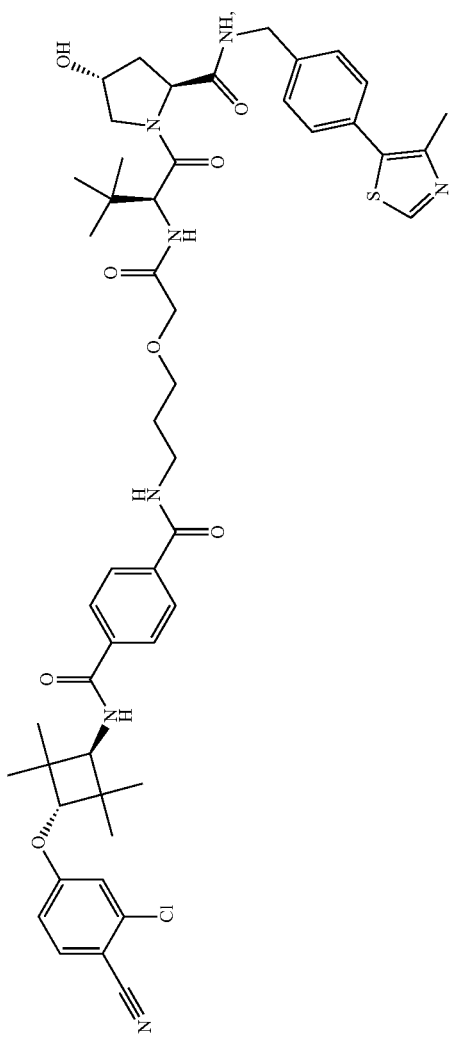
(410)
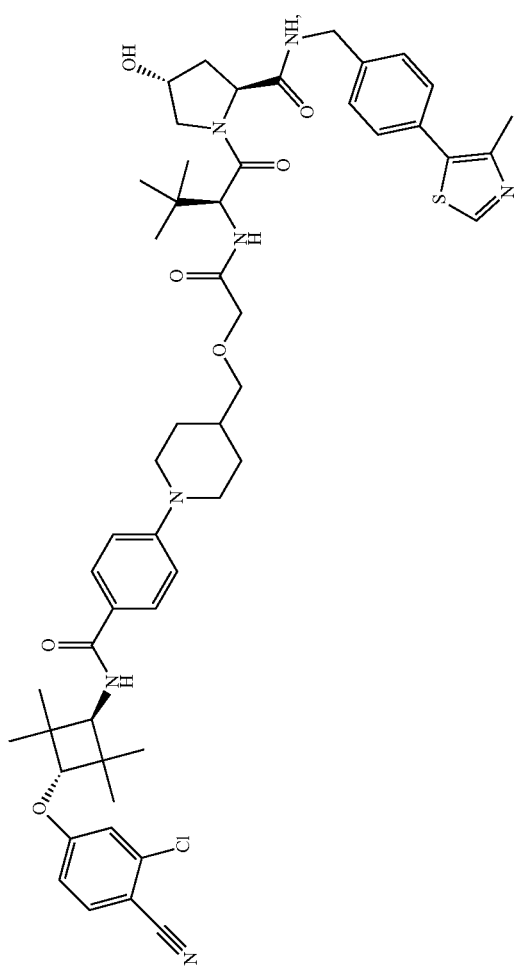

(411)
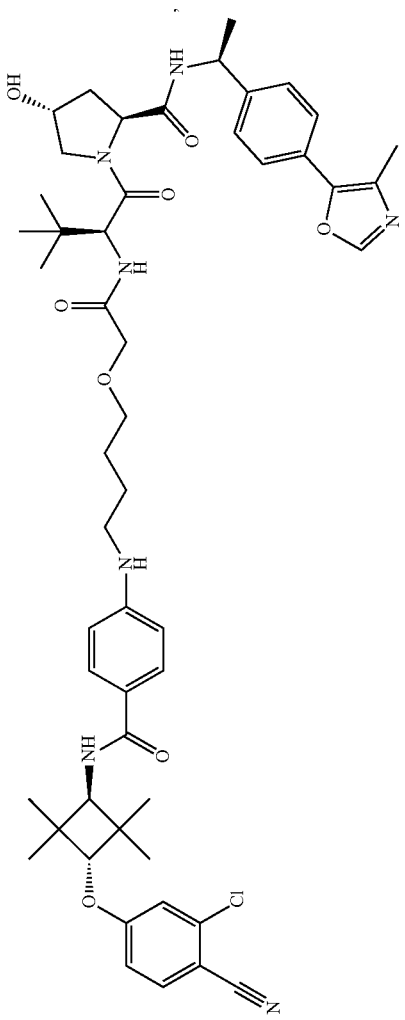
(412)
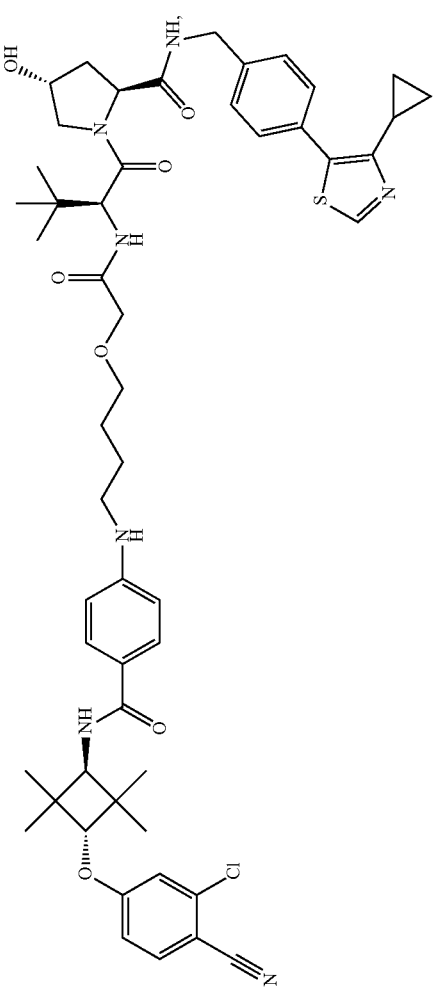

(415)
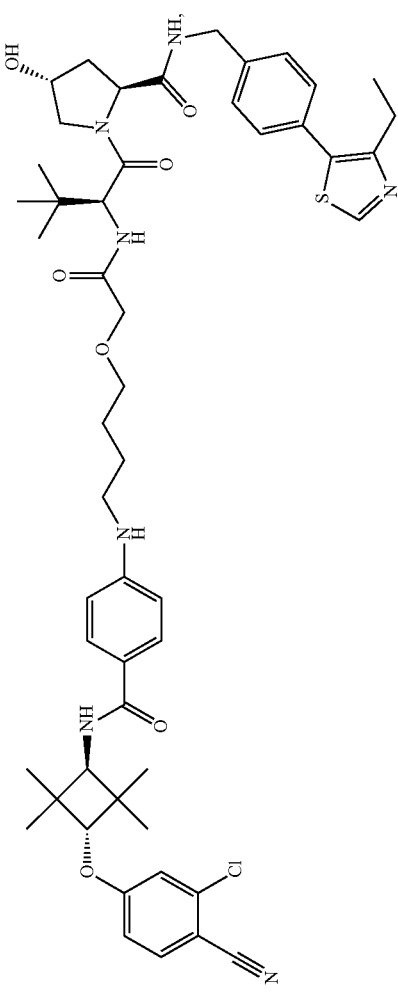
(416)
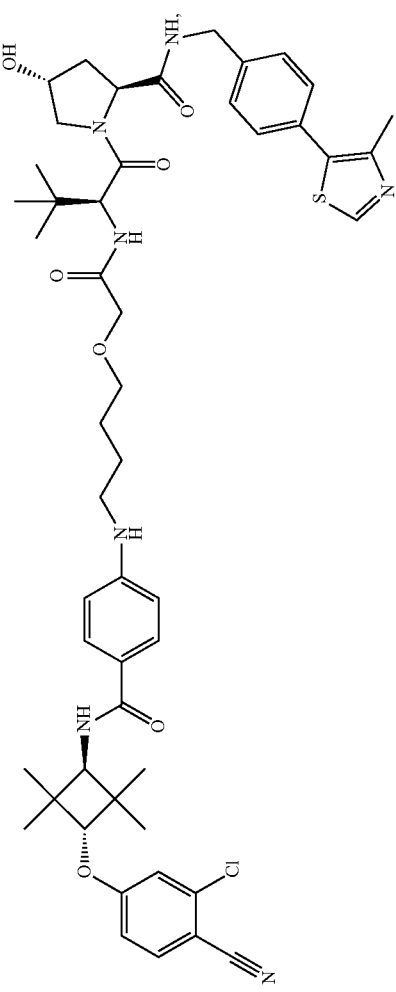

(417)
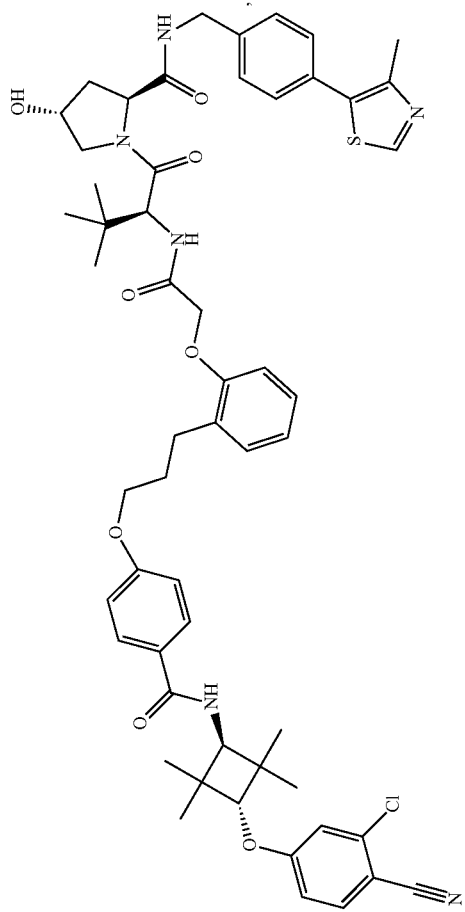
(422)
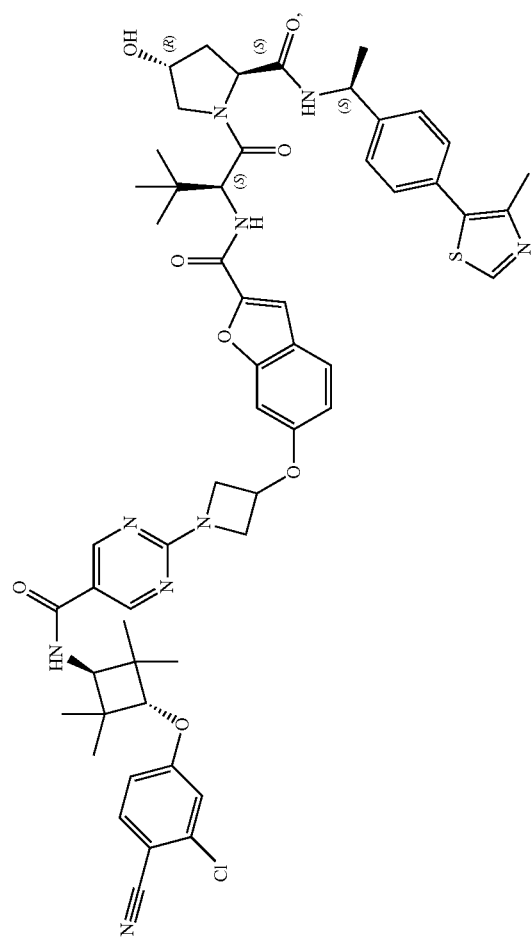

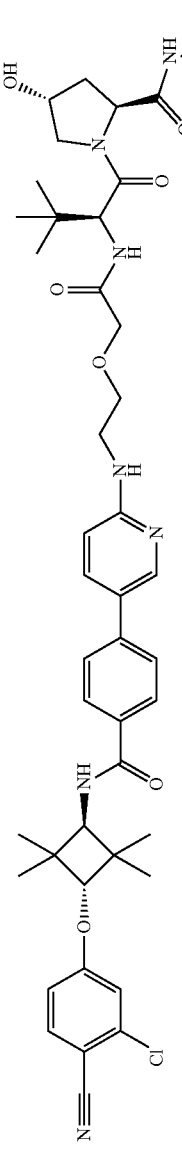 (425)
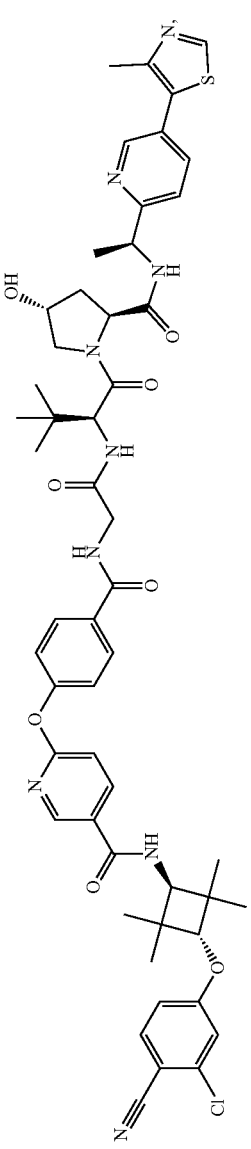 (432)
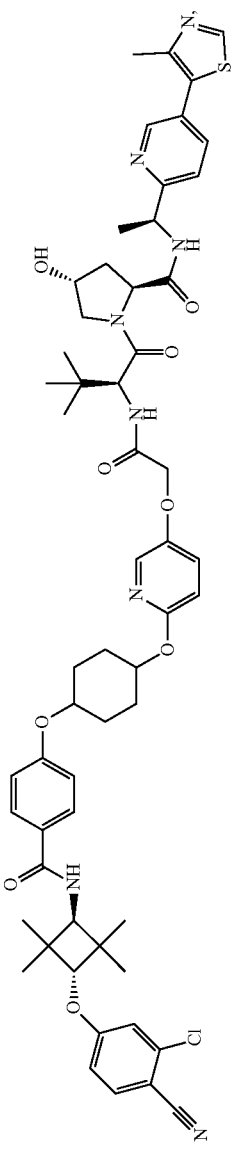 (433)

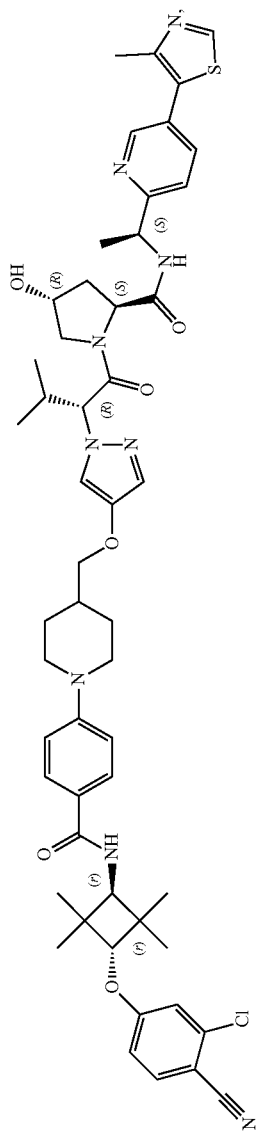
(436)
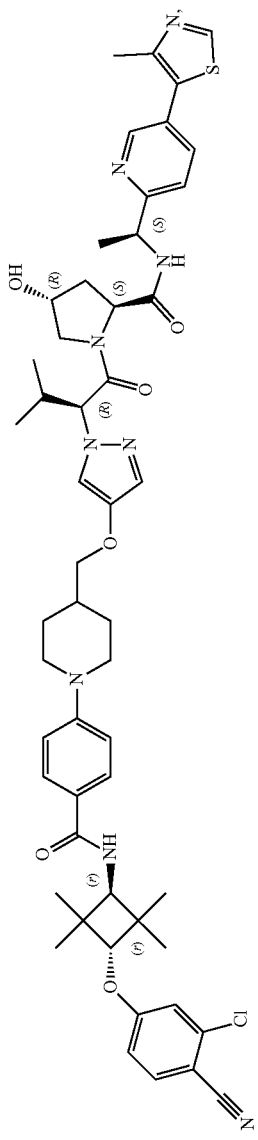
(437)
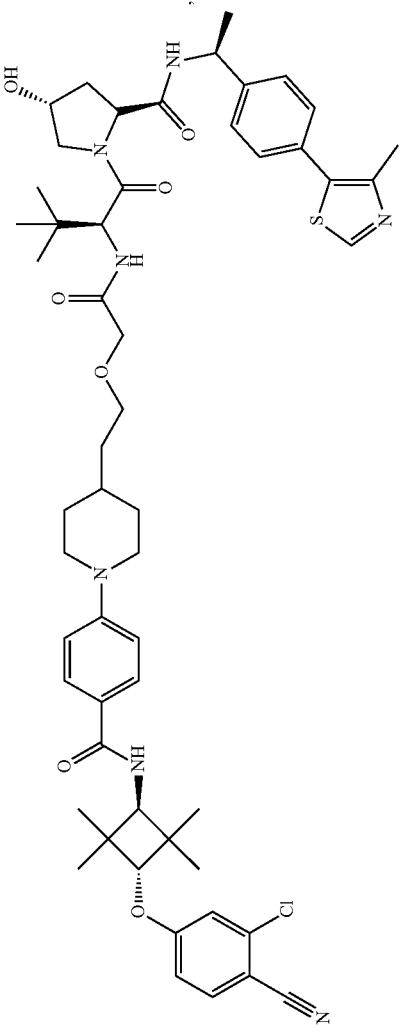
(438)

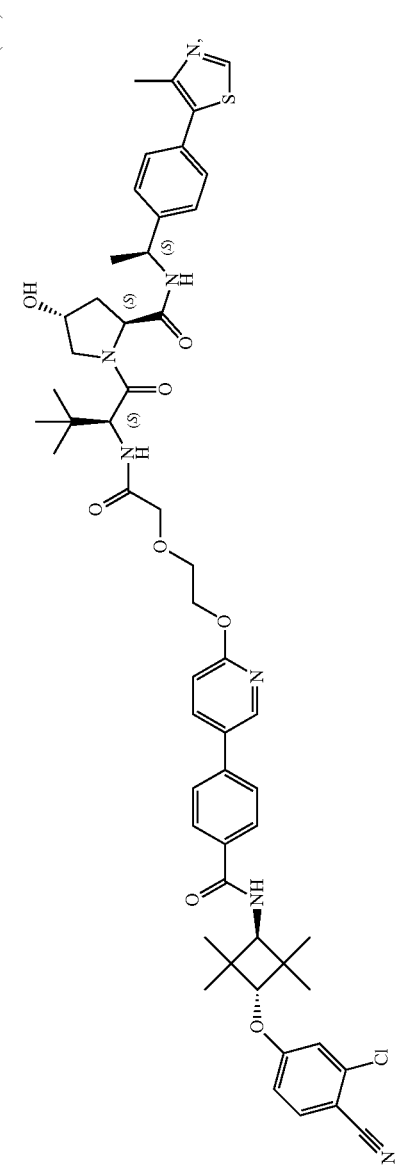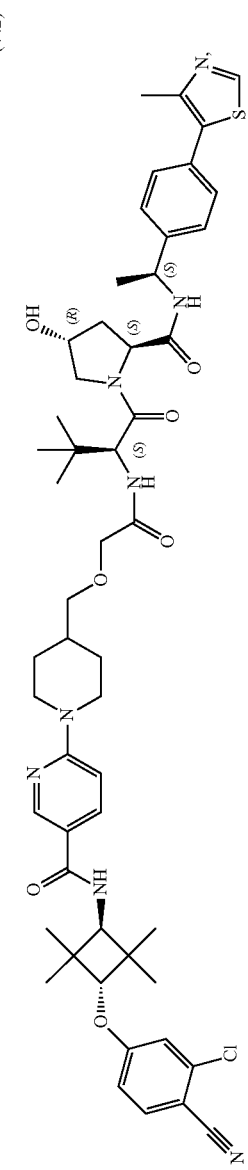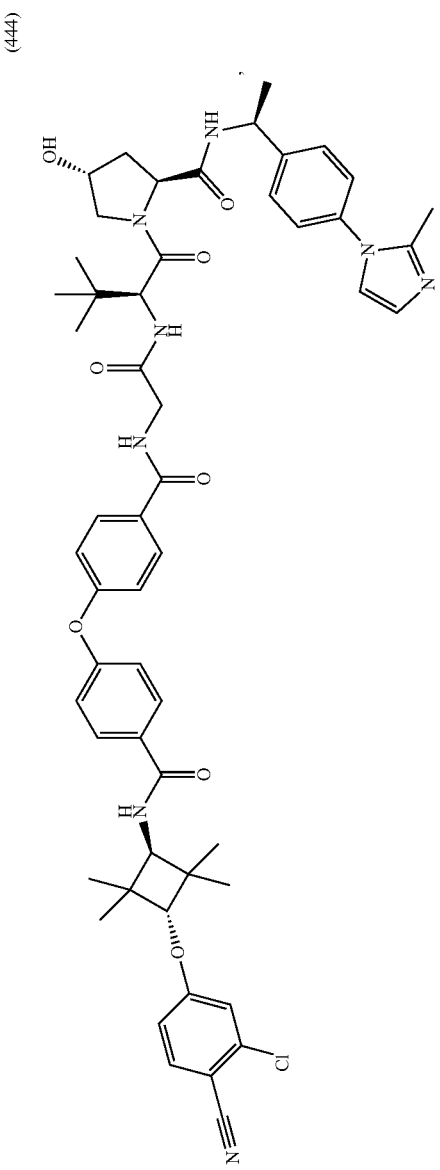

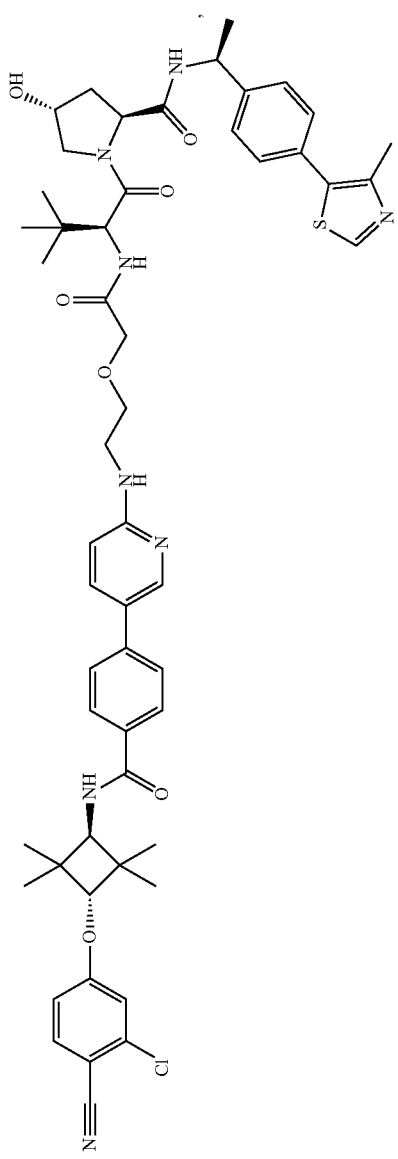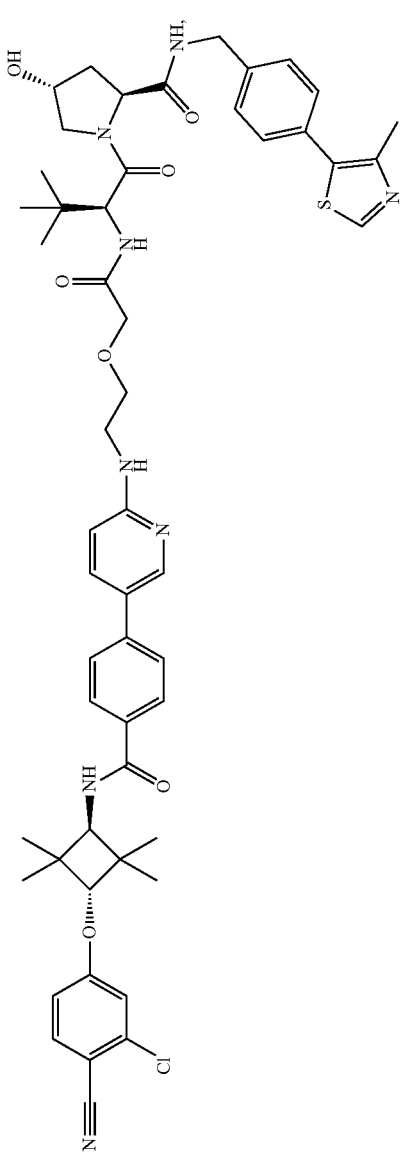

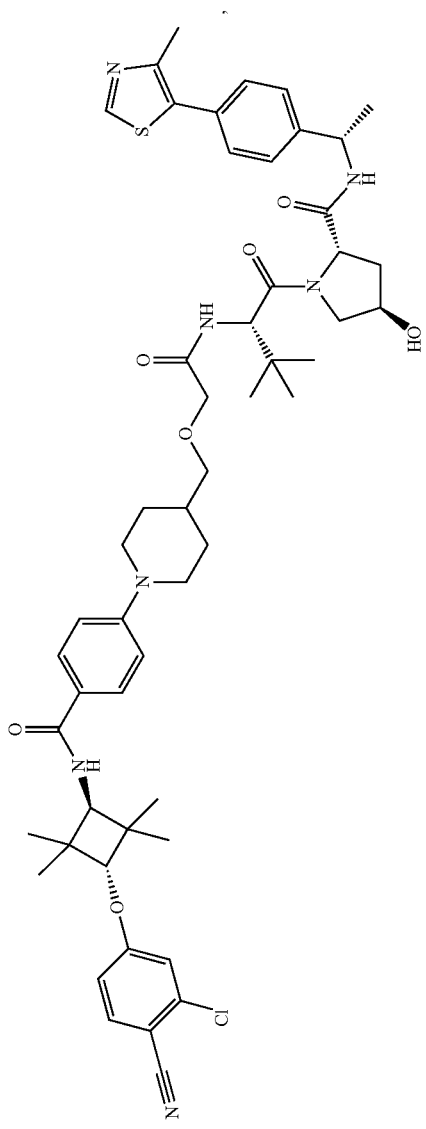
(447)
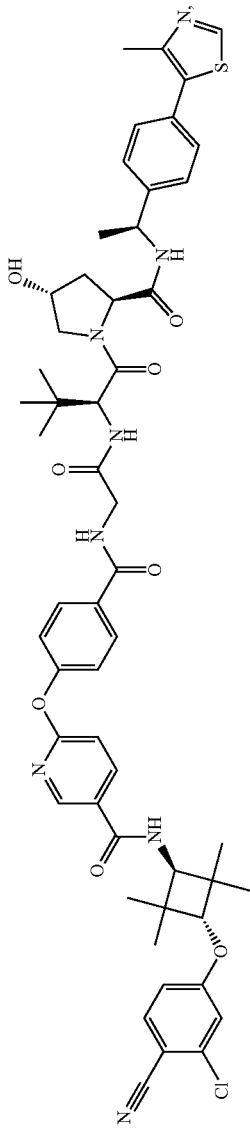
(448)

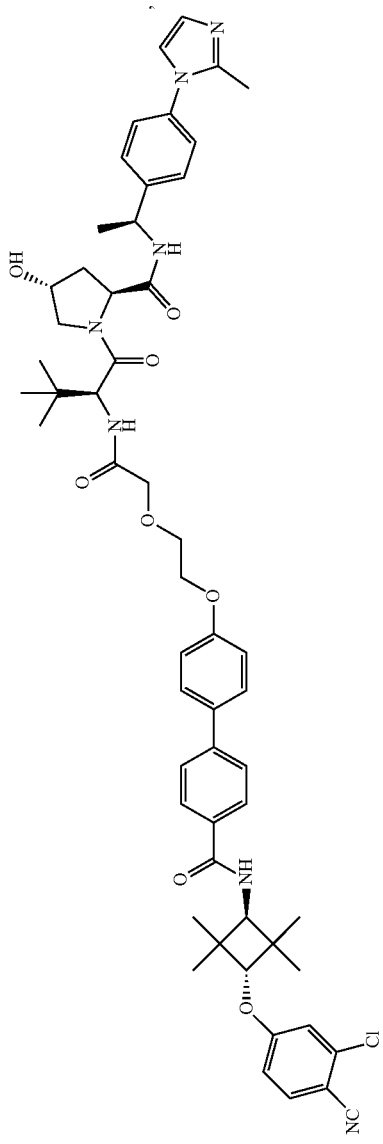
(449)
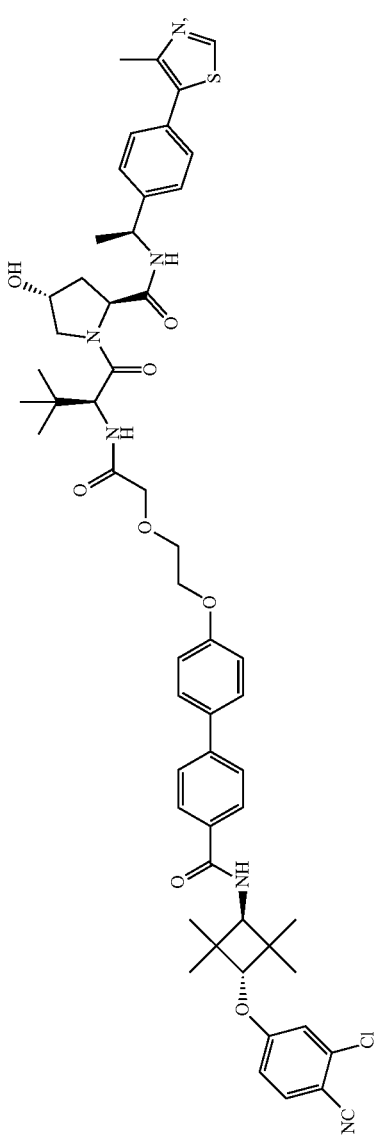
(450)

(454)
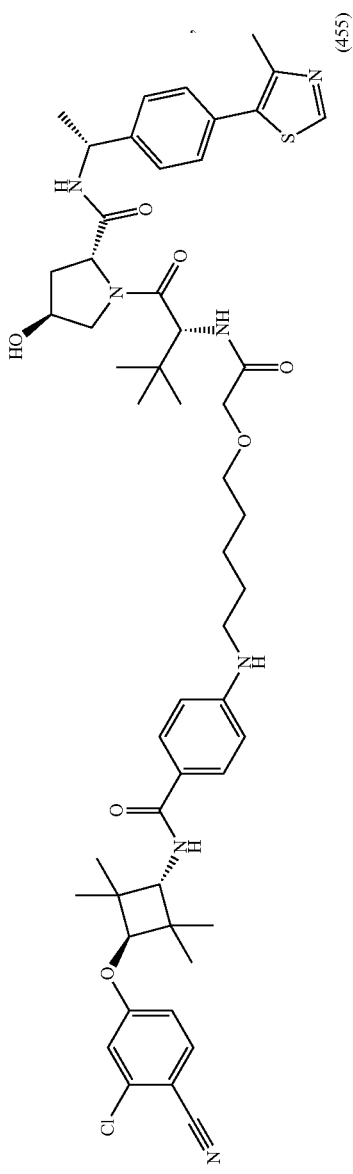
(455)
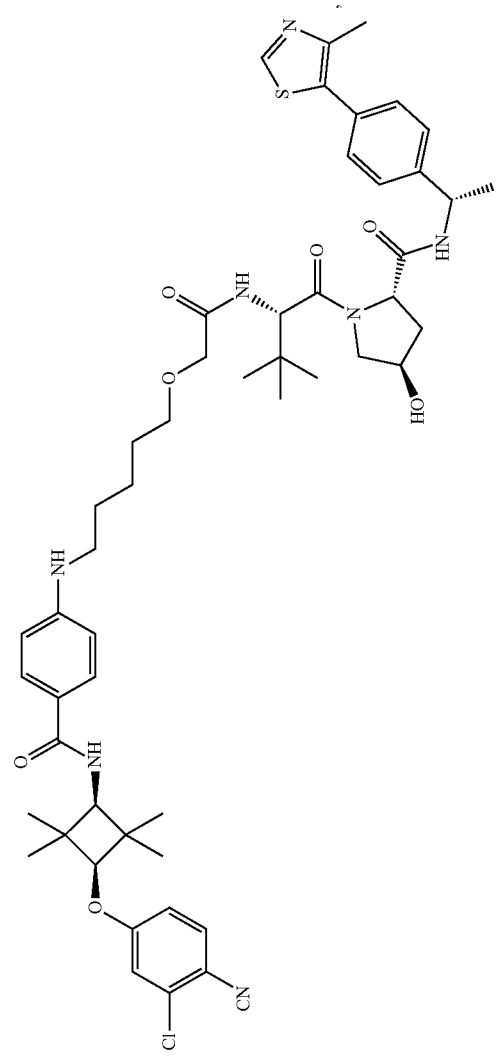

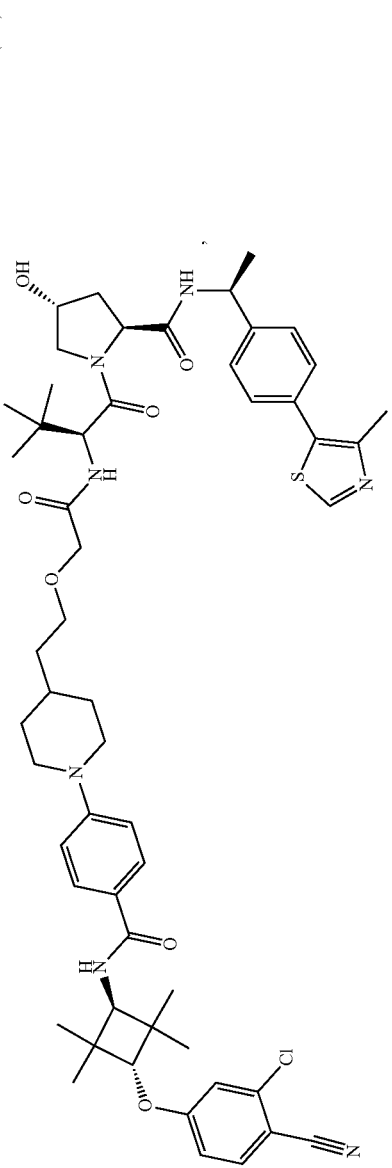
(456)
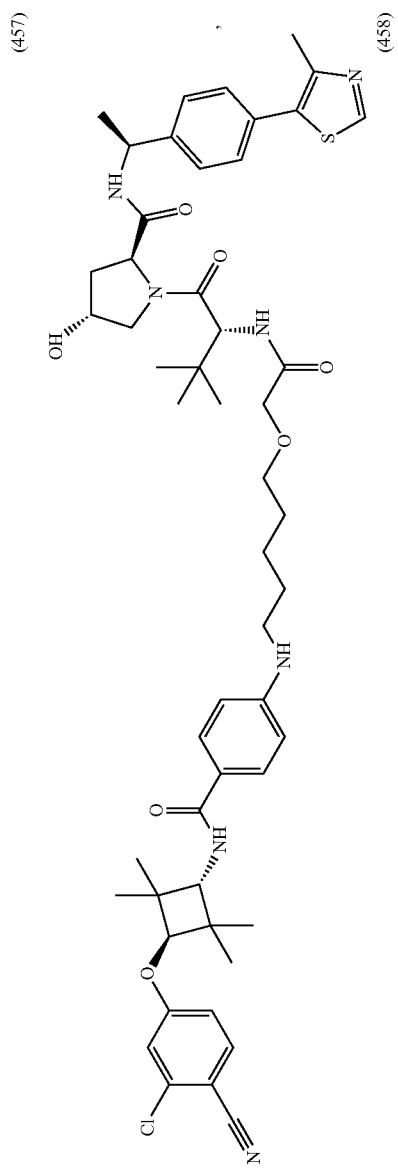
(457)
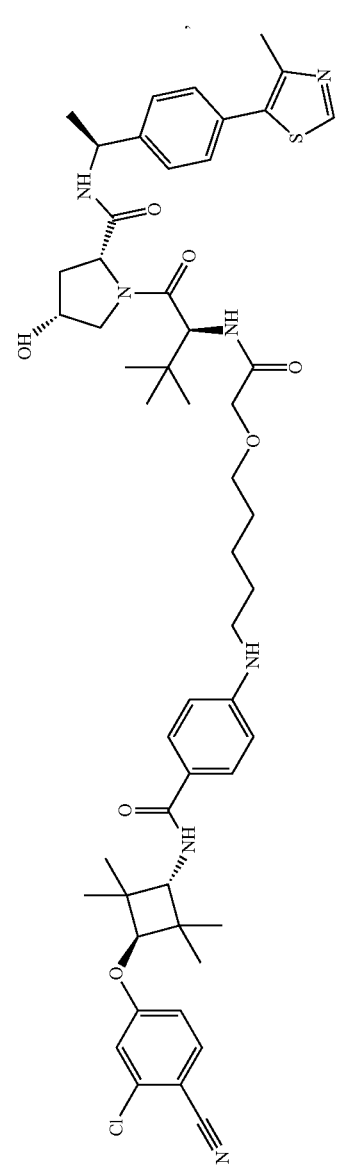
(458)

-continued
(459)
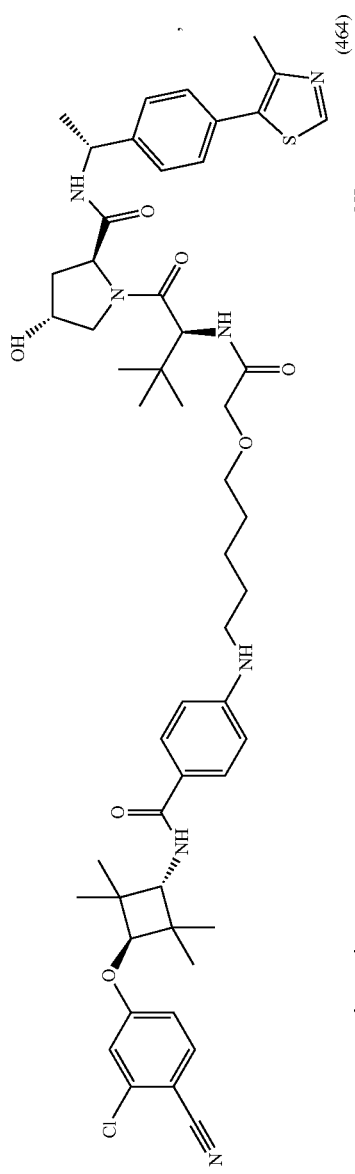
(464)
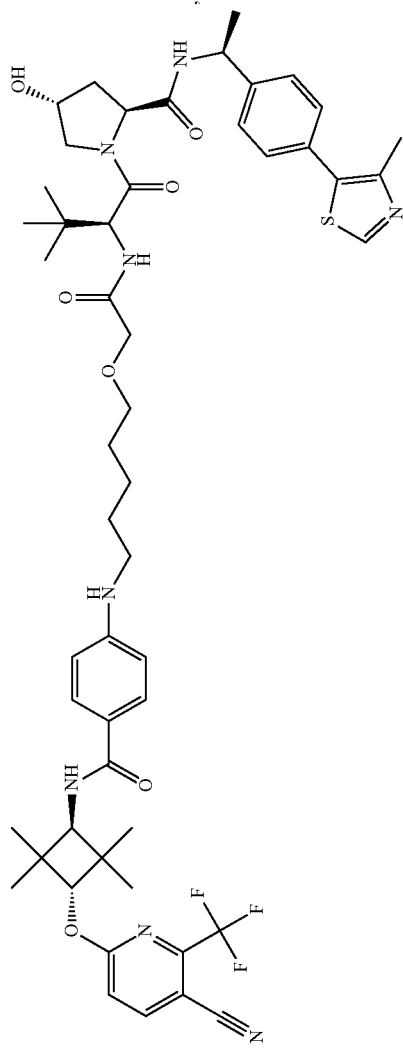

(465)
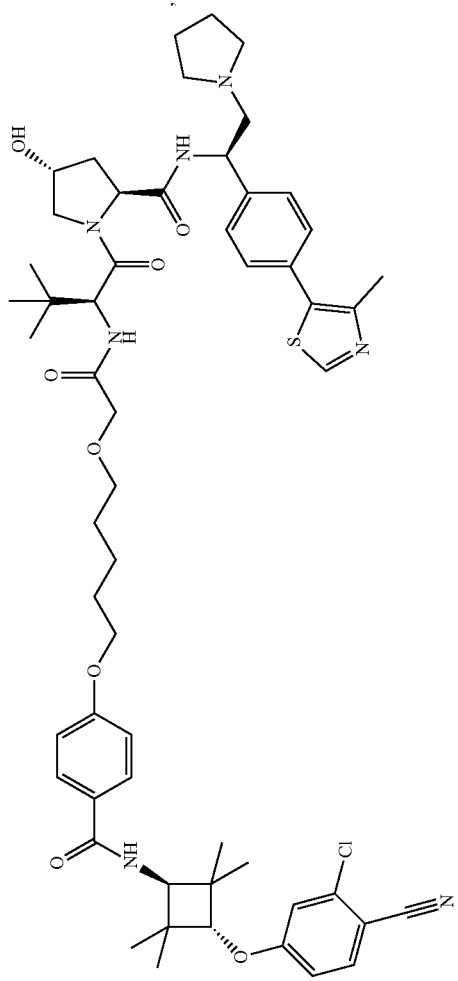
(466)
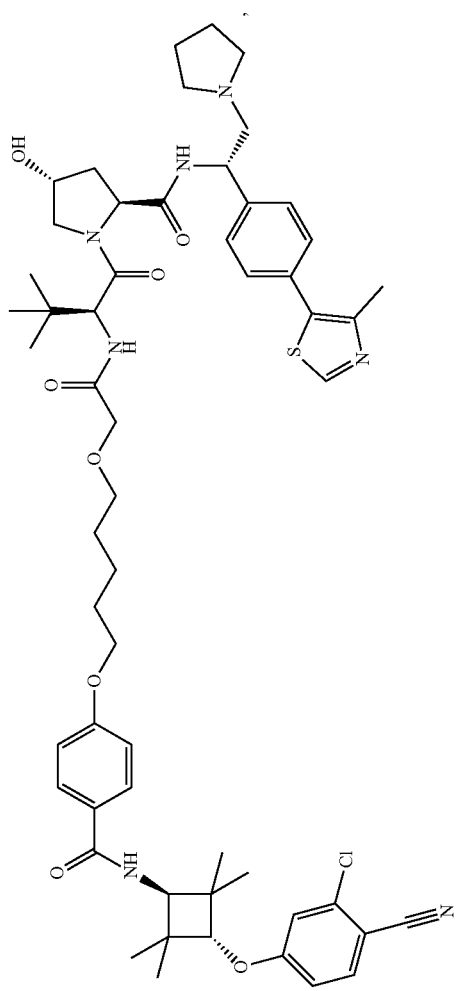

-continued
(470)
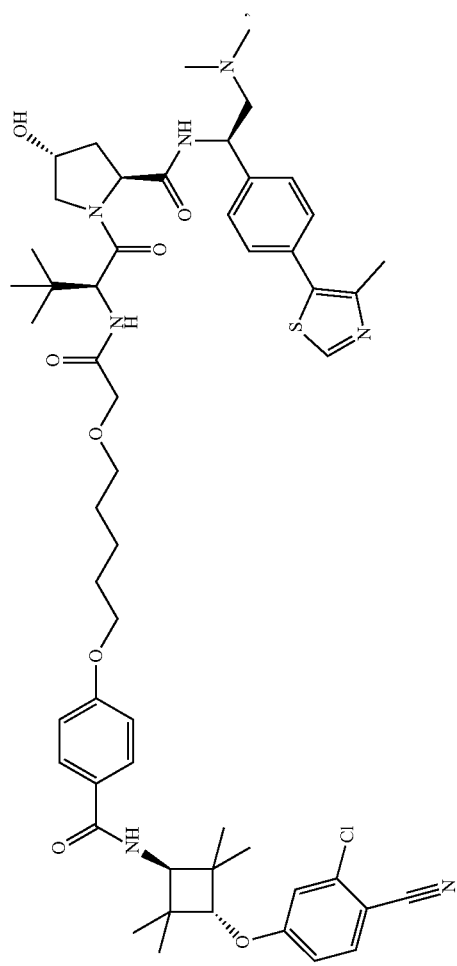
(471)
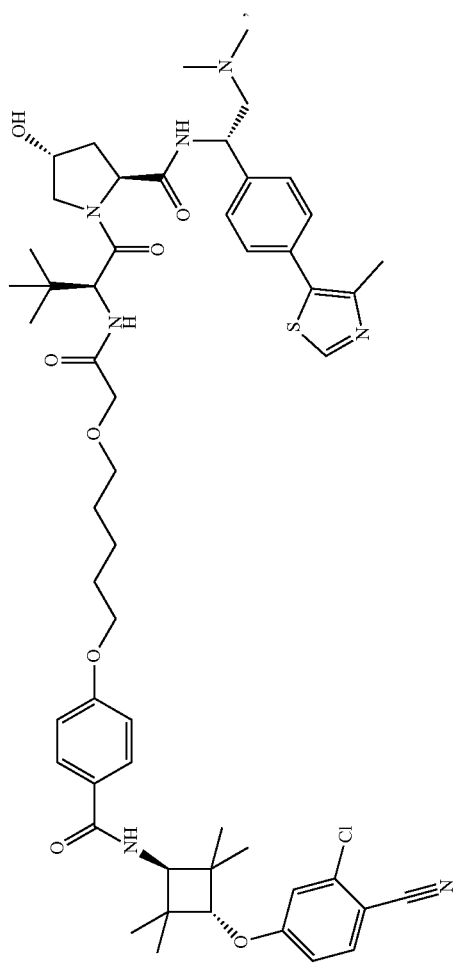

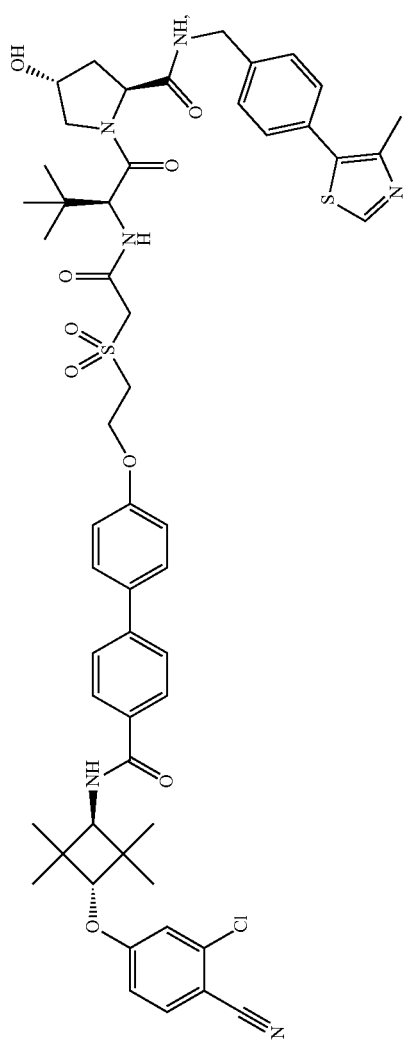
(472)
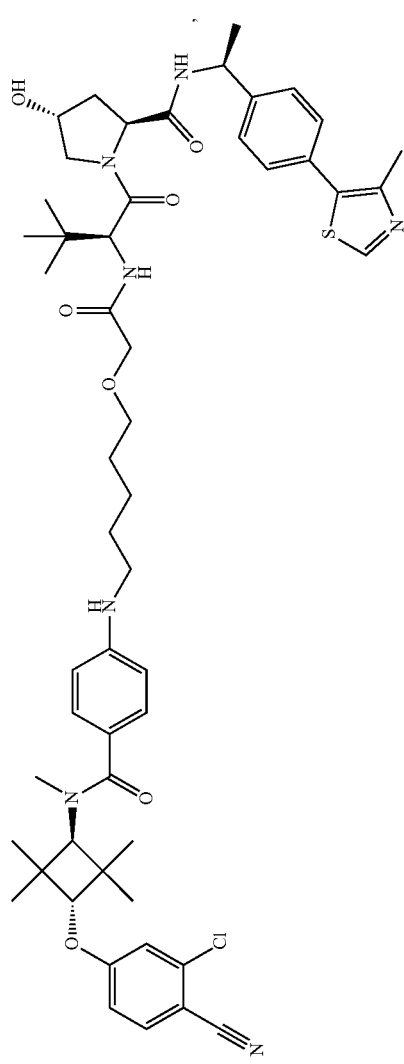
(473)

(474)
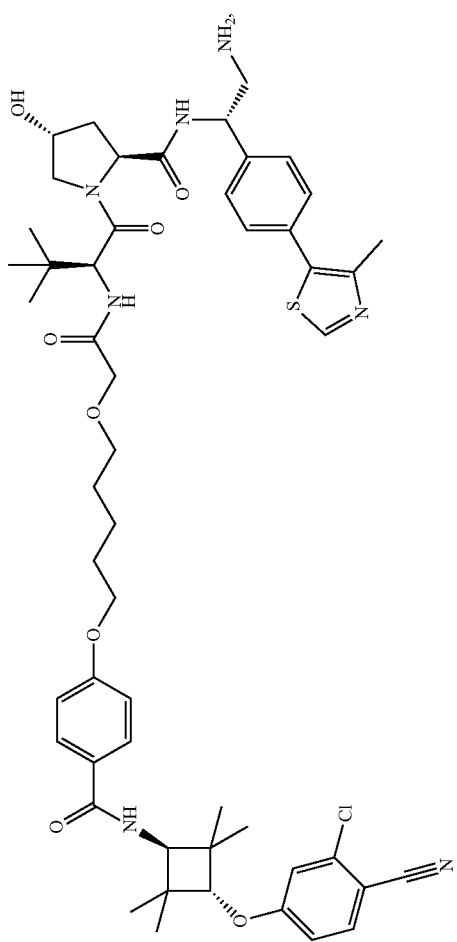
(475)
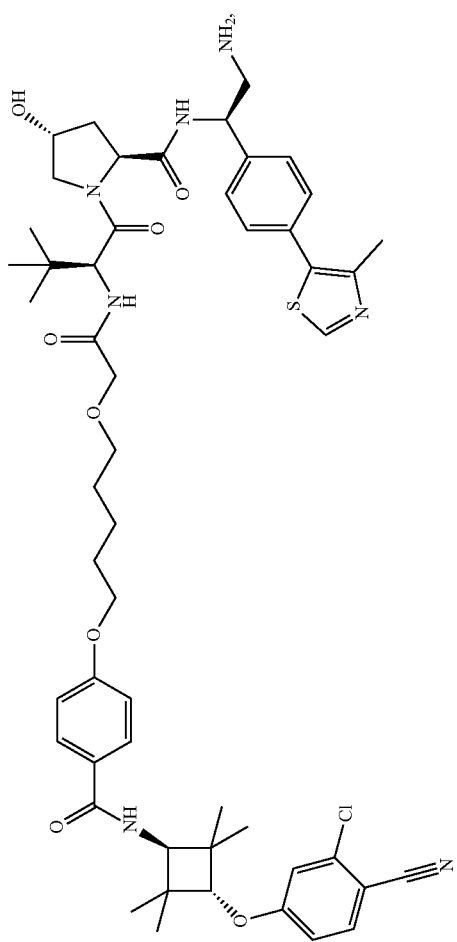

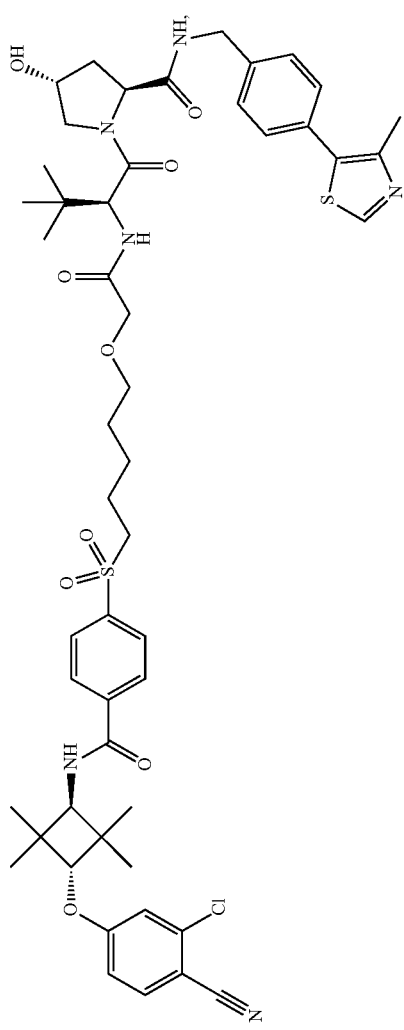
(476)
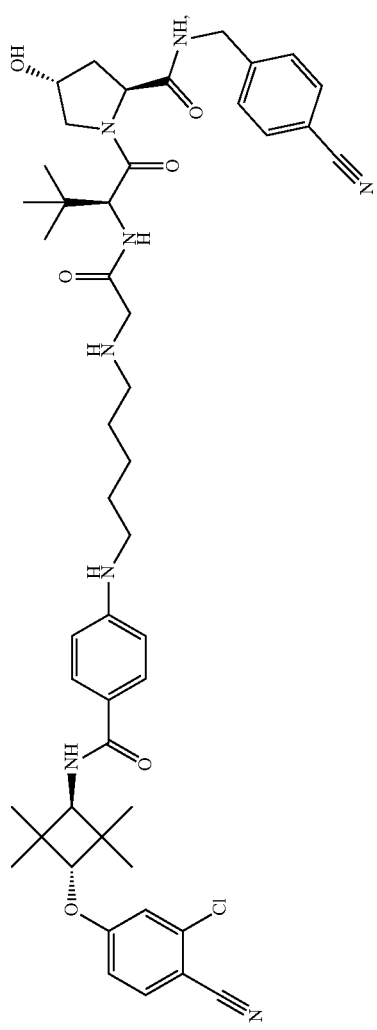
(480)

(481)
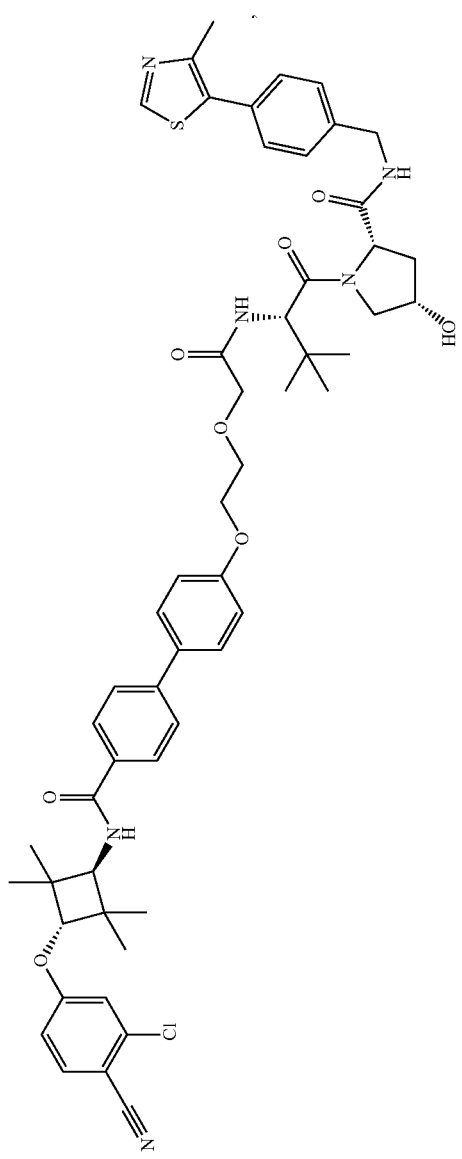
(482)
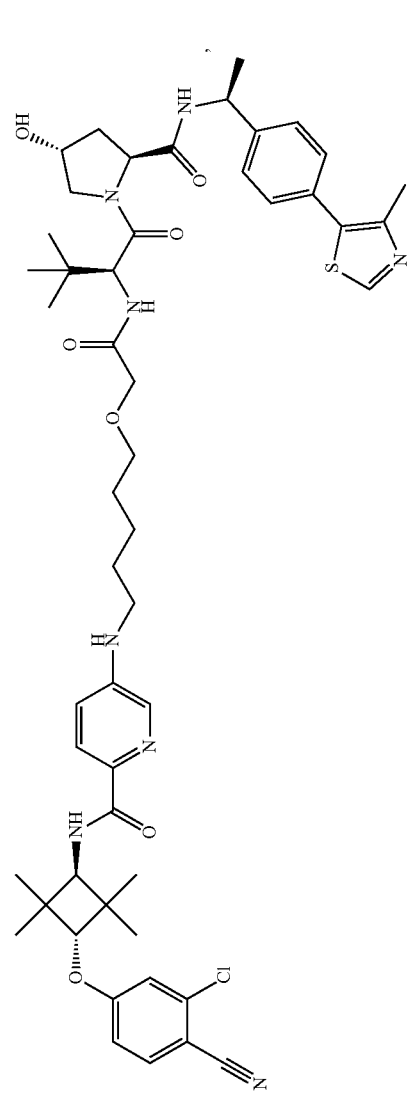

(483)
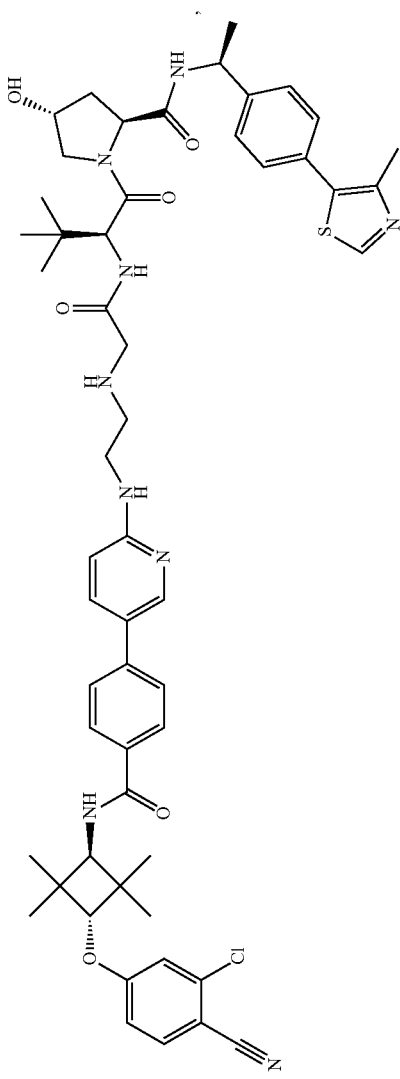
(484)
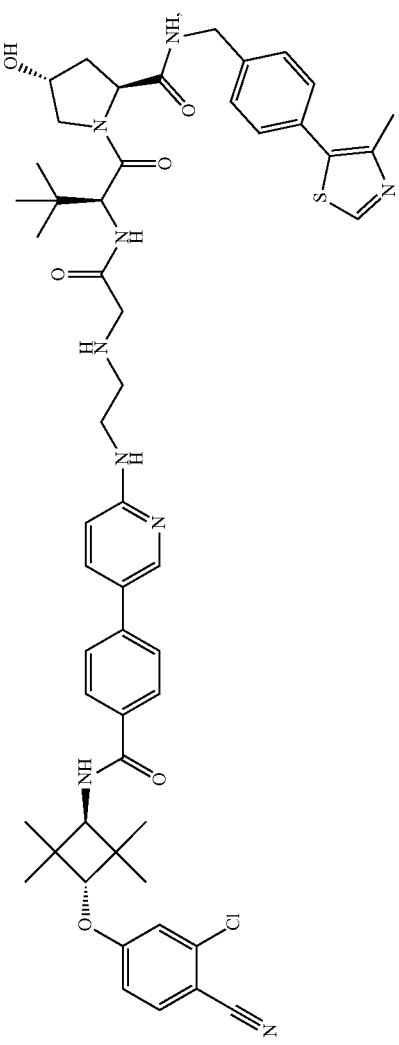

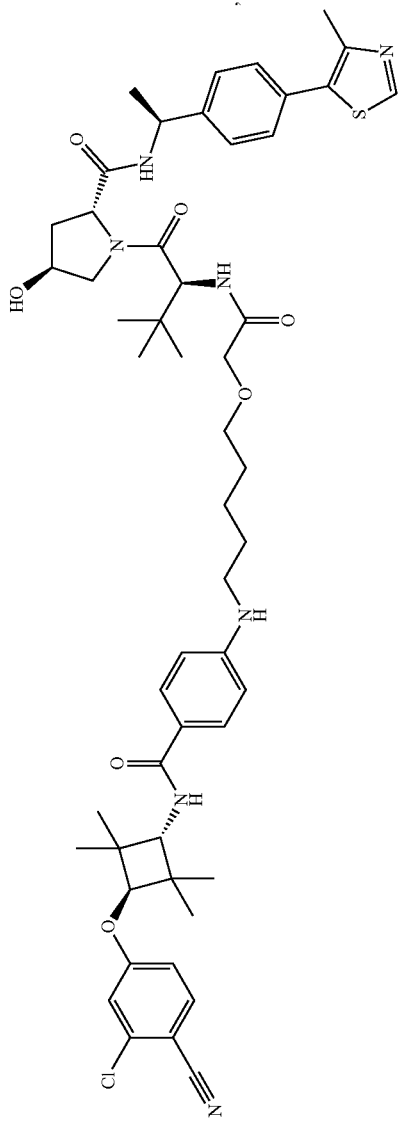
(485)
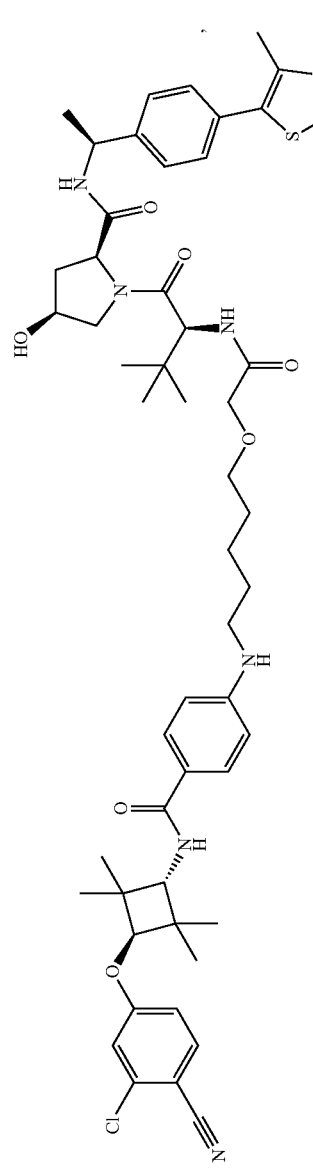
(486)
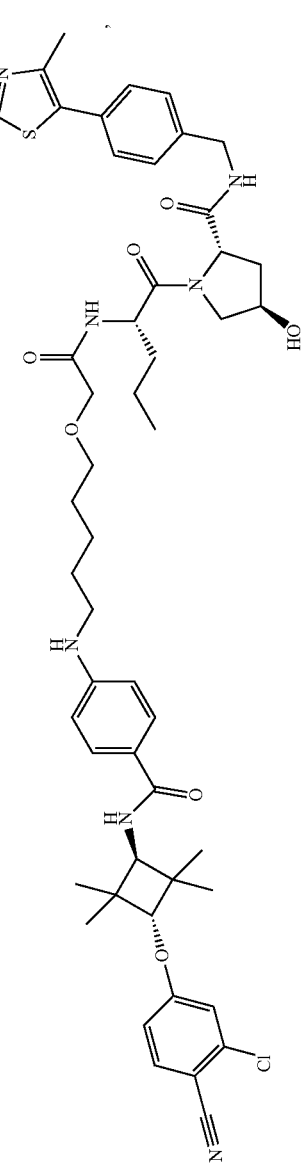
(487)

881
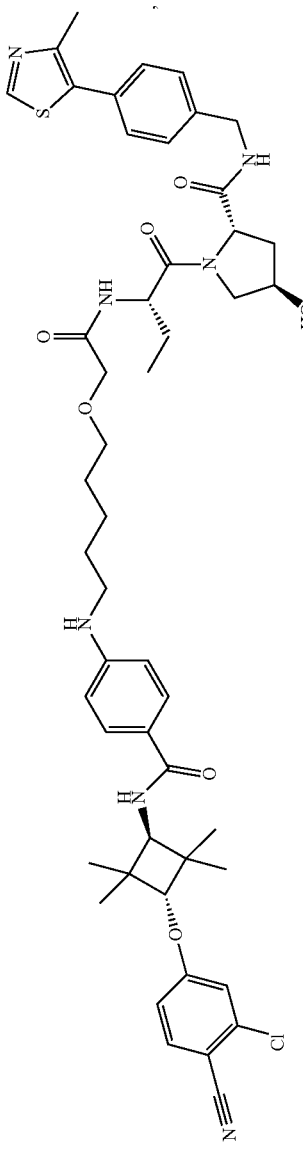
(488)
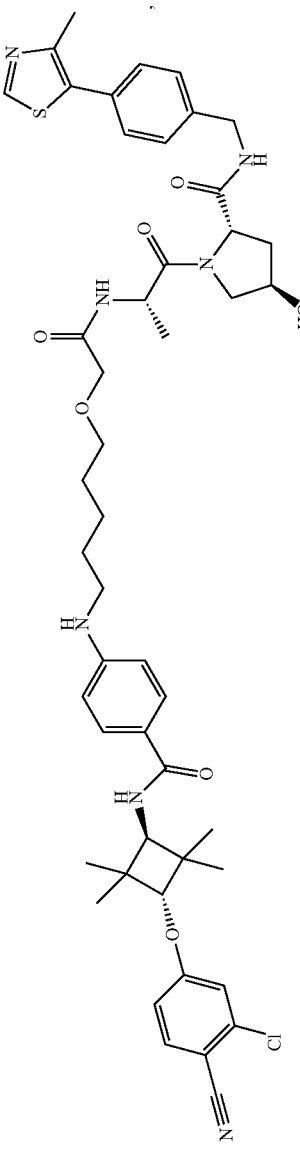
(489)
882
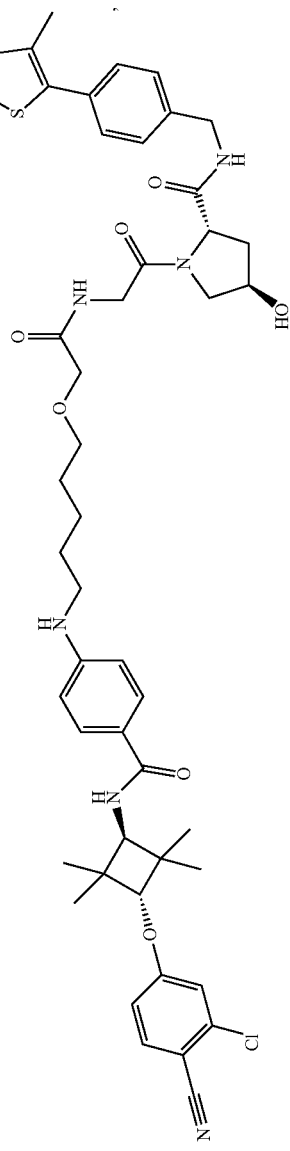
(490)

(491)
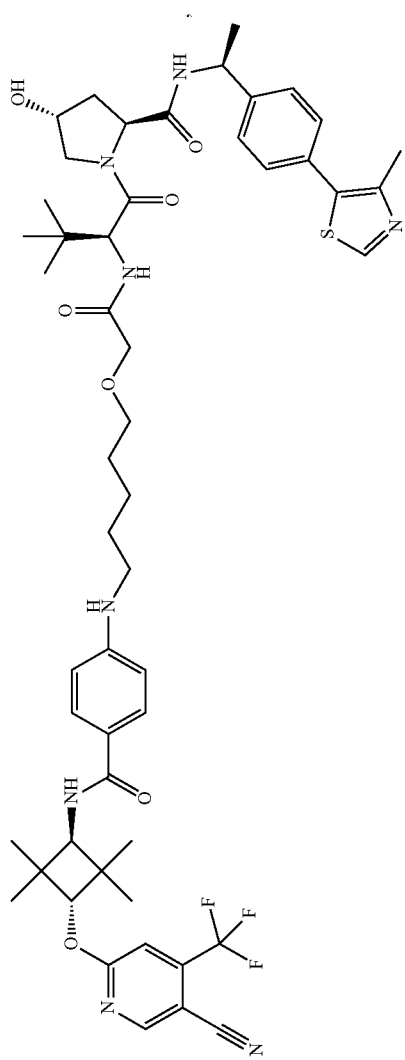
(492)
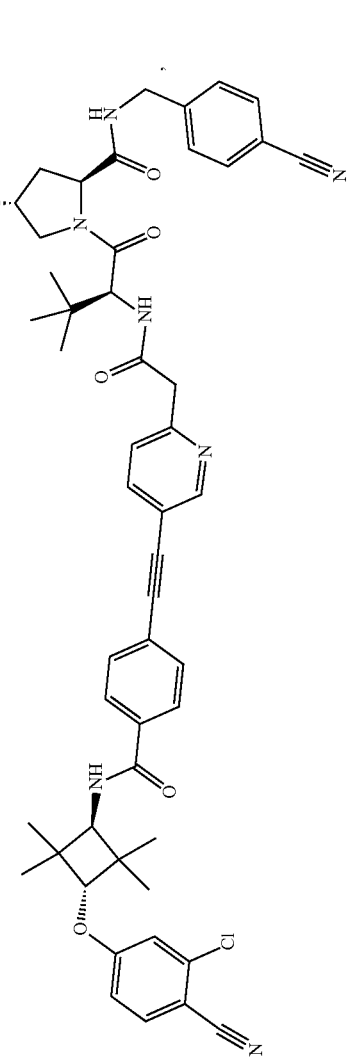

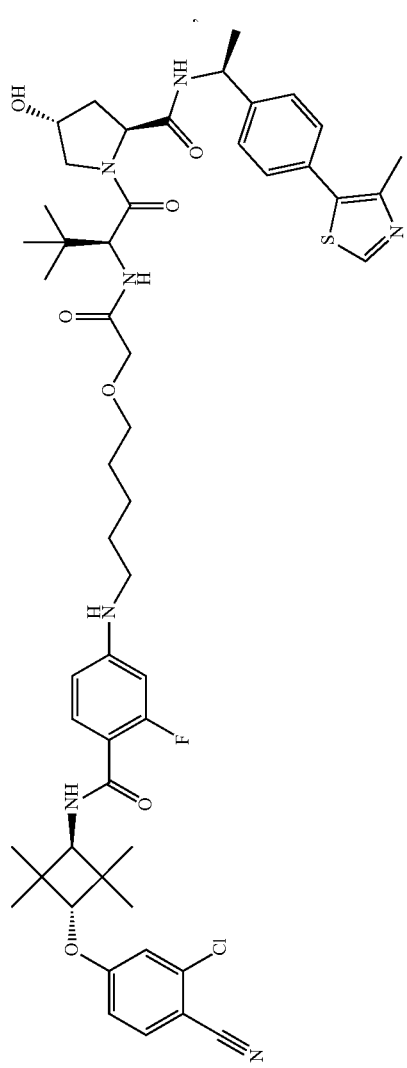
(495)
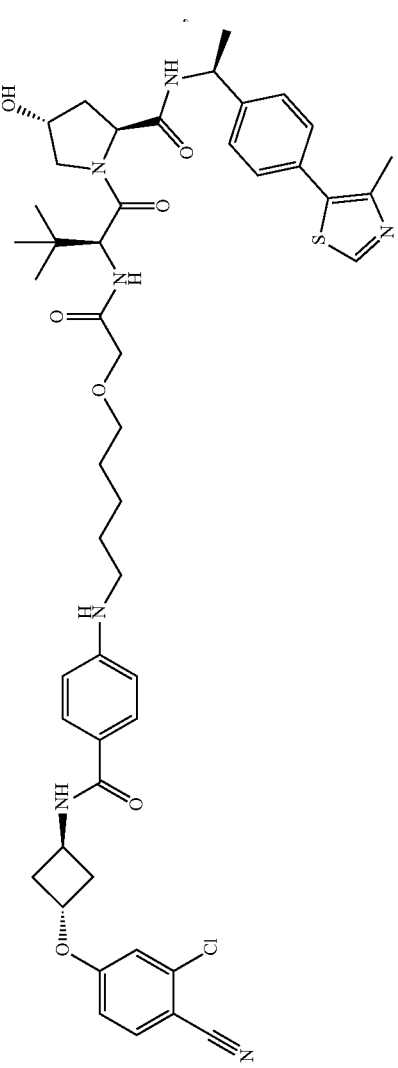
(496)

(497)
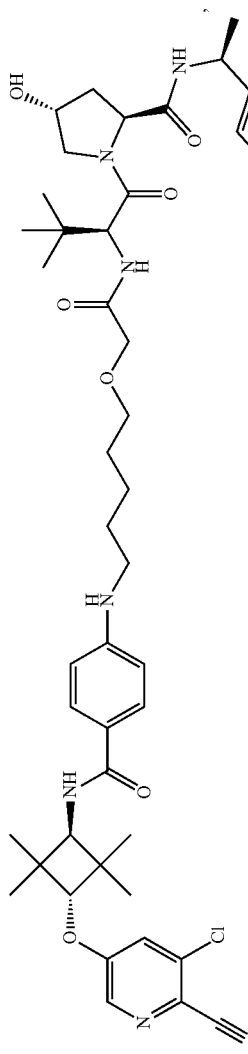
(498)
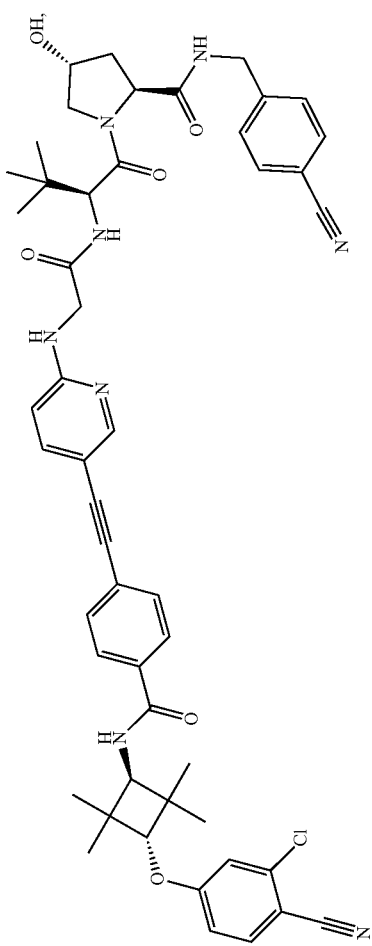

(499)
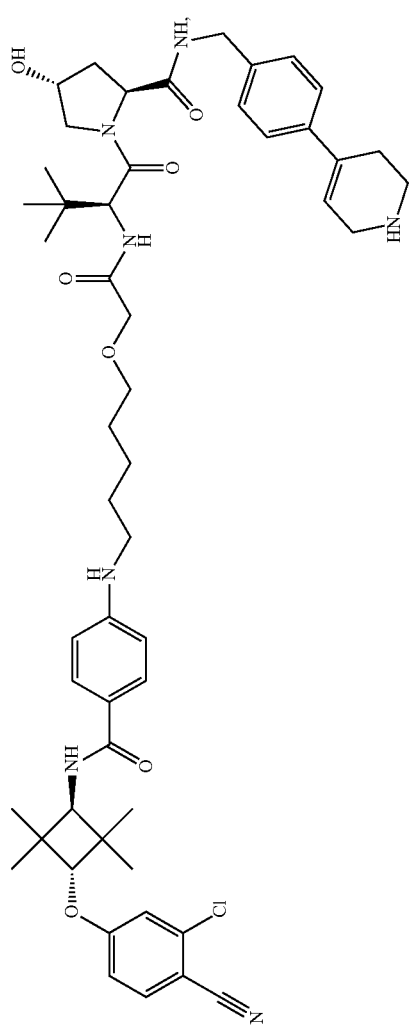
(500)
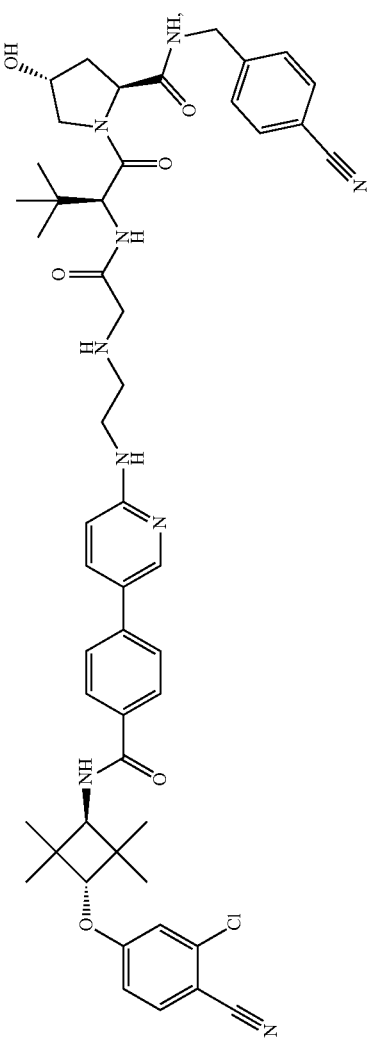

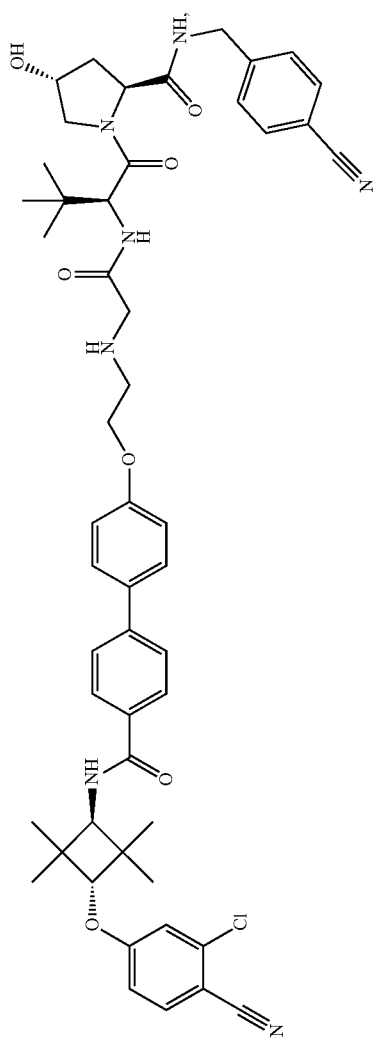
(501)
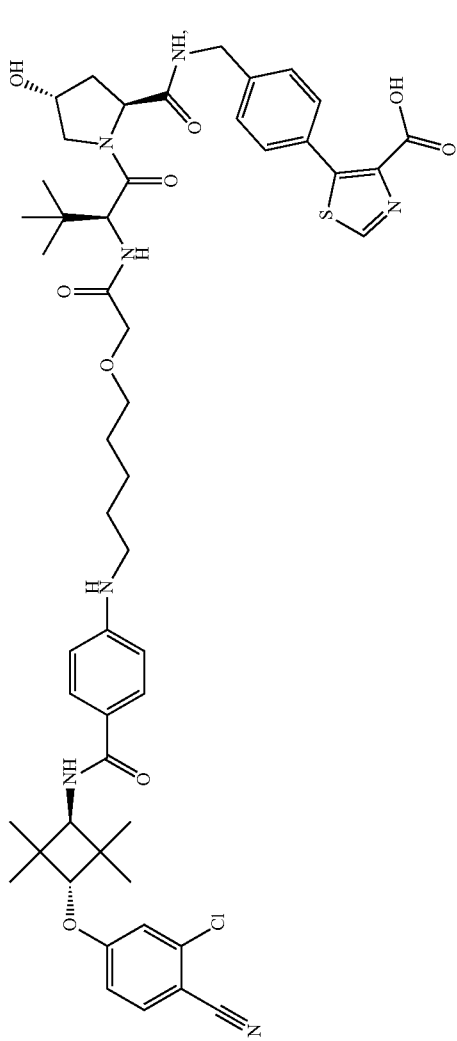
(502)

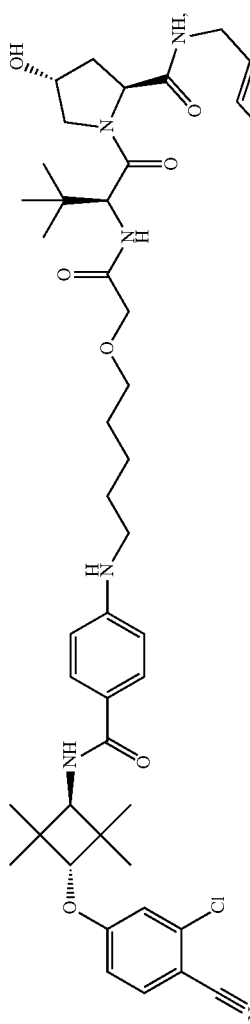
(503)
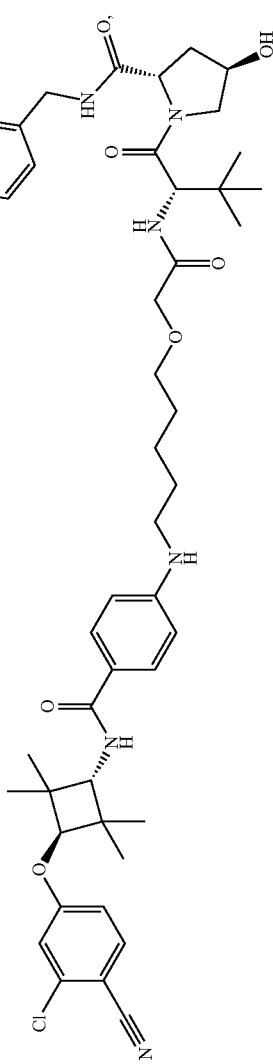
(504)

(505)
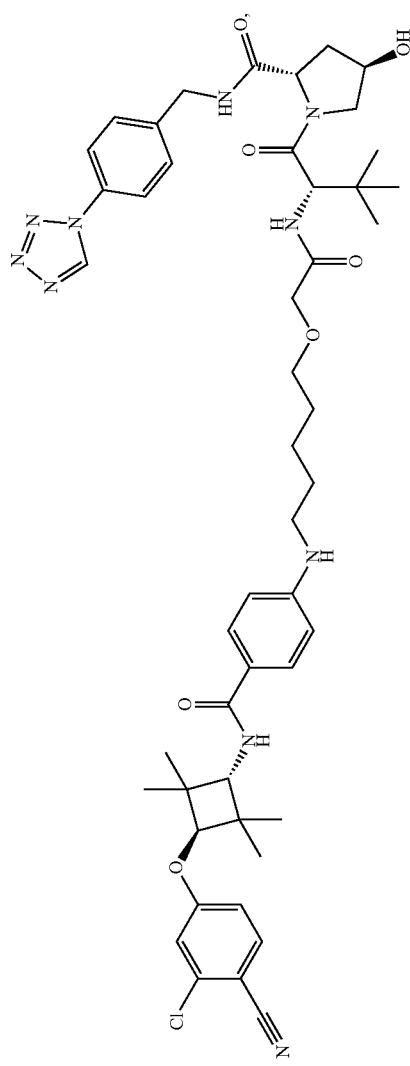
(506)
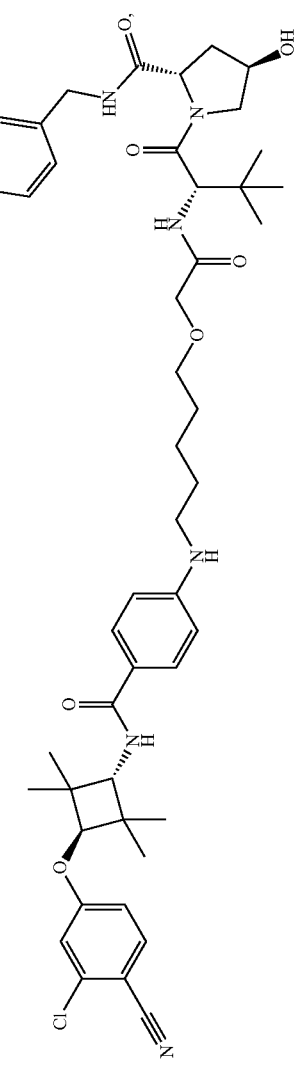

(508)
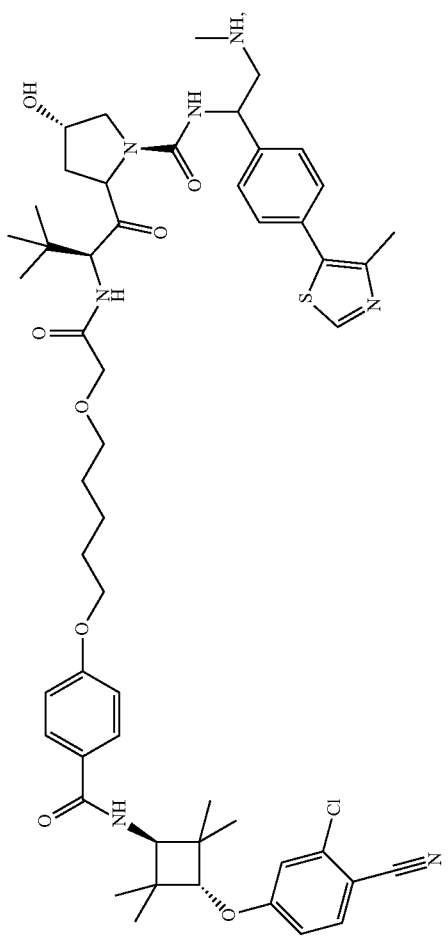
(510)
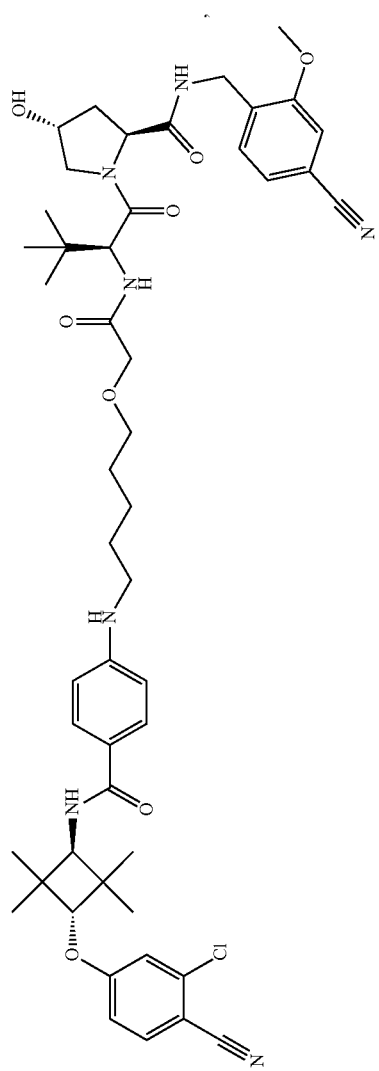

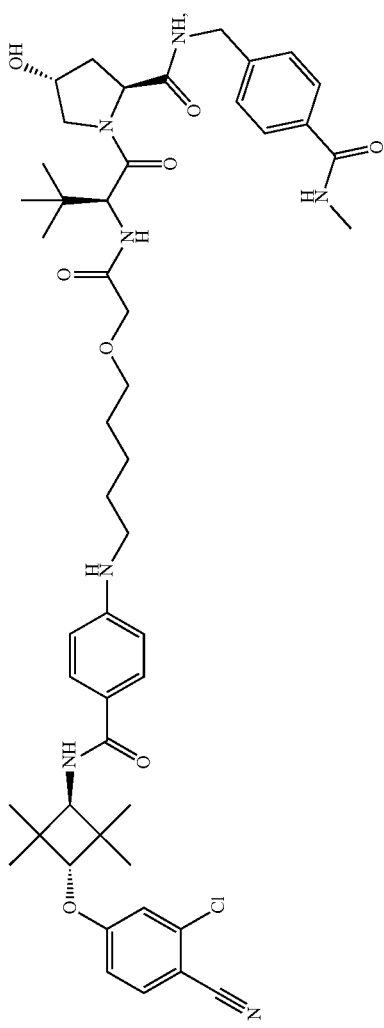
(511)
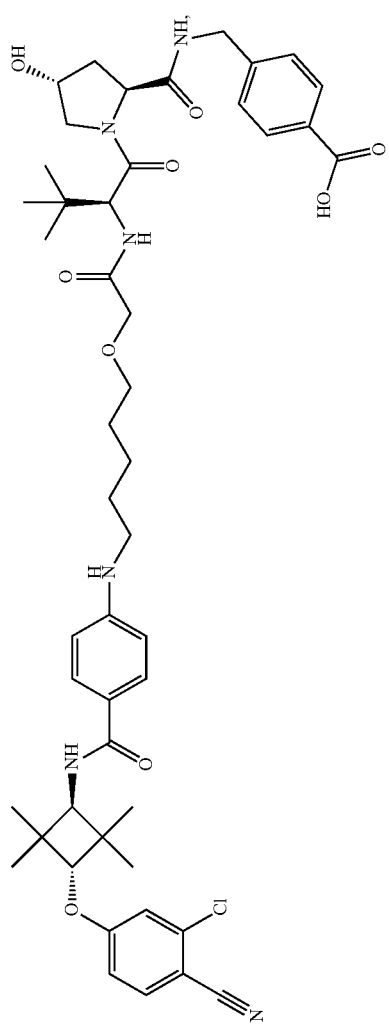
(512)

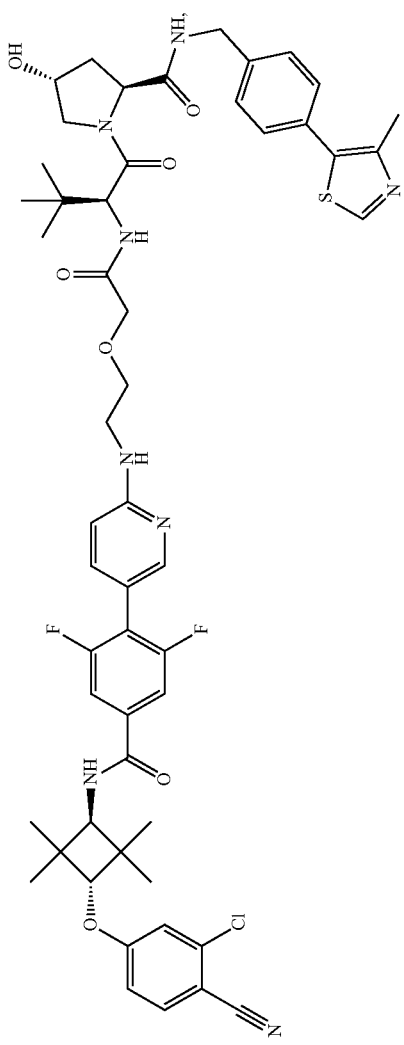
(513)
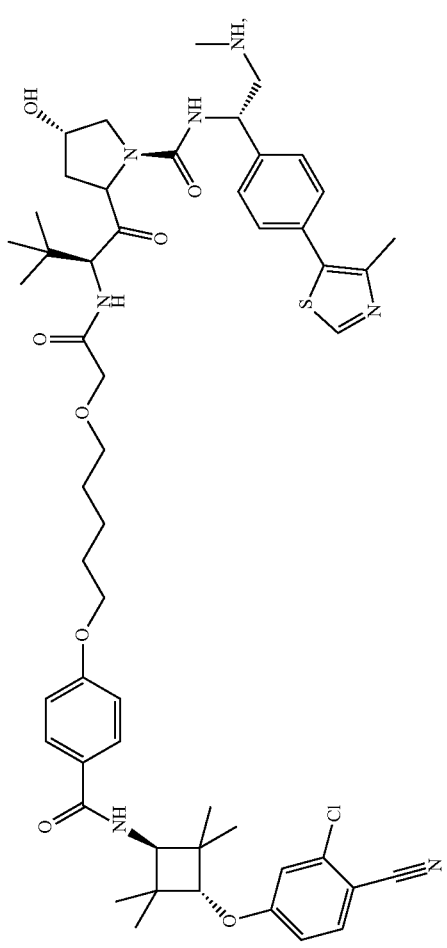
(514)

(515) 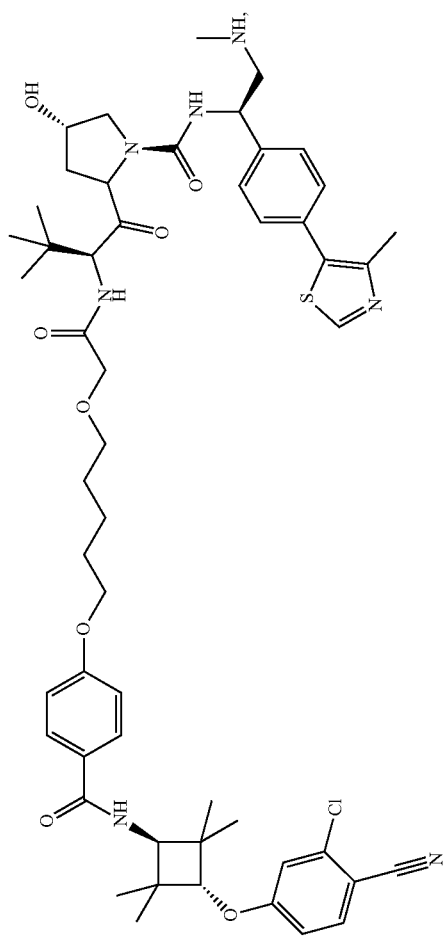
(516) 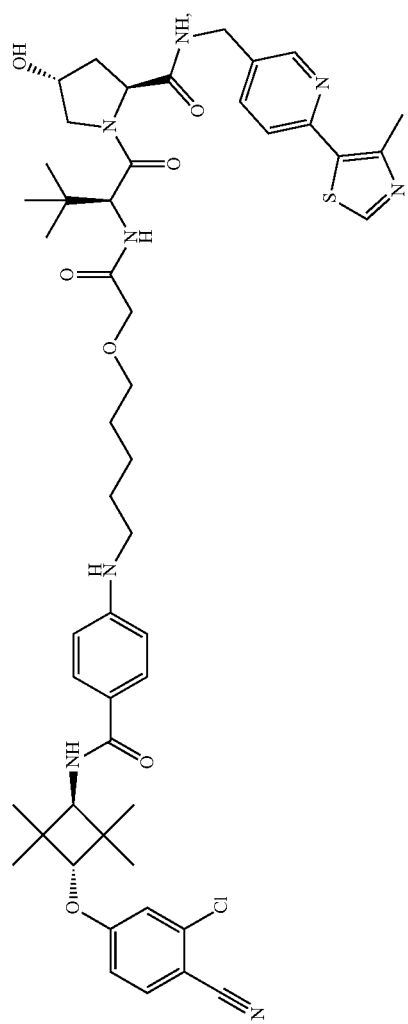

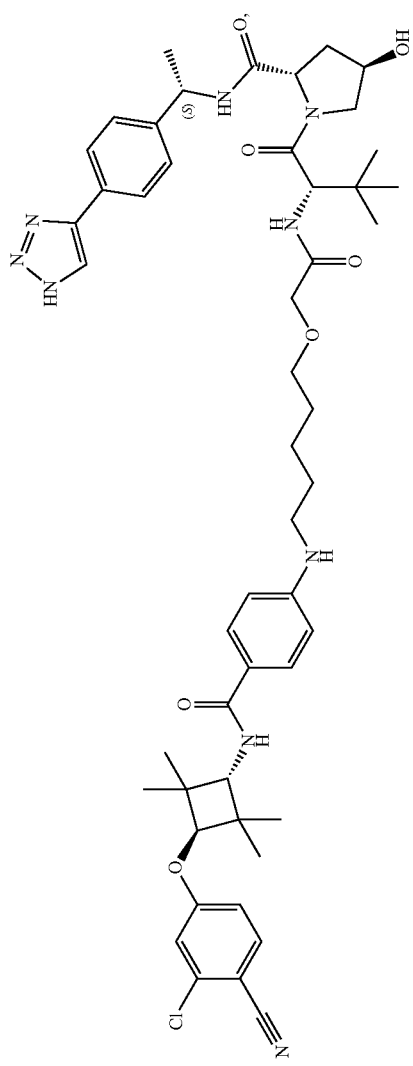
(517)
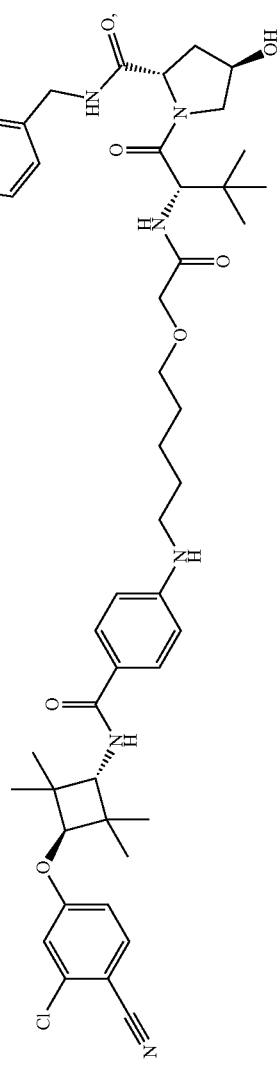
(518)

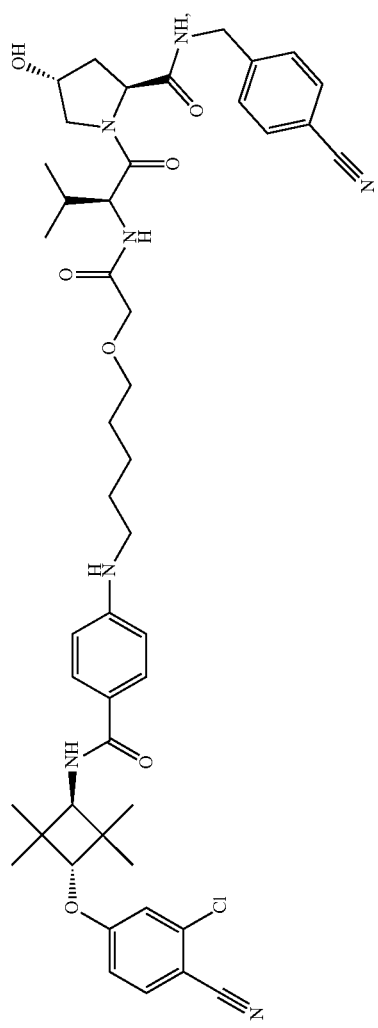
(520)
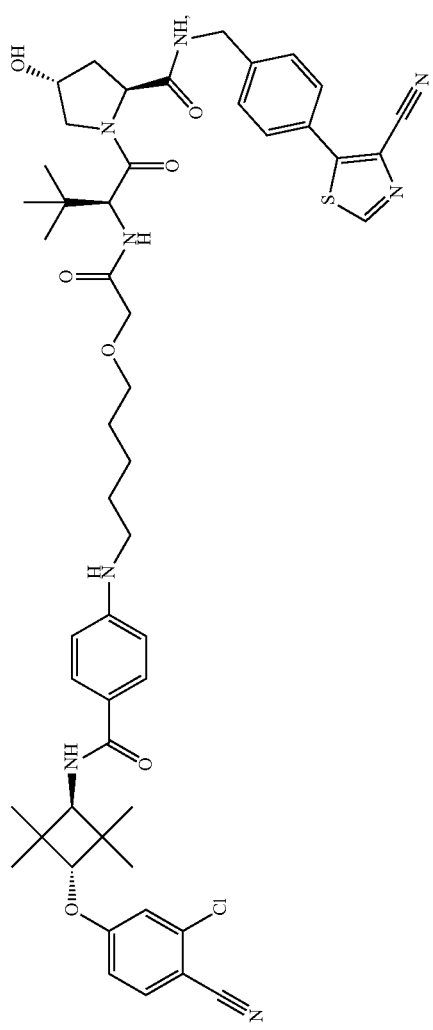
(521)

909 910
(522) 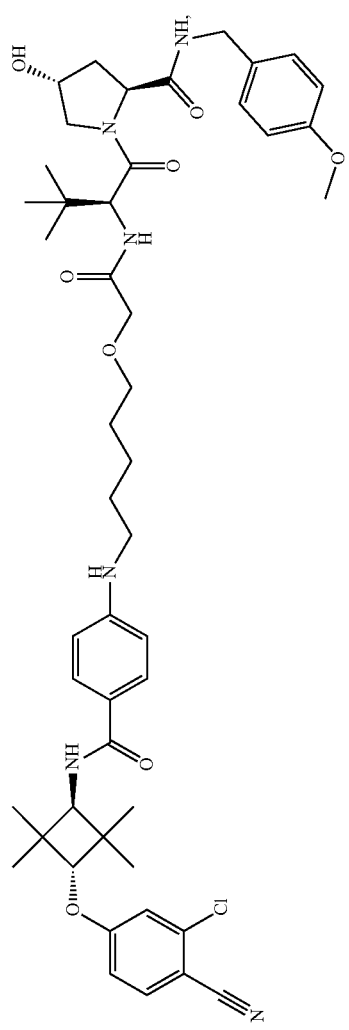
(523) 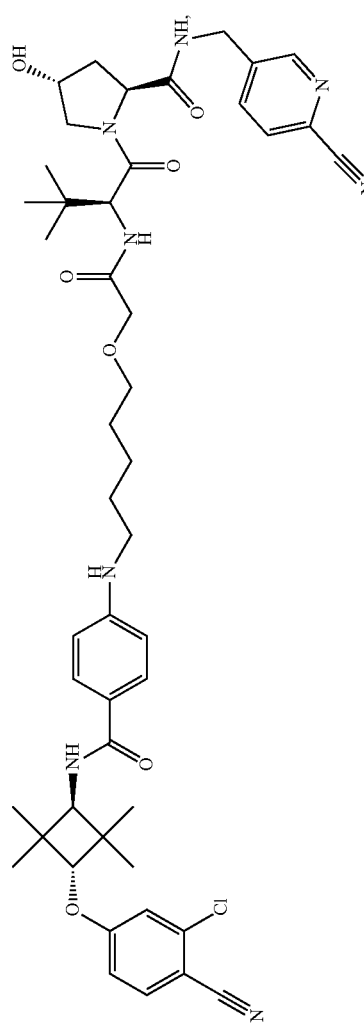
(524) 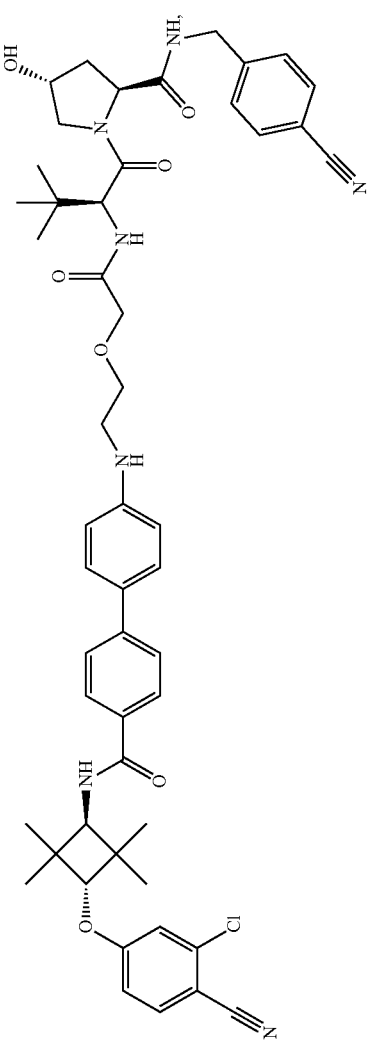

(525) 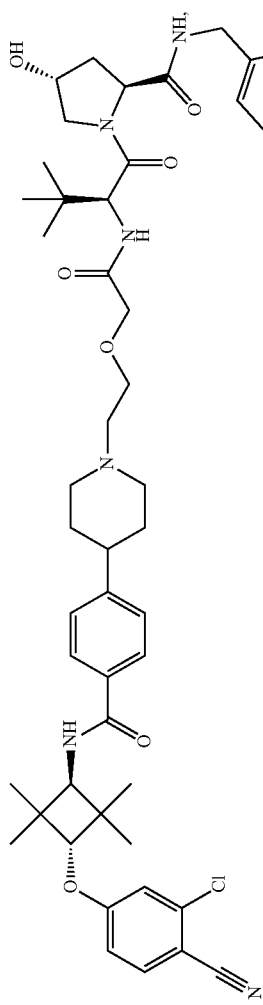
(526) 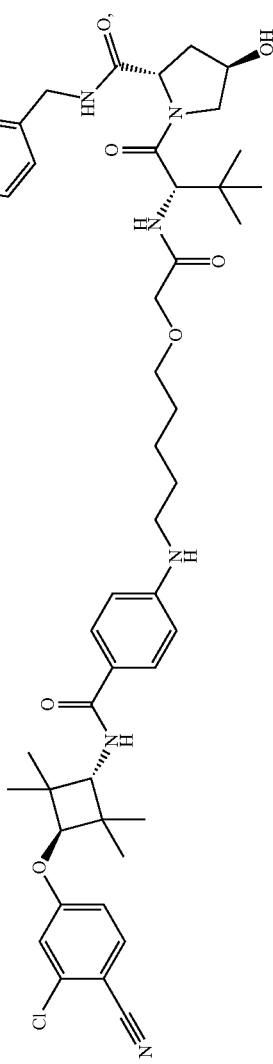

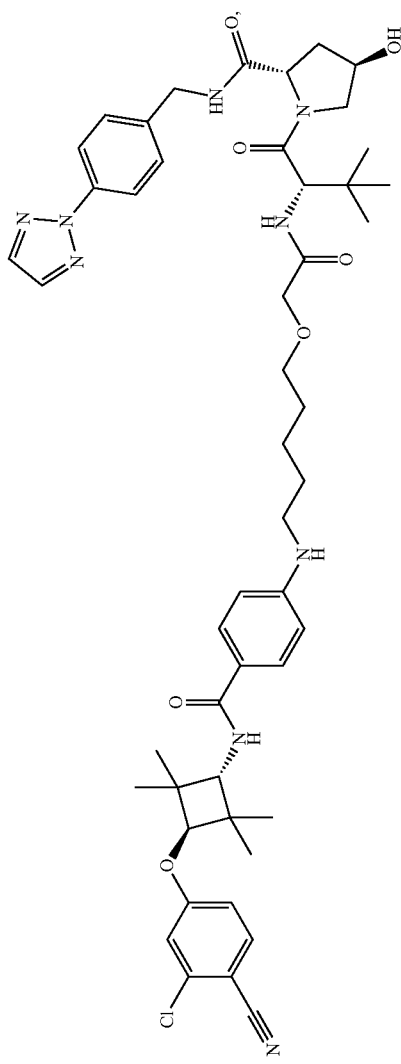
(527)
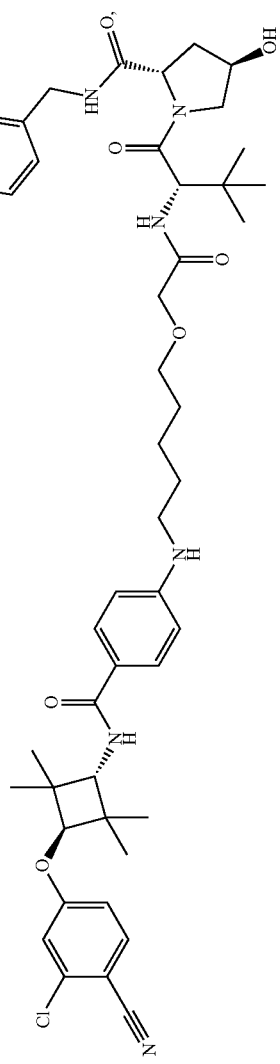
(528)

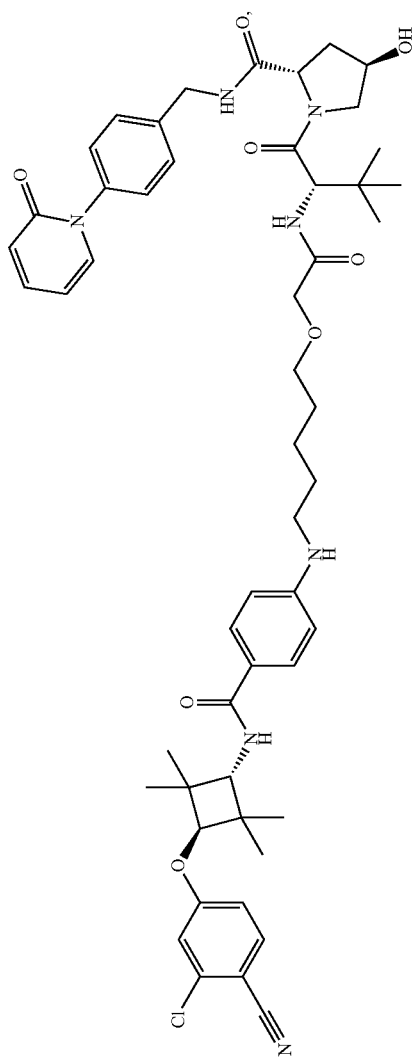
(529)
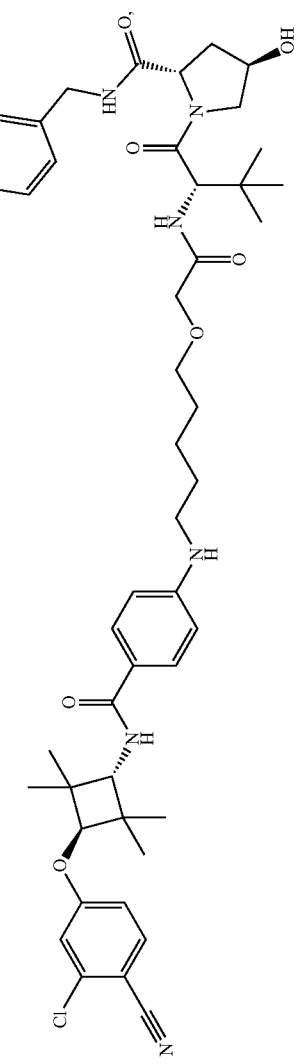
(530)

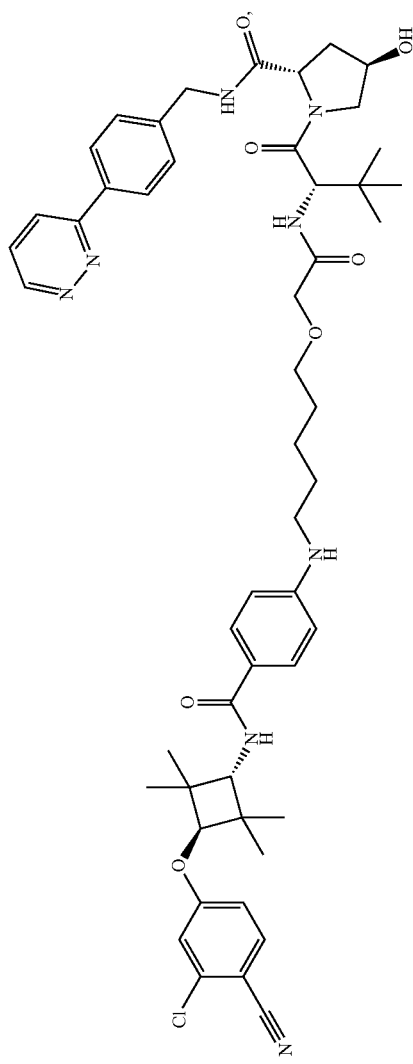(531)
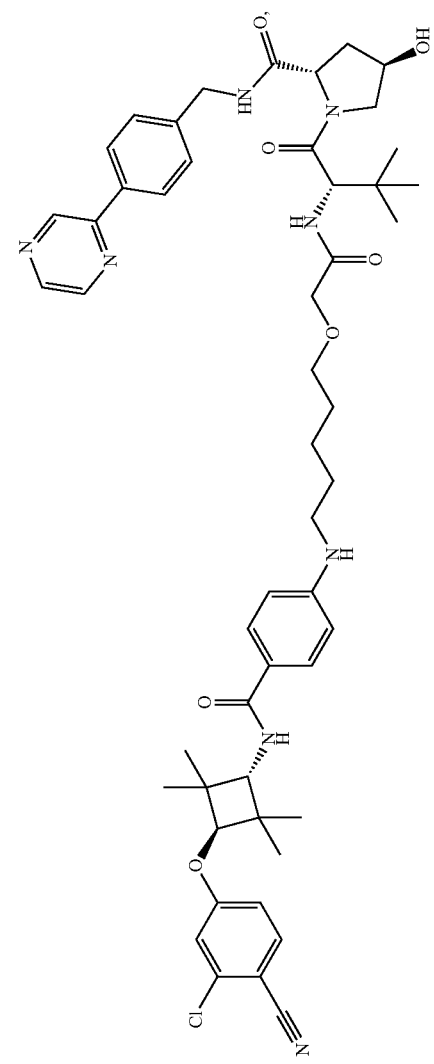(532)

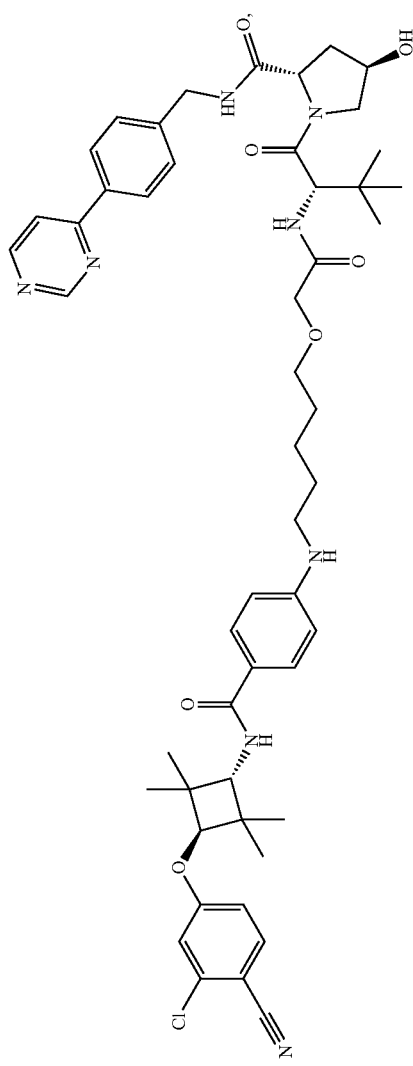
(533)
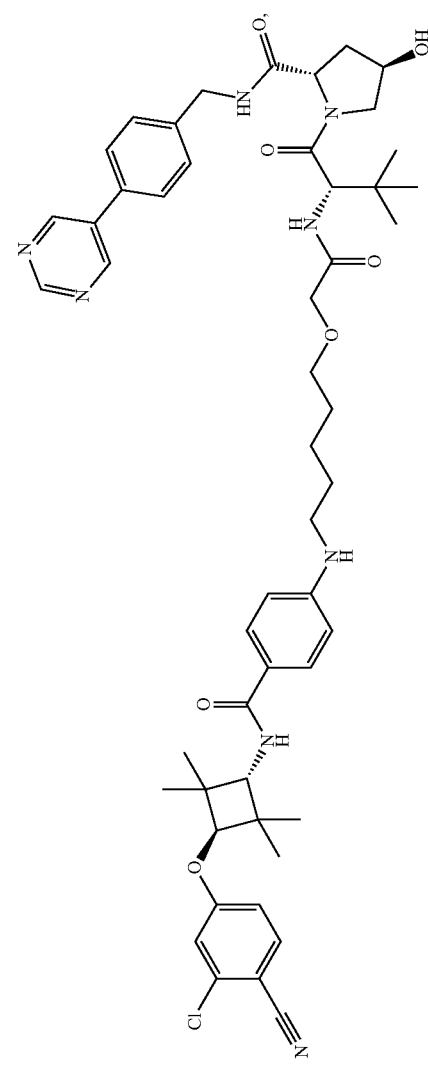
(534)

921 922
(535) (536)
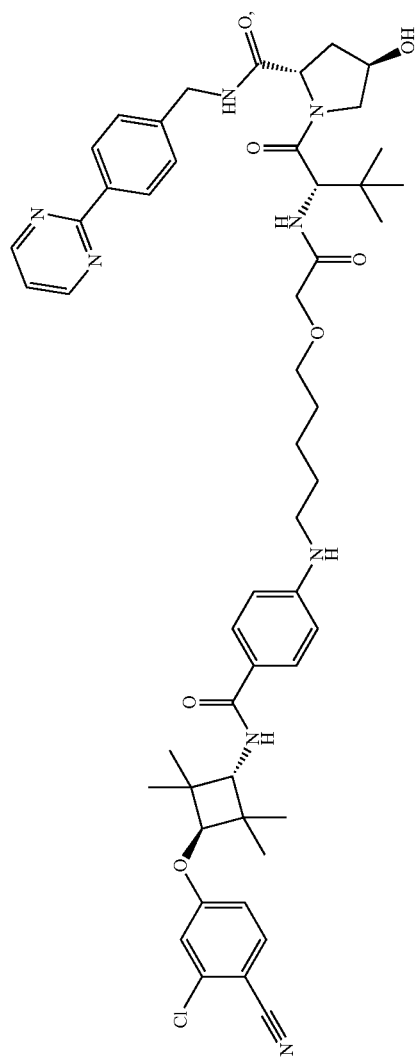
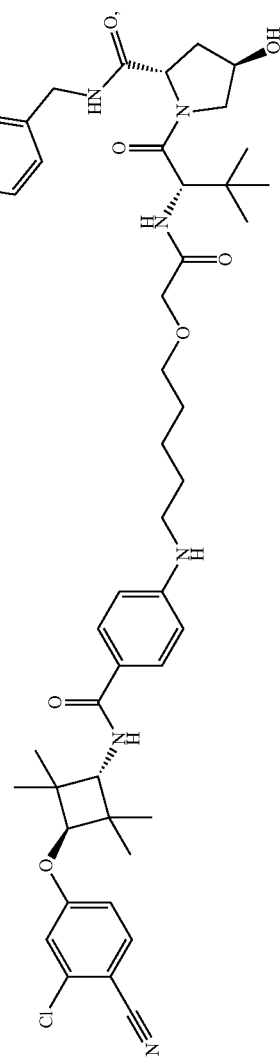

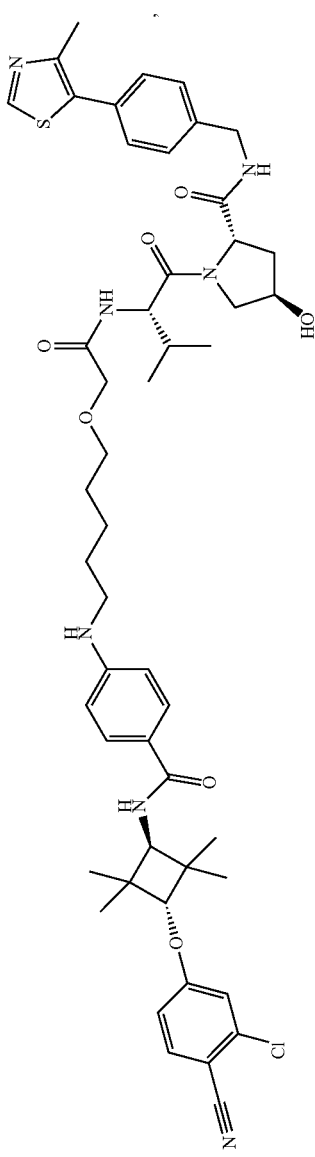
(537)
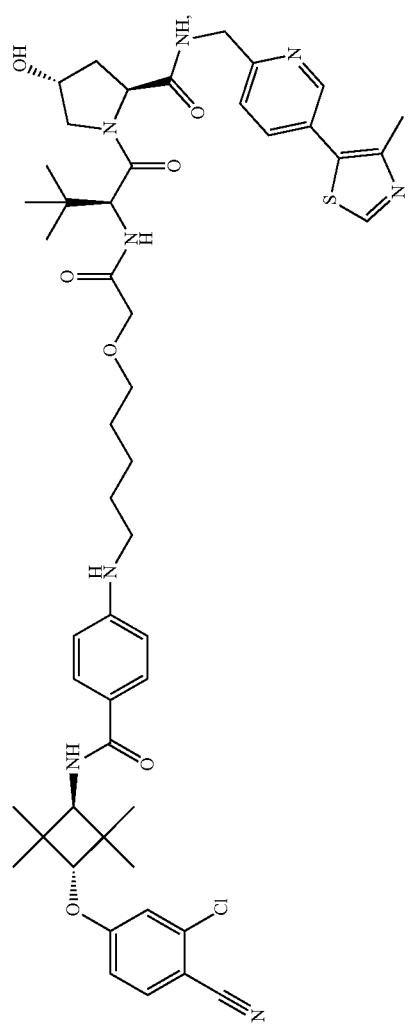
(538)

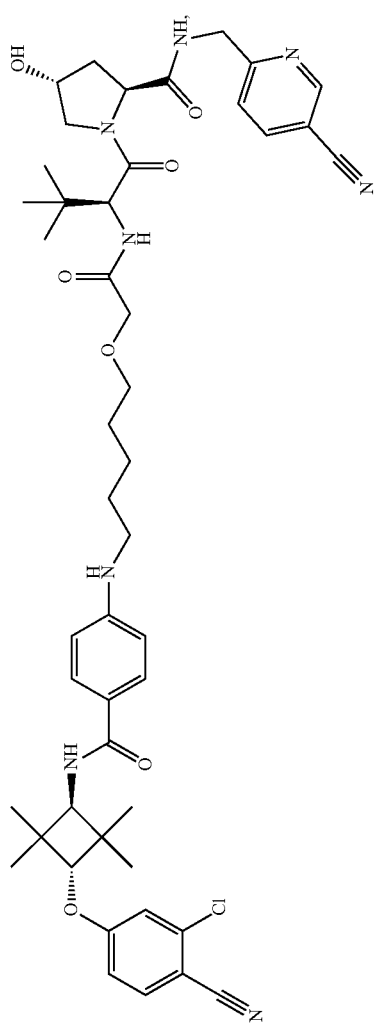
(539)
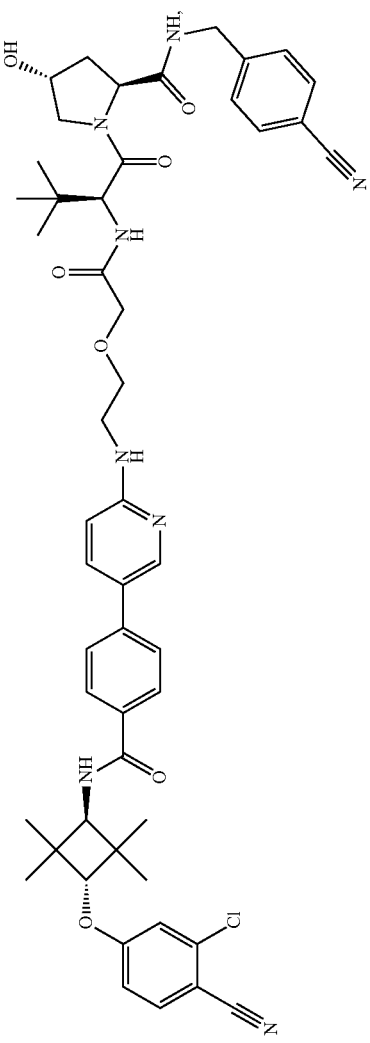
(540)

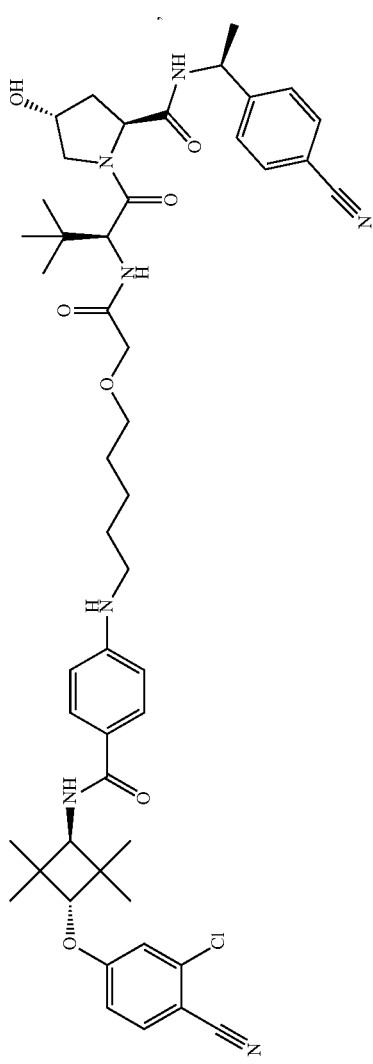
(541)
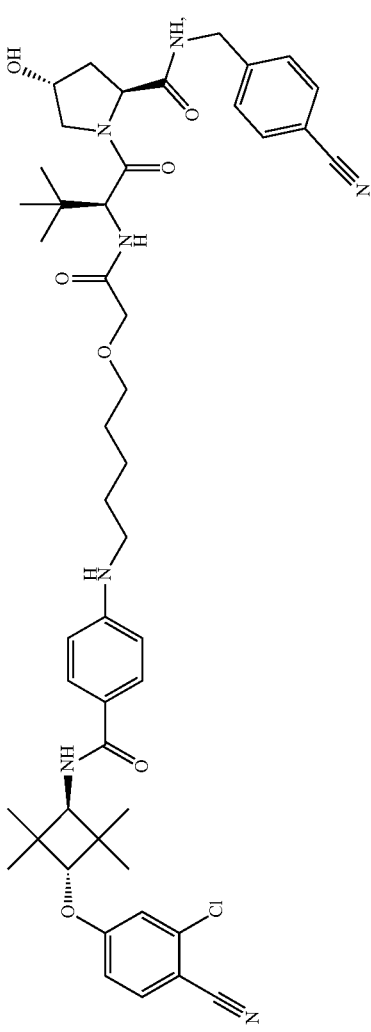
(542)

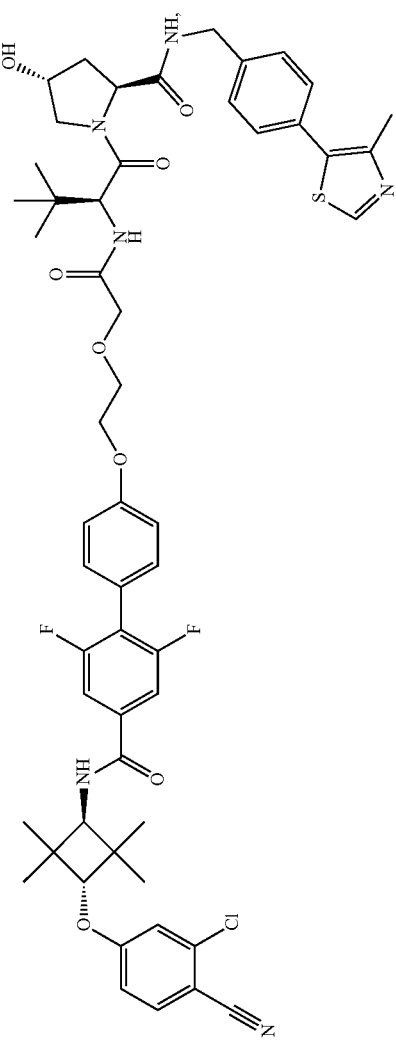
(543)
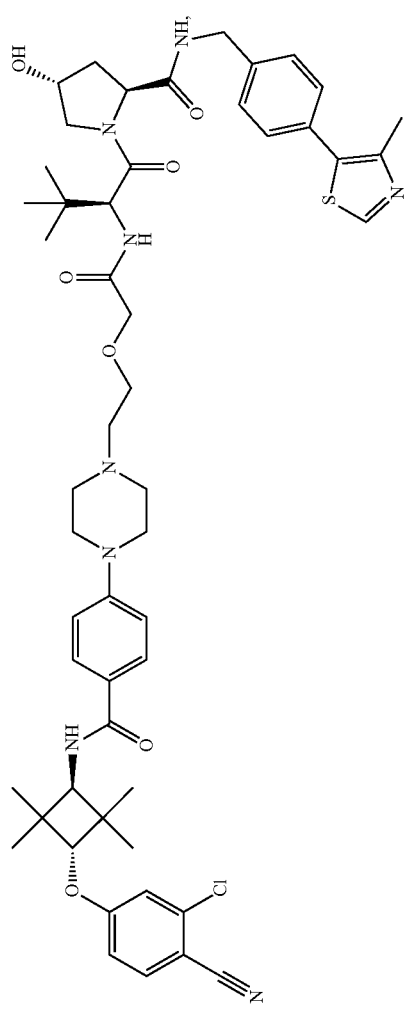
(544)

(547)
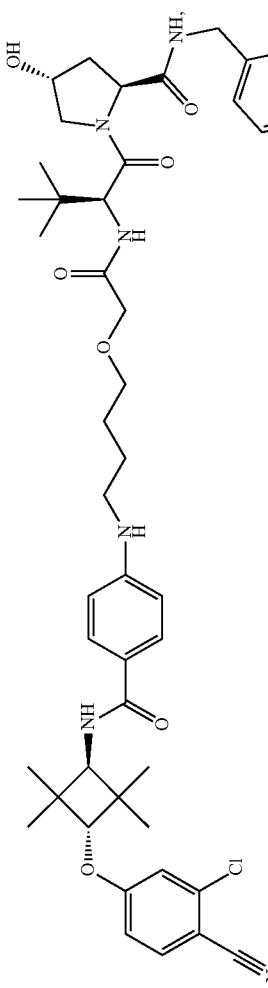
(548)
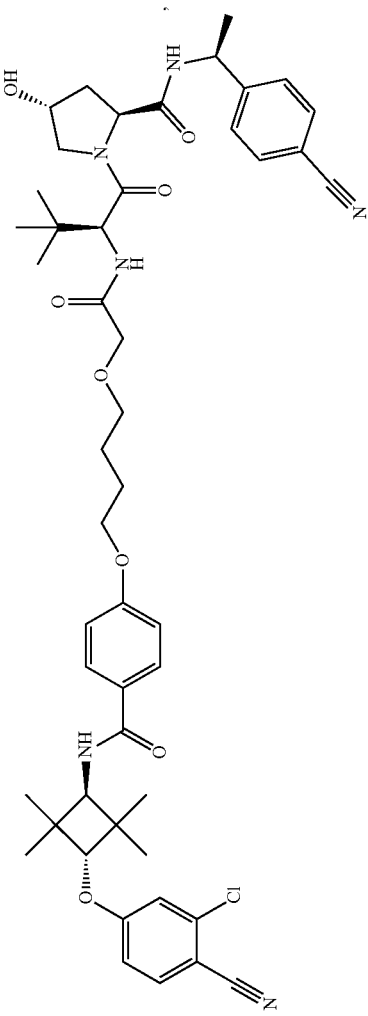

(549)
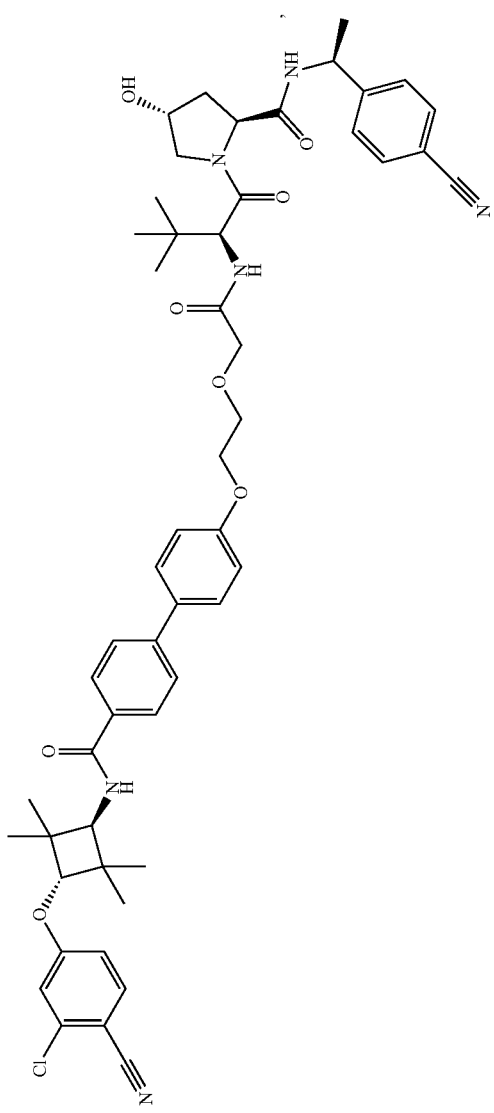
(550)
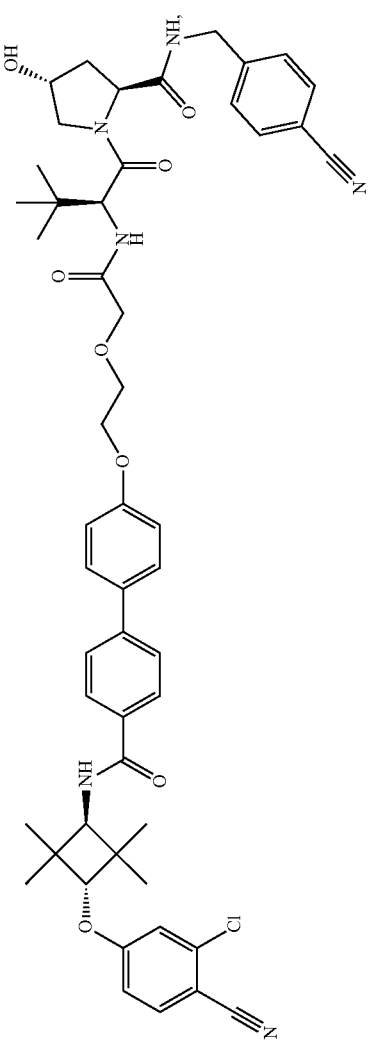

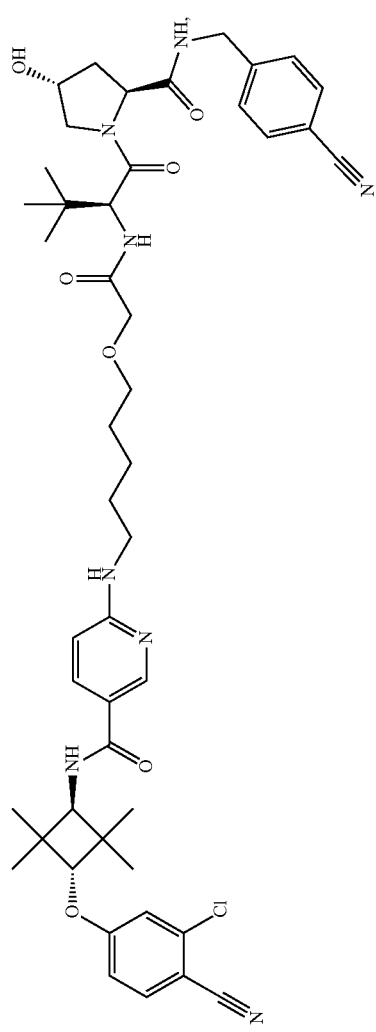
(551)
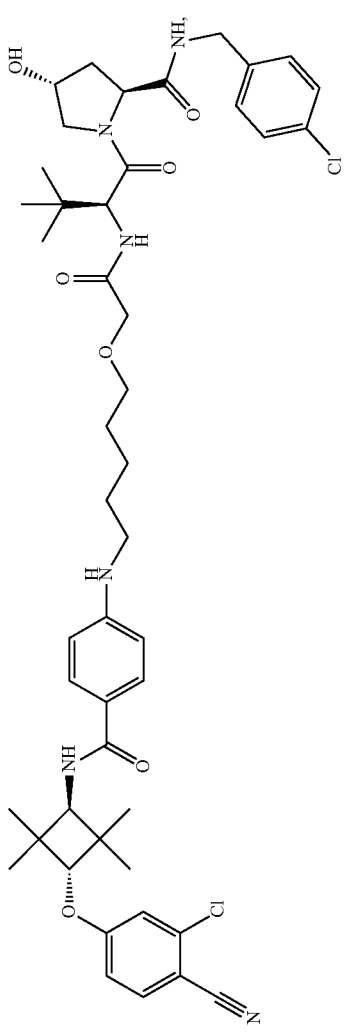
(552)

-continued
(553)
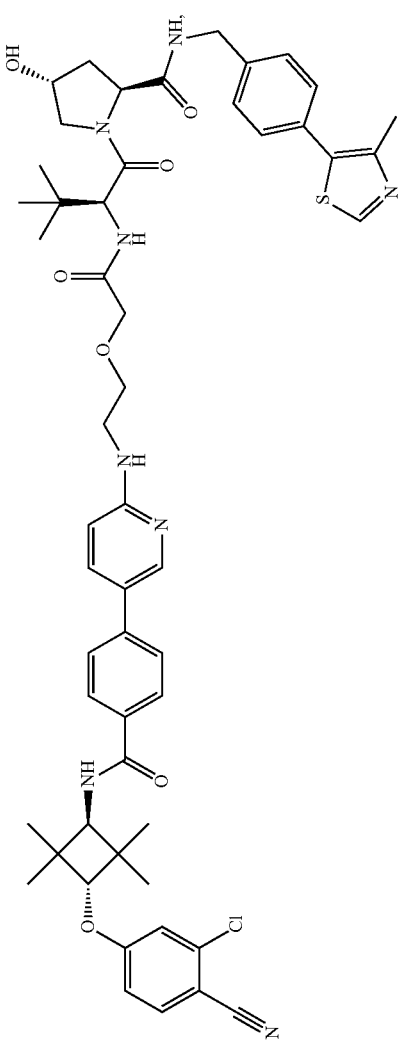
(555)
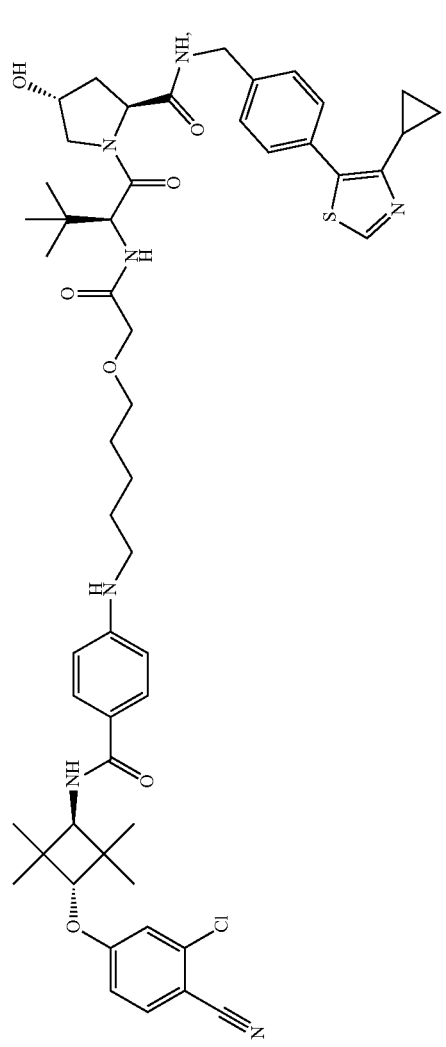

(557)
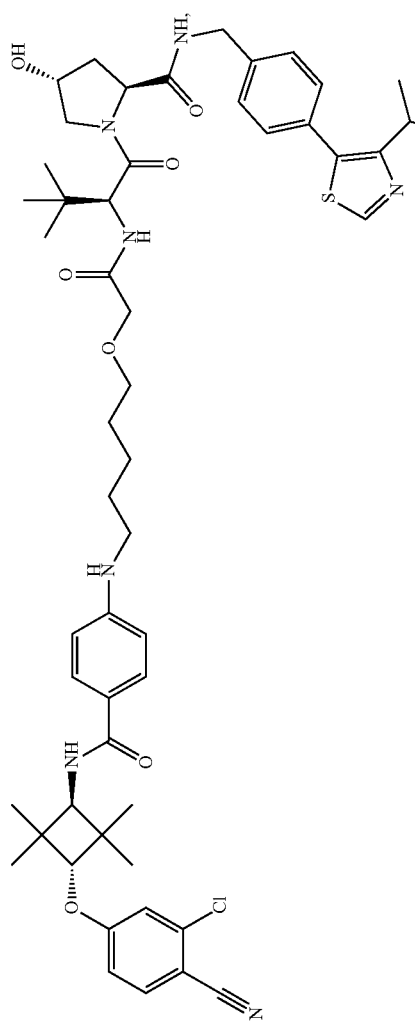
(558)
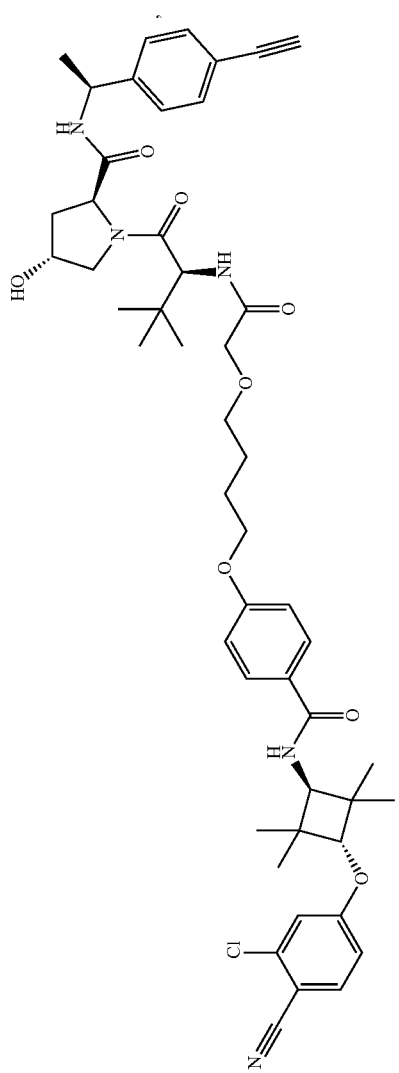

(560) 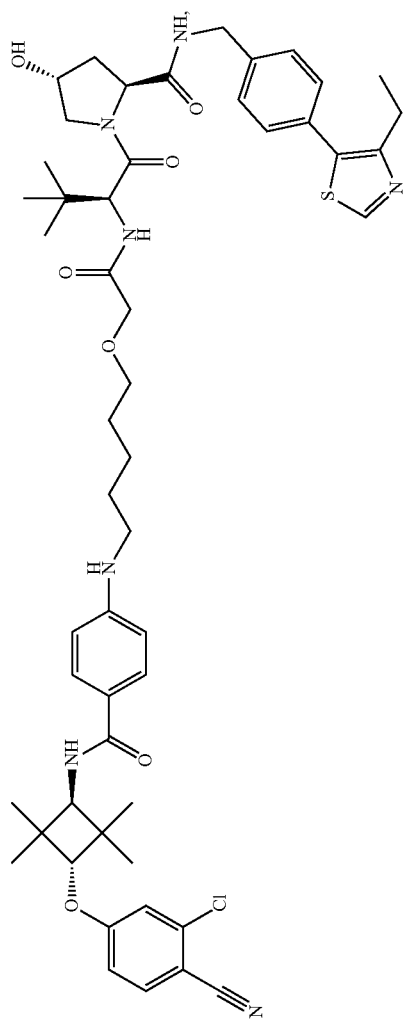
(561) 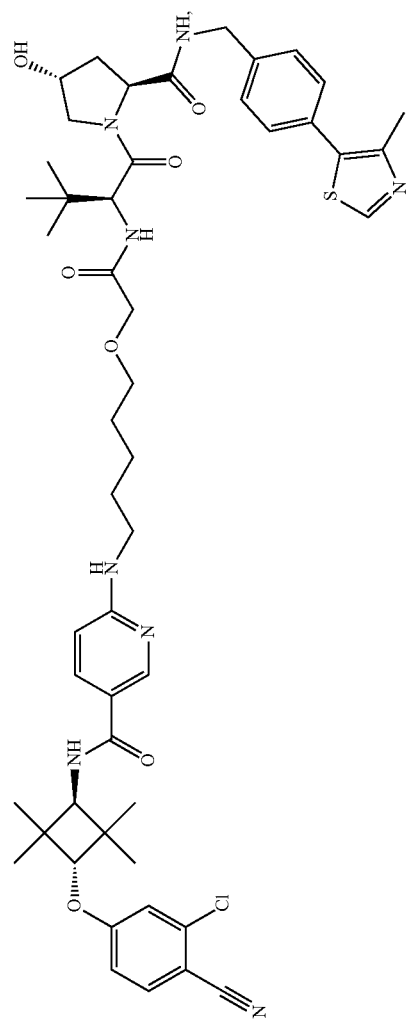

(562)
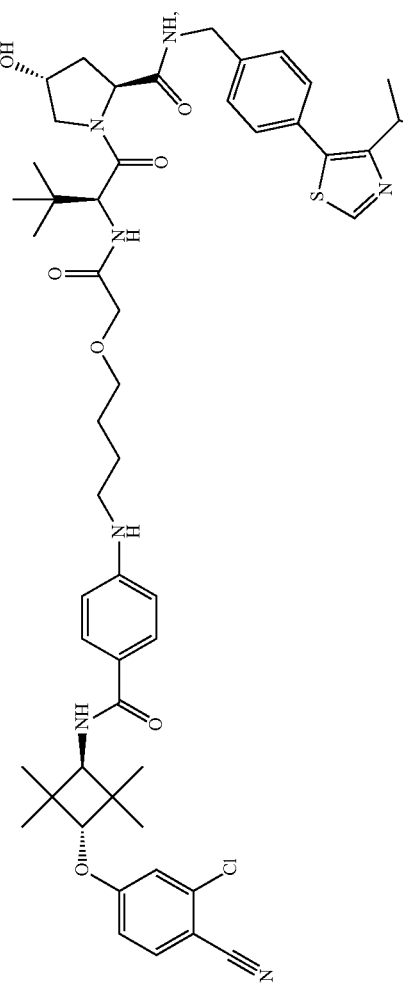
(563)
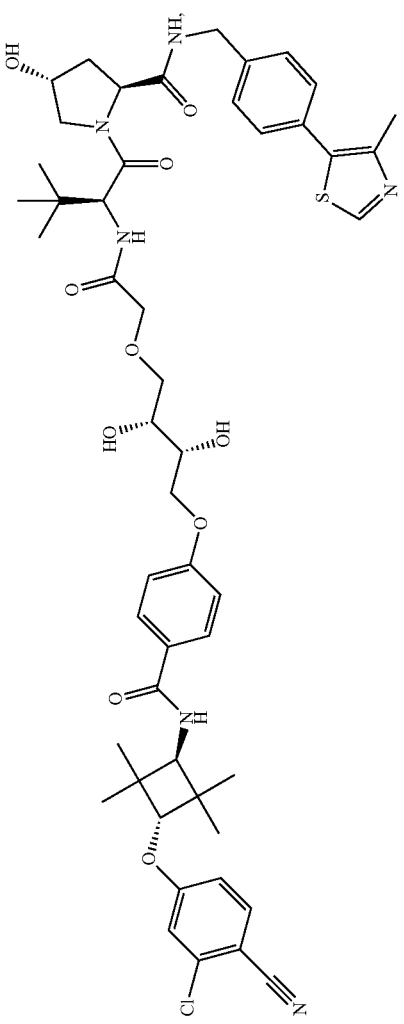

(564)
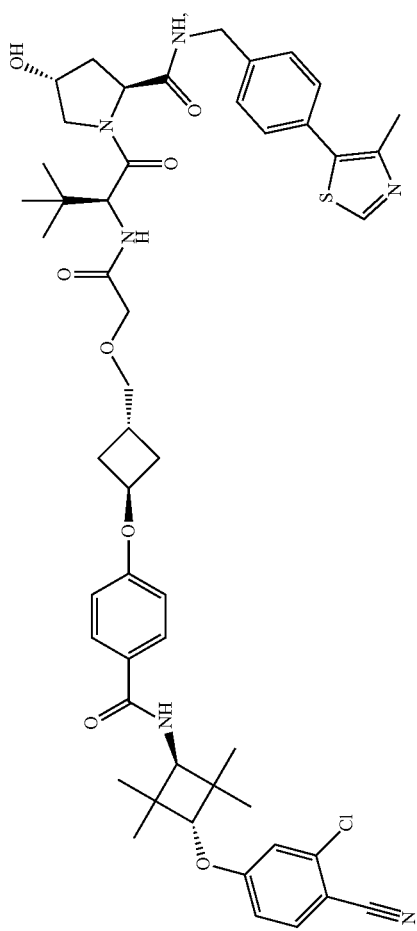
(568)
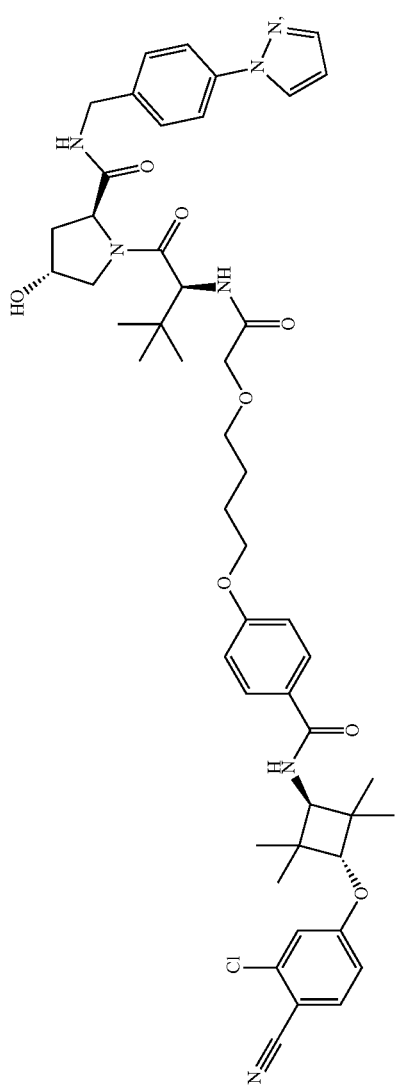

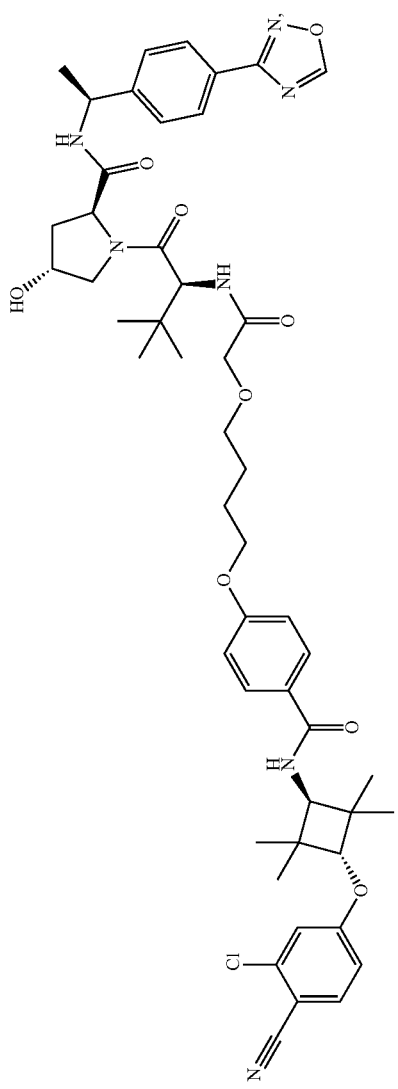
(569)
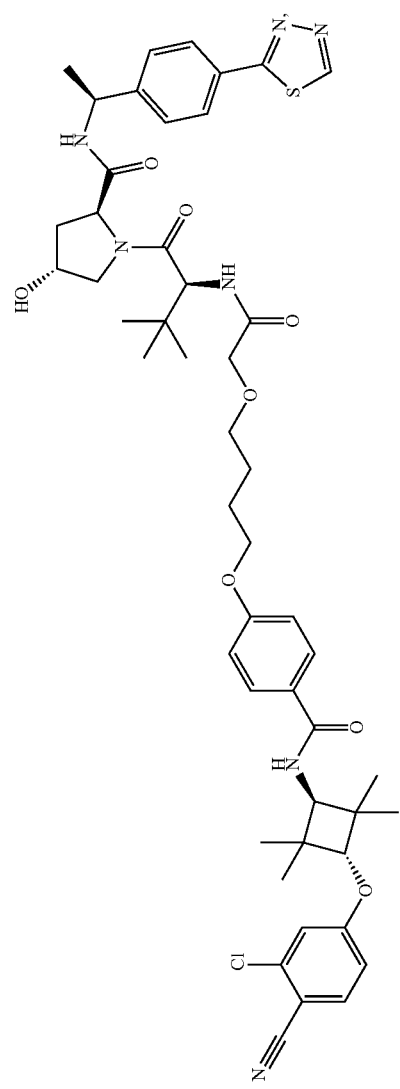
(570)

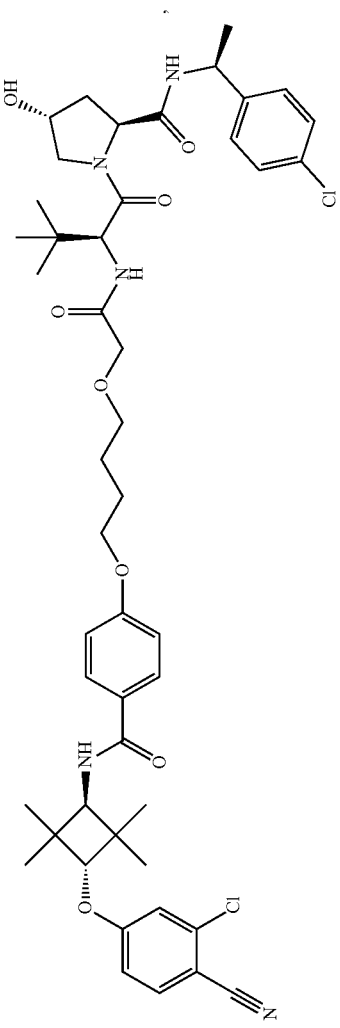
(572)
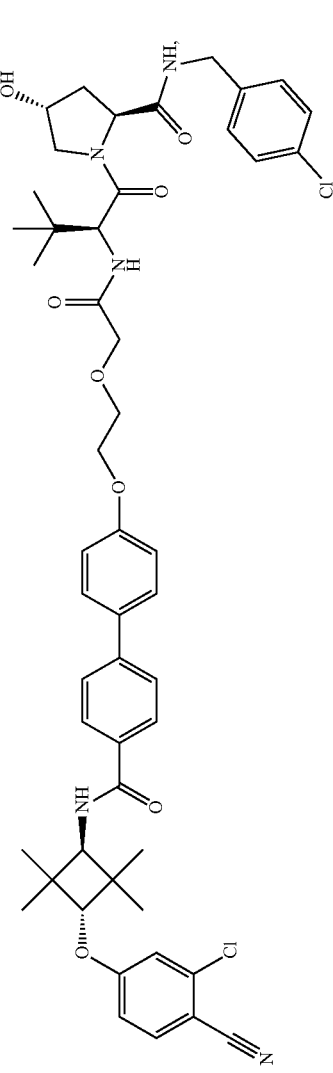
(573)
and

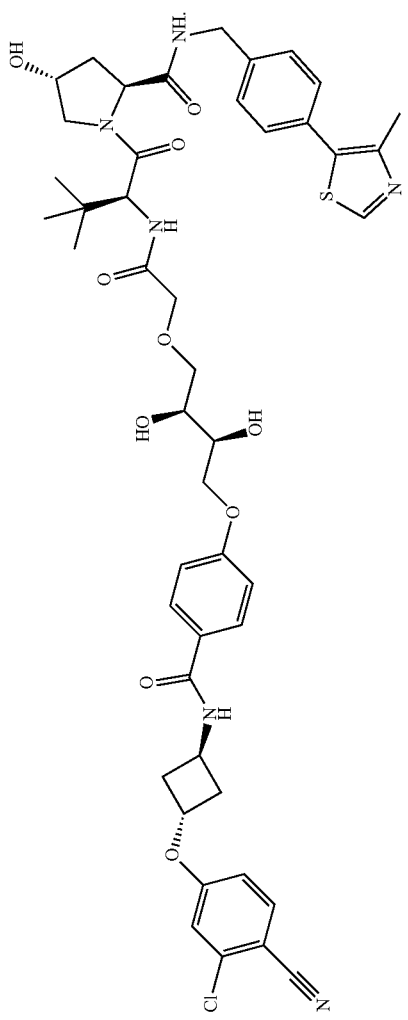
(577)

7. The bifunctional compound of claim 1, wherein the compound is selected from the group consisting of:
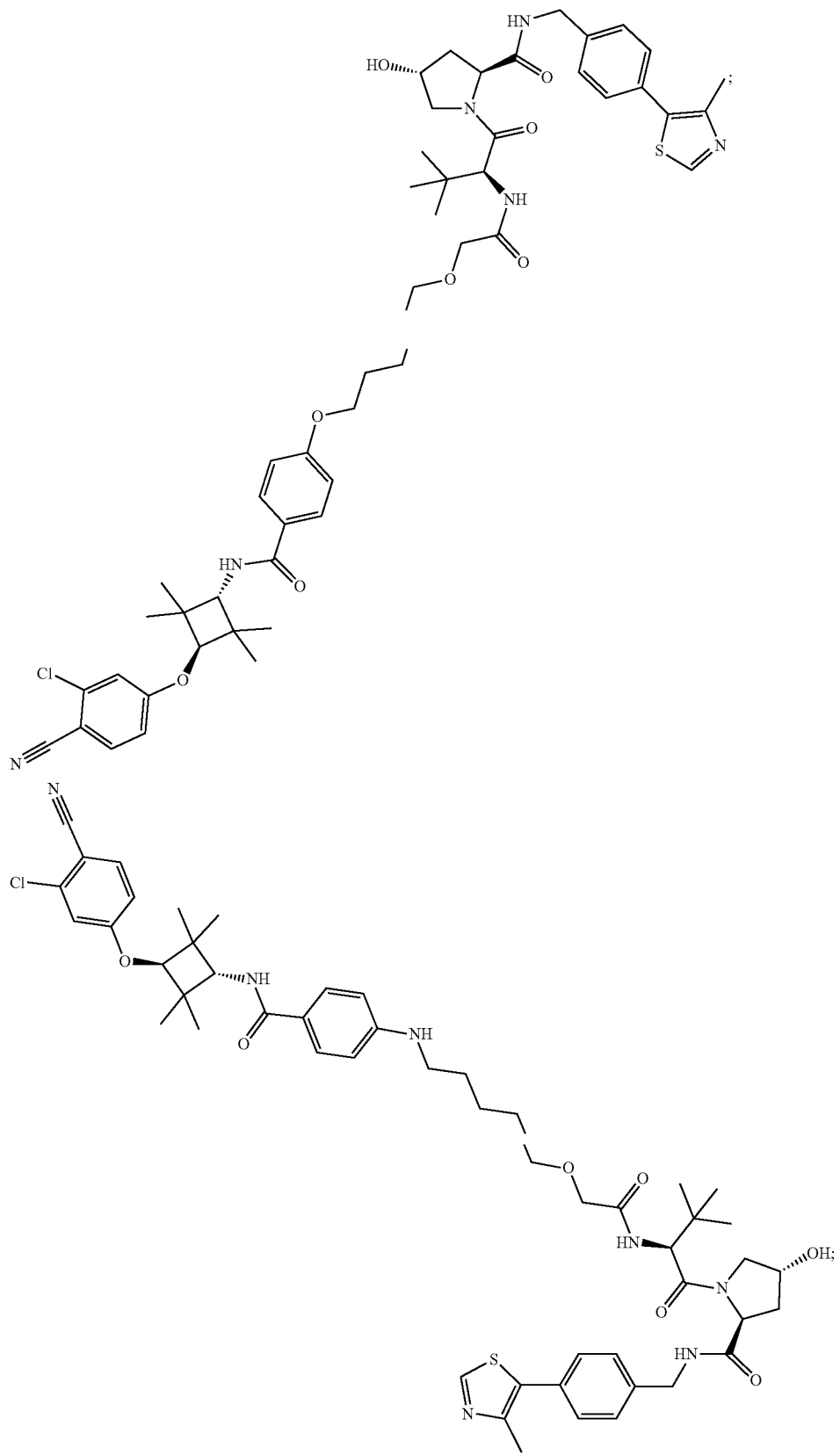

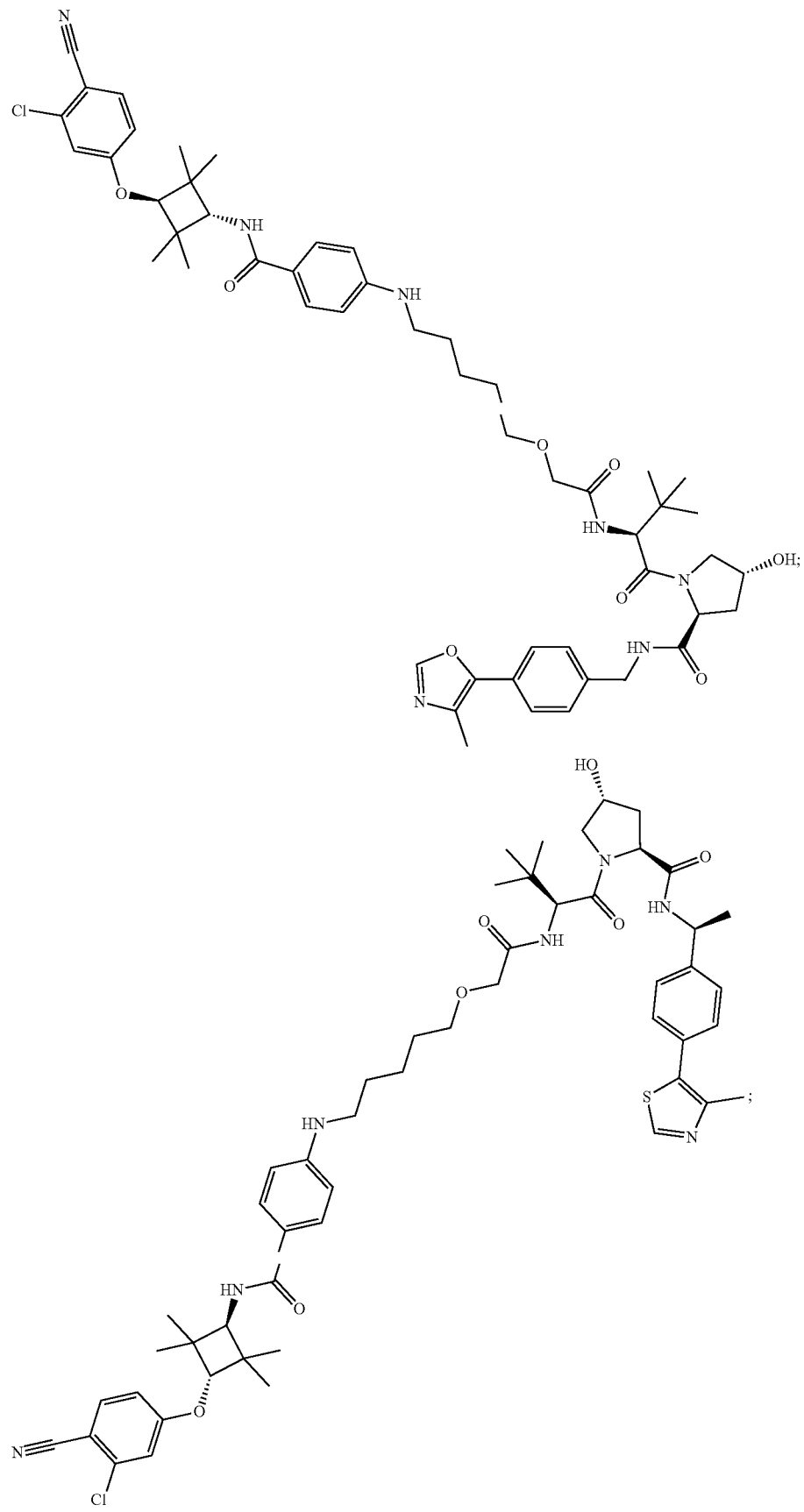

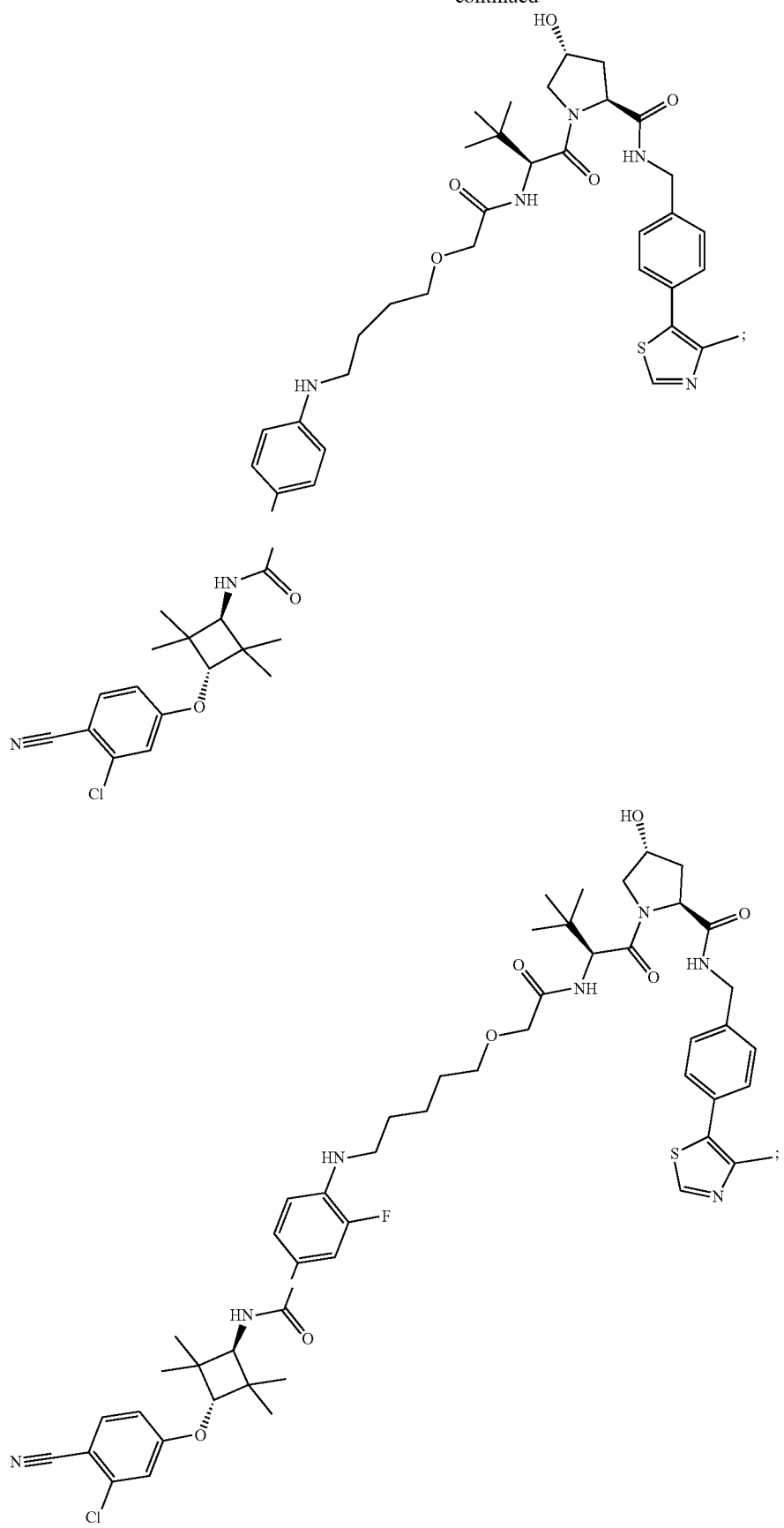

-continued
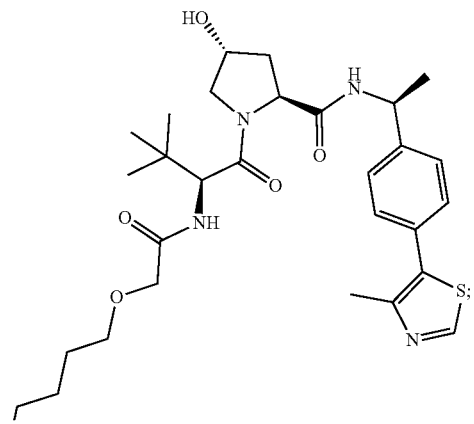
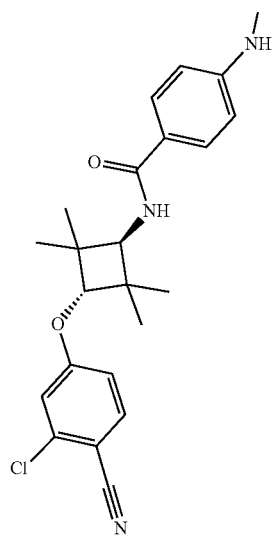
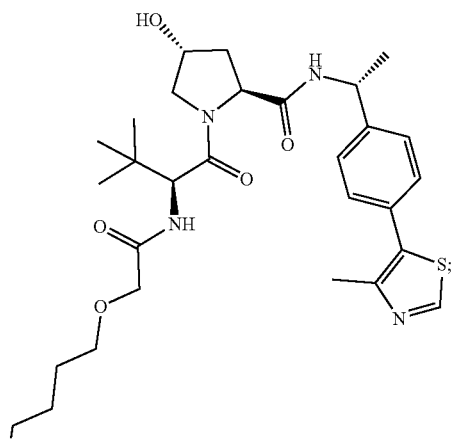

961
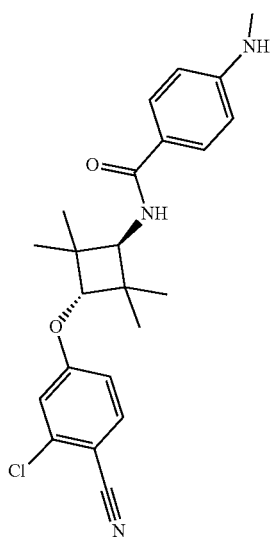
-continued
962
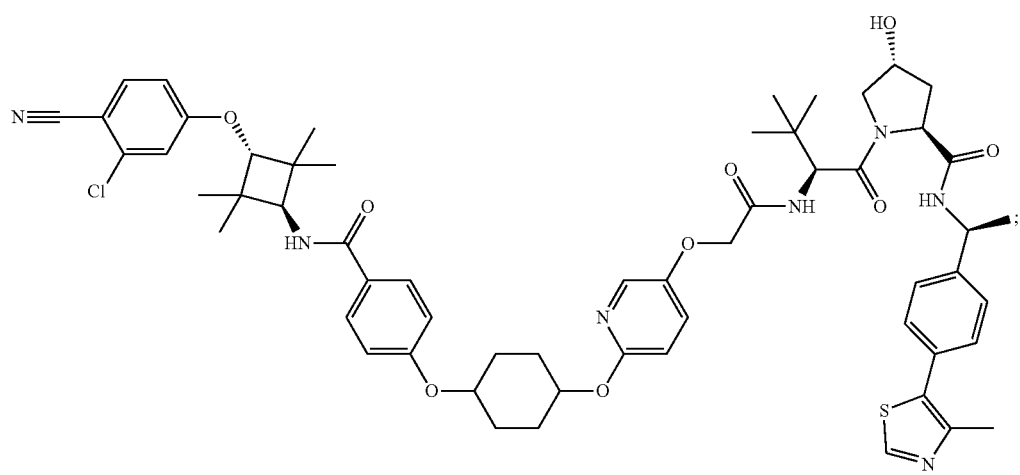
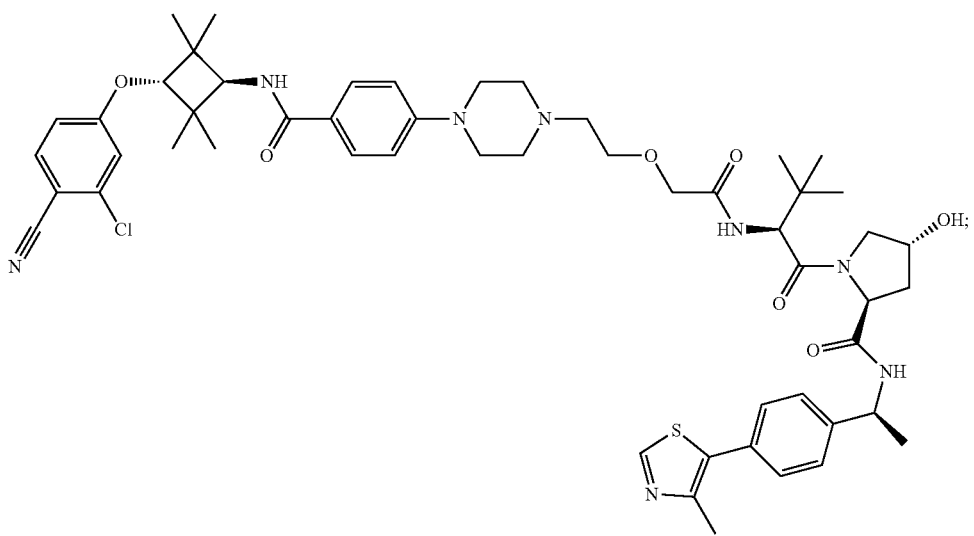

963
-continued
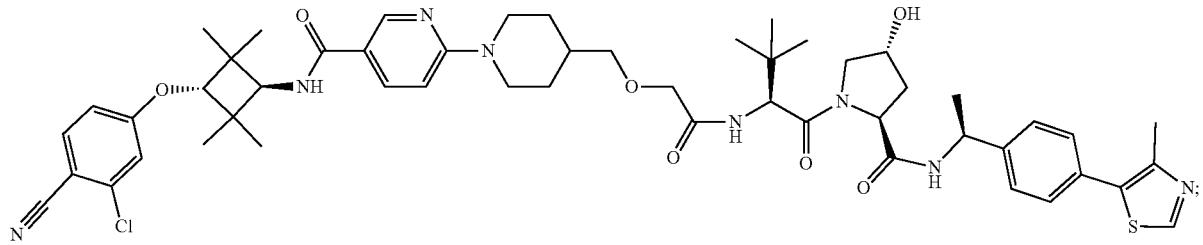
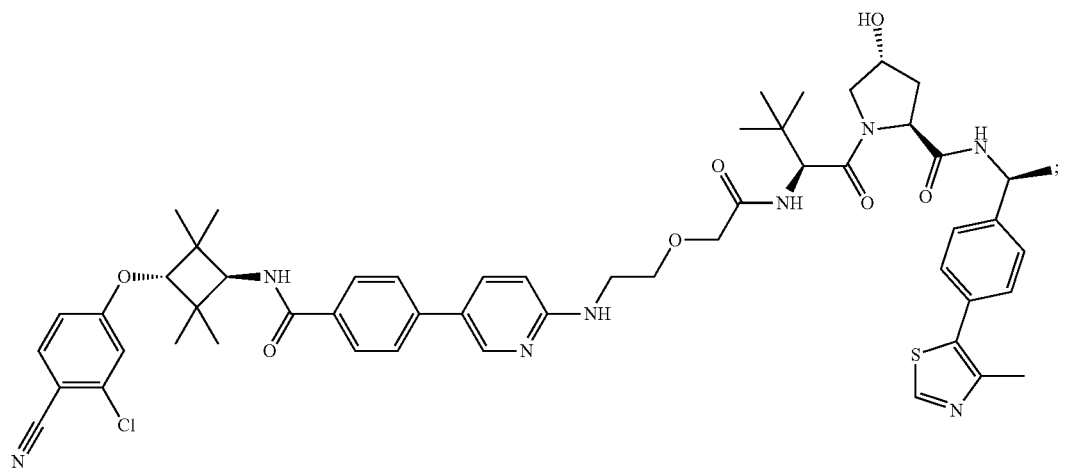
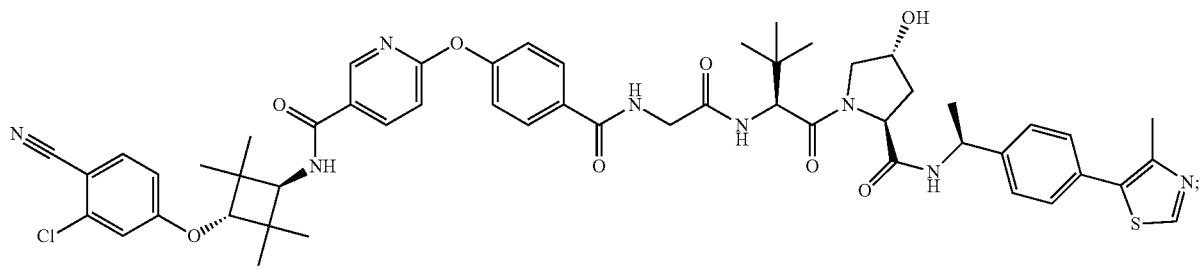
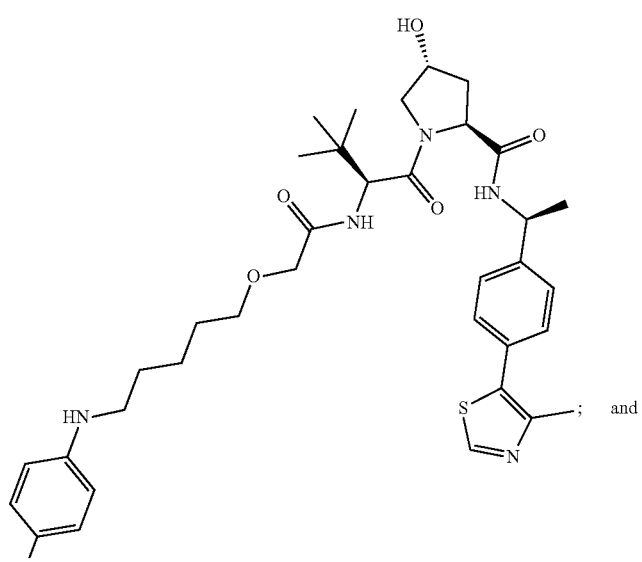
; and
964

965
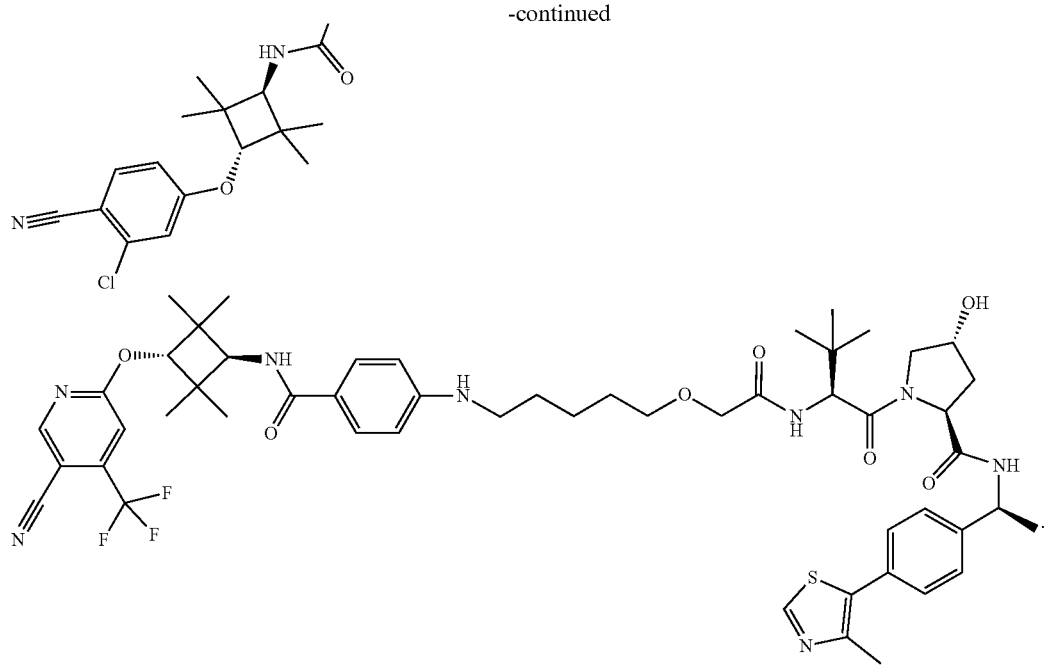
966
-continued
8. A compound selected from the group:
(578)
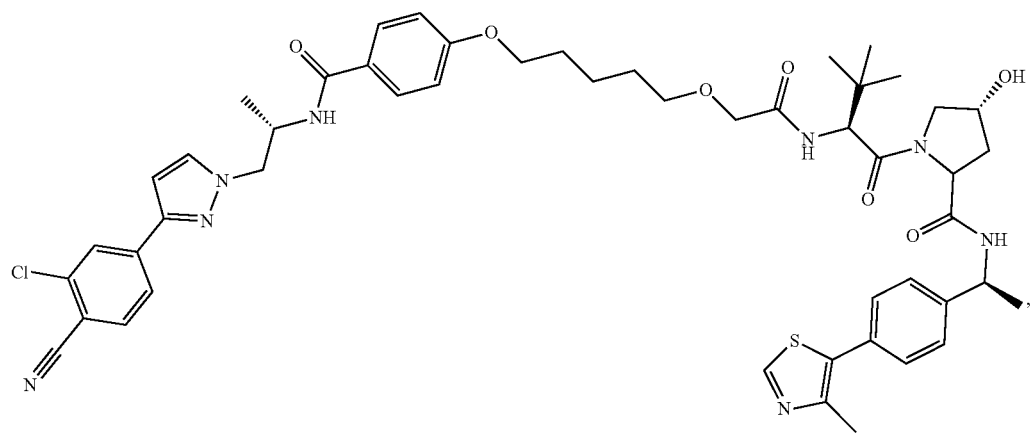
(579)
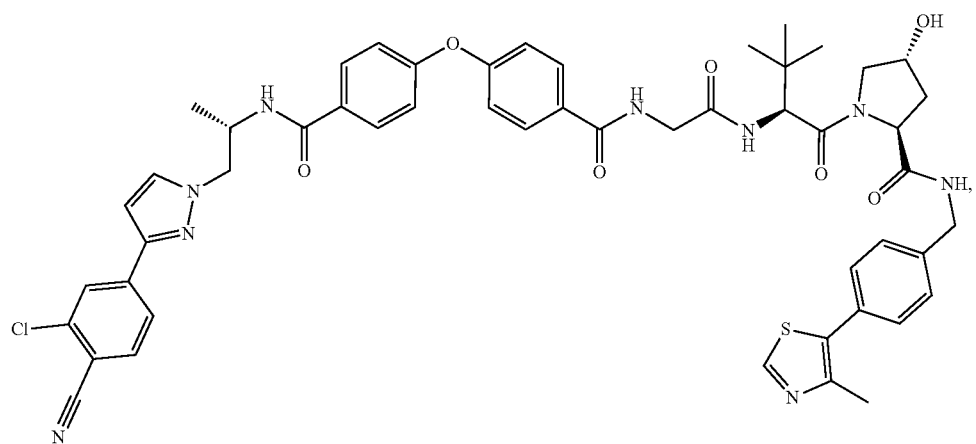

(580)
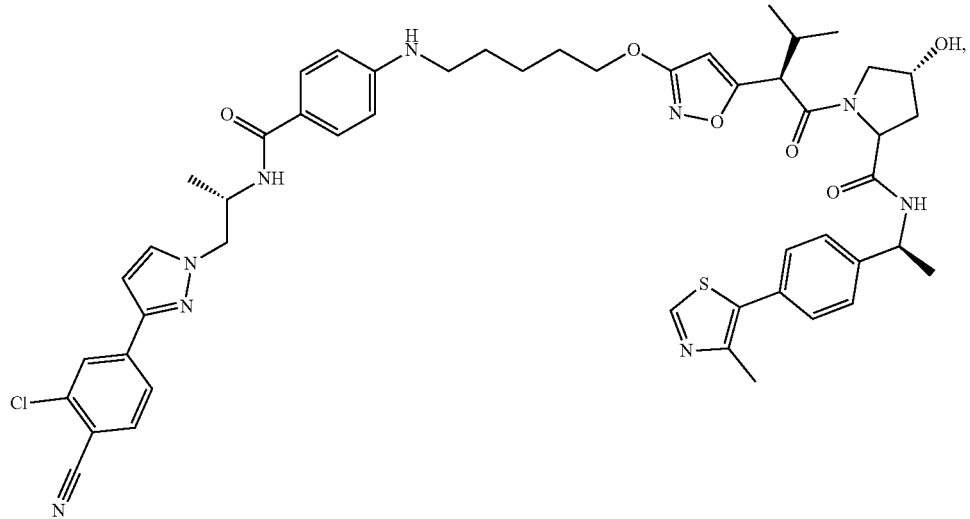
(581)
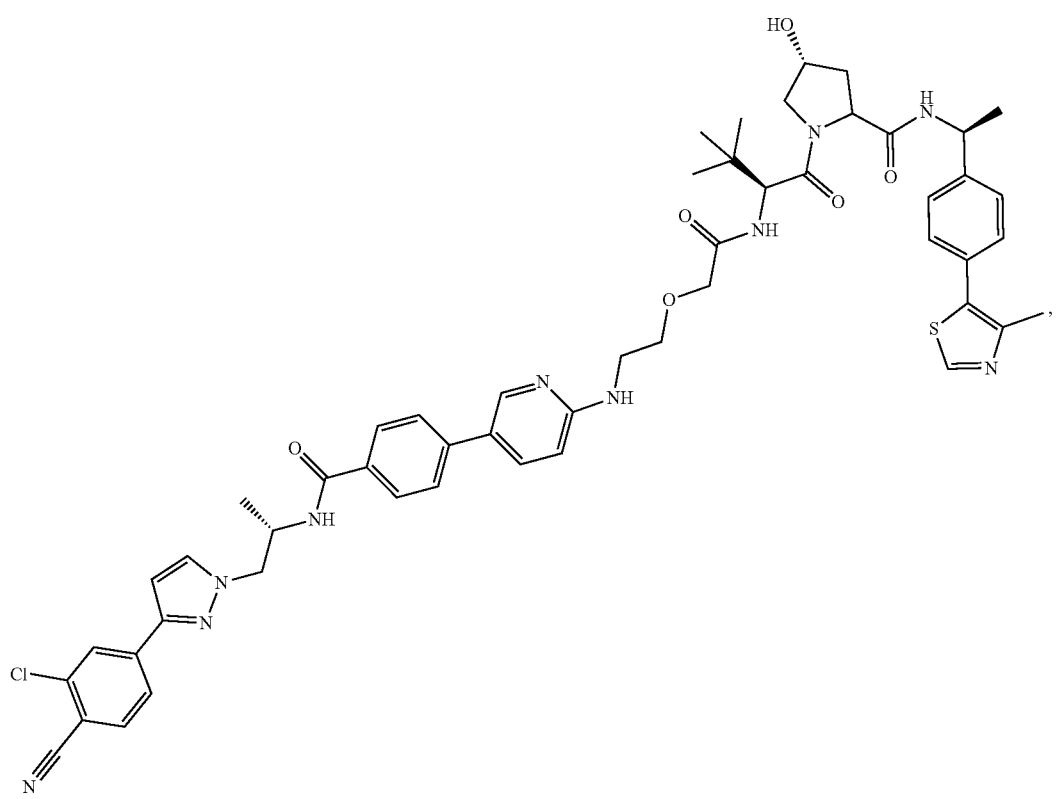

-continued
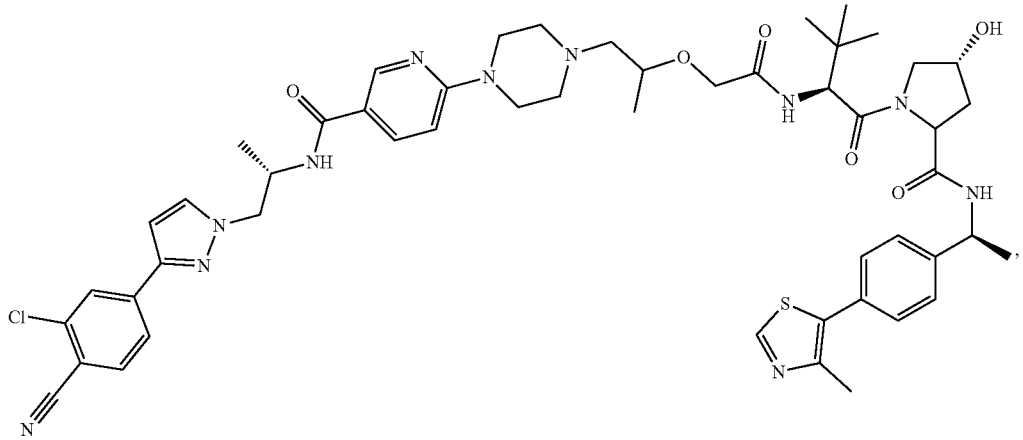
(582)
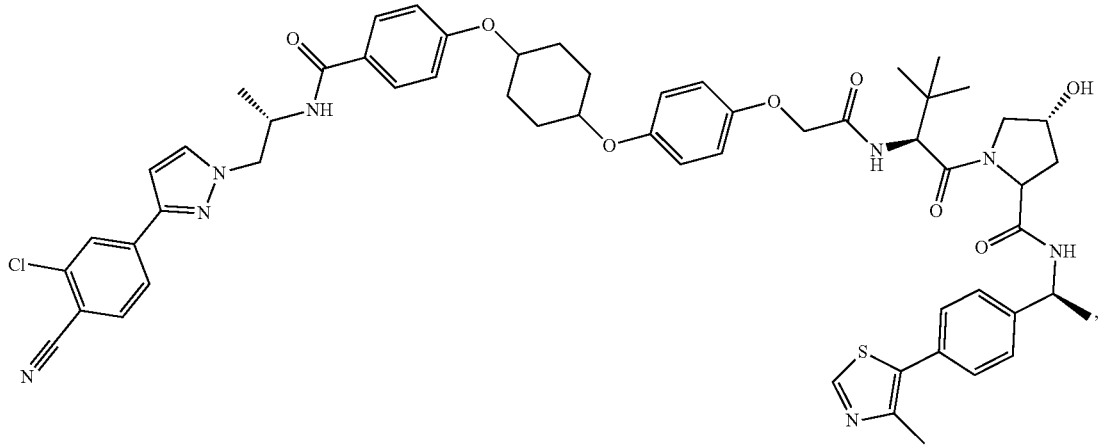
(583)
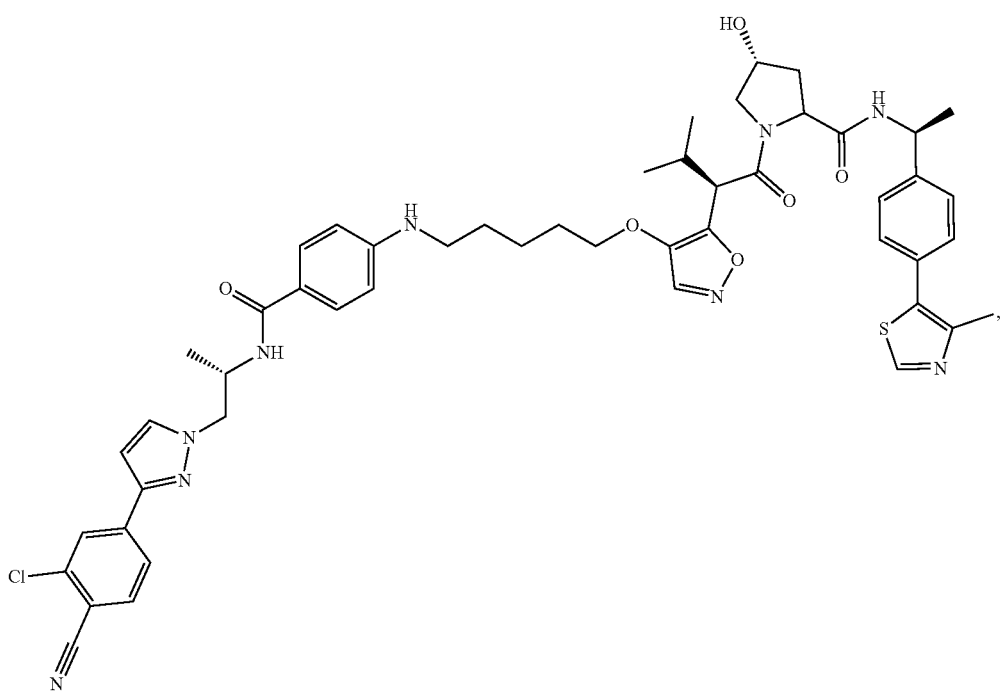
(584)

(585)
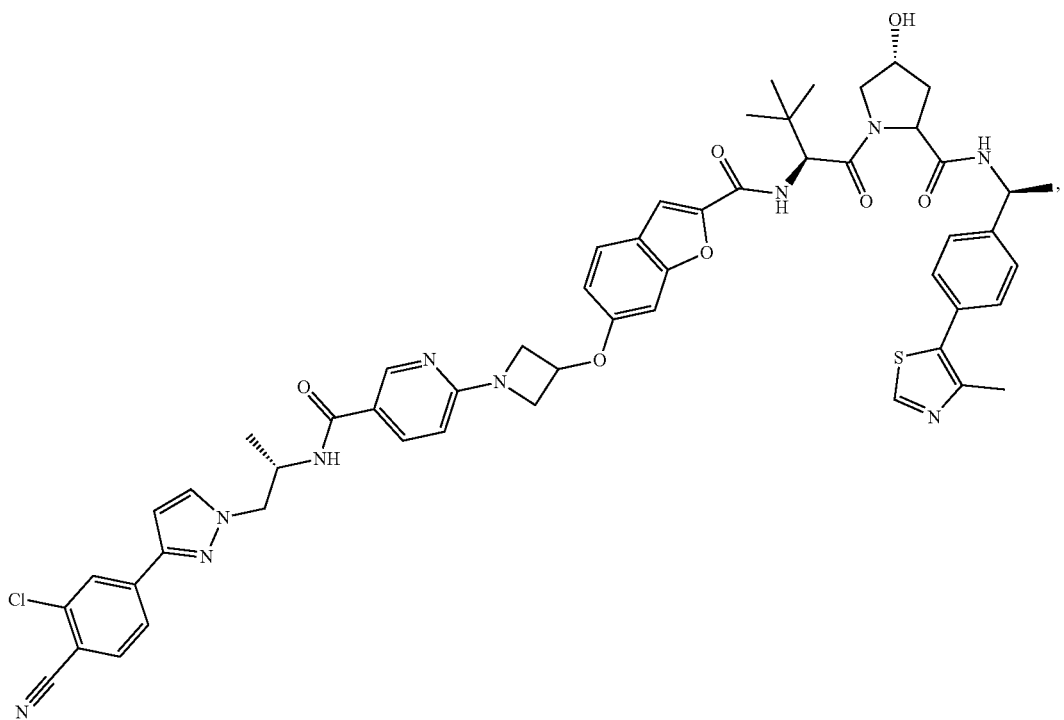
(586)
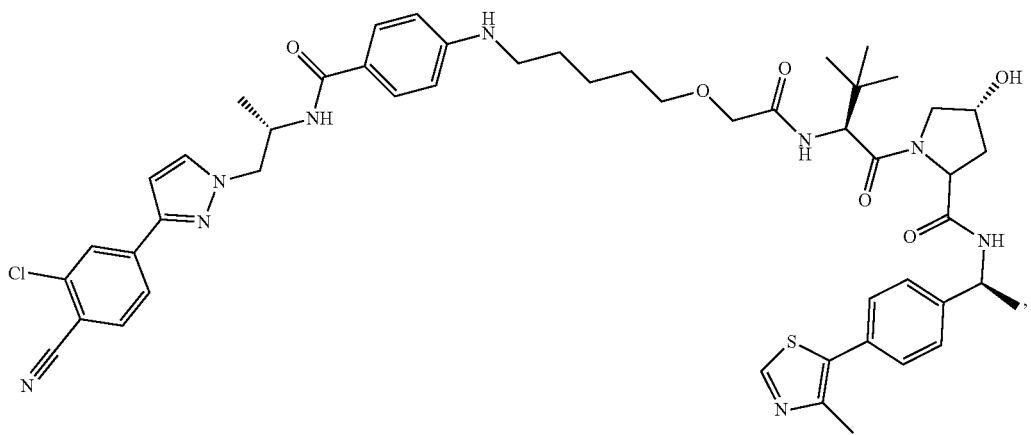

(587)
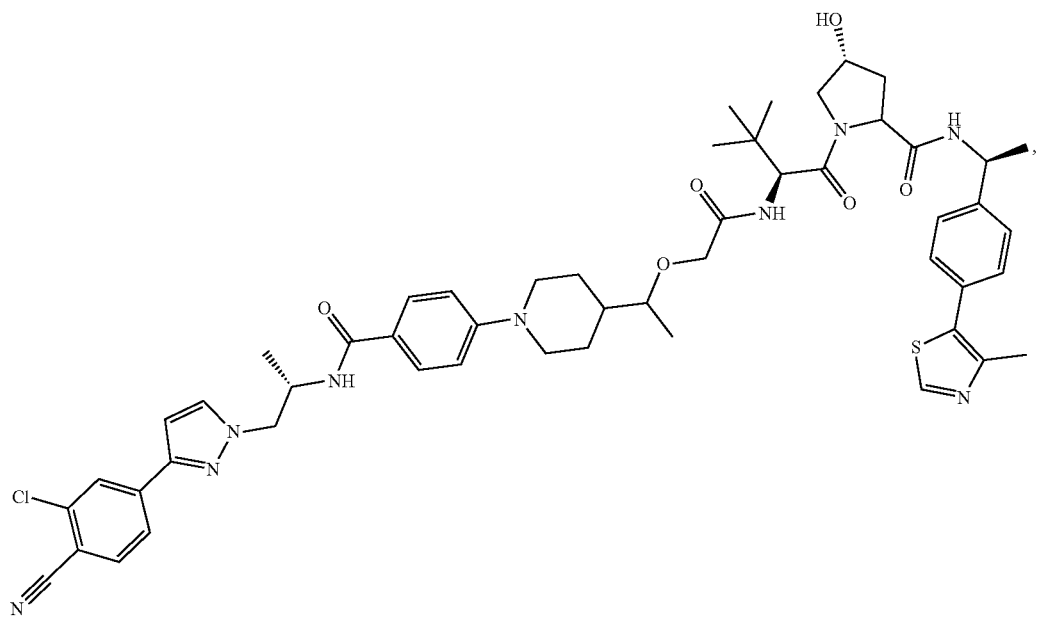
(588)
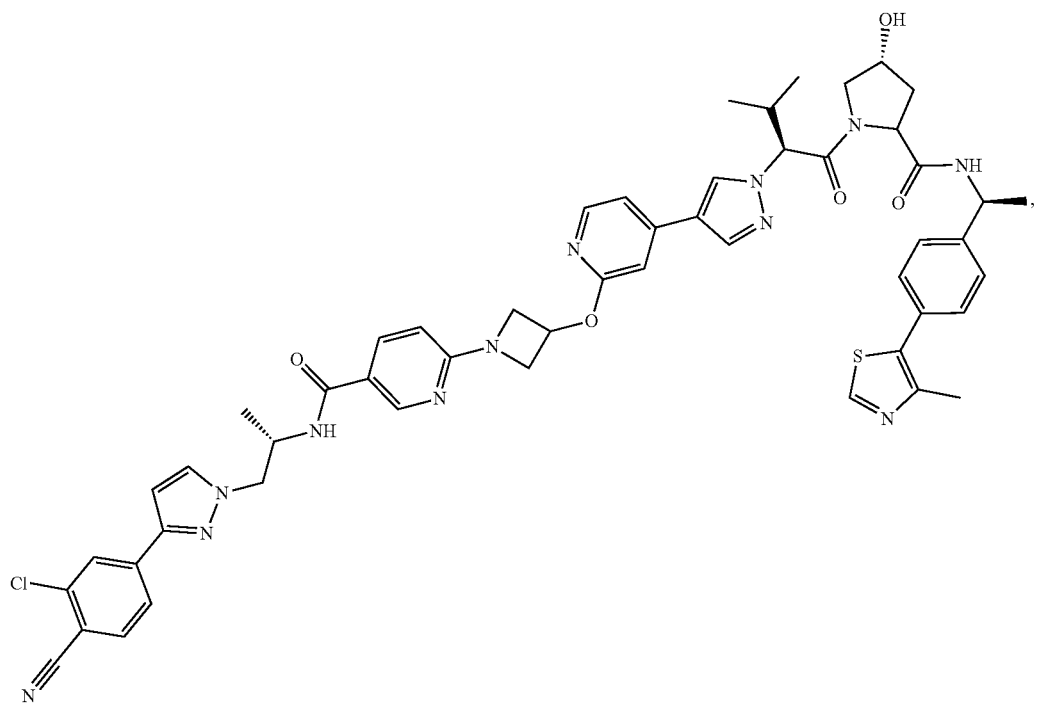

(589)
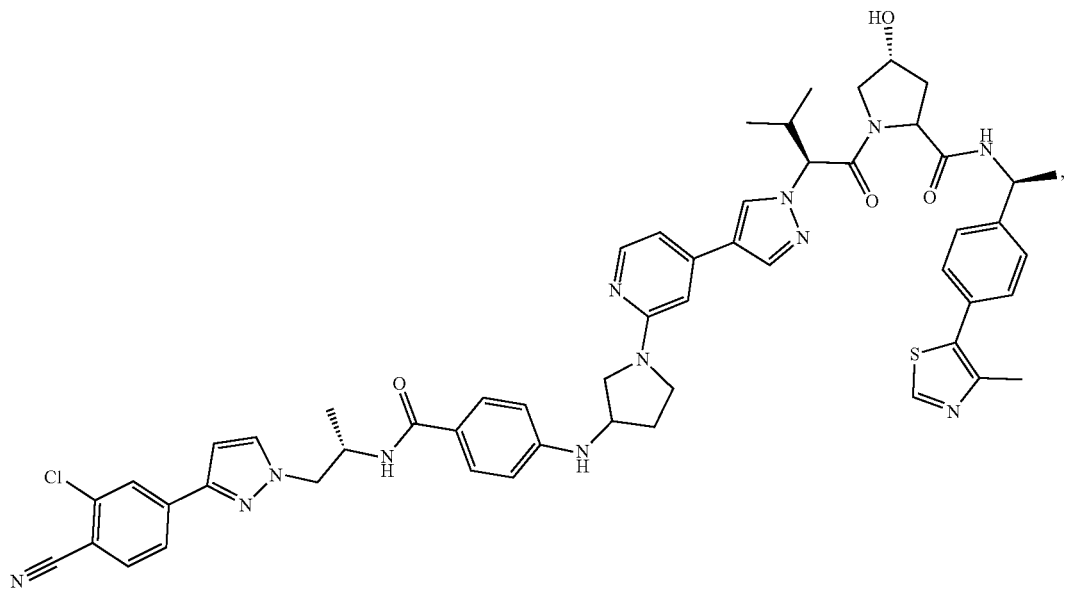
(590)
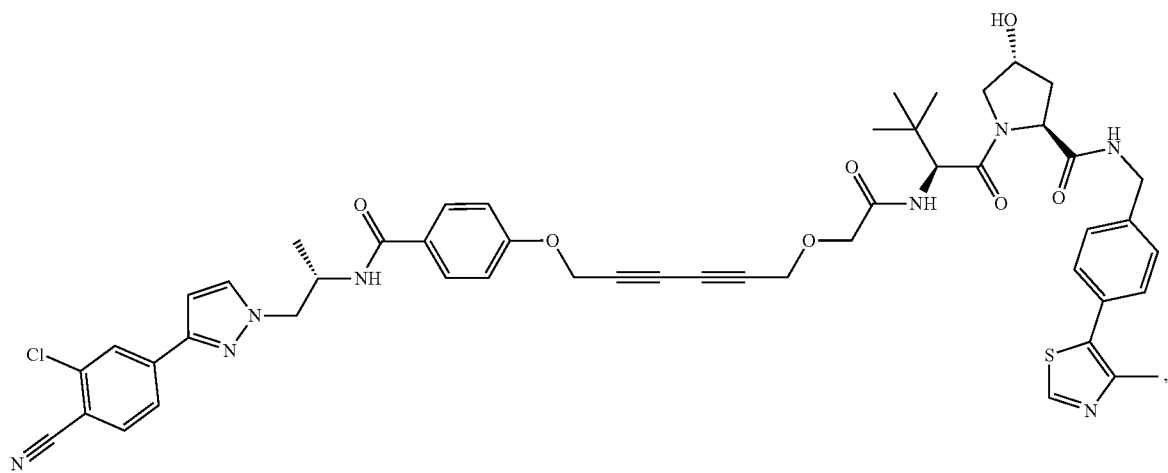
(591)
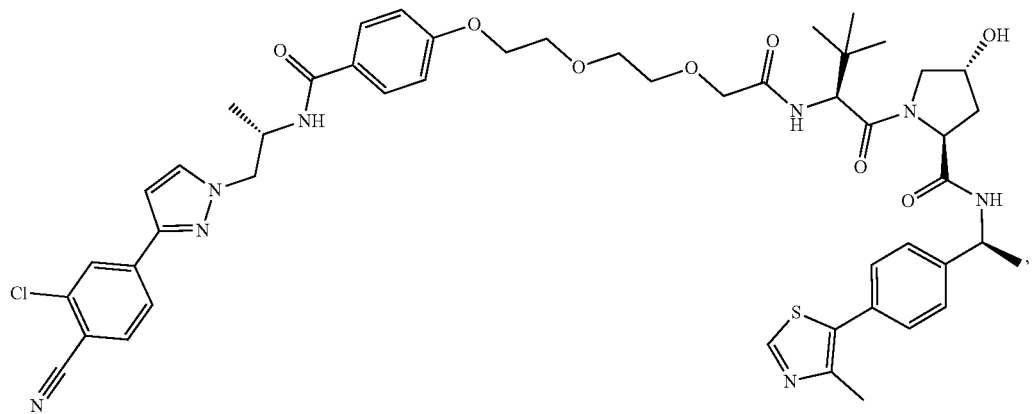

-continued

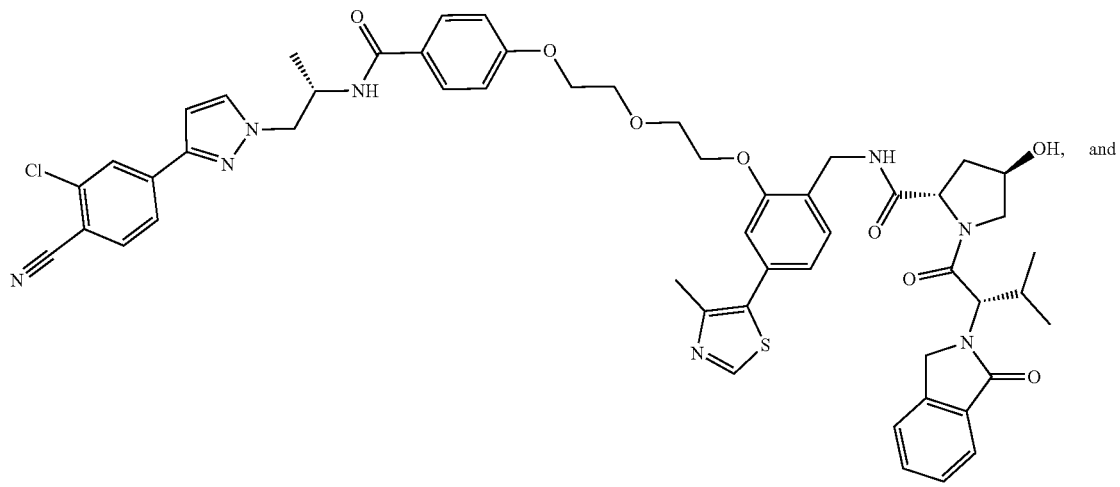
(592)

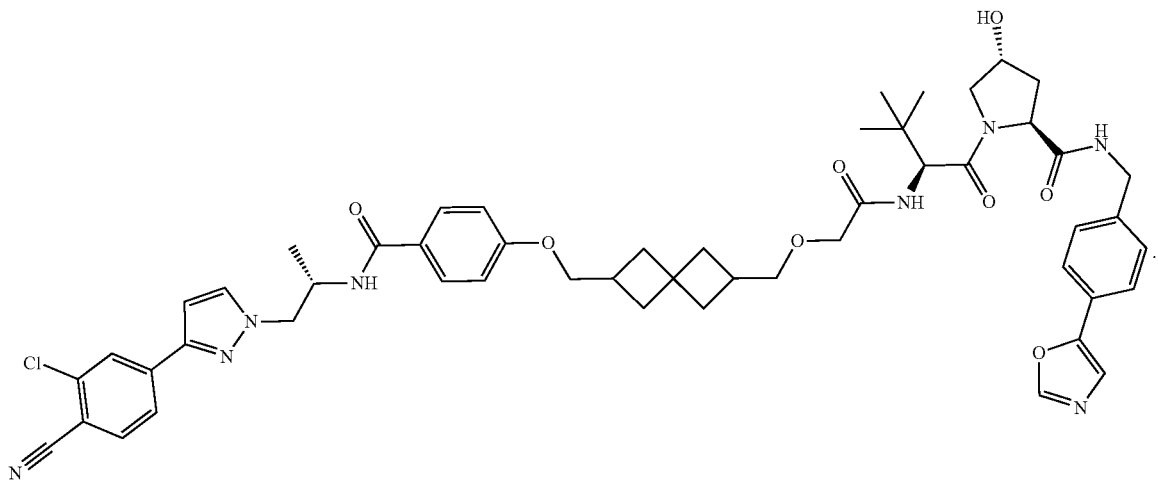
(593)

9. A composition comprising an effective amount of a bifunctional compound of claim 1, and a pharmaceutically acceptable carrier.

10. The composition of claim 9, wherein the composition further comprises at least one additional bioactive agent.

11. The composition of claim 10, wherein the bioactive agent is an anti-cancer agent.

12. A therapeutic composition comprising an effective amount of at least two different bifunctional compounds as described in claim 1.

13. A method of treating a disease or disorder related to androgen receptor (AR) activity in a subject having said disease or disorder comprising steps of administering a composition comprising a pharmaceutically acceptable carrier and an effective amount of a bifunctional compound as described in claim 1 to the subject, wherein the compound is effective in treating or ameliorating at least one symptom of the disease or disorder.

14. The method of claim 13, wherein the disease or disorder is cancer or Kennedy's Disease or both.

15. The method of claim 14, wherein the cancer is prostate cancer.

16. The method of claim 15, wherein the composition further comprises an effective amount of at least one additional anti-cancer agent.

* * * * *